US012698514B2

(12) United States Patent
Goren et al.

(10) Patent No.: US 12,698,514 B2
(45) Date of Patent: Aug. 4, 2026

(54) MAMMALIAN CELLS COMPRISING INTEGRATED CAS9 GENES TO PRODUCE STABLE INTEGRATION SITES, AND MAMMALIAN CELLS COMPRISING STABLE INTEGRATION SITES AND OTHER SITES

(71) Applicant: Regeneron Pharmaceuticals, Inc., Tarrytown, NY (US)

(72) Inventors: Michael Goren, Tarrytown, NY (US); Darya Burakov, Tarrytown, NY (US); Gang Chen, Yorktown Heights, NY (US); Yu Zhao, Willison Park, NY (US); Dipali Deshpande, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 766 days.

(21) Appl. No.: 18/047,357

(22) Filed: Oct. 18, 2022

(65) Prior Publication Data

US 2023/0287460 A1    Sep. 14, 2023

Related U.S. Application Data

(60) Provisional application No. 63/256,675, filed on Oct. 18, 2021.

(51) Int. Cl.
| | |
|---|---|
| *C12N 15/90* | (2006.01) |
| *C12N 5/00* | (2006.01) |
| *C12N 9/22* | (2006.01) |
| *C12N 15/11* | (2006.01) |

(52) U.S. Cl.
CPC ............. *C12N 15/907* (2013.01); *C12N 5/00* (2013.01); *C12N 9/22* (2013.01); *C12N 15/11* (2013.01); *C12N 2310/20* (2017.05); *C12N 2800/80* (2013.01); *C12N 2820/002* (2013.01)

(58) Field of Classification Search
None
See application file for complete search history.

(56) References Cited

U.S. PATENT DOCUMENTS

| | | | |
|---|---|---|---|
| 5,464,758 | A | 11/1995 | Gossen et al. |
| 5,658,785 | A | 8/1997 | Johnson |
| 5,981,225 | A | 11/1999 | Kochanek et al. |
| 5,985,846 | A | 11/1999 | Kochanek et al. |
| 5,989,910 | A | 11/1999 | Mermod et al. |
| 6,423,544 | B1 | 7/2002 | Hardy |
| 6,558,948 | B1 | 5/2003 | Kochanek et al. |
| 7,232,899 | B2 | 6/2007 | Von Seggern et al. |
| 7,771,997 | B2 | 8/2010 | Chen et al. |
| 8,734,809 | B2 | 5/2014 | Gao et al. |
| 8,852,926 | B2 | 10/2014 | Mo et al. |
| 9,315,773 | B2 | 4/2016 | Schiedner et al. |
| 9,371,512 | B2 | 6/2016 | Schiedner et al. |
| 9,469,856 | B2 | 10/2016 | Dou et al. |
| 9,534,233 | B2 | 1/2017 | Kochanek et al. |
| 9,777,291 | B2 | 10/2017 | Chatterjee |
| 9,783,825 | B2 | 10/2017 | Chatterjee |
| 9,803,218 | B2 | 10/2017 | Chatterjee |
| 9,816,110 | B2 | 11/2017 | Shen et al. |
| 9,834,789 | B2 | 12/2017 | Chatterjee et al. |
| 10,081,798 | B2 | 9/2018 | Wissing et al. |
| 10,544,429 | B2 | 1/2020 | Farley et al. |
| 10,647,999 | B2 | 5/2020 | Cawood et al. |
| 10,711,274 | B2 | 7/2020 | Mueller et al. |
| 10,815,497 | B2 | 10/2020 | Kyostio-Moore et al. |
| 10,858,631 | B2 | 12/2020 | Vink |
| 11,643,666 | B2 | 5/2023 | Colloca et al. |
| 11,697,824 | B2 | 7/2023 | Cawood et al. |
| 2003/0192066 | A1 | 10/2003 | Zhang et al. |
| 2009/0191597 | A1 | 7/2009 | Samulski et al. |
| 2013/0023033 | A1 | 1/2013 | Wilson et al. |
| 2015/0152437 | A1* | 6/2015 | Mauro ................. C12N 15/907 |
| | | | 435/325 |
| 2016/0177300 | A1 | 6/2016 | Feary et al. |
| 2018/0030480 | A1 | 2/2018 | Shen et al. |
| 2018/0216118 | A1 | 8/2018 | Chen et al. |

(Continued)

FOREIGN PATENT DOCUMENTS

| | | |
|---|---|---|
| EP | 1230354 A2 | 8/2002 |
| EP | 1362096 A2 | 11/2003 |

(Continued)

OTHER PUBLICATIONS

Chai et al ( Biochem engineer. J , 2020,v, 161, pp. 1-7).*

(Continued)

*Primary Examiner* — Michail A Belyavskyi

(74) *Attorney, Agent, or Firm* — McCarter & English, LLP

(57) ABSTRACT

The present inventions provide mammalian cells that comprise multiple Stable Integration Sites. The inventions provide sites introduced genomically into a Genomic Safe Harbor and introduced genomically outside of that particular Genomic Safe Harbor, including but not limited to another Genomic Safe Harbor. Polynucleotides of interest that encode polypeptides or RNAs of interest can be inserted into the Stable Integration Sites provided according to the inventions. The cells and methods of the inventions can be used for the high yield production of any protein, including viral proteins. Additionally, the cells and methods of the inventions are useful for production of viral vectors, such as AAV, antibodies and other proteins.

37 Claims, 18 Drawing Sheets
Specification includes a Sequence Listing.

(56) References Cited

U.S. PATENT DOCUMENTS

| | | |
|---|---|---|
| 2018/0267516 A1 | 9/2018 | Fister et al. |
| 2019/0078099 A1 | 3/2019 | Zhou et al. |
| 2019/0171188 A1 | 6/2019 | Fister |
| 2019/0175716 A1 | 6/2019 | Gilbert et al. |
| 2019/0233544 A1 | 8/2019 | Babb et al. |
| 2020/0032221 A1 | 1/2020 | Tiernan et al. |
| 2020/0066369 A1 | 2/2020 | Downey et al. |
| 2020/0102578 A1 | 4/2020 | Farley et al. |
| 2020/0157567 A1 | 5/2020 | Cawood et al. |
| 2020/0199627 A1 | 6/2020 | Gu et al. |
| 2020/0208121 A1 | 7/2020 | Hewitt et al. |
| 2020/0239909 A1 | 7/2020 | Cawood et al. |
| 2020/0277626 A1 | 9/2020 | Roska et al. |
| 2020/0277628 A1 | 9/2020 | Hein et al. |
| 2020/0325455 A1 | 10/2020 | Tiernan et al. |
| 2021/0163991 A1 | 6/2021 | Gillmeister et al. |
| 2022/0098619 A1* | 3/2022 | Nakamura ............. C12N 15/11 |
| 2022/0154215 A1 | 5/2022 | Greene |
| 2022/0162636 A1 | 5/2022 | Cawood et al. |
| 2022/0177854 A1 | 6/2022 | Chanas et al. |
| 2022/0259572 A1 | 8/2022 | Gu et al. |
| 2022/0307052 A1 | 9/2022 | Pechan et al. |
| 2022/0364103 A1 | 11/2022 | Xue et al. |
| 2023/0048994 A1 | 2/2023 | Smith et al. |
| 2023/0076955 A1 | 3/2023 | Cawood et al. |
| 2023/0193312 A1 | 6/2023 | Goren et al. |
| 2023/0257444 A1* | 8/2023 | Lim ................... C07K 14/7056 |
| | | 530/396 |
| 2023/0257770 A1 | 8/2023 | Cawood et al. |
| 2023/0257831 A1 | 8/2023 | Cawood et al. |
| 2023/0279427 A1 | 9/2023 | Hu et al. |
| 2023/0304062 A1 | 9/2023 | Zhao et al. |
| 2023/0313228 A1 | 10/2023 | Cawood |
| 2023/0357794 A1 | 11/2023 | Cawood et al. |
| 2024/0168012 A1* | 5/2024 | Haig .................... G01N 33/505 |
| 2024/0352483 A1 | 10/2024 | Abbott et al. |
| 2025/0154524 A1 | 5/2025 | Goren et al. |

FOREIGN PATENT DOCUMENTS

| | | |
|---|---|---|
| EP | 1743041 A1 | 1/2007 |
| EP | 2606128 A1 | 6/2013 |
| EP | 3456822 A1 | 3/2019 |
| EP | 3649239 A1 | 5/2020 |
| WO | 1999/53085 A2 | 10/1999 |
| WO | 2001/034940 A2 | 5/2001 |
| WO | 2002/066620 A2 | 8/2002 |
| WO | 2003/101189 A1 | 12/2003 |
| WO | 2005/106046 A1 | 11/2005 |
| WO | 2007/133797 A2 | 11/2007 |
| WO | 2012/041311 A1 | 4/2012 |
| WO | 2013/190032 A1 | 12/2013 |
| WO | 2015/092440 A1 | 6/2015 |
| WO | 2017/140406 A1 | 8/2017 |
| WO | 2017/221031 A1 | 12/2017 |
| WO | 2018/150269 A1 | 8/2018 |
| WO | 2018/150271 A1 | 8/2018 |
| WO | 2018/177758 A1 | 10/2018 |
| WO | 2018/189535 A1 | 10/2018 |
| WO | 2019/020992 A1 | 1/2019 |
| WO | 2019/030069 A2 | 2/2019 |
| WO | 2019/057691 A1 | 3/2019 |
| WO | 2019/073059 A1 | 4/2019 |
| WO | 2019/126634 A2 | 6/2019 |
| WO | 2019/141993 A1 | 7/2019 |
| WO | 2019/155016 A1 | 8/2019 |
| WO | 2019/157239 A1 | 8/2019 |
| WO | 2019/175600 A1 | 9/2019 |
| WO | 2020/16148 A1 | 1/2020 |
| WO | 2020/043869 A2 | 3/2020 |
| WO | 2020/072480 A1 | 4/2020 |
| WO | 2020/077411 A1 | 4/2020 |
| WO | 2020/084034 A1 | 4/2020 |
| WO | 2020/086881 A1 | 4/2020 |
| WO | 2020/132165 A1 | 6/2020 |
| WO | 2020/165603 A1 | 8/2020 |
| WO | 2020/183133 A1 | 9/2020 |
| WO | 2020/232366 A2 | 11/2020 |
| WO | 2021/127432 A1 | 6/2021 |
| WO | 2021/188892 A1 | 9/2021 |
| WO | 2022/020712 A1 | 1/2022 |
| WO | 2022/038369 A1 | 2/2022 |
| WO | 2022/112218 A1 | 6/2022 |
| WO | 2022/221397 A2 | 10/2022 |
| WO | 2022/223954 A1 | 10/2022 |
| WO | 2023/173105 A2 | 9/2023 |

OTHER PUBLICATIONS

Ayuso et al., Production, purification and characterization of adeno-associated vectors. Curr Gene Ther. Dec. 2010;10(6):423-36.

Douin et al., Use and comparison of different internal ribosomal entry sites (IRES) in tricistronic retroviral vectors. BMC Biotechnol. Jul. 27, 2004;4:16.

Pinto et al., Precise integration of inducible transcriptional elements (PrIITE) enables absolute control of gene expression. Nucleic Acids Res. Jul. 27, 2017;45(13): 15 pages.

Sergeeva et al., Multicopy Targeted Integration for Accelerated Development of High-Producing Chinese Hamster Ovary Cells. ACS Synth Biol. Sep. 18, 2020;9(9):2546-2561.

Shin et al., Streamlined Human Cell-Based Recombinase-Mediated Cassette Exchange Platform Enables Multigene Expression for the Production of Therapeutic Proteins. ACS Synth Biol. Jul. 16, 2021;10(7):1715-1727.

International Search Report and Written Opinion for Application No. PCT/US2022/078266, dated Feb. 17, 2023, 24 pages.

Invitation to Pay Additional Fees for Application No. PCT/US2022/078275, dated Feb. 17, 2023, 14 pages.

Brown et al., Synthetic promoters for CHO cell engineering. Biotechnol Bioeng. Aug. 2014;111(8):1638-47.

Ede et al., Quantitative Analyses of Core Promoters Enable Precise Engineering of Regulated Gene Expression in Mammalian Cells. ACS Synth Biol. May 20, 2016;5(5):395-404.

Gaidukov et al., A multi-landing pad DNA integration platform for mammalian cell engineering. Nucleic Acids Res. May 4, 2018;46(8):4072-4086.

Hamaker et al., Site-specific Integration Ushers in a New Era of Precise CHO Cell Line Engineering. Curr Opin Chem Eng. Dec. 2018;22:152-160.

Hilliard et al., Systematic identification of safe harbor regions in the CHO genome through a comprehensive epigenome analysis. Biotechnol Bioeng. Feb. 2021;118(2):659-675.

Kolling et al., State-change decisions and dorsomedial prefrontal cortex: the importance of time. Curr Opin Behav Sci. Aug. 2018;22:152-160.

Lagrange et al., New core promoter element in RNA polymerase II-dependent transcription: sequence-specific DNA binding by transcription factor IIB. Genes Dev. Jan. 1, 1998;12(1):34-44.

Lee et al., Site-specific integration in CHO cells mediated by CRISPR/Cas9 and homology-directed DNA repair pathway. Sci Rep. Feb. 25, 2015;5:8572, 11 pages.

Liu et al., Rapid establishment of a HEK 293 cell line expressing FVIII-BDD using AAV site-specific integration plasmids. BMC Res Notes. Sep. 10, 2014;7:626, 6 pages.

Morita et al., Attenuated protein expression vectors for use in siRNA rescue experiments. Biotechniques. Aug. 2012;0(0):1-5.

Papapetrou et al., Gene Insertion Into Genomic Safe Harbors for Human Gene Therapy. Mol Ther. Apr. 2016;24(4):678-84.

Pellenz et al., New Human Chromosomal Sites with "Safe Harbor" Potential for Targeted Transgene Insertion. Hum Gene Ther. Jul. 2019;30(7):814-828.

Ramachandra et al., Efficient recombinase-mediated cassette exchange at the AAVS1 locus in human embryonic stem cells using baculoviral vectors. Nucleic Acids Res. Sep. 1, 2011;39(16):e107, 13 pages.

Ramos et al., The TetR family of transcriptional repressors. Microbiol Mol Biol Rev. Jun. 2005;69(2):326-56.

(56)        References Cited

OTHER PUBLICATIONS

Russell et al., Phage Bxbl integrase mediates highly efficient site-specific recombination in mammalian cells. Biotechniques. Apr. 2006;40(4):462-464.

Sajgo et al., Dre—Cre sequential recombination provides new tools for retinal ganglion cell labeling and manipulation in mice. PLoS One. Mar. 7, 2014;9(3):e91435, 15 pages.

Saxena et al., Design of Synthetic Promoters for Gene Circuits in Mammalian Cells. Methods Mol Biol. 2017;1651:263-273.

Suzuki et al., VCre/VloxP and SCre/SloxP: new site-specific recombination systems for genome engineering. Nucleic Acids Res. Apr. 2011;39(8):e49, 11 pages.

White et al., Use of a negative selectable marker for rapid selection of recombinant vaccinia virus. Biotechniques. May 2011;50(5):303-9.

Wissmann et al., Tn10 tet operator mutations affecting Tet repressor recognition. Nucleic Acids Res. May 27, 1986;14(10):4253-66.

Bae et al., Design and Testing of Vector-Producing HEK293T Cells Bearing a Genomic Deletion of the SV40 T Antigen Coding Region. Mol Ther Methods Clin Dev. Jul. 9, 2020;18:631-638.

Chen, Intron splicing-mediated expression of AAV Rep and Cap genes and production of AAV vectors in insect cells. Mol Ther. May 2008;16(5):924-30.

Li et al., Engineering adeno-associated virus vectors for gene therapy. Nat Rev Genet. Apr. 2020;21(4):255-272.

Quinn et al., Genetic Modification of Target Cells by Direct Delivery of Ative Protein. Molecular Therapy. May 1, 2015;23;S50-S51.

Renaud-Gabardos et al., Internal ribosome entry site-based vectors for combined gene therapy. World J Exp Med. Feb. 20, 2015;5(1):11-20.

Su et al., Self-attenuating adenovirus enables production of recombinant adeno-associated virus for high manufacturing yield without contamination. Nat Commun. Mar. 7, 2022;13(1):1182, with supplementary information, 32 pages.

Sun et al., Expression of heme oxygenase-1 and GFP gene mediated by recombinant adeno-associated-virus in transplanted liver in rats. Zhonghua Wai Ke Za Zhi. Jun. 1, 2008;46(11):851-3.

International Search Report and Written Opinion for Application No. PCT/US2024/022809, dated Jul. 19, 2024, 17 pages.

International Search Report and Written Opinion for Application No. PCT/US2022/078275, dated Apr. 11, 2023, 20 pages.

Hein et al., Establishment of a Scalable Production Process using Stable Helper-Virus Free AAV Producer Cell Lines based on CEVEC's CAP Suspension Cell line. CEVEC Pharmaceuticals GmbH. Poster presentation, 1 page, (2020).

Lee et al., Construction of an rAAV Producer Cell Line through Synthetic Biology. ACS Synth Biol. Oct. 21, 2022;11(10):3285-3295. Pre-publication edition.

Luo et al., AAVS1-Targeted Plasmid Integration in AAV Producer Cell Lines. Hum Gene Ther Methods. Jun. 2017;28(3):124-138.

Tripp et al., Vector engineering of pRep-Cap and pHelper enhanced AAV productivity by triple transfection in suspension HEK293 cells. Lonza, ASGC Virtual. 17 pages, May 11-14, 2021.

Wang et al., Adeno-associated virus vector as a platform for gene therapy delivery. Nat Rev Drug Discov. May 2019;18(5):358-378.

Weitzman et al., Adeno-associated virus biology. Methods Mol Biol. 2011;807:1-23.

Wentz et al., Influence of lactate, ammonia, and osmotic stress on adherent and suspension BHK cells. Enzyme Microb Technol. Jan. 1992;14(1):68-75.

Wissing, Elevecta®—Helper virus-free AAV production with stable CAP® and HEK293 producer cells. Digital Week, Cell & Gene Therapy Manufacturing & Commercialization. 34 pages, Feb. 19, 2021.

Worner et al., Adeno-associated virus capsid assembly is divergent and stochastic. Nat Commun. Mar. 12, 2021;12(1):1642, 9 pages.

U.S. Appl. No. 18/047,341, filed Oct. 18, 2022, 2023-0193312, Published.

U.S. Appl. No. 18/626,156, filed Apr. 3, 2024, Pending.

U.S. Appl. No. 18/047,349, filed Oct. 18, 2022, 2023-0304062, Published.

Brent et al., A eukaryotic transcriptional activator bearing the DNA specificity of a prokaryotic repressor. Cell. Dec. 1985;43(3 Pt 2):729-36.

Gossen et al., Tight control of gene expression in mammalian cells by tetracycline-responsive promoters. Proc Natl Acad Sci U S A. Jun. 15, 1992;89(12):5547-51.

Gossen et al., Transcriptional activation by tetracyclines in mammalian cells. Science. Jun. 23, 1995;268(5218):1766-9.

Iida et al., Inducible gene expression by retrovirus-mediated transfer of a modified tetracycline-regulated system. J Virol. Sep. 1996;70(9):6054-9.

Jaubert et al., Tetracycline-regulated transactivators driven by the involucrin promoter to achieve epidermal conditional gene expression. J Invest Dermatol. Aug. 2004;123(2):313-8.

Labow et al., Conversion of the lac repressor into an allosterically regulated transcriptional activator for mammalian cells. Mol Cell Biol. Jul. 1990;10(7):3343-56.

Louvion et al., Fusion of GAL4-VP16 to a steroid-binding domain provides a tool for gratuitous induction of galactose-responsive genes in yeast. Gene. Sep. 6, 1993;131(1):129-34.

Mattioni et al., Regulation of protein activities by fusion to steroid binding domains. Methods Cell Biol. 1994;43 Pt A:335-52.

Murphy et al., Estrogen regulation of protein expression and signaling pathways in the heart. Biol Sex Differ. Mar. 10, 2014;5(1):6, 7 pages.

No et al., Ecdysone-inducible gene expression in mammalian cells and transgenic mice. Proc Natl Acad Sci U S A. Apr. 16, 1996;93(8):3346-51.

Ortiz et al., Tetracycline-inducible gene expression in Trichomonas vaginalis. Molecular and Biochemical Parasitology. Apr. 25, 2003;128(1):43-49.

Pedone et al., A tunable dual-input system for on-demand dynamic gene expression regulation. Nat Commun. Oct. 2, 2019;10(1):4481, 13 pages.

Sadowski et al., GAL4-VP16 is an unusually potent transcriptional activator. Nature. Oct. 6, 1988;335(6190):563-4.

Sato et al., Generation of mouse iPS cells using an inducible expression of transgenes via the cumate gene-switch. Anal Biochem. Jun. 15, 2020;599:113748, 7 pages.

Schmidt et al., Adeno-associated virus type 2 Rep78 induces apoptosis through caspase activation independently of p53. J Virol. Oct. 2000;74(20):9441-50.

Sisson et al., Expression of the reverse tetracycline-transactivator gene causes emphysema-like changes in mice. Am J Respir Cell Mol Biol. May 2006;34(5):552-60.

Song et al., Investigation of arc repressor DNA-binding specificity by comparative molecular dynamics simulations. J Biomol Struct Dyn. 2015;33(10):2083-93.

International Search Report and Written Opinion for Application No. PCT/US2022/078271, dated Feb. 6, 2023, 22 pages.

U.S. Appl. No. 18/047,341, filed Oct. 18, 2022, Pending.

U.S. Appl. No. 18/047,349, filed Oct. 18, 2022, Pending.

Deckert et al., The anatomy of a hypoxic operator in *Saccharomyces cerevisiae*. Genetics. Dec. 1998;150(4):1429-41.

GeneCopoeia, Datasheet for HEK293/LoxP-Cas9-hyg-AAVS1 Cell line. Catalog No. SL554. 8 pages, (2018).

GeneCopoeia, Genome-CRISP CRISPR-Cas9 stable cell lines. 4 pages, (2017).

Mullick et al., The cumate gene-switch: a system for regulated expression in mammalian cells. BMC Biotechnol. Nov. 3, 2006;6:43, 18 pages.

* cited by examiner

MAMMALIAN CELLS COMPRISING INTEGRATED CAS9 GENES TO PRODUCE STABLE INTEGRATION SITES, AND MAMMALIAN CELLS COMPRISING STABLE INTEGRATION SITES AND OTHER SITES

This Application claims priority to U.S. Application Ser. No. 63/256,675, filed Oct. 18, 2021, which is hereby incorporated by reference in its entirety.

FIELD OF THE INVENTIONS

The present inventions provide mammalian cells (including cell lines), including human and rodent cells (including cell lines), that comprise multiple Stable Integration Sites (SIS), which can be produced using integrated Cas9 genes. The inventions provide Stable Integration Sites (1) introduced genomically into Genomic Safe Harbors (GSH), for example AAVS1 (Adeno-Associated Virus Integration Site 1) and AAVS1-like, and (2) introduced genomically outside of that particular Genomic Safe Harbor, such as a different Genomic Safe Harbor or other region that is not a Genomic Safe Harbor. Polydeoxyribonucleotides of interest that encode polypeptides or RNAs of interest can be inserted into the Stable Integration Sites provided according to the inventions.

REFERENCE TO ELECTRONIC SEQUENCE LISTING

The application contains a Sequence Listing which has been submitted electronically in .XML format and is hereby incorporated by reference in its entirety. Said .XML copy, created on Oct. 7, 2022, is named "135975-97402.xml" and is 709,205 bytes in size. The sequence listing contained in this .XML file is part of the specification and is hereby incorporated by reference herein in its entirety.

BACKGROUND OF THE INVENTIONS

Mammalian cell lines are the preferred approach for producing commercial quantities of therapeutic proteins, such as antibodies. However, it has been reported that modified mammalian cells often exhibit production decreases due to genetic and epigenetic instability. Hilliard and Lee, *Biotech. Bioeng.* 118: 659-75 (2021).

Integration of polynucleotides is the preferred approach for creating and maintaining transformed cells. Integration of particular sequences into human AAVS1 is discussed in Liu et al., *BMC Research Note,* 7: 626 (2014) and Ramachandra et al., *Nucl. Acids Res.* 39: e107 (2011). Human AAVS1 is known as a Genomic Safe Harbor. Papapetrou et al., *Molecular Therapy* 24: 678-84 (2016). Gaidukov et al., *Nucl. Acids Res.* 46: 4072-86 (2018) have disclosed sites for DNA integration into landing pads.

Chinese hamster ovary (CHO) cells and baby hamster kidney cells (BHK) are used in the production of therapeutic proteins, and hamster genomes have been extensively studied. Hamaker and Lee have reported on CHO chromosomal loci as potential sites for stable integration and refers to them as "genomic hot spots". *Curr. Op. Chem. Eng.* 22: 152-60 (2018) at 153. At Table 1, Hamaker and Lee identify 30 hot spot loci, of which 17 are identified by gene and 13 are unannotated. *Curr. Op. Chem. Eng.* 22: 152-60 (2018) at 154. This work was followed by Hilliard and Lee, who sought to identify safe harbor regions in CHO using an epigenome analysis. Hilliard and Lee, *Biotech. Bioeng.* 118: 659-75 (2021). The authors determined that 10.9% of the CHO genome contained chromatin structures with enhanced genetic and epigenetic stability. The authors further determined that of the 30 hot spots identified Table 1 by Hamaker and Lee, five of which overlapped with stable regions determined by high throughput chromosome conformation capture (Hi-C). The closest genes to the regions were ALDH5A1, SMAD6 and CLCN3, and two other regions were unannotated. Hilliard and Lee, *Biotech. Bioeng.* 118: 659-75 (2021) at Supplementary Table 3 (S3). Gaidukov et al., *Nucl. Acids Res.* 46: 4072-86 (2018) at Table 1 also identifies loci for integration in CHO cells. Lee et al., *Scientific Reps.* 5: 8572 (2015) identifies the COSMC locus.

The present inventions advantageously employ an integrated Cas9 gene to efficiently create mammalian cell intermediates that are further modified to provide mammalian cells having multiple Stable Integration Sites for stable integration of multiple DNA cassettes and other polydeoxyribonucleotides of interest. According to the inventions, a Stable Integration Site can be located in a Genomic Safe Harbor or other regions, including newly-identified Genomic Safe Harbors.

SUMMARY OF THE INVENTIONS

The inventions provide mammalian cells, wherein any cell thereof can comprise a first Stable Integration Site located in a Genomic Safe Harbor and a second Stable Integration Site that is not located in the Genomic Safe Harbor, wherein the first Stable Integration Site comprises a first reporter gene encoding a first reporter protein and the second Stable Integration Site comprises a second reporter gene encoding a second reporter protein, wherein the first reporter protein and the second reporter protein are different. The first and second Stable Integration Sites can comprise recombinase recognition sites (RRSs). The first and second reporter genes can be under the control of SV40 promoters. The first and second reporter genes can be fluorescent proteins. The cells can further comprise a polynucleotide encoding a repressor protein under the control of a CMV promoter. The cells can be a Human Amniotic Epithelial, HEK 293, CHO or a BHK Cell. The polynucleotide encoding a protein of interest can be inserted into the first Stable Integration Site or the second Stable Integration Site. The second Stable Integration Site can be located in a second Genomic Safe Harbor that is different from the first Genomic Safe Harbor or in a region that is not a Genomic Safe Harbor.

The inventions also provide mammalian cells, wherein any cell thereof can comprise a first Stable Integration Site located in a Genomic Safe Harbor and a second Stable Integration Site that is not located in the first Genomic Safe Harbor, wherein the first Stable Integration Site comprises first polynucleotide encoding a first protein and the second Stable Integration Site comprises a second polynucleotide encoding a second protein. The first and second proteins can be viral proteins, such as an adenovirus associated virus protein or an adenovirus protein. For example, mammalian cells can comprise a polynucleotide encoding an adeno-associated virus protein and a polynucleotide encoding an adenovirus protein. Other polynucleotides encoding proteins include, but are not limited to, antibody genes, for example. Cells can have the second Stable Integration Site located in a second Genomic Safe Harbor that is different from the first Genomic Safe Harbor that the first Stable Integration Site is located in, or in a region that is not a Genomic Safe Harbor.

The inventions further provide a mammalian cells, wherein any cell thereof can comprise a first Stable Integration Site located in a Genomic Safe Harbor and a second Stable Integration Site that is not located in the Genomic Safe Harbor, wherein the first Stable Integration Site comprises a polynucleotide encoding a first reporter gene encoding a first reporter protein and the second Stable Integration Site comprises a polynucleotide encoding Cas9 and a polynucleotide encoding a second reporter gene encoding a second reporter protein, wherein the first reporter protein and the second reporter protein are different. The second Stable Integration Site can further comprise a selection marker gene and an internal ribosome entry site (IRES). The first and second Stable Integration Sites can comprise recombinase recognition sites. The first and second reporter genes can be under the control of SV40 promoters. The first and second reporter genes can be fluorescent proteins. The cell can further comprise a polynucleotide encoding a repressor (for example TetR) under the control of a promoter (for example, CMV). The cell can be a Human Amniotic Epithelial Cell, HEK293, CHO or a BHK Cell. The polynucleotide encoding a protein of interest can be inserted into the first Stable Integration Site or the second Stable Integration Site. The selection marker protein can confer drug resistance. The second reporter gene, the selection marker gene, the IRES and an SV40 promoter can be arranged on a DNA cassette. The cell can further comprise a polynucleotide encoding a repressor protein under the control of a promoter (for example, CMV). The second Stable Integration Site can be located in a second Genomic Safe Harbor that is different from the first Genomic Safe Harbor that the first Stable Integration Site is located in or in a region that is not a Genomic Safe Harbor. The first reporter gene can be flanked by a 5' genomic safe harbor homology arm and a 3' genomic safe harbor homology arm. The 5' genomic safe harbor homology arm can comprise a CRISPR sgRNA target site and the 3' genomic safe harbor homology arm can comprise a CRISPR sgRNA target site.

The inventions further provide methods for making at least one protein of interest, wherein any method thereof can comprise: (a) providing mammalian cells comprising a first Stable Integration Site located in a Genomic Safe Harbor and a second Stable Integration Site that is not located in the first Genomic Safe Harbor, wherein the first Stable Integration Site comprises a first reporter gene encoding a first reporter protein and the second Stable Integration Site comprises a second reporter gene encoding a second reporter protein, wherein the first reporter protein and the second reporter protein are different, and wherein the first and second Stable Integration Sites comprise recombinase recognition sites; (b) introducing a polynucleotide encoding the protein of interest into a Stable Integration Site by recombinase mediated cassette exchange, and (c) culturing the mammalian cell of under conditions that allow expression of the polynucleotide encoding the polynucleotide of interest. The first and second reporter genes can be under the control of SV40 promoters. The first and second reporter genes can be fluorescent proteins. The cell can further comprise a polynucleotide encoding a repressor protein under the control of a CMV promoter. The cell can be a Human Amniotic Epithelial, HEK 293, CHO or a BHK Cell. The polynucleotide encoding a protein of interest can be inserted into the first Stable Integration Site or the second Stable Integration Site. The second Stable Integration Site can be located in a second Genomic Safe Harbor that is different from the first Genomic Safe Harbor that first Stable Integration Site is located in, or in a region that is not a Genomic Safe Harbor.

The first Stable Integration Site comprises a first polynucleotide encoding a first protein and the second Stable Integration Site comprises a second polynucleotide encoding a second protein. The first and second proteins can be viral proteins, such as an adenovirus associated virus protein or an adenovirus protein. For example, the mammalian cell can comprise a polynucleotide encoding an adeno-associated virus protein and a polynucleotide encoding an adenovirus protein. Other polynucleotides encoding proteins include, but are not limited to, antibody genes, for example. The second Stable Integration Site also can be located in a region that is not a Genomic Safe Harbor.

The inventions further provide methods of creating mammalian cells with multiple Stable Integration Sites, wherein any method thereof can comprise: (A) providing a mammalian cell comprising a first DNA cassette comprising in 5' to 3' order a polynucleotide encoding the first lox site, a promoter, a selection marker gene encoding a selection marker protein, an IRES, a first reporter gene encoding a first reporter protein, a promoter operably linked to an operator, a Cas9 gene and the second lox site; (B) integrating a second DNA cassette comprising in a 5' to 3' order a polynucleotide comprising a first Genomic Safe Harbor homology arm containing a CRISPR sgRNA target site, a third lox site, a second reporter gene encoding a second reporter protein, a fourth lox site and a second Genomic Safe Harbor homology arm containing an CRISPR sgRNA target site, wherein the first lox site, the second lox site, the third lox site and the fourth lox site are different, wherein the first and second guide arms can contain a region with alterations (if needed to avoid recreating a targetable site), and wherein the second reporter protein is different from the first reporter protein; (C) exchanging the first DNA cassette with a third DNA cassette, wherein the third DNA cassette comprises in a 5' to 3' order a polynucleotide encoding the first lox site, a promoter, a third reporter gene encoding a third reporter protein, and the second lox site, wherein the third reporter protein is different from the second reporter protein, thereby providing the mammalian cell with multiple Stable Integration Sites. The mammalian cells can be Human Amniotic Epithelial Cells, HEK 293 Cells, CHO Cells or BHK Cells. Reporter genes for use can be fluorescent proteins. The cell of step (A) can further comprise a polynucleotide encoding a repressor (for example, TetR) under the control of a promoter (for example, CMV). The cell of step (B) can further comprise a polynucleotide encoding a repressor (for example, TetR) under the control of a promoter (for example, CMV). The cell of step (C) can further comprise a polynucleotide encoding a repressor (for example, TetR) under the control of a promoter (for example, CMV). The selection marker protein can confer drug resistance. Lox sites are the most commonly used type of RRS; however, different RRSs can be used as well.

The inventions also provide methods of creating a mammalian cell with multiple recombinase-mediated cassette exchange sites, wherein any method thereof can comprise: (A) randomly integrating a promoter and polynucleotide encoding a repressor into the cell genome, wherein the repressor can bind to a ligand; (B) randomly integrating into the cell genome a first DNA cassette comprising in 5' to 3' order a polynucleotide encoding a first lox site, a promoter and optionally an operator, a first reporter gene encoding a first reporter protein, an IRES, a first selection marker gene encoding a first selection maker protein and a second lox site, wherein the first lox site and the second lox site are different; (C) exchanging the first DNA cassette with a second DNA cassette, wherein the second DNA cassette comprises in 5' to 3' order a polynucleotide encoding the first lox site, a promoter, a second selection marker gene encoding a second selection marker protein, an IRES, a second reporter gene encoding a second reporter protein, a promoter and an optional operator, a Cas9 gene and the second lox site, wherein the first and second selection marker proteins are different and the first and second reporter proteins are different; (D) integrating a third DNA cassette comprising in 5' to 3' order a polynucleotide comprising a first Genomic Safe Harbor (GSH) homology arm containing an sgRNA (single guide RNA) target site, a third lox site, a third reporter gene encoding a third reporter protein, a fourth lox site and a second GSH homology arm containing an sgRNA target site, wherein the first lox site, the second lox site, the third lox site and the fourth lox site are different, wherein the first and second guide arms can contain at least one region with alterations (if needed to avoid recreating a targetable site), and wherein the third reporter protein is different from the second reporter protein and can be the same or different from the first reporter protein; and (E) exchanging the second DNA cassette with a fourth DNA cassette, wherein the fourth DNA cassette comprises in a 5' to 3' order a polynucleotide encoding the first lox site, a promoter, a fourth reporter gene encoding a fourth reporter protein, and the second lox site, wherein the fourth reporter protein is different from the third reporter protein and the second reporter protein and preferably different from the first reporter protein, thereby providing the cell with multiple Stable Integration Sites. Lox sites are the most commonly used type of RRS; however, different RRSs can be used as well.

The inventions further provide mammalian cells comprising a modified genomes, wherein a given genome is modified by insertion of at least three DNA cassettes within different regions of the genome, wherein the modified genome comprises (1) a first deoxyribonucleic acid sequence that is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of SEQ ID NOS: 1 and 2 prior to modification; (2) a second deoxyribonucleic acid sequence that is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of SEQ ID NOS: 5 to 10 prior to modification; and (3) a third deoxyribonucleic acid sequence that is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, 99% identical to at least one selected from the group consisting of SEQ ID NO: 11 and SEQ ID NO: 12 prior to modification, wherein the first deoxyribonucleic acid sequence is modified by insertion of a first DNA cassette, the second deoxyribonucleic acid sequence is modified by insertion of a second DNA cassette, and the third deoxyribonucleic acid sequence is modified by insertion of a third DNA cassette. The mammalian cells can each have (a) the first DNA cassette comprise a promoter and at least one selected from the group consisting of a selectable marker gene and a reporter gene; (b) the second DNA cassette comprise a promoter and at least one selected from the group consisting of a selectable marker gene and a reporter gene; and (c) the third DNA cassette comprise a promoter and at least one selected from the group consisting of a selectable marker gene and a reporter gene. Moreover, the mammalian cells can each have (a) the first DNA cassette comprise a promoter, a selectable marker gene and a reporter gene; (b) the second DNA cassette comprise a promoter, a selectable marker gene and a reporter gene; and (c) the third DNA cassette comprises a promoter, a selectable marker gene and a reporter gene. The first deoxyribonucleic acid sequence comprises a Stable Integration Site, and a gene of interest inserted therein. The gene of interest can encode a polypeptide of interest selected from the group consisting of antibodies, antibody chains, receptors, Fc-containing proteins, trap proteins, enzymes, factors, repressors, activators, ligands, reporter proteins, selection proteins, protein hormones, protein toxins, structural proteins, storage proteins, transport proteins, neurotransmitters and contractile proteins. The mammalian cells can be human cells and the first deoxyribonucleic acid sequence is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to SEQ ID NO: 1. Alternatively, the mammalian cell can be a CHO cell and the first deoxyribonucleic acid sequence is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to SEQ ID NO: 2. The first deoxyribonucleic acid sequence can comprise a Stable Integration Site produced using a guide sequence selected from the group consisting of SEQ ID NOS: 13 to 419. Additionally, the first deoxyribonucleic acid sequence can comprise a Stable Integration Site produced by using a guide sequence that binds to and/or is complementary to target sequences in SEQ ID NO:2 at nucleotide position ranges selected from the group consisting of: (a) 1 to 2000; (b) 2001 to 4000; (c) 4001 to 6000; (d) 6001 to 8000; (e) 8001 to 10,000; (f) 10,001 to 12,000; (g) 12,001 to 14,000; (h) 14,001 to 16,000; (i) 16,001 to 18,000; (j) 18,001 to 20,000; (k) 20,001 to 22,000; (l) 22,001 to 24,000; (m) 24,001 to 26,000; (n) 26,001 to 28,000; (o) 28,001 to 30,000; (p) 30,001 to 32,000; (q) 32,001 to 34,000; (r) 34,001 to 36,000; (s) 36,001 to 38,000; (t) 38,001 to 40,000; (u) 40,001 to 42,000; and (v) 42,001 to terminus (44,232).

Additionally, there are provided mammalian cells comprising a modified genomes, wherein a modified genome comprises a deoxyribonucleic acid sequence comprising an AAVS1-like region modified by insertion of at least one DNA cassette, and wherein a guide sequence selected from the group consisting of SEQ ID NOS: 13 to 419 that binds to and/or is complementary to a sense or antisense strand of the AAVS1-like region. The mammalian cells can further comprise a second deoxyribonucleic acid sequence that is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of SEQ ID NOS: 5 to 10 prior to modification; and a third deoxyribonucleic acid sequence that is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of SEQ ID NO: 11 and SEQ ID NO: 12 prior to modification, wherein the first deoxyribonucleic acid sequence is modified by insertion of a first DNA cassette, the second deoxyribonucleic acid sequence is modified by insertion of a second DNA cassette, and the third deoxyribonucleic acid sequence is modified by insertion of a third DNA cassette. The second deoxyribonucleic acid sequence is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of one selected from the group consisting of SEQ ID NOS: 5 to 10 prior to modification; and the third deoxyribonucleic acid sequence is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of SEQ ID NO: 11 and SEQ ID NO: 12 prior to modification. The first deoxyribonucleic acid sequence comprises a Stable Integration Site produced by using a guide sequence that binds to and/or is complementary to at least one target sequence having at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identity to SEQ ID NO-2 at nucleotide positions: (a) 1 to 2000; or (b) 2001 to 4000; or (c) 4001 to 6000; or (d) 6001 to 8000; or (e) 8001 to 10,000; or (f) 10,001 to 12,000; or (g) 12,001 to 14,000; or (h) 14,001 to 16,000; or (i) 16,001 to 18,000; or (j) 18,001 to 20,000; or (k) 20,001 to 22,000; or (l) 22,001 to 24,000; or (m) 24,001 to 26,000; or (n) 26,001 to 28,000; or (o) 28,001 to 30,000; or (p) 30,001 to 32,000; or (q) 32,001 to 34,000; or (r) 34,001 to 36,000; or (s) 36,001 to 38,000; or (t) 38,001 to 40,000; or (u) 40,001 to 42,000; or (v) 42,001 to 44,232.

There are also provided mammalian cells comprising a modified genome, wherein a modified genome comprises a Stable Integration Site in a AAVS1-like region, wherein the Stable Integration Site is produced by using a guide sequence that binds to and/or is complementary to at least one target sequence having at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identity to SEQ ID NO:2 at nucleotide positions: (a) 1 to 2000; or (b) 2001 to 4000; or (c) 4001 to 6000; or (d) 6001 to 8000; or (e) 8001 to 10,000; or (f) 10,001 to 12,000; or (g) 12,001 to 14,000; or (h) 14,001 to 16,000; or (i) 16,001 to 18,000; or (j) 18,001 to 20,000; or (k) 20,001 to 22,000; or (l) 22,001 to 24,000; or (m) 24,001 to 26,000; or (n) 26,001 to 28,000; or (o) 28,001 to 30,000; or (p) 30,001 to 32,000; or (q) 32,001 to 34,000; or (r) 34,001 to 36,000; or (s) 36,001 to 38,000; or (t) 38,001 to 40,000; or (u) 40,001 to 42,000; or (v) 42,001 to 44,232.

There further provided mammalian cells according to the preceding paragraph, further comprising a second deoxyribonucleic acid sequence that is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of SEQ ID NOS: 5 to 10 prior to modification; and a third deoxyribonucleic acid sequence that is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of SEQ ID NO: 11 and SEQ ID NO: 12 prior to modification, wherein the first deoxyribonucleic acid sequence is modified by insertion of a first DNA cassette, the second deoxyribonucleic acid sequence is modified by insertion of a second DNA cassette, and the third deoxyribonucleic acid sequence is modified by insertion of a third DNA cassette. The mammalian cell can have the second deoxyribonucleic acid sequence at least is 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of one selected from the group consisting of SEQ ID NOS: 5 to 10 prior to modification; and the third deoxyribonucleic acid sequence is at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, or 99% identical to at least one selected from the group consisting of SEQ ID NO: 11 and SEQ ID NO: 12 prior to modification.

Additionally, there are provided methods of producing proteins of interest, wherein the method comprises the steps of: (1) culturing the above mammalian cells; and (2) harvesting the protein of interest. There also are provided cells made according to any of the above methods, as well as methods of using the disclosed cells.

BRIEF DESCRIPTION OF THE FIGURES

The below figures illustrate an exemplary progression and creation of intermediate cells useful for creating cells having Stable Integration Sites in different regions of the genome, and thereafter creating cells having Stable Integration Sites in different regions of the genome. These figures illustrate embodiments of the invention, and do not limit the inventions in any manner.

FIG. 11, left side indicates the location of 5' genome primer and 3' insertion primer used with 5' junction PCR. FIG. 11, right side indicates the location of 5' insertion primer and 3' genome primer used with 3' junction PCR. Instead of lox sites, other RRSs can be used as well. A promoter 5' of the color 1 gene is depicted as a 5' arrow.

DETAILED DESCRIPTION OF THE INVENTIONS

Definitions

Unless defined otherwise, all technical and scientific terms used herein have the same meaning as commonly understood by one of ordinary skill in the art to which this invention belongs.

The term "about" in the context of numerical values and ranges refers to values or ranges that approximate or are close to the recited values or ranges such that the invention can perform, such as having a sought rate, amount, degree, increase, decrease, or extent of expression, concentration, or time, as is apparent from the teachings contained herein. Thus, this term encompasses values beyond those simply resulting from systematic error. For example, "about" can signify values either above or below the stated value in a range of approx. +/−10% or more or less depending on the ability to perform.

"AAVS1" can be a Genomic Safe Harbor and refers to Adeno-associated virus integration site 1, and is reported to be located on human chromosome 19 in nature and contains approximately 4.7 kilobases. The AAVS1 locus can be used according to the inventions.

"AAVS1-like" refers to an AAVS1 homolog found in CHO cells, and is disclosed herein. An AAVS1-like region containing an AAVS1-like Genomic Safe Harbor (GSH) can be used according to the inventions. SEQ ID NO:2 is an example of an AAVS1-like region.

A "DNA cassette" or "cassette" is a type of nucleic acid moiety that comprises at least a promoter, at least one open reading frame and optionally a polyadenylation signal, for example an SV40 polyadenylation signal. Other nucleic acid moieties, such as operators, also are optional. A DNA cassette thus is a polynucleotide that comprises two or more shorter polynucleotides. A cassette can comprise one or more gene and promoters, enhancers, operators, repressors, transcription termination signals, ribosomal entry sites, introns and polyadenylation signals.

"COSMC" has reportedly been found in hamster cells. Homologs of a partial or whole COSMC locus are candidates for use according to the inventions.

"CCR5" refers to C—C chemokine receptor type 5 gene, and has been reportedly found in human, mouse and rat cells. Homologs of a partial or whole CCR5 locus are candidates for use according to the inventions.

"Genomic Safe Harbors" or "GSH" refers to sites in the cell genome that can accommodate insertions of polynucleotides, such as DNA cassettes, and permit the inserted polynucleotide to function and not pose an undue burden on a transformed cell. Accordingly, Genomic Safe Harbors are ideal locations for creating Stable Integration Sites for the insertions of DNA cassettes through the practice of the inventions. Genomic Safe Harbors that can be utilized herein include, but are not limited to, AAVS1 and AAVS1-like. Reported loci that are candidates include, but are not limited to, CCR5, COSMC and Rosa26.

Figure 4:
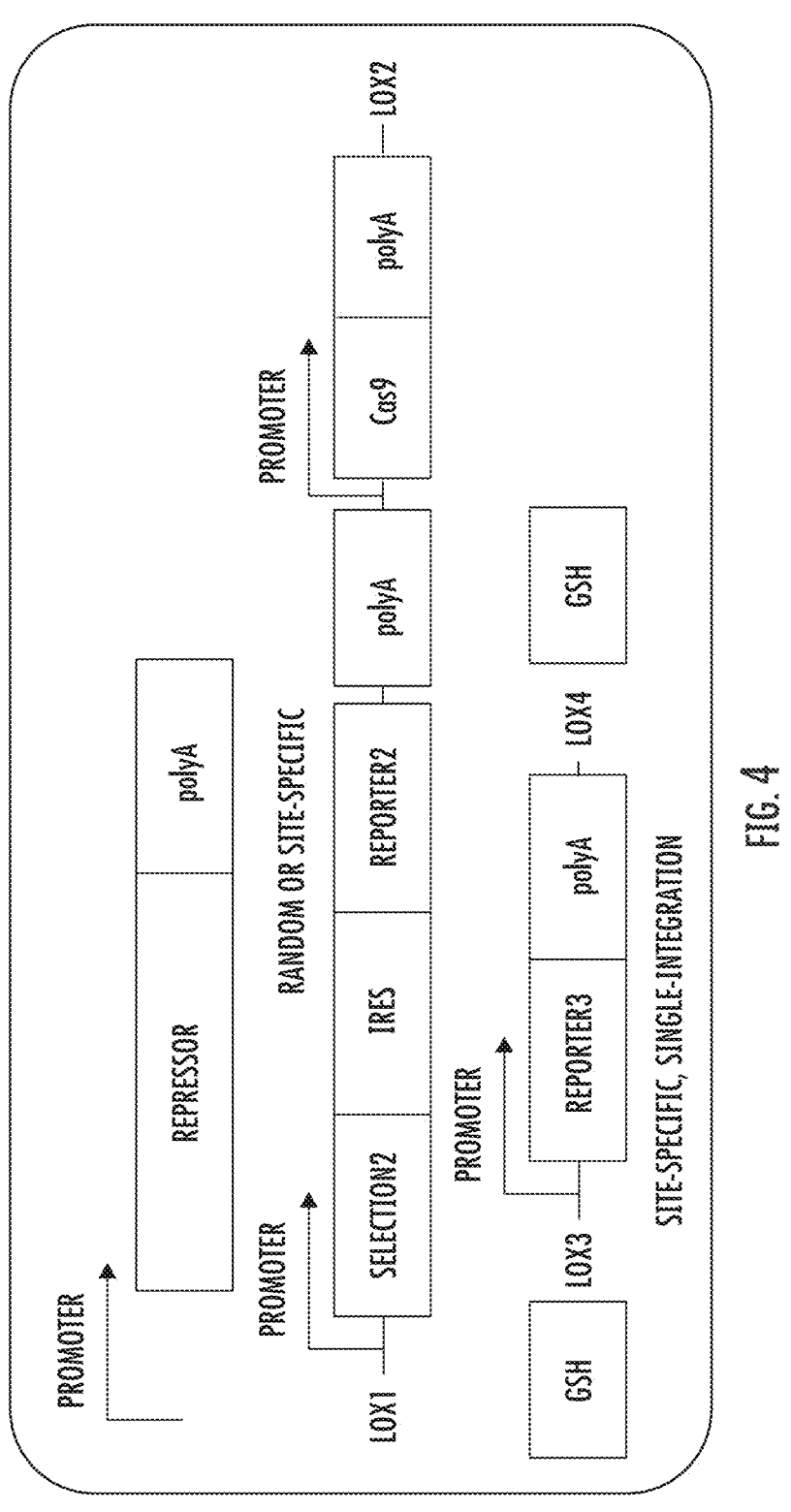
FIG. 4 schematically depicts the modification of the cell of FIG. 3 that has a DNA cassette (3) comprising flanking Genomic Safe Harbor (GSH) homology arms, lox sites (3 and 4) and a reporter gene (3) with a polyadenylation signal under the control of a promoter inserted into the Genomic Safe Harbor. The insertion is a site-specific integration and creates a Stable Integration Site between Lox3 and Lox4. Instead of lox sites, other RRSs can be used as well.
Figure 5:
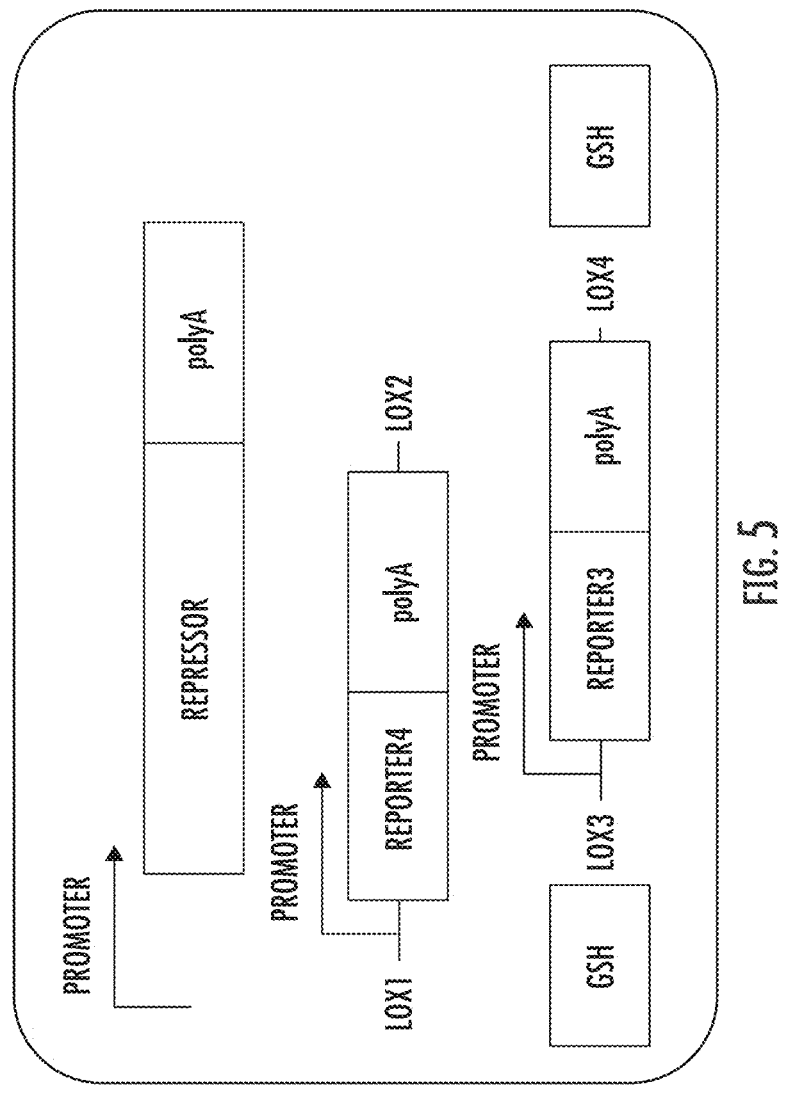
FIG. 5 schematically depicts the modification of the cell of FIG. 4, wherein DNA cassette (2) is replaced by recombinase mediated cassette exchange with DNA cassette (4). DNA cassette (4) comprises flanking lox sites (1 and 2), reporter gene (4) and a polyadenylation signal under the control of a promoter. This exchange removes the Cas9 gene. Instead of lox sites, other RRSs can be used as well.

"Genomic Safe Harbor homology arm" or "GSH homology arms" is derived from Genomic Safe Harbors, and have homology to the Genomic Safe Harbor. Preferably, the Genomic Safe Harbor homology arm comprise about 100 to 2000 bases, more preferably about 300 to 1800 bases, more preferably about 400 to 1600 bases, more preferably about 500 to 1500 bases, more preferably about 500 to 1300 bases, more preferably about 500 to 1100 bases, more preferably about 500 to 1000 bases, more preferably about 600 to 1000 bases, more preferably about 700 to 1000 base, more preferably about 800 to 1000 bases, and still more preferably about 900 to 1000 bases. Typically, a polynucleotide to be inserted into a Genomic Safe Harbor will be flanked by a 5' GSH Homology Arm and a 3' GSH Homology Arm. For example, see FIGS. 4 and 5 showing a lox site-flanked DNA cassette that is further flanked by GSH Homology Arms.

"hRosa26" refers to the human homolog of the murine Rosa26 locus ("Reverse Orientation Splice Acceptor"). "Rosa26" refers to a partial or whole Rosa26 locus, and has been reportedly found in hamster cells in addition to mouse and human cells. Homologs of a partial or whole Rosa26 locus are candidates for use according to the inventions.

An "Intron" is a section of DNA located between exons. An intron is removed to form a mature messenger RNA. Preferred introns are those that can affect the starting point of translation, and exemplars are the hCMV-IE intron (Human cytomegalovirus immediate early protein) and FMDV intron (Foot and Mouth Disease Virus).

A "nucleic acid moiety" includes any arrangement of single stranded or double stranded nucleotide sequences. Nucleic acid moieties can include, but are not limited to, polynucleotides, promoters, enhancers, operators, repressors, transcription termination signals, ribosomal entry sites and polyadenylation signals.

"Operably linked" refers to one or more nucleotide sequences in functional relationships with one or more other nucleotide sequences. Such functional relationships can directly or indirectly control, cause, regulate, enhance, facilitate, permit, attenuate, repress or block an action or activity in accordance with the selected design. Exemplars include single-stranded or double-stranded nucleic acid moieties, and can comprise two or more nucleotide sequences arranged within a given moiety in such a way that sequence (s) can exert at least one functional effect on other(s). For example, a promoter operably linked to the coding region of a DNA polynucleotide sequence can facilitate transcription of the coding region. Other elements, such as enhancers, operators, repressors, transcription termination signals, ribosomal entry sites and polyadenylation signals also can be operably linked with a polynucleotide of interest to control its expression. Arrangements and spacing to achieve operable linkages can be ascertained by approaches available to the person skilled in the art, such as screening using western blots and RT-PCR.

"Operator" indicates a DNA sequence that is introduced in or near a polynucleotide sequence in such a way that the polynucleotide sequence may be regulated by the interaction of a molecule capable of binding to the operator and, as a result, prevent or allow transcription of the polynucleotide sequence, as the case may be. One skilled in the art will recognize that the operator must be located sufficiently in proximity to the promoter such that it is capable of controlling or influencing transcription by the promoter, which can be considered a type of operable linkage. The operator may be placed either downstream or upstream of the promoter. These include, but are not limited to, the operator region of the Lex A gene of *E. coli*, which binds the Lex A peptide and the lactose and 45 tryptophan operators, which bind the repressor proteins encoded by the Lad and trpR genes of *E. coli*. The bacteriophage operators from the lambda Pi and the phage P22 Mnt and Arc. Preferred operators are the Tet (tetracycline) operator (TetO or TO) and the Arc operator (ArcO or AO). Operators can have a native sequence or a mutant sequence. For example, mutant sequences of the Tet operator are disclosed in Wissmann et al., *Nucleic Acids Res.* 14: 4253-4266 (1986).

The Tet operator is preferred, and can be used to control transcription using a repressor, such as the Tetracycline repressor (TetR). Appropriate ligands for the repressor are tetracycline (tet), doxycycline (dox) and derivatives thereof. When the ligand binds to TetR, the affinity of the Tet repressor for the Tet operator is lessened and the Tet repressor separates from the operator, and thereby the operator becomes permissive for transcription. Other repressors can be paired for usage with their own respective operators.

The phrases "percent identity" or "% identical," in their various grammatical forms, when describing a sequence is meant to include homologous sequences that display the recited identity along regions of contiguous homology, but the presence of gaps, deletions, or insertions that have no homolog in the compared sequence are not taken into account in calculating percent identity. As used herein, a "percent identity" or "% identical" determination between homologs would not include a comparison of sequences where the homolog has no homologous sequence to compare in an alignment. Thus, "percent identity" and "% identical" do not include penalties for gaps, deletions, and insertions.

A "homologous sequence" in its various grammatical forms in the context of nucleic acid sequences refers to a sequence that is substantially homologous to a reference nucleic acid sequence. In some embodiments, two sequences are considered to be substantially homologous if at least 50%-99%, 75%-99%, 85%-99%, 90%-99%, 95%-98%, 98%-99%, 50%, 55%, 60%, 65%, 70%, 75%, 80%, 85%, 90%, 91%, 92%, 93%, 94%, 95%, 96%, 97%, 98%, 99% or more of their corresponding nucleotides are identical over a relevant stretch of residues. In some embodiments, the relevant stretch is a complete (i.e., full) sequence.

"Polynucleotide" includes a sequence of nucleotides covalently joined, and includes RNA and DNA. Oligonucleotides are considered shorter polynucleotides. Genes are DNA polynucleotides (polydeoxyribonucleic acid) that ultimately encode polypeptides, which are translated from RNA (polyribonucleic acid) that was typically transcribed from DNA. DNA polynucleotides also can encode RNA polynucleotides that is not translated, but rather function as RNA "products". The type of polynucleotide (that is, DNA or RNA) is apparent from the context of the usage of the term. A polynucleotide referred to or identified by the polypeptide it encodes sets forth and covers all suitable sequences in accordance with codon degeneracy. Polynucleotides, including those disclosed herein, include percent identity sequences and homologous sequences when indicated.

"Polypeptide" and "peptide" refers to sequence(s) of amino acids covalently joined. Polypeptides include natural, semi-synthetic and synthetic proteins and protein fragments. "Polypeptide" and "protein" can be used interchangeably. Oligopeptides are considered shorter polypeptides.

"Promoter" indicates a DNA sequence that cause transcription of a DNA sequence to which it is operably linked, i.e., linked in such a way as to permit transcription of the nucleotide sequence of interest when the appropriate signals are present and repressors are absent. The expression of a polynucleotide of interest may be placed under control of any promoter or enhancer element known in the art. A eukaryotic promoter can be operably linked to a TATA Box. The TATA Box is typically located upstream of the transcription start site.

Useful promoters that may be used include, but are not limited to, the SV40 early promoter region, SV40 E/L (early late) promoter, the promoter contained in the 3' long terminal repeat of Rous sarcoma virus, the regulatory sequences of the metallothionein gene, mouse or human cytomegalovirus major immediate early (CMV-MIE) promoter and other CMV promoters, including CMVmin promoters. Plant expression vectors comprising the nopaline synthetase promoter region, the cauliflower mosaic virus 35S RNA promoter, and the promoter of the photosynthetic enzyme ribulose biphosphate carboxylase; promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I; insulin; immuno globulin; mouse mammary tumor virus; albumin; C.-feto protein; C.1-antitrypsin; 3-globin, and myosin light chain-2. Various forms of the CMV promoter can be used according to the inventions.

Minimal promoters, such as CMVmin promoters, can be truncated promoters or core promoters and are preferred for use in controlled expression systems. Minimal promoters and development approaches are widely known and disclosed in, for example, Saxena et al., *Methods Molec. Biol.* 1651:263-73 (2017); Ede et al., *ACS Synth Biol.* 5:395-404 (2016); Brown et al., *Biotech Bioeng.* 111:1638-47 (2014); Morita et al., *Biotechniques* 0:1-5 (2012); Lagrange et al., *Genes Dev.* 12:34-44 (1998). There are many CMVmin promoters described in the field.

"Protein of interest" or "polypeptide of interest" can have any amino acid sequence, and includes any protein, polypeptide, or peptide, and derivatives, components, domains, chains and fragments thereof. Included are, but not limited to, viral proteins, bacterial proteins, fungal proteins, plant proteins and animal (including human) proteins. Protein types can include, but are not limited to, antibodies, bi-specific antibodies, multi-specific antibodies, antibody chains (including heavy and light), antibody fragments, Fv fragments, Fc fragments, Fc-containing proteins, Fc-fusion proteins, receptor Fc-fusion proteins, receptors, receptor domains, trap and mini-trap proteins, enzymes, factors, repressors, activators, ligands, reporter proteins, selection proteins, protein hormones, protein toxins, structural proteins, storage proteins, transport proteins, neurotransmitters and contractile proteins. Derivatives, components, chains and fragments of the above also are included. The sequences can be natural, semi-synthetic or synthetic. Proteins of interest and polypeptides of interest are encoded by "genes of interest," which also can be referred to as "polynucleotides of interest." Where multiple genes (same or different) are integrated, they can be referred to as "first," "second", "third," "fourth," "fifth," "sixth," "seventh," "eighth," "ninth," "tenth," etc. as is apparent from the context of use.

"Recombinase recognition sites" (RRS), also known as "heterospecific recombination sites," are used in recombinase mediated cassette exchange (RMCE). Cre/Lox, Dre/Rox, Vre/Vlox, SCre/Slox and Flp/Frt are suitable RRS systems, for example. Suitable RRSs for use according to the inventions include Lox P, Lox 66, Lox 71, Lox 511, Lox 2272, Lox 2372, Lox 5171, Lox M2, Lox M3, lox M7 and Lox M11. These sites can be referred to generically as first (1), second (2), third (3), fourth (4), fifth (5), sixth (6), seventh (7), eighth (8), ninth (9), tenth (10), etc., as is apparent from the context of usage. Cre/Lox is most commonly used RRS, but other RRSs can be used instead of Cre/Lox according to the inventions.

"Reporter proteins" as used herein, refers to any protein capable of generating directly or indirectly a detectable signal. Reporter proteins typically fluoresce, or catalyze a colorimetric or fluorescent reaction, and often are referred to as "fluorescent proteins" or "color proteins." However, a reporter protein also can be non-enzymatic and non-fluorescent as long as it can be detected by another protein or moiety, such as a cell surface protein detected with a fluorescent ligand. A reporter protein also can be an inactive protein that is made functional through interaction with another protein that is fluorescent or catalyzes a reaction. Accordingly, any suitable reporter protein, as understood by one of skill in the art, could be used. In some aspects, the reporter protein may be selected from fluorescent protein, luciferase, alkaline phosphatase, p-galactosidase, p-lactamase, dihydrofolate reductase, ubiquitin, and variants thereof. Fluorescent proteins are useful for the recognition of gene cassettes that have or have not been successfully inserted and/or replaced, as the case may be. Fluid cytometry and fluorescence-activated cell sorting are suitable for detection. Examples of fluorescent proteins are well-known in the art, including, but not limited to Discosoma coral (DsRed), green fluorescent protein (GFP), enhanced green fluorescent protein (eGFP), cyano fluorescent protein (CFP), enhanced cyano fluorescent protein (eCFP), yellow fluorescent protein (YFP), enhanced yellow fluorescent protein (eYFP) and far-red fluorescent protein (e.g. mKate, mKate2, mPlum, mRaspberry or E2-crimson. See, for example, U.S. Pat. No. 9,816,110. Reporter proteins are encoded by polynucleotides, and are referred to herein as "reporter genes" or "reporter protein genes." Reporter genes and proteins can be referred to generically as first (1), second (2), third (3), fourth (4), fifth (5), sixth (6), seventh (7), eighth (8), ninth (9), tenth (10), etc., as is apparent from the context of usage. Reporters can be considered a type of marker. "Color" or "fluorescent," in their various grammatical forms, also can be used the more specifically refer to a reporter protein or gene.

A "repressor protein", also referred to as a "repressor," is a protein that can bind to DNA in order to repressor transcription, and is encoded by a polynucleotide, also referred to herein as a "repressor gene" or a "repressor proteins gene." Repressors are of eukaryotic and prokaryotic origin. Prokaryotic repressors are preferred. Examples of repressor families include: TetR, LysR, LacI, ArsR, IclR, MerR, AsnC, MarR, DeoR, GntR and Crp families. Repressor proteins in the TetR family include: ArcR, ActII, AmeR, AmrR, ArpR, BpeR, EnvR, EthR, HemR, HydR, IfeR, LanK, LfrR, LmrA, MtrR, Pip, PqrA, QacR, RifQ, RmrR, SimReg2, SmeT, SrpR, TcmR, TetR, TtgR, TrgW, UrdK, VarR YdeS, ArpA, BarA, Aur1B, CalR, CprB, FarA, JadR*, JadR2, MphB, NonG, PhIF, TyIQ, VanT, TarA, TyIP, BM1P1, Bm3R1, ButR, CampR, CamR, DhaR, KstR, LexA-like, AcnR, PaaRR, PsbI, Th1R, UidR, YDH1, BetI, McbR, MphR, PhaD, Q9ZF45, TtK, Yhgd, YixD, CasR, IcaR, LitR, LuxR, LuxT, OpaR, Orf2, SmcR, HapR, Ef0113, HlyIIR, BarB, ScbR, MmfR, AmtR, PsrA and YjdC proteins See Ramos et al., *Microbiol. Mol. Biol. Rev.,* 69: 326-56 (2005). Still other repressors include PurR, LacR, MetJ and PadR, "Selectable" or "selection" marker proteins include proteins conferring certain traits, including but not limited to drug resistance or other selective advantages. Selection markers can give the cell receiving the selectable marker gene resistance towards a certain toxin, drug, antibiotic or other compound and permit the cell to produce protein and propagate in the presence of the toxin, drug, antibiotic or other compound, and are often referred to as "positive selectable markers." Suitable examples of antibiotic resistance markers include, but are not limited to, proteins that impart resistance to various antibiotics, such as kanamycin, spectinomycin, neomycin, gentamycin (G418), ampicillin, tetracycline, chloramphenicol, puromycin, hygromycin, zeocin, and/or blasticidin. There are other selectable markers, often referred to as "negative selectable markers," which cause a cell to stop propagating, stop protein production and/or are lethal to the cell in the presence of the negative selectable marker proteins. Thymidine kinase and certain fusion proteins can serve as negative selectable markers, including but not limited to GyrB-PKR. See White et al., *Biotechniques,* 50: 303-309 (May 2011). Selectable marker proteins and corresponding genes (selectable marker genes) can be referred to generically as first (1), second (2), third (3), fourth (4), fifth (5), sixth (6), seventh (7), eighth (8), ninth (9), tenth (10), etc., as is apparent from the context of usage. In the figures, the selectable markers are positive selectable markers unless otherwise specified as a negative (neg.) marker.

"Single guide RNA" or "sgRNA" is used for targeting Cas9 to a site, and is usually 17-24 nucleotides long.

A "Stable Integration Site" or "SIS" is a region for site-specific integration of DNA polynucleotides of interest, including cassettes that comprise genes and/or other open reading frames, promoters and optionally other elements. Stable Integration Sites comprise an exogenously-sourced DNA cassette, and can be created according to the methods of the inventions described and depicted herein, preferably in a GSH. Constructs can be inserted into an SIS by a variety of approaches. Multiple Stable Integration Sites can be created and located on different chromosomes, different regions of the same chromosome or different positions in a same region of a chromosome.

A "Tetracycline Response Element" or "TRE" comprises seven copies of the 19 nucleotide TetO spaced apart by spacers comprising 17-18 nucleotides, and are commercially available. TetO sequences can vary and nucleotide substitutions are known. For example, altered sequences based on the Tet operator are disclosed in Wissmann et al., *Nucleic Acids Res.* 14: 4253-66 (1986). The spacers are not sequence specific. The spacers can be similar, but all should not be identical. A TRE is considered a type of operator as used herein.

All numerical limits and ranges set forth herein include all numbers or values thereabout or there between of the numbers of the range or limit. The ranges and limits described herein expressly denominate and set forth all integers, decimals and fractional values defined and encompassed by the range or limit. The ranges and limits described herein expressly denominate and set forth all integers, decimals and fractional values defined and encompassed by the range or limit. Thus, a recitation of ranges of values herein are merely intended to serve as a shorthand method of referring individually to each separate value falling within the range, unless otherwise indicated herein, and each separate value is incorporated into the specification as if it were individually recited herein.

DETAILED DESCRIPTION

The inventions provide mammalian cells with multiple Stable Integration Sites, and are suitable for production of proteins of interest, including viral proteins, and the production of viral vectors, including adeno-associated virus vectors (AAV). One or more Stable Integration Sites can be within the Genomic Safe Harbor and one or more Stable Integration Sites can be outside of the particular Genomic Safe Harbor. Multiple Stable Integration Sites can be created and located on different chromosomes, different regions of the same chromosome or different positions in a same region of a chromosome.

Genomic Safe Harbors are discussed in Pellenz et al., *Hum. Gene Therapy* 30: 814-28 (2019); Papapetrou et al., *Molecular Therapy* 24: 678-84 (2016).

Preferably, the Stable Integration Sites contain recognition sites to allow for Recombinase-Mediated Cassette Exchange (RMCE). Stable modification of cellular genomes can be undertaken with known approaches employing heterospecific recombination sites (also known as RRSs), such as Cre/Lox, Flp/Frt, transcription activator-like effector nuclease (TALEN), a TAL effector domain fusion protein, zinc finger nuclease (ZFN), a ZFN dimer, or a RNA-guided DNA endonuclease system, such as CRISPR/Cas9. See U.S. Pat. No. 9,816,110 at cols. 17-18; Sajgo et al., *PLoS ONE* 9: e91435 (2014); Suzuki et al., *Nucl. Acids. Res.* 39: e49

(2011) Integration using Bxb1 integrase in human, mouse and rat cells also can be undertaken. Russell et al., *Biotechniques* 40: 460-64 (2006).

Recombinase recognition sites, also known as heterospecific recombination sites, are referred to generically as first (1), second (2), third (3), fourth (4), fifth (5), sixth (6), seventh (7), eighth (8), ninth (9), tenth (10), etc., as is apparent from the context of usage. Suitable Lox sites for use according to the inventions include, but are not limited to, Lox P, Lox 66, Lox 71, Lox 511, Lox 2272, Lox 2372, Lox 5171, Lox M2, Lox M3, lox M7 and Lox M11. Other RRSs can be used as well. Lox sites are the most commonly used type of RRS; however, different RRSs can be used as well.

Homology arms preferably start within about 10 to 20 bases, more preferably 10 to 15 bases, of the cut site. A greater distance can be used as well, but with lower efficiency. In order to ensure that the DNA cassette(s) inserted into the Genomic Safe Harbor(s) maintain stability in the event that the homology repair could possibly recreate a targetable site, as determined by the skilled person, the guide arm region of the DNA cassette can be made to contain alterations (for example, base mismatches) that disrupt the function of CRISPR target site. There are two approaches that can be employed independently or together. The first approach is to insert base substitutions to create base mismatches in the CRISPR twenty base target site or the protospacer adjacent motif (PAM), which is usually 2 to 6 bases. The second approach is to create a donor plasmid where insertion divides the CRISPR target site or divides the CRISPR target site from the PAM.

Human cell lines include amniotic cells (such as Human Amniotic Epithelial cells), Hela cells, Per.C6 cells and HEK 293 cells. Examples of HEK 293 cells include, but are not limited, to HEK 293, HEK 293A, HEK 293E, HEK 293F, HEK 293FT, HEK 293FTM, HEK 293H, HEK 293MSR, HEK 293S, HEK 293SG, HEK 293SGGD, HEK 293T and mutants and variants thereof. Rodent cell lines, such as Sp2/0 cells, BHK cells and CHO cells and mutants and variants thereof, also can be used according to the inventions. CHO cells include, but are not limited to, CHO-ori, CHO-K1, CHO-s, CHO-DHB11, CHO-DXB11, CHO-K1SV, and mutants and variants thereof.

The mammalian cells of the inventions are produced by advantageously producing and utilizing a cell intermediate that has a cassette comprising a Cas9 endonuclease gene flanked by recombinase recognition sites and integrated into the genome via RCME. Without being bound by any theory, the inventive use of an integrated Cas9 gene when expressed appears to increase the efficiency of homology arm integration into Genomic Safe Harbors by increasing the occurrence of cuts in genomic DNA caused by the Cas9 endonuclease. The use of stably integrated Cas9 gene of the inventions provides 10, $10^2$, $10^3$, $10^4$, $10^5$, $10^6$, $10^7$, $10^8$, $10^9$, or $10^{10}$ greater HDR efficiency than HDR without a stably integrated Cas9 gene. Ultimately, this intermediate cell can be further subjected to RMCE to remove the cassette containing the Cas9 gene.

As a starting point for engineering of cells, polynucleotide sequences of interest, as well as the operably linked promoter and optional operators, may be introduced into the cell by transfection of a plasmid containing said polynucleotide sequences and elements. Accordingly, the inventions include the generation of cells as described.

Suitable plasmid constructs can be made by those of skill in the art. Useful regulatory elements, described previously or known in the art, can also be included in the plasmid constructs used to transfect the cells. Some non-limiting examples of useful regulatory elements include, but are not limited to, promoters, enhancers, sequences encoding suitable mRNA ribosomal binding sites, and sequences that control the termination of transcription and translation. Suitable plasmid constructs also may comprise non-transcribed elements such as an origin of replication, other 5' or 3' flanking non-transcribed sequences, and 5' or 3' non-translated sequences such as splice donor and acceptor sites. One or more selectable marker genes may also be incorporated. Useful selectable marker proteins and reporter proteins for use with the present inventions are known and can be readily identified by those of skill in the art.

A plasmid construct encoding a gene of interest may be delivered to the cell using a viral vector or via a non-viral method of transfer.

Non-viral methods of nucleic acid transfer include naked nucleic acid, liposomes, and protein/nucleic acid conjugates. A plasmid construct that is introduced to the cell may be linear or circular, may be single-stranded or double-stranded, and may be DNA, RNA, or any modification or combination thereof.

A plasmid construct may be introduced into the cell by transfection. Those of skill in the art are aware of numerous different transfection protocols, and can select an appropriate system for use in transfecting cells. Generally, transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect.

The inventions are further described by the following Examples, which are illustrative of the many embodiments and aspects of the invention, but do not limit the inventions in any manner. In the Examples, the selectable markers are positive selectable markers unless otherwise specified as a negative (neg.) marker.

Example 1

Figure 1:
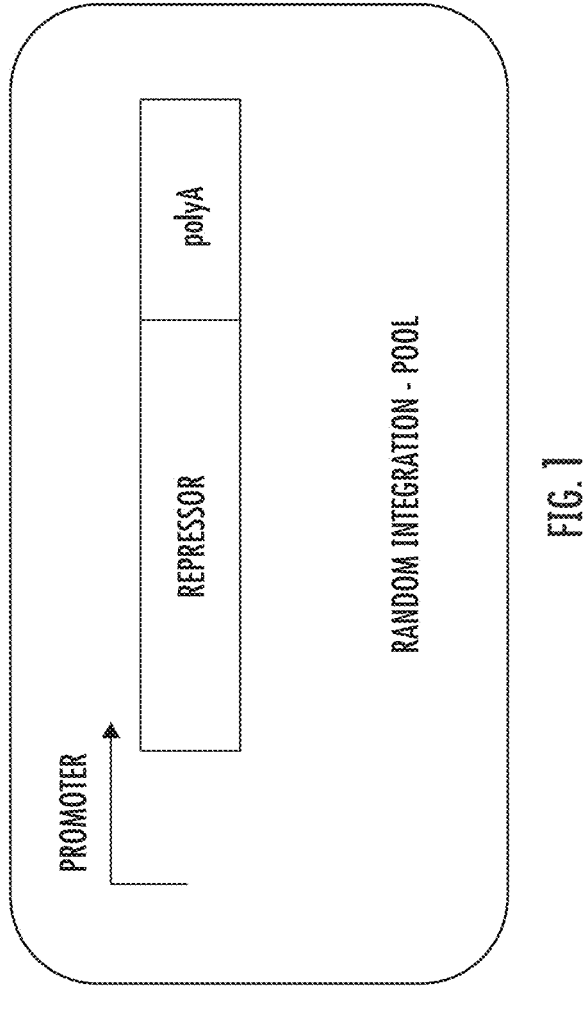
FIG. 1 schematically depicts the modification of a cell that has a polynucleotide encoding a repressor protein and a polyadenylation signal under transcriptional control of a promoter, wherein the polynucleotide is randomly inserted in the cell genome.

This example concerns the creation of mammalian cells comprising a repressor, such as TetR, under control of a promoter, such as a CMV promoter. See FIG. 1. The cell is transfected with a polynucleotide comprising the promoter and the repressor gene. The polynucleotide is randomly inserted into the cell genome. Western blots and Taqman can be used in the cell pool to identify transformants and determine average copy number. The integration of a repressor, such as TetR, allows for control of transcription of polynucleotides that under control of a promoter and an operator.

Example 2

Figure 2:
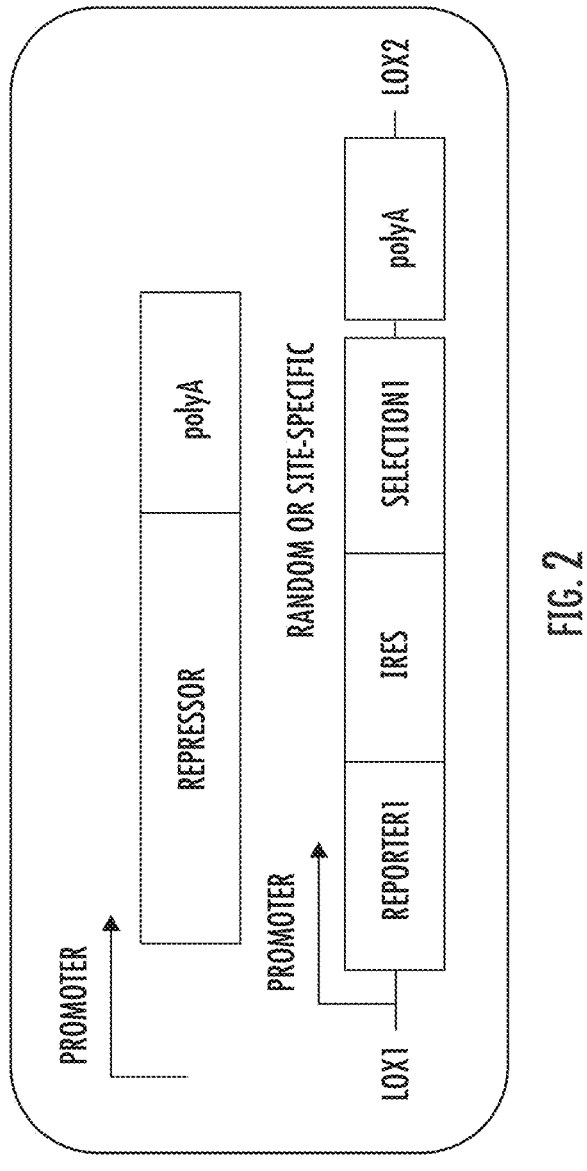
FIG. 2 schematically depicts the modification of the cell of FIG. 1 after a DNA cassette (1) is randomly or site-specifically inserted into the cell genome. DNA cassette (1) comprises flanking lox sites (1 and 2), a promoter, a reporter gene (1), an IRES, selection marker gene (1) and a polyadenylation signal. Instead of lox sites, other RRSs can be used as well.

This example concerns further engineering of the cells of Example 1. DNA cassette 1 is schematically depicted in FIG. 2 and comprises flanking lox sites (1 and 2) and further comprises in 5' to 3' order a promoter, reporter gene (1) encoding reporter protein (1), an IRES and selection marker gene (1) encoding selection marker protein (1) and a polyadenylation signal. DNA cassette (1) optionally can include an operator operably linked to the promoter. DNA cassette (1) is randomly or site-specifically inserted into the cell genome. The first lox site and the second lox site on DNA cassette (1) are different.

Where the tet operator is used in DNA cassette (1), multiple rounds of −ligand/+ligand sort and single cell sort will identify Lox-site stable cells for dox-regulated expression. Thus, when the ligand, such as doxycycline or tetracycline, is present, TetR will not bind to the operator, and thereby conditions are permissive for transcription of reporter gene (1) and selection marker polynucleotide (1).

Example 3

Figure 3:
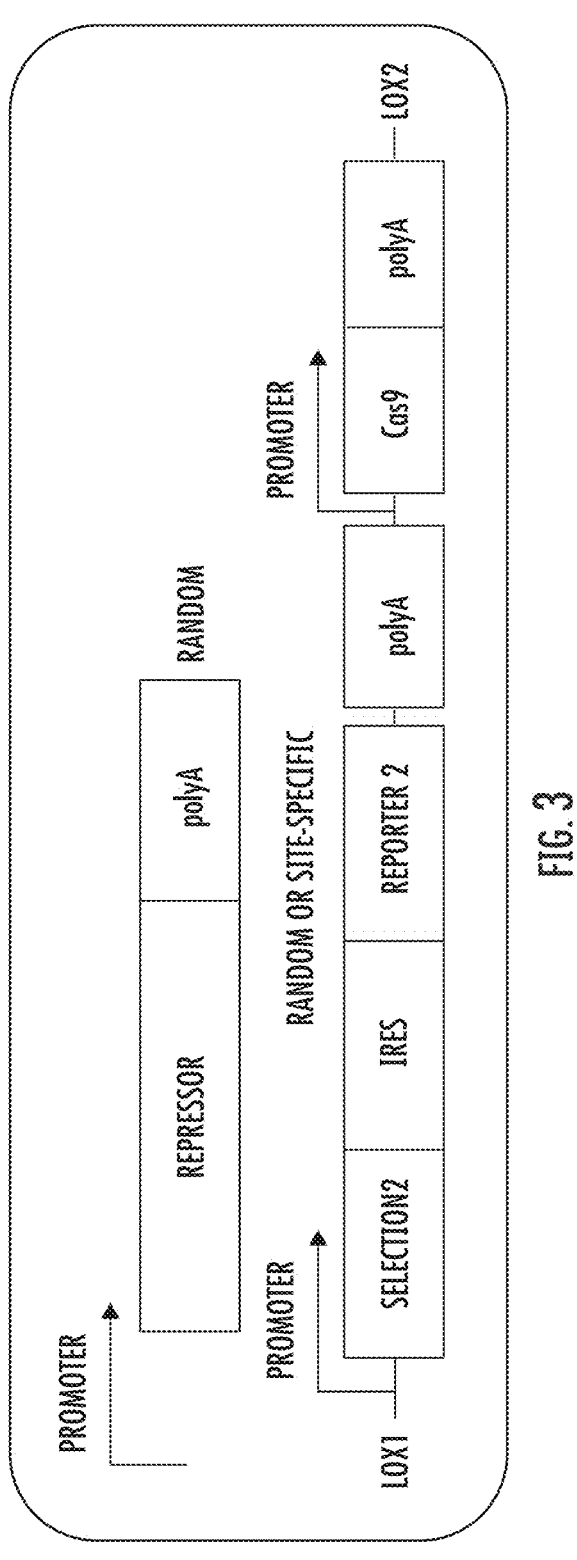
FIG. 3 schematically depicts the modification of the cell of FIG. 2 wherein DNA cassette (1) is replaced by recombinase mediated cassette exchange with DNA cassette (2). DNA cassette (2) comprises flanking lox sites (1 and 2), a promoter, selection marker gene (2), an IRES and reporter gene (2) and polyadenylation signal, and a Cas9 gene with a second polyadenylation signal under control of a second promoter (an operator is optional). Instead of lox sites, other RRSs can be used as well.

In this example, RMCE is performed to replace DNA cassette (1) with DNA cassette (2) in the cells of Example 2. As schematically depicted in FIG. 3, DNA cassette (2) comprises flanking lox sites (1 and 2), and further comprises in 5' to 3' order a promoter, selection marker gene (2) encoding selection marker protein (2), an IRES and reporter gene (2) encoding reporter protein (2), and a Cas9 gene under control of a second promoter (optionally operably linked to an operator).

In an embodiment, a CMV promoter is operably linked to a tet operator to control transcription of the Cas9 gene. When the cells are in the presence of doxycycline or tetracycline, TetR is no longer able to bind the tet operator, and thus allow transcription of the Cas9 gene to occur. Reporter protein (1) is different from reporter protein (2), and selection marker protein (1) is different from selection marker protein (2).

Example 4

This example concerns the integration of DNA cassette (3) into a Genomic Safe Harbor. See FIG. 4. DNA cassette (3) comprises in 5' to 3' order a polynucleotide comprising a first Genomic Safe Harbor homology arm containing an sgRNA target site, lox site (3), a promoter operably linked to reporter gene (3) encoding reporter protein (3), a polyadenylation signal, lox site (4) and a second Genomic Safe Harbor homology arm containing an sgRNA target site, wherein the first and second guide arm target sites each can contain a region with alterations if needed to avoid recreating a targetable site. Lox site (1), lox site (2), lox site (3), and lox site (4) are different from one another. Reporter protein (3) is different from reporter protein (2). Reporter protein (3) and reporter protein (1) can be the same or different. Homology arms of about 1000 bases are used in this example.

When the Cas9 endonuclease is expressed, the efficiency of DNA cassette 3 integration is increased. Without being bound by any theory, the inventive use of an integrated Cas9 gene appears to increase the efficiency of integration by increasing the occurrence of cuts in genomic DNA caused by the Cas9 endonuclease. The use of stably integrated Cas9 gene of the inventions provides 10, $10^2$, $10^3$, $10^4$, $10^5$, $10^6$, $10^7$, $10^8$, $10^9$, or $10^{10}$ greater HDR efficiency than HDR without a stably integrated Cas9 gene.

If needed, alterations in the first and second Genomic Safe Harbor homology arms ensue that the DNA cassette (3) will stay integrated by avoiding recreation of a targetable site. The smaller cassette therein, namely the region between lox site (3) and lox site (4), is available for RMCE and is referred to as a Stable Integration Site.

Example 5

This Example concerns the final form of the cell line, and is schematically depicted in FIG. 5. To ensure stability of a cell line over time, it is preferred to remove the Cas9 gene. Accordingly, DNA cassette (2) is replaced by RMCE with DNA cassette (4), and removes the Cas9 gene. DNA cassette (4) comprises flanking lox sites (1 and 2) and reporter gene (4) encoding reporter protein (4) under the control of a promoter. Reporter protein (4) is different from reporter protein (2) and reporter protein (3) and preferably different from reporter protein (1).

The resulting cells will have two integration sites within the genome, one integration site within a Genomic Safe Harbor (for example, a Stable Integration Site) and one integration site outside of that particular Genomic Safe Harbor. It is possible to create still further integration sites by applying the approaches described above, including the use of an integrated Cas9 gene and the use of additional and different GSH homology arms.

Example 6

This example is a comparison of the efficiency of using Cas9 with homology directed repair (HDR) as disclosed herein compared to conventional HDR. As reported in the literature, HDR is precise, but desired recombinational events occur infrequently: 1 in $10^6$-$10^9$ cells (0.0001% to 0.0000001%). Hsu et al., *Cell* 157: 1262-78 (2014).

In order to assess the advantages of a stably integrated Cas9 gene, a CHO cell having the sites disclosed in U.S. Pat. No. 7,771,997 ("Stable Site 1") and U.S. Pat. No. 9,816,110 ("Stable Site 2") was modified. Regeneron provides a suite of goods and services referred to as EESYR®. CHO cells with integrated sequences in Stable Site 1 and Stable Site 2 are disclosed in US 2019/0233544 A1, and each is referred to as an "enhanced expression locus" therein. Sequences set forth in these patents and Examples 11 and 12 can be used according to the inventions described and depicted herein.

A CHO cell was modified to include a cyano fluorescent protein reporter gene under control of a promoter in Stable Site 1, and a selection marker gene and a yellow fluorescent protein reporter gene under the control of the same promoter in Stable Site 2. Additionally, a Cas9 gene under control of a second promoter with an operator also was inserted into Stable Site 2. The Cas9 gene can be eventually removed in accordance with the teachings contained herein.

The cyano fluorescent protein can be change to fluoresce green by changing the tyrosine residue at position 66 to tryptophan. The sgRNA Delivery Plasmid comprise a selection marker (Ampicillin resistance), a POL III promoter (RNA Polymerase III promoter), a target sequence and gRNA scaffold, a POL III Terminator and Digest Sites 1 and 2. Pol III promoters include H1 and U6.

Figure 6:
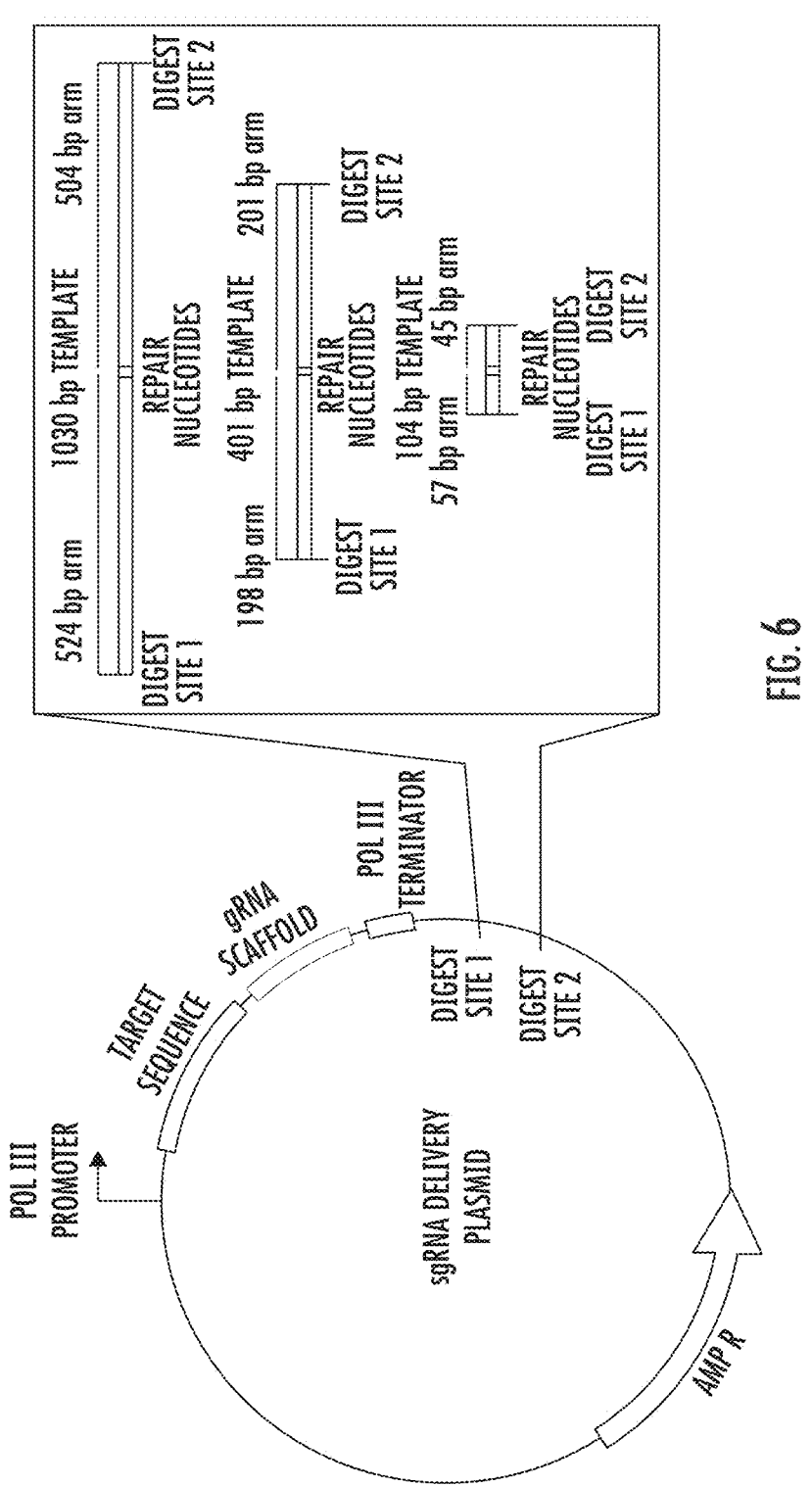
FIG. 6 schematically depicts an sgRNA plasmid used in Example 6.
Figure 7:
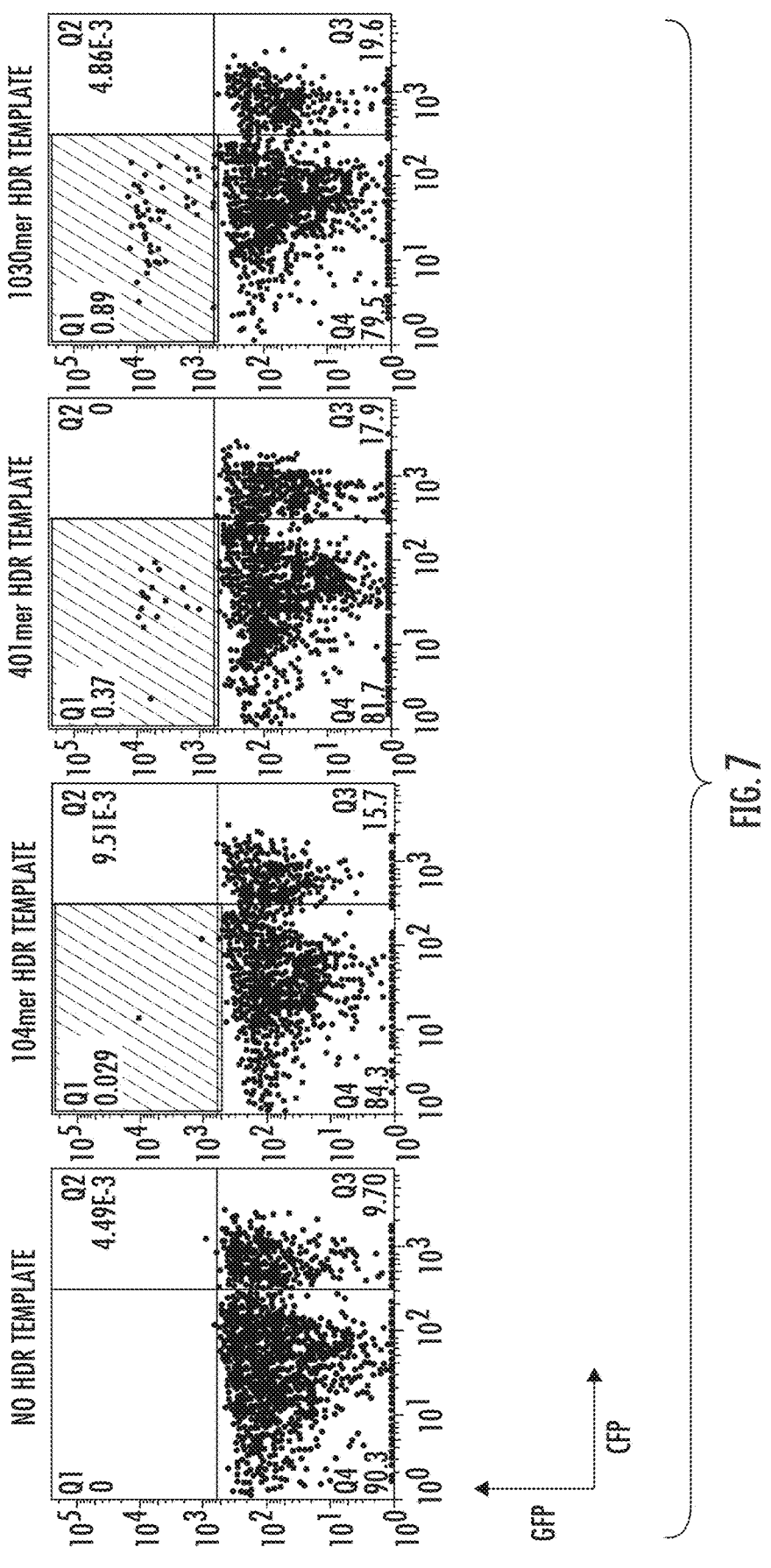
FIG. 7 depicts plots of Example 6 showing green fluorescent protein positive populations (Q1) for No HDR Template (control), 104 mer HDR Template, 401 mer HDR Template and 1030 mer HDR Template. GFP positive is the vertical axis and CFP positive is the horizontal axis.

As depicted in FIG. 6, sgRNA delivery plasmids were constructed containing HDR Templates: a 104 mer insert (having a 57 bp arm and a 45 bp arm), a 401 mer insert (having a 198 bp arm and a 201 bp arm) or a 1030 mer (having a 524 bp arm and a 504 bp arm) insert containing homology arms and the sequence to effect the change from cyano to green, which in this example was composed of 2 nucleotides ("repair nucleotides"). The HDR templates were inserted into the Digest Sites (for example, NotI and/or other appropriate sites) of the sgRNA delivery plasmid to form a sgRNA target plasmid. A sgRNA delivery plasmid without an insert (No HDR Template) was used as a control FIG. 7 shows that the control exhibited no green positives in Q1. The cells with HDR Template exhibited green positives in Q1, and the green positive population in Q1 consistently increased with the increased size of the HDR Template (left to right). The cells with the 1030 mer HDR Templates showed the greatest efficiency in repair, which was about 6.5 percent.

The cells of this example possesses Stable Site 1 and Stable Site 2 and the SIS created in a GSH according to the inventions. Thus, this cell possess three sites for stable integration of genes of interest.

Example 7—Generation of an Intermediate Human Cell Comprising a Stable Integration Site in a Genomic Safe Harbor (AAVS1)

In this example, the starting point is HEK293 cell with stably integrated Cas9 gene flanked by Lox sites 3 and 4. The Cas9 gene is under the control of at least a promoter (not depicted). AAVS1 also is schematically depicted. See FIG. 8. This cell can made according to Examples 1-4 and FIGS. 1-4.

Targeting plasmids containing sgRNA target site, left homology arm (here a GSH homology arm) for insertion into a region, such as a Genomic Safe Harbor (here AAVS1), Lox 1 site, a reporter gene (color 1), Lox 2 site, a right homology arm (here a GSH homology arm) for insertion into a region, such as a Genomic Safe Harbor (here AAVS1). See FIGS. 9A and 9B for alternative targeting plasmids. At the 3' end, one targeting plasmid has reporter gene (Color 2), See FIG. 9A. The other targeting plasmid has at the 3' end a negative selection gene (Negative Selection 1). See FIG. 9B. Promoters and optionally other moieties (such as operators) are represented by arrows pointed in a 5' to 3' direction in FIG. 9A and FIG. 9B. Both plasmids insert color 1 into a region, such as a Genomic Safe Harbor (here AAVS1).

Figures 9A, 9B:
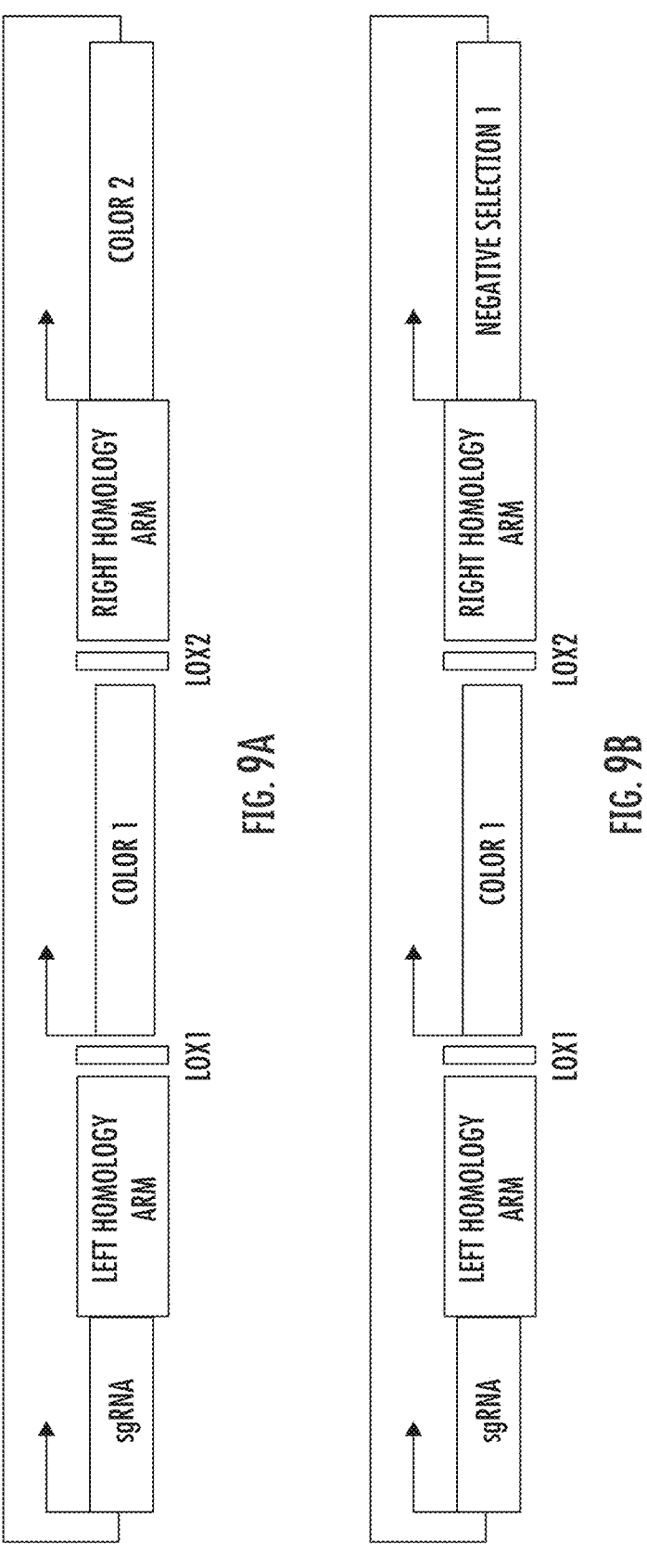
FIG. 9A and FIG. 9B schematically depict targeting plasmids containing sgRNA target site, left homology arm (here a GSH homology arm) for insertion into a region, such as a Genomic Safe Harbor (here AAVS1), Lox 1 site, a reporter gene (color 1), Lox 2 site, a right homology arm (here a GSH homology arm) for insertion into a region, such as a Genomic Safe Harbor (here AAVS1). At the 3' end, FIG. 9A schematically depicts a reporter gene (Color 2), and FIG. 9B schematically depicts at the 3' end a negative selection gene (Negative Selection 1). Promoters and optionally other moieties (such as operators) are represented by arrows pointed in a 5' to 3' direction. Both plasmids insert color 1 into a region, such as a Genomic Safe Harbor. Instead of lox sites, other RRSs can be used as well.
Figure 10:
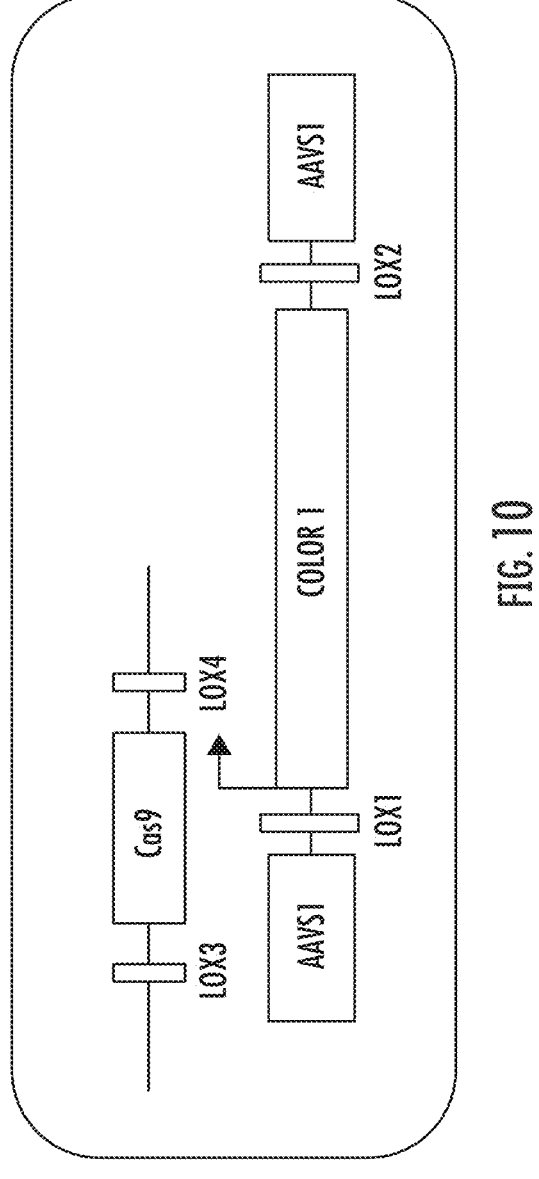
FIG. 10 schematically shows the results after Cas9 mediated integration into the Genomic Safe Harbor (AAVS1) of the mammalian cell (HEK293, for example). Color 1 is flanked by Lox 1 and Lox 2. A gene of interest can replace color 1 via RMCE. When a targeting plasmid according to FIG. 9A is properly integrated, the cell will be color 1 positive and color 2 negative. When a targeting plasmid according to FIG. 9B is properly integrated, the cell will be color 1 positive and will be able to propagate because the negative selection gene is removed. Instead of lox sites, other RRSs can be used as well. Promoters and optionally other moieties (such as operators) are represented by arrows pointed in a 5' to 3' direction.

Cas9 mediated integration of a targeting plasmid (for example, FIG. 9A or FIG. 9B) into the Genomic Safe Harbor (AAVS1) of the HEK293 cell is schematically depicted in FIG. 10. Color 1 is flanked by Lox 1 and Lox 2. A gene of interest can replace color 1 via RMCE.

Figure 8:
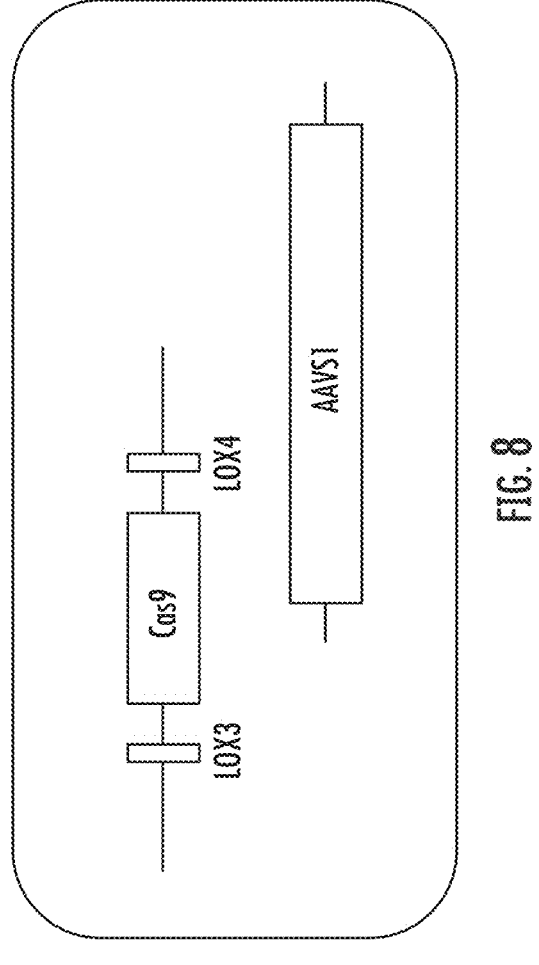
FIG. 8 schematically depicts a mammalian cell (HEK293, for example) with stably integrated Cas9 gene flanked by Lox sites 3 and 4. The Cas9 gene is under the control of at least a promoter (not depicted). AAVS1 also is schematically depicted. Instead of lox sites, other RRSs can be used as well. Promoters are present 5' of genes, but are not depicted.

When a targeting plasmid according to FIG. 9A is properly integrated, the cell will be color 1 positive and color 2 negative. When a targeting plasmid according to FIG. 9B is properly integrated, the cell will be color 1 positive and will be able to propagate because the negative selection gene is removed. This cell is considered an intermediate. Ultimately, the cell can be further subjected to RMCE at lox sites 3 and 4 to remove the cassette containing the Cas9 gene, as shown in FIG. 8. See, for example, Example 5.

Figure 11:
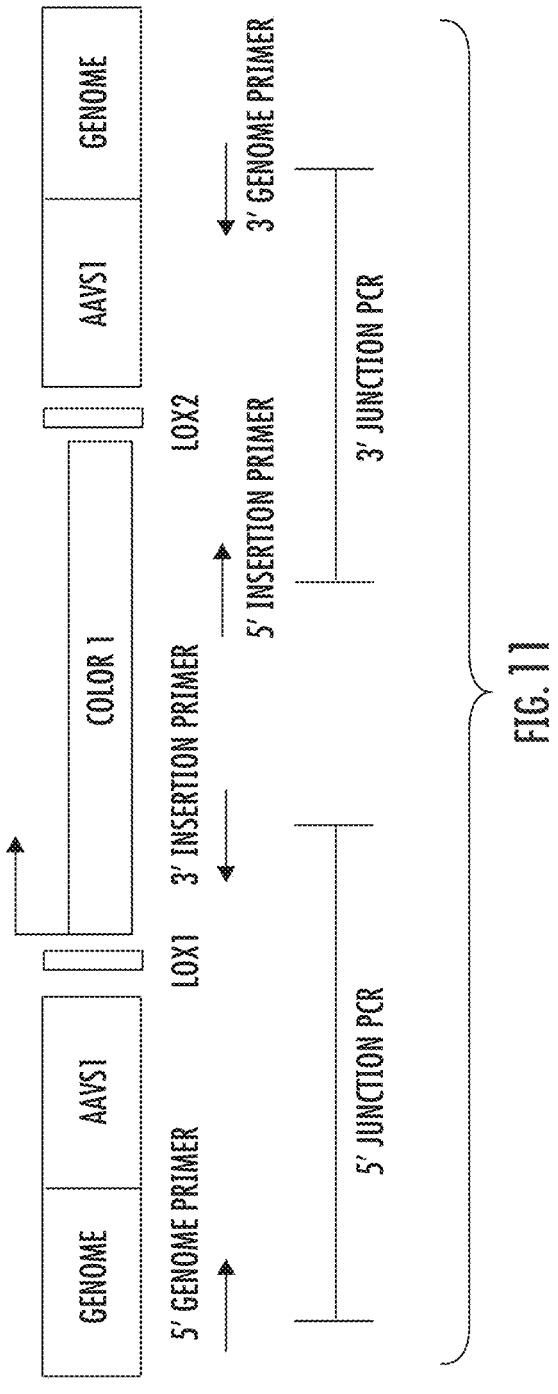
FIG. 11 schematically depicts the insertion of FIG. 10 in greater detail. The cellular genome, including AAVS1, flanks the insert and the 5' and 3' ends. Color 1 is flanked by Lox 1 and Lox 2.

The precision of this inventive methodology is shown in FIGS. 10 and 11. FIG. 11 depicts the insertion of FIG. 10 in greater detail. The cellular genome, including AAVS1, flanks the insert and the 5' and 3' ends. Color 1 is flanked by Lox 1 and Lox 2. FIG. 11, left side identifies the location of 5' genome primer and 3' insertion primer used with 5' junction PCR. FIG. 11, right side identifies the location of 5' insertion primer and 3' genome primer used with 3' junction PCR.

Figure 12:
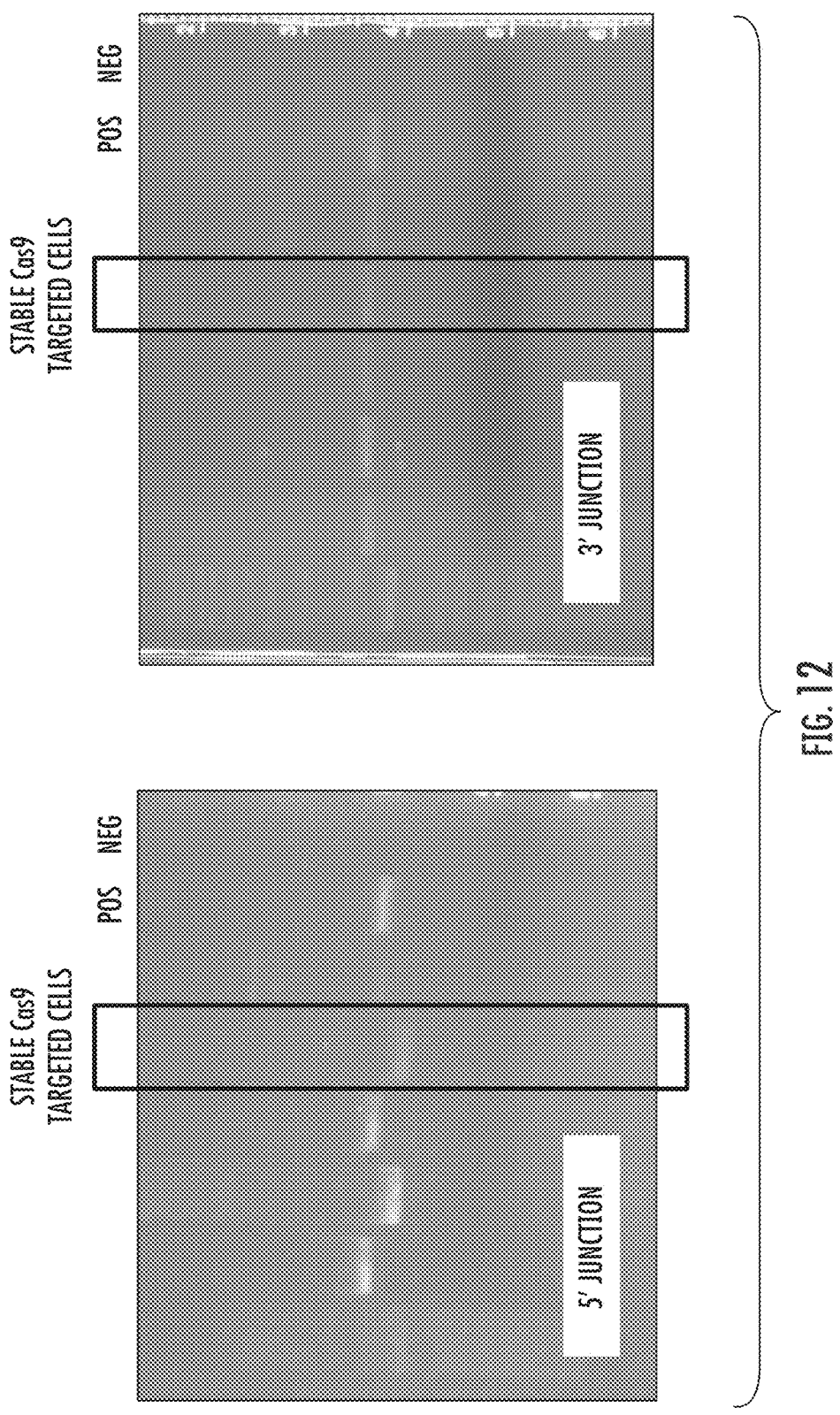
FIG. 12 shows that correct size fragments are amplified in HEK 293 cells by the junction PCR schematically depicted in FIG. 11. Stable Cas9 targeted HEK293 cells and the 5' junction and the 3' junction are obtained and detected, which establish correct insertion.
Figure 13:
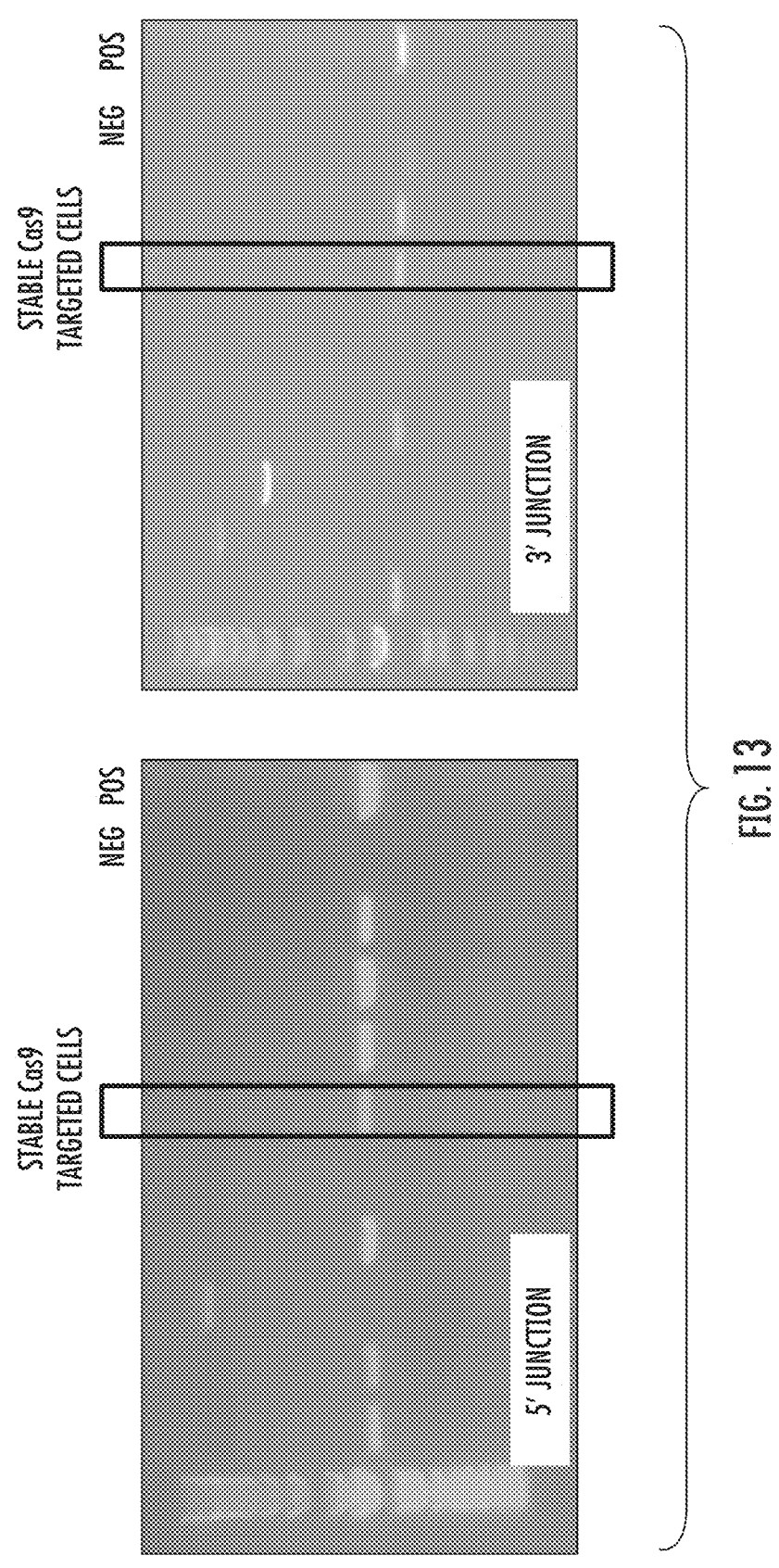
FIG. 13 shows that correct size fragments are amplified in CHO cells by the junction PCR schematically depicted in FIG. 11. Stable Cas9 targeted CHO cells and the 5' junction and the 3' junction are obtained and detected, which establish correct insertion. Instead of lox sites, other RRSs can be used as well.

Junction PCR shows that correct size fragments are amplified and labeled as "Stable Cas9 targeted cells." See FIGS. 12 and 13. Stable Cas9 targeted cells and the 5' junction and the 3' junction are obtained and detected, which establish correct insertion. Positive and negative controls are at the right hand columns of each gel.

Example 8—CHO Regions and Sequences

For CHO cells, the sequences set forth in U.S. Pat. No. 7,771,997 (Stable Site 1) and U.S. Pat. No. 9,816,110 (Stable Site 2) can be utilized. The sequences and homologous sequences within the percent identity values of U.S. Pat. Nos. 7,771,997 and 9,816,110 are hereby incorporated by reference. An AAVS1-like region disclosed herein can be used to create Stable Integration Sites according to the inventions.

Candidate loci for use according to the inventions are reported in the literature. Hamaker and Lee, *Curr. Op. Chem. Eng.* 22: 152-60 (2018) identify 30 hot spot loci. Hilliard and Lee, *Biotech. Bioeng.* 118: 659-75 (2021) sought to identify safe harbor regions in CHO using an epigenomic analysis for Hi-C stable regions, and found an overlap with 5 of the 30 regions identified by Hamaker and Lee. See Supplementary Table 3 of Hilliard and Lee. Gaidukov et al., *Nucl. Acids Res.* 46: 4072-86 (2018) also identifies loci for integration in CHO cells, including a putative Rosa26. Lee et al., *Scientific Reps.* 5: 8572 (2015) reported a COSMC locus in hamster cells. In sum, these papers identify several unannotated regions and gene regions in CHO, and the gene regions are set forth below:

| BMP5 | SSBP2 | TRMT6 | CLCC1 | FAM114A1 |
|---|---|---|---|---|
| | | | | (NOXP20) |
| LRBA | DCN | CEP128 | AACS | ALDH5A1 |
| SMAD6 | PTPRQ | ROSA26 | ADGRL4 | GPM6A |
| K1AA1551 | HPRT | CLCN3 | FER1L4 | COSMC |
| (C12ORF35) | | | | |

Example 9—CHO Cells with Three or More Insertion Sites

CHO cells containing multiple insertion cites using the cells disclosed in US 2019/0233544 A1. Stable Site 1 and Stable Site 2 can be used initially in accordance with the teachings contained herein that utilize an integrated Cas9 gene. Once one or more Stable Integration Sites are created in Genomic Safe Harbors, such as in the AAVS1-like region (see, for example, SEQ ID NO:2) and counterpart guide sequences (see, for example, SEQ ID NOS:13 to 419). Guide sequences can bind to target sequences in SEQ ID NO-2 at nucleotide position ranges selected from the group consisting of: (a) 1 to 2000; (b) 2001 to 4000; (c) 4001 to 6000; (d) 6001 to 8000; (e) 8001 to 10,000; (f) 10,001 to 12,000; (g) 12,001 to 14,000; (h) 14,001 to 16,000; (i) 16,001 to 18,000; (j) 18,001 to 20,000; (k) 20,001 to 22,000; (l) 22,001 to 24,000; (m) 24,001 to 26,000; (n) 26,001 to 28,000; (o) 28,001 to 30,000; (p) 30,001 to 32,000; (q) 32,001 to 34,000; (r) 34,001 to 36,000; (s) 36,001 to 38,000; (t) 38,001 to 40,000; (u) 40,001 to 42,000; and (v) 42,001 to 44,232.

Stable Site 1 and Stable Site 2 of U.S. Pat. Nos. 7,771,997 and 9,816,110 can be used for expression of genes of interest to encode proteins of interest. Cells with SISs ultimately can have 3, 4, 5, 6, 7, 8, 9, 10 or more sites for expressing genes of interest.

Preferably, a CHO cell comprising Stable Sites 1 and 2 is modified to create a third site in a Genomic Safe Harbor, namely a Stable Integration Site. Preferred Genomic Safe Harbors for creation of such a CHO cell are in the AAVS1-like region. Other CHO cell types can be used to create multiple sites according to the teachings contained herein.

Figure 14:
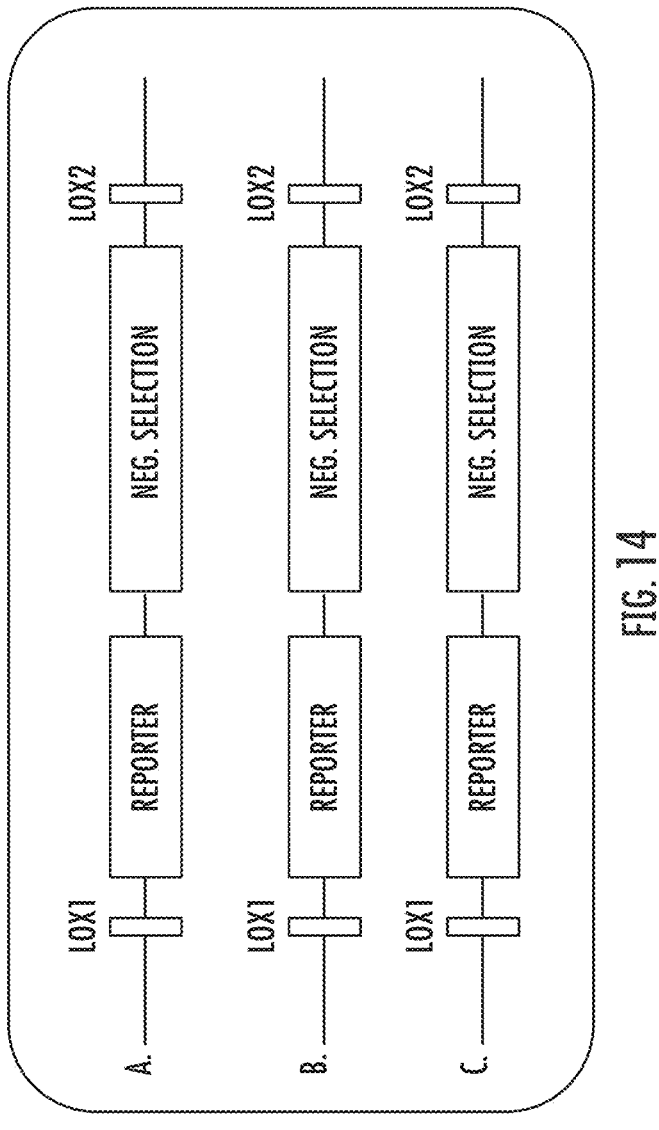
FIG. 14 schematically depicts an exemplary cell comprising three cassettes integrated into regions of the genome with flanking RRSs (here lox 1 and lox 2). Depending on the cell type, each of the three cassettes can be integrated into different Stable Integration Sites (for example, AAVS1-like) schematically depicted at position A, and other available sites (such as Stable Site 1 and Stable Site 2) schematically depicted at positions B and C. The reporter genes can be the same or different. The negative selection genes can be the same or different, but preferably the same. The cell can contain additional Stable Integration Sites and integrated cassettes according the teachings contained herein. Promoters are present 5' of genes, but are not depicted.

FIG. 14 schematically depicts an exemplary cell comprising three cassettes integrated into regions of the genome with flanking RRSs (here lox 1 and lox 2). Depending on the cell type, each of the three cassettes can be integrated into different Stable Integration Sites and other available sites (such as Stable Site 1 and Stable Site 2) schematically depicted as positions A, B and C. The reporter genes can be the same or different. The negative selection genes can be the same or different, but preferably the same. The cell can contain additional Stable Integration Sites and integrated cassettes according the teachings contained herein.

Figure 15:
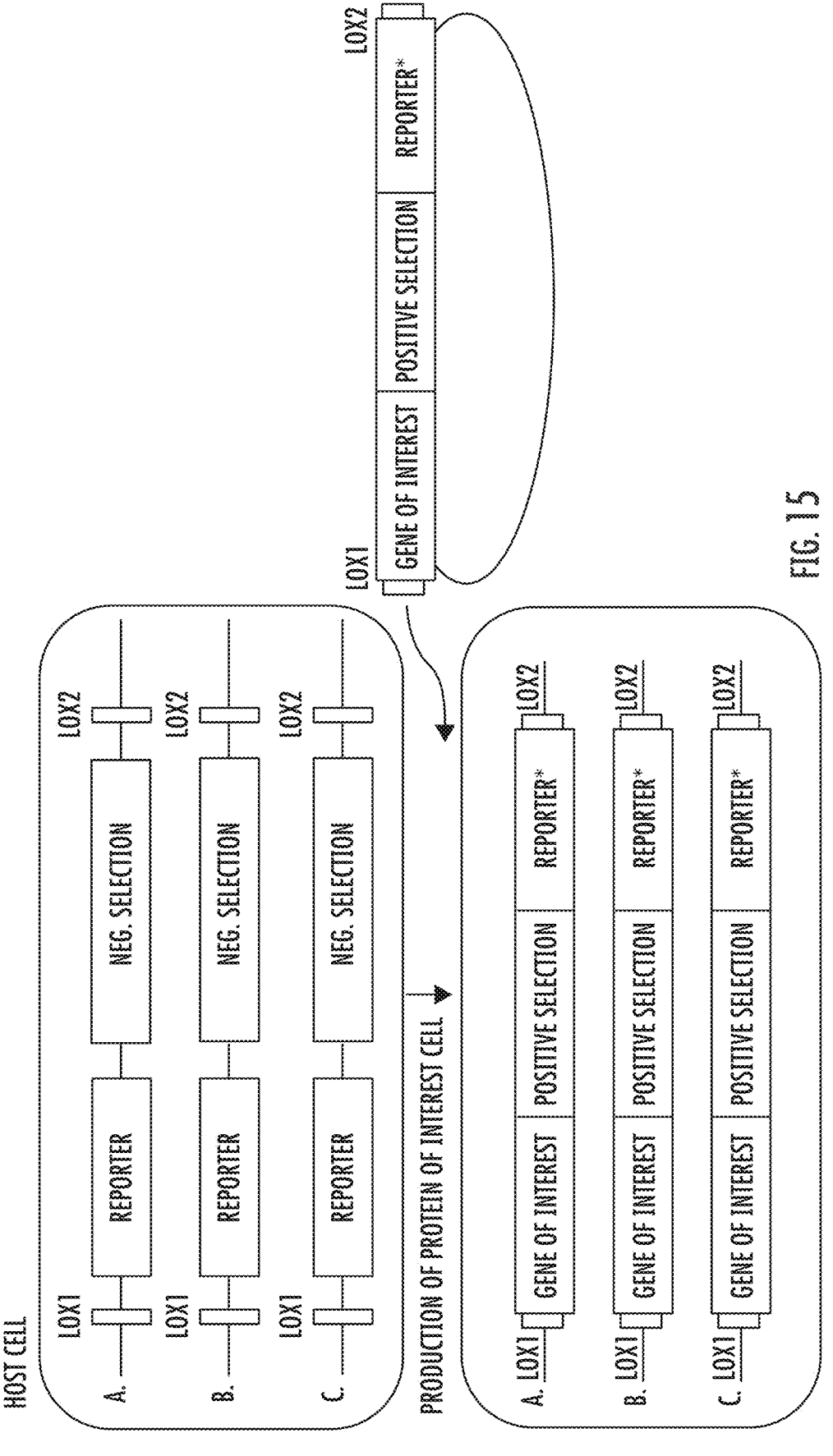
FIG. 15 schematically depicts the modification of the cell of FIG. 14 at schematically depicted positions A, B and C. Three cassettes each comprise flanking RRSs (here lox 1 and lox 2), a gene of interest, a positive selection marker gene, and a reporter* gene. The positive selection marker genes can be the same or different, but preferably the same. The reporter* genes can be the same or different, but each must be different from any of the reporter genes in the cell of FIG. 14. The genes of interest can be the same or different. The cassettes of FIG. 14 are replaced by the cassettes of FIG. 15 by RMCE. The cell can contain additional Stable Integration Sites and integrated cassettes according the teachings contained herein. Promoters are present 5' of genes, but are not depicted.

FIG. 15 schematically depicts the modification of the cell of FIG. 14 at schematically depicted positions A, B and C. Three cassettes each comprise flanking RRSs (here lox 1 and lox 2), a gene of interest, a positive selection marker gene, and a reporter* gene. The positive selection marker genes can be the same or different, but preferably the same. The reporter* genes can be the same or different, but each must be different from any of the reporter genes in the cell of FIG. 14. The genes of interest can be the same or different. The cassettes of FIG. 14 are replaced by the cassettes of FIG. 15 by RMCE. The cell can contain additional Stable Integration Sites and integrated cassettes according the teachings contained herein.

The combination of negative and positive selection assures isolation of cells that underwent recombination in all sites. If the gene of interest is the same in each of the three cassettes, the cell can result in high yield protein expression. For example, 7, 8, 9, 10 or more grams per liter (g/A) of protein production is possible.

Figure 16:
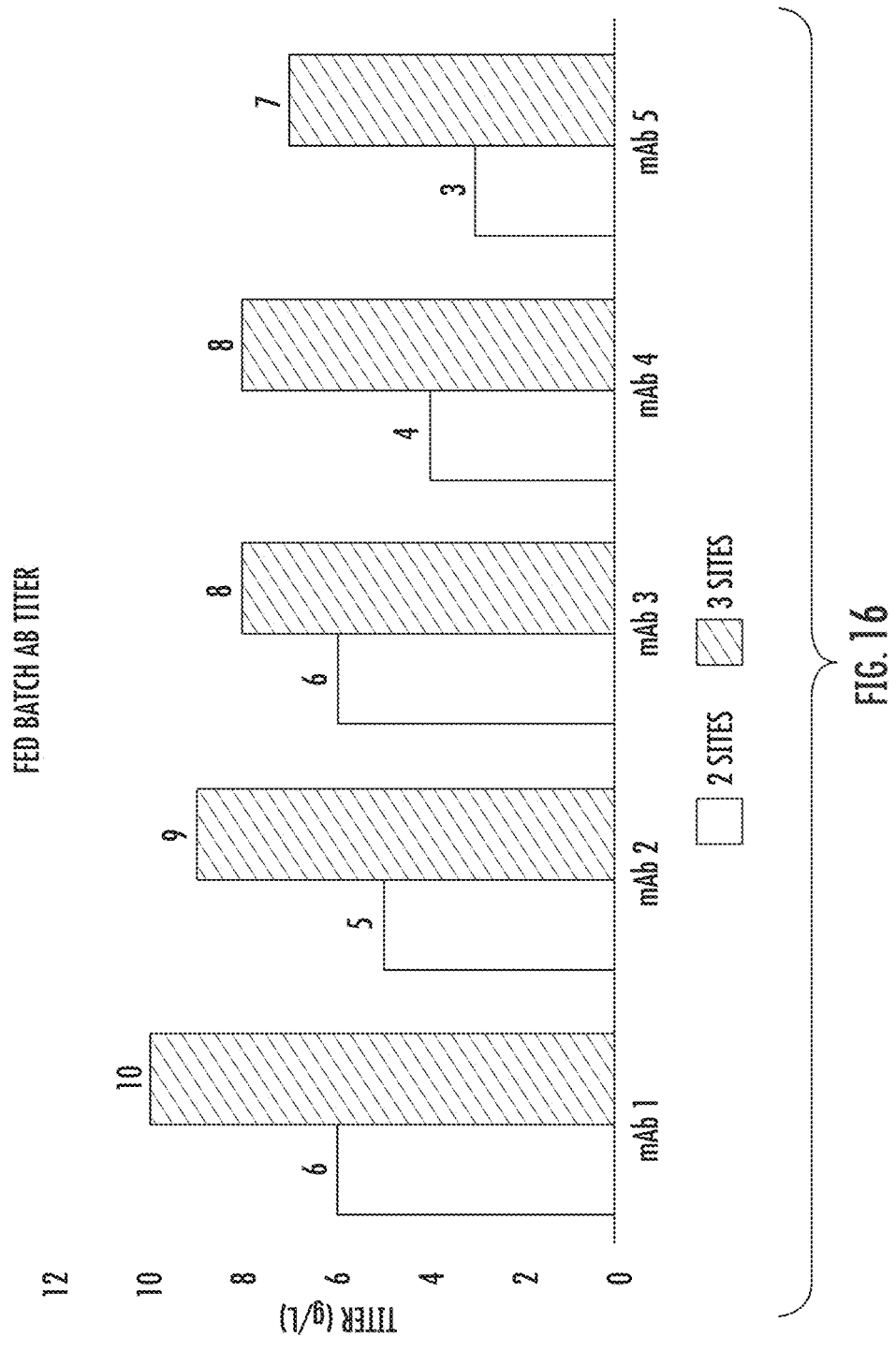
FIG. 16 is a bar graph comparing protein produced by a three-site CHO-K1 cell (A, B, and C) compared to a two-site CHO-K1 cell (B and C).

FIG. 16 shows the results from five different human IgG antibodies that were stably integrated using Cre-lox recombination into CHO K1 derived hosts engineered with either 2 integration sites (Stable Site 1 and 2) or 3 integration sites (Stable Site 1, Stable Site 2 and AAVS1-like (see SEQ ID NO:2)). Isogenic cell lines (ICLs) were isolated using flow cytometry. Fed batch production of ICLs were inoculated into chemically defined production media, and production cultures were carried out for 13 days. Antibody titer in conditioned media was determined using a protein A HPLC based method, and each three-site cell expressing a given antibody (1, 2, 3, 4, or 5) expressed a greater amount of protein than the comparison two-site cell. The three-site cell can provide increases of 10%, 20%, 30%, 40%, 50%, 60%, 70%, 80%, 90%, 100%, 110%, 120%, 130%, 140%, 150% or more over the two-site cell.

Alternatively, different genes of interest can be used in the cassettes. For example, heavy chain and light chain sequences of an antibody can be gene of interest.

Turning to a four-site cell, preferably a CHO cell comprising Stable Site 1 and 2 is modified to create a third and fourth site in a Genomic Safe Harbor, namely a Stable Integration Site. Preferred Genomic Safe Harbors for creation of such a CHO cell are in the AAVS1-like region, which can be the third site. A fourth site can be created in other loci, including but not limited to:

| BMP5 | SSBP2 | TRMT6 | CLCC1 | FAM114A1 (NOXP20) |
|------|-------|-------|-------|-------------------|
| LRBA | DCN | CEP128 | AACS | ALDH5A1 |
| SMAD6 | PTPRQ | ROSA26 | ADGRL4 | GPM6A |
| K1AA1551 (C12ORF35) | HPRT | CLCN3 | FER1L4 | COSMC |

Other CHO cell types can be used to create multiple sites according to the teachings contained herein.

Figure 17:
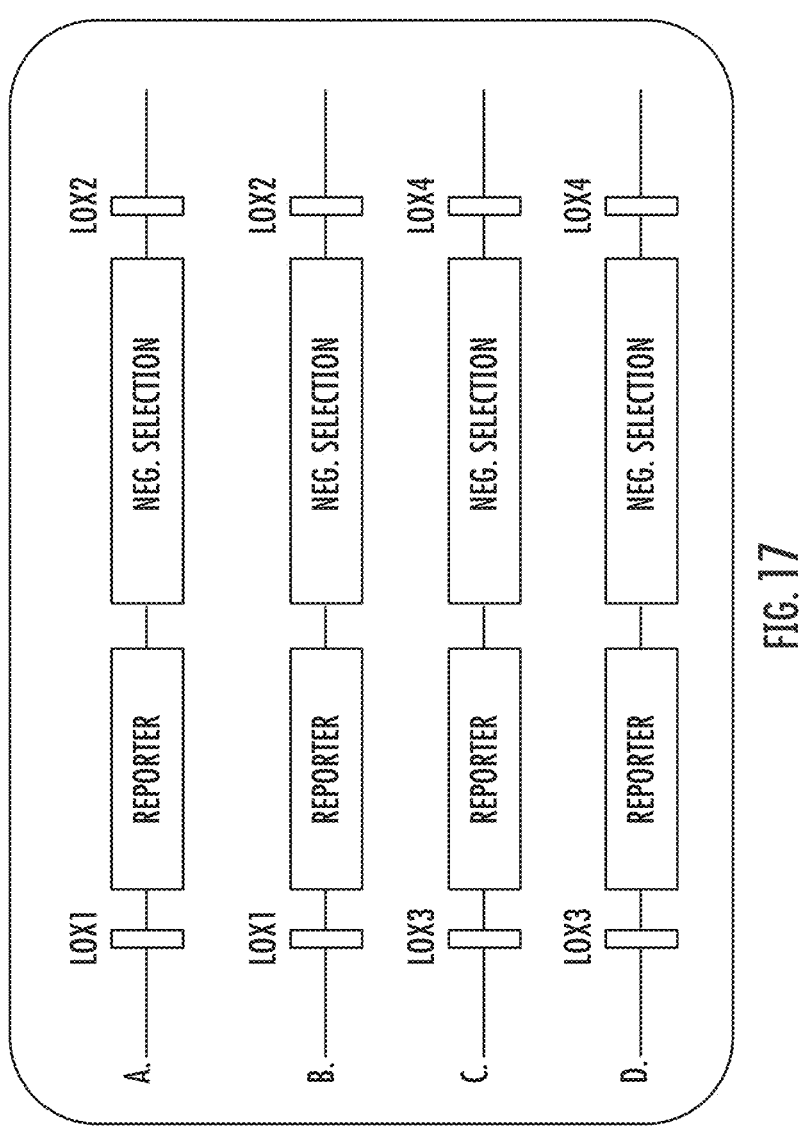
FIG. 17 schematically depicts an exemplary cell comprising four cassettes integrated into regions of the genome with flanking RRSs (here lox 1 and lox 2, or lox 3 and lox 4). Depending on the cell type, each of the four cassettes can be integrated into different Stable Integration Sites (and other available sites (such as Stable Site 1 and Stable Site 2), and schematically depicted as positions A and B (SISs) and C and D (Stable Sites 1 and 2). The reporter genes can be the same or different. The negative selection genes can be the same or different, but preferably the same. The cell can contain additional Stable Integration Sites and integrated cassettes according the teachings contained herein. Promoters are present 5' of genes, but are not depicted.

FIG. 17 schematically depicts an exemplary cell comprising four cassettes integrated into regions of the genome with flanking RRSs (here lox 1 and lox 2, or lox 3 and lox 4). Depending on the cell type, each of the four cassettes can be integrated into different Stable Integration Sites and other available sites (such as Stable Site 1 and Stable Site 2) schematically depicted as positions A, B, C and D. The reporter genes can be the same or different. The negative selection genes can be the same or different, but preferably the same. The cell can contain additional Stable Integration Sites and integrated cassettes according the teachings contained herein.

Figure 18:
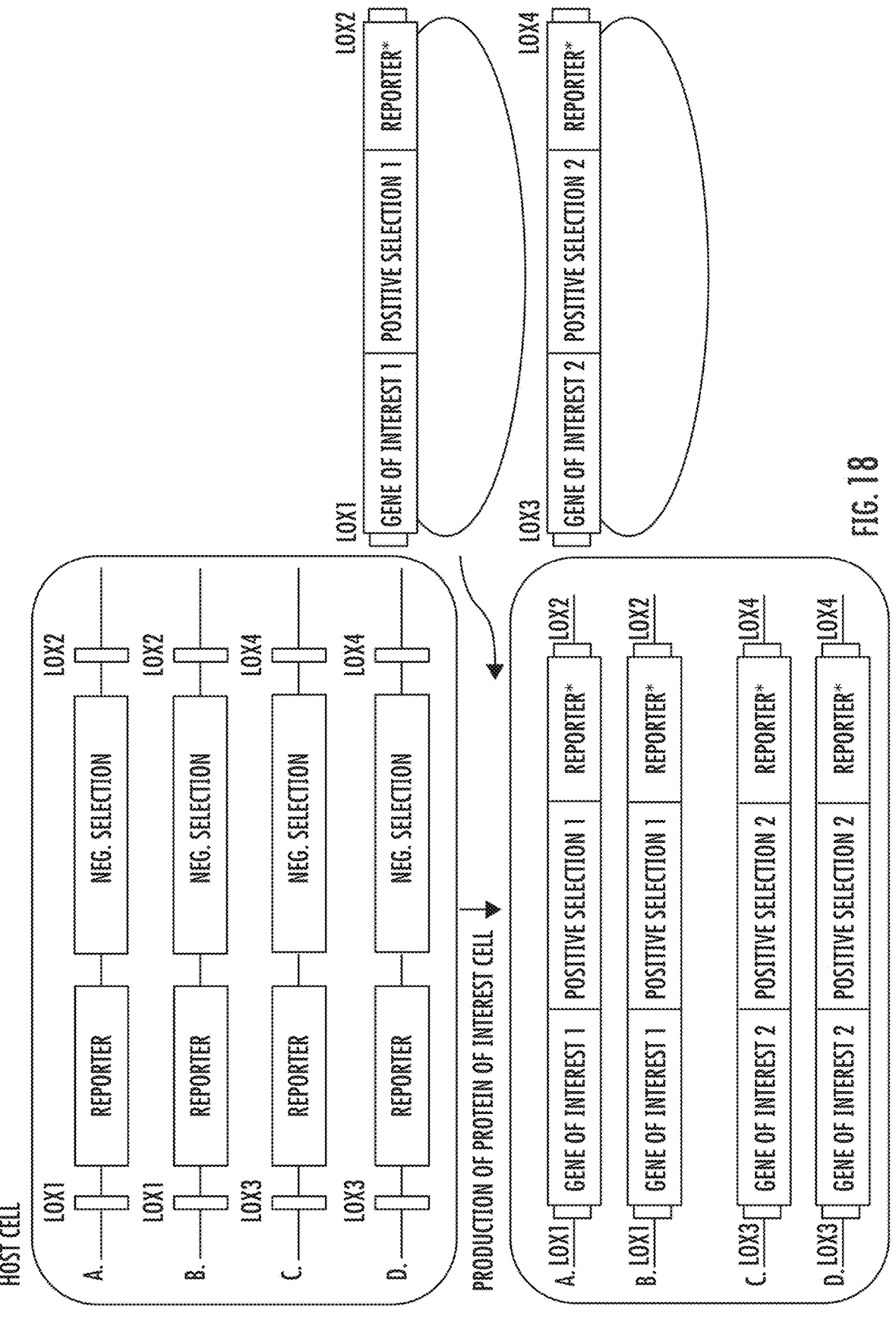
FIG. 18 schematically depicts the modification of the cell of FIG. 17 at schematically depicted positions A, B, C and D. Four cassettes each comprise flanking RRSs (here lox 1 and lox 2, or lox 3 and lox 4), a gene of interest, a positive selection marker gene, and a reporter* gene. The positive selection marker genes can be the same or different, but preferably the same. The reporter* genes can be the same or different, but each must be different from any of the reporter genes in the cell of FIG. 17. The genes of interest can be the same or different. In this figure, there are two copies of Gene of Interest 1 and two copies of Gene of Interest 2. The cassettes of FIG. 17 are replaced by the cassettes of FIG. 18 by RMCE. The cell can contain additional Stable Integration Sites and integrated cassettes according the teachings contained herein. Promoters are present 5' of genes, but are not depicted.

FIG. 18 schematically depicts the modification of the cell of FIG. 17 at schematically depicted positions A, B, C and D. Four cassettes each comprise flanking RRSs (here lox 1 and lox 2, or lox 3 and lox 4), a gene of interest, a positive selection marker gene, and a reporter* gene. The positive selection marker genes can be the same or different, but preferably the same. The reporter* genes can be the same or different, but each must be different from any of the reporter genes in the cell of FIG. 17. The genes of interest can be the same or different. In this figure, there are two copies of Gene of Interest 1 and two copies of Gene of Interest 2. The cassettes of FIG. 17 are replaced by the cassettes of FIG. 18 by RMCE. The cell can contain additional Stable Integration Sites and integrated cassettes according the teachings contained herein.

The combination of negative and positive selection assures isolation of cells that underwent recombination in all sites. A four-site cell is useful for making bispecific antibodies, wherein two distinct heavy chain/light chain plasmids can be targeted into distinct sites.

Example 10—Genomic Safe Harbor Sequences

Genomic Safe Harbors Sequences and the like are described herein, and many are in the literature and are publically available. Exemplary sequences are set forth below.

```
Human AAVS1 sequence
Human AAVS1 (Native RBS and guide RNA site for safe harbor insertion indicated)
                                                               (SEQ ID NO: 1)
GAATTCCTAACTGCCCCGGGGCAGTCTGCTATTCATCCCCTTTACGCGGTGCTACACACACT

TGCTAGTATGCCGTGGGGACCCCTCCGGCCTGTAGACTCCATTTCCCAGCATTCCCCGGAGG

AGGCCCTCATCTGGCGATTTCCACTGGGGGCCTCGGAGCTGCGGACTTCCCAGTGTGCATCG

GGGCACAGCGACTCCTGGAAGTGGCCACTTCTGCTAATGGACTCCATTTCCCAGGCTCCCGC

TACCTGCCCAGCACACCCTGGGGCATCCGTGACGTCAGCAAGCCGGGCGGGGACCGGAGATC

CTTGGGGCGGTGGGGGGCCAGCGGCAGTTCCCAGGCGGCCCCCGGGGCGGGCGGGCGGGCGG

GTGGTGGCGGCGGTTGGGGCTCCGGGCGCGTCGCTCGCTCGCTCGCTGGGCGGGCGGGCGGT

GCGATGTCCGGAGAGGATGGCCGGCGGCTGGCCCGGGGGCGGCGGCGCGCGGCTGCCCGGGAGC
```

-continued

```
GGCGACGGGAGCAGCTGCGGCAGTGGGGCGCGGGCGGGCGCCGAGCCTGGCCCCGGAGAGCG

CCGCGCCCGCACCGTCCGCTTCGAGCGCGCCGCCGAGTTCCTGGCGGCCTGTGCGGGCGGCG

ACCTGGACGAGGCGCGTCTGATGCTGCGCGCCGCCGACCCTGGCCCCGGCGCCGGAGCTCGA

CCCCGCCGGCCGCCGCCCGCCCGCGCCGTGCTGGACTCCACCAACGCCGACGGTATCAGCGC

CCTGCACCAGGTCAGCGCCCCCCGCGGCGTCTCCCGGGGCCAGGTCCACCCTCTGCGCCACC

TGGGGCATCCTCCTTCCCCGTTGCCAGTCTCGATCCGCCCCGTCGTTACTGGCCCTGGGTTT

NCACCCTATGCTGACACCCCGTTCCAGTCCCCTTACCATTCCCTTCGACCACCCCACTTCCG

AATTGGAGCGCTTCAACTGGCTGGGCTAGCACTCTGTGTGACACTCTGAAGCTCTACATTCC

CTTCGACCTACTCTCTTCGATTGGAGTCGCTTTAACTGGCCCTGGCTTTGGCAGCCTGTGCT

GACCCATCGAGTCCTCCTTACCATCCCTCCCTCGACTTCCCCTCTTCCGATGTTGAGCCCCT

CCAGCCGGTCCTGGACTTTGTCTCCTTCCCTGCCCTGCCCTCTCCTGAACCTGAGCCAGCTC

CCATAGCTCAGGTCTGGTCTATCTGCCTGGCCCTGGCCATTGTCACTTTGCGCTGCCCTCCT

CTCGCCCCCGAGTGCCCTTGCTGTGCCGCCGGAACTCTGCCCTCTAACGCTGCCGTGCCGTC

TCTCTCCTGAGTCCGGACCACTTTGAGCTCTACTGGCTTCTGCGCGCCTCTGGCCCACTGTT

TCCCCTTCCCAGGCAGGTCCTGCTTTCTCTGACCAGCATTCTCTCCCCTGGGCCTGTGCCGC

TTTCTGTCTGCAGCTTGTGGCCTGGGTCACCTCTACGGCTGGCCCAAGATCCTTCCCTGCCG

CCTCCTTCAGGTTCCGTCTTCCTCCACTCCCTCTTCCCCTTGCTCTCTGCTGTGTTGCTGCC

CAAGGATGCTCTTTCCGGAGCACTTCCTTCTCGGCGCTGCACCACGTGATGTCCTCTGAGCG

GATCCTCCCCGTGTCTGGGTCCTCTCCGGGCATCTCTCCTCCCTCACCCAACCCCATGCCGT

GTTCACTCGCTGGGTTCCCTTTTCCTTCTCCTTCTGGGGCCTGTGCCATCTCTCGTTTCTTA

GGATGGCCTTCTCCGACGGATGTCTCCCTTGCGTCCCGCCTCCCCTTCTTGTAGGCCTGCAT

CATCACCGTTTTTCTGGACAACCCCAAAGTACCCCGTCTCCCTGGCTTAGCACCTCTCCATC

CTCTTGCTTTCTTTGCCTGGACACCCCGTTCTCCTGTGGATTCGGGTCACCTCTCACTCCTT

TCATTTGGGCAGCTCCCCTACCCCCCCTTACCTCTCTAGTCTGTGCTAGCTCTTCCAGCCCCC

TGTCATGGCATCTTCCAGGGGTCCGAGAGCTCAGCTAGTCTTCTTCCTCCAACCCGGGCCCT

ATGTCCACTTCAGGACAGCATGTTTGCTGCCTCCAGGGATCCTGTGTCCCCGAGCTGGGACC

ACCTTATATTCCCAGGGCCGGTTAATGTGGCTCTGGTTCTGGGTACTTTTATCTGTCCCCTC

CACCCCACAGT***GGGGCCACTAGGGACAGGAT***GGTGACAGAAAGCCCCCATCCTTAGGCCT

CCTCCTTCCTAGTCTCCTGATATTCGTCTAACCCCCCACCTCCTGTTAGGCAGATTCCTTATC

TGGTGACACACCCCCATTTCCTGGAGCCATCTCTCTCCTTGCCAGAACCTCTAAGGTTTGCT

TACGATGGAGCCAGAGAGGATCCTGGGAGGGAGACTTGGCAGGGGGTGGGAGGGAAGGGGGG

GATGCGTGACCTGCCCGGTTCTCAGTGGCCACCCTGCGCTACCCTCTCCCAGAACCTGAGCT

GCTCTGACGCGGCTGTCTGGTGCGTTTCACTGATCCTGGTGCTGCAGCTTCCTTACACTTCC

CAAGAGGAGAAGCAGTTTGGAAAAACAAAATCAGAATAAGTTGGTCCTGAGTTCTAACTTTG

GCTCTTCACCTTTCTAGNCCCCAATTTATATTGTTCCTCCGTGCGTCAGTTTTACCTGTGAG

ATAAGGCCAGTAGCCACCCCCGTCCTGGCAGGGCTGTGGTGAGGAGGGGGGTGTCCGTGTGG

AAAACTCCCTTTGTGAGAATGGTGCGTCCTAGGTGTTCACCAGGTCGTGGCCGCCTCTACTC

CCTTTCTCTTTCTCCATCCATCCTTCTTTCCTTAAAGAGCCCCCAGTGCTATCTGGACATAT

TCCTCCGCCCAGAGCAGGGTCCGCTTCCCTAAGGCCCTGCTCTGGGCTTCTGGGTTTGAGTC

CTTGCAAGCCCAGGAGAGCGCTAGCTTCCCTGTCCCCCTTCCTCGTCCACCATCTCATGCCC

TGGCTCTCCTGCCCCCTTCCTACAGGGGTTCCTGGCTCTGCTCTTCAGACTGAGCCCCGTTCC
```

-continued

CCTGCATCCCCGTTCCCCTGCATCCCCCTTCCCCTGCATCCCCCCAGAGCCCCAGGCCACCTA

CTTGGCCTGGAACCCCACGAGAGGCCACCCCAGCCCTGTCTACCAGGCTGACCTTTTGGGTG

ATTCTCCTCCAACTGTGGGGTGACTGCTTGGGCAAACTCACTCTTCGGGGTATCCCAGGAGG

CCTGGAGCATTGGGGTGGGCTGGGGTTCAGAGAGGAGGGATTCCCTCCAGGTTACGTGGCCA

AGAAGCAGGGGAGCTGGGTTTGGGTCAGGCTGGGTGTGGGGTGACCAGCTTATGCTGTTTGC

CCAGGACAGCCTAGTTTTAGCGCTGAAACCCTCAGTCCTAGGAAAACAGGGATGGTTGGTCA

CTGTCTCTGGGTGACTCTTGATTCCCGGCCAGTTTCTCCACCTGGGGCTGTGTTTCTCGTCC

TGCATCCTTCTCCAGGCAGGTCCCCAAGCATCGCCCCCCTGGCTGTTCCCAAGTTCTTAGGT

ACCCCACGTGGGTTTATGAACCACTTGGTGAGGCTGGTACCCTGCCCCCATTCCTGCACCCC

AATTGCCTTAGTGGCTAGGGGGTTGGGGGCTAGAGTAGGAGGGGCTGGAGCCAGGATTCTTA

GGGCTGAACAGAGCCGAGCTGGGGGCCTGGGCTCCTGGGTTTGAGAGAGGAGGGGCTGGGGC

CTGGACTCCTGGGTCCGAGGGAGGAGGGGCTGGGGCCTGGACTCCTGGGTCTGAGGGTGGAG

GGACTGGGGGCCTGGACTCCTGGGTCCGAGGGAGGAGGGGCTGGGGCCTGGACTCGTGGGTC

TGAGGGAGGAGGGGTCGGGGGCCTGGACTTCTGGGTCTTAGGGAGGCGGGGCTGGGCCTGGA

CCCCTGGGTCTGAATGGGGAGAGGCTGGGGGCCTGGACTCCTTCATCTGAGGGCGGAAGGGC

TGGGGCCTGGCCTCCTGGGTTGAATGGGGAGGGGTTGGGCCTGGACTCTGGAGTCCCTGGTG

CCCAGGCCTCAGGCATCTTTCACAGGGATGCCTGTAC

CHO AAVS1-Like Region Sequence
(Guides for Insertion are shown further below in Example 13)
                                         (SEQ ID NO: 2)
CCAGCACCCACATGGTGGCTCACAACTGTCCGTAACTCCAGTTCCAGAGGATCTGATGCCCTCTTCTG

TCTCCCGCGAGCACCTGGCACACACGTGATGCACACTTAAACACATGCAAGCAAACCATCAGACACAT

AACTTTTTTTTCCAATTTTTTAAAGATTTAGTTATTATTATTTACTTAATAAATATTTATTATATTTA

TTACATATACAGTTTCTGCCTACATGCCAGCAGAGGGCACCAGATTGAATTGTAGATGGTTGTGAGCC

ACCATGTGGTTGCTGGGAATTGAACTCAGGACCCCTGGAAGAGCAGTCAGTGCTCTTAACCTCTGAGC

CATCTCTCCAGCCCCTCCATTTTTTTTTTTTTTAAATAAAGAAATGTAATGTCCTAAGTGGGGCTTAGA

GAGTGGAAGCAGATAAAGAAAGATGGAGTTAAGAATTTTAAGAAGCCAGTTGGCGGTTGTGCATGCCA

GCACTCAGGAGGCAGAGGCAGGTGGATGGATCTCTATGAGTTCGAGGCCAGCCTGGTCTACAGAGAGA

GAGTTCCAGGACAGACTTCTCCAAAGCTACAGAGAAACCCTGTCTGAACCCACCACGACCACCACAAA

GAAAAAAAGGATTTCAAGAGGAGAGCCAGGTTTATAGCAAGAGAGAAAGTTGTGAACTAATGCCCAGG

GCTTAGTGTGGCCTACCTCTGGGCTGGGTCTCTCTCTGAACACAGGGTGGAGCTGCCCCGGGAGGAAG

AAGCGGCTCCGTACAGTCCCGAATTCTACAGTGGCTGGGAGCCTCCCGCCACTGACCCGCAGGGCCGC

GCCTGGGAGGACCCGGTGGAAAAACAGCTACAGCATGAGAAGAGGCGCAGGCAGGTGAGGCAGGGTTG

CCGGGGGAGCACTGGGCTCCCCGTTTCTGCACAACATGGGCGAGCAGGACGTCTGAGGTCTAGCCTGC

CTGACCCCAAGCTCTCTCTCTTCCCGCAGCAAAGCGCCCCCCAGATCGCTGTCAATGGGTGAGTGACC

GCTGCAGGGTGGCCAGGGATGGGGTTGGGAGGACTGAGTCCCGGGGTCACCCCGGCTCTGACTCCGAC

CCTCCCCCTTTTTTCTTGTCTTTTTTTTTTTTTTTTTTTTTTTAAACCTCTGCCTTCCCGGCTCTT

TGCAGGTGGGTGAGGTGGTGAGGAGGCGGGGCTGGGGTGGGGGTGGGGGAGGAGCCAGGAGGGAGGGG

GGGAGGAGCCCAGAACTCTGGGTCCAAGGGAAGAGGGAAAGGAGGCTTAGTTTGCTGAAGCTATGAGA

GTTAGGGGCTGAAAGTGGGTGGGTCTAAAGGCTTGGACCCCACACCCCCACCCCCGGCATCCTCAAAA

GATTGAAAAGGTGCAGTTTGGTGTTCTAGGACCTGGGAGAGCACCATGCTTGAGTCCCCAGAGCACAG

AGCACTGGGTGTCAGAGAAAAAAAAAAAATGGAGACCAAAAAGCAGGGTTGGGACTTCCGAGGATTCA

-continued

```
GGGACAAGTTTGAGGAAACGTGAGAAAGTGCTGGCATCCCTGGACCACTAACTGAGGTGGGACTTCCG

GCTTCCTAATGCGCAAAGGAATAGCACGTACTGAGCAAACTGGAATGCTCCCAGGGCTGAAAGAATGG

AGGAAATTGAAGGTCAAGGCACGGACTCCTGCCTAGGTCCCTGGGAAGGAAAGAACTAGGGACCTAAA

TTTACAGTTCTACCAAACTATGGAAGCTGAGGGCTGCAGGTCCAGGTGAGGAAGTGATGGAGAGGGGG

TCACAGCCCTAGGATCCTTGGGGAAATAGGGGCCAGGAGTGGAGGGCGTGGATGTGGCTTGAGAACAA

AATGATAGACTTGGAGGAGAGGAATTGGGGGCCTAGGTGAGAGCCCCAGCAGAGGGTCTCAGCAGGGA

CGGCATACTGGGAGCTGTCAGTCCCACACATGGGGCGCCGAGGCCCTGAAGAGTCCCCTCCTCCCTTC

CACAGGTAGGCCTGATCCGGGATGAGGTCTCTCTTGCTGGGGGCGCCAGAGCTAATCGTCCCCCAGGC

TGCCTGGTGCTGCAGGGCCCTCTTGTCTGTCTGTCTGCTTCTGAATCTTGGGCTCAGCACCTGCAAGC

TGTTTACTCGCCTTCTCTGGCTGTAATTTCTTTGCCTGGAAGGGTGAGGACTCTCTGGCGCTGTAAGG

GGCTTGCAAAGAGCTCAGTGCCGTGACTCAGCCTGAGTTCAAATCCAGCTGCATGAAGAACAGTACAG

AGTGACCCTGACAAGGGCAGCCTAGGGCCAGCTCAGTCACACCTTTCTCTTTCTTGTGCACTGGCCGT

TACTACAGTATCCCTCGGTTCCTTCATATAGAAAGAGAAATAGTGAGCCGGGCAGTGGTGGCGCACAC

CTTTAATCCCAGCACTTGGGAGGCAAAGGCAGGTGGACCTCTGTGAGTTCAAGACCAGCCTGGTCTAC

AAGAGCTAGTTCCAGGATAGTCTCCAAAGCCACAGAGAAACCCTGTCTCGAAAAACCAAAAAAGAAAA

AAGAAAGAAAGAGAAATAGTGAGACCGGCAGTGGTGGTGCACGTCTTTAGTCCCAGCACTGGGGAGGC

AGAGGCAGCCGGATTTCTGTGAGTTCAAGGATAGACTGGTCTACAGAGTGAGTTCCAAGACAGCCAGA

ACTAAACAGTGAAACCCTGTCTTGGAAAAAAAAAAAAGTGAAATAATGGCCATATTCTGGTGATGGTG

TAGGCCTGTGGTCCCAGCTACTCAGAGACATGAAGCAGGAGAATAAAAATCAAGGCCTGCTTTGACTA

CAAAGTGAGCTTCAAAGGCCAGCCTGGGCAAAGCAACAAGGCCTTGCCTCAAAATGAAAAAATAAAAA

TAAAAGAGGCTGGAGAAATGGCTTAGTGGTTAAGAGTACTGGCCGCTCTTCCAGGGGACCAGGGTTCA

ATTCCCAGCACCCAGACATACAGCAGCTCACAACTCCAGTTTCAGGGAATCCGGTGTTCTCTCTGGTC

TCTGTAGGCACCAGGCACTCAAGTTGTGCAGACATAAAATAACACAGAGGGCTGGGCTGGGGCTCAGT

GGCAGGCATTTGCCCAGAATCCCCCAGTAAAGACATAGCTCAGTGAATCCAGAGCTGAGGGGCTGGGC

GTATATTAATGGTGGAATCCTTGCCTAGAATTCAACCAGCGAAGGGCTGTGGCCGTGGCTCGGCTGTA

GAACCCTGTCCTGGTATCTACCATGAAGGGCTGGGACATGGCTCAGAGATAAAACACTTGCCTAGACT

CTACCGCTGAGAGCCTGGGGTGTGGATCAGTGGACAGTGCCCGCCTAGCATGCACAAGGCCCCTGGGT

TCAATCCCCTGTACCACAAAAAAAAGGGGGGGTGGAGGGAGGGTAAGAGTGAGATCTCAGGAGAAGGA

AGGAACCAAATTCATGGAACTACAAGGGAACTCCAGGAGAATCGAAGCGTTTCTGGCGTACGTTGCTG

TGTAAGCACAAGGGTCGGCTATTTTTGCACCCTGTTCATTATCCTAGCGGGTGATGGGAATAGATCTG

CTGTCTCTAGCCGATTCCTCATGATCCTCACTGATGAAAATGCAGGTGAGGGGCTGGAGAGATTAAGA

ACACTGTCTGCTCTGGCACTGGACCTAGGTTCATTCAGCTCCCCACAGCACATGGTGGCCCACAAATA

TCTGTAACTCCAGCTCTAAGAACCCAGGTCTAGGACACCCTCTCCTGGACTCTGTGGCTACTGCACAC

AGGTGATGCACATACACACACATGCATGCAGGCAACACACACACACACACACACACACACACACACAC

ACACACAATGCATGTGAACGACTGGGGATGAAGCTCGGAAGCTAAGCACTTCCCTGGCATGCACGGGC

CCTGGGTTCAATCCCCAGCACCCCATAATGAATTAAATCGTTATCATGATACGGTGTGTTTACTGCAT

GGTGCCAGGCAAGGAAATGAGCTAACTCCATTCAAGCTGTGACTCCAGTGTCAAGCCTGTATTAACAT

ATTAACCTGGGCCTCTGCTCTGACCCCCTGCTTGGCTCTAACCCCACCTCACACCTTAGAGTCCAGAC

CAGCAGGGCTGGCTACCTCCTAATCTCCTGCTGGTTTCTTTCTCCCCAGTCATCAAGATCCAGACCTG

GAAGCCGCCGAGCTAGAAGAGAGAGCCAGAAAGTGGGTTCTGTGTAACTATGACTTCCAGGCCCGAAA
```

-continued

```
TAGCAGCGAGCTGTCTGTCAAGCACGGAGATGTGTTGGAGGTTAGCGGTGTGGGGGGCCTGAGACCCT

GAAATTGGTCAATTTAGCCCTAGGTATAGAACCGGAGCGTGAATTCTCTCCTTATACGCCACCTAGGT

CCTGGATGACAGGCGCAAGTGGTGGAAGGTTCGGGACCATCAGGGACAGGAGGGTTATGTACCCTATA

ACATCCTGACACCCCACCCTGGACCTCAGGTGCACCGCAGCCAAAGTCCTGCAGGAAACCTAGTAAGT

CGGCGTGTTCTTGCTTCTTCGGGGAGAAAGGGGGGCAAGATCCTAGGTCCTGGGGATGAGGACAGAGA

AAATCAGGTGTGAAGGTTGCTGTTTGGAAAGGGGGGGGGGTGGTCAGATGTTTATTGGGAAAGGAGCT

GGAAGCCTCTCTTCATTCCCTTCCAGGAGACGAGTACTCCTCCTCCCCCACCCGCACCAGCTCCAGCC

CCTGCTCAGGTGCGACCCCACTGGGACAGTTGCGACAGTCTCAACAATTTGGACCCCAGCGAGAAGGG

TGAGTGGTGGAGCGTCACTCTGGGAAGTGATCCTTGTCTTCGCTTTTCAGGCTCCACCCTGGGCACCC

TAGCGGCTCCCAGCCCCCTGACCCCAGAACCCCTGAGCGCGCACTCCCCTCCGCCCCCCCCCCTCACG

GTTTCGCTTCTGCAGAGAAATTCTCCCAGATGCTCAGTGTCAATGAGGAGCTGCAGGCGCGCCTTGCG

CAGGGCCGTTCGGGTCCCAGCCGGGTAGCCCCGGGACCCCGCGCCCCGGAGCCTCAGCTCAGCCCGCG

CTCTGAGGCCTCGGTGGTCCGTGCCTGGCTGCAGACCAAGGGCTTTAGCTCGGGGTGAGTGGGGCTCC

CCCCGGGGCTAGTCTGAAGAGACCTGTGCTTGAACTGAAAGGCGAGGTTCCCATTGGTCCAGGGGTGG

GGGCGTGGAAACTGTGGAGCAGGCCCAAATTGCAACGCCCAATGCCCAGGGACAGGCTCCAAACGGAG

GCCACAGGAAAGGAAGTCCCATCCCCTTTCCGAAGCCCCAAATCTCCAAGAGTTTGAACATCCCCCCC

TCCCCCCAGCTTCCTTGTTTGAGAACTCTGATTGCACAAGCAGCTAGGTAGGTGTGGCGTGATTGGTG

GAGGGCCGAGGGAGCTTGATGAGCTGTGATGGCCCCTGCTGCCTCGCTCAGGACTGTGGACGCGCTCG

GCGTGCTGACCGGAGCACAGCTCTTCTCGCTGCAAAAGGAAGAGTTGCGGGCGGTGTGCCCCGAGGAA

GGGGCGCGGGTGTACAGCCAAGTCACCGTGCAGCGCGCGCTGCTGGAGGTGAGCGAATCCTTGGGGCC

GGACAAGGCGACGGAGGGTAGGGTGGGGATGGGGGACCTGGGGGGAGGGGGTCGTCCAGGGTTCACAT

ACTAAGATCTTGATTTCTACCCCGCTCTGCAGGACAGAGAAAAAGTGTCGGAGCTGGAGCCGTGATGG

AGAAGCAAAAGAAAAAAGTGGAAGGCGAGACCAAAACAGAAGTTATTTGATCCTTCCTGACTCGGTCA

CAAAACGTGATGGCATGGCGGGGCTCCCAGCGCCCCCTAGGACAACAGTCGCCAGACTCCTCCCCGTG

ACCGGGGACAGTAGATGTCCCGAAGGATCGCCCACCCTCATCTCCCGGCTCACTCGCTCGCTCGCTCT

CCTGGCGGGCAGGCTGCGCTGACAGTGCCGGCTGGAATCCTTCCGGGGGACCTCAGACTGACGGGGAC

GGGGACGGGGACGGGGACGGGGACGGAGCATACAGACACTACCAGAGAGGCACGCCCAAGAGGCGCAC

GGAGGGAGGGCCCTGGGCGTCGTGACGTGCTATAAACAGCCTCCTTTCTAGACCATGCGTGTCACCTG

CTGTCCCCTTCTCTCGCCGGCTACCCAGGAGCCAGGAATCTGAGAGATGCCCCACGCTTCCTCCCCAT

AAACCTGGAGAGTCCAGCCCAGGCTTCCTAATCACCAGTCTATCCTCGCACTGGCCCCATCTACATCC

CTTCTCCTGTTCAAAACCCTCGCCTGGCTGGCTCCTCGTTGTTCTCAGTCCTGTCTCCTGGTGTTTAA

GGCCTGGGCTTTTCTCATTGTCTCCGCCCACCCTGCATTTCGGCCCAGCCGCTCCAGACCACAAGCGG

TTTGCACTTAACGCTTCTGAGGGTTGGAGCGGCCCCCATCACCCTGGCTCGGCTCTCCTAGCCACACC

GTGGACACCCGTGTCCAGCCTCTAAGGACCGGCCATGCAGATCTGGACGCTCCCGGGGCATGCCACGG

GCTCTTGGTTCTTCCTGGCCCCTCAACAACTTTCTCCCTGCCAAGCCCTGCAACTTGTCCAGGTTATG

CAGGTGGATGGTAAGAGCCGGTTTTCTCATCCGCGCTAGGTTTATCTAAGGCCTTTCTTTTCCCTGCA

TCCTTGGAACACTCCCAAGAGTCCCACCGTTGCAGTCGGCCTCTGCTCCCCGCGCAGCTCAGTCCTTA

CCTGGGCCACCAGGTGGCGCACCTCGAATCTGACCCAGGAGGGCCAGCCTTGGGCTGACTTCACTAAG

CCCCCTTTCCTTCTGGAACACTGTAGCGTTCCAGTAAGCCTTTAGTGTCCATTCCCTTGGTTTCTCCT

GGTACATGAGATAAAACCTAACTCCAGCATGACAGCCGATGGCCTGTGACCCCTATGGGCTCAGGTCG

CCCTTCCTCTCTGTTCGGGACTCCAGGCACTGGTCCATGCTGTTGGTTCTGTTGGGATGTCTTGGCTC
```

-continued

```
CATGGTGTCTTATCACTGCCTGGGGCGTCATTTCTTATGTCGCGCTTGGTTGGTTTGTTGGAGGCCGT

CTGGGTACAGCCCCAAACTCTCGGTCCTCCAGTTTCAGTTTCCTGCATGTGGGGATATTGGCAGGCGC

CCTGCTGCCACCCTCTTTTCTAATCGAGAAACCAAAAGTACAAGCAGTTGCCCAAGCTGTTTTGATTC

CGGCAGTGAGGTCCCAGACTACAGACTGAAATGCCAGCAGGAGCCATCTGGCTTGCTGGGACATCAGG

TGATCAGGTGCCTGTGGCTGGCTCTCTGTGGTTTGGAGTCTGACCTTTTCATCCTGACTTGACCCTCT

GTCGATCACTTTGTCCATCCATCACTCCCCAAGTCTACATCCAGCCAGGGGCACCTGTCAGAGCTCAA

GCCGGATGGTAACCTGGTGGTCAGGCCTCCCAGCTCAGGTGGAGCTCAAGTTCTTAACAGAGCCATGA

TCACACACAAAGCCATCACCTCAGCGCCACAGCACGCCAGGCCTGCTCTACCCCACGCTGCACACGGT

TCTCATCATCATGCAAAAGGTGCTTCCTTCAGATACAGGGCTCACCGTCACCTTCTAGCATCTGTCTG

TGCAGCTTGTCATGGGGCCTACTTTTGACTGTCATAAACACCACACACGCACATATATATACACACCA

GATACACACACCACACACATGCCCAATACACTGTGCATGCGCACACACAAACACACACATACCT

CATACACCATACACCCTATAACCCACACCAGCCATACCACACACCACATATACACAGTTCACCTCAGA

CAGCATGGCACACCACACACACACACACACACACACACGCGCGCGCGCACACACACACACAC

ACACACACACTCCGCACTCTCCCCTTCTCCACAGCACTGTAGCTGAAATCCACACAGTGGCAACCT

TCCTCAGTGTACTGGCTGCTGGACCAAGCTGTTCACTCCTGTGACGCCAGCTGGCAGAACAGCCCATT

CCTGACTGTCAGGATGGAGGAGGCACCACGCGATCCATCTCAAGACTGATTCCTGGCTCTGCCCCAGT

CACTGTGGCCACGAAGGACTACTTACCATCACCTACTCCTTTCCCAGAAAACCTAGACTTGCGGTTTC

CTATGTTGGCCATCCTACCTTTTCAATGTTAAGCCACTGACTCCGCTCACTTCCAAAGCACTGAGGGT

CAATGTGAGCACCCGGATCAGGTCACAGGCTTCCTTCTGACCCCCCCCTACCTCACCTGGGGCTCTTTC

TCTCCAGCTGCTCACTCGAGCAAGCTCCCCTCCCCACACCTGTGAGCAAGCTCCCAGCCACCCACTGG

CCCTCATCCAAATGGATGAGCGGTTTCAGTCAGATACACAGGCTGAGTATACAAGCAGGAACCAGTGC

CCCACACCCAGGGGGAGACAAGTCACTGAGTGGCAATGTCACGACTTTATTTGTGGTGCCTGTGCTTT

GTCTCAAAAATACCTTCTCCCCCTCCCCAGACAATGGGTGGGAAGGAGGCAGCAAAAATAGAAGACAA

CCCTCCCTATTGCACACGGACCCTATATACAGGCCCACCTGGCAGAGGCCAGTGGGGCTCTTGGCACA

TTCCTGGATCCCTGCTGGGGAGGGAAGGGATACTGGGTAGCATCACACGTGAGGTGGGCCCGGGGCAG

CCACTCTGCTCCTGGATACTGATCCTGGCTTCCTTGGTCCTTGCTTCCTTCCTGGTCCCATCTCTGGT

GCCTGCCCACTCTCGGCAACATTTCCCTACCTGGCTCAGCCTCCCACCTCCACCCTGGTTCTGGGGAC

TCTGTGCTTTCCTCCGGGTTCTGAGGTCCCGAGAGGAGGTTATGGCTTCTCAACAACTTCCCCCGGAG

CCCTGTCACTCATGTTCACTCGGGGGAAGGGGTGCGTGTGTCAAAAGCAGCTGTATAAATACGGTGCG

GGAGCCCCTCCAGAGTCACTTGGAGAGCTTGCTAATGACGCGGATCAGTGCTGCATTCTCATCCTTGA

GCCGCTGGTTGTCAGCGCGGAGGTCGGACAGGGCCTAGGGGGCAGGGTGGAGTCAGCTGGGCAGGGCG

GGGCAGGGTGGGCTCTGGCCACCGCCCTTCACAAGCTCGTTACCTTCAGCTCCTCCTCCAGCTCTGCG

GCCTTGCGCTCCAGGGCCCTGCGCTCCTGCAGGAATGGGCTGGGCTCAGAAGCAGGGTAAGGGCAGGG

GACAGGGCAAGGGCGGGACACCACCCCAGCGGCCCAAACTCACGAATCTCTCCAGCTCCAGGAGGGCG

GGCCTCTCGGCAAAGCGTTCCTGCCGCTGGTAAGGGCAGAGAAGACTGGGCGTCAGGAGCTGCTTCTT

ACCCCTAGGACATCAGAGCCCTGCCCCCCCCCCCCCGAGTGGGGGACCTCCAACCTCCCAGCCACGGCC

AGGCCCCTTGCCACTGGGGCTCTGACTCCCACTGCCCCAACAGCTGGTTCTTAGGTCTCAGTATCTGC

ACCTGCGTGGCCCGCTCAAGCTCCACCTTGAGCTGTGCCAGCCGCAGGGTGGTCTCTGTCAGGGCCTC

ACGAAGCCGCTCGTTCTCCCTCCGAAGCTCCATGTACAGCTAGGGACACAGAGGAAGCAGGCAGGCTC

AGAAGGGCCCGGGAAGGGGCCAGGACAGGGTGGGGTGGGGCAGGAGGTAGCATGCGGCACCTTCCGGA
```

-continued

```
AGCTTCCATCGGGTTCTTCCTGTTCCTGCTTGGATTCTGGATTGAGGTCTCTCTGCAAACGCTGTCTA

CGGGCAGTGGAGCCGCCATCCACGGTGCTGGACAGAAATTCAGGCCTTAGGGCCCAGGCCCTGCCCGA

GGGGTGCCCCAGCCCCCACGCATGACCCGGCCTACCTGCACTCCAGGCTCCGTTCTGCCGGCCCCGCC

TCCTCCCCCTGCAGAAGAGCCCTGAGAGTTCAGTCTCCATGCAACGTCCTCCCTCCAGCCCGCCCGGC

CTCCACACAGCATCCTCACCTCCGCGGCCCCTCCCTCCAGCCCGCCCGGCCTCCACACAGCATCCTCA

CCTCCGCGGGCCCCTCCCTCCAGCCCGCCCGGCCTCCACACAGCATCCTCACCTCCGCGGCCCCTCCC

TCCAGCCCGCCCGGCCTCCACACAGCATCCTCACCTCCGCGGCCCCTCCCTCCAGCCCGCCCGGCCTC

CACACAGCATCCTCACCTCCGCGGCCCCCTCCCTCCAGCCCGCCCGGCCTCCACACAGCATCCTCACC

CTCCGCTGCCCCTCCCTCCAGCCCGCCCCCCGCCTCCACACAGCATCCTCACCTCCGCGGCCCTCCCTC

CAGCCCGCCCGGCCTCCACACAGCATCCTCACCTCCGCGGGCCCTCCCTCCAGCCCGCCCGGCCTCCA

CACAGCAGCATCCTCACCTCCGCGGGCCCTCCCTCCAGCCCGCCCGGCCTCCACACAGCATCCTCACC

TCCGCGGCCCCTCCCTCCAGCCCGCCCGGCCTCCACACAGCATCCTCACCTCCGCGGCCCCTCCCTCC

AGCCCGCCCCGCCTCCACACAGCATCCTCACCTCCGCGGCCCCTCCCTCCAGCCCGCCCGGCCTCCA

CACAGCATCCTCACCTCCGCGGCCCCTCCCTCCAGCCCGCCCCGCCTCCACACAGCATCCTGACCTCC

GCGGCCCTCCCTCCAGCCCGCCCGGCCTCCACACAGCATCCTCACCTCCGCGGGCCCTCCCTCCAGCC

CCCCCCCCCCGCCTCCACACAGCAGCATCCTCACCTCCGCGGCCCCTCCCTCCAGCCCGCCCCCGGC

CTCCACACAGCAGCATCCTCACCTCCGCGGCCCCCTCCCTCCAGCTCCGCCCGGCCTCCACACAGCAT

CCTCACCTCCTCGGCCCCTCCCTCCAGCCGCCCCCCCCCCGCCTCCACACAGCATCCTCACCTCCGCG

GCCCTCCCTCCAGCCCGCCCGGCCTCCACACAGCAGCATCCTCACCTCCGCGGGCCTCCCTCCAGCCC

GCCCGGCCTCCACACAGCATCCTCACCTCCGCGGCCCCTCCCTCCAGCCCGCCCCGGCCCTCCACACA

GCATCCTCACCTCCGCGGCCCCTCCCTCCCCGCCCGGCCTCCACACAGCATCCTCACCTCCGCGGGCC

CTCCCTCCAGCCCGCCCGGCCTCCACACAGCATCCTCACCTCCGCGGCCCCTCCCTCCAGCCCGGCCC

CCCCCCCCCCACCCCCCGCCTCCACACAGCATCCTCACCTCCGCGGGCCCTCCCTCCAGCCCGCCCGC

CTCCACACAGCATCCTCACCTCCGCGGGCCCTCCCTCCAGCCCGCCCCGCCTCCACACAGCAGCATCT

CACCTCCGCGGCCCCTCCCTCCAGCCCGCCCCGGCCTCCACACAGCAGCATCCTCACCTCCGCGGCCC

CTCCCTCCAGCCCGCCCCGCCTCCACACAGCAGCATCCTCACCTCTGCGGCCCCTCCCTCCAGCCCGC

CCGGCCTCCACACAGCATCCTCACCTCCGCGGCCCCTCCCTCCAGCCCGCCCCGGCCTCCACACAGCA

TCCTCACCTCTGCGGCCCCTCCCTCCAGCCCGCCCGGCCTCCACACAGCATCCTCACCTCCGCGGGCC

CCCTTCGCTCGTGGCCGACCTTTCGATGCTCCCTGGCCGCCTGTGGTCCCTGGCCCTGCCCGTCGGGC

GCCTCTGCTGGGGAACCAGTGGGAATCAGCTCAGACACCACCATAGGGGCCCCTGTCTACTGTGCAGG

GAACCTGACTTAGCCCCCAGTGAACAAAGACACTTTATGGGGAGACAGGATGGCTCCCTGGGGAGCGA

CTTCCCAGAAAGCCGACCTCACCTCTCTGGGCAGGGCCCTCAGCGTTCTCCACGCCAGGGACCCGAGG

TCTCCGAGAAGGGTCCTGCCGGGGAGGAGCACAGTCAGAAACAGGGAGACGGGTCCACCCGCCCCAGT

TCACCTGACCCTGCTCACCAGGCTGGGCAGGGCAGGCTGCTCTGGCTCTGGAGCCTTCCCTGCCACCT

TCTCTGCTTCCTTCAAGTCTGTCAAGGTCACGCCCTAGTGTAGAGAACTCGGTCAAGGAAAAAGGGCC

TAGACTTCCACAGGACTCAAGTTCAAGACCCCGGCCCTCCTCCCTCAGACCCGGGAGCACAGCCCCAG

CCCCATCCCACACCTGTGTAGACCTCCGAGACTGGCGCATAAGGCGGGAGCGAGCCTTCCGCTGAGAC

TCGGACTCTTCATCACGCACAGGCATCTGGTAGGACCTGAGTGGAGAATGTCCCCTTGGGTGCTGTCG

CACTGTGAATGACACCTTAGGGGAGTGCACATTCTGGCAGAGAACGTGTCAACTGGGCAAACAGGACC

CCAGGAGCCTACCCAGAGCCCCAGAGACCCCTAAACACTGTCTTCCCCTAGCCTCTTTACCTCCGCCG

ATCCCTGGAGTCAGGTAGGGCTGCTGCAGAGGCTGCGAGGGCATTTGGCTTCACTGGGGATCCAGGCT
```

-continued

```
CCCTCCTGGAGGATGGGGCGGAGTGATCCGAAGAAGGAGGCATGGCAGCCTCACACCTGTATGGATTC

ATTCATTCATCAGCAAATATTCCTCAAGCCCGCATTCTGTGTCAGGCATAGGAGAGACCACAGAGAAG

GAGCCAATCATGGCTGCTGATGAGCCATTTCTGGGCAAAACAGATAAAACAAACAGCAGCCAAAGAGA

CCAGTGTGGAGCTTGGGGAGAAAAGGTGCTTGGAAAAAATAAAGAGAATAAGCAATTATTTGATGCAC

CCTAAGGGCTTTCTCAGATCTCAAATGCCAGGATGGCACCAGACCTGTCCCCTTGCCCCAGCCACTGG

TACTTACAGGGTAGAGGGCTCTGGCACTTTCTGGGCAGGGGTAGGGGTTATTCTGGCAAGACGGGGTT

CCCTGGCCTGTGGAGACAGGAGAGAAGCAAAGGAGGCACTGTCTGCCCCAAGGCAGGAGCCTGTACCC

CACACACTTCACGGCACCTACCTGAGAGGAGGCCTTTTCTAGGAGGGAGGAGGAGGCTGAGCGCTGCA

GACCGAGAACCCCCTCTGCACCCCTCCTCTCTGAGGGACCCAGGGCACCAGAGCTTCCTGTCTTCTGG

AGACCGCCGCGCCTGGAGAAGGGAGCCTCTTCTGGCGGCTGGGAGAGGAAGAAGGTCTTCATTACTGA

GCAAAGCAATGACCCTTCTCCTCAGAGCCTACGCGTGTAACTCCAGGGGAATTACAGTAAACCACAGC

CAAAGCAATGACCCTCCTCCTCAGAGCCTACGCGTGTAACTCCAGGAGAATCACAGTAAACCACAGCC

AAAGCAATGGCCCTTCTCCTCAGAGCCTACGCGTGTAGCTCCAGGGGAATCACAGTAAACCACAGCCA

AAGCAATGACCCTTCTCCTCAGAGCCTACGCGTGTAGCTCCAGGGGAATCACAGTAAACCACAGCCAA

AGCAATGGCCCTTCTCCTCAGAGCCTACGCGTGTAGCTCCAGGGGAATTACAGTAAACCACAGCCAAA

GCAATGACCCTTCTCCTCAGAGCCTACGCGTGTAACTCCAGGAGAATCACAGTAAACCACAGCCAAAG

CAATGGCCCTTCTCCTCAGAGCCTACGCGTGTAACTCCAGGAGAATCACAGTAAACCACAGCCAAAGC

AATGGCCCTTCTCCTCAGAGCCTACGCGTGTAACTCCAGGAGAATCACAGTAAACCACAGCCAAAGCA

ATGGCCCTTCTCCTCAGAGCCTACGCGTGTAGCTCCAGGGGAATTACAGTAAACCACAGCCAAAGCAA

TGACCCTTCTCCTCAGAGCCTACGCGTGTAACTCCAGGAGAATCACAGTAAACCACAGCCAAAGCAAT

GACCCTTCTCTTCAGAGCCTAAGAGTGTAACTCCAGGAGAATCACAGTAAACCACAGCCCAGGCAGGT

GCCACCAAAAAAAAAAAAAAAAAAAACATTACTTCTTGGTCCACAAGGACCTAAGAACCAAGTCAAAA

AGCCACTTTCCTCAGCGGAAGCAGAAGTATTTACCGTATCCCACCCGCTGCCCCAAACCTCACATCTG

CTCAGGGCGCTCAGGCTCACCACAGGGCTCTTGGGGCTGGAGGACACAGGAGAAGACACGCCATTGAG

GGCTCTTGGTTGCACAGGAGGGTGATCTGTGTGCAGGAACAGGAGAGGGGGGTCACAGGAGAGGCCGG

CCGCCTCTGAGATTGGGGACCCACAAGTCCAGCTCCTTCCTCAGACCCAGGGTCCAGCATCCCTACCA

GCTGCCTCTTCTTCTCCCTCATCCTCATCCCCAAGAGAGGGGCCCGCGGCCCCACCAGGCCGGCGCTC

CTTCGACAGATCCTGCAGGGAGATCTTCTCACGGCTGCTCAAACGACACACGGAGCTCCTAGGAGGAC

AGGGTGTCCGTGTCCAAGTCTGGGGGCGAGTCCGACCCACCCCAGGCCTAGGCATCTCTTACCTTCTG

TGCTTGCTGTTGGAGGGCACCTGTGGCTCTTGGCCTCGGCTCTGAGAGGCTTCCTTTTGGTTCCGAAG

CTACAAGGATGGAAGGGGGCAACTGGGGAGGGGCAGAGAGCACAAGCCCTCCAGGGTCTCCTGGCCGC

CCCCTCTGTGCCACCTCTCCACCTCGAGGGCCATCACGCATAACTGGGCTAGTCACACTTTATGCAGG

GTCCTGCAAACATGGGGGACTCAGTAACCCGGCAGCACACTGGCTCTGGGGCTTATTCAGGCTCTCCC

AGGCTTGGCCTGGTCCAGCTGTCACTGCCTCCAGCCTCATTCCCAGGGGGATTCGTCTTCTTCCCAGG

AGCGAGCACCTTGCTCAGACTTCCCCCTACCCTCCAGCACATCCAGGGCAGGACAGGGCAGGTGGCTC

TTTCTGGTTATCACAGGCCAGCTCTCAGCTCAAGGACAACGGCCACCGTCCCATACTAAGCAGTCTGG

TGTCGTAACCCCAGGAACACCTCTTGCCCATGCCCTCCTTGCATCCCAGTGTGCCACGGGACTCCTCT

CTGGACAATGTTCCCGATGGTTCCACGAGGCCCGGGCCACCTCACTAAATAATGGAATTGCAGCCATG

CCGTCTGCTTGGGGCCACACCCATGATGCCTCACTCTCCACTTTCCTAGCAAAAGTGCTAACTAGAGT

GGGGGGGGGGGTAGATACAGGTTCAACCTGTGTCACACACAGCTGTCTTCCCAAGCGAGCAGGCAGGAA
```

-continued

```
ACTCTGGGCATAGCCTCAAGTCCTCCAGATATGGAGGTGCCTCTGTTCTTAGCCCTCCACCAGAGCTG

GGCTGACAGGTGGGAATAGCGGGTCTCAGTACTGAGGGTGTCAAGGGACAAAGACTGTCAGCCCTCCC

GGTTACTGTTACCTCCTCAGAGCTGCCAAGTAAAGAGGCAAACTAGAGTCGAGACTCACGTCCTCCTG

TTTCTGGGCCAGTTCCTCCAAAAGGTTCATCACTTCCTCATCAGCCAGGTCACAGGGCCGCTGCCCCT

GAGTAGGAGAAGGAGGCAGATGACGGTGATGGTGGTGGTGTAGTAGGGGCTCCCCGCCACCCTGCCC

CACCATCTGAGATGGCCCTTACCGCATGGGTCAGCGAATCCATGCCCCCACCGTGCTCAGCCAGGAGA

CGGCAGGCGTCCTCCACACCCCAGTGGGCTGCTGCGTGCAACGGTGTCCAGCCATCTCCATCCCGGAG

CTCTGTGTCGTAGCCAGCTTGGAGTAGCAGCCTAAGGGCCAGGGAGGCTTGGGTCAGATGGCAAGCTA

GGCCAATGGCTGATCTCAACTTCTGTTCTGTGGCCACAGGACTACTGATCAATACCCAAGCGTTACTA

GTTTTACCAGCAACCAGCCCCACCCCAAGCTCAACTGAGCCCTCCCTTGGACCAGCAGCTACTAATGA

AAAAGCTCCCTCATACCACAGGGATCCCACTCCTCAGGCCCCAGGGTAAAGGGTTAGGGCAGTGGTGA

GGCGATGAGGTGGATGCAGGACTCCCCACTAACGCAAGCCCATGGAGAGGATGGACCCTGAAGGGGCT

GTGATGCTGGAACCACTGGAACCACGCGGTTTTAGGACACGGATCCTCAACAGTGTCAAGCAGCTCTC

ACACCCTCTCTACAACTGGAGACATCACCACTAGAATCCTAACTTACGGGTACAAGCAGGAAGCACCA

GTGTGTGGGAGCTGGAGAGGCTGCTCAACCCCCTCCCACGCACAGGACAGCCCTACCACAGCACGGTA

AGACCCCAAACATCACAGTGCCGGAGGAGAGCGAGCCTGGCTCAGCCTTCCAGAAGGTAACAACCTGG

AGCTCTCAAAACTCAGCATGGCACGAGGCGAGGCCTCTTTTGGAAGCAGTGTGATGAGGTCCTGTGTC

AGTGAGGAAGGCTTCAAGCCCAGGGAGGCAGAGGTACAAGGCACAAGGTGCTGTGTGGCCCTGGGACC

CTCCTCCCTCACACTTCCCAAGATTCCCCTGTCCCCTTGCAGCAGGGCACGCTGGGCTTCTTGTTACA

TTCCCACATGCCAGGGTCTCTAGCCAGCTGTGCGCTCCTTCTGGTCAGTATCCTAGGAGCCTGAAGCG

TGCCACCCAGCCACACCCCCTAGTCCATCAGCACTTCCTCACCTGGCAGTTTCTTCACCACCATCTCT

GCCAGGGGGCCTCCCTACTGCCCACTAGTTATAGCCTCCCAAGGCCAAGGTTTTCTTTGTATAAGCTT

AGTGTTATTTACCATTAGTGTGTGTGTCTGTGTGTGTGTGTGTGTGTGTGTGTGTGTGTGTGTGTCTG

TGTGTGTGTGTGTGTCTGTGTGTGTCTGTGTGTGTCTATGTGTGTGTGTGTCTGTGTGTGTCTGTGTG

TGTGTGTGTCTGTGTGTGTGTGTGTGTCTATGTGTGTGTGTGTCTGCGTGTCTGTGTTTGTGTGTG

TGTGTGTCTGTGTCTGTGTGTTGTGCATAAATGCCAACACACATGCCCCAGTATGAAGATCATGGA

TGAAGATCAGAGGACATATTCAGGATTCACTTTCTCCTTCCACCACCGGTTCCAGGACCTAACACAAG

TCACCAGGCTCTTGTGTGGCCAACACTTTTACCTCTGAGCTATCTCACTGGTCTAGAAGCCAACGTTT

GCAGCTGGACCCTGCTACTCCCCAGAGGACCTGTGGCAATGTCTACAGTCATCACACAACTGGGTCAG

AGGTGCTGCAATGGACTGGACAGCCATCAGAATAGAATGACCCAGCCCATCAAGTCTCTCATTGGCTA

CGGTGGGTACACATCTGAAACACCACGACCAGCCCAGGAGGCTAGCCCCTAACAGACACCAATATTTA

CCTGTACTTCAATGAGTACAATCATAGAAGACTTTTAATACAGTCAGAAACAATAGATAACTATAAAT

TCAGTGAACAGGAGTCTAAACGCAAACTCACACAAAGGGGGCCATCACAAAATTACAAAATTCAGTAT

GATGGCTCACACCTGCAATCCCAGAACACAGAAGCTGAGGCAGGAGGACAGCTGTGAGTGCAAGGCCA

ACCTAGGCTATCTATCCAGTACCAGGCTAGTCAGGACTACATAGCAAGACCTTGTCTCCATTAGAAAA

GAAAGAAGCCAGAGGGGAGGGAGGCAAGCATGGTGGCTCTCACCTCTATCCCACAGGAAGGTGAAGGA

ACAAAGAGTAGAAATTCAAGACCAGTGAACTAGAGGCGATCATGACCGACATGAGCTATTTATGGAAG

AGGCCAAATAAACAAACACAAAAGTTGTCATCAGTGCATTTTTTTTTTCAGGGCTGGGACTGGAACCC

AGAACGCTAGGCAAGTGCTCTATCCCTGAGGCACCCCCCCCTTCCCTCACGGGTAGACACCAGGGAAG

CATCTATCTACCTATGGCCTGCGACCACAGCCCAGTGCTTCAGTTCTGGGACAAGTATTGGCTCACTT

TCTCTACTAACTAGCCCCCCGGACCTATGCAGGTGACACCGGGGAAAGCATTTAAGCACAAAGACAGG
```

-continued

```
AAGGAGTTCTGATCACCAGAATCCACTTAAAAACTCAGTGGATAGCTGTTATAAAAAAATGACATCAG

GGTGGAGAGAGATAGATGGCTCTGCTCTTCCAGAGACCCGGGTTCAATTCCCAGCACCCACACGGCAG

CTCCAGGGGTTCTGACCCCTCACACTGACATAACACAGACAGGCAAAGCACTAATTAATGCACATTAA

AAAAAATAACATCATGAAATCTGCAGGCAAATGGATGGAACTGGAAAAAAAAAAAAAAAAAAAAAAACA

TCCTGGGTGAGGTAACCCAGCCCCAGAAAGACAAACATGGTGTGTACTCATTTACAAGTGCACATTAG

CTGTTCAGTGAAGGACAATCGTGCTACAATCCACAGACCCAGAGAGGCTAGGTAACAAGGAGGGCTCC

GGGGAGGGACGGTGCACGGATGCCCCAGGGAAAGGGAAAGAGAAAAGACTTTGCAGATGGAATGGGCA

GGTAGGGATGGAAACAGGAGAGGTGGGGAGAGGGAGTGGAGGGGAAATACTGGGGGGGGTGGCTGCAA

TGGGGGCTCACTTTGGGGGTGTTAAGGAAACCCAGCACAGTGGGAACTCCTGGACTCTGCAAGGGTGG

ACCTAGCCAAGTAACGAGGGACACAGAGTCTGAACCGGCTACTTTGGGTAACAGGCAAGGCTCCCAGC

AGTGGGACATCAACCCGGCCACAAAACTTTTGACCTACGATGTGCCCTGCCTGCAAGGTGTGCTGAGG

TAATGGTGGCGCAGAGCTTGTGGGAGTGGCCAACCAATGACAGGTCCAGCTTGAGGTCCATGCCACAA

GAGGGAGCCCACGCCTGACACAGCCTTGATGGCCAGGAGCCTGGATAGCCCGAGACCTGGGGTAGAAC

CAAATACAATTGGGGGAAAAGAAAAAAAGGCAAGAAACAATTCTTAATGATATTCTGCTGTTCTCATG

GATCTGTGGCTAGCCCAACTGTCGTCAGAGAGCTTTTTCCAGCAGTTGACGGGAGCAGATGCAGAGAC

CCACAGCTCAGGGAACCCCACAGGAAGGATTATGGGGGGGGGGGGCGCGAGGACACCAGGAGAACAAA

GCCCACAGAATCAACTAAGCAGGGCTCCTTGGGGCTCATGGAGACTGAAGGAGCTAGCCATCAGGACC

TGTATGGGTCTGCGCTGGGTCCTCGCCTGGTGCTCTTGCGGGACTCCTTAACACTGGGACTGGAGCTG

TCGCTGACTCTTGTGCCTGTTTGGGGACCCAGACAAGCATAACTGGTTACGCTGTGCTTGGCTGTCAT

CTCTGAGATGCCTGTTCTTTTCTGAAGGGAAACAGAGGACTGGATCTGGAGGAGGGGTGGAGGGGAAC

AGGGCAGAGGGGAGGGAGGAATGTAATATGAGAGGAAAAAACAACAACTACAATTATTGAGTGGACAT

GGCAGCCCATCTGCAGAGACAGGCCACCCTCAGACGGAGATGGCAGCTAAACTTGCCAAAAAGGCAAG

CTGAGGGATCGGCCAGAGGCCCTGCCTCAATATTAGAGTGGAGAGCAACCAGAGAAAGTACTACATGC

CAACACACACACGAGTGTGAACACACACACACACACAAGTCATACCCATACACATGCACACGCGCGCG

CGCACACACACACACACCACAACCTTTAACCAGACATATAGTTGTGTGGAAACAAACCTAGTTTTC

CTTGCAACTAGGACTGGCCAATGGTGAGAACTGGGTTAATGGAACACAGATATTAAATATGCACACTT

CTGGAATGTTCTCCTGAAAAGGAATAGACATTCGCTCCCTTTGCCTCTGCTTCCCACCAACTTGAGAT

ATAGACGCAAAGGCAGGTGAGGCAAGTCACCCTCAAGTGAGAGGCACCGCTAGAGCAGGGCGCAAGCT

CTGCACTCGGAGATTTAGGGCATCCTGTCCCCCAAAAGGAATGGGCTCAGAGCGCACTGGGACTCATG

CTGTAACTACAGAGACTGATGCCCCTCCCCCAGGAGCACAACTATGCAGGCAGGCTGTAAGTCTGGGG

GTGGCACGAGGTCTTAAATCCTGCTGGAGAAAACCTGCCTGCAACCTTACCAGTATGAAAAGCAGAGA

GGTTCATCTTAATTCAATTTGGGTCTTTGTTTTTTTGTTGTTTTTTTTTACAACAGGATCCCTCTATA

AAGCACTAGCCTCACACTCAGTATATAGACAAATCTATCCTGGAATTCCAGTAATCCTCCTGCCTCTG

ATTCTCAAGTGTAATTATAGACATATAACACCGTATCAAGCAAGCAAGTGCACACACGCACGCACACG

CTCTTGTTACATAGCCTGGGCTAGCCTACAACTCACAGCAATCCTGCCTCGACCTCCCAAGTGAGGAA

ATTAAAAGCGTATACCACCATGCCTGGCTTAATGCCATTTTTTTAGGTTGGTATTATTTTTATGCGTA

TATGTTTTGCCTACATGTATGTATGCATACAAATACACACAGACACAGAGATAAATAAATGTAATTTT

TAAACCTCTTTGGCTTTAGGTATGTAAACCAGGAGAAGAAAAGGACAAGAGCCCCGAAAAGCTTCCAG

ACACAAAACAATCACTCTGGCCTCGCTCACCTCATCACCTCGATGTAGCCCTTGGCGGCAGCCACATG

CAGGGCAGAGGCCCCGGTCCGGGGGTGGCGGGCCTCTGGCATGGCACCCCCATTCAGCCAGCACCTTG
```

-continued

```
TGTCATGAAGCAGCAGTTCTTCTTCAGCCCGCTTGGCTGCCTCGACATCCACACCTGGGAGAATGAGA

GGTGACAGGTGGACTCACACAGGGTGGCCTAGGAAACCCCGGCTGCGGTCTCAACTAGTCACAGCCCG

GCCCCGTGACTCATCAAGTCTCTGGACCACTCAGGAGACCGGGACTGCCCCAGTGTTTCCCAACTGTG

CTCCCTGAAGACCTGGGCACCACCGAGGGGGCCAAGACAGGCCAGGAATGGAAACCACAGGTCCTGAC

CCCTGTGGGTCAGTATCCTCTTTATGTTTTTCTAATAGAAAACCCCACACCGGATTCCATCTAGGTTT

TCCTACCCCTCCAGCTATAAGCTAAAGCCAGCGCCTTCACACAATGTCACTGCTGGTTCTTCTCCCTT

TGAAGTACGATAGGCCAAACAAAACTTCACTACGGCGTTGTACGTGGTGGCTCCGGCCTCTATTCCAG

ATCTCAGCCTTGGCAGGATGACCGGTGGCCTCGAATCTGAGAACAGCCTGAGCTACATACATGGTGTC

AAGCCAACCAGGACTAGAGAGACAGACTCTGTCTTAGACAACAGTAAAAACTAAAACTCAAAAGCTTC

TGGGCGGTGGTGCACACCATTAATCCCAGCACTCGGGAGGCAGAGGCAGGCGGATCTCTGTGAGTTCG

AGACCAGCCTGGTCTCCAGAGTGAGTGCCAGGATAGGCTCCAAAGCTACACAGAGAAACCCTGTCTCG

AGAAAAAAAAAAAAAAAAAAAAAAAAAGCTATTTCCCAAACTATTTGCATGCATAGTTTCATTCTTGCC

CAGATGTCCAGGCATTTGACACCTCGCTGGCCCACGACAGAAGTGAGAAGTGAGTGACTGCCTTGGCA

CTTTGTGCTTATGCGGGTATGCTGCATGCCTGTGACCCCAACACAGGCAAGAGGCAAGAGACCAGCAG

GGCTCCACAGAGACCCTGAGTCAAAAGACAAACAGAGGGGGAGGGGCTGGAGAGATGGTTTAGAGGAT

GAAGTGCCAAGCCCGATGACCCAAGTTCAATCCTGGGAACTCATGAGGCAAAGGAAAGAATCAAGTTG

CACAAGGGGTTTCCCTTTGTGAACCCAGCTTGGCCTCAAACTCACAGCAATCCTCAGTCTCTGGAAAG

CTGAGATTAAGAGGGGGTTTTTTTGTTGTTTATTTGTTTTTTTTGGTTTTGGTTTTACGAGACAGGGT

TTCTCTGTGTATCTTTGGAGCCTATCCTGGCACTCGCTCTGGAGACCAGGCTGGTCTCCAACTCACAG

AGATCCACCTGCCTCTGCCTCCCGAGTGCTGGGATTAAAGGCGTGCACCACCAACACCTGGCTAAGAT

TAAGAGTTACACACCACACCTGTACTCCCTGCACTCAAAGAGGCTGAGGCAGGAGGATTGCTCCAAGT

CCAAGGTCAGCCTGGGCGCCAGCATGAGAGCCTGTCTCAAACACCTCAGGGGGGAAACAGAAAGCCAG

GCAGACTAGCTGAGGCTGAAGCACTCCAGCCCTCACTGTGACCCTCATCCCTTAAAGCACCCCTAACT

CACTGAGACCACAGCAAAATGGCCTCTGCTGAATAACTTCCTCCTGGGAAGGTTATTACTGCCCATGC

TTTTGCAGTTGTGAAACTCTTGACTTGCCGAAGTTCCTCAGAGTTGAGCTGTTGTATCCAGTAGCCGG

CAGCTATGTGGAACTGCCGAGCGAGCACTCGAAACTGAGACATGCTGTGAACGTCAAGTGCACTCGGG

ATTTCAAAACACAGGAAAAGGTAAGGGCTCTCGTGGACAGTTGTCTCTAAACTGTTTTGTGCACACGT

GCATGGCAGCGTGGTCAGGGGGCAATTCTGAGGAGCCGAGTCCTGCTTCCCACCTTGCTGAGGCTGGG

TCTCTGGATTCTGCGGCTGTGCTGTGTACTCTAGGCTACCCGGCCCACAGGGCGTCCCCACAGTTCTC

CCACCTTCCTCTAGGACCTGGGAGTACGGACGTGCACCAGTGCCGCCGCCGGCTTTTTACAAGGGTTC

TAGAGGTGGTAACTTGGGTGCATCTAACATCTTTACTGGCTGAGCTATCTCCCCAGTTCCCCTTACTG

TGTTGATTGCACCCAACGGAATACTGGGTTTGTTTTTTGTTCTGGAGCGTGCGTGAGAGAGAGAGAGA

GAGAGAGAGAGAGAGAGAGAGAGAGAGAGAGAGAGAGAGAGAGAGAGAGAGATACAGACACAGAATCT

TAACAGAGAGACAGAGTCTTACATTATATAGTGGAGGCTGAATATCTAGTCTTCCTGCCTCCCAAGTA

CTATGGGATAGTCCTTCTGTACGCTACGAATATGGACTCTTCTCATTGGTTAATAATAAAGCTGAGTT

GGCCCACAGCCAGGCAGAATAAGGGTAGGCGGGAAAGCCAAACAGAGATACAGGGAGAAAGAAGGGCA

GAGTTGAGTGAGACGTAAGCAGCCACCAGGGAAGCAAGATGCCAGGTGACAGGTAAAGCCACGAGCCA

TGTGGCAAAACACAGGCTAATAGAAATGGGTTGATTTAAGTTGTAAGAGCTAGTTAGTAATAAGCCTG

AGCTATAAGCCGAGCATTCCGTAATCAATACGAGCTCTTGTGTATTTATTTGGGGCCTGGCGATTGGA

ACTAAAGGGAAGCTTAGACTACGGACTTGCACCTCCATGCTTAGTTTATGGGTTCAGAGGACCATGCT

AATGGATAAGCACTCTACCAACTAAGCTACACCCCCAGCCTATGGCTTGCAAGTTTCAAACTACATCT
```

-continued

```
GTGGCTCATTCAGGATTTCCACTGGGCGTCACTGGCAAAGGCCTTCAGGTCCCACCTGGAGCGCTGGC

TCAGCCATTAGAGCCATTAATGGTAGACTCACAACCTACACAAGAGACAAAAACCCACACAAGGGGTG

GAATGCAGAGACTCAACCAGTTCCAAGCCAGCCGGGACTAACAAAGCAAGATCCTGGCTCATAAACCC

AGGAGCAGGGTTTAGCCCAGTGGTGGTATGCCTGCCTGGAAAGGGATGGCCCCAGGTTCAGGCCTCTA

CACAGAGGGCTGCTTTCCTCACCACACTCCCTCTTAACCAAGGTGAGCAGCCGCTCCCCTCAGCACAC

ACATTGTACACTGCCACCATAAAGCTTTACATGGGACCCAAGAAACAGTCCTGAAAGCTGGTTCGGGA

TGTTCTTTCTCATTGCAAGGCAAGGCCAACTCCATGCGGACACCGGCTGCAGCTTGGTGCTACCTGGC

GGCAGCCGGGTCCTAGCTCCTTGTGTCTCCTGGCCAACTAGGGTTTCCCTTGTGGTGGCAGAGTTCAA

GAATGCATGGCGAAAGTCCACCCGCAGCACAGTCACAGGGAACAGGGCAGGGAGGGCCAGGCCCGCCC

TCGTCCTCCAGACTCCTGCTTCCTTAAAGGGAGTCTCCCACAGTTCCACCTACTGTGGGGGGAAGGGG

AAGGGGAAGGGCGGAGCTCCCTTGCTGTTCTTCAACCACCAGCCAGTACTCCCGTGCAGGCTCAAGGG

CAGCCTGTGCTCTCCACACAGCCAAGACCTGCTTGCTTGTTACTCAGTTTTTCTTACACAGGCCGTTA

GCTGATTAATTGGGTTTTTATTTTATGTGTATGGATGTGTTGCCTGTGTGCATGAATGTATACATGTG

TGCTGGTGCCCGAAAAGGCCAGAAGAGGGTGTCAGATTCCTCTGGAAATGGAGTTACAGGTGTCATGT

GGGTGCTAGAGTTGAACCCGAGTCTTAACCACCGAGGCATAGCCACTGATTCAGCCAGACTGACCAGC

CTGCAAACCCCAGGGATCCTCTGTATCGGCCTTGCCCCACACCTGCTAGGATTACAGGTGGTGGTGGG

CTTGGCTTTGTGGTTGCTGGGGAACTGAACTTAAGACCTCAGTATGTGCACCAAACCCTTCTACTGAC

TTAGCAACATTCCCGTGGAAGTCCTGAAAATGAAGGACGGGGGGAAGGATACTGACTCTGCTGTAAGA

AAATTCTTACATTTATGTTATTGTGTGGATGTGTGTGCACTCAAGCACAAATGAGAGCTAGAGAGGGC

CTGCAGAAGTCACTTCTCTCCTCCCACCAAGCGGATCCCAGGGACTGAGCCCAGGGGTCAGGCTTGGT

GGTGAGCGCCTTCGCCCACTGAAGCACCTCACCAGCCTGAAAATAAAGCTCTCATGGCACCCAGCCAC

GTCTGCTTTTTCTCATCCCGTCGCTGGCTCATTTCCCCCGATAGCAGCTGGTAGAGTCATTATAGCAA

GACCGTGCACCCTGTAAGGCCTGAAACACATACTGACCAGCCCTCCACAGGTCCCAGCTGACTCCTGC

TGGGACCACTGAGTTATAAATCAGAGCGTCATCTACCGGCTGCAGAGGCGACAGCTTTTTGGTGTCAC

CAACAGCAAACACTGTGCTGTATTCCTGTGCACTCACCACCTGTGAGAAAATGCACCAGGGCAGGAGC

TCAGGCCTGCAGCTTCAGCCAGGTTAAGGCCGGCCTGAGCTCTCCTTCCAGGCACAGCCTTGCACTAC

TCTAGCTGGCATCTGTAACTACCGCAGTCCACTGTGCCCATCTCTGCATGCTACAGCCCTCACTGTCC

TTCCTGGATGTCAGTTTCCATGGGAGACAGCTTCGCCTTTCTCCAAAGCACATCCTAAGTCTCCTTCC

TACCCTGTCCCCCCAAGGGGGGGCTCCTCCTCCACGGACACTGTGCTTTCAGTCTTTGCCAGGGGTCTG

ACCTAGGCCTGGGCCGCACCAACACTGCTAGGACCTGGCAGCACCCACTCTTCCTCCTTCAGGAACCA

CGTCCTGACTTTCCTCGCCCACAGGGCTTCAGTGTGACACTTGTCACAAGGTGACAAGTCCTCCTGCA

CACTGGTGGGCTCTGGGACTGACATGAGATCATGTGCCAGTGTCACACAGAGAGCTGTGGCTCAGCCA

CTGAGGGGGTAGGGCTACTGTACCCCACCTAGGCATTAGCCCTGCTAAGCACCACAGGGAGAGACCA

GACCCCACCAGGAGGCCAAAGCGGCTGGTGGCATTAGGGATCCACTGCCAAAGACTGGAACTCTAGGG

CTTGGACAGACAGATGGCTCAGTTGGTAAAGTGTTCACCACACAAGCTGCAAACCTGAGTTCAACCCC

CAGCACCCATGTAAAATGCCAGGCATGGTGGAGCATGTGTAATCCCAGTACTGGGGAGGTAGAGACTG

GAGGACAACCGGGGTTCACTGGCCAGCCAAACTAGCCCAATCGTGGAAGCTACTGAGACACCCTGACT

CAAAAATCAAGGTAGACGGCTCCTGACGAACATTCGATTGACCTCTGGTCTCCAAACACACCTGTGCA

CGCACACATGCACACACAAACATATGAAGGACTGAGATTCTGCATACGTTAAACAGCAACTCTCTCCT

CCCCCTTTTTATTGCATTCATTTACTGGTGTGTGTGGCTGAGAACAATCTATGGGGTCAGTTCTCTGG
```

-continued
```
TCCACCAAGTGGGTCCAAGGAATCAGACTCAGTTGTAGGCTTGGCAGCAAGCACCTTGACCCACTGAG

CCATCCAGCCAACTCTCTTTTTGTTTGTTTAGTTTGTTGGGTCAGAATCTCTCTGTGTAGTCGTGGC

TGTCCTGGAAGCCACTCTGTAGACCAGGCTGGCCTCAAACTCAGAGATTCACCTGTCTCTGCCTCCAG

TGCTGGGAATAAGGCATGTGATAGGGTTAAACCCACCACACCCAGCTCTACTCCCAGGGTTGTTAGCG

CCTGGAAACCACATTGGATGCTCTGTGGCTATGACTTTGGGAGCGCTATTATTTTCATTACGCTTGGT

GTCTCACACAAATGGAAACCTCGCACTTGTCTTTGAGTGGCTGACTTGCTCCATGTAGGTCCTTAAGT

CTCATCCAAATCTGGCAGGCGGTGGTGGCGCACGCCTTTAGTCCCAGTACTCAGGAGGCAGAGGCAGG

CGGAGTTCGAAGCCAGCCTGGTCTACAGAGACAGTTCCAGGACAGGCTCCAAAGCAATACAGAGAAAC

CCTGCCTCAAAAAACCAAAAAAAAAAAAAAAAAAAAAAAAAAAAAAAAAAAAAAAAAGAAAGAAAAAG

TTTCATCCACATCGTTAGACGTGTTGGTTTCCTTCCCTGTTAAGGATGAGCAGCATTCTTTTATCTGT

ATAGACCACATTTTGCTTATCCAGCCAGTGATGGACTTCCTACCCTCCCTGGTCCTGAGGCTGGAATT

CTCATACCAGACCAAGTGCCACAGGCTGGAGTACTAAGCAACACCCAAGTCCTAGGCTACTGTAAATA

CGCCTGCAGGTGGCTTTCTCTTTGCCCAACACCACAAAACATAAAGAAGGGAGCCAGACATAGAGGCA

ACTACTACAATCCAGACCCTCAAGAGGCTGAAGCAGAAGGATCCAAAACCGTACTACAGTCAGTTTCG

CCGCAGCCGAGGCCAACTAACTAATTAATTAACAAAATAATACGTATTGTGGGTGTGCATCTTGCGAT

GCTTGTGTTGTGGTGTGGGGATTGAACCTGCCTACGCTCAGCAAACGCTCTGCCAGTATGAAGTGTCC

AGTCCTCTCCCACACACACGCGAACACACGCGAACACACGGGAACACACGCACACACACACACACACA

CACACACACACACACACACACACGCACACGTATATTTAAGATCTTTCCTCTCTCTCTCTCTCTC

TCTCACACACACACACACACAGGGGTTAGTTAAGACCTTATTTGTATTACTTTTAATTGTGTGTGCG

TGTGTCTGTGCAGGGCACGCACACACGTGTTTCAGTACCGGAAGAGGTGTGGGATCCCCCAGGTGCTG

GAGCTACAGTGAGCCAGACACTGGTGCTCTGAACTGAACTGAATCCTCTGCCAAAGCAGAAAGCACTC

TCTGGACTCCTGCTTTTGTTGGTTTTGTTTTGTTTTGTTTTGTTTTGTTTTGTTTTCTTTGTACTTTT

CAACAGATTCTCACTAAACTGTCCAAGTTGGCTTGAACTCCCTCTGTAGTTCAGGCAGGCCTTGAACT

CACAATTCCTCAGGCCTGGGAGAGCGGAATCTTTTCGTCAAGAAAACACCCCATTTGAAAACTGAGGA

ATGCTGTATCAGCACAGGAAGGGGGAAGCTCAGGCCTTGTGGCTTAGAGAAGCGGCCTTGTGCCATGG

GGTTAAGAGCCCCAGGCTGCCCCATCTCGTTGGCTGAGGGAGGCGCTTCCCGTTATCTGAGCAGAGCT

TCCAGCATCAGCAACATAGTCTCCAAGTGGCTGAGGAATGGAAGGAGGATGGACTGGAAAGGAGAAAA

CAGGAAGGGTACTGCCGCCTGTGTGTGGGGAAAGGGGCAGAGCTGGACAAAACAGTAAAGGCGTCTAT

TTAAAGTGTGCGATTCCATCTGCACGAAATGTCCGCAACAGACAGATCCCTAATGAGAGAAACCTTAG

AGGCTTGCCCAGGGATGGGACAGGGGACTAGACTTTTGAGGGTGACTTTAAAATGCTCTGAAATCAAT

GTGGCATCGACTCCGACAACTCTGTGGACCACAGCACAACCAGGAAGTGCACTTTGGATGGGCAAACT

TCTGGGCATATTAATTACAGCCCCAAAGGCTGCTTTGTTATAAAAAGCACTGGTGGGCTGGCCGGCTA

GCTCAGCAGGTCAGGCGCTTGCCACCAACAACCTGAGTCCCAGACCAAGGCCACATGGTGGAAGGAGA

GGCCTGCCAGAAATTGCCCTCTGACCCCCACAGTGCCGAGCACTCACACTCATGATAAACTAAATAAA

TCTAAAAAACAAAACAAGACTTCAAAAGCAGCAGATGGAGCGCTGACACAGACACTCGGGAGGCTTGG

GCAGGACGGCTCCAAATTCAAGGCCAGCCTGATCTACGCAGTGAGTACCAAGCCAGCCAGGACTTCGT

AGCAAGACCCTGTCTCAAAGACATAAACAGGGCTAAAGGGCTGCCTCAGTGGTTAACAGCGCTGGATG

CTCTTCCTGAAGACCCCAGGTTCAATTCCCAGCACCCCGGGCAGGCAGCTCACAACCATCTGTAACTAC

ACTCCCAGGGATCCAGTGCCATCTTCTAGCCTCCGCAGACACCAGGCACACATGGAACAAAATACCGG

GACATAAAGAACACACTGTGTGGTGAAGCCCAGGGAAGGATCTGTGGTGGCTGTCACAGTACCGAGGC

GACTCTTCTGAGTTTGAATCAGGGGACGGGAAGGAGAGCTCAGCTCAACCGCTGCTACCTGTGGCTCC
```

-continued

```
TGACCACTGCCCTTCAGCTCTTGGTGCCCACTGGCTACCAAGCATTCCCAAGTGACTCGCAGTCACCT

GAAATTCAATATGCCAACATGGTGAACCCACTGTCTCTCCATCCTGCGTAGCAACACGCAAGGACGGG

GAGCCAAGACTATGCCTCCCATGAACTATCTGTCCTCTGTCCCCGCTTATCTCCTAACTGGACAGTCC

CCAGTCTGGAACTGGTGCCTTATGTTCCTGGAGAGCCTGCAAAGCTGCCTGTTTGCTGATCCCTTTCC

TTCCAGACCCTGCACTACAGAGCTGAGAGCCACCCAGCTATAACCCAGTGTTTCGTTTGTAGCTGACA

GGGACTCACAGAGCCCAGGCTGCTCACAAACTTACTATGTGGGGAAGCCTGACCTAAACTCCTGATCT

TCCTGCCCTGCCTCCCAAGGCTGGCTGGGATTACAGGCCTGTGCCGGGACACCTGGCCGGGACACTAG

CTTGTCAGGCAGGCAGAGAGGGCTCTCAAGCCCTGTTAAGAACTTGCTATTGGGAACACACACGCCCC

ACCCAGGAAAATGAATAGGACCCAACATGGAGTTTCAAGGGGCATGATGGGAGCTCAGGAGAGAATCC

TCTGCATGCTCCAGTGCCTCCTAACACGAGCTGGGTCTAGCCATCTTGCTGCTTACTCCTCGACAGGC

CCTTGCTGACAGCACCTCCCTCCTTCAGTTCCTCAGACACTCACAGCAGTTGGGGCTCTTACTCTGTG

TCTGGCAGTGTCTCACTAGACCCTTGGCAACCCACCCTGGGGACACGTACCACCCCCACTTCACAGGG

AAGGAAACTGAGGCACAAAGAGCAAGAGTACAAGGAAATGGGCTGGGCCTTTGAGCCCAGACTCCCAG

ACGCCAAAGCTCTCGATCCCACAGGCCCACCTCGGCGGGCGATCTCCGCCTTCAGCAGCCCCTCCATG

GCATCCGACTCAGCCAGGTCCAAAGACAGGTCTCCATCACTGTTGACGGCGGCGATGTTGGCCCCATG

GCTCAGGAGGTACCTAGGGGCAGGGGAAGGTCAGAGCCACCAGGCCTGGACCTAACGCCTAACCCAAG

CCCTGCCCTTCAACCCCAGCCTCACCTGGCAATGTCCAAGTACCCACAGGAGGCTGCCACATGCAGCG

GCGTCCAGCCCTCGTTGTCCGCCTGGTTCACAGTAGCACCCTGCTCCACCAGGAAGCGCACCACCTCC

AGGTTCTCGTCTATGCAGGCCTGGGGACGGGGACAGGCCCATCAGCTCCCGGCCGGGCCAATGAGAGG

TGTGGAAAGCAACGCCGATGGGCTGCAGCACAGATTCCAGGGGCCCTCTGGTCAGTGGCCGCCTAAAA

TATGCCTCGTTACCCATGCTTGGGTAATCTATGCATGCAGAGCTCATGGAGACTAGAGCAGGCTCCAA

AAGGCAGATTGAAAAGGCGACCAGGGAAGAGGCGGAGCTGCCATCCCTGCATGTGACTGCTGAACATA

CCCTATGAGGCAGAGGAACCCCAGAGCCCAGCCATGTTCTTCCAAGGGGCAGGGCAAGGCTAGGTTGA

GGCAAAACGCTCACCTAGCCCTGGGTTCCATCCACAACACAGGAAAAAGAGAGATCACCACAAAGAGA

CACACGCACATCCCAGAGTTGAGGGCTTGGGGCACAGTTCCCAAAAGGGATGAGTAGGCTATGTTCCC

GGTGTCCAGGGATCCAAGCAGACCAAGCTCTGGGTCACTGAGGGCCTACCGTGCACAGGTCTCCTCAG

AACTTCTTTTCTAAACACCCCACACCACACTAATCCCCCACCTCCTCACCCTTCGAACCAACAGCTCA

GGAGAGGAAGGCCTCACCCTAGCCAGCACAGCACCCAGGGCCACAAGAGAGCTGGTCTCAATCCCTGA

TGACACTGCTTGGACACTGGAACCACTGAGTCTAGGGAGGGGGTTAGGTCCGGACTCCTGGGTCCTCA

TGAAAATTAACCCCCTTCTACAAGCGCGACCATCTGGAGAAAGAGGGAAGGAAGCTACGAGGGCCAAG

TGCATGAAGTCATGGAAATTTAGGCTGGGGGGGGGGGGCACGTGCCCTGGGAACGGGATGAACTCTGGG

CTTCACTCTGGGCTCAGTTTATTTCCACCCTGTTGTCATGGTGATGGGAGGGGGGGCAAGGAGGCAGA

TGGGGCCTTTCCCTTTCAAGGACCTGGCCGGGTACGGGCATCCATGTGAAAGATGCCTGAGGCTGGGCA

CTGGGGACCCAAGAATCCTCCTCCCTCAGATGTAGAACTCTAGCCAATCCTCTTTCCTTAGACCCAGG

GATCCAGACTTGGCCCTCCTCCCTCAGGCCCAGGTGCTAGGGCTCCCCATCTCTCCCCTGCTCAAACC

TAGGACTCTTAACTCCCAGCCCTACCTACTCCAGACCCAACTCATAGCCATTATTGGACAAGGCAATT

ATTGGACAAGGGAAAGAGGAAGGAATGTCCCTGCCTTGCTAAGGCAGAGGCTGGGGCTTAGGAAATGT

CATTGCAGGAGGCTGATGCCCCAAGGAGGGTCTAGAACCGGAAACACTAAAAAGTCTGAGGTGTAGAA

ATCACCACAGACTGGGTGGCTCAATGCCCCTGCTTTCCTGGGACTGAAACTAGTTTCAGGAGTTTTCA

CTGCTGAAGCCAGGGCAGTGGTACTAGGAGGTGATGCTACGTACGCACCACTCCAAACCCCAGCCCCC
```

-continued

```
TCTGCGTTCTGGCCCTGAAAGCCAAATGATCTCACTGAATCTGATCTCCAGTCTCCCAAGCCTCCTGC

AAAGGCCTGAAGAGTCAGGTCACCAAGGTGTCTGCATGGCGGGAGGAGAGTCCCCACCTGGAAGGCTGA

CACGTCAGGCCTGAGGTCACAGGTTCCTGTCAGAGAGGATGCTCTAGGGACCTCCAGCAGATGCAGAG

GAAGGGGATGCAGTTGGGAGGGAACTCTTGGGAGGGCCAGGGACTTTGGTGATCATGTGAGCAGCCTG

AGCTGATCTCCTGGACTGGTCAAAGACGCTGACACCCTGAGTGTGGCCTCGGGAAAACAGGACCCTGC

TATATATAGAGGACGATGTCCCACACAGCTCACGCCGGCCCCATAAAGGAAGTTTTCCACAGGACGCC

TCTCACCATAGAGTCCCTCTGGGGACAGGGGTGACCACTGGTCCCATTCTACAGGTAAAAAAACTAAG

GCGCACCGAGAAAAGACACTCAAGATACAAGACACAAGAAGCAGACTGACACAAAAAGTCAGCACGGA

CTTTTTTTGTTTGGTCAAGATTTTGCAACTGGGTCTCATGTGGGCTATCAAGATGGCCTCAAAGTCAC

TGTGTAGATGAAGGTGACACTGAATTCCAACCCTCCTGCCTCTACTTTCCAAGCACCTGATTTCTGTG

GTATTGGGGTTGGAACCTGAGGCTTCCTGCACTCTAGGCAAGCACTCTGTCTAAAAGACAGCCCAGCC

CAGGACAGACGGATTCTGTTTTTCCTCTGCCTGGATGAGTGAAACACTGAACCTTTATTCCCCACCTC

CACGAGCATCCTAGCAAGAGGACGACAACCCAGGAGATGGAAGTTGCCATGAAAGACTGAAAGTGAAC

CAACACTGTGGCCAGGAGGAAGAAGAACGGGGATGGGGGCTCTGCTGTGACTAATCTTGTCCCTGACA

ATGCCAGCTTTTGGATGACGGGGAGATAAAAGCATCCCGAATCCAGAAGGATCCCGGCAATACAAGAT

GGTCCTCACTCTCGGGGCACAGATCACTGGAAAAAGATAATCACAGTGTCTGAGTCGCCCAGGGTCCT

GGTGGGGTAGGTTCTAGAAGGTGACAGGGTGGAAATCTAAGAGACAGGGCATAGTTTTTAAAGCAGGA

TGCTGCCCAAATATAGTCCATGGGGTGGTAGGTGGAGTGGGCATGCCTGTAATCCCACAAATGAGGGG

GTCAGAGACACAGGACCTGTATTTGAGGTTGGCCTGGGCTACACAGGGGAAAAAACAAAAAACAACAA

CAAAAACAAAACCAGAGGAGAGAGAGAAATAGGGCTTGGAAGACCGAATGCTTAGAAGTTTCCAGAAAGG

CAAATCAATGTGGACACAGAGAGAGAAAGACAGAGAGAGAGAGAGAGAGAGAGAGAGAGAGAGAGAGA

GAGAGAGAGAGAGAGAGTTGAGGAGAAACCTATGGGGGGTGGGGGTGGGTGGCAAGATCACCAAAAGG

GGATGAGCCGAGAATTGAATTAATAGGACATGGGGAGGGGAGGAAGGTTATGGGATGGGGCCCAACAG

ACGGTGGAGCGCCTCTTCTCCAGGGGAACAAAGGGGTACACTGCCTTGGAGGGGCAAAGGACCCTCCT

GAGGCCACAGCGGACAGCACGGGTCACAGGAAGTGGGGTAGGGAACAAGGTGGACCCCCCAAAAGAAG

TGACACTGAAGGGCCTGGGCCTGGCTAGCCTCAGAGGAGGGAGTGGGGGATTGGGGGGGGGGCGTCA

AGTCAGAGCTGGGCCCTGGAAGCCTGCGGCACAGCCAGGGCAGCCACCAGCCTGGAAAGGCACGGGGT

GTAAGCCATCCGTGTGCGGAAGACGCCGCCGGGGAGAGCGGTGACAGCGCGGATGACAGGGGCGAGGC

GGCCCCTGCAGGGCAGGAGGCGGGGAGGGAGGAGGGGTGGCTCGGGGGGGCCCCGGGGAGGGAGGATGC

TCGGGGGCCGCTGACCTGGTGCAGGGCGCTGATGCCGTCGGCGTTGGTGGAGTCGAGCACCGCTCGGG

CAGGCGGCGGGACGCCGGCGTCCGATTCCCCGCTGGCGCCGGGATCGGGGCCCCGGGGTCCCCGGGA

TCCCCGGGGTCGGCTGCGCGAAGCATCAGGCGAGCCTCATCCAGATCGCCGCCCGCACAGGCCGCCAG

GAACTCGGCGGCGCGCTCGAAGCGCACGGTGCGAGCACGACGCTCCCCGGGGCCCGGCTCAGCCCCCG

CCCGCGCCCCCCACCGCCGCAGCTGCTCCTGCCGCCGCTCGCGGGCTGCCGCCGCCGCCGAAGACGAC

GACGACGACGACGACGACGACGCCGCCCCGGGGCCGTCCTCGCCCGACATCGCGCCCCACACCGG

GCCGCTCGCCCGCTCACCCACCGAGCGAGCGAGCGAGCGAGCTGAGCGAGCGCCCGCCCGAAGGCCGG

CCGGCGACGAACAGCCGCCACCCGCCCGCTCGCTCGCTCGCCCGCCCGCCCGCCAGCCCCGGGGGCCG

CCGGGAACCGCCGCCGCCGCCGCCGCCGCCGCACAAGCACCGCCCCGAGGCTCAGGCTGGGCCCCAC

CCCTCCCCCCACGGACGGGCGTTGACGTCACGACGCTGCCCCACAGCCCTCTGGGAAATGGAGTCCTC

CGTTGAGAAGCCCGCAGGGTTTTTTCAGCAGACTCGCTAACTGCTGAGGGAACGGTCGGGGTGGCACG

GAAGCCGCCAGCAGGCGCGCCTACAGCCCCCAGCACCTGAGAGGCAAACTGCTCTCTCGAGTTCGAGG
```

-continued

```
TCAGCCTGGGCTACAGAGGCAGTGCCAGGGTAGCACCAATTGCCTAAAGCAGGACACGCCCCCCCCCG

GGAATGCTGGAAATCTGAGTTTAGAGGCGGGACGGGATGCCCGGGGGGATGCTGGGAGATGTAGTTTT

TTTGGTAAAGCGGCGCAAAGGATGGCGCGTGGGAAATGATGGCGTGTAGCGGAACCCGAGAGACGCAG

AAATAAGACTCGCGTACTTTCAGTTGTGTTTTTGCTGTGAGATGGGTTTGCCCTCGAGCTCGCTGTGT

GACTGCGATTGTCTGTTTTAAACTCCCGACCTTCCTGCCTCCGTCTCCTAATTGCTGGGGTTGCAGAC

GTTTGTTTGGGTTTTGTTGGTTTGGTTTGGGTTGGGTTTTTTCTTGGGGGCGGGGGTATTTTGTTGTT

TTGTTTTTGTTTTTGTTTTGAGACAGCGTCTCACTATGTAGCCCTGCCTGGCCTGAAACTCGCTACGT

AGACCAGGCTGGCCTCGAACTCATAGAGACTCCTCCCCCCACACTTCTGCCTGGTATGAAGGGGGCGC

CACCAGGTCCCGCTTGTTTTGGTTTTGGAATCTGCCCCTCCCTCCCTCCCCATCAACACCCGATGAAG

GACAAGGATTTGTGAATGAATGAATGAATGCATGAGTGCATGAATGAATGGGCTCCCCAAGACGTCGG

GGAGACCAGGGGCCCACGGGAAACTGAGTCCTGAAACCAGATTAAACACCAATCGCCGCCAAACTCCT

CTGGGTAACTAAGGTTCCCGTGCAAAATCCAAGGGTATCGGGTAGCATGGGGCAAGCTGGGAAATGTA

GTCCCAGGGCCACGCCTCCTAAAGAGTTCAGCCCCCAGACTTCCAAAACTGCCTGAGATGCCAAGGTA

CCCCGGAAAGTCAGTTTCCAGATGAAGACAAGCCTCCGGTCTCCAGCGGTAATCCCTTGAGCACCCGG

GAAGAAGGGTCCCCAAAGAACCACACATTTCTCCTTAGCCCACTCGGGGCTGCGGGGGACGCTAGGAG

ATGCTCTCCCGGCTGCATCAATGCTCTCCTGGAATTCTGGGATCGGTAGCACAAAATGTGATGCTCCG

ATAGGTTTGGAAGTTTTGTTAGTAGACCCAACAGATAAAAGAACACCTTGATCTTTCAAGAATCTTCC

CCCCACCCCCACCCCCACCCCCACCTCCACCCCAAAAATTGCAATTTGAGAAGGACAGAAACACTTTT

GAGACAGGAACACAGACTCACACACACACACAAAAAAGTAGAACAGAAAGCTGTCAAGTTTATAGA

GAGAAAACACGTCTTCCTAAGGGTCGTTAGGGCAGCCCCGTTCACACTGTGACCCTTGGATTTGTGAA

TGAGAGATAAATTACAGACCCTGGCAGAGTCTAGGGAATAACGACCATAAATCCAAAAGGATAACCCT

GTGGTTTTTAAGATGTGAGATCACACACACACACACACACACACACACACACACACACACACACACAC

CATTCTTCCCCAAGGCAAGAAATCAGATATTTCAACCCCTGGGGTCCAGAAGGAAGGAGGTCGCTGAC

TCCAAAAACTGTCTTCTGATTTCCACCATGGATTTCCACACACACACACCCTATCAACACACACACTA

AATAGACGTTTATAAAATGATCCACAAAATAAGGCTACACCAACACACAGAGGTAAGACTGTTGTTAG

ACAGTTTTGGTCTGGTTGGGTTTTTTTTTTTTTTTTTTTTTTTTTGAGTAGCCTTCTCCTGTCCCAT

TTCTCATGCCTCTACACACACCTGGCCTCTGGGTGTGTTATTTTAAAACATCCTTAGAAGAATTAATG

ACCTTGTACAACCAGTTTAAATGCAAGAGGCAATTAATTTTGTTTTGTTTTGTTTTTCGAGACAGGGT

TTCTCTGTGTAGCTTTGGAGCCTGTCCTGGCACTCGTTCTGTAGACCAGGCTGACCTCGAACTCACAG

AGATCCCCCTGCCTCTGCCTCCCGAGTGCTGGGATTAAAGGCGAGCCCGGCAGCACTGGAGATTTAAC

TCAAGGTCTCCTGAGTGCTCGACAAGCTACTCCCAGCCATGAACTTGATATCTCTTTAATGGCAGCTG

ATGTCTCTCCCGGGCAACATGGAGCTGTCCAGCCAAGCCGCACAGCCAGCCACGCATAATGACAACAC

GGAAGAACTCAAGCGGATGTCTGGAGGGCCTTTATTTTGAGTTACAGATGGGGGACACACTCCAGAGG

CTCCCAGGCTCCATGCAGTGGGGCGTGTCCTGGCAGTCTCACTTCCAGCGGCCTCCAACTCGACCCTT

CCCAGCCCCCTTTCGGCTGTGGGAGAAGAAGGTGGAGTCAGGAAGAAGCCCGGAGCCTCCGAGATAAG

CTTAACACAGTCCCTTTAAAATTAAGGAAGTCCACCAAATACCCACCCCCACCCAGAGGGAAGAGAGA

GCAGAGGTCAGCAGAGCTGTTTTTTTTTGTTTGTTTTTTGGGTTTTTTTTTTGCAGTAGTGAGCATAA

AGTCAAGGCCTCACACGTGCTAAGTATGTTCTGTACACTGAGCCACGCCCCTTGCCTCTCACTGGCGA

TTCTAAGCAAGGGCTCTACCACTGAGCCACATCCCCAGCCCCTCACTGGGGGATTCCAGGCAGGGGCT

CTACCACTGAGCCACGCCCCCAGCCCCTCCTCACTGGGGGGATTCTAGGTAGGGGCTCCACCACTGAG
```

-continued

```
CCACACCCCCAGCCCCTCCTCACTGGGGGGATTCTAGGCAGGGGCTCCACCACTGAGCCACGCCCCCA

GCCCCTCCTCACTGGGGGGACTCTAGGCAGGGGCTCTACCACTGAGCCACGCCCCCAGCCCCTCCTCA

CTGGGGGGACTCTAGGCAGGGGCTCTACCACTGAGCCACGCCCCCAGCCCCTCACTGGGGGATTCTAG

GCAGGGGCTCCACCACTGAGCCACACCCCAGCCCCTCACTGGGGGATTCTAGGCAGGGGCTATACCACT

GAGCCACACCCCCAGCCCCTCACTGGGGGATTCTAGGCAGGGGCTCCACCACTGAGCCACGCCCCCAG

CCCCTCACTGGGGGATTCTAGGCAGGGGCTCTACCACTGAGCCACACCCCCAGCCCCTCACTGGGGGA

TTCTAGGCAGGGGCTCCACCACTGAGCCACGCCCCCATTAAGGGCATCTCTTTCAGATAATTCCCAGT

AGGGGGTTGGTGGCCATGTTGGAGTTGACTTTCTTGGGTTAGTTCGGAGAACACATGCAAATTTATGA

GTAAGGGGCCTGAGGGAGAAGGAAGGGTGAGCTGGAGTTGGTGACTTGCATGCAACAATGTTGAGTGA

GGCTGGAACAGTACAGAAAATGCTAGAAAAAGGCAGAGACTGAGCAGTGAGCGGCCTGGATACGGTGG

AGCACATCGGTAATCTCTGCACTCTGAAGGGGATGAGGCAGGAGGATCACCGAGAGTTTGAGGACAAC

CTGGGCTATATAGCAAGAGCCTGACTCAAATGAAAACAACAACAACAGCAAAAAAGTCGGGTATGATG

GCTCTGTAATCCCTGAACTTGGGAAGCAGAGGCAGGAAAGTGTCAGGAGTTCAAGGACACCCTCAACT

ACAAATGGAGTTCAAGGTCATTCACGCTTACAGGAGACCTTGTCTTAAAGCAAGAAATAGAAGGAAAA

GGGGCAGGAAGTGGACAGACAGATGGAGAAGGGGGGAGGGGGGAAAGAAAGGAAGAAAGAGAGAGAGA

GAGAGAGAGAGAGAGAGAGAGAGAGAGAGAGAGAAAGAAAGGCAGACAGAGGGGGGCACTGAGATGGCTC

AGCAGGTAAAGGAGCTTGCAGCCAAGCCTAGGCCCTGAGTTTCAACTCTGGGACCCACATGATAGAAG

GAGAAAACCGACTTGTTCGAGTCATCCTTCGGCCACATCTGCACCATAACAGCACACACACACACACA

CACACACACACACACACACACGCACGCACGCACGCACGCACGCGCGCGCACACACACACACA

CACTATGCGGTGTGATATGATACAAAAAAAAGTGTAAAAGAAAATGTACTCAGAAAGAAAGGGTTGGA

GGGAGGCAGAGAGGCGGGGAGATTGAGACCAAAGAGTTGATAAAGAGAAGCAAGAGATTGGAGTGCAG

GCCAATAAACACAGCACTCAGCAGGCTGAAGCCAGGGGACCAGGAGGAGTTCAAGGTCAGCCTCAGCT

ACCTAGTGAGACTGGGCTGCATGAAACCTTGCCTTAAAAATAAATAGACAGAGCCGGGCAGTGATGCG

CACGCCTTTAATCCCAGCACTTGGGAGGCAGAGGCAGGCGGATCTCTGTGAGTTCGAGACCAGCCTGG

TCTACAGAGCTAGTTCCAGGACAGCCTCCAAAGCCACAGAGAAACCCTGTCTCGAAAAAACCAAAAAA

TAAATGAATAAATAAATAAATAAATAAATAGACATACCAAAAAAAAAAAAAAAAAACAGGAACAGTGAG

TCATGCCAATCATCCCCACATACATGGGATTAAAGCAAGAGGATCTCCTACAGGTTCAAAGAAAGCCT

GGTCTACATAGTGAGTACCAGGCCAGCCTGGGCTACAAAGTAAGACTTCCTCGAAATAATAAACAAAC

TAAACAAACAAACAAACAAATAAATAAACAAACCCGAGAGAACAGATACAGAAAGGATGTCTCAGGGA

GCAAGGAACAAAGACATATAAGATGCCAAAAGGAGGGCTGGAGAGATGGCTCAGCAGTTAAGAGCACT

GGCTGCTGTTCTGGAGGTCCTGAGTTCAATTCCCAGCAACCATATGGTGGCTCACAGCCATCTATAAT

GAGATCTGGTGCCCTCTTCTGGCCTGCAGGCAGGCATACAAGCTGGCAGAACACTGCATACATAAATA

AATAAATCAAAAAAAGATAACACTTTAAAGAAAATGATACTTTGAGAATTCTATGTATAGAGCCAGGC

GGTGGTGGCGCACGCCTTTAATCTAGGTCCTCAGGAGGCAGAGGCAGGAGGATCTCTGTGAGTTCGAG

GCCAGCCTGGTCTACTGAGCAAGTTCCAGGACAGGCTCCAAAGCTACAGAGAAACCCTGTCTCAGAAG

AAGAAAAAATAAAAGATCCCAAAGGGCAGTGGTATGCAGAAGACAGGGAGGAAGGGAGGGAGGGAGGG

ACAGAGGGAGGGACAGAGGGAGGACAGCAGGCCTTTTGTGGAAGCAGCACTTACAATTTCTGGGCATG

GCTGATTCGGTTGTACAGCACATTGATCTGTAGAACGAGAAGCCAGGCTAGGTGCAGATGTCCAACCA

AAGCCCTGCCCTGCCTATCACCCCTGTCACCCCAGCCTGGACCCCAACAGAGGCAGGTCCCACCTCGT

ATTTCTGTTGCTTCAGTTTCTCCATCAGATCAAATTTCTCTGACTCGAGCTGGTGGATCCATTCCGAC

AGCTCCTGGGCCTTCTCCCTGGCAGAATGAGAATAACTGGGATGCAGCGAGACTATGTTCTGGGCCCA
```

-continued

```
GAAAGGTTGAGACACCTACCCCAAGCCTCAAGGCAAGTCTCTCTGAGCTTGATACAGTTGGTATGCTA

AGCCACTATGAGCCTGATACAGTTGGTATGTTGTGGAATGTTACTTTAACTATGTAAAGATGCCTTAC

ATTTGTTTACTTTGTGGAATGTTACTTTAACTATGTAAAGATGCGTTACATTTGTTTACTTTGTGGAA

TGTTACTTTAACTATGTAAAGATGAGTTACATTTGTTTACGCTGTGGAATGTTACTATAACTATGTAA

AGATGCGTTACATTTGTTTATATTGTGGAATGTTACTTTAACTATGTAAAGATGCGTTACATTTGTTT

ACGTTGTGGAATGTTACTATAACTATGTAAAGATGCGTTACATTTGTTTAGGTTGTGGAATGTTACTT

TAACTATGTAAAGATGCGTTACATTTGTTTACTTTGTGGAATGTTACTCTAACTATGGGAAGGTGTGT

TGCATTTGTTTCTGCTGCATTTGTTGAGTTGGATAAAGGTGTGTTGCTGTTTCACCTTGCCTGCCTAA

GGCACCTGATTGGTCTAATAAAAAGCCGAACAGCCAATAGCTAGGCAGGAGAGGGATAAGCGGGGCTG

GCAGGCAGAGAGAATAAGTAGGAGGAGGAATCTAGGATGCAGGGAGGGAGACCAAGGGAGAAAGAGAG

GGAGATGCCTGGAGCCAACCAGACATGGAGTAGTCAAAATGCAGATGAAGAGAAACAGGTTAATTTAA

GTTATAAGAGCTGGTAGGACAAGCATAAGCTAAGGCCAAGCTTTCATAACTAAATTATCTCTCCACGT

CTTGATTTGCGAACCGGTTGGTGGCCCGAAAGGAAGGCAGCTACACTGGTAAATTCTTGTTAAGATTG

GAGGCTGAAGTTTTAAAATATGGCCACTTTCTGAAACGGAGGTCTCCCAAAGGAGAGAAGGAAGTGAT

GACTGGGAGCCCCAGAATCGGAAAGATGTTTGGTTTTTATTTATTGCTTATGTAGTGTGTGTGTGTGT

GTGCGTGTGTGTGTGTTTAATTTTGATTTCTGAGACAAGGTCTCGTGTAACCCAAGCTTCAATATATA

GGAGAGGATGACCCAGAACTTCTGATCCTCCTGCCTCCCCCTCCTGAGTGCTAAGATTCCACCTAAAT

GAGGGAGAGAGCACTGTCAATGCCAGACTCCACAGGCCATGCCAGGCACAGGACAGATTGCACCCGAG

TGACATTTTGAACAGAGAAAGCAACAGTGGCCCAGAAAAGGAATGTCACTTGCCTAAAGTGACACAGC

ACCAAGGCTCACACCTGGAACATCACCCACGGAAACCTTAGGAGAGCCACAGGTGTTGCTGTAGTTCC

TTGTCCCACCAGGTCCCTTCGTCCTTCTCAGCCCCAAATAAACACACAGATACTTATATTAATTATAA

AACTGTTGGCTGATGGCTAGGGCTTCTTATTGGCCAGCTCTGTCTTAATTGACCCATTTCTATAACTC

TATGTATCTCCACGTGGTCTTGGCTTACCGGAGAATGGCCGGACCTGTTACTCCTTTTGGCAGCTACA

TGGTGTCTTCCCTGTGGCCCCTCTCTACCTACCTTTCCCAGAATCCTCCTCGTCTCCTAGCCCCGCCT

ATCTTGCTGCCTTTATTGGCCAAGCAGTGTTTCATTCATCAACCAATAAGAGAAACACATATACAGAA

AGGCATCCCCCATCACACAGGCACTTACCGGAGTTGGTCCTCCCCCATGTAGTCGATGTTCAAGGGTT

TTTTCCTCTCAGACAGGATCCTGAGCTTCATCTCCCGGCCGGTCTGCCGCTTCCCACGTTTCTGCTCA

GCCTGGAGGGGGAGGAATCCCAAGCCAGGGATGGGACCTGGAGGCCAAATCCACTCAGGGTCCTACAG

TCATGGCCAGGGCCTCCACCACTTGCAAGGGGCCCAGGCTGCAGCCCTCCTCCCCCAGACCCAGGAAT

CCAAGCTCCATGCCTCCTCCATCAGACACGGGAGTACAGGCCCACTCTTCCCTTGCACCCAGGCACCA

CCAGAATGTTATCTAAAGCGACAGCTGCCCCCCCTTACCCAAACCCCAACGGGATCCAGGCTCAGTGC

CCTTCCTGAGGACCAGCATTCTGCAGCTCCCCTTCCCTCCTCCTTGTAAACGCAGACACCCCCCCCCC

AGGGCTAGACTCACCTTGACCAGGTAGCCCCCAAAATGAGCCCCCATGTTGGAGAGAACCTTCTTCTT

CTTGGCATCGTCCTCGGCTCGCTTCTTGGCTTCCTCCTCCTCTTTGCGCATCTTCTCTTCCTGTGAAA

ACAGAGGGGTTCCCTCCATGTGGCCCTACTAAGGAAGGCACGAGCCTGGGTAGTGCATGGCTAGGCTC

CATAGACGGGGCCGCAGAGGGATCCACTCCTAAACTTGATATATAGTTCACCGAGCCCTCAGGTTGGC

AGAAATCCTCCTGCCTCAGCTTCTCCAGGGCTGGGATCACAGGTCTGAGCCCACCGCAGGCAGCAAAG

CTCAGTCATTGTGCTATGGTTTTGAGTCTCTTGATCCAGCCATGCCTGAACTTTTTAAAATTTATATG

CAGTTCATCCTTTCACTAGGAAAAACAAAAAACAAAAACAAAAACAAAAAAACCTTGCGCTGTACATT

ACAGGGACTTTCTGAGAACCACAGGGGACATCAACGGCAGGAAAGGAAAGTATTCGTCTCCAAGAAAG
```

-continued

GGGCAGACACCTACCGCCAGCTTGGCCTGCCGCTCCCGCTCCTTTTCGGTTCTGAATCGCTGCTGCTC

AGCTCTCTCTGCACGACGCCTCTCCTGGGGTGGGGTTGGGGATGGAAGAGAGGAAGATAGCGGAGGGG

GATTGGAGGCTACCCTCTCCCCCAGTTTATCCCTCCCTCCACCAGTAGACAGCAAGAGAGGTAAGTGC

GGTTTCTTTTGTTTTCTTTTCCTTTTTTGAGATAGTCTCAGAGAGCCCAGGCTGGTCTCAAATTCGTG

GCAATCTACCTTCCTTGTCCCTCTAAGAGCACGCCTGGCCGAAATACGCATTGGAGTGCAACCACCCG

GTGTCCCCATTGTTTCTCCCGGAGACCCCAAAGCACTTCACGGAGGAAGGGACGAGGAGGGACCGAAG

GACCCGGCCTCCCCGGCCTCCCCGGCCTCCCAGGCTCACGATGCGATCTTTCAGCGCAATGAGCTCCT

CTTCCTCCTTTTTGCGCTGCTCGAAGTGCACGTCAATCAGAGTCTGCAGCTCCAGTAAGTCTTTCTCC

ATGCGCTTCCGGTGGATGTCCTGCAGAGGGAGCCCGTGAGGCAGAGGGACCAGACCCTAGAGCCGCCC

CTCTCCGGCCCCAGGGGATGATGATTGACAGCCAGCTGGGACGGCTTCCAGCAGAGGTCAGCAAAGCA

TTCCTGGCTGGCAACAGGGCACCGAGGTAAATGCAGGCATTTTCAAGAAAGGAGCAAAGAGGGGCGCC

TATCAGAATGGGCTCAAGGCGCTGAGGAGCCAGCAAGTATGTCTGGGGTGGGACACCTGTCGCTTACA

TCAAAGTCCACACGCTCCCCTTCTGGGATCTTGGGGGGGATCAAAGGAGGCACCACAGGACGGCTGTC

GGGACAGAAATGGGAAGAGATCATTAGCAGGCTGGCCTCCTCATCCCCCCTCACCACAGACAGTTCAA

AGTGACAGCTGCCCCTGAGTCTAAGCAGAGACCAGTCAGAAAGTACACCGTCTGAGCATGTTGGGTTT

AATAAAACGTGTAAGACGGTGTGTTTTGCCTGTTTTGACATACTTGTAAAAAAAAAAAAAAAAATGGAC

AGAGCCTGATGGCACAAACCTGTCACCCGATCTACTTGGGAATCAGAGACAAGTTCCGGGCCTGCCTG

ATCTACAGTAAAGCTAAAGCCATCCCTGGAAACTTGTGAGACCCGGCCTCAAACTAAAAAGTAAAAAC

AGGACTGGGACTGTGGCTCAGGGGTAGAGCCCCTGCCTAGAATCCCCCAGTGAGGGGCTGGGGTGTGG

CTCAGTGGTGGAGCCCCTGCCTAGAATCCCCCAGTGAGGGGCTCGGGTGTGGCTCAGTGGTAGAGCCC

CTGCCTAGAATTCCCCAGTGAGGGGCTGGGGTGTGGCTCAAGACGGAGCCCTTGTGTCAAACATATAA

GGCCACAGGTTGGACACTGGACATTAAAAGGG

CCR5 sequence
(a putative guide for insertion of a integration site is *indicated*)

(SEQ ID NO: 3)

GTAAACAGAGTCCTGTAATGCAAGGTCCGGCCTTGGCAGCCCCAGCCTGGAGCCACAGTGAG

ATGTGAGCCGAGGGTTATGCTGGGAAAAACCTCTCCCTCCCAGCACCTGAAAGGCTCTGCAG

GCCCAGCAGCTCAGCAAGCAAGGGTAAGGGCATGGACTAACATCTTATTTCATACTATCCCT

TATAACACATCCTAATGTAATCAGCTCACAATATGAAATTATTTCATTTCTCTCCAGTCATT

GTTTCAATGGGCCTTAGGGTTGACTGGATTCTGGAGGGCCCTGCCTAGAGGAGGGGGTGCA

TTCTGTCCCTATGTCCCCTCCTGCTCCATCCTCCACAGCACGTGCCTAGTGGTCTACCTTGT

GGGGAATTCTTGTACCTCCCTCTTCTAGGCATGGACTAGCATTGAGAAGTGGGAGAGGAGTG

TTAGGAAAAAGGGCAAATATAGACATACCTTGTCTTATTGTGCTTTACAGATATTGTTTTTG

TTGTTGTTGTTGTTTACAAATTGAAGGTTTGTGGCAACCCTGCCTCGAGCAAGTCTATT

GGTGCTGTTTTTCCAACAGCATGTGCTTGTTTTACATCTCTGTGTCACATTTTGGTAATTCT

CCCAATATTTCAAACTTTGTCATTATTTCTATATCTGTTATGGTAATCTGTGATCAGTGATC

TTTGATGTCACTATTGTAGTTGTTTTGGGGCACCATGAAGTGCACCCATGTAAGATGGCAAA

CAATCAATAAATGTTGTGTGTGTTCTGACTGCTCCATGGACTGCCTGTTCCTGAGACACAAT

AATGTATATATAACAATTATATATATATATATTTATAACAATTATATATATATATATATATA

TTTTTTTTTTGAGGCAGAGTCGCACTCTGATTGCCCAGGCTGGAGTGCAATGATGTGATTTC

AGCTCACTGCAACCTCTGCCTCCCCAGGCTCAGGTGATTCTCCCACTTCAGCCTCCCAAGCT

GGGACTACAGGTGTGCACCATCACACCCGGCTAATTTTTTTTTTTGTATTTTTAGGAGAGACA

-continued

```
GGGTTTTGCCATGTTGCCCAGGCTGGCCTTAAACTCCTAGACTCAAACAATCCACCTGCCTC

AGCTTCCCAAAGGGCTGGGATTACAGGCATGAGCCACTGTGCCCAGCCCAAGACACAATAAT

ATTGAAATTAAGCCAATTAATAACCCTACAATGGCCTCTAAGTGTTCAAGTGAAGGGAAAAG

TCCCACGTCTCTCACTTTAAATCAAAATCTAGAAATGATTAAGCTTAGTAAGGAGGACATAT

TGAAAGTCAAGGCCAAAAGCTCACCTCTGCACCAGTTAGCCAAATTGCGACTTCACAGGAAA

AGTTCTTGAAGGATATTTAAGCTCTACTCCAGGGAACATGCAAATGAAGAGAAAACAAAGCA

GCCATATTGCTAATATGGAGAAAGTTTGAGTGGTCTGGAGAAAAGATCCAACCAGCCACAAC

ATTTCCTTAAGTCAAAGCCTAATCCAGAGCAAGACTCTAACTCTCTTCAATGCTATGAAGGC

GGAGAGAGGTGAGGAAGCTGCAGAAGAAAAGTTTGAAGCTAGCGGAGGTTGGTTTGTGAGGT

TTAATGAAAGACAACATCTCCATAACATAAAAATGCAAGATGAAGCAGCAAGTGCAAAGGGA

GAAGCTGTGGCAAGTTATCCAGAAAATCTAGATAAGATAATTGATGAAAGTGTCTACACGAA

ACAACAGATTTTCAGTGTAGACAAAACAGTCTTATGTTGGAAGAAGATGCCATCCAGGACTT

TCACAGCTAGAGAGGAGATGTCAAGGCAAGCTGCAAAGCTCCACAGGACAGGCTGACTCTCT

TTTTAGAGGTGAATGCAGCTGATGACTTTAAGTTGAAGTAAATGTTCATTTACTATTTTGTA

AATCCTGGTGTCATTAAGAATTATGCGAAATCTACTCTATCTGTGCTCCATAAATGGAACAA

TAAAGCCTGGATGACAACACATCTGTTTACAGCATGGTTTACTGAATATTTCAAGCCCACTA

TTGAGAACTATTGCTCAGAAAAAAAGATTCCTTTCAAAATATTACTGCTCTGCACCATGTCG

ATCAAGAGCTGTGTTGGAGATGTACGAGAATATTCATGTTGTTTTCATCCCTGCTAACACAA

ACATCCATTCTGCAGTCCATGGACCAAGACTTTCAAGTCTTATTAAGAAATATATTTCATAA

GGCTATTAAGAAATAGCTATATATATATATATAGCCTTATATAGTTTATATAGCTACCATTG

ATAGTGATTCCATTGATGGATCTGAGCAAAGCAAATTGAAAAGCTTCTGGAAAGTAGTCATT

ATTCTAGATGCCATTAGGAACATTTGTAATTCATGGGAGGAGGTCAAAATACCAACATTAAC

AGGAGTGTGAAAGACATTGATTCCAACCCCCATAGATGACTTTCAGGGGTTCACGTCTTCAG

TGGAGGAAGTCGCTGTAGATGTGGTGGAAACAGCAAGAGAACTAGAACTAGAAGTGGAGCCT

GAAGTTGTGACTGAATTGCCGCACTCTCATGATCAAACTTGAACAGATGAAGAGTTGCTTCT

TACATATGAGCAGTGAAAGTGGTCTCTTGAGATGGAATCTCCTCCTGGTGAAGATGCTGTGA

ACACGGTTAAAATGACAACAATCGATTTAGAATATTACATAAATTTAGTTAATAAAGCAGTG

GCAGGGTTTGAGAGGATTGACTCCAATTTTGAAAGAAGTGGGTAAAATGCTATCAAATAGCA

TCACATGGTATGGAGAAATCTTTTGTGAAGGGAAGAGTCGACCAAGGTGGCAAATTGCATTG

TCATCTTATTTTAAGAAATTGCCACAGCCACCCCCAGCTTTAGCAACCACCACCCTGATCAG

TAAGCAGCCATCAACATCAAAACAAGACCGCCATCCTCTTCAGCAAAAACACTATGACTTGC

TGAAGGCTCAGATGATGGTTAGCATTTTTAGCAATACAATATTTTTAATTAAGGTATGCACA

TTGGTTTTTCTGACATAATACTATTGCATACTTAATAGACTACAGTATAGGATAAACACAAC

TTTTATATGCACTGGGAAACCAAAAAGGTTATTTTTGAGATATTTGCTTTACTGTGGTGGTC

TGAAGCTGAACTCACAATCTCACCAAGGTGTGCCTGAACCTCTTTAGCTAACTGGCCACTGC

CACAGTCCACTCTGTGTTGGTCAAGATGCCCCAGAGTGGCAGGCACACTGTGTGGTCACATC

CAAGGGCCTAGATATGGTGGGGGCTCCAAATGGATCTAGATATGTGAGATCTCTCTTTGATT

TGACTTCTTCCAACCCACCATTTTCTGGGTGCTGGGCTCATCTCACCCAGAAAGTAGGACCC

AATGTGACAGTTCCTGCCCAGTTCCCTCCTGTGGTAGCCACTTGACCCAGGGGCACTCTTGA

TCCTTGCAGCCTCACTTACACACCCTATCTCTACCCCTATTAACTCTCTCCAATCCCCACTC

CCCCTGCTCAGCTTGTCTGCTGCCCAGTGGGGGCCCCACCCATGCTGGCCTCTCCTTTTGCA
```

```
AGTCCCCATTCCTCATATGGTTTCTTCAGAGCCCCTTTCTTTGGCTTTGAGGAGAGATGCCC

TCACTCGCTTCCCCACCAATCCTGCCCACTTCTACAATCCATTCATTATCCTAATTGCCTCC

GTATACAGACTGGAGTGAGAGGAGTTGATGTGATGGGTGTGGATACAGGGCTGGTGCTGTCA

TCTTCTAGTAAGCCCTGGGAGAGGTGTCTGAGCCCAGGTGTCAGTGGTTTTCTTTGGAACTG

TGAGTGCATAACACTTCTTTGCCTTCAGCCTTAGGCCATAGTTGCTAGTTCTGGGACAACCA

GAAAAGCCCTACATAATCTCGTGTTATGTGCAGAGCTGAGTATAGAGCTCCAGGTATGATCT

GACTCACTTAAGATCACAGTGAGTCTATTGTATTGTTGAACTGTTAGCTTAGACATCTGTTA

CTGTACCTACATGGCACTAGCCTCACGCCTAGACACCGATCTGAAAGAAATCCCCTAAATGC

ATAGAGAAGACTTCTCAGCTGAGCTAAGGGGCTCCCACCAGGTTTGAGCCTATCTAATGAAT

CCATGAGGTAGACAGCCTGCACATGTCCACTTGGTTTGATGAATTGCACAAATCCCTATGGG

GGATGTGGTTCATGGGCTGGGAAGTGGGTTACCCTGGGAAAGGTCTACAGGACAGAGGCAGG

GATGGAGACAACAGCATGGTGAGTTCCCAACCCACCCACGATGATAGGTGTCTGAGGCAGAA

GGTAAAGAGGCTGTCACCTGGTGGGTGTCATAAGACTCAAGTGTCATTGTTGAGGCACATGG

GTAACAAAGCGTGGCACTGGATGGGGGTAGATTCTTCCTATTTCTGTGAGGATCAGGGGGAC

TCCCTGGCTCTCCTGCTAAAGGTGGCTCTAGGGACAGGAAGAGTGTACTTCTTGACAGGGAT

GTCAGAGCACTGATGGTGACAATCAGTGTGACACTGCTCACATGACTGAACAACCGAGAAGA

GCCCGACTGTCTACTGAACAACGGGAAGAGCCCGACTGTCAATGACGGAGCTCTGTTAAATA

TAGTTAAGGCTATTTTGTTGAATGAATGAAGCCAGACAGGAAAGAGGACAGTATCTTTAATC

CATTTATAGAAGTTAAAGACAGGCTTATTTAATCTCTATGAAGACAGAGTGGCCCTTACCTC

TGGGTGGAGCAAAAGGCACCTTCTGAAGTGATAGGGATGTTCCTTATCATCTTGATCCGGAG

TGGTAGTTACATGCATGTGTGCATATCAAAACTCACCAAGCTGTACCACTAAGTGTGTTCTT

CCTCAATAAAAATAATAAAGAACTACACTTATAAAGAATTTTTTAATAATATAGGAAAATGT

CTACACTATAATCTTTAGCTAAAAAAAAAAAAAAAAAGAAGCCGCCTACAGAATGGTATATGC

ATGAGAACAATTAATCGAAAAGTGCATGGGAAAAGTCAGGATTGAAACATCATGTTTTAAAA

GACATTGTTTTGATACTGTGAGAATGTACCTAAGTTTTTCCTTTTTTCTGTTTTTCCCAATT

TTATACAATGAGCATGTGTTGGTTTTATAATTAGACATTTTGTTTGTTTGGTTTGGTTTTGA

GACACAGCTTGCTGTCACCCAGGTTGGAGTGCAATGGCCCAATCTTGGTTCACTGCAACCTC

CATCTCCTGGGTTCAAGAGATTCTCCCACTTCAGCCTCCTGAGTAGCTGGGACTATAGGGGC

GCACCACCACATCCAGCTAATTTTGTGTATTTTTAGTAGAGATGGGGTTTCACCATGCTGGC

CAGGTTGGTCTCAAACTCCTGACCTCAAGTTATCCACTCGCCTTGGCTTCCCAAAGTGCTGG

GATTATAGGCATGAGCCACCGCACTTGGCCTAGACATTTGTTTTTAAAAATAAAAGATTCAT

TTGCTCTTTTTACAGCCCGTCTCACTGTTGACTGATATTGACCAGGAGTCAACTCAGGCCCC

AGGGATTTTCACAACAGCTGCTGTATGGCAGGGTTTCTGCTCACTGTGCTCATGTAGTTGGC

CCTTGCACCCAAAGTGAATAATTAACATTCTCCCCATCCTGTTGACGATGCTCTGAAAATAT

GGTCCAGAAATGGTGTGAGCAAGGAGACAGCAAAGCAATGCTTGGAACATAGGTGCAGTGAC

TAGACATGGGGCAGCTGTTTAAAGACAAAAAGGCCCCAAAAAGGAGGGATGGCACGAAACAC

CCTCCAATATGGGCATGGAGTCTAGAGTGACAAAGTGATCAAAAGTTCATTTCCTATGGGGT

GTCCGAATGTACTTAATAATAAAAAGAGAACAAGAGCCATGCAAACTGAGAGGGACAAAGTA

GAAAGAGTAGCAGACACCAAGCAACTAAGTCACAGCATGATAAGCTGCTAGCTTGTTGTCAT

TATTGTATCCAGAACAACATTTCATTTAAATGCTGAAGAATTTCCCATGGGTCCCCACTTTC
```

-continued

```
TTGTGAATCCTTGGGCTGAACCCCCCTGTCCTGAGTGGTTACTAGAACACACCTCTGGACCA

GAAACACAAAAGTGGAGTAACGCACACTGCAAAGCTGTGCTTCCTTGTTTCAGCCTGTGAAT

CCTCACCTTGTTTCCCATCTAGCCTATATTTTTCAAACTAACTTGGCCATAGAATCATGTAG

TATTTAGGGTGGAAGCTGCCCCAGGTCTAGCACGTCATTTAACAGATGAGGAAATGGAAGCT

TGGGCAGTGGAAGTATCTTGCCGAGGTCACACAGCAAGTCAGCAGCACAGCGTGTGTGACTC

CGAGCCTGCTCCGCTAGCCCACATTGCCCTCTGGGGGTGAGTATGTCTTCACATCCTCCAAT

ACCCTAATGACAGACAAACAGAACATGGCAAAGCCTCAGCTCTGCATGGTGAAAGTAAGAAC

CAGCAATTGCCACAAACAGAAATACAGTGTTGGTCCGGCAGCCTCCGGGGGTTCTGCACAAG

TGGATTACCAGTGAATACAAGGCTATCTATCTTTCGAAAAACCAAAGTTGTATTTATGCTAT

CTATTTTCTATAAAATTTTATATTAATTTATTTGTTACCTATTTTTGAACTCTTTCAAAAGC

ACACTTTATATTTCCCTGCTTAAACAGTCCCCCGAGGGTGGGTGCCCAAAAGGCTCTACACT

TGTTATCATTCCCTCTCCACCACAGGCATATTGAGTAAGTTTGTATTTGGGTTTTTTTAAAA

CCTCCACTCTACAGTTAAGAAAACTAAGGCACAGAGCTTCAATAATTTGGTCAGAGCCAAGT

AGCAGTAATGAAGCTGGAGGTTAAACCCAGCAGCATGACTGCAGTTCTTAATCAATGCCTTT

TGAATTGCACATATGGGATGAACTAGAACATTTTCTCGATGATTCGCTGTCCTTGTTATGAT

TATGTTACTGAGCTCTGTTGTAGCACAGACATATGTCCCTATATGGGCGGGGGTGGGGGTG

TCTTGATCGCTGGGCTATTTCTATACTGTTCTGGCTTTTCCCAAGCAGTCATTTCTTTCTAT

TCTCCAAGCACCAGCAATTAGCTTTACCTTTTCAGCTTCTAGTTTGCTGAAACTAATCTGCT

ATAGACAGAGACTCCGGTGAACCAATTTTATTAGGATTTGATCAAATAAACTCTCTCTGACA

AAGGACTGCTGAAAGAGTAACTAAGAGTTTGATGTTTACTGAGTGCATAGTATGTGCTAGAT

GCTGGCCGTGGATGCCTCATAGAATCCTCCCAACAACTCATGAAATGACTACTGTCATTCAG

CCCAATACCCAGACGAGAAAGCTGAGGGTAAGACAGGTTTCAAGCTTGGCAGTCTGACTACA

GAGGCCACTGGCTTAGCCCCTGGGTTAGTCTGCCTCTGTAGGATTGGGGGCACGTAATTTTG

CTGTTTGGGGTCTCATTTGCCTTCTTAGAGATCACAAGCCAAAGCTTTTTATTCTAGAGCCA

AGGTCACGGAAGCCCAGAGGGCATCTTGTGGCTCGGGAGTAGCTCTCTGCTGTCTTCTCAGC

TCTGCTGACAATACTTGAGATTTTCAGATGTCACCAACCGCCAAGAGAGCTTGATATGACTG

TATATAGTATAGTCATAAAGAACCTGAACTTGACCATATACTTATGTCATGTGGAAAATTTC

TCATAGCTTCAGATAGATTATATCTGGAGTGAAGAATCCTGCCACCTATGTATCTGGCATAG

TGTGAGTCCTCATAAATGCTTACTGGTTTGAAGGGCAACAAAATAGTGAACAGAGTGAAAAT

CCCCACTAAGATCCTGGGTCCAGAAAAAGATGGGAAACCTGTTTAGCTCACCCGTGAGCCCA

TAGTTAAAACTCTTTAGACAACAGGTTGTTTCCGTTTACAGAGAACAATAATATTGGGTGGT

GAGCATCTGTGTGGGGGTTGGGGTGGGATAGGGGATACGGGGAGAGTGGAGAAAAAGGGGAC

ACAGGGTTAATGTGAAGTCCAGGATCCCCCTCTACATTTAAAGTTGGTTTAAGTTGGCTTTA

ATTAATAGCAACTCTTAAGATAATCAGAATTTTCTTAACCTTTTAGCCTTACTGTTGAAAAG

CCCTGTGATCTTGTACAAATCATTTGCTTCTTGGATAGTAATTTCTTTTACTAAAATGTGGG

CTTTTGACTAGATGAATGTAAATGTTCTTCTAGCTCTGATATCCTTTATTCTTTATATTTTC

TAACAGATTCTGTGTAGTGGGATGAGCAGAGAACAAAAACAAAATAATCCAGTGAGAAAAGC

CCGTAAATAAACCTTCAGACCAGAGATCTATTCTCTAGCTTATTTTAAGCTCAACTTAAAAA

GAAGAACTGTTCTCTGATTCTTTTCGCCTTCAATACACTTAATGATTTAACTCCACCCTCCT

TCAAAAGAAACAGCATTTCCTACTTTTATACTGTCTATATGATTGATTTGCACAGCTCATCT

GGCCAGAAGAGCTGAGACATCCGTTCCCCTACAAGAAACTCTCCCCGGTAAGTAACCTCTCA
```

-continued

```
GCTGCTTGGCCTGTTAGTTAGCTTCTGAGATGAGTAAAAGACTTTACAGGAAACCCATAGAA

GACATTTGGCAAACACCAAGTGCTCATACAATTATCTTAAAATATAATCTTTAAGATAAGGA

AAGGGTCACAGTTTGGAATGAGTTTCAGACGGTTATAACATCAAAGATACAAAACATGATTG

TGAGTGAAAGACTTTAAAGGGAGCAATAGTATTTTAATAACTAACAATCCTTACCTCTCAAA

AGAAAGATTTGCAGAGAGATGAGTCTTAGCTGAAATCTTGAAATCTTATCTTCTGCTAAGGA

GAACTAAACCCTCTCCAGTGAGATGCCTTCTGAATATGTGCCCACAAGAAGTTGTGTCTAAG

TCTGGTTCTCTTTTTTCTTTTTCCTCCAGACAAGAGGGAAGCCTAAAAATGGTCAAAATTAA

TATTAAATTACAAACGCCAAATAAAATTTTCCTCTAATATATCAGTTTCATGGCACAGTTAG

TATATAATTCTTTATGGTTCAAAATTAAAAATGAGCTTTTCTAGGGGCTTCTCTCAGCTGCC

TAGTCTAAGGTGCAGGGAGTTTGAGACTCACAGGGTTTAATAAGAGAAAATTCTCAGCTAGA

GCAGCTGAACTTAAATAGACTAGGCAAGACAGCTGGTTATAAGACTAAACTACCCAGAATGC

ATGACATTCATCTGTGGTGGCAGACGAAACATTTTTTATTATATTATTTCTTGGGTATGTAT

GACAACTCTTAATTGTGGCAACTCAGAAACTACAAACACAAACTTCACAGAAAATGTGAGGA

TTTTACAATTGGCTGTTGTCATCTATGACCTTCCCTGGGACTTGGGCACCCGGCCATTTCAC

TCTGACTACATCATGTCACCAAACATCTGATGGTCTTGCCTTTTAATTCTCTTTTCGAGGAC

TGAGAGGGAGGGTAGCATGGTAGTTAAGAGTGCAGGCTTCCCGCATTCAAAATCGGTTGCTT

ACTAGCTGTGTGGCTTTGAGCAAGTTACTCACCCTCTCTGTGCTTCAAGGTCCTTGTCTGCA

AAATGTGAAAAATATTTCCTGCCTCATAAGGTTGCCCTAAGGATTAAATGAATGAATGGGTA

TGATGCTTAGAACAGTGATTGGCATCCAGTATGTGCCCTCGAGGCCTCTTAATTATTACTGG

CTTGCTCATAGTGCATGTTCTTTGTGGGCTAACTCTAGCGTCAATAAAAATGTTAAGACTGA

GTTGCAGCCGGGCATGGTGGCTCATGCCTGTAATCCCAGCATTCTAGGAGGCTGAGGCAGGA

GGATCGCTTGAGCCCAGGAGTTCGAGACCAGCCTGGGCAACATAGTGTGATCTTGTATCTAT

AAAAATAAACAAAATTAGCTTGGTGTGGTGGCGCCTGTAGTCCCCAGCCACTTGGAGGGGTG

AGGTGAGAGGATTGCTTGAGCCCGGGATGGTCCAGGCTGCAGTGAGCCATGATCGTGCCACT

GCACTCCAGCCTGGGCGACAGAGTGAGACCCTGTCTCACAACAACAACAACAACAACAAAAA

GGCTGAGCTGCACCATGCTTGACCCAGTTTCTTAAAATTGTTGTCAAAGCTTCATTCACTCC

ATGGTGCTATAGAGCACAAGATTTTATTTGGTGAGATGGTGCTTTCATGAATTCCCCCAACA

GAGCCAAGCTCTCCATCTAGTGGACAGGGAAGCTAGCAGCAAACCTTCCCTTCACTACAAAA

CTTCATTGCTTGGCCAAAAAGAGAGTTAATTCAATGTAGACATCTATGTAGGCAATTAAAAA

CCTATTGATGTATAAAACAGTTTGCATTCATGGAGGGCAACTAAATACATTCTAGGACTTTA

TAAAAGATCACTTTTTATTTATGCACAGGGTGGAACAAGATGGATTATCAAGTGTCAAGTCC

AATCTATGACATCAATTATTATACATCGGAGCCCTGCCAAAAAATCAATGTGAAGCAAATCG

CAGCCCGCCTCCTGCCTCCGCTCTACTCACTGGTGTTCATCTTTGGTTTTGTGGGCAACATG

CTGGTCATCCTCATCCTGATAAACTGCAAAAGGCTGAAGAGCATGACTGACATCTACCTGCT

CAACCTGGCCATCTCTGACCTGTTTTTCCTTCTTACTGTCCCCTTCTGGGCTCACTATGCTG

CCGCCCAGTGGGACTTTGGAAATACAATGTGTCAACTCTTGACAGGGCTCTATTTTATAGGC

TTCTTCTCTGGAATCTTCTTCATCATCCTCCTGACAATCGATAGGTACCTGGCTGTCGTCCA

TGCTGTGTTTGCTTTAAAAGCCAGGACGGTCACCTTTGGGGTGGTGACAAGTGTGATCACTT

GGGTGGTGGCTGTGTTTGCGTCTCTCCCAGGAATCATCTTTACCAGATCTCAAAAAGAAGGT

CTTCATTACACCTGCAGCTCTCATTTTC***CATACAGTCAGTATCAATTCTGG***AAGAATTTCCA
```

-continued

```
GACATTAAAGATAGTCATCTTGGGGCTGGTCCTGCCGCTGCTTGTCATGGTCATCTGCTACT

CGGGAATCCTAAAAACTCTGCTTCGGTGTCGAAATGAGAAGAAGAGGCACAGGGCTGTGAGG

CTTATCTTCACCATCATGATTGTTTATTTTCTCTTCTGGGCTCCCTACAACATTGTCCTTCT

CCTGAACACCTTCCAGGAATTCTTTGGCCTGAATAATTGCAGTAGCTCTAACAGGTTGGACC

AAGCTATGCAGGTGACAGAGACTCTTGGGATGACGCACTGCTGCATCAACCCCATCATCTAT

GCCTTTGTCGGGGAGAAGTTCAGAAACTACCTCTTAGTCTTCTTCCAAAAGCACATTGCCAA

ACGCTTCTGCAAATGCTGTTCTATTTTCCAGCAAGAGGCTCCCGAGCGAGCAAGCTCAGTTT

ACACCCGATCCACTGGGGAGCAGGAAATATCTGTGGGCTTGTGACACGGACTCAAGTGGGCT

GGTGACCCAGTCAGAGTTGTGCACATGGCTTAGTTTTCATACACAGCCTGGGCTGGGGGTGG

GGTGGGAGAGGTCTTTTTTAAAAGGAAGTTACTGTTATAGAGGGTCTAAGATTCATCCATTT

ATTTGGCATCTGTTTAAAGTAGATTAGATCTTTTAAGCCCATCAATTATAGAAAGCCAAATC

AAAATATGTTGATGAAAAATAGCAACCTTTTTATCTCCCCTTCACATGCATCAAGTTATTGA

CAAACTCTCCCTTCACTCCGAAAGTTCCTTATGTATATTTAAAAGAAAGCCTCAGAGAATTG

CTGATTCTTGAGTTTAGTGATCTGAACAGAAATACCAAAATTATTTCAGAAATGTACAACTT

TTTACCTAGTACAAGGCAACATATAGGTTGTAAATGTGTTTAAAACAGGTCTTTGTCTTGCT

ATGGGGAGAAAAGACATGAATATGATTAGTAAAGAAATGACACTTTTCATGTGTGATTTCCC

CTCCAAGGTATGGTTAATAAGTTTCACTGACTTAGAACCAGGCGAGAGACTTGTGGCCTGGG

AGAGCTGGGGAAGCTTCTTAAATGAGAAGGAATTTGAGTTGGATCATCTATTGCTGGCAAAG

ACAGAAGCCTCACTGCAAGCACTGCATGGGCAAGCTTGGCTGTAGAAGGAGACAGAGCTGGT

TGGGAAGACATGGGGAGGAAGGACAAGGCTAGATCATGAAGAACCTTGACGGCATTGCTCCG

TCTAAGTCATGAGCTGAGCAGGGAGATCCTGGTTGGTGTTGCAGAAGGTTTACTCTGTGGCC

AAAGGAGGGTCAGGAAGGATGAGCATTTAGGGCAAGGAGACCACCAACAGCCCTCAGGTCAG

GGTGAGGATGGCCTCTGCTAAGCTCAAGGCGTGAGGATGGGAAGGAGGGAGGTATTCGTAAG

GATGGGAAGGAGGGAGGTATTCGTGCAGCATATGAGGATGCAGAGTCAGCAGAACTGGGGTG

GATTTGGGTTGGAAGTGAGGGTCAGAGAGGAGTCAGAGAGAATCCCTAGTCTTCAAGCAGAT

TGGAGAAACCCTTGAAAAGACATCAAGCACAGAAGGAGGAGGAGGAGGTTTAGGTCAAGAAG

AAGATGGATTGGTGTAAAAGGATGGGTCTGGTTTGCAGAGCTTGAACACAGTCTCACCCAGA

CTCCAGGCTGTCTTTCACTGAATGCTTCTGACTTCATAGATTTCCTTCCCATCCCAGCTGAA

ATACTGAGGGGTCTCCAGGAGGAGACTAGATTTATGAATACACGAGGTATGAGGTCTAGGAA

CATACTTCAGCTCACACATGAGATCTAGGTGAGGATTGATTACCTAGTAGTCATTTCATGGG

TTGTTGGGAGGATTCTATGAGGCAACCACAGGCAGCATTTAGCACATACTACACATTCAATA

AGCATCAAACTCTTAGTTACTCATTCAGGGATAGCACTGAGCAAAGCATTGAGCAAAGGGGT

CCCATAGAGGTGAGGGAAGCCTGAAAAACTAAGATGCTGCCTGCCCAGTGCACACAAGTGTA

GGTATCATTTTCTGCATTTAACCGTCAATAGGCAAAGGGGGGAAGGGACATATTCATTTGGA

AATAAGCTGCCTTGAGCCTTAAAACCCACAAAAGTACAATTTACCAGCCTCCGTATTTCAGA

CTGAATGGGGGTGGGGGGGGCGCCTTAGGTACTTATTCCAGATGCCTTCTCCAGACAAACCA

GAAGCAACAGAAAAAATCGTCTCTCCCTCCCTTTGAAATGAATATACCCCTTAGTGTTTGGG

TATATTCATTTCAAAGGGAGAGAGAGAGGTTTTTTTCTGTTCTGTCTCATATGATTGTGCAC

ATACTTGAGACTGTTTTGAATTTGGGGGATGGCTAAAACCATCATAGTACAGGTAAGGTGAG

GGAATAGTAAGTGGTGAGAACTACTCAGGGAATGAAGGTGTCAGAATAATAAGAGGTGCTAC

TGACTTTCTCAGCCTCTGAATATGAACGGTGAGCATTGTGGCTGTCAGCAGGAAGCAACGAA
```

-continued

```
GGGAAATGTCTTTCCTTTTGCTCTTAAGTTGTGGAGAGTGCAACAGTAGCATAGGACCCTAC

CCTCTGGGCCAAGTCAAAGACATTCTGACATCTTAGTATTTGCATATTCTTATGTATGTGAA

AGTTACAAATTGCTTGAAAGAAAATATGCATCTAATAAAAAACACCTTCTAAAATAATTCAT

TATATTCTTGCTCTTTCAGTCAAGTGTACATTTAGAGAATAGCACATAAAACTGCCAGAGCA

TTTTATAAGCAGCTGTTTTCTTCCTTAGTGTGTGTGCATGTGTGTGTGATGTATACAAAGAG

AGAGATAATTGTATTTTTGTATTTTCTTTTAAATAATTTTTAAAATTGACCCTTTTCCTGAG

ACAAATTGCCAGAATAGTTTGTATTTAGAGATGGTACCTCTAAGAGTAAGGTTGCTGGTTGC

TGAGCAATTGACTTGAAAACTTTTAAAATTCAAATTTTAATTCCACTACTCAAAAGAATTGC

CATGTTTTAAAAAAGAGAATTGGTGCCATAAGTTAGTTGTCTATGTTTGAAAATGAAGAAGA

TATGCAACGTCATGGCCTGGTCACTTACCCGCAGCCCTGAGTTGTAGGCACATCATATGTGA

GAATGAGGATGCTTTTCTTTCATTTAAAATCCCTCCCCAAAACTTGGCTCTAATTGCAGTCA

TGACAATCATGTACATTTGGATTTATGTGCACGAGTCTCTTACCCTGAGAGAGGACAGGTGC

TACAGGTGGAGGGGACCCGTCTGGGTCACGTTCACATTTTGAACATGCTGGTTTTCAGTCAC

TGCACACTCATCTCCCAGCACAGGTCATGGGCAGCAGATGCAAAAGCTGCCCGTGGTCCTAT

TTGGAGGTGCATGAAATGAGCAGAAGACAGAACAGCTTGATCTGACTAGAAGGGCAGCTTGT

CCCTACCAAGACTTGAAGGATTGCCTTTCATCTGTTAGGGTAAAAGGTAGAATGAACCAAGG

AAGGGCAGGAGGGGGCTGGGGTTAGGGTAGAAGGAAGGGGCCATGGAGAAGGGAGATCCATC

CCATAGGAGGAAGGCAGTGCGGCAGGGAGGTTTGAAGGTATCAGCTTTTGTGGCTGACATAC

ATGCAGTCATGTCAATTGCTCGTTTTTCCTTTTCCATCTTATTAAATGTCTTCCAACGTTAG

CACGAAGAAAGCTATTTGCAGTGTTGCCAGCCTTTCCAGAGCCCGTCCCCATTACCTCCCC

AGGCCCATGCCTTTACTCCTTGGAGTTTCAACTCACGACCTTCAGGATCTGACTTTATTCAC

CAACTCTGGGGTGAACGTACCTTCTGTCTCCACCCAGAGGTCTCTATCAAAGAGGAGATTGC

ATGCCATGGATAAAGTCAAAGTAGAGGTGACTGTCCTTAGGAAGAGTAATGTGAAAATTCAT

AAACTGGGATTCTGTTTACATTTTGTACTCCAGGGGTTCTTAGTTTAAATCGCTCTGAATAA

ATTAAGATGCAATGGCATTTCAACTGTTATGATTAAATTTACAAATCATTTATTTTCTATCA

CGGGGAGAGATAGAGCTCCAAATGCAAACATAACTGCTCAAGTGTTAACACTTATAATGAAA

ACATAAGAATTACCACCAACTACCCTGGGGGCTAGAAGCAGAAATGTGAACCAGAAAACAAA

TCATGAACTTTCCTTTTTTTTTTTGAGATGGAGTCTCGCTCTGTTGCCCAGGCTGGAGTGCA

ATGGTGCGATCTCGGCTCACTGCAACCACTGCCTCCCGGGTTCAAGCAATTCTCCTGCCTCA

GCCTCCTGAGTAGCTGGGACTACAGGCATGCACCACCACGCCTGGGTAATTTTTTGTATTTT

TAGTAGAGACAGGGTTTCACCGTATTAGCCAGGATGCTCTCGATCTCCTGACCTCGTGATCT

GCCCGCCTCGGCCTCCCACCGAAGTGCTGGGATTACAGGCATGAGCCACTGTGCCCGGCCAA

CAAATCATGAACTTTCTAACTGCAGTTCCTTGTAGCTTGTTAACACATCCACTTACTTATTG

TCAGAGTACGTGGAGATTTTCCACAACCCTCGGGGATAAGGCTGAACAGAAGAGGCAAAAAC

GTGAAAACATTTCGATAGCTCCTATACTTTGAAATAAAATTCACTGTAAAAGTTGCTTGTAT

TTTTCCAAAACAGAGTCAACCCTTAATATTTAAGATTCTGTATACAAATACATATTTTTATA

TAATTAATATATATTGTCATATGACATATATCTTTATATTAATATGCATGCATATAATATAT

ATTTCCTTCCTAATTTTCTATAAGCAATTTTACAAGACTGACTTCTATTTGCCTCCTTATTG

TTACTACGTGGTTTGATAATCCGTTTTGTGTCATTGTGATTCTGTCATGTTTTGGGGACTTA

TTTTTGTTTCTCTGGGTGGTCACTAGTTTTTTTAAAGCATTCATGGAAGAGTGTGAATCTTT
```

-continued

```
TACAAGCTAGGAAGCCATGGCAAGCCTTGGGTCATACTGCCCCCGCGAGGCCACATTGGCAA

ACCAGCAAGGGTGTTCAACTTCCAGACTTGGCCATGGAGAAGACACACGAGGAGGCTTTTCA

CATTCAGCTCTTTAATGTTTGTCTCTGCCGGCACCATCCCAGTTGTGAAAAAGAGGTATTTC

CACAGCGGCTCAGGGTAGGTAGTGCACAGCTCACATTCATCATTTCTGAAAACCGAGAGGAG

TCTCCATTCGGGGTACAGGTTGATGCCTGTCGTGGAATGAAGGTTCCAACACCCAGACCAAT

CTCTGCAGTGTGCTGCTCTCATGAGCTTGCAACAAGATCAGAAAATGTTTTGTGACTAAGCA

TTTTTCATATTGCATAAAATGCTTCAAGCTCCTCCCTTGTTTCTCTCTATAATCCTGTATAT

CTGATGATTGTGGGTACCAAGTGTTTGAAATAATCAAATGTGATTTGATGTTGGTAAATTTC

TTTTTTTTTTTTTTTTTACTTCTATTTTTTTTTATTATACTTTAAGTTTTAGGGTACATGTGC

ACATTGTGCAGGTTAGTTACATATGTATACATGTGCCATGCTGGTGCGCTGCACCCACTAAC

TCGTCATCTAGCATTAGGTATATCTCCCAATGCTATCCCTCCCCCCTCCCCCCACCCCACCA

CAGTCCCCAAAGTGTGATATTCCCCTTCCTATGTCCATGTGATCTCATTGTTCAATTCCCAC

CTATGAGTGAGAATATGCGGTGTTTGGTTTTTTGTTCTTGCGATAGTTTACTGAGAATGATG

GTTTCCAATTTCATCCATGTCCCTACAAAGGACATGAACATAGCAAAGACTTGGAACCAACC

CAAATGTCCAACAATGATAGACTGGATTAAGAAAATGTGGCACATATACACCATGGTAAATT

TCTTTATCATTCGCACTCTCCTTTCTCTATTATTGTTATTGTAACTGAACCGCAGATTAGTC

ACTCATTGCTTGCAGAATCCAATTAACAAGAGCGAGGTCAGATATAAAGAAAATGATTTATT

CCAAACCTCCTTCAGGGAAGAGGTGCAGCCTCCTGCCTCTAAATGCACTGCTTCGCCAGGCG

TGGTGGCTCACACCTGTAATCCCAGCACTTTGGGAGACCGAGGAGGGCAGATCACTTAAGGT

CAGGAGTTCAAGACCGGCCTGGCCAATATAGTGAAACCCCTGCCTCTACTAAAAATACAAAA

AATTAGCCAGACGTGGTGGCGGGTGCTTGTAATCCCAGCTACTCGGGAGGCTGAGGCAGGAG

AATCGCTTGAACCTGGGAGGTGGAAGTTGCAGTGAGCTGACATCTAGCCACTGCACTCCAGC

CTGGGTGACAGAGTGAGACTCTGTCTCAAAATAAATAAATAAATAAATAAATAAATAAATAA

ATAAATAGTAAATGCACTGCTTTGCTTTTGGAGCAGAAAGCAGGCACTTTGAAAAGGCAGGG

GAGGAAGTGAGCAAGGGCAGGGGGTCTGCACACTGGCATGGTGCCTGATCTATCCAGGCAGT

TGAATTGGCACTTTCATAGGCAGAAATAAGTTGAAAAAGTGGCCTAAAACTCTCTAGGTGGG

AGTGGATAGTGGGCATGCCTTCAACCTGCCTTTCTGGAGGGTGAGTTCCATGGCAACCCCCT

GAAGGGTGAGAGTTCCATGGAGATCATGCTTTGGTCTGTAAATCAGCTGTTAACTCTCTAGA

AAGTTCTGTCTTGGAGCATATAGTTAGATGAACTTGCCCTGTAAAGAATGTCTGGTGAAGGG

GAAGTAAAAGGTGAGATTTGCATTTCTAAAGGGCTAAGTAGAAAGTGGGGTACAAGAGGAAA

GGAGAAAAGAGAAAATAATTTAAAAAATAATTGTAACTTATTCCCTTTTACTTAGAAAAAAG

GGAATACTCAGTTACATTATCACCTCGTTTACATCAAACCCTCTTATGGAATCCTATGGTTT

GAAAACAAAAAGGTTGTTGAGGACCAGTGAGCCCAACCCCTTTGCTTTATAAATGAAGAGCA

TTGCCTGCCCTAAGCCCCAGAGACTCTGATGTCGTGGGTCTGGAGTGGGCTCCAACAGCGGC

ATGTTTTGATGGTGCTTCCCAGTGGCACGCCAGCGATGAGCCTTTGAGTAGGGAAAGTAGGA

GCACTCGTGACTCCCTTCACGATCAGCACCTGTGTGCTAATAAATTCACAAAAGCCAACATA

TTGGAGTCACTCAGGGAGTTTTACAAATAGTGAGGTTAAATCCAACCTCAAATAGTTCTGAT

TCGATCTGCCTGCATTGCTGCCCTGTGGTTCCCCACTGTAGAAGCTCCCCAGGTGATTCTAA

GTGTAGCCAAGTCTGAGAAATACTGCCTAAAGCCTGTTGGACTGACAGCAAGGGCTGTTGTC

TGAGCAAGACTTTGCCTGGCCTGGGGTGGCATGTGCACCAGGAAGAGTCTCAACTTTCATAA

CAGAACATTCCCCAAGCTGGTTTTTTTAAAGCATGTGAATCTAGACTTCATTGGCAATACCA
```

-continued

```
AAGATCTGTATTTGAGGCTCCAAGTATTTCACTTTCATTTTTGGTTTTGGGTTATGTTTTCA

CCCTTCCTTTCCAAGTGAAAAGTAAACAGAAGTGGGATGTCTGGCGCCCATGCTGAGCTTGG

CAACTTCAAATTCAATAGAGAAGAAGTCTCTTGTATAGAAAAGGGCCTGTCTGAGATGTTTC

TCAAATAAATATAGATTTTGCTTATGTGGCTAAAGGATTCTTCTCCCCCCATTTCCTTATCC

CTGCAGTGAGCCATCCTTCTTAACTCTTTCCATGAAAGCATTATTCCTGAAGAACTGGGAAC

TCATGCCAGCCCTGATCAGGCAATGATAATTCTGCAGAGAATTAGAATTTAGATTTAAATTG

TCAACTCTTATACATCCTGGCATATGGTTTAAACACATGTACACACACACAAACACCTCCTA

CTATTTACTGAAGAGCAGATATCTGATAACTTAATCTTTTTGGTTTTGAGTCAAGACAATTC

CTCCTTTTGAAACTGCATACCGCTGAATATAATAAAATGTAATTAAGATTAAAAATAAGAAA

CTAATGGGAGAATTTCAATATTGTCTATGTTCACTTTAAAATTCCTCTACTTAGGTTTACTG

CCATTACCAAAGACTATTCAAAAATCCTTTTTAGGAGAATCCTAATGGTTTCCTGACATATA

ATCAAATAAGGACTCTGTTGATTGGCTAACTCAATCTTCCTGTGCCAAAAAGCAGAGCCCAG

CAGAGAAGAGGGCAGGGACTTGAAAGTCAGACTGACTCGAGTTCCAGCCTTGGGGCTGTGGG

AGCTTGGGCAAGTGACTTAACGTCTCTGGCTCTCAGGATCTAAAAGGATTTCCAGTAGTAAT

TTGGGGTGTTACTGATACAGGAGCTAAAAAGAAATTATTTAGGTGGTTAGTGAGGGTCAGAG

AGTCCTCGGTAAGATTTGCCTTTTAACAAAAAGCAGCCCCAAAATCATTTGTTTGCTAACAA

AGAGAAGCCTGTAAAATTGAGCTGCAGACATAGATAAGCAAGCTGGAAGCTTGCACGGGTGA

ATGCCGGCAGCTGTGCCAATAGGAAAAGGCTATCTGGGGGCCAGGCATGTTCAACATGGATT

CTCCATCTTCCCTTTTCTTTGTCAACCAAGTGTACAGTAAAGGAACAGGCAACATGGCACGG

GCCAGGTAGAGAACCCTTCTGCATAATAAAAGATTAGGGTGAGATGGCCAGCTTCTTCCCGT

GCTATGTAAATGGCATACCTGGTCCAACCAGTCTTTTGGGCCCTGTGTAAATCAGACACCGC

CTCCTCAAGTTAGTCTATAAAACCCCATGCATTTTACCGTGAAACTGGGAGATCCACTCGGA

ACCCCCTCCTGCACGAGAGACCTTTTCTCTTTTGCCTATTACACTTCCGCTCTTAAACTCAC

TGCTCATGTGTTAGCATCCTTGATTTCCTTGGCATGAGGCAACGAACCTTGTGTATTACCCC

ATACAAATGATGCTGCTTCATTACTAATAGCAACCTGACAGGGTTGTGTTGGGGTATAAATT

ATCTAGACCAGGGAGATCCAATATAATTTTTTTGTAATGACGGGAATGCTTTGTATCTGCAT

CATCCAAAATGGTAGCCACCAGGCCAGGGTGAAATGTGGCCAGTGTGACTGAGGAACTGAAT

GTTTTCCATGATTTAATTTAAATGTGGCCAATGGCTACTGTAGGAGACAGTGTGAGTCTGGC

ATATTATAAATAATAAATATTAATATAATTTGAACTTTGGCATCAGTGTTTCCTAGATTTGA

ATTACTATGCAAGTTGCTTACTGTTTCCAAGCCTCAGCTTTCTAATCTGTAATTGGGGCTAA

TAATAGTATCTGCCTTACAGGTTTGTTCAGAGGATAAATGAGAAATTGCATGTTGAGGGCTT

AACACAGTGCCTGGCACATAAAAGCTCTGGTAACAGTTAGCCACTTTAATAATTTGCTAATA

ATGGCTATTTCTTCTTCAGATTAGGATGTGCTCCCCCAAACAGTGCACTTAGACATAGCGGG

CAATCCAGCTCACTCTCTGCAGTGAGAGAGAAGCACTGGCCGACCAGAGTCAGCCAGGGGCT

CATGGGTATGAAATCAACAGCATGATTTTGTAAGTAATGGATGGAAAGGGCCTCACAACTTT

ATGGCACTGTGTTCAATTTGCTTGGTCTTCTGTAGCTCCTTTTGAAAGCCTTTTAGGGTGGA

TTAACCTGCTACCAATAATTCTGGTCAGATGTAGACTCCATAGCTCAAAGCAAACTGAGAGA

GTGAGGGCAGCAGGCCAATTCCCCACCCCTTCCTTCTGGACTCTGACAGAAGCTTACACTCA

AGGAAGAGCAAGTAGGAATTAACGTGTTAAGAGCTAGGTAAGCAAAACCCAATGAGAAGTTC

TGGCAAAGCCCCATGGGCAGGGGTGGCTTAGGCACAGGAAACAAGTAGGATTTCATACCACG
```

-continued

```
CGCCTCAGTCTACTTCCGGGGCCCTCATCCTCAGCTGTGCCTATGCAAAGGAGAGCAACCAA

TAAACCCCACCGCCACTCTCCTACTGTGGAGGCCAGGGATGGCCAGGGGTAAGAGAGGGATG

GGAAGTGTTTCCTCCAGCCGTCCTCTGAGAAGGAGAGGAAACTGGGCAGAGCTTCTGTCCTC

CTTCAAGCAGAAACAGAAACAAAAGAAACCCCTAAGGGGGTTCTTACTTCCCCTCTAGTTCA

GTTGTGCACTAACCATCTGCAGCTCAACATTCAGCATTCATTCATTGATTCAGCAAACATTG

AAGGAGGGCCAGCTATGTGCCAGATGCCAACTCATGCCATGAAAGAGAGTCCCTGTCCTTAT

GAAATTCACTATTTAGAGAGAAAAGCAAGCAAAAAGGCAAAGTTTGAAAAGTACTGTTGAAG

TGGCATCATTGTCTGGGGTGAATACCTGAGGTTTGTGGTCTCACGCCAAGGGAATCAAGGAC

TCAGGCACACAAGAAGTGAGTTTAAGAGCAGAGGTTTAATAGGCAAAAGAAAGAGAAAAAAG

AATAGCTCTCTTGCCTGCACAGAGAGAGGGGCACCTGAGTGGATCTTCCTGTTTTGTGGTGA

AATGCAAGGCATTTTATAGACGAGCTTGAGGAAGTGGTGTCTGATTTACTTAGGACCCGAGA

GATTGGTCAGACCAGGTGTGATGTTTACATAGCATACAAAGAAGCTGGCCATCCCATCCTAA

TCTTTTATTACGCAGACGGGGTCTATACCTGGCTGGTGCCATGTTGTCTGTTCCTTACTGTA

CACGTGGTTGACAAAGAAAAGGGAAGATGAAGAATCCATGTTGAACATGCCTGGCCCCCAGA

TAGTCTTTTCCTATTGGCACAGCTGCCGGCATTCACTCTTGCAAGCTTCCAGATTGCTTATC

TATGTCTGCAGCCCAATTTTACAGGTTGCTCTTTGCTAGAAAAGAAATGATTTGGGGGCTGC

TTTTCATTAA
``` hRosa26 sequence (SEQ ID NO: 4)

(Putative guides for insertion of a integration site are *indicated*)

```
ACCATTTAAACCTCAAATTAAGCAACCCACAGAACCAGGAAGTTCAAGGACCATGTCTGTTT

TCACCACGATGTCTTTCCCCACCCCCCCACCCCCCACTCCACCCCCCACTAAGGGCAGGGTA

TTGTATCTGCCAGACTGGGTATTTGTTGAACAAGCGAGTATTTTCGCCTATTAGCTTAGTTT

TTAAGGAAATCATTTTTTACTTGATTCATCATAGCTTTAATTCTATTACATACTACAATAAA

AATTTGACAAGACTGATACAAATATGTAGTGGGCAATAGTTTGCCGTCTTCTTCCCTAGTAT

GGTGTTTTTCAATCTGGTGACTAGAATAGGCAGTGGGCTATAAGCAGGATTCATAAGGCCTG

GAGCTGAGTTATATGTGACACTGCCACCTATTCATTGTGTGACCTTGGTTTTAACCTTCAAA

GTGGGTCTCCTGGACTAAAAGAATGTGAAAAGATGGGGAAATAAATCTGTAATCTGAACATG

GAATGACTTAGTTACAGACCAGACATATTGTTACTGGGAATGAAAAAGTCAATATATTTGAG

GGGAAAAAAATGTAAATAAATATTGAGAAAGATTTTACAAATCTAATTAGGGGAAGATAGTT

ATCTCCCAATACTAGAGGGTACCAGAGTGCTTTTAAGGGGAACATTTGGTTACCCTTATTTC

TTTAAAAAATGGCAGTTTAGGAAATTCTGCCCTAACTGTAGTCCCAATGTCAGATAGGACTC

AGGTCTCCACTGCAAGGACCAAAATGTTAAGTTGAAGACTGAAAATGGGAAAATTTGGAAAT

GTCTTTGGAACCTCAAGTACATAAAAGCCTGTAAGTGCTTCATACTCATTAACAACATAGGC

ATAGAAAAAGATATCCTTATTCTCAAGCATAGCCTTTTCTAATAAGTTCATGTTAGATGTC

ATGAAGTTTAGTGAGGAGTGAAAATCTATGAGGAAAAACATGAACCATTCTACTCTGGCAAA

AGTTCAGGACAAACACCATAGGCCTGTATACCAAATTTTAAACCATGTTGAATAATGTGAAA

AAAAGCATCACATTGCTTATGAAAGGCTTTCCTGTCGCCCCTTAATACTTCTGTCTCAGGCT

AACATGTTTGTTAATGAGTTACAGTGGTGAAGTTAAGGAAATCTGCTTCCTGTCCTAGCATG

CCCATTATCCCAGCCATACAGATTTAATACCAGGAGTCACTTTAACTCCATGAAGTCATTCA

ACAGGTACTTGAGTATTTACTATGTGCGTTTGTGCTAGAGTAGCCATTTCTTAAACTTTGTG

GCCTCAGAGAATCCCTTCACATTCTTAAAGATTGAGGGCCCCAAATCACTTTACTAGTATCT
```

-continued

```
TACCATATTAGAAAGTAAAATATTTAAATATTATAGCAACAAATGCATATTTTTAAAAAAAT

AGGTGCATTGTTTTACATTTTGGCAATTGTTTCCCTAAATGTCTGACTTAAATAGAAGACAA

CTGAATTGTTTCTTTTGCATTCAATTGGTTACAATGTTACTAGCAGTTTTCTATAATCTCAC

GTATTAGTCATTAGGAAAATATAGCTTCACTGAGTTATGTCAATCTCCCAAATGTTGGCCCA

TTTTACTGTATACTACCTAAAATATCATTGGCCGGGCACAGTGGCTTAAACCTGTAATCCTA

GCACTTTGGGAGGCCAAGGTGGATCACCTGAGGTCAGGAGTTCAAGACCACCCTGGCCAACA

TGGTGAAACCCCATCTCTACTAAAAATACAAAAATTAGCCGGGTACAGTGGTACACACCTGT

AGTCCCAGTTATGCAGGAGGCTGAGGCAGGAGAATTGCTTGAACCCAGGAGACAGAGGTTGC

AGTCAGCCAGATGTCCCAAAAAAAAAAAAAAATTATTTTCAATATCACTATCTCATGAAGTA

TTGGGAAGCTGTCAAGTTCCTGATATTAGACACAAGTTTTCCCGAAATTCTGATTTTGACTC

AACGTTTGGATTTTATCATTGAAAACAATTGCTGTCAGTTGTTAGGCTCCAAGGAAATAGCA

GATAATTCAGCTTACATGAGTGCTTTTTCTTGAGACAACCATTTCAAAAAGTTATGTACTGT

AGGGTTTAAGATTTAACAAAATGTCACTGCTTTCACAAGGACATTCTTGAGTGAAACTGGTT

TTTTTCTTTTGTGGGGGTTCACACCACAAATGCATGGCAGTGAAAAATAACTTAGAGTTTGA

TGCCACTGCCACAGTTTGTGCCAAGGTGCCTGAAATTTTACTTTTACCTACTGTTGCCTTAT

CACCACTCTTATGTCAACATATAGTTTAGCATAAACCATGAGATTTTAAAAAGTTATTCTAC

ACTTGCATTATTTCAGGACATGTGTTTGTTGCCAAGCTTTCACGTAAGAGTATCTTTAACTA

GTTGGTGCTGATGCCTGGCAAATACAAGCCAAGTAACAAGTCCAGCCATGTTTATGCACGCA

TCCATTGATAACGTATTAGCACAGTCAGCCCTCCATATCCTCAGGTTCTGCATCTGCAGATT

CAACCAAATGTGCTTGAAAATATTTGAGAATATTTAATACAATAGTACAAATATAAGTACAC

AATGTAACAACTATTTATATAGCATTCACATTGTATGAAGTATAAGAAATCTGGAAATGATT

TAAAGTATATGGGAGGATGTGTGTAAGTTGTATGCAGATACAGCGCCATTTTATAAAAGGGA

ATTCAACATCCTTGGGTTTTGGTGTCCTTGGCAAATGGCCAGCAAGGGTGGGGGAGTGCTGT

CCAGAAACCAATCCCAAAGCAAGGGACAAATATATACTTCTACAGATGAGATATTAACTCAG

AATCCATGTCTGCACACACATCTTTAATGACAAGTTGCTTTATCACTCAACAGCGGCACTAC

TATGATCTTTTACTTACACTTCAGCCAGCAGAGACATTCAGCAGTGTGAGATTTTTTAAGTT

TTTCAGCTATTGTGTATGTTTCTAGTGTATAATAAAGTAACTTATCCTTTAAGATACTTAAG

TAGCTTTTCATTTCTAGCTTTAAAACCTGTTTTTTTTTTTTTCCCAGTAGTGGCATACCTGC

ATTAAAAAATAATGCCTTACCAAAAAAAGCACTCTGAATGATTGGTTTCAAAATGATGCCAC

AACATAGGTGGCACCAACACTATTCAAGATCATTCCATTCCCATCTCTAAAAAAATTTTTGG

CTGGGTATGGTGGCTCACGCCTATTAACTCAACATTTTGAGAGGCCCAAAGCAAGATCACTC

AGGGCTAGGAGTTGAAGACTAGCCTGAGCAACATGGCAAGATCCTGTCTCAAAATTCTTTTT

AAAATTTTTTTAAAAGCCCAGGCTTGGTGGCGCATGCCTATAGTTCCAGCTACTCAGGAGGC

TGAGGCAGAAGGATCTCTTGAACCCAGGAGTTTCAGGCTGTAGTTCACTATGATGGCAGCTG

TGAATAGCCTGGGCAACACAGCAAGACCTCATCTCCAAAAAAAGACAAAAGAACTAAATTAT

TCTACTGCAGAACATGATTAGGTAAATATCTCCAAAGCAGAAAGACAGGTTTCATATTTTCG

TTAGTTTGAGTCAGTCCTTCCAAATCAAATCTTGTTTTTTATTAGTATACAGATGGTATAGC

CAGTAAGTAAATGAGAAGCAGTCTTTTTAAGCCGATCCATTCTTAAATGAAAAAATATATAA

ATATTTTAGAATAAATTTATTAAATTCTAAAGTTGTAGAATTTTTAAATTTGGATATTTTGG

GAAAATATTTAAACCACTATTGCAAACAAAACAACAAAATGTACTTATGTTTATACTTAGGC

ACAAAGAAAACTACAGTATTTTAAAGTAACCATTACACAATATTGAGGTTGCAAAGATTACT
```

-continued

```
GAAGGCATAACCTAAAAAATGAGTTGATTTCTAAAAATGGGAAAAAGGAAAAAAATAATTTC

TAAAAACAAGTATGCATACCTAAACCTACCTAATGACACCTTAGAAAATTCAAGTATAGCAC

CATTCATTAACATCAATGAGGATGTCATCACACATCATGTAGCCTCTGCACACCGTGAGAAT

AAATGAAAAAGACAGGCATCTTGCTATCATGACAATAGTTTTGACCTCGCAGACCTCTCTGT

GCTTACGCAACGGATAAAGCCATAAGAACTGTCCTGCCCTCAAGGAGCAACCTAAAGTAGGA

AAAAAAAAACAAAATTACACAATTATTATTTACAATTGTGAGAAGAGCTCTTGACAACATTC

AAATGGAGGATACAGTGTAGTAAGGGTGAGGGTATCAAGGCTTCCTTGAGAAGTGATGTTTT

GAGGCCATTCTTTCTTCTCAATAACTGGTATTTGGTTCCTGAATCCTTTAACTTCCTTACCA

TTGTCACTCCTAAGCCAAATCTCATTACGTCATGTCTAGACTACTGTTAAGAGAACCACTTA

AGTGGTCTCTGCAGCCCTCAATTTATTGGTGTTATCTATGGGAAAATTGCTCAAACTCTAAG

CCTTAGTTTCCTACCCTATAAAATGGGGTTTTATATACAAGGAACATACTAAATACACAGGT

ATACCTCAGAAACACGGCAGGCTCAATTCCAGAGCACTACAATAAAGCGAATCTCATGAATT

TGTTGGTTTCCCAGTGCATAAATTATGGTTACACTATACCATAGTCTATTAAGAAGTGTACA

ATAGCATTATGTATAATTGATAAATACATCACTGCTAAAAAAATGCTAACAATCTTTTTGCT

GGTGGAGGGTCTTACGCCAACGTTAACGATGGCTACTGACTCATCAGGGTGGTGGTGGTTGA

AGATTACGATAGCTGTGGCAATTTCTTAAAAGACAATGAAGTTTGCCACACTGACATCCTTT

CACAAGACTTCTCTGTAGCATGTGATGCTGTTTGATAGCATGATAGCATTTTACCCACAGTA

GAACTTTTTTTTCCTTTTCCTTTTTTTTTTTTTTTAAACGCAAGGTCTCACTCTGTCACCCA

GGCTGGAGTGCAGGGGCGCCATCTCGGCTTACTGCAACCTCCTCCTCCCTGGTTCAAGAGAT

TCTCCTGCCTCAGCTTCCCAAGTAGCTGGGACTACAGGTGTGCACCACACCTGGCTAATTTG

GTAGAGGTGGGGTTTCACCATGTTGGCAAGGCTGGTCTTGAACTCCTGACCTCAAATGATCT

ACCAGTCTCGGCCTCCTAAAGTACTGGGATTGCAGGTGTGAGCCACCACACCCAGCCAGTGG

AACTTATTTCAAAATTGAAGTCAACTCTCTCACACCCTGGCACTGCTTTATCAACCAGGTTT

CTGTAATTCCTAAATCCTTTATTGGCATTTTAACAATGTTCACAGCAACTTCACCAGTAGAT

TCCATCTCGAGAAACCACTTTCTTTGCTCATCCCTAAAAAGCAACTCCTCATCCATTCAAAT

TTGATCATGAGATTGCAGCAATTCAGTCACATCTTCAATGCTTTACTTCCAGTTCTAGTTCT

CTTCCTGTTTCCACACCTGCAGTACACAAAAAGCATTCAATAACTATTACTTCATTTCTTCT

ACCTATGTTTCCATTAGCTTTTGCCTATAGTACGCACTAGAGTATGTTACCATTATTTGTTA

TAAGTAGTACCTCATTATTACACTATTCGTAAGCAATACCTCAAGGTCTAAGATTAGATTTT

AAATCAAGGTCAGTAAAAATAGAAAAGGCTGTGAAGACTGTTGACTGACTTTACCAGAATCC

ATACACTAGAGGTGAGATTAGTTAGGTGATGAAATAACCATTCTATAAACATGATCTGAAAC

TCTGTTACTGTTGTCAGCAGGAAAAGCCAATGTTACATATGTTTAAAAAAGAAAAAAAAAAC

CCAAAACCAGAAACAAAAGGTGACAAAGTATCAAGACAAAAGGTCACTGATGACTGATCTC

TAGGAAAAGCTGGAAAGCAGGATTATTAAATGTAACCACGACTAAGATAAAAATCAGAGACA

GAAAAGTCTTTGTCACCAAGAAGATATACTCCATGAGAGAGCAGAAACAATTCATCAGGTTT

AACCCTGCTCTAGATAAAATAAAACTATCTGATTCAATACTCACACTTCTCTAATAATCCAA

TACATTATCCCATCTCAAGAAGAGAGAGTCACAGATAAGAAAAAAAAGGCTTCTTGAGAAGT

ATGTGCTCTAATATAAACTAATATGCCACTAAGAAAGCAACCTGCAAAGTCCAGTACCAGAC

TTCTGGATTTGTGACCTAACAAGGTGCTCTACAATTAACCTAACAGTCAAACCAGAGTGTTG

TAAAAGAGAATTATGTAATTATGCCAAACCTCCACTCACAAAAAATATATGGAAGTAACCTA
```

-continued

```
AGTTTACATTTTGCAAATCTCACACACACACTAGCCCTGACAAAAGTTTCACCAGCTTTCTC

ATCCAAGTACAAGCGTGTAATATACTTAATAAATTTGTCTTATAAGGGTAAGAAATAGTATG

TAACTACTTGAAAAGGAGATAGGTAGCTGGTTAATTTAAACAAAAAGCCCAAGGAAGTAAGG

TGCAGGAAAAGGATAACTGCAATGATTAGTACAGGAAACCCAAAGAAGAACTGAATGGTGGG

ATAGATGTACTCAGAGACCATGAGGCATCAGTTTCCTCTATGAATAGAATATTAGGAGATGT

AGGTTAAATGGGACCCTGAAGTCTCTCCCAAAAAGCCTTGTTTATATGTTTTCTGAGCTTAA

CTATTACTTGAGAATCAATTTCACGTATAAACCAACAAAACTAACATTTATTGAGCTTCCAG

CTCTGTGCTTAGGCACTGAAAAATCACTTTCCTTAAGGATTGCAATTAAGCAGGAGAAACAC

AAATAAGGTGAACTTCTCTTGTTCGAAAGAATATATTTCAACATTCCTTTTAAAAGGAAAAC

CTGACCTGCAAGTTTCCAAAAATATTAATTACTATTCCTCTTTGCCTCTCAAAATTCCCATT

CTGTTATTTTTTAGGAGGAGGAAAAAACAGTTCATTTGAGGAAAAATTGAGGGTCACATACT

ATACAATTGAGAAGAGTTTCTCTGAAACTGTAATCATTTTTGGCAGGTAAATAGGCATATCC

GAGTCAGCAAATGAACTTGAAGATACTGAGTTATACTGCCTGCCCTGTGGGGTTCCACCTTC

CCCAAAAGAATTCAGAATTTTTGGGTGATCTGAGAATCTACATTAAGACAACTGTCTCCACA

CACAGGAGGCCTGAAGATCGCTGACATAAGGGTCTTTTTAAAAAGTATATTTAATGGCCTAG

GGCGGTGGCTCACACCTGTAATCCCAGGACTTTGGGAAGCTTAGGGCAGGAAGATCACTTGA

GCCCAGGAGTTCTAACCTGTGCAGCACAGCAAAAACCCATCTCTACAAAAAAAAAAACACAA

AAAAATTAGCTGGGCATGGAAGCGTGTGCCTGTAGTTCCAGCTACTCAGGAGGCTGAGGCAG

GAGGATCACTTGAGCCCAGGAAGTCAAGGCTGCGTGAGCCATGATCATGCCATTGCAATCCA

GTATGTGACACTAAGACTCCGTCTCAAAAAAAAAAAAAAAGATAATTAAAATGTGTAAGATAC

TGTATTAGCAATATAAAAAGCATTTGGTGTTAAAATGTTGGTATTATAATTCCTCAGGATAA

AACTTACTTTGTGATTGTTTTCTATAACTCAAGATATGATGCTTAGAGCTCCTCCAATCAAG

TGTTTCCAGGAAGTGAAAACTTGTAGGACAGAAATTTAGGCTGGGTTCATTTGTATCACACA

GACCTATTCTTCATTCAAGTTCTGATATATTTAACTATGTAGCTCCTGTAACAGTTTAATGG

AATCTCACCTCCCTAAAATTCATTATGCATTTTTTTTTGAAATCCAAACTCATTAACGCTTG

CTTTCACTGTTGTCCAAGGCAGGCACATCTTTAAAAATGGTTTGTTGGACTTAGCTTTCAGC

TAAATATATAATAAATAAAACAAAACAAGCAGTTAAATGAAATGTAATGGGCCAGAGAGCTT

CAGCTTTTATTTCCTTACTGCTCAGTAAAAAGAGAAAACCATCAATGTCCACGTATTCTGTA

ATCCACAGAACAAGTCCGGGGCTACAGCTATACTGTCCACAGTTGCAATTCAAATTAGATAA

AAAATAAAAATTCAGTTCTTTAGTCATACCAGCCACTTTTCCAATGCTCAAGATTAATAAAA

TGTCAAACCATAAAGACATTTACATGTCGCTCACTCCATTTACTTAAAGTTGGCTAGACATC

AGAGTATACTAGGAGCTCAGGAGTACAAGACACTATTCCTTCAAAAAGCTCAGAATAGTTAA

GGTAATTTAAATCAGCAATGACAACAACCCCAGAATTACTATGACCCACGCAGTACAAACTG

CTCAGGAGTCAGAAGAAAACTGCTTTTTTAAAAGGGCAGTTTGGGTCATAGAACAACAGACC

ATGGAAGGCATGACCAAAGGGGAGATGACATTTGAATCTGCAGGATTAAAAGCAGCAAGGGT

AGCATTCCAAAAAGAACCACCCCACAAAGATATATGACGTCTCTATGATTTGGGTAACTGCA

ATTCATTCCATGTGACTTCAGGAGAGAGGTCATATTTGTGTGTGTAGTATGTGGAAAATAGT

GAAAAATGAAAAAGCTGTTAAATTGAGGAAAGTCTATCCAGGGACCTTATGCATCACATTCA

CGAGAACAGAATTCATCCTGTAAACCAGGGGTGTCCAATCTTTCGGCTTCCCTGGGCCACAC

TGCAAGAACTGTCTTGGGCCACATATAAAGGACAGCTGATGAGCAAAAAAAAAAAACAGACA

ACAACAACAAAAAAAACACCCCGCAAAAAAAACTCCTAAAACTTTAAGAAAGTTTACGAATT
```

-continued

TGTGTTGGGTCGCATTCAAAGCTGTCCTGGGTCCCATGCGGCCCGCGGGTTAGACAACTTGC

TGTAAACAGTACAAGCCAGTAATGGAGTTTCACCTGTCATTTTCATGCTCTATCTTCCTTTA

GGACAATCATCCTAACAAGATGTAAGATGGATCAAAAGATAACACTAAAGACAGAGACAGCA

ATTTGGAAGCTATCACACAGGCATCTGAGATCAGTTACTAACTGGTAAGAACAGAAATGAGA

GGTATTTAGAGGAAGAAAAAGGGAGATGTTGCCTAACCTCAGATCCAATTCTCTGTAAAGCA

GTAGTCAAGATCACCTGGACTGTGAAGACGGTCAGGGACAGAATCCCAGCTAAGGAAAAAGG

ATAAAATGAAAATCAAGATAAACATTTAAGAACGTGAACTAGGGAGGAATAAAAGCACTGCT

GGGTAAGAGTCAAGCCCCAGCTCAAGCCTTAATTTGTGGTGGAACCAATCTGTCTGGTTTCG

CGAGACACCAGGCTACCCAAGATCAAGAGAGGGAGAAAGCTAGTGCTATGTCTGAATACTAG

AGGAGCAAGTACAACAAATGGAAAATGGGATCAAGTATGAGTGAGAGTTGCTAAGATGCCTG

GTAGGGATGCAAAGGGGTAGAGAGCCTGGGGAGAGAGGGTGAGGGAGGGAAGCACTGGTTTC

TCAAGCAAAAGCTAAAATTTTTCTATTAAGATTTAACCTGATGCTACACTTTGGTGGTGCAG

CAAGGGTCTCAAATGGTATAAAACTCAGGTGATCATGCTTTATGTCTGTCTCTAGAAAAATG

CTCCAAAAATGATAAGTAGTGATAATCCGCAGTCTCGTTGCATAAAATCAGCCCCAGGTGAA

TGACTAAGCTCCATTTCCCTACCCCACCCTTATTACAATAACCTCGACACCAACTCTAGTCC

GTGGGAAGATAAACTAATCGGAGTCGCCCCTCAAATCTTACAGCTGCTCACTCCCCTGCAGG

GCAACGCCCAGGGACCAAGTTAGCCCCTTAAGCCTAGGCAAAAGAATCCCGC*CCATAATCGA*

*GAAGCGACTCGAC*ATGGA*GGCGATGACGAGATCACGCGAGG*AGGAAAGGAGGGAGGGCTTCT

TCCAGGCCCAGGGCGGTCCTTACAAGACGGGAGGCAGCAGAGAACTCCCATAAAGGTATTGC

GGCACTCCCCTCCCCCTGCCCAGAAGGGTGCGGCCTTCTCTCCACCTCCTCCACCGCAGCTC

CCTCAGGATTGCAGCTCGCGCCGGTTTTTGGAGAACAAGCGCCTCCCACCCACAAACCAGCC

GGACCGACCCCCGCTCCTCCCCCACCCCCACGAGTGCCTGTAGCAGGTCGGGCTTGTCTCGC

CCTTCAGGCGGTGGGAACCCGGGGCGGAGCCGCGGCCGCCGCCATCCAGAAGTCTCGGCCGG

CAGCCCGCCCCCGCCTCCAGCGCGCGCTTCCTGCCACGTTGCGCAGGGGCGCGGGGCCAGAC

ACTGCGGCGCTCGGCCTCGGGGAGGACCGTACCAACGCCCGCCTCCCCGCCACCCCCGCGCC

CCGCGCAGTGGTTTCGCTCATGTGAGACTCGAGCCAGTAGCAAGGGCCCGGTCCCACAGCTT

CGACAGCCAATCAGGTGTCGAAGACAAGCAGGCGGCGGGTAAACCGACTCCCCCGAAGGAAG

GGGAGGGTGGGAGGACGCCCGCGCCAGAGCCGATTTCACTGACCCTCCCCTCCCGCCGCAGG

AGGCCGGCCGCGCCCGCACACCCAGCATCTCTACACCCCACCTACCTACCCGCCCCCACCCAG

GGGGCAACGCGAGAGTCGCTAAGCGGCTGCGTACTCCCGACGGCGTAACTGACAGGAGCTTT

ACTCCAACCAGAATACGCCATTTGTGTTTTCACACACGGCGGGAGGAGAAACGGCCAATCGG

CGACAAGAGGCTAGCCGGAAGCGCTCCTCCCTCTGCGAGAGCAATGGCTCCGTCCGGTTTCG

AGCATTTTCCGCTCCCTTCTCCCTCCCCCTCCGGTTGCCGCAGGGCGGGCCTCCCTCCCGCC

TGCATCCAGCCACCCCTTTCCCTCCCAACGTAACAAACATTATGTTCCCGACTTCCCACGGG

AAAGGCAACCCCCGCAAGCCACCAGACGGCCCCCCTAGCCACCCATCCCCCCCAGTGTACCGC

ACCTCCCCTCCCACCAGAGTTCCGCTCCCCTACCTAGCCGAGGCTCTCTGAGGAGCCGGAGC

GCCGAAGCACAGCCTCTTCTCTAGGCGGCCCCGGCGGCTTCCGCTGATTGGCGGCGAGTGGG

CCAATGGGTGCGGGGCGGTGGGCGGAGAGGCCAATGGCGCGGCGGGAGGGGGCGTGTCCCGG

GTGCCCCTGGCGCCGGCGCTGGGAATCCCCGTGCGGTCAGTGGCGTTTCCGCTCGGGCAGCG

GGCTGAGTGAGCTGCCGCCGCCGCCGCCGCCGCCGCCGCCGCCGCCGCCGCTGCCGGGGGAGGGG

-continued

```
CGGCCGCCGCCCGCCTGCGCTCAGAGACTCACGCAGCCCCAGTCCCGCCAGTCCGCCAACAC

AGTAGTGCCGGCCCCCCTCTTTCCCTGGCCCTGCCCCCCCTCCCCGCCTTTGGCTCGCTCCG

CCTTTCTGCCCCCCACCCCCACCTCACGGGTACGGGCCATTCCCGGCCAGGAAACGCCGTGG

CGCCGCGTTGGGCCTAACTCGAGTCCTGCCGCCTCCCGGGAGTGCCGTGCGCCGCAGCCCGG

GCCCAGGCCCCGGCAGCGCCTGGGACAAGGTAAGGGTCCGACAGAAAAGAGACCGAACCTCA

CGATCGGGCCCCAGGGGAGGGAAGGGTCACCTCCTCCGTCTCCCCGCGCTCGCTCTCCTTGG

GTCGTGGGCCTGGCCCTCCCCAAGCTCTTAGGAGGATGCTGCCACTTCTCACCCCCCTCGCC

GCCTTGCACACACCGTTGCAACACCCCATTTTCCCAGGGAGAGAGATCCCCCTCTAATCTAG

GCGACCCAACTCCCCCTTTCATGTTTTTCCTGGGTCAGGACGCTTCCCCTCCCCCAACGCCT

CTTCACCCCCTTTCCTGGGAACTGCCTACTCCACGTTTACCTTTCCCTTGAGGAGAGGCCTC

TTGCTGCCCTCCGCTCGAAATACACAGGCATACTTTTTTTCTCTCCCCGATCCCCCACTCCC

TACCCCCGTTCTCGCGGCCTTGTGACAGACAACTCTGATCGCTCTGGGGGCCGCGATCTCCC

CTCCGTAATCTTCCTGGACGCCTTCCCTCTCGTTTTCTGGCTTCCCACCTCAGATGGCTGCT

TCCCAAAGGCATTACCTTCGCCACCCCCACCACACGTTCTCTGGCTCCCCGTGGCGTGTGCC

ACAGCGTGTCTGAGATAGCCTCGTTGAATGTGTAGGGTTCGAGCCTGGAGTTGAGCCAGATT

GTGTCGTTTTACTTGCCTTGGGCGTGGAGAACGATCTTGTGAGAATATCTTCAAAGGCAGAA

AAATATTCCCTTTATGAATTCTCTTTCCCTCTGCGTGTAAGTCGGGAATGTGAAGAGGAGTG

TAGGAAAGAGCCCTGGTTCAAGTAGGTAAATCGCATGAGAGGGAAAGTTAAACTGTTGGGAA

AGCCCCTTCTATGCTAATTGATTCTATAGAGTCCTTGCTTGTCTCACTTCTTGGGCGTCAGT

GGTCTTTCTCTTGGATATGGATGCTGCAGTCAGCTCTGCTGGTCTGGGTCAGGGGTGCGTGT

ATGACCTGCATTTTCTGCTTTCTCATGTTACTTGTGCAATGTATTCACCGGTAACTCATTTC

TTTCCCAGACCTCTGGGTTCCACTGGGCTTTGTCTATATTTAAGTTCATTTCTCCAGTTTCC

TTCCTGCACATAGGTACTGAACGAATCCCCAAGTTCTGTGCTAATTACCTTCATCAGTTGAC

TAAACAAGTTTTTAGATGACATATTTGTGACCAAGGTCATATTTACATTTCTTTGTTGGACA

GATGTTACATAGCTATACTTGTGATTGGGGAGGATCCAGCTGAGTGGAGTGTGCTGAGCTTT

TTAGGAGAGTGTGTACTCCCTATTTGAAATTATTTTTTGGTTGTTAATTTTATATTATTAAT

GTTTTTAGGTCACAGAAAGTTCTAAGTGGTAATTTTAGATGTGTGGGATCTGAGCTAGGACT

AAAGCAGAGAATACCCACGTAATCAGAGGTTTCTGGGCTCCATAGAGGACGTAGGGCTTTTT

TTTTTCTATTGGATTTCTTCCAGTTTTCTCAGGATCATTAGTTCTCTTCTGTAGCCAAAAAT

TCTGGCCTGTTATGGGATTAGAGTCTTTAAGGTTTACTCAGACTGTCATTATGTGTAGAAAA

ATGAATTATGCCCTTTGGTAGGACATGACACAAGGCTCTGTTTCTAGCTGCAAATTTAAATT

AGATTGTAGAGTGCTTGGGAAATTGGCTTTCAAAAGACCAAAGCTTAATCTTCACTCCTAAA

CTGCTGGCTTAATTAAAATGGATATTTAGAATTTGGTAAATGTTGATTTTTCTAATAAAAGG

CCTTGGTTTAAAAGGGTGACCTTAGGATTGTTTCTTTCTTAAAAGCATAATTCCAGCCCTTC

TGGCATGGAGCACTGGTCCAAAAAAAAAAAAAAAAAAGTGTGTAAGGAGTGGGGGTGGGGT

AAAGAGAAGGTTGTTCCTTTGGGTTGGATCACAGGGGTGAGTATACAAGGCAGCAGCAGCTG

CTGGCTCTGGAGCTCTGGTTGCTACGTGAGAAGCTTGAGTAGTGCTGGCTGCTGTCTCCAGG

GAAGGACAGCAGTGCAGCGTCCATTAATGCTGCTGGCTGCAGGGAGCAGCACTTAGGCGATG

GCTGCTTCAGGACTAAGAAGAAACCTTGCTTTTCTGGGAATTTTCACTGCTGAGCTGGTTTG

CTTTTTATTGGTGGGGAGATGGGAATTAGTAATTCATAATCTCCTACCCATTTATGGATATT

GGCATCTGGAAACTGGATCATGGTTAAAGCCTTTCTTTTTTTGTTTGTTTGATTTGATTTTT
```

-continued

```
GTTTTTTGGCAGATTTTTGTTTTTTATCTAGACATTTGTGCTTGGATAGGACTAAAAGTTCC

ATTAGAGTTTTAATTTTTCAATCAGTTTAAAAACCCAAGTAATAATTTTAAGAATCTTTCTG

ATAACCACAATAGGAAGAAAATAACAGGAATTTTTTCCTGCAGCTCACATATCATGCCTTCC

TCCATCTCTTTAATCATAGAATCAATTCTTATTATTTTGTTATGTGTCTCCATCCTTTCGAT

TAGACCACATTTACCTTATAGACGATTTGCTAAACATTTTACTAAGCTTGAACTCTTAAACT

CTAAAAAGGTGCCATTTTGGAGTGGTTTCTAAATAAATATTTTTAATTTGTATATTAGTAAT

AAACTTCTCCAGATTAGATATTTTCTTTGGAGTTTGACTTATAAGATTGATTCATTATATAC

ATGTTGGATATAGCCTTCTGACATCACAAATATATGTCTTTGGCCATAATCCATCTGAAATG

TAGGACAGACCAGAAGAAATATGCAGAAATCGAATAAGTCTAGTTCAGGATACTGAGAAGAT

GGCCTCTGAGCCCCTTAGGTGATCTCCCCTCCCCCACAACTCCTGAACATTAGGATGATCTC

TGATTAAGCAAAACAGTCTGAGCGTGGAAAAACTTGAAGGAGAACCACCACCACCAATTATA

TGCAATACTGGACATATTCCTGTGTGCTGTTTTTCTTCCCCAAGACTCGTGTATCCTATACT

TTTTTCTCTCAGAATTTTGATTTGTTCATTTTCGTGTAAATGTACTTAAATCTCACAAACAT

CTATAATTTGTAGTATCACTCTGGCATTTGTGGCAGAGAACCAAAAAGAATGGAAATGAGTT

TTGTCATTCACAAATGTGGCTCACATTGTTTTCCCAGTAATAAAAGCAGACCAATGAAACAG

AACCTTTAATGGATACTATTTTAGGAGGTTCCAATTCTTATTACTATCACATAGATAAGATG

CAATAGCAGATAAATATGATTTCATGTATACTGGCTGTTTGACATACTTAGGGTTTAAGATA

AAAATGTTTGTAGTTTTTTACTCTGTGGCTTAAGTTGCTATATAAAATAATTGCTTTTACAC

TCGAATTTCCTGTTGTTTGGAACCTTTTGTGCTCTTGATATTATCATTTTTTAGAGGATCAT

ACAGGCCCTTTTCATAGAAGGATTTACTTAAGTTATACCCTTGAAAACTTTTTTATATCTTT

TGATACTGTTTTGTGTCCAGGAACTGACTTTCTGAAATTATTCTGGCTTTTCTGGGGAGAAT

GACTATTTCATTTTTACCTTTGAATGGGGAAATAATAAAGTGCAAAGTACAGATTTGCAGAT

AATTACTTTTGCTTTATCCTCTCCATGTTGAAATAACTTATGAAAAATTAGGCCATAGTTAA

CAGCAGTCAATGACTATTGGATACATTTTATCAGAGGGGAACTGGATCATGAATAAAATAAA

ATTTTAAAAATAATTTTTGGCTGAACTCTGGTGATTCATCAGTTTAATTTGAAGTCAGAAGG

TCTAGCAGTGAATTTTATTTATAAAAATTGTATTTCAAGTGTTGAAAACTGAAACTTCTTGA

CCAGTATATTTTGTTTGAGGCATCAAACTTTGCAAAATGTGCATCGTATATTTAGTGATATA

ACTGGTAGTCATTTGTAATTTAAAGTATTCTTTCAAAGGCACTCTTTAGAAAGTAATGTAGT

GTACCCGTGATGGGCAGGGATTGGTACCATTCCTTACTGCCAAAAATTCCAAAATATGTGGC

AAAATGATTGATTTATCTTGTGGGTGGGATTCTGGGAAGTTCATGAAAGGTGGAGAGAATAT

AGTTTCCTTCACTTGTCTATATACATTTTGTTAAATAAGTCTTAGGAAAACTGTTTTATTGT

ATCTTTAATTATGAATTGCGTAAAAGATACCCAGTAACTTTGGGGGGAGGTGCTGTTAGAAA

GCATTACATTGGAGAGAATTCCCCTACCCTGGGACAAAATGCATTCTGTCTTTAATACTTAG

CGAAGGGAACTATGGGATAAAATAAACAATGAAGGTAAGCTCAGTCTGCTTTATATGTGCCC

TCACTGAGCAAGGAATTTGTAATCGCATCGTGCCTCATTCGTTTATACCATCATATTGATTT

TGTTTGCTGAGTACCTGAGGGAATACCTTACTTAATGTAAGGTCACATTAAGTATGTTTGAT

ATGAAGACAGGGAAAGGAATTTTCTGCTTCTTGGAGTAATGTCTTAGTATTTTTAAAACACT

TAAGTTTTTACATCAGGCCAGTTTTGCCTGATGCTCATGTCTGTTGCTTTGGTTGGGCTGCT

GCTTTCTCTTCTGTGTTCTTATGGGTTCGTTGTGGTATAAGGATTCCCACAGCTTTCATGGC

AGTATGAAGTAATGAGAAGCATTGCCTTAGCCATGTTAGTTACATGTATACTTTTGGCCTAT
```

-continued

```
GTTATGAATCACAAAAAGCGGTAGCTATAGGAATGTATACAAAATAGATTTCTGTCTGGGGA

ATCAAGTTTTTGATTTGTGCTACCTAATGGAGGGGAAAATGCTGAATTTCTTGCTGCTCTGT

TTGAGAAATAGATGGAAGCATGGGAGGAGCCAGAGACCTCTGCAGCAGGATTTGGTCTAAGT

AGAAAAGGAAGATTTTTGTTTCAAATTGCCAGCTGCTTATGTCAGACTGACTCCCTTATTAT

GCCTCCAGTAGGCCTGTCAATATGGCCAAACAGCTAGATAAGTGCGGGGCAGGACAAAGGGC

TCTTTGCACAGCAGGGAGGCAATGTTGGTGGGGGAGGGGCAGGAGGTAGGAAAGGCAAGAGG

AGGAGGTTCTTTTCCCTGGGAGATTATTCAGTTTGGCATACAATTAAAGAAATCATTTTTAG

TTCCCACTCAAGCATTGAATTTTTGCCAACCACATACTATTAACCCCAAATTTGATACATTT

CAGAATATCTTGTAGGGATCCATTCTCGCCAAGGAAAAATAAAAAAATAAATAAAGCTCTGT

ATAGGTTAAAATAAAATAAATCCCACACTCTGCACCCTCCTAGGTGCAAGTCACCTCCCGAG

GAGACCCGTTCTAGAGCTGAATTCTCATTAAGAAATGGAAAAGAATACTCTATCTGAATAAA

AACACATTGTAATACAATGTGTTTATTTGGGTTGGGATTGGACCTGAACATGTAGAATAATT

TGTTTCCCTTTATGAAATAGTTGCTCGTAGTTGTCTACAATTTTATTTCATTAAGATAGGTA

GCACATTACAGCTTTCATGTGTTGGGTTGCCATATGTAAAATGCTAACTGAAGAAAGGCTAC

TTTTTAATTTCAGCCTCATCCTTAGTTCCTGGAGAACCTGATATTTCCTGGAGATTACTCCC

TCCCCCACCTTTTAGTTTAGGCAACCTCTTTTGATACATTTGTGTTCAGCTCGCATACAAGT

GGGATAGTTGCATCCAGTTTATTAAGACTTAGTATGAATCATAGAGTTGGAAAAGATCTGTT

GGTTATCTGGTCCTTTAAACCAAAATCATAATGAAATATTTTGAAATTTGGGTCCCTATTGA

AGTTTTCATTAAAATGTTAAAGGATCGGTGTTCTGAACAACATTTTTAGTTACTTTTAAAAT

AAATGTTTTGCGTCAGTTCTTTTTTTAAAAATAAAGAATTTCATTTATAGGCAAATTAGCTG

GCAATTATTTGAATTGTGATAGGATTTCTCTTTTATGAAGGAATATATGACAAGGTTTTTCA

AAATGCTTAATATATTTTAAAAGACTTTAATTTTTAGAAATAATTGGTTTGAACAGTTTTCC

AAGAGCACATTTGTTGCTTGGGTTGAGGTACCACCTATATTGCAATGTTACTAAACTAGCCT

TAAAGTTTTCCCTTCTGTCTATACTGCATGCAACAATAAAGGGAACTGGAATGTTAATTTCC

ATTTATGGATTAGCAGAGGAGATGTTTTAACCGATTAATAACCAAAAAACTGCCTTTCGTAC

ACGTAATATTAAGCAAGCCTGACCAAGTTTTGTGTTATTTCTCTCTGTTAAAGAAAACTGGA

TGTGTTACTACTTAACATTATATTGTTATTTAATGGTCTTGGCAGTAATGATATAATATTTC

GACCAAAAGAAATTTTGAGTAATTAATTATTATTGTAATTAGTTGGAAGTTTCTCATCAGTA

AAATAGCAACAGCATTAACACAAATCTAGTGAGCTATATTTTATATTACTACAGAAATTTA

GGGTAGTCATTTCTTTCTTTATAATTTATTCACATGGATTATTTCCATAAATTTGTGGGACT

AAAATAGAAGCCATCTAGTCAAGCACCAGTCTCCATACCAGACAGTTTTCTCTGCATGTGCT

ATGACCCACATTGCCAGTATTAAACATCCTTTACACCCTCCCCCTTCCCAGATAATTAGAAA

TCTCTTCAGGGTAGCTTCCATTGCTCCTATTACCTGGATCTTGCTAGAGGCTCTAAGAAGTT

CCTGGTAAAAGTGAGACAGTAAGGGACCACATTTTGATTCCAAAGGTTTTGATAACTGTTAG

GGCTCCCCAAACAGCTAATCTCATTTTCACCAAGACTTAGCCAGCAGAGGGCTGGAATGGAG

GTGAAACACAAGCACTGTACCTCATCTTGCCTGTGCAGCTGCTCCACCTTATTTCCTGCTAT

TATTATCTCACAACGCCTCCTCCCATCAAAAAGAAACTAGGACAAAGGGGGAAAATTGGATG

GGCTAATGTGATTTTTATTATGCTAGGTTGTGGGCTTGTTTATATGTACTTAAATACAAAGC

TAATTTGCCCCATTCTTAAAAGTCTTTAGTGATAGAGATTTTGTAACTTCTGTATCTTCTAC

TTTCTTTCTTGATAAACCATTTCAGATTCTCAGCCTTACAGAAAGAAAGGTTTTAAGCATAC

TTAATTTTCGTTGGCCGTTCACAGTCATTATTACCACCAGATGCCACTGTATTATTAGCTTG
```

-continued

AAGAAAGGTGGGCTCTCTTCTGTACATAATATCTGCAATTTGTTTTGGAAAATACTAATTTG

TATAAATCTGATTTATGACTAAAATAAGGTTAAAAATTAGACCTCTATGTATGTTTACCCTA

TTACCTTAGTGGGGGTGAAATTAATTAGCTCTTTGAACATAAATTTTTCATGTCTTAGAGTT

CTTTTTTCAAGCTGCATAATTTATGTTCTTCAAGCCATTTTTATCCCATACCACCCCCACAA

AGGGGGAAATTTTATTTTTTATCATTTTTATTGTCTTTCAATGGTGAGATTTTCGCCACCCC

ACTCCTGAAATGTGAAGACTCAAATAAAACTGAGTAATCTAATAAGGTATATGCGTTGCTGA

ATGTAGTAAGATGATTGTTTCATCATTCTTAGATATTATGATCTAGTTTGAATCTGGTTTCC

AGTATCATGTTAGCATATTTAATACTGTTGATATGTTAATTTTAATACATGCCCAGGTGGAT

CTCCTTGCTTTCTATTTGTGCCCCTTGTTTGTCGTTTTGTATGAAGGGGGTTTTTGTTGTTG

GATTTTCTTCCCCATCTCTGTGTCCTGTTATGTTCTTTGGCTTATGTTTCAAAAATTCTGTT

TCCTACCACCAACCTCTGTACATGCCACAACACATACAATTTGTACTTTCACAGTTTCTGTG

AAGTAGGATGATCTGCAGTTAATAATCAACTGTTTGGGCATTCTTGGTATCCAAGGAAGGTT

TTACTTAGAAGGAAGAACCTGGAAGGACCTGTTGGCAATTAGACTACTTCTGCGTTTATTTT

ACATTTTCCCTTATTAACGTAGGCTGTTGAGAGTTGACTTGTTTTATAAGAGAAACCAGATT

GACAGAGAAGACCCCCAATCAGATAGAGTTATTTTAAAAATAAATGTGTTTATTATGGTAAC

ATTTGGGGTAGAATCTAAAGGGCATATTTTTAAAAAAACTTTTAGTTCTAAAGACAAAAGAG

TTTAACCTAAAACAGAACAAAGAGAAGGGCCTTTGAAGCAGTATGATTGATTATAT

EXAMPLE 11 - CHO and Mouse Stable Site 1 Sequences - U.S. Pat. No.
7,771,997
211> 6473
<212> DNA
<213> *Cricetulus griseus*
<400>    1
                                                                    (SEQ ID NO: 5)
tctagaaaca aaaccaaaaa tattaagtca ggcttggctt caggtgctgg ggtggagtgc        60
tgacaaaaat acacaaattc ctggctttct aaggcttttt cggggattca ggtattgggt       120
gatggtagaa taaaaatctg aaacataggt gatgtatctg ccatactgca tgggtgtgta       180
tgtgtgtgta tgtgtgtctg tgtgtgtgcc cagacagaaa taccatgaag gaaaaaaaca       240
cttcaaagac aggagagaag agtgacctgg gaaggactcc ccaatgagat gagaactgag       300
cacatgccag aggaggtgag gactgaacca ttcaacacaa gtggtgaata gtcctgcaga       360
cacagagagg gccagaagca ctcagaactc caggggggtca ggagtggttc tctggaggct       420
tctgcccttg gaggttcctg aggaggaggc ttccatattg aaaatgtagt tagtggccgt       480
ttccattagt acagtgacta gagagagctg agggaccact ggactgaggc ctagatgctc       540
agtcagatgg ccatgaaagc ctagacaagc acttccgggt ggaaaggaaa cagcaggtgt       600
gaggggtcag gggcaagtta gtgggagagg tcttccagat gaagtagcag gaacggagac       660
gcactggatg gcccccacttg tcaaccagca aaagcttgga tcttgttcta agaggccagg       720
gacatgacaa gggtgatctc ggtttttaaa aggctttgtg ttacctaatc acttctatta       780
gtcagatact ttgtaacaca aatgagtact tcgcctgtat tttagaaact tctgggatcc       840
tgaaaaaaca caatgacatt ctggctgcaa cacctggaga ctcccagcca ggccctggac       900
ccgggtccat tcatgcaaat actcagggac agattcttca ctaggtactg atgagctgtc       960
ttggatgcaa atgtggcctc ttcattttac tacaagtcac catgagtcag gaggtgctgt      1020
ttgcacagtg tgactaagtg atggagtgtt gactgcagcc attcccggcc ccagcttgtg      1080
agagagatcc ttttaaattg aaagtaagct caaagttacc acgaagccac acatgtataa      1140
actgtgtgaa taatctgtgc acatacacaa accatgtgaa taatctgtgt acatgtataa      1200

-continued

```
actgtgtgaa taatctgtgt gcagccttc  cttacctact accttccagt gatcaggttt      1260
ggactgcctg tgtgctactg gaccctgaat gtccccaccg ctgtcccctg tcttttacga      1320
ttctgacatt tttaataaat tcagcggctt cccctctgct ctgtgcctag ctataccttg      1380
gtactctgca ttttggtttc tgtgacattt ctctgtgact ctgctacatt ctcagatgac      1440
atgtgacaca gaaggtgttc cctctggaga catgtgatgt ccctgtcatt agtggaatca      1500 gatgcccca  aactgttgtc cagtgtttgg gaaagtgaca cgtgaaggag gatcaggaaa      1560
agaggggtgg aaatcaagat gtgtctgagt atctcatgtc cctgagtggt ccaggctgct      1620
gacttcactc ccccaagtga gggaggccat ggtgagtaca cacacctcac acatactata      1680
tccaacacac acacacacac acacacacac acgcacgcac gcacgcacgc acgcacacat      1740
gcacacacac gaactacatt tcacaaacca catacgcata ttacacccca aacgtatcac      1800
ctatacatac cacacataca caccctcca  cacatcacac acataccaca cccacacaca      1860
gcacacacat acataggcac acattcacac accacacata tacatttgtg tatgcataca      1920
tgcatacaca cacaggcaca cagacaccac acacatgcat tgtgtacgca cacatgcata      1980
cacacacata ggcacacatt gagcacacac atacatttgt gtacgcacac tacatagaca      2040
tatatgcatt tgtatatgca cacatgcatg cacacataca taggcacaca tagagcacac      2100
acatacattt gtgtatgcac acatgcacac accaatcaca tgggaagact caggttcttc      2160
actaaggttc acatgaactt agcagttcct ggttatctcg tgaaacttgg aagattgctg      2220
tggagaagag gaagcgttgg cttgagccct ggcagcaatt aaccccgccc agaagaagta      2280
ggtttaaaaa tgagagggtc tcaatgtgga acccgcaggg cgccagttca gagaagagac      2340
ctacccaagc caactgagag caaaggcaga gggatgaacc tgggatgtag tttgaacctc      2400
tgtaccagct gggcttcatg ctattttgtt atatctttat taaatattct tttagtttta      2460
tgtgcgtgaa taccttgctt gcataaatgt atgggcactg tatgtgttct tggtgccggt      2520
ggaggccagg agagggcatg gatcctccgg agctggcgtt tgagacagtt gtgacccaca      2580 gtgtgggggtc tgggaactgg gtcttagtgt tccgcaagtg cagctggggc tcttaacctc      2640
tgagccatcc ctccagcttc aagaaactta ttttcttagg acatggggga agggatccag      2700
ggctttaggc ttgtttgttc agcaaatact cttttcgtgt attttgaatt ttattttatt      2760
ttactttttt gggatagaat cacattctgc agctcaggct gggcctgaac tcatcaaaat      2820
cctcctgtct cagtctacca ggtgataaga ttactgatgt gagcctggct ttgacaagca      2880
ctttagagtc cccagcccctt atatattgtg tgtgtgtgtt tgtgtgtgta tgagacactt      2940
atatatatat atatatatat ctggacactt gttccaagta taatatatat atatatatat      3000
gctctaaggg tatcatatat atccttgatt tgcttttaat ttatttttta attaaaaatg      3060
attagctaca tgtcacctgt atgcgtctgt atcatctata tatccttcct tccttctctc      3120
tctttctctc ttcttcttct caccccaag  catctattt  caaatccttg tgccgaggag      3180
atgccaagag tctcgttggg ggagatggtg aggggcgat  acaggggaag agcaggagga      3240 aaggggaca  gactggtgtg ggtctttgga gagctcagga gaatagcagc gatcttccct      3300
gtccctggtg tcacctctta cagccaacac catttttgtgg cctggcagaa gagttgtcaa      3360
gctggtcgca ggtctgccac acaaccccaa tctggcccca agaaaaggca cctgtgtgtg      3420
actctggggt taaaggcgct gcctggtcgt ctccagctgg acttgaaact cccgtttaat      3480
aaagagttct gcaaaataat acccgcagag tcacagtgcc aggttcccgt gctttcctga      3540
agcgccaggc acgggttccc taggaaatgg ggccttgctt gccaagctcc cacggcttgc      3600
```

-continued

```
cctgcaaacg gcctgaatga tctggcactc tgcgttgcca ctgggatgaa atggaaaaaa      3660
gaaaaagaag aagtgtctct ggaagcgggc gcgctcacac aaacccgcaa cgattgtgta      3720
aacactctcc attgagaatc tggagtgcgg ttgccctcta ctggggagct gaagacagct      3780
agtgggggcg gggggaggac cgtgctagca tccttccacg gtgctcgctg gctgtggtgc      3840
atgccgggaa ccgaaacgcg gaactaaagt caagtcttgc tttggtggaa ctgacaatca      3900
acgaaatcac ttcgattgtt ttcctctttt tactggaatt cttggatttg atagatgggg      3960
gaggatcaga gggggagggg aggggcgggg agacggaggg aggaggggag gaggggagga      4020
ggggaggagg ggaggagggg aagggatgga ggaaaatact aacttttcta attcaacatg      4080
acaaagattc ggagaaagtg caccgctagt gaccgggagg aggaatgccc tattgggcat      4140
tatattccct gtcgtctaat ggaatcaaac tcttggttcc agcaccaagg attctgagcc      4200
tatcctattc aagacagtaa ctacagccca cacggaagag gctatacaac tgaagaaata      4260
aaattttcac tttatttcat ttctgtgact gcatgttcac atgtagagag ccacctgtgt      4320 ctagggctg atgtgctggg cagtagagtt ctgagcccgt taactggaac aacccagaac      4380
tcccaccaca gttagagctt gctgagagag ggaggccctt ggtgagattt ctttgtgtat      4440
ttatttagag acagggtctc atactgtagt ccaagctagc ctccagctca cagaaattct      4500
cctgttccgg tttccaaagt actggagtta tgagtgtgtg ttaattgaac gctaagaatt      4560
tgctgattga agaaaacctc aagtgggttt ggctaatccc cacgacccca gaggctgagg      4620
caggaggaat gagagaattc aaggtttgcc agagccacag ggtgagctca atgtggagac      4680
tgtgagggtg agctcaatgt ggagactgtg agggtgagct caatgtggag actgtgaggg      4740
tgagctcaat gtggagactg tgagggtgag ctcaatgtgg agactgtgag ggtgagctca      4800
atgtggagac ctgtatcaag ataataatag tagtagtaac aatgcaggcg agggtgtggt      4860
tgagtggtag agcagttagt tgatttgaca tgcttgaggt ctcccggtcc atctgtggcc      4920
ctgcaacagg aagggaggga ggaaggggg gaacgagaga gaggaaagag agacagaagc      4980
taagataggg aatgagagag gaaggaagaa acgggaagaa attcagactc cttcctgagt      5040
tccgccaacg cctagtgaca tcctgtgcac accctaaggt ggcctttgtg tggcactggc      5100
ttgggtggtc gggaaaggca ttttcagctt gttgcagaac tgccacagta gcatgctggg      5160
tccgtgaaag tttctgcccg ttaacaagaa gtctctacta cttgtgacct caccagtgaa      5220 aatttctta attgtctcct ggtgttctgg gttttgcatt tttgtttcta aggatacatt      5280
cctgggtgat gtcatgaagt ccccaaagac acagtggggc tgtgttggat tgggaaagat      5340
gatttatctg gggtgtcaaa aggaaaagaa gggaaacagg cacttgggaa aatgtcctcc      5400
cgcccacccg aattttggct tggcaaccgt ggtggaggag caagaaacac gtggacgttt      5460
gaggaggcat ggggtcctag gaggacagga agcagaagga gagagctggg ctgacagcct      5520
gcaggcattg cacagtttca gaaggagatt acagcatgac tgagtttttta gggatccaac      5580 agggacctgg gtagagattc tgtgggctct gaggcaactt gacctcagcc agatggtatt      5640
tgaataacct gctcttagag ggaaaacaga catagcaaac agagccacgt ttagtgatga      5700
aactctcact ttgcctgagt catgtgcggc catgcccagg ggtcaggctg acactcaact      5760
caaaaacaag tgagaaattg aagacaatcc gtggtggcag ctactggaag ggccaccaca      5820
tccccagaaa gagtggagct gctaaaaagc catttgtgat aggcacagtt atcttgaatg      5880
catggagcag agattacgga aaaatcgaga atgttaatga ggcaacattc gagttgagtc      5940
attcagtgtg ggaaacccag acgcttccat cccctaaaag gaacatcttg ctctcagtca      6000
aaatggaaat aaaaattggg gcttgaattt ggcaaatgat tcagaactct gtgtaggtat      6060
```

-continued

```
tttcacacgc acagtggata attttcatgt tggagtttat ttgtgctaaa aggcagaaaa      6120
gggtaaaaag cacatcttaa gagttatgag gttctacgaa taaaaataat gttacttaca      6180
gctattcctt aattagtacc cccttccacc tgtggtaatt tcctgagata gtcagtgggg      6240
aaaagatctc tccttctctt ctttctcccc ctcccctcct ctccctccct ccctccctcc      6300
ctccctcctc tccctccctc cccctttcct tctttctttg ctccttctcc tctgcctcct      6360
tctccctttc ttcttcattt attctaagta gcttttaaca gcacaccaat tacctgtgta      6420
taacgggaaa acacaggctc aagcagctta gagaagattg atctgtgttc act            6473
```

```
<211> 7045
<212> DNA
<213> Cricetulus griseus
<400>    2
```
                                                                     (SEQ ID NO: 6)
```
actagcgtgc aattcagagg tgggtgaaga taaaaggcaa acatttgagg ccatttcctt        60
atttggcacg gcacttagga agtggaacat gcctaatcta ctggtttgta ccacctttcc       120
ctataatgga ctgtttggga agctcctggg caaccgattc tggcatctca ttggtcagag       180
gcctgttaaa tggtactctt atttgcaaag aaggctgtaa cttgtagctt taaaagcctc       240
tcctcaagaa agaagggaga aaggatatgg ctagacatat ctaatagact taaccactgt       300
gaaaagcctt agtatgaatc agatagaacc tatttttaac tcagttttga aaaaaataat       360
ctttatattt atttgtgtgt gtgtgtgtgt gtgtgtgtgt gtgtgtgtgt gtgtgtgtgt       420
gaaccacatg tagcaggtgc tggaggaggc cagaagaggg caccagatct cctggaactg       480
acaccacaca tggttatgag ctgcctgatg tgggtgctgg gaactgaact ctcgtgttct       540
gcaagagcag caactgttct cttaactgat gagccatctc tccagccccc cccataattt       600
taattgttca ttttagtaaa ttttattcat aatcaattat cacagtataa aacaatgatt       660
ttatatatat catatacata tcaaggatga cagtgagggg gatatgtgtg tgtgtgtgtg       720
tgtgtgtgtg tgtgtgtgtg tgtgttattt gtgtgtgtgc tttttaagaa ggtgccatag       780
tcactgcatt tctctgaagg atttcaaagg aatgagacat gtctgtctgc caggaaccct       840
atcttcctct ttgggaatct gacccaaatg aggtattctg aggaactgaa tgaagagctc       900
aagtagcagt gtcttaaacc caaatgtgct gtctagaaa agtcaacgtc atcagtgagc       960
tgaggagaga tttactgagc ggaagacaag cgctctttga tttaagtggc tcgaacagtc      1020
acggctgtgg agtggagcct gtgctcaggt ctgaggcagt ctttgctagc cagctgtgat      1080
gagcagtgaa gaaagggtgg agatggaggc agggtgggag cagggctatg gttcagacta      1140
ggtatcgtga gcacaccagc tggttgactt gtggtctgtg ggtcaggcgt tgtaaacgcc      1200
ctcagggtca ggcagtcaca ttgcttgaag ctgaatgggt gaggcaacac agagagtgca      1260
aagaaggcaa agtaccacct cttccccgac ccaggtcact tctgggttat agctgagact      1320
ccggacagca tgcaaccagc tggttagagc ttcagggaaa acttgatgtc tgcatgttgc      1380
tatgaaatgt gattcggtac atctggagaa aatttataat gctggctcag tcaagcactg      1440
aacaaaggta ccttggcttt gggagctaca tgacattgac ttgtaggcag actttttttt      1500
ttctgcccgc caattcccag ataaccaata tggaggctca atattaatta taaatgctcg      1560
gctgatagct caggcttgtt actagctaac tcttccaact taaatgaacc catttctatt      1620
atctacattc tcccacgtga ctttaccttg tacttcctgt ttcctctcct tgtctgactc      1680
tgcccttctg cttcccagag tccttagtct ggttctcctg cctaacctta tcctgcccag      1740
ctgctgacca agcatttata attaatatta agtctcccag tgagactctc atccaggga      1800 gacttgggtg ctccccctc ctcattgcca tccgtgtctt cctcttccct cgcttccccc      1860
```

-continued

```
tcctcttcct gctcttcctc ctccacccct cctttcatag tattgatggc aagggtgttc          1920
tagaatggag gagtgcccat aggcatgcaa agaaaccagt taggatgctc tgtgaggggt          1980
tgtaatcata agcgatggac acaattcaag ccacagagtg aagacggaag gatgcactgt          2040
gctctagagc aacttctggg gcagaatcac agggtgagtt tctgacttga gggcgaagag          2100
gccacgagga agggagtgag tttgtctgag ctagaagcta cggcccacct cttggtagca          2160
gacctgccca caagcatgct ttgttaatca tgtgggatct gattttcctc taaatctatg          2220
ttcaactctt aagaaaatgt gaattctcac attaaaattt agatatacgt cttttggtgg          2280 gggggtgta aaaaatcctc aagaatatgg atttctgggg gccggagaga tcgctcagag          2340
gttaagagaa ctggttgctc ttctagacat tctgagttca attcccagca accacatggt          2400
ggctcacaac catctgtaat gcgacctggt gccatcttct gacatgcatg gatacatgca          2460
ggcagaaagc tgtatacata gtaaattgat aaatcttttt ttaaaaagag tatggattct          2520
gccgggtgtt ggtggcgcac gcctttaatc ccagcactct ggaggcagag gcaggtggat          2580
ctctgtgagt tcgagaccag cctggtctat aagagctagt tccaggacag cctccaaagc          2640
cacagagaaa ccctgtctcg aaaaaccaaa aaaaaaaaa aaaaaaaaaa aaaaaaagaa          2700
gtatggattc taagaaagcc gtaacagctg gagctgtgta cggagttcag cgtggtacta          2760
gaagaacaga cattcatgat gaaacacccc aggattttta cttagtatct agtttccatt          2820 gttgtttttga gaccggctct tatgctctcc aggctggcct caaactgctg atcttcccgc          2880
ctctacctct caagtcctgg gactacttgg ctcataaaac agtttttgtc gggctccctg          2940
aagttatggt tgtacaaacc gtggggggtca atatactcac ttgggcagag agagaaggtc          3000
tgaatcccag acaatgactg catctcagga cagttgggaa gaggacaatg gcagaaggac          3060
ttagaaaaga tagactggag ggtggaaaag cagcaggaac agagaaacaa aacaggaagc          3120
ttgctatcca gggccactct ggagtcctgt ggcaagatgg aagcgggcta ggggaataca          3180
tttgtgctac tgtgtgtgtg tgtgtgtgtg tgtgtgtgtg tgtgtgtgat caatgcctat          3240
caatgttgaa gggggaaatat gtataccaca ttgattctgg gagcaattct cagtatctgg          3300
cctagagaaa ggaatggccc ctgcagaata gacagagtga atggtgccct ttatcatttg          3360
ctaaagtgaa ggagaaataa acatccttcc atagagtttc aggtaaatga accccacagt          3420
tcatctgtgc cgtggtggag gcctggccaa cagttaaaaa gattagacac ggacaaagtc          3480
tgaaggaaac acctcgaata ggaagaggag agccacctca ttctgtaact ttcctcaagg          3540
ggaagatgtt ccaagagtgg gaataaatgg tcaaaggggg gattttttaat taggaaaacg          3600 atttcctgta tcacttgtga aactggaggt tgatttgggg cataggacaa tagatttgat          3660
gctttgcaaa aagctgtttc aaagcagaga aatggaatag agacaattat gtagcgagga          3720
gggagggtgg ggcgaagatg gagacagaga agtggaagct gactttaggg aagaggaaca          3780
tagaccacag gggcggggcg gggggcaggg gcggggggcg gggctcaaag gaggcagtgg          3840
gaacgttgct agtgttcgca gcgtaagcgt gaatgtgcaa gcgtctttgt ggtgtgtgac          3900
caggagtagc gtggctggct tgtgtgctgc ttgtaatccc agtctttgag gtttccacac          3960
tgttccacag tgggtgtgat tttccctcgg agagcatgag ggctctgctt tccccacatc          4020
ctccccagcg ttcgttggta tttgtttcca agatgttagt gggtgagaca aagcctctct          4080
gttgatttgc ctttaacagg tgacaaaaaa agctcaacca ggagacattt ttgccttctt          4140
ggaaggtaat gctcccatgt agagcaatgg gacccatctc taaggtgagg ctactcttgc          4200
agtttgcacc cagctcttct gatgcaggaa ggaagttggt gggcaagcaa gactgtttgc          4260
```

-continued

```
ttcttgcgat ggacacattc tgcacacaaa ggctcaggag gggagaaggc tgtttgatgt      4320
ttagcactca ggaaggcccc tgatgcatct gtgattagct gtctccatct gtggagcaga      4380
cacggactaa ctaaaaacca gtgtttttaa attgtcaagc ctttaaggtg aggaaattga      4440
cttattgtgc tgggccatac gtagagcaag tgctctgcat tgggccaacc cccggctctg      4500
gtttctaggc accagaatgg cctagaacta actcacaatc ctcccattcc aggtctcagg      4560
tgctagaatg aaccactata ccagcctgcc tgcctgccta cctgccttcc taaattttaa      4620
atcatgggga gtaggggaga atacacttat cttagttagg gtttctattg ctgtgaagag      4680
acaccatgag catggcaact cttataaagg aaaacattta gttgggtggc agtttcagag      4740
gttttagtac attgtcatca tggctgggaa catgatggca tgcagacaga catggtgctg      4800
gagaaaggga tgagagtcct acatcttgca ggcaacagga cctcagctga gacactggct      4860
ggtaccctga gcataggaaa cctcacagcc caccctcaca gtgacatatt tccttcaaca      4920
aagccatacc tcctaatagt gccactccct atgagatgac agggccaatt acattcaaac      4980
tgctataaca ctttaaagta ttttattttt attattgtaa attatgtatg tagctgggtg      5040
gtggcagccg aggtgcacgc ctttaatccc agcacttggg aggcagaggc agatggatct      5100
ctgtgagttc aagaccagcc tggtctataa gagctagttg caaggaagga tatacaaaga      5160
acagttctag gatagccttc aaagccacag agaagtgctg tcttgaaaac caaaaattgt      5220
gctgggacct gtctctgctt tggttgcttc ccactccccc agagctggac tcttggtcaa      5280
cactgaatca gctgcaaaat aaactcctgg attcctctct tgtaacagga gcccgaagtc      5340
aggcgcccac ttgtcttctc gcaggattgc catagacttt ttctgtgtgc ccaccattcc      5400
agactgaagt agagatggca gtggcagaga ctgggaaggc tgcaacgaaa acaggaagtt      5460
attgcaccct gggaatagtc tggaaatgaa gcttcaaaac ttgcttcatg ttcagttgta      5520
cacagactca ctcccaggtt gactcacacg tgtaaatatt cctgactatg tctgcactgc      5580
ttttatctga tgcttccttc ccaaaatgcc aagtgtacaa ggtgagggaa tcacccttgg      5640
attcagagcc cagggtcgtc ctccttaacc tggacttgtc tttctccggc agcctctgac      5700
acccctcccc ccattttctc tatcagaagg tctgagcaga gttggggcac gctcatgtcc      5760
tgatacactc cttgtcttcc tgaagatcta acttctgacc cagaaagatg gctaaggtgg      5820
tgaagtgttt gacatgaaga cttggtctta agaactggag caggggaaaa aagtcggatg      5880
tggcagcatg tacccgaaat cccagaactg gggaggtaga gacggatgag tgcccggggc      5940
tagctggctg ctcagccagc ctagctgaat tgccaaattc caactcctat tgaaaaacct      6000
ttaccaaaca aacaaacaaa caaataataa caacaacaac aacaacaaac taccccatac      6060
aaggtgggcg gctcttggct cttgaggaat gactcaccca aacccaaagc ttgccacagc      6120
tgttctctgg cctaaatggg gtgggggtgg ggcagagaca gagacagaga gagacatgac      6180
ttcctgggct gggctgtgtg ctctaggcca ccaggaactt tcctgtcttg ctctctgtct      6240
ggcacagcca gagcaccagc acccagcagg tgcacacacc tccctccgtg cttcttgagc      6300
aaacacaggt gccttggtct gtctattgaa ccggagtaag ttcttgcaga tgtatgcatg      6360
gaaacaacat tgtcctggtt ttatttctac tcttgtgata aaaaccgggg aactccagga      6420
agcagctgag gcagaggcaa atgcaaggaa tgctgcctcc tagcttgctc cccatggctt      6480
gccgggcctg ctttctgcaa gcccttctct ccccattggc atgcctgaca tgaacagcgt      6540
ttgaaatgct ctcaaatgtc actttcaaag aaggcttctc tgatcttgct aactaaatca      6600
gaccatgttt caccgtgcat tatctttctg ctgtctgtct gtctgtctgt ctgtctatct      6660
gtctatcatc tatcaatcat ctatctatct atcttctatt tatctaccta tcattcaatc      6720
```

-continued

```
atctatcttc taactagtta tcatttattt atttgtttac ttactttttt tatttgagac       6780
atctatcttc taactagtta tcatttattt atttgtttac ttactttttt tatttgagac       6780
agtatttctc tgagtgacag ccttggctgt cctggaaccc attctgtaac caggctgtcc       6840
tcaaactcac agagatccaa ctgcctctgc ctctctggtg ctggggttaa agacgtgcac       6900
caccaacgcc ccgctctatc atctatttat gtacttatta ttcagtcatt atctatcctc       6960
taactatcca tcatctgtct atccatcatc tatctatcta tctatctatc tatctatcta       7020
tctatcatcc atctataatc aattg                                             7045
```

<211> 6473
<212> DNA
<213> *Cricetulus griseus*
<400>    3

(SEQ ID NO: 7)
```
agtgaacaca gatcaatctt ctctaagctg cttgagcctg tgttttcccg ttatacacag         60
gtaattggtg tgctgttaaa agctacttag aataaatgaa gaagaaaggg agaaggaggc        120
agaggagaag gagcaaagaa agaaggaaag ggggagggag ggagaggagg gagggaggga        180
gggagggagg gagaggaggg gaggggagga agaagagaa ggagagatct tttccccact         240
gactatctca ggaaattacc acaggtggaa ggggtacta attaaggaat agctgtaagt         300
aacattattt ttattcgtag aacctcataa ctcttaagat gtgctttttta ccctttttctg        360 cctttttagca caaataaact ccaacatgaa aattatccac tgtgcgtgtg aaaataccta        420
cacagagttc tgaatcattt gccaaattca agccccaatt tttatttcca ttttgactga        480
gagcaagaty ttcctttttag gggatggaag cgtctgggtt tcccacactg aatgactcaa        540
ctcgaatgtt gcctcattaa cattctcgat ttttccgtaa tctctgctcc atgcattcaa        600
gataactgtg cctatcacaa atggcttttt agcagctcca ctctttctgg ggatgtggtg        660
gcccttccag tagctgccac cacggattgt cttcaatttc tcacttgttt ttgagttgag        720
tgtcagcctg acccctgggc atggccgcac atgactcagg caaagtgaga gtttcatcac        780
taaacgtggc tctgtttgct atgtctgttt tccctctaag agcaggttat tcaaatacca        840
tctggctgag gtcaagttgc ctcagagccc acagaatctc tacccaggtc cctgttggat        900
ccctaaaaac tcagtcatgc tgtaatctcc ttctgaaact gtgcaatgcc tgcaggctgt        960
cagcccagct ctctccttct gcttcctgtc ctcctaggac cccatgcctc ctcaaacgtc       1020
cacgtgtttc ttgctcctcc accacggttg ccaagccaaa attcgggtgg gcgggaggac       1080
attttcccaa gtgcctgttt cccttctttt ccttttgaca ccccagataa atcatctttc       1140
ccaatccaac acagccccac tgtgtctttg gggacttcat gacatcaccc aggaatgtat       1200
ccttagaaac aaaaatgcaa aacccagaac accaggagac aattaaagaa attttcactg       1260
gtgaggtcac aagtagtaga gacttcttgt taacgggcag aaactttcac ggacccagca       1320
tgctactgtg gcagttctgc aacaagctga aaatgccttt cccgaccacc caagccagtg       1380
ccacacaaag gccaccttag ggtgtgcaca ggatgtcact aggcgttggc ggaactcagg       1440
aaggagtctg aatttcttcc cgtttcttcc ttcctctctc attccctatc ttagcttctg       1500
tctctctttc ctctctctcg ttcccccccct tcctccctcc cttcctgttg cagggccaca       1560
gatggaccgg gagacctcaa gcatgtcaaa tcaactaact gctctaccac tcaaccacac       1620
cctcgcctgc attgttacta ctactattat tatcttgata caggtctcca cattgagctc       1680
accctcacag tctccacatt gagctcaccc tcacagtctc cacattgagc tcaccctcac       1740
agtctccaca ttgagctcac cctcacagtc tccacattga gctcaccctc acagtctcca       1800
cattgagctc accctgtggc tctggcaaac cttgaattct ctcattcctc ctgcctcagc       1860
```

-continued

```
ctctggggtc gtggggatta gccaaaccca cttgaggttt tcttcaatca gcaaattctt      1920
agcgttcaat taacacacac tcataactcc agtactttgg aaaccggaac aggagaattt      1980
ctgtgagctg gaggctagct tggactacag tatgagaccc tgtctctaaa taaatacaca      2040
aagaaatctc accaagggcc tccctctctc agcaagctct aactgtggtg ggagttctgg      2100
gttgttccag ttaacgggct cagaactcta ctgcccagca catcagcccc tagacacagg      2160
tggctctcta catgtgaaca tgcagtcaca gaaatgaaat aaagtgaaaa ttttatttct      2220
tcagttgtat agcctcttcc gtgtgggctg tagttactgt cttgaatagg ataggctcag      2280
aatccttggt gctggaacca agagtttgat tccattagac gacagggaat ataatgccca      2340
atagggcatt cctcctcccg gtcactagcg gtgcactttc tccgaatctt tgtcatgttg      2400
aattagaaaa gttagtattt tcctccatcc cttcccctcc tcccctcctc ccctcctccc      2460
ctcctcccct cctccctccg tctccccgcc cctcccctcc ccctctgatc ctcccccatc      2520
tatcaaatcc aagaattcca gtaaaaagag gaaaacaatc gaagtgattt cgttgattgt      2580
cagttccacc aaagcaagac ttgactttag ttccgcgttt cggttcccgg catgcaccac      2640
agccagcgag caccgtggaa ggatgctagc acggtcctcc ccccgccccc actagctgtc      2700
ttcagctccc cagtagaggg caaccgcact ccagattctc aatggagagt gtttacacaa      2760
tcgttgcggg tttgtgtgag cgcgcccgct tccagagaca cttcttcttt ttctttttc      2820 catttcatcc cagtggcaac gcagagtgcc agatcattca ggccgtttgc agggcaagcc      2880
gtgggagctt ggcaagcaag gccccatttc ctagggaacc cgtgcctggc gcttcaggaa      2940
agcacgggaa cctggcactg tgactctgcg ggtattattt tgcagaactc tttattaaac      3000
gggagtttca agtccagctg gagacgacca ggcagcgcct ttaaccccag agtcacacac      3060
aggtgccttt tcttggggcc agattggggt tgtgtggcag acctgcgacc agcttgacaa      3120
ctcttctgcc aggccacaaa atggtgttgg ctgtaagagg tgacaccagg gacagggaag      3180
atcgctgcta ttctcctgag ctctccaaag acccacacca gtctgtcccc ctttcctcct      3240
gctcttcccc tgtatcgccc cctcaccatc tcccccaacg agactcttgg catctcctcg      3300
gcacaaggat ttgaaaatag atgcttgggg gtgagaagaa gaagagagaa agagagagaa      3360
ggaaggaagg atatatagat gatacagacg catacaggtg acatgtagct aatcattttt      3420
aattaaaaaa taaattaaaa gcaaatcaag gatatatatg ataccttag agcaagtgtc      3480 tcatacacac acaaacacac acacacaata tatatatata tatatatata tatatata      3540 tatatatata ttatacttgg aacaagtgtc cagaagggct ggggactcta aagtgcttgt      3600
caaagccagg ctcacatcag taatcttatc acctggtaga ctgagacagg aggattttga      3660
tgagttcagg cccagcctga gctgcagaat gtgattctat cccaaaaaag taaaataaaa      3720
taaaattcaa aatacacgaa aagagtattt gctgaacaaa caagcctaaa gccctggatc      3780
ccttccccca tgtcctaaga aaataagttt cttgaagctg gagggatggc tcagaggtta      3840
agagccccag ctgcacttgc ggaacactaa gacccagttc ccagacccca cactgtgggt      3900
cacaactgtc tcaaacgcca gctccggagg atccatgccc tctcctggcc tccaccggca      3960
ccaagaacac atacagtgcc catacattta tgcaagcaag gtattcacgc acataaaact      4020
aaaagaatat ttaataaaga tataacaaaa tagcatgaag cccagctggt acagaggttc      4080
aaactacatc ccaggttcat ccctctgcct ttgctctcag ttggcttggg taggtctctt      4140
ctctgaactg gcgccctgcg ggttccacat tgagaccctc tcattttaa acctacttct      4200 tctgggcggg gttaattgct gccagggctc aagccaacgc ttcctcttct ccacagcaat      4260
```

-continued

```
cttccaagtt tcacgagata accaggaact gctaagttca tgtgaacctt agtgaagaac      4320
ctgagtcttc ccatgtgatt ggtgtgtgca tgtgtgcata cacaaatgta tgtgtgtgct      4380
ctatgtgtgc ctatgtatgt gtgcatgcat gtgtgcatat acaaatgcat atatgtctat      4440
gtagtgtgcg tacacaaatg tatgtgtgtg ctcaatgtgt gcctatgtgt gtgtatgcat      4500
gtgtgcgtac acaatgcatg tgtgtggtgt ctgtgtgcct gtgtgtgtat gcatgtatgc      4560
atacacaaat gtatatgtgt ggtgtgtgaa tgtgtgccta tgtatgtgtg tgctgtgtgt      4620
gggtgtggta tgtgtgtgat gtgtggaggg gtgtgtatgt gtggtatgta taggtgatac      4680
gtttggggtg taatatgcgt atgtggtttg tgaaatgtag ttcgtgtgtg tgcatgtgtg      4740
cgtgcgtgcg tgcgtgcgtg cgtgtgtgtg tgtgtgtgtg tgtgtgtgtt ggatatagta      4800
tgtgtgaggt gtgtgtactc accatggcct ccctcacttg ggggagtgaa gtcagcagcc      4860
tggaccactc agggacatga gatactcaga cacatcttga tttccacccc tctttttcctg      4920 atcctccttc acgtgtcact ttcccaaaca ctggacaaca gtttgggggc atctgattcc      4980
actaatgaca gggacatcac atgtctccag agggaacacc ttctgtgtca catgtcatct      5040
gagaatgtag cagagtcaca gagaaatgtc acagaaacca aaatgcagag taccaaggta      5100
tagctaggca cagagcagag gggaagccgc tgaatttatt aaaaatgtca gaatcgtaaa      5160
agacagggga cagcggtggg gacattcagg gtccagtagc acacaggcag tccaaacctg      5220
atcactggaa ggtagtaggt aaggaaaggc tgcacacaga ttattcacac agtttataca      5280
tgtacacaga ttattcacat ggtttgtgta tgtgcacaga ttattcacac agtttataca      5340
tgtgtggctt cgtggtaact ttgagcttac tttcaattta aaaggatctc tctcacaagc      5400
tggggccggg aatggctgca gtcaacactc catcacttag tcacactgtg caaacagcac      5460
ctcctgactc atggtgactt gtagtaaaat gaagaggcca catttgcatc caagacagct      5520
catcagtacc tagtgaagaa tctgtccctg agtatttgca tgaatggacc cgggtccagg      5580
gcctggctgg gagtctccag gtgttgcagc cagaatgtca ttgtgttttt tcaggatccc      5640
agaagtttct aaaatacagg ccaagtactc atttgtgtta caaagtatct gactaataga      5700
agtgattagg taacacaaag cctttaaaa accgagatca cccttgtcat gtccctggcc      5760
tcttagaaca agatccaagc ttttgctggt tgacaagtgg ggccatccag tgcgtctccg      5820
ttcctgctac ttcatctgga agacctctcc cactaacttg cccctgaccc ctcacacctg      5880
ctgtttcctt tccacccgga agtgcttgtc taggctttca tggccatctg actgagcatc      5940
taggcctcag tccagtggtc cctcagctct ctctagtcac tgtactaatg gaaacggcca      6000
ctaactacat tttcaatatg gaagcctcct cctcaggaac ctccaagggc agaagcctcc      6060
agagaaccac tcctgacccc ctggagttct gagtgcttct ggccctctct gtgtctgcag      6120
gactattcac cacttgtgtt gaatggttca gtcctcacct cctctggcat gtgctcagtt      6180
ctcatctcat tggggagtcc ttcccaggtc actcttctct cctgtctttg aagtgttttt      6240
ttccttcatg gtatttctgt ctgggcacac acacagacac acatacacac acatacacac      6300
ccatgcagta tcgcagatac atcacctatg tttcagattt ttattctacc atcacccaat      6360
acctgaatcc ccgaaaaagc cttagaaagc caggaatttg tgtatttttg tcagcactcc      6420
accccagcac ctgaagccaa gcctgactta atatttttgg ttttgtttct aga           6473
```

-continued

<211> 7045
<212> DNA
<213> *Cricetulus griseus*
<400>    4

(SEQ ID NO: 8)

```
caattgatta tagatggatg atagatagat agatagatag atagatagat agatagatga      60
tggatagaca gatgatggat agttagagga tagataatga ctgaataata agtacataaa     120
tagatgatag agcggggcgt tggtggtgca cgtctttaac cccagcacca gagaggcaga     180
ggcagttgga tctctgtgag tttgaggaca gcctggttac agaatgggtt ccaggacagc     240
caaggctgtc actcagagaa atactgtctc aaataaaaaa agtaagtaaa caaataaata     300
aatgataact agttagaaga tagatgattg aatgataggt agataaatag aagatagata     360
gatagatgat tgatagatga tagacagata gacagacaga cagacagaca gacagcagaa     420
agataatgca cggtgaaaca tggtctgatt tagttagcaa gatcagagaa gccttctttg     480
aaagtgacat ttgagagcat ttcaaacgct gttcatgtca ggcatgccaa tggggagaga     540
agggcttgca gaaagcaggc ccggcaagcc atggggagca agctaggagg cagcattcct     600
tgcatttgcc tctgcctcag ctgcttcctg gagttccccg gtttttatca caacagtaga     660
aataaaacca ggacaatgtt gtttccatgc atacatctgc aagaacttac tccggttcaa     720
tagacagacc aaggcacctg tgtttgctca agaagcacgg agggaggtgt gtgcacctgc     780
tgggtgctgg tgctctggct gtgccagaca gagagcaaga caggaaagtt cctggtggcc     840
tagagcacac agcccagccc aggaagtcat gtctctctct gtctctgtct ctgccccacc     900
cccaccccat ttaggccaga gaacagctgt ggcaagcttt gggtttgggt gagtcattcc     960
tcaagagcca agagccgccc accttgtatg gggtagtttg ttgttgttgt tgttgttatt    1020
atttgtttgt ttgtttgttt ggtaaaggtt tttcaatagg agttggaatt tggcaattca    1080
gctaggctgg ctgagcagcc agctagcccc gggcactcat ccgtctctac ctccccagtt    1140
ctgggatttc gggtacatgc tcccacatcc gactttttc ccctgctcca gttcttaaga    1200
ccaagtcttc atgtcaaaca cttcaccacc ttagccatct ttctgggtca gaagttagat    1260
cttcaggaag acaaggagtg tatcaggaca tgagcgtgcc ccaactctgc tcagaccttc    1320
tgatagagaa aatggggga ggggtgtcag aggctgccgg agaaagacaa gtccaggtta    1380
aggaggacga ccctgggctc tgaatccaag ggtgattccc tcaccttgta cacttggcat    1440
tttgggaagg aagcatcaga taaaagcagt gcagacatag tcaggaatat ttacacgtgt    1500
gagtcaacct gggagtgagt ctgtgtacaa ctgaacatga agcaagtttt gaagcttcat    1560
ttccagacta ttcccagggt gcaataactt cctgtttcg ttgcagcctt cccagtctct    1620
gccactgcca tctctacttc agtctggaat ggtgggcaca cagaaaaagt ctatggcaat    1680
cctgcgagaa gacaagtggg cgcctgactt cgggctcctg ttacaagaga ggaatccagg    1740
agtttatttt gcagctgatt cagtgttgac caagagtcca gctctggggg agtgggaagc    1800
aaccaaagca gagacaggtc ccagcacaat ttttggtttt caagacagca cttctctgtg    1860
gctttgaagg ctatcctaga actgttcttt gtatatcctt ccttgcaact agctcttata    1920
gaccaggctg gtcttgaact cacagagatc catctgcctc tgcctcccaa gtgctgggat    1980
taaaggcgtg cacctcggct gccaccaccc agctacatac ataatttaca ataataaaaa    2040
taaaatactt taaagtgtta tagcagtttg aatgtaattg gccctgtcat ctcatagga    2100 gtggcactat taggaggtat ggctttgttg aaggaaatat gtcactgtga gggtgggctg    2160
tgaggtttcc tatgctcagg gtaccagcca gtgtctcagc tgaggtcctg ttgcctgcaa    2220
gatgtaggac tctcatccct ttctccagca ccatgtctgt ctgcatgcca tcatgttccc    2280
```

-continued

```
agccatgatg acaatgtact aaaacctctg aaactgccac ccaactaaat gttttccttt        2340
ataagagttg ccatgctcat ggtgtctctt cacagcaata gaaaccctaa ctaagataag        2400
tgtattctcc cctactcccc atgatttaaa atttaggaag gcaggtaggc aggcaggcag        2460
gctggtatag tggttcattc tagcacctga gacctggaat gggaggattg tgagttagtt        2520
ctaggccatt ctggtgccta gaaaccagag ccggggggttg gcccaatgca gagcacttgc        2580
tctacgtatg gcccagcaca ataagtcaat ttcctcacct taaaggcttg acaatttaaa        2640
aacactggtt tttagttagt ccgtgtctgc tccacagatg gagacagcta atcacagaty        2700
catcaggggc cttcctgagt gctaaacatc aaacagcctt ctcccctcct gagcctttgt        2760
gtgcagaatg tgtccatcgc aagaagcaaa cagtcttgct tgcccaccaa cttccttcct        2820
gcatcagaag agctgggtgc aaactgcaag agtagcctca ccttagagat gggtcccatt        2880
gctctacatg ggagcattac cttccaagaa ggcaaaaatg tctcctggtt gagctttttt        2940
tgtcacctgt taaaggcaaa tcaacagaga ggctttgtct cacccactaa catcttggaa        3000
acaaatacca acgaacgctg gggaggatgt ggggaaagca gagccctcat gctctccgag        3060
ggaaaatcac acccactgtg gaacagtgtg gaaacctcaa agactgggat tacaagcagc        3120
acacaagcca gccacgctac tcctggtcac acaccacaaa gacgcttgca cattcacgct        3180
tacgctgcga acactagcaa cgttcccact gcctcctttg agcccgccc cccgcccctg        3240 cccccgccc cgcccctgtg gtctatgttc ctcttccta aagtcagctt ccacttctct        3300
gtctccatct tcgcccacc ctccctcctc gctacataat tgtctctatt ccatttctct        3360
gctttgaaac agctttttgc aaagcatcaa atctattgtc ctatgcccca aatcaacctc        3420
cagtttcaca agtgatacag gaaatcgttt tcctaattaa aaatccccc tttgaccatt        3480 tattcccact cttggaacat cttcccttg aggaaagtta cagaatgagg tggctctcct        3540
cttcctattc gaggtgtttc cttcagactt tgtccgtgtc taatctttt aactgttggc        3600 caggcctcca ccacggcaca gatgaactgt ggggttcatt tacctgaaac tctatggaag        3660
gatgtttatt tctccttcac tttagcaaat gataaagggc accattcact ctgtctattc        3720
tgcaggggcc attcctttct ctaggccaga tactgagaat tgctcccaga atcaatgtgg        3780
tatacatatt tccccttcaa cattgatagg cattgatcac acacacac acacacac        3840 acacacac acacagtagc acaaatgtat tcccctagcc cgcttccatc ttgccacagg        3900
actccagagt ggccctggat agcaagcttc ctgtttttgtt tctctgttcc tgctgctttt        3960
ccaccctcca gtctatcttt tctaagtcct tctgccattg tcctcttccc aactgtcctg        4020
agatgcagtc attgtctggg attcagacct tctctctctg cccaagtgag tatattgacc        4080
cccacggttt gtacaaccat aacttcaggg agcccgacaa aaactgtttt atgagccaag        4140
tagtcccagg acttgagagg tagaggcggg aagatcagca gtttgaggcc agcctggaga        4200
gcataagagc cggtctcaaa acaacaatgg aaactagata ctaagtaaaa atcctggggt        4260
gtttcatcat gaatgtctgt tcttctagta ccacgctgaa ctccgtacac agctccagct        4320
gttacggctt tcttagaatc catactcttt tttttttttt tttttttttt tttttttttgg        4380 tttttcgaga cagggtttct ctgtggctttt ggaggctgtc ctggaactag ctcttataga        4440
ccaggctggt ctcgaactca cagagatcca cctgcctctg cctccagagt gctgggatta        4500
aaggcgtgcg ccaccaacac ccggcagaat ccatactctt tttaaaaaaa gatttatcaa        4560
tttactatgt atacagcttt ctgcctgcat gtatccatgc atgtcagaag atggcaccag        4620
gtcgcattac agatggttgt gagccaccat gtggttgctg ggaattgaac tcagaatgtc        4680
```

-continued

```
tagaagagca accagttctc ttaacctctg agccatctct ccggcccca gaaatccata          4740 ttcttgagga ttttttacac cccccccacc aaaagacgta tatctaaatt ttaatgtgag          4800
aattcacatt ttcttaagag ttgaacatag atttagagga aaatcagatc ccacatgatt          4860
aacaaagcat gcttgtgggc aggtctgcta ccaagaggtg ggccgtagct tctagctcag          4920
acaaactcac tcccttcctc gtggcctctt cgccctcaag tcagaaactc accctgtgat          4980
tctgccccag aagttgctct agagcacagt gcatccttcc gtcttcactc tgtggcttga          5040
attgtgtcca tcgcttatga ttacaacccc tcacagagca tcctaactgg tttctttgca          5100
tgcctatggg cactcctcca ttctagaaca cccttgccat caatactatg aaaggagggg          5160
tggaggagga agagcaggaa gaggaggggg aagcgaggga agaggaagac acggatggca          5220
atgaggaggg gggagcaccc aagtcctccc tggatgagag tctcactggg agacttaata          5280
ttaattataa atgcttggtc agcagctggg caggataagg ttaggcagga gaaccagact          5340
aaggactctg ggaagcagaa gggcagagtc agacaaggag aggaaacagg aagtacaagg          5400
taaagtcacg tcgcagaatg tagataatag aaatgggttc atttaagttg gaagagttag          5460
ctagtaacaa gcctgagcta tcagccgagc atttataatt aatattgagc ctccatattg          5520
gttatctggg aattggcggg cagaaaaaaa aaagtctgcc tacaagtcaa tgtcatgtag          5580
ctcccaaagc caaggtacct ttgttcagtg cttgactgag ccagcattat aaattttctc          5640
cagatgtacc gaatcacatt tcatagcaac atgcagacat caagttttcc ctgaagctct          5700
aaccagctgg ttgcatgctg tccggagtct cagctataac ccagaagtga cctgggtcgg          5760
ggaagaggtg gtactttgcc ttctttgcac tctctgtgtt gcctcaccca ttcagcttca          5820
agcaatgtga ctgcctgacc ctgagggcgt ttacaacgcc tgacccacag accacaagtc          5880
aaccagctgg tgtgctcacg atacctagtc tgaaccatag ccctgctccc accctgcctc          5940
catctccacc ctttcttcac tgctcatcac agctggctag caaagactgc ctcagacctg          6000
agcacaggct ccactccaca gccgtgactg ttcgagccac ttaaatcaaa gagcgcttgt          6060
cttccgctca gtaaatctct cctcagctca ctgatgacgt tgactttctc tagacagcac          6120
atttgggttt aagacactgc tacttgagct cttcattcag ttcctcagaa tacctcattt          6180
gggtcagatt cccaaagagg aagatagggt tcctggcaga cagacatgtc tcattccttt          6240
gaaatccttc agagaaatgc agtgactatg gcaccttctt aaaaagcaca cacacaaata          6300
acacacacac acacacacac acacacacac acacacacac atatcccct cactgtcatc          6360 cttgatatgt atatgatata tataaaatca ttgtttata ctgtgataat tgattatgaa          6420
taaaatttac taaaatgaac aattaaaatt atgggggggg ctggagagat ggctcatcag          6480
ttaagagaac agttgctgct cttgcagaac acgagagttc agttcccagc acccacatca          6540
ggcagctcat aaccatgtgt ggtgtcagtt ccaggagatc tggtgccctc ttctggcctc          6600
ctccagcacc tgctacatgt ggttcacaca cacacacaca cacacacaca cacacacaca          6660
cacacacaca caaataaata taaagattat tttttttcaaa actgagttaa aaataggttc          6720
tatctgattc atactaaggc ttttcacagt ggttaagtct attagatatg tctagccata          6780
tcctttctcc cttctttctt gaggagaggc ttttaaagct acaagttaca gccttctttg          6840
caaataagag taccatttaa caggcctctg accaatgaga tcccagaatc ggttgcccag          6900
```

-continued

```
gagcttccca aacagtccat tatagggaaa ggtggtacaa accagtagat taggcatgtt        6960
ccacttccta agtgccgtgc caaataagga aatggcctca aatgtttgcc ttttatcttc        7020
acccacctct gaattgcacg ctagt                                             7045
```

```
<211> 13515
<212> DNA
<213> Cricetulus griseus
<400>       5
                                                          (SEQ ID NO: 9)
tctagaaaca aaaccaaaaa tattaagtca ggcttggctt caggtgctgg ggtggagtgc          60
tgacaaaaat acacaaattc ctggctttct aaggcttttt cggggattca ggtattgggt         120
gatggtagaa taaaaatctg aaacataggt gatgtatctg ccatactgca tgggtgtgta         180
tgtgtgtgta tgtgtgtctg tgtgtgtgcc cagacagaaa taccatgaag gaaaaaaaca         240
cttcaaagac aggagagaag agtgacctgg gaaggactcc ccaatgagat gagaactgag         300
cacatgccag aggaggtgag gactgaacca ttcaacacaa gtggtgaata gtcctgcaga         360
cacagagagg gccagaagca ctcagaactc caggggtca ggagtggttc tctggaggct          420
tctgcccttg gaggttcctg aggaggaggc ttccatattg aaaatgtagt tagtggccgt         480
ttccattagt acagtgacta gagagagctg agggaccact ggactgaggc ctagatgctc         540
agtcagatgg ccatgaaagc ctagacaagc acttccgggt ggaaaggaaa cagcaggtgt         600
gaggggtcag gggcaagtta gtgggagagg tcttccagat gaagtagcag gaacggagac         660
gcactggatg gccccacttg tcaaccagca aaagcttgga tcttgttcta agaggccagg         720
gacatgacaa gggtgatctc ggttttaaa aggctttgtg ttacctaatc acttctatta         780
gtcagatact ttgtaacaca aatgagtact tggcctgtat tttagaaact tctgggatcc         840
tgaaaaaaca caatgacatt ctggctgcaa cacctggaga ctcccagcca ggccctggac         900
ccgggtccat tcatgcaaat actcagggac agattcttca ctaggtactg atgagctgtc         960
ttggatgcaa atgtggcctc ttcattttac tacaagtcac catgagtcag gaggtgctgt        1020
ttgcacagtg tgactaagtg atggagtgtt gactgcagcc attcccggcc ccagcttgtg        1080
agagagatcc ttttaaattg aaagtaagct caaagttacc acgaagccac acatgtataa        1140
actgtgtgaa taatctgtgc acatacacaa accatgtgaa taatctgtgt acatgtataa       1200
actgtgtgaa taatctgtgt gcagcctttc cttacctact accttccagt gatcaggttt        1260
ggactgcctg tgtgctactg gaccctgaat gtccccaccg ctgtcccctg tcttttacga        1320
ttctgacatt tttaataaat tcagcggctt cccctctgct ctgtgcctag ctataccttg        1380
gtactctgca tttttggtttc tgtgacattt ctctgtgact ctgctacatt ctcagatgac        1440
atgtgacaca gaaggtgttc cctctggaga catgtgatgt ccctgtcatt agtggaatca        1500 gatgcccca aactgttgtc cagtgtttgg gaaagtgaca cgtgaaggag gatcaggaaa         1560
agaggggtgg aaatcaagat gtgtctgagt atctcatgtc cctgagtggt ccaggctgct        1620
gacttcactc ccccaagtga gggaggccat ggtgagtaca cacacctcac acatactata        1680
tccaacacac acacacacac acacacacac acgcacgcac gcacgcacgc acgcacacat        1740
gcacacacac gaactacatt tcacaaacca catacgcata ttacaccca aacgtatcac         1800 ctatacatac cacacataca cacccctcca cacatcacac acataccaca cccacacaca        1860
gcacacacat acataggcac acattcacac accacacata tacatttgtg tatgcataca        1920
tgcatacaca cacaggcaca cagacaccac acacatgcat tgtgtacgca cacatgcata       1980
cacacacata ggcacacatt gagcacacac atacatttgt gtacgcacac tacatagaca       2040
tatatgcatt tgtatatgca cacatgcatg cacacataca taggcacaca tagagcacac       2100
```

-continued

```
acatacattt gtgtatgcac acatgcacac accaatcaca tcggaagact aagattgctg      2160
actaaggttc acatgaactt agcagttcct ggttatctcg tgaaacttgg caggttcttc      2220
tggagaagag gaagcgttgg cttgagccct ggcagcaatt aaccccgccc agaagaagta      2280
ggtttaaaaa tgagagggtc tcaatgtgga acccgcaggg cgccagttca gagaagagac      2340
ctacccaagc caactgagag caaaggcaga gggatgaacc tgggatgtag tttgaacctc      2400
tgtaccagct gggcttcatg ctattttgtt atatctttat taaatattct tttagtttta      2460
tgtgcgtgaa taccttgctt gcataaatgt atgggcactg tatgtgttct tggtgccggt      2520
ggaggccagg agagggcatg gatcctccgg agctggcgtt tgagacagtt gtgacccaca      2580
gtgtggggtc tgggaactgg gtcttagtgt tccgcaagtg cagctggggc tcttaacctc      2640
tgagccatcc ctccagcttc aagaaactta ttttcttagg acatggggga agggatccag      2700
ggctttaggc ttgtttgttc agcaaatact ctttttcgtgt attttgaatt ttatttttatt      2760 ttacttttt gggatagaat cacattctgc agctcaggct gggcctgaac tcatcaaaat      2820
cctcctgtct cagtctacca ggtgataaga ttactgatgt gagcctggct ttgacaagca      2880
ctttagagtc cccagccctt ctggacactt gttccaagta taatatatat atatatatat      2940
atatatatat atatatatat atatattgtg tgtgtgtgtt tgtgtgtgta tgagacactt      3000
gctctaaggg tatcatatat atccttgatt tgcttttaat ttatttttta attaaaaatg      3060
attagctaca tgtcacctgt atgcgtctgt atcatctata tatccttcct tccttctctc      3120
tctttctctc ttcttcttct cacccccaag catctatttt caaatccttg tgccgaggag      3180
atgccaagag tctcgttggg ggagatggtg aggggcgat acaggggaag agcaggagga      3240 aaggggggaca gactggtgtg ggtctttgga gagctcagga gaatagcagc gatcttccct      3300
gtccctggtg tcacctctta cagccaacac cattttgtgg cctggcagaa gagttgtcaa      3360
gctggtcgca ggtctgccac acaaccccaa tctggcccca agaaaaggca cctgtgtgtg      3420
actctggggt taaaggcgct gcctggtcgt ctccagctgg acttgaaact cccgtttaat      3480
aaagagttct gcaaaataat acccgcagag tcacagtgcc aggttcccgt gctttcctga      3540
agcgccaggc acgggttccc taggaaatgg ggccttgctt gccaagctcc cacggcttgc      3600
cctgcaaacg gcctgaatga tctggcactc tgcgttgcca ctgggatgaa atggaaaaaa      3660
gaaaaagaag aagtgtctct ggaagcgggc gcgctcacac aaacccgcaa cgattgtgta      3720
aacactctcc attgagaatc tggagtgcgg ttgccctcta ctggggagct gaagacagct      3780
agtgggggcg ggggaggac cgtgctagca tccttccacg gtgctcgctg gctgtggtgc      3840
atgccgggaa ccgaaacgcg gaactaaagt caagtcttgc tttggtggaa ctgacaatca      3900
acgaaatcac ttcgattgtt ttcctctttt tactggaatt cttggatttg atagatgggg      3960
gaggatcaga gggggagggg aggggcgggg agacggaggg aggaggggag gaggggagga      4020
gggaggaggg ggaggagggg aagggatgga ggaaaatact aactttttcta attcaacatg      4080 acaaagattc ggagaaagtg caccgctagt gaccgggagg aggaatgccc tattgggcat      4140
tatattccct gtcgtctaat ggaatcaaac tcttggttcc agcaccaagg attctgagcc      4200
tatcctattc aagacagtaa ctacagccca cacggaagag gctatacaac tgaagaaata      4260
aaattttcac tttatttcat ttctgtgact gcatgttcac atgtagagag ccacctgtgt      4320
ctaggggctg atgtgctggg cagtagagtt ctgagcccgt taactggaac aacccagaac      4380
tcccaccaca gttagagctt gctgagagag ggaggccctt ggtgagattt ctttgtgtat      4440
ttatttagag acagggtctc atactgtagt ccaagctagc ctccagctca cagaaattct      4500
```

-continued

```
cctgttccgg tttccaaagt actggagtta tgagtgtgtg ttaattgaac gctaagaatt      4560
tgctgattga agaaaacctc aagtgggttt ggctaatccc cacgaccca gaggctgagg       4620 caggaggaat gagagaattc aaggtttgcc agagccacag ggtgagctca atgtggagac      4680 tgtgaggtg agctcaatgt ggagactgtg agggtgagct caatgtggag actgtgaggg      4740
tgagctcaat gtggagactg tgagggtgag ctcaatgtgg agactgtgag ggtgagctca      4800
atgtggagac ctgtatcaag ataataatag tagtagtaac aatgcaggcg agggtgtggt      4860
tgagtggtag agcagttagt tgatttgaca tgcttgaggt ctcccggtcc atctgtggcc      4920
ctgcaacagg aagggaggga ggaaggggg gaacgagaga gaggaaagag agacagaagc        4980 taagatagg aatgagagag gaaggaagaa acgggaagaa attcagactc cttcctgagt       5040
tccgccaacg cctagtgaca tcctgtgcac accctaaggt ggcctttgtg tggcactggc      5100
ttgggtggtc gggaaaggca ttttcagctt gttgcagaac tgccacagta gcatgctggg      5160
tccgtgaaag tttctgcccg ttaacaagaa gtctctacta cttgtgacct caccagtgaa      5220
aatttcttta attgtctcct ggtgttctgg gttttgcatt tttgtttcta aggatacatt      5280
cctgggtgat gtcatgaagt ccccaaagac acagtgggc tgtgttggat tgggaaagat       5340
gatttatctg gggtgtcaaa aggaaaagaa gggaaacagg cacttgggaa aatgtcctcc      5400
cgcccacccg aattttggct tggcaaccgt ggtggaggag caagaaacac gtggacgttt      5460
gaggaggcat ggggtcctag gaggacagga agcagaagga gagagctggg ctgacagcct      5520
gcaggcattg cacagtttca gaaggagatt acagcatgac tgagttttta gggatccaac      5580
agggacctgg gtagagattc tgtgggctct gaggcaactt gacctcagcc agatggtatt      5640
tgaataacct gctcttagag ggaaaacaga catagcaaac agagccacgt ttagtgatga      5700
aactctcact ttgcctgagt catgtgcggc catgcccagg ggtcaggctg acactcaact      5760
caaaaacaag tgagaaattg aagacaatcc gtggtggcag ctactggaag ggccaccaca      5820
tccccagaaa gagtggagct gctaaaaagc catttgtgat aggcacagtt atcttgaatg      5880
catggagcag agattacgga aaaatcgaga atgttaatga ggcaacattc gagttgagtc      5940
attcagtgtg ggaaacccag acgcttccat cccctaaaag gaacatcttg ctctcagtca      6000
aaatggaaat aaaaattggg gcttgaattt ggcaaatgat tcagaactct gtgtaggtat      6060
tttcacacgc acagtggata attttcatgt tggagtttat ttgtgctaaa aggcagaaaa      6120
gggtaaaaag cacatcttaa gagttatgag gttctacgaa taaaaataat gttacttaca      6180
gctattcctt aattagtacc cccttccacc tgtggtaatt tcctgagata gtcagtgggg      6240
aaaagatctc tccttctctt ctttctcccc ctcccctcct ctccctccct ccctccctcc      6300
ctccctcctc tccctccctc ccccttttcct tctttctttg ctccttctcc tctgcctcct      6360 tctcccttc ttcttcattt attctaagta gcttttaaca gcacaccaat tacctgtgta       6420
taacgggaaa acacaggctc aagcagctta gagaagattg atctgtgttc actagcgtgc      6480
aattcagagg tgggtgaaga taaaaggcaa acatttgagg ccatttcctt atttggcacg      6540
gcacttagga agtggaacat gcctaatcta ctggtttgta ccacctttcc ctataatgga      6600
ctgtttggga agctcctggg caaccgattc tggcatctca ttggtcagag gcctgttaaa      6660
tggtactctt atttgcaaag aaggctgtaa cttgtagctt taaaagcctc tcctcaagaa      6720
agaagggaga aaggatatgg ctagacatat ctaaatagact taaccactgt gaaaagcctt      6780
agtatgaatc agatagaacc tattttttaac tcagtttttga aaaaaataat ctttatattt     6840
atttgtgtgt gtgtgtgtgt gtgtgtgtgt gtgtgtgtgt gtgtgtgtgt gaaccacatg      6900
tagcaggtgc tggaggaggc cagaagaggg caccagatct cctggaactg acaccacaca      6960
```

-continued

```
tggttatgag ctgcctgatg tgggtgctgg gaactgaact ctcgtgttct gcaagagcag        7020
caactgttct cttaactgat gagccatctc tccagcccccc cccataattt taattgttca       7080
ttttagtaaa ttttattcat aatcaattat cacagtataa aacaatgatt ttatatatat        7140
catatacata tcaaggatga cagtgagggg gatatgtgtg tgtgtgtgtg tgtgtgtgtg        7200
tgtgtgtgtg tgtgttatt gtgtgtgtgc tttttaagaa ggtgccatag tcactgcatt         7260
tctctgaagg atttcaaagg aatgagacat gtctgtctgc caggaaccct atcttcctct        7320
ttgggaatct gacccaaatg aggtattctg aggaactgaa tgaagagctc aagtagcagt        7380
gtcttaaacc caaatgtgct gtctagagaa agtcaacgtc atcagtgagc tgaggagaga        7440
tttactgagc ggaagacaag cgctctttga tttaagtggc tcgaacagtc acggctgtgg        7500
agtggagcct gtgctcaggt ctgaggcagt ctttgctagc cagctgtgat gagcagtgaa        7560
gaaagggtgg agatggaggc agggtgggag cagggctatg gttcagacta ggtatcgtga        7620
gcacaccagc tggttgactt gtggtctgtg ggtcaggcgt tgtaaacgcc ctcagggtca        7680
ggcagtcaca ttgcttgaag ctgaatgggt gaggcaacac agagagtgca aagaaggcaa        7740
agtaccacct cttccccgac ccaggtcact tctgggttat agctgagact ccggacagca        7800
tgcaaccagc tggttagagc ttcagggaaa acttgatgtc tgcatgttgc tatgaaatgt        7860
gattcggtac atctggagaa aatttataat gctggctcag tcaagcactg aacaaaggta        7920
ccttggcttt gggagctaca tgacattgac ttgtaggcag actttttttt ttctgcccgc        7980
caattcccag ataaccaata tggaggctca atattaatta taaatgctcg gctgatagct        8040
caggcttgtt actagctaac tcttccaact taaatgaacc catttctatt atctacattc        8100
tgccacgtga ctttaccttg tacttcctgt ttcctctcct tgtctgactc tgcccttctg        8160
cttcccagag tccttagtct ggttctcctg cctaacctta tcctgcccag ctgctgacca        8220
agcatttata attaatatta agtctcccag tgagactctc atccagggag gacttgggtg        8280
ctcccccctc ctcattgcca tccgtgtctt cctcttccct cgcttccccc tcctcttcct        8340
gctcttcctc ctccacccct cctttcatag tattgatggc aagggtgttc tagaatggag        8400
gagtgcccat aggcatgcaa agaaaccagt taggatgctc tgtgaggggt tgtaatcata        8460
agcgatggac acaattcaag ccacagagtg aagacggaag gatgcactgt gctctagagc        8520
aacttctggg gcagaatcac agggtgagtt tctgacttga gggcgaagag gccacgagga        8580
agggagtgag tttgtctgag ctagaagcta cggcccacct cttggtagca gacctgccca        8640
caagcatgct ttgttaatca tgtgggatct gattttcctc taaatctatg ttcaactctt        8700
aagaaaatgt gaattctcac attaaaattt agatatacgt cttttggtgg gggggtgta        8760 aaaaatcctc aagaatatgg atttctgggg gccggagaga tggctcagag gttaagagaa        8820
ctggttgctc ttctagacat tctgagttca attcccagca accacatggt ggctcacaac        8880
catctgtaat gcgacctggt gccatcttct gacatgcatg gatacatgca ggcagaaagc        8940
tgtatacata gtaaattgat aaatcttttt ttaaaaagag tatggattct gccgggtgtt        9000
ggtggcgcac gcctttaatc ccagcactct ggaggcagag gcaggtggat ctctgtgagt        9060
tcgagaccag cctggtctat aagagctagt tccaggacag cctccaaagc cacagagaaa        9120
ccctgtctcg aaaaaccaaa aaaaaaaaaa aaaaaaaaaa aaaaaaaaga gtatggattc        9180
taagaaagcc gtaacagctg gagctgtgta cggagttcag cgtggtacta gaagaacaga        9240
cattcatgat gaaacacccc aggattttta cttagtatct agtttccatt gttgttttga        9300
gaccggctct tatgctctcc aggctggcct caaactgctg atcttcccgc ctctacctct        9360
```

-continued

```
caagtcctgg gactacttgg ctcataaaac agtttttgtc gggctccctg aagttatggt    9420
tgtacaaacc gtgggggtca atatactcac ttgggcagag agagaaggtc tgaatcccag    9480
acaatgactg catctcagga cagttgggaa gaggacaatg gcagaaggac ttagaaaaga    9540
tagactggag ggtggaaaag cagcaggaac agagaaacaa aacaggaagc ttgctatcca    9600
gggccactct ggagtcctgt ggcaagatgg aagcgggcta ggggaataca tttgtgctac    9660
tgtgtgtgtg tgtgtgtgtg tgtgtgtgtg tgtgtgtgat caatgcctat caatgttgaa    9720
ggggaaatat gtataccaca ttgattctgg gagcaattct cagtatctgg cctagagaaa    9780
ggaatggccc ctgcagaata gacagagtga atggtgccct ttatcatttg ctaaagtgaa    9840
ggagaaataa acatccttcc atagagtttc aggtaaatga accccacagt tcatctgtgc    9900
cgtggtggag gcctggccaa cagttaaaaa gattagacac ggacaaagtc tgaaggaaac    9960
acctcgaata ggaagaggag agccacctca ttctgtaact ttcctcaagg ggaagatgtt   10020
ccaagagtgg gaataaatgg tcaaaggggg gatttttaat taggaaaacg atttcctgta   10080
tcacttgtga aactggaggt tgatttgggg cataggacaa tagatttgat gctttgcaaa   10140
aagctgtttc aaagcagaga aatggaatag agacaattat gtagcgagga gggagggtgg   10200
ggcgaagaty gagacagaga agtggaagct gactttaggg aagaggaaca tagaccacag   10260
gggcggggcg gggggcaggg gcggggggcg gggctcaaag gaggcagtgg gaacgttgct   10320
agtgttcgca gcgtaagcgt gaatgtgcaa gcgtctttgt ggtgtgtgac caggagtagc   10380
gtggctggct tgtgtgctgc ttgtaatccc agtctttgag gtttccacac tgttccacag   10440
tgggtgtgat tttccctcgg agagcatgag ggctctgctt tccccacatc ctccccagcg   10500
ttcgttggta tttgtttcca agatgttagt gggtgagaca aagcctctct gttgatttgc   10560
ctttaacagg tgacaaaaaa agctcaacca ggagacattt ttgccttctt ggaaggtaat   10620
gctcccatgt agagcaatgg gacccatctc taaggtgagg ctactcttgc agtttgcacc   10680
cagctcttct gatgcaggaa ggaagttggt gggcaagcaa gactgtttgc ttcttgcgat   10740
ggacacattc tgcacacaaa ggctcaggag gggagaaggc tgtttgatgt ttagcactca   10800
ggaaggcccc tgatgcatct gtgattagct gtctccatct gtggagcaga cacggactaa   10860
ctaaaaacca gtgttttttaa attgtcaagc ctttaaggtg aggaaattga cttattgtgc   10920
tgggccatac gtagagcaag tgctctgcat tgggccaacc cccggctctg gtttctaggc   10980
accagaatgg cctagaacta actcacaatc ctcccattcc aggtctcagg tgctagaatg   11040
aaccactata ccagcctgcc tgcctgccta cctgccttcc taaattttaa atcatgggga   11100
gtaggggaga atacacttat cttagttagg gtttctattg ctgtgaagag acaccatgag   11160
catggcaact cttataaagg aaaacattta gttgggtggc agtttcagag gtttttagtac   11220 attgtcatca tggctgggaa catgatggca tgcagacaga catggtgctg gagaaaggga   11280
tgagagtcct acatcttgca ggcaacagga cctcagctga gacactggct ggtaccctga   11340
gcataggaaa cctcacagcc caccctcaca gtgacatatt tccttcaaca aagccatacc   11400
tcctaatagt gccactccct atgagatgac agggccaatt acattcaaac tgctataaca   11460
ctttaaagta tttttatttt attattgtaa attatgtatg tagctgggtg gtggcagccg   11520
aggtgcacgc ctttaatccc agcacttggg aggcagaggc agatggatct ctgtgagttc   11580
aagaccagcc tggtctataa gagctagttg caaggaagga tatacaaaga acagttctag   11640
gatagccttc aaagccacag agaagtgctg tcttgaaaac caaaaattgt gctgggacct   11700
gtctctgctt tggttgcttc ccactccccc agagctggac tcttggtcaa cactgaatca   11760
gctgcaaaat aaactcctgg attcctctct tgtaacagga gcccgaagtc aggcgcccac   11820
```

-continued

```
ttgtcttctc gcaggattgc catagacttt ttctgtgtgc ccaccattcc agactgaagt    11880
agagatggca gtggcagaga ctgggaaggc tgcaacgaaa acaggaagtt attgcaccct    11940
gggaatagtc tggaaatgaa gcttcaaaac ttgcttcatg ttcagttgta cacagactca    12000
ctcccaggtt gactcacacg tgtaaatatt cctgactatg tctgcactgc ttttatctga    12060
tgcttccttc ccaaaatgcc aagtgtacaa ggtgagggaa tcacccttgg attcagagcc    12120
cagggtcgtc ctccttaacc tggacttgtc tttctccggc agcctctgac acccctcccc    12180
ccattttctc tatcagaagg tctgagcaga gttggggcac gctcatgtcc tgatacactc    12240
cttgtcttcc tgaagatcta acttctgacc cagaaagatg gctaaggtgg tgaagtgttt    12300
gacatgaaga cttggtctta agaactggag caggggaaaa aagtcggatg tggcagcatg    12360
tacccgaaat cccagaactg gggaggtaga gacggatgag tgcccggggc tagctggctg    12420
ctcagccagc ctagctgaat tgccaaattc caactcctat tgaaaaacct ttaccaaaca    12480
aacaaacaaa caaataataa caacaacaac aacaacaaac taccccatac aaggtgggcg    12540
gctcttggct cttgaggaat gactcaccca aacccaaagc ttgccacagc tgttctctgg    12600
cctaaatggg gtgggggtgg ggcagagaca gagacagaga gagacatgac ttcctgggct    12660
gggctgtgtg ctctaggcca ccaggaactt tcctgtcttg ctctctgtct ggcacagcca    12720
gagcaccagc acccagcagg tgcacacacc tccctccgtg cttcttgagc aaacacaggt    12780
gccttggtct gtctattgaa ccggagtaag ttcttgcaga tgtatgcatg gaaacaacat    12840
tgtcctggtt ttatttctac tcttgtgata aaaaccgggg aactccagga agcagctgag    12900
gcagaggcaa atgcaaggaa tgctgcctcc tagcttgctc cccatggctt gccgggcctg    12960
ctttctgcaa gcccttctct ccccattggc atgcctgaca tgaacagcgt ttgaaatgct    13020
ctcaaatgtc actttcaaag aaggcttctc tgatcttgct aactaaatca gaccatgttt    13080
caccgtgcat tatctttctg ctgtctgtct gtcgtctgtct ctgtctatct gtctatcatc    13140
tatcaatcat ctatctatct atcttctatt tatctaccta tcattcaatc atctatcttc    13200
taactagtta tcatttattt atttgtttac ttactttttt tatttgagac agtatttctc    13260
tgagtgacag ccttggctgt cctggaaccc attctgtaac caggctgtcc tcaaactcac    13320
agagatccaa ctgcctctgc ctctctggtg ctggggttaa agacgtgcac caccaacgcc    13380
ccgctctatc atctatttat gtacttatta ttcagtcatt atctatcctc taactatcca    13440
tcatctgtct atccatcatc tatctatcta tctatctatc tatctatcta tctatcatcc    13500
atctataatc aattg    13515
```

<211> 14553
<212> DNA
<213> *Mus musculus*
<400>    6

(SEQ ID NO: 10)

```
cttgaagaac acatgttttc caagagggag cacccatgtt ggaatgacaa tgtagttagt    60
gctcctctcc tgtaggttag tgctcctttg ctataggtaa gtgctcctct cctataggtc    120
agtgctcctc tcctataggt tagtgctcct ctcctatagg ttagtgctcc tctcctacag    180
gttagtgctc ctctgctcta ggttagtcct gctctcctat agtacctaga gagctagggc    240
aaatgggcta ggcccgaagt gcagagacaa acagctatgg aagactgggt aagcacttcc    300
aagctacgaa agagcagtgt gaaggtcag ggcttgtgca gttagtaggg gagatcttcc    360
agttgaagaa acagaagaac tgagagccac tgggtatcat cctcctgcgc catgccttcc    420
tggatactgc catgctccca ccttgatgat aatggaatga acctctgaac ctgtaagcca    480
gccccaatga aatattgttt ttatgagagt tgccttggtc atgctgtctg ttcacagcag    540
```

-continued

```
taaaaccccta aataaggcag aagttggtac cagtattgct gtgatagacc tgaccatgct    600
ttcctttgaa agaatgtgga tttggtgact ttggatttgc aacacagtgg aatgctttaa    660
atggagatta atgggtcatc aattcctagt aggaatatgg aagactttgt tgctgggagt    720
atttgaactg tgttgacctg gcctaagaga tttcaaagga gaagaatttc agaatgtggc    780
ataaagacag tttttgtggt attttggtga agaatgtggc tactttttgc ccttgtctga    840
aaagtctgcc tgagactaaa gtgaagagaa tcagattaat tgcattgaca agggaagttt    900
gtggctgcgc tatctggaaa cttacagcca gcctcttgga cctcgggtga cttacgcaaa    960
tactcaggga cagagatgct tgactctgta ctgatgagtt gtcttggatg caaatatggg   1020
ctcttcattt gactacatgt cacgatgagt caggagctgc tctctccaga gtgtgacaaa   1080
gcgagggggt gctgacggta gctgttctag ctttgaaggt aagcctgcac ttatgctaaa   1140
gtcacacata cacgagccgg gtggagaacc tgtctgtgtg gagacacctt tcattacctg   1200
tggcatccag cctctcaagc ttggactgcc tgtgtgctcc tggactctgg aggtcccact   1260
gctctgtcct ctgctgctta tgatactgac attttaaaag aatccagtgg ttccccctg    1320 tactcggtgt ctacttctac ctggatgttc ctcatttatg ttctgtgaca cttctctgtg   1380
actctgctgc attcctgggt gacatgtgga caccctgtcc ctttgcagac catgatgtca   1440
ctgtcactag tggaatcaga tgccccaagt gttgtcctgt gtttgggaac gtgacaggca   1500
gtacagaagc agaagaggaa gggtgaaaac ggaaatgtca cagcagcatc tgatgtgtgc   1560
ctcagtcacg catgctgctg attggaacta ctcagcatga gagagggcca tggtgaatac   1620
acaaccctat acacactgtg tccatttctc tctctctctt acacagagag agagggagga   1680
gggggagggg gaggcggagg gggaggggga gggagaggga gtgggagagg gagagggaga   1740
gggagaggga gagggagagg gagagggaga gggagagttt aatgtctgtg aagagatacc   1800
atgaccaaag caactcttat aaaggacaac atttaattgg ggctggctta caggttcaga   1860
aattcagtcc attctcacca tggtgggaag catgcaggta gatgtggtgc tggaggaacc   1920
aagagttcta tatcctgatc tgaaggcagc caggagaaga ctgcctcttc tgcacagggc   1980
agagcttgag catagaacat caaagccctt ccccacactt cctccaacaa ggtcatacat   2040
acttcaacaa agacacacct cctaacggtg ccactccctg tggaccaacc atttaaacgc   2100
atgagtctat gagggtcaaa gctcttcaaa ccaccacact catgtacaca cacacacaca   2160
cacacacaca ctctcataca cacacacaca cacactcaca cacacacaca cacacacaca   2220
cacacacaca ccacacacac acacacacac agagttctat tttgcactgt ttcactgtca   2280
caaggttcta cttatctcag acacactgcc aggaattgtg tcggaagact ttcagtttct   2340
ttgggttcac atggacttag cagttcttgg tgatcctgaa agatttctgc agaaagaagc   2400
caaagtgttg agcccaaggc ctggccacac attagtcctg tctagatgaa caggggttta   2460
aaaataaggg tcgaagtcaa tgaagccagc aggggctgac ttagagagga gacccaccca   2520
agccaactgc ggcatcaagg aagcgatgaa tcccatatc cagctgtgcc cggtgctgtc    2580
ttgctacatc tttagtaaat gttcttttag ttgtatgcgt atgaatattt tgcttgcata   2640
tatttgtgta caccataggt gttcctaggg cctatggagg ccagaagagg gcatcagatc   2700
ctttggaact ggaattatag acacttgtta cccatagagt agattgtggg aaatgagcct   2760
ttagtcttcg agagcggcca gtgctcttaa cctttggtcg tttctccagg tctttgagac   2820
tttattttct tggacatcag gacaggatcc agggctttga gcttgtttct tcagccagct   2880 ttctttttcat gtatattaaa ttttatgtta ttttgctttc ttttccccca agacagaatc   2940
```

-continued

```
acactctata tagctcaggc tgggtttgaa ttcagtttcc ctgtctcagt ctaccgggta    3000
atatgattac agatgtgagt ctgactttgg tatcaaagtc cccagccctt ctggatatgt    3060
gttttaagga tatcagatat atccttgatt tgctttgaat tttcttttta gttacaacat    3120
aattagttcc gtgtcacctg aatatgtgta tgtcacctac atagtcttcc ttcttctctt    3180
cttccctctc ccaccttccc aggtacctgt ctgtcttcat atccttgtgc tgagagtctt    3240
gttgagggag atgatgaccg agacagagcc actgggaag ggagatgggc tagtgcaggt    3300
cttcagagag gagctcgtga atattgtagc ccctttagtc cctggcatgt cctcttgtat    3360
agccaccgcc atgctgtggc ctggcagaag tgaataagtt gtccagctgt tgacaggcct    3420
gccctccaga cccagtctga tcccaagaaa gggcatctgt gtctgtctct gaggccgtaa    3480
gtgctgcctg gttgtctcca gcttgacttg acactccctc cttaataaga gtaccacaga    3540
acagggtctg cagagtccct gggccaggtc cctgtgctgt cctggaatgc caggcgtgaa    3600
tttcctgtga gtaggactt tgctcgccaa gctcccacgg cttgcccttc agatagccag    3660
aattatctgg taccctgcat tgccgttcaa tacgcagagt atcactggaa gcgcgcgcgc    3720
gcacacacac acacacacac acacacacac acacacacac acacgcccac tccatcttta    3780
aaccccaccc cccagcaacg gcggtgtaaa cactctccat caggaagctg aaacgcagtt    3840
gccctctgct ggggagatga aggcagcttg ctgggggcga ggaccgtgct agcaaccttc    3900
cctggtgcac acgggctctg gtgcatgacg ggaacggaaa cgcggaacta aagtcagtcc    3960
tgcttttttt ttttttttt ttttttttt ttttttttt ttttttttt ggcgttggtg    4020 gtggactgag tgacaatcag tgaaatcact taggttgttt ttctcttctt cgttgggttt    4080
gatagacggt gggagaggt cagaggagaa ggggagggat ggggagagag ggaggaggga    4140
ggggcgggag gcggggggcg aggaaaacgt gctaacttct ccaatcctac aagacaaagg    4200
tttggagaaa gccgcactga gtgacccagc agaaggaatc caggaatgtc cgctggaatc    4260
tgactgttga ttccagcgcc atgcagagaa tctaggctgg taggaacatt ctttgtccta    4320
tccgacataa taactccaac caacacggaa aagaaaggct atacaagtga agaaatggca    4380
ttttcacttt catgactata caatcacttc caggtagtaa cacgtgtcta gcacagcggt    4440
tctcaacctg ggggtcacga tccccacctt ttctgcatat cagacatttt tacgttgtta    4500
ttcataacag tagcaaaatt gcagctatga agtaacaatg aaatgcattt atggtgcgtg    4560
tgtgtgtgtg tgggggggta tcaccttaac atttactgta agaaggttga gaatactgct    4620
ccagcagcta gtgtgttgga cttaggttct gggtatatta ttagcaatag ccaaccagaa    4680
tccccaccca ccacagcatt gaggccccat gcagggcttg ctgggagagg cactgataag    4740
acttctttat gtatttattt agagacgaat actcattagg taggccaagc tagcgtcaaa    4800
ctcatggcaa ttctcctcct ccagtttcct aagtactgga ctcaggagtg tcttgccatc    4860
atatacagta aggatttatt gactgaagaa aatctcaagt ggctttggtt aatccctact    4920
acgccagagg ctgaggcagg aggcgcgcaa ggtcaaggct tgcctgggct acatatagag    4980
tgagctcaat tttgacactt ggtgcggtgt tagtagtaat agtaaagatg aaggtgtggc    5040
tcaggtgggg ccggtgattg dacacacttg gggtctcctg gtccatctgc agctgtgcaa    5100
caggaagagc ggagaatgag aggaaagaga gaaaagacag aatgagagag agggaggaag    5160
agagaaaaag gaaagagag aggaaaggaa aaaggaaat gaggaaagcg agaaagaaga    5220
aatgagaaag aggaaaggga gaaagaaatg agagagagaa aagaaaagac agaatgcgag    5280
agagggagga agagagaaaa aggaaaagag agaggaaagg aaaaaggaaa atgaggaaag    5340
cgagaaagaa gaaatgagaa agaggaaagg gagaaagaaa tgagagagag aaaagaaaag    5400
```

-continued

```
acagaatgcg agagagggag gaagagagaa aaaggaaaag agagaggaag ggaaaaagga    5460
aaatgaggaa agcgagaaag aagaaatgag aaagaggaaa gggagaaaga aatgagagag    5520
agaaaagaaa agacagaatg cgagagaggg aggaagagag aaaaaggaaa agagagagga    5580
agggaaaaag gaaaatgagg aaagcgagaa agaagaaatg agaaagagga aagggagaaa    5640
gaaatgagag agagaaaaga aaagacagaa tgcgagagag ggaggaagag agaaaaagga    5700
aaagagagag gaagggaaaa tggaaaatga ggaaagcgag aaagaagaaa tgagaaagag    5760
gaaagggaga aagaaatgag cgagataaaa gacagaattt gagagaggga ggaagaaata    5820
ggaaaagaga ggaaaggatg gagaaaagag agaaagaaag agagatgaaa gagagaaagg    5880
agaaatgaaa tgagagagag agagagacac aaagagccag agagagaaga aaaaaggga    5940 aagagaaaga gaaagaggaa ggctcctctt ggacacatct tcctttatct ttccctgggg    6000
accgccaaag cctggtggca tactgtacat tctgtacact gttcattcaa aacaggctct    6060
gtcttaaaga tggtctgagc ggtcagaaaa gggtattgtt aacttgtttg caaaactgcc    6120
tcaggagagt gctgagtgcg tgaaagttgc tgcccgttaa ggagaagtct ctactacttg    6180
tgatctcacc atcgaaaatt tctttaattg tctcctggtg ttctgggttt tgcagttttg    6240
tttctaagga tacattcttg ggtgatgtca caaagtcccc aaagacacgg tggagctgtg    6300
ttagatgggg aaagacagtc tgctgaggat ttatctggaa ctgtcagaag gaaaagaagg    6360
taaatggggc acttgggaaa gtggcctcta gtttgacttc tggcttagca aaggttgtgg    6420
ggagataagg catacacagt agttagcagg aggcaacagg gtcctgggag gacgcgaggc    6480
agaaggagag gctgggctga cagcatgcaa tcattgcata gtctccaaag gagattgcaa    6540
catggctgag ttttcagagg tcctacagag cccgtggtag agattctgtg ggttctgaga    6600
caacttgact ttagccagat ggtatttgag taatctggga gagagaaaac agctacagca    6660
aacagggcca catttagtga cgaaactctc actttgactg ttgagtcatt tgcagtgggc    6720
cctgaggtca ggctggccct cagctcaaaa acaagcgagg aactgaagca attactcaga    6780
taatccacag ccacagccac tggaaagggc cacatcccca gagacagcac agcaggggtg    6840
ggggtggggc tatgagaaag ttagtgattg tagcagttat ctagaatgtg cggagcagag    6900
gaggttacac aaaaacctag aatgtcattc aatgtgggaa accgagaggc tcccaagccc    6960
taaaaggaac agtttgcttt cagccaaaat ggaaataaaa tttggggctt aaatctggca    7020
aatgattcag accttctgtg taggtgtctt taaatgcaca gcagattgat tttcatgttg    7080
gagtttattt gaactaaaag acagaaatgg tgaaaagcac acctgaagaa attgagatgc    7140
tatgaataaa atcatttact tacagctatc acttaattag tacctccttc caccttgctg    7200
atttattggg ctagtcaagg aagaaaagat cttccctcct ccttctctcc tcctcccccct    7260 cctctcctcc tcccctcccc tccttgacct tcctctcctc cttttcccctc ctccccctct    7320 tcttctcttc accccctcct ccccctccccct cctctgtact cctccccttt cctcccaatc    7380
tcttttttct ccccccttctt ctctttctcc ccccctcctct tccctcctct tcctccctcc    7440
ctccctcctc ctcctcatcc tcctcttcct cttcatcctc ttctccttcc tccctctcct    7500
cctcctcctt ttccagccct acctacctc cctttcttct tcatttattc aaagtagctt    7560
tgaacagcac tactcggttt agttgtgtat aaaaggaaaa tgcaggtcca agcagcttgg    7620
ggaagattgc ttttttgctct ctggaggcag atgatgacag ttcaagatca ttccttttgc    7680
tccatgtcac aggaaggggg acatgccgaa tctaccagtt tgcagccacc tacacaggat    7740
ccaccttcac ttctaaggaa atgtttggga agctacctac caaccacttc tggcatctca    7800
```

-continued

```
tgggctagag gactcttaaa tggcactctt atttgtttaa taaaggaggt tgtgacgtgt      7860
agttttaaat cccttccaca caacaattgc tactctctga ccaaaaaaga agggagacag      7920
gatacggcta ggtgtctagt agactttacc actttgaaaa gccttaatat aaatcaggta      7980
gatacatctt tttaacttat tcttgtaaag acaaaaacaa aactttattt ttatttgtgt      8040
gtatgcttgt gtgtgtgtgc ctgtgtgtat accacatgtc gctggtgccg gagaacacca      8100 gaagaggggga cctgatctcc tggagctaaa gctatccatg gttctgagct gcctgatgtg      8160
ggtgctggga acagaactct ggtcttctgc aagagcaaca agcctcctct taactacgaa      8220
tctcctcccc atccccccaa atacatttaa ttattcattt tagcagcttt atttcgtaac      8280
tacttatcac agcataaaac aaggatttta tatatattac atgcaatcga ggataagagt      8340
tgaggggaga tgcgtgtgct ccttctgggt gtctgtgctt ttgaagaatg taagcagtgc      8400
acaagggacc gaggcgtgcc tgtctgccag gagctgtctt cttcccttgg actctgagct      8460
gagtgcagtg ctccgaagaa gtaaaagacg acctcatgaa gcaatgtctt caacccaaac      8520
atgctgtcca gacaaagtcc agcttcatta gtgctctgag gagagactta ctgagcctca      8580
ggaaagcccc cctcagcatg gcgaaagtcc actttgattg aagtgactcg aaagccatgg      8640
cagtgcggcg gcggccgcgt ggagcttgtg ctcgagtcgg aagcggcatc tttgtcaggc      8700
ggctgtgatt agcacgggga ggcaggactg gagtgaagga agagttgggg gcggggctta      8760
gcgctctggt ctcctaagct gtagtcagcg cctcaagatt tgtaacctgc cttctgcctt      8820
cccagccagg cagtcaagtg gctccaagct gaagactgca aagtgcccct aaccttttgg      8880
ttatagcgag gctgaagaca ccgtgctctt tcatgaaagc cggatgtctg aaatccgatt      8940
tgataaatat ggataaaacg tataacgctc gatcaatcga atcgaaggag ctcacgattg      9000
gcaccacggc tttggggaca acagagtact gactcgttgg gaggacttgg atacttcccc      9060
tcctcttcca tctcttcccc tttcctcact tcctcctcct tccttctcca ttttctccct      9120
cttcactgtt tcttactatt tttacaaaag attttattta tttatttatt tatttatttta      9180 tttatttatt tatttatttta tttatttaat gtatgcgagt acactgtagc tgtcttcaga      9240
cacaccagaa gagggcgtca agttccatta gagatggttt cgagccacca tgtggttgct      9300
ggggcctctg gaaggaccgc cagtgctctt aacccctgag ccatttctcc agtacccttc      9360
tcaccgtttc tcttcaatct tcttcctctt ccttctccac tttccttgtc ttcttggttt      9420
cattatcttt ctcccctttct tcctcttctc ccctcttcc tcctccactg tagttttcct      9480
tccctactct tttcctgcct ccctcctcct cccctctcat tcccctcct ctttcctcct      9540 tctccctcct cctccttcct tctcccttctc ccctctcccc tctcccttct cccttctccc      9600
cctcctcttc ctctttctcc ttctccaccc ctcctgtcac agtatcaatg gcaagggtgt      9660
tctagaatgg aggagtgtcc cctaggcact aacgaaagcc agttaggatg ctctgagacg      9720
ggtacaattc agggagggcc gtggggatgg aagggttgtg ctgcgattca ttctggagca      9780 accccccaggc agaatcatga ggttggttcc ggattcgcag ggcacaattc agaagaggaa      9840
ggtttcagga aggacgagtt tgtctgagat aggagttaca tctgatgtct ggcagcaga      9900 gccactgtac aagcgtgctt tattaaccac gtgggattaa atcttctttt aaatttattt      9960
tcaactctta aggaaacgtg aactttcaca ttcaaattta gacttgcagc tcttatgggg      10020
aaaaaaaggg gatcttaaga atattaagca taggcggctg gagagatggc tcagcggtta      10080
agagcactct ctgctctccc agaggtcctg agttcaattc ctagcaacca cataatagtt      10140
aacaacagtc tttaatgaat tctaatgccc tcttctggtg tgtctgaaga cagttacagt      10200
gtactcatat aaataaaata aagaaattta aaaaaatgaa tattaggcat agattcctgg      10260
```

-continued

```
atcctaagaa agccatcaga gctggagcca tgtgtgggat cctgcttggt gctggagggg      10320
cagagttcat gcccccgggg ttttttactta ttatcacatt ttcatcgttg ttttgaaaca      10380
gggtcttgtg tggtccaggc tggccttgaa ctcatctttc agcctctacc tcacaggttc      10440
tgggattact tggttcctaa aagtatctcc gtcaagctcc ctggtgttat ggctgtgcca      10500
accaggaggg tctatacact cgctcaggta gagggagaag atccgaatct ctgacaggga      10560
ctgctgcctc tcggggcaaa tggagtgaag acagcggca gaaggattta ggaaagatgg       10620
acgggagagt ggaaatgctg cagaagccag aaaacaaagc aggaagcctg ctgtccagtg      10680
gggctcaaga gcggagggat gcgagggggc tgcgcaggaa catttagcgt ctgcgtctat      10740
gggggtaggg gcggggtgcc agcacctagt cacctgaagg ggaaatgctt gcccagggag      10800
caggtctcag tagctgacct agagaaagga gcggcccta cagaggagac acgggtcact      10860
gtttgttaaa gtgaaggaga aataaatatt ctttcaaaga atcttaggtg agcccagttc      10920
atctgcgctg tggaggcctg gggaacagtt aaaaagaccc tgacacacac ccaaggcaaa      10980
caagcaacac acggctcctt ccgtaagggt ccatgattct ctgaagaatc agccccggaa      11040
tcagccccgg aatcaggtag tccgtaaaca caatgagtgt tttactctgc agaagtccag      11100
cctgctggcg tctcccatta ccaaaataga gggatagtca cgtgagctca ccggctcgat      11160
ttaaggcacg tcgtttttcca gggtagatga gctttggctt ctggaaccat tatgggggcac     11220 gaaggatgga gccaggattt tttttttttt tttttttttc tattagcaat tgatttgctt      11280
gggcttggct ggacttgccc agttcttagg cccagtcttc ttaactgccg atctgaagtc      11340
tgtcatggag tcagcctagc cttctcactt cccttcagct cgaataggaa gaggaggtgc      11400
acaccagatg gtctgagagc agggataaat ggtgtgcctt tgtctttcag tatttcgtta      11460
ttttaagtag gaagatgctt ttctgtatta cattgcttgt gaaaccggaa gttgattcgg      11520
ggcacaggac aatggatttg gtgttttgca aggactgttt cagaagagag aggagtggaa      11580
gggtggttag agtgaggagt ggggtgggac gggatggggg aagagaagga agggccagac      11640
aggctaggta gggctgagag gaggcggtgg gaacttcttg agttagcgca gcagtaaact      11700
tggatgtgcg tgtatctttg tgatatatga cccggagccg tgtagctggc tccgatagta      11760
ctgctaatgt cagtgtcggg gggggggggt cccatactgt tccacagggg ctgcacattc      11820
ccatcgagag caggagggct cctctctcca tacatcctcg ccagcattcc ttgttgtttc      11880
tgtgatgaca gggggtggga tgaaatctct ctgttggttt gagagaccgt gaagaagctc      11940
aaccccagga cattttgcag tcttggaagg cagtgcctcc atgtggagcc gtggagccca      12000
tctctgagtc caggtcactc ttgcagttcg cactcagctc ttcagatgca ggagagacgt      12060
tggtgggaaa gcaagattgt ttgcttgttg agatagacac attctccaca caaaggctca      12120
cgtggggcaa aggctgattg acgtacagcg ttcaggaacg cctgtggtag agctatgatt      12180
agctgtctcc atcatgaag cagacaaaga gttataaaaa aaatcaatgt tttcaaattg       12240
tcaaactttt aacccgacag caagcgctct gtccctgggc taatccctag ccctggtttc      12300
ttgagatggg gtcttttgtg cactagactg gcctagaact cacgatctta gtgttccagc      12360
ctcccagctg ctgggatgag ccgctataac cagtctgcct gccttcctaa attttaagtg      12420
atgggaagtg gggagaaata cagtttaaag tatgcagatc tgagagcagg aacctggcaa      12480
agccaagggg ccggagttac aggcggctaa catgggtgct gggaactgac ccaggtcctt      12540
gagaggagca gtgtgtactc ttgaccaaac aggtccgtct ctccagtccc cgtagtatta      12600
aaaataggta ctacgggcat ggtggtgcac acctttaatc ccagcactag ggaggcagag      12660
```

-continued

```
gcaggtggat ttctgagttt gaggccagcc tggtctacaa aatgagttcc aggacagcca      12720
cggctataca gagaaaccct gtcttgaaaa caaaacaaca acaaaatagg tactacaaag      12780
cgatgtaatt gtgctcaaac atgcaaaccg aggggactgt atgcataaga aagagaaaga      12840
cggccacact ggttctatct gggtgacagg aaatcagtat ttttattttt cacattcatt      12900 ttttgttgt tgttgttgac acagtgattt ttctatcaaa aacattattt cttttatagt       12960
tcccctgagg agctgttttt aaagccgtgc tttgaaaaac cattgaagga gcagaggcag      13020
ggagactcct gtgtggcagt cggtgaagca ggccctctgc aggcaggctg gccctggact      13080
tgggagtctc tttccctccc tcctgtgctc aaatagcaaa tgtcaggctt caatgtagct      13140
agaaggttct agaatgatta agtttccaag gctgaagagc ttccctgttt gcctttcact      13200
tccctggaga ggtcgttgtg tgttccggag tctgcaaggt gcctttggtg atgcgggtgg      13260
ttcatctcgg gagattccgc ctggaggacc caagttcaag ccctgcctga gctacagagt      13320
gactttcagg tcttctgcgc aattcagtga gacccagtct acaaataaaa agtaaaaaga      13380
aggctgtgga tggaactcgg tggtagagtt ctgggtttac tccctagagg aggggagaag      13440
gaggaggagg gaggaggaag aggaagaaag aagaagagaa gggaagagga gaaggaaggg      13500
agggaagggg ctgacaagaa gagagaagag ggagggaggg gagggaaagg aaggggaaag      13560
gaagggaggg aaggggctga caagaagaga gaagagggag ggaggggaga aaggaaggg      13620 ggaaagaaga gaagggtaag aagaaactgt tccaatggtc tgggccacag agtgatggcc      13680
ttttgtggtg atcagctgta atccttgatt tgacacaacc tagaatctgg gaagcgagtt      13740
tctgtgaagg agcattcaca ctggctggcc tgtgggcgtg catgtgggag actgtcataa      13800
ttaggttcat taatacagga agtcccagcc cactacaaat ggcttcgttc catacccaag      13860
agatgctaac tgtagacggt tggagaaagc aagcaagctg tggatacccc acgctctttc      13920
acctcggctc ctgggggggtg ggtgcactgt gtctcttggt attttaaagt cctgccttga      13980
cgtccctgct gtgacagact gtaactggaa ttgtgagctt tagtcctta gttttctacg       14040 ttggttttc tcaggatatt ttatcgcagt aacagaaaca agaccaggac acttgatctc       14100
ctctgatcaa cactgaagag ttacaaaaca ggctgaggaa acaaactttc ttctccctct      14160
cccccttctg tccctcccct tccttctcgc tccctccctt gcccctctc tccctgtctc       14220 tgtctctgtc tctgtctctg tctctgtctc tgtctctgcc tctcccctcc cctccctcc      14280 ctctgtctct gtctctgtct ctgtctctgt ctctgtctct gtctctgtcc ctttctcctc      14340
tatctcctaa atggctggag gccatgctag ctcaatgttg aactttgaac acgtatttag      14400
gaaatctttg ttcttaacag ttctgaagtg ctgaagtggt ggtttagtct ctcggcctga      14460
caagctcact tcctctcact ctgtcttaat gaccaaatct gccatttccc taaaacagca      14520
caggctccag ctccaggttg ctccggagcg gag                                   14553
```

EXAMPLE 12 - CHO Stable Site 2 Sequences - U.S. Pat. No. 9,816,110
<211> 4001
<212> DNA
<213> *Cricetulus griseus*
<400> 1

(SEQ ID NO: 11)
```
ccaagatgcc catcaactga ttaatagatg ataaaattat tgtacatttc agtgtaatat           60
tattcagttt ttaagaaaaa tgaaattatg taataagcat gtaaatggat atatcttgaa          120
acaaccattc cccattatat tacctaaaca ttgaaagtcc aaaatcatat gatcttttta          180
gtggatctac taatcttttg ctatatgtat tttattgaac tacccatgga tgtgagataa          240
ttggtaacaa cagcacatgg gagagcatgg gatcattcaa ggaagattag agagaatgca          300 tttttttagga gataatggag gagcaataga aaggattaaa tgaggttact gatgaaagtg          360
```

-continued

```
atggttagag aaggcaatat gaggagggat aactagcact tagggccttt tgaaaaagac      420
atagagaaaa tactattgta gaaacttcct ataattggtg tatagttata tacaccaaag      480
agctcagatg gagttaccct ataatggaaa tattaactac tttttatcac tgtgataaaa      540
catcctgaac agagcaacat agattgggaa gcatttactt tggcttacag ttctaacggg      600
ataaaaattc atgatgaaag aatgaatatg tcagcaaaca gcagtagcaa tggcctgaga      660
agcaggtgag agctcacatc ttgaagtgta agaatgtagc agagagaaca aactgcaaat      720
gaccagaaaa tgcttttgga tcagagccca tacccctctg actgacttct ccagaaattc      780
tgaacaaata aaactcccca aacagagcca taactgaagg tccagtgtct gagactacta      840
ggggtatttc ttattcaaac cactacaatg gggtggggg agcaatcctc caagtaggca      900
ctacacacag acaaataaaa actctagtaa ctggaatgga ttgacttatt tgaattactt      960
gccagtggag ctacatagag cacaattatt gtatttaaat tacccttat gatcttacaa     1020 aacttgacag taagatcata ttgctaaaga aaccacatat ttgaatcagg gaacatggtg     1080
atatctagtt gttcttcaac tggaaacttc atgctttctg cccagcattc atgttgctgg     1140
aaagagcaat gtacactacc agtgtagaaa ttaaatcatc aatcttatca agatgtggat     1200
cctataagtt acaataaaaa ttagcctgat aagatatccc caccagaaga atattcacat     1260
aaatgctatg ggagcaacaa gctattttct aaattagctt taatcctatt ctacaagaga     1320
gaatccatat ctagaatagt tatagggatc aagaacccat ggcttgattg gtcataggcc     1380
caatgggaga tcctaatatt attgttctac aaaatgaaaa taactcctaa tgacttgttg     1440
ctgcagtaat aagttagtat gttgctcaac tctcacaaga gaagttttgt cttacaataa     1500
atggcaatta aagcagcccc acaagattta tatcataccg atctcctcat ggcctatgca     1560
tctagaagct aggaaacaaa gaggaccta agagagacat acatggtccc cctggagaag     1620 gggaagggg caagacctcc aaagctaatt gggagcatgg gggagggag agggagttag     1680 aagaaagaga aggggataaa aggagggaga ggaggacaag agagagaagg aagatctagt     1740
caagagaaga tagaggagag caagaaaaga gataccatag tagagggagc cttgtatgtt     1800
taaatagaaa actggcacta gggaattgtc caaagatcca caaggtccaa ctaataatct     1860
aagcaatagt cgagaggcta ccttaaaagc ctttctctga taatgagatt gatgactacc     1920
ttatatacca tcctagagcc ttcatccagt agctgatgga agcagaagca gacatctaca     1980
gctaaacact gagctagttg cagacaggga ggagtgatga gcaaagtcaa gaccaggctg     2040
gagaaacaca cagaaacagc agacctgaaa aaaatgttgc acatggaccc cagactgata     2100
gctgggagtc cagcatagga cttttctaga aaccctgaat gaggatatca gtttggaggt     2160
ctggttaatc tatggggaca ctggtagtgg atcaatattt atccctagtt catgactgga     2220
atttgggtac ccattccaca tggaggaatt ctctgtcagc ctagacacat gggggaggtt     2280
ctaggtcctg ctccaaataa tgtgttagac tttgaagaac tcccttgaga agactcaccc     2340
tccctgggga gcagaaaggg gatgggatga gggttggtga gggacaggag aggaggggag     2400
ggtgagggaa ctgggattga caagtaaatg atgcttgttt ctaatttaaa tgaataaagg     2460
aaaagtaaaa gaagaaaaga aaacaggcca aaagattata aaagacagag gtggtgggtg     2520
actataaaga aacactatta tctaaataaa aacatgtcag aagcacacat gaacttatag     2580
tgtttatgaa agtatgtata ataactacat aatctcaagc caagaaaaaa atatcatctt     2640
tcagtgatga aggtgatttt atttctccca gaattaaagc caaagaccta atgaaagtaa     2700
ttatcttcaa aaggttgaaa atacatactt tccaatacac agatctgcct agaaatctca     2760
```

-continued

```
tcttcacaat acacatgatg ctcaattgaa ttccattcaa tgttacagtt tagataaaca      2820
gtttgtagat aaactcacaa tgtatcattt ctttttattt tttgaccaaa cagcttctca      2880
tctgttattc agaataattc ctcgatggca ggatatccat cccaattggg ggaaggggag      2940
aatttgaaga aaacctagac cacatacata tttgccattg ggaaacaaag tctaaaatga      3000
tgttgttcac atcttctcta ctagtcctct ccccgtccca aagaaccttg gtatatgtgc      3060
ctcattttac agagagagga aagcaggaac tgagcatccc ttacttgcca tcctcaaccc      3120
aaaatttgca tcattgctca gctctgccct tctcatatga cagttacaag tcaaggcttc      3180
caaagtccct ctgtcatgtt tggtgtcaat agtttataca gatgacttca tgtcttcata      3240
tctaatgtct tatatagatt aatattaaac aatgttattt ctctaaccac attttaaatt      3300
aatttaaaaa tccattaatt gtgtctataa aatgcagaca gagtgctgag acacaatata      3360
agcctgatga tctgaatttg aaactcacac ccaccacatg gagaatcaac ttccaaaaat      3420
tttcctatta cttccacact tacaccattg tacaaacaca ataataatga acaaatgaa      3480 atgaaataaa aaattaagtc tctgtaggta atgctactgt gcagcaaaag taaaaatggc      3540
agcttaagct tgctttatgg ttacacttta ccatcttcca ttaattataa ggacttcaat      3600
catggcagaa ctatgctgtt attgtctcag tgtaacctaa ccaggtgttc cagatgttct      3660
taatgtggac acctaaacta tttgatattt gggttaagat ctttccctct ttcagaagaa      3720
acctcaggac agagggaatc ttgtctttta attttgagtc tgtagacttt ttccatttca      3780
aatatacatg aaacaagtga tgaagaaaat taatcaaaag gtgggaattg caatgatatt      3840
aggttcaata ttaagcttca atattatcat ggaatcgcct gttatacact gagtgtttgg      3900
caataaggga tttttagaag aaggagtttt tattctcaac aggttcctta agtttagctc      3960
aaataaatct aagcaatcca ctctagaatt aaatagtttc c                          4001
```

```
<211> 14931
<212> DNA
<213> Cricetulus griseus
<220>
<221> misc_feature
<222> (2176) . . . (2239)
<223> n is a, c, g, t or nucleotide is missing
<400>    4
```
(SEQ ID NO: 12)

```
catgtacact tatgcaagta tgatatggcc caacacagta ttttacacca attttatct        60 ataaaatata catgtacatc aaaatatatt attaataata acatcattat tctttctttc      120
caagtaataa acacatacac tgaaattttg gttcttgtgg ataattttaa tgaaacagga      180
aatgcaaatt tatcttagca tctttacttc actttctttg catagataac cagtaatcac      240
attgatggat catgtagtga aatgtatttt taggtatcta aggaattttg gcttcgtttt      300
gtgcttgttg acactgaatt ctattcctaa caacagtgtg taaggattct gtctgatttc      360
ttttaccagt atttgtccat ttgcatttc tttattattc atggctgctg ttctagaaag        420
tggaaggtag tgtgtcaagt ctgtttaaca tctttccctg atgatcagtg tcttaacacc      480
tctctgagta catgttggcc aatgtcgttt ctagacccat ctattcttgc ttgacttatc      540
ctggtacatg cctgccaaga aatttctcct catcctttct gtctcttcac tgatttactt      600
gatgtgtgga tttcacattg atcatatgga aatagaagat acaattttct ttattcacag      660
tttggaagac tttcaatctc atagatcatc attatttttt gctactgttc cctatgctat      720
ggtgaaattt ccatttgaat aattgcttaa acaattaaca agaaagaatc tatttttact      780
tgcaataact tccatttcag aacatttact acactgttac tatatccaaa aactagtttt      840
atatatcatg tgagaaatga ctaattcata atttggccat gacattttt tcagaaacag        900
```

-continued

```
aaaaagtgac caatacatac acaatgctat aaatattaag acttcagcaa attaaatatt        960
tattcatgat atcacataaa attcatttat tatgtttttat ttaaatgtgt ttttaaaaca      1020
gtggtatcac taaatattaa gttagatgtg tttatgtgct taatgaattt atattttaga      1080
atgttataag ttgtatatag tcaaatatgt aataaatttt attttttagg tctttctcat      1140
taaggtattt taattttggg tcccttttcc agagtgactc tagctcatga tgagttgaca      1200
taaaaactaa acagtacaaa atgtacattg cattccagtat tgcacttgat ctttgcactg      1260
aagtttgagt cagttcatac atttagtact tcggaagtac attaagctaa ctttcattgc      1320
tctggcaaaa tgctcgataa gataagagtc tattgtggaa agccatggca gcaggaaagt      1380
aagactgctg atgatgttta atccatagtc aagacgcaga aggagatgaa tgctggtatc      1440
caacattttt tgctgttcat tttctctaga accctagtcc ataaagatgt atgacttgca      1500
ttcaaaatgc gtcccttca gttgttcaac ttttctgtaa atatcctttc aggcatgtct        1560
agaagattgt ttcgcaaata cttctcaatc cattcaagtt gatagtgcag attaatcact      1620
gcagaataaa agcctgtaac ttggctcacg tcccaaggaa tatgcacact cctgacacat      1680
caataagtaa atcaaagtgt agcttttgcc tttaacattg ccagacttat gtaatgttct      1740
gcacgttctt cctccatcac tttttattct aatggtgttt ccttgacatt gaatcacgct      1800
gtggaagctg cttagaatta acattgaaat ctactgatat atttatgatg cagcaattta      1860
gatttactat tttacttaga atttttttata attgagagaa tataatattt tcacagttat      1920
ctatctgctg taaatagagg attttaaaaa aaatctctat aactttttt tacaacacac         1980 agtaaaatta agttaaaatt taataaagtc actatgttga tttcaaagtg tgctacgccc      2040
acggtggtca cgcaggtgta gcagaagatg ccactaaggt gggctaaggc cgatgggttg      2100
gggtctgcgc tccctggaga tgagccccag gcggttccct ggcaatcagc tgcgatcatg      2160
atgcccgatg agccannnnn nnnnnnnnnn nnnnnnnnnn nnnnnnnnnn nnnnnnnnnn      2220
nnnnnnnnnn nnnnnnnnnc tgggtgactt tatggaaaga atttgataga tttcatgatg      2280
tagaagaatt ttattaggct tattttacag gagactaaga ccctgggacc taaagatatc      2340
tgggtcctga gaatcaggaa atgggtagag acgtggttga tggtatgaga cagattttag      2400
agaactctta gatcatgggc aatgaccgca atctgatgct tagaatagat catctataaa      2460
caattatgct gttctttttc tttctgttgt atgatctgat gatgtagccc ccttgccaag      2520
ttccctgatc cccccttgcca agttccctga ttgtaacagt atataagcat tgcttgagag      2580
catattcaac tacattgagt gtgtctgtct gtcatttcct cgccgattcc tgatttctcc      2640
ttgagccttt tcccttgttc tccctcggtc ggtggtctcc acgagaggcg gtccgtggca      2700
aaagtgtata aatgttctaa aacatttgaa ctctaaaaca tccaaaatga aaaattaaaa      2760
taaataaaca tgaaaattaa aatatattag ctgctaaaag ttaaacaata ctatataata      2820
ttttgttatt agaattcaaa atcacattag ttggatttaa tttgaacatt gcattctttc      2880
aataataatt tcaataaaaa aagtttcccc atgatagtag aaaataataa catatgtatc      2940 tatctatttta tttaactaca catatatagc atttgtttca actaaataaa atgaatgagc      3000
aaagcaccta agtaattggt gtctattata tttatgaagc caatagtttc aaataaatta      3060
tcatgcataa ggaggtattg caaatgttaa acctttttttg aaacagatat tcccagttac      3120
agaaattata atttctaatc tttcctataa gtagaatgat gataattaat ataggccatt      3180
tgtaaataat gttcagatta aaatattctc tatttcacta gagaagaatg atattaaatg      3240
tattatattt tatttcccat tttgtttgca ccactattct atatccctca gcagtttaaa      3300
tttgtttcac catatgtgtg tgtgtttgta tcttaaatat ggcactaaaa ttagaataat      3360
```

-continued

```
ttaatataaa tctttaggag aaaagatatt gaattatttt atgttgatag gaaaatatct      3420
tttaattgtc caagaatact ttttcttcta ttttaggact gatcagaccc aggactaata      3480
ttttatatgt actaattcta tgtaccaaaa tatgttatta tctcatgaat tctgtctcaa      3540
tattgaggta ataaaaatag tccatcatga actttaaaat taaaataatg attaattaat      3600
ttttattcat attttgtttg tatgaatggt tatacatcac atgtgtgcct ggtgactgtg      3660
aatgtcagga gaaggtatga aagccactgg aattggaata agagataata tttgagatgt      3720
tatgtgggtg ctgagaatta gacgcaagcc atcttcaaga atagccagca tactatacca      3780
ctgagtaatc cattcatccc tcaataatta tctttgtaga cagtaaatat atttctaaac      3840
tataaatgac cagaaaaatt aatgtattat taatgaagac attcatctca tgtgacacac      3900
ttcacctgtc taaatcagta acactctctc cactaattaa gattttctaa gtgcatgaca      3960
cttactattt ctaaagctgt ccaatggggg ccagtcccca gtcagcaccc agtgagataa      4020
tccatgaatg catttatatc ttaggaaaaa ttcttatcta tgtagtattt agaacatttt      4080
catgtgaggg gataaacaag gaagcacaga tgctttctga tagaaacttt ctctttaatt      4140
catctagaaa aaaaaaacct ctcaggaaaa tctctcttgc tctcctccca atgctctatt      4200
cagcatcttc tccctactta attctagatc tttttctcta tgcctccttg ctgctgccct      4260
gctggctctg ctctatgcct ccccatgtca ctttttcttg ctatctcacc gttaccttct      4320
ctgcctcact ctctgccttc ttctctgctt ctcacatggc caggctctgg acaattatag      4380
ttatatgtta cattctcata acacatgata tgtcacatag tttctctcag gctagggata      4440
tcacaatgac tggccaatga gcaagtggcc ttgcatgtag ctctaagttg gtgatggttc      4500
ccagacagta agtagccatt tggttgaaat ttgaggttgg gtagtacatg aagactgaat      4560
tttcttcaaa ctctggcctt gaaatagtaa aacaacacct atgaaaatga cgacctgtat      4620
ttgtctttag aggcaaccac atattgtctg cagggcctgc tttgaatttg ctctgaagtt      4680
agcttgtttg tgtaaaagga agaatcctat atcagcctga gaaatgtaaa atatcctagc      4740
atttcaagtc atcaaaatta tatggagagt ataaatcatc cttctgacta ttcatagtca      4800
tatttgtgtc caccaagtat aaaacacact accaaagggc tgtggaaaaa atcgccataa      4860
ctgttcttat tagggaggca tagcagtggt acctgaggaa gttacagcaa caaccagtca      4920
tccagtcaat aaccccatgg ctttgccact tggaggtacc caataatgtt tggctttgcc      4980
gagtaggact ccaacaaatt cagagggtca attttttaaat gctggttgtc actgctgaac      5040
agtcccattg ccctctgcat aattccacaa tggaaagctt tttacactga ttgccaatca      5100
ttaaacagcc tactcagcat aaacaggtat gatattattc tccattttgt tacattacta      5160
gatgaattcc tatttcttcc tacaatagtg gaactgaaaa aagatacaca atcatactac      5220
ccctctacta atcttatgac ttatatcatt tcaattttca gaccataatg caaactattg      5280
accaaaacat gtgaagatga aaaatagaaa tgtagaataa tattacatat aaaaagaaaa      5340
ggcggactta ttttgtttta tttcttagca tgcatagcaa tacatgattt gaggtttata      5400
taataaaggg acaataaatc ttcaagaaac ttacccctac tgaattaaaa tattaaagaa      5460
ggtcacacat ttactcaaat atattagact actgggcaaa tagacatgaa aagtagagtt      5520
aatattgagg taggccttct gtgaaatgtc taaggaaatt atgtttcata cagtgtgtaa      5580
ccaagtggga atcatatcag aaagcagtca aaagcttata ttacaagtaa cagatgcttg      5640
gttatatgac ctcccagagc ttgactgtct atacacaaaa agtggtgtta ataaaactgt      5700
aatttgggct atgttttttt aaatggcttc accaacatga aaggaaggga atgagcatgt      5760
```

-continued

```
catggatgct tagagattat gcttccagca agaagaattg agctttggct cttattacag      5820
aaacatgaca aggtgtgagt tttatttatt agaaattata taatatttta agctggggac      5880
taaaaatttt attgaaacaa acaggcaagg gataggcatg tactagaagc aaaaatagga      5940
tgtcaatgct gtaatgttat ttttttggacc aaaatagtat ttcctataga aatgacaatg      6000
atcttaggtt attattcttc ataaagatga caagttcaca agatatccta gttcattaaa      6060
atcgttttag tcatttaata gagtgctgtg atagattaca caaaggaaag cacttacgat      6120
gagaaataat gatatccaca attattttct taattcttag aaacattcta ttgttatatc      6180
tcaatctcag aagccactta ttgctttatt attgaaacat atgaaattgt aagttatata      6240
ttgtctatgg tgacatttca aagaacatgt gacgtacagt gtagcacaga taaagaacat      6300
aactgcagct gaatcagtaa ctaaacttac atacattaaa tctgccatgt tggcaacagt      6360
gtgtgcacta ccaaaggatg tactaatgct cacgacactc ccctatgtca cccttttgttc      6420 atcattacat cataggtcta tttttgtttgc ttttgaaatc tagaccaagt cttttgtgtc      6480
tttccaagca cagagctcat taatttacct catagacttg ttaaacttct tctggttcat      6540
caattgaata gaaatactca ctactaatta tgtgagaccc tcccagtacc atagcacatg      6600
gataattttt acataaaaca tgcatacaag taagattatt cagactgaac atgaatttta      6660
gagaaatcag gaaggagtat atgggagtgg ttggagtgag actagagaaa tgtaattaaa      6720
ctataatctc aatacaaaga tctactaagc aaaaaacatg aaacattgtc attcaagtga      6780
aacatcagtc ttcaaattgg aaagatattt ttactaggaa aatgtctggt agatggttat      6840
tatctagaaa acacaaaaat tagaaaacgg taaactttaa taaaaagaat aatacaatga      6900
gactacatga aaagttctta actaatgaaa caaatatctt gaaactttttt tcttaaaagt      6960 ttaatatcaa taaccatcat ggaaattcaa attaaaacta tttacatatt acccctgaaa      7020
taataactaa tacccaataa aaataatata aacaaaaaat ggcaatgcat gccatcatgg      7080
atttgggaga gagaatgttc attgcagttc tgaatggata ctggtgccac cacggtgaaa      7140
atctctgtat aggtccttcc aaaagctgaa aatagacata tcacaagacc tcccacacat      7200
ttttcaagca aatacccaaa ggactctacc tgactgcaga gacactttct cataaaatat      7260
tattgttgat ctattcataa tatctggaaa atagaaacag ccaagatgcc catcaactga      7320
ttaatagatg ataaaattat tgtacatttc agtgtaatat tattcagttt ttaagaaaaa      7380
tgaaattatg taataagcat gtaaatggat atatcttgaa acaaccattc cccattatat      7440
tacctaaaca ttgaaagtcc aaaatcatat gatctttttta gtggatctac taatcttttg      7500
ctatatgtat tttattgaac tacccatgga tgtgagataa ttggtaacaa cagcacatgg      7560
gagagcatgg gatcattcaa ggaagattag agagaatgca tttttttagga gataatggag      7620 gagcaataga aaggattaaa tgaggttact gatgaaagtg atggttagag aaggcaatat      7680
gaggagggat aactagcact tagggccttt tgaaaaagac atagagaaaa tactattgta      7740
gaaacttcct ataattggtg tatagttata tacaccaaag agctcagatg gagttaccct      7800
ataatggaaa tattaactac tttttatcac tgtgataaaa catcctgaac agagcaacat      7860
agattgggaa gcatttactt tggcttacag ttctaacggg ataaaaattc atgatgaaag      7920
aatgaatatg tcagcaaaca gcagtagcaa tggcctgaga agcaggtgag agctcacatc      7980
ttgaagtgta agaatgtagc agagagaaca aactgcaaat gaccagaaaa tgcttttgga      8040
tcagagccca tacccctctg actgacttct ccagaaattc tgaacaaata aaactcccca      8100
aacagagcca taactgaagg tccagtgtct gagactacta ggggtatttc ttattcaaac      8160
cactacaatg gggtgggggg agcaatcctc caagtaggca ctacacacag acaaataaaa      8220
```

-continued

```
actctagtaa ctggaatgga ttgacttatt tgaattactt gccagtggag ctacatagag    8280
cacaattatt gtatttaaat taccctttat gatcttacaa aacttgacag taagatcata    8340
ttgctaaaga aaccacatat ttgaatcagg gaacatggtg atatctagtt gttcttcaac    8400
tggaaacttc atgctttctg cccagcattc atgttgctgg aaagagcaat gtacactacc    8460
agtgtagaaa ttaaatcatc aatcttatca agatgtggat cctataagtt acaataaaaa    8520
ttagcctgat aagatatccc caccagaaga atattcacat aaatgctatg ggagcaacaa    8580
gctattttct aaattagctt taatcctatt ctacaagaga gaatccatat ctagaatagt    8640
tatagggatc aagaacccat ggcttgattg gtcataggcc caatgggaga tcctaatatt    8700
attgttctac aaaatgaaaa taactcctaa tgacttgttg ctgcagtaat aagttagtat    8760
gttgctcaac tctcacaaga gaagtttttgt cttacaataa atggcaatta aagcagcccc    8820
acaagattta tatcataccg atctcctcat ggcctatgca tctagaagct aggaaacaaa    8880 gaggaccccta agagagacat acatggtccc cctggagaag gggaaggggg caagacctcc    8940
aaagctaatt gggagcatgg gggagggggag agggagttag aagaaagaga aggggataaa    9000 aggaggggaga ggaggacaag agagagaagg aagatctagt caagagaaga tagaggagag    9060
caagaaaaga gataccatag tagagggagc cttgtatgtt taaatagaaa actggcacta    9120
gggaattgtc caaagatcca caaggtccaa ctaataatct aagcaatagt cgagaggcta    9180
ccttaaaagc ctttctctga taatgagatt gatgactacc ttatatacca tcctagagcc    9240
ttcatccagt agctgatgga agcagaagca gacatctaca gctaaacact gagctagttg    9300
cagacaggga ggagtgatga gcaaagtcaa gaccaggctg gagaaacaca cagaaacagc    9360
agacctgaaa aaaatgttgc acatggaccc cagactgata gctgggagtc cagcatagga    9420
cttttctaga aaccctgaat gaggatatca gtttggaggt ctggttaatc tatgggggaca    9480 ctggtagtgg atcaatattt atccctagtt catgactgga atttgggtac ccattccaca    9540
tggaggaatt ctctgtcagc ctagacacat gggggaggtt ctaggtcctg ctccaaataa    9600
tgtgttagac tttgaagaac tcccttgaga agactcaccc tccctgggga gcagaaaggg    9660
gatgggatga gggttggtga gggacaggag aggagggggag ggtgagggaa ctgggattga    9720
caagtaaatg atgcttgttt ctaatttaaa tgaataaagg aaaagtaaaa gaagaaaaga    9780
aaacaggcca aaagattata aaagacagag gtggtgggtg actataaaga aacactatta    9840
tctaaataaa aatatgtcag aagcacacat gaacttatag tctttatgaa agtatgtata    9900
ataactacat aatctcaagc caagaaaaaa atatcatctt tcagtgatga aggtgatttt    9960
atttctccca gaattaaagc caaagaccta atgaaagtaa ttatcttcaa aaggttgaaa   10020
atacatactt tccaatacac agatctgcct agaaatctca tcttcacaat acacatgatg   10080
ctcaattgaa ttccattcaa tcttacagtt tagataaaca gtttgtagat aaactcacaa   10140
tgtatcattt ctttttattt tttgaccaaa cagcttctca tctgttattc agaataattc   10200
ctcgatggca ggatatccat cccaattggg ggaaggggag aatttgaaga aaacctagac   10260
cacatacata tttgccattg ggaaacaaag tctaaaatga tcttgttcac atcttctcta   10320
ctagtcctct ccccgtccca aagaaccttg gtatatgtgc ctcattttac agagagagga   10380
aagcaggaac tgagcatccc ttacttgcca tcctcaaccc aaaatttgca tcattgctca   10440
gctctgccct tctcatatga cagttacaag tcaaggcttc caaagtccct ctgtcatgtt   10500
tggtgtcaat agtttataca gatgacttca tgtcttcata tctaatgtct tatatagatt   10560
aatattaaac aatgttattt ctctaaccac attttaaatt aatttaaaaa tccattaatt   10620
```

-continued

```
gtgtctataa aatgcagaca gagtgctgag acacaatata agcctgatga tctgaatttg          10680
aaactcacac ccaccacatg gagaatcaac ttccaaaaat tttcctatta cttccacact          10740
tacaccatty tacaaacaca ataataatga acaaaatgaa atgaaataaa aaattaagtc          10800
tctgtaggta atgctactgt gcagcaaaag taaaaatggc agcttaagct tgctttatgg          10860 ttacactta ccatcttcca ttaattataa ggacttcaat catggcagaa ctatgctgtt          10920
attgtctcag tgtaacctaa ccaggtgttc cagatgttct taatgtggac acctaaacta          10980
tttgatattt gggttaagat ctttccctct ttcagaagaa acctcaggac agagggaatc          11040
ttgtctttta attttgagtc tgtagacttt ttccatttca aatatacatg aaacaagtga          11100
tgaagaaaat taatcaaaag gtgggaattg caatgatatt aggttcaata ttaagcttca          11160
atattatcat ggaatcgcct gttatacact gagtgtttgg caataaggga ttttttagaag          11220 aaggagtttt tattctcaac aggttcctta agtttagctc aaataaatct aagcaatcca          11280
ctctagaatt aaatagtttc ctaagggcac agctatgaat agagctcaat ttacatataa          11340
aattttgttc accatttatg tcattccagt tttcattagt acaaggaaaa tacaaaatat          11400
ttagatgtca atatcaagtg aatagttcat ctcctttttt aatatatatc acctaaatca          11460
ccattttctc agaaaaatct ggcctgaagt tctgtctgga acttcaacat gaaaaatatg          11520
cacagcttgc tattataaat cctagttgat ttttaagatt catgtctggt gtctgactca          11580 gagggggccag aggctagaca aatatttttt gaatcttcat tgtgaagatt tttaatgatt          11640
attttaatat aaataacaaa gatgatggat aatgtaactt tgtacagttc atagacgctg          11700
aactactttg tgcttaaaat gttagttccc tatcataaat gataggtgat aagtgtatgt          11760
ttaatacttt ccctctgagc tatattcatg tactagagaa ttattttaaa catgaaaaga          11820
ctgtgtttat agtctcagct cctgagaact ggtccaacct taggcaggtg aatgccagga          11880
gcaacgtttt tcttctacag aggatgcttt gctgccaagc aacctggttg tgtggaaatg          11940 ttccttttt aatcaagttt aaagggtctt catcatgctg ttgctccaca tattttcagg          12000
ttagagcttg gtccttggag tattatcttt taccagaaaa ttcatagtat tctttcaata          12060
actaacaact aaacttttcg ataaaaaaga attggaattt caattttaaa gcctgagtaa          12120
aattcttgtg aatcaggata ttttatttta agtcttatct tttaaaaagt tattttattt          12180
tttaaaaaat tataatatac tttcataatt tccctccttc acttttcttt acaaacactt          12240
ctatagatca ccatgtgttt ttttttttac atttatggcc tctttctgtt cattgttatt          12300
acatacaaat agtcttgcct atagaagaac accacaattt gttacctgat aacaaattat          12360
caacccttaa aacctacaaa ctattgatat tactgaaaag actatactta tagatgtaaa          12420
gatatatgtg tgtgcacata tatagataca catatatgta ggatttttaa ttttagattt          12480
tagacatcaa aattatttat atgactgaga aactagacac tataaatgag cattcagtat          12540
tcaacaccgt gatttagat attgtcacaa tgacagaaaa ttttcttata gaaaattta           12600 agttttgtga ttgctctgtg cacttagtga agtctcacag aaaaagaatc atagtatttt          12660
tagtttataa taaaaagtac atataattaa aatggttggc acaaacaac atttgagcat           12720 ttttcctatt tactatcaag tagtatcatt ttgaaataat aatttgacta gtttcaaaaa          12780
tgaaaacaaa atttaaacta aatgcctaat ctagcctgat aacatttta tgaatgaaat           12840 tattcaatag tcttatcaat taggggccca aaacttttcc taaaataaaa ctttttaattt         12900 ttttccattt ttatttaaat tagaaacaaa attgttttac atgtaaatca gagtttcctc          12960 accctccccct tctccctgtc cctcactaac accctacttg tcccatacca tttctgctcc         13020
ccagggaggg tgaggccttc catggggaaa cttcagagtc tgtctatcct ttcggatagg          13080
```

-continued

```
gcctaggccc tcacccattt gtctaggcta aggctcacaa agtttactcc tatgctagtg      13140
ataagtactg atctactaca agagacacca tagatttcct aggcttcctc actgacaccc      13200
atgttcatgg ggtctggaac aatcatatgc tagtttccta ggtatcagtc tggggaccat      13260
gagctccccc ttgttcaggt caactgtttc tgtgggtttc accaccctgg tcttgactgc      13320
tttgctcatc actcctccct ttctgtaact gggttccagt acaattccgt gtttagctgt      13380
gggtgtctac ttctactttc atcagcttct gggatggagc ctctaggata gcatacaatt      13440
agtcatcatc tcattatcag ggaagggcat ttaaagtagc ctctccattg ttgcttggat      13500
tgttagttgg tgtcatcttt gtagatctct ggacatttcc ctagtgccag atatctcttt      13560
aaacctacaa gactacctct attatggtat ctcttttctt gctctcgtct attcttccag      13620
acaaaatctt cctgctccct tatattttcc tctcccctcc tcttctcccc ttctcattct      13680
cctagatcca tcttcccttc ccccatgctc ccaagagaga tgttgctcag gagatcttgt      13740
tccttaaccc ttttcttggg gatctgtctc tcttagggtt gtccttgttt cctagcttct      13800
ctggaagtgt ggattgtaag ctggtaatca tttgctccat gtctaaaatc catatatgag      13860
tgatgtttgt cttttgtga ctgggttacc tcactcaaaa tggtttcttc catatgtctg      13920
tggatttcaa tagcacaaac aacatacagt atcttggggc aacactaacc aaacaagtga      13980
aagaccagta tagcaagaac tttgagttta aagaaagaaa ttaaagaaga taccagaaaa      14040
tggaaagatc tcccatgctc tttgataggc agaatcaaca tagtaaaaat ggcaatcttg      14100
ccaaaatcca tctacagact caatgcaatc cccattaaat accagcacac ttcttcacag      14160
acctgaaaga ataatactta actttatatg gagaaacaaa agacccagga taggccaaac      14220
aaccctgtac aatgaaggca cttccagagg catccccatc cctgacttca agctctatta      14280
tagagtaata atcctgaaaa cagcttggta atggcacaaa aatagacagg tagaccaatg      14340
gaattgagtt gaaaaccctg atattaaccc acatatctat gaacacctga ctttgacaaa      14400
gaagctaagg ttatacaatg taagaaagaa agcatcttca acaaatcgtg ctggcataac      14460
tggatgctgg catgtagaag actgcagata gatccatgtc taatgccatg cacaaaactt      14520
aagtccaaat ggatcaaaaa cctcaacata aatccagcca cactgaacct catagaagag      14580
aaagtgggaa gtatccttga ataaattggt acaggagacc acatcttgaa cttaacacca      14640
gtagcacaga caatcagatc aataatcaat aaatgggacc tcctgaaact gagaagcttc      14700
tgtaaggcaa tggataagtc aacaggacaa aatggcagcc cacggaatgg gaaaagatat      14760
tcaccaatcc tatatctgac agagggctgc tctctatttg caaagaacac aataagctag      14820
tttttaaaac accaattaat ccgattataa agttgggtag agaactaaat aaagaattgt      14880
taacagagca atctaacttg gcagaaagac acataagaaa gtgctcacca t             14931
```

<table>
<tr><td colspan="2">EXAMPLE 13 - Guide Sequences for<br>AAVS1-Like Region Sequences in CHO<br>(The below guides can be sense guide<br>sequences or antisense guide<br>sequences)</td></tr>
<tr><td></td><td>SEQ ID NO</td></tr>
<tr><td>CCCCGCTGGCGCCGGGATCGGGG</td><td>13</td></tr>
<tr><td>GAGTCGAGCACCGCTCGGGCAGG</td><td>14</td></tr>
<tr><td>TTCCCCGCTGGCGCCGGGATCGG</td><td>15</td></tr>
<tr><td>GTGTGCGGAAGACGCCGCCGGGG</td><td>16</td></tr>
</table>

-continued

<table>
<tr><td colspan="2">EXAMPLE 13 - Guide Sequences for<br>AAVS1-Like Region Sequences in CHO<br>(The below guides can be sense guide<br>sequences or antisense guide<br>sequences)</td></tr>
<tr><td></td><td>SEQ ID NO</td></tr>
<tr><td>CGGTGACAGCGCGGATGACAGGG</td><td>17</td></tr>
<tr><td>CAGCGCGGATGACAGGGGCGAGG</td><td>18</td></tr>
<tr><td>GCCGGCGTCCGATTCCCCGCTGG</td><td>19</td></tr>
</table>

-continued

-continued

| EXAMPLE 13 - Guide Sequences for AAVS1-Like Region Sequences in CHO (The below guides can be sense guide sequences or antisense guide sequences) | |
|---|---|
| | SEQ ID NO |
| CGTGTGCGGAAGACGCCGCCGGG | 20 |
| GAGGCGCTCCACCGTCTGTTGGG | 21 |
| GTCCGATTCCCCGCTGGCGCCGG | 22 |
| GACCCCGGGGGCCCCGATCCCGG | 23 |
| CGGCGTCTTCCGCACACGGATGG | 24 |
| TCGAGCACCGCTCGGGCAGGCGG | 25 |
| AGCTCACGCCGGCCCCATAAAGG | 26 |
| CATCGTCCTCTATATATAGCAGG | 27 |
| AGAGGCGCTCCACCGTCTGTTGG | 28 |
| GGTCGGCTGCGCGAAGCATCAGG | 29 |
| TGCTTCGCGCAGCCGACCCCGGG | 30 |
| GGCCCCGATCCCGGCGCCAGCGG | 31 |
| TCCGATTCCCCGCTGGCGCCGGG | 32 |
| TCCCGGCGCCAGCGGGGAATCGG | 33 |
| TGGTGGAGTCGAGCACCGCTCGG | 34 |
| CAAGATGGTCCTCACTCTCGGGG | 35 |
| GCTTCGCGCAGCCGACCCCGGGG | 36 |
| GTGGAGCGCCTCTTCTCCAGGGG | 37 |
| GACGTGTCAGCCTTCCAGGTGGG | 38 |
| GCCAGCGGGGAATCGGACGCCGG | 39 |
| TCTCCCCGTCATCCAAAAGCTGG | 40 |
| GGTGGAGTCGAGCACCGCTCGGG | 41 |
| GCTGCCCAAATATAGTCCATGGG | 42 |
| ATGCTTCGCGCAGCCGACCCCGG | 43 |
| GCGGTGACAGCGCGGATGACAGG | 44 |
| ATGCTCGGGGGCCGCTGACCTGG | 45 |
| TTGTATTGCCGGGATCCTTCTGG | 46 |
| TCCCCGCTGGCGCCGGGATCGGG | 47 |
| CTCGACTCCACCAACGCCGACGG | 48 |
| GGTGGCAAGATCACCAAAAGGGG | 49 |
| GGCGCTGATGCCGTCGGCGTTGG | 50 |
| TCCACGAGCATCCTAGCAAGAGG | 51 |
| AGGCTGACACGTCAGGCCTGAGG | 52 |
| GGGTGTAAGCCATCCGTGTGCGG | 53 |
| AGGATCCCGGCAATACAAGATGG | 54 |

| EXAMPLE 13 - Guide Sequences for AAVS1-Like Region Sequences in CHO (The below guides can be sense guide sequences or antisense guide sequences) | |
|---|---|
| | SEQ ID NO |
| GGATGGGGCCCAACAGACGGTGG | 55 |
| GAGGACCATCTTGTATTGCCGGG | 56 |
| AGTCGCCCAGGGTCCTGGTGGGG | 57 |
| GGCGGGAGGAGAGTCCCACCTGG | 58 |
| ACCTACCCCACCAGGACCCTGGG | 59 |
| TCAGCGTCTTTGACCAGTCCAGG | 60 |
| CGTCCCGCCGCCTGCCCGAGCGG | 61 |
| GTCCCCGGGATCCCCGGGGTCGG | 62 |
| AGCACCGCTCGGGCAGGCGGCGG | 63 |
| CGGTGGAGCGCCTCTTCTCCAGG | 64 |
| GCCCCGATCCCGGCGCCAGCGGG | 65 |
| ATCGGGGCCCCCGGGGTCCCCGG | 66 |
| ATTCTCGGCTCATCCCCTTTTGG | 67 |
| ACCACCCCATGGACTATATTTGG | 68 |
| TAGCAAGAGGACGACAACCCAGG | 69 |
| GCTGATGCCGTCGGCGTTGGTGG | 70 |
| TACAAGATGGTCCTCACTCTCGG | 71 |
| TGCCGGGATCCTTCTGGATTCGG | 72 |
| CCCAAATATAGTCCATGGGGTGG | 73 |
| TACCTGTAGAATGGGACCAGTGG | 74 |
| TCTTGCTAGGATGCTCGTGGAGG | 75 |
| ATGCCAGCTTTTGGATGACGGGG | 76 |
| ATAGTCCATGGGGTGGTAGGTGG | 77 |
| CAGGACCCTGCTATATATAGAGG | 78 |
| GGGGCCGGCGTGAGCTGTGTGGG | 79 |
| ACCTGGAAGGCTGACACGTCAGG | 80 |
| CAGCGGACAGCACGGGTCACAGG | 81 |
| CGCCGGGATCGGGGCCCCCGGGG | 82 |
| GCGCCGGGATCGGGGCCCCCGGG | 83 |
| GCCGGGATCCTTCTGGATTCGGG | 84 |
| GCTGTCACCGCTCTCCCCGGCGG | 85 |
| GGTGACAGCGCGGATGACAGGGG | 86 |
| GAAGACGCCGCCGGGGAGAGCGG | 87 |
| AAGGGGTACACTGCCTTGGAGGG | 88 |
| CTTCTAGAACCTACCCCACCAGG | 89 |
| GGGGCCGCTGACCTGGTGCAGGG | 90 |

-continued

160
-continued

| EXAMPLE 13 - Guide Sequences for AAVS1-Like Region Sequences in CHO (The below guides can be sense guide sequences or antisense guide sequences) | |
| --- | --- |
| | SEQ ID NO |
| TCCCGAATCCAGAAGGATCCCGG | 91 |
| TCACAGTGTCTGAGTCGCCCAGG | 92 |
| GCTAGGATGCTCGTGGAGGTGGG | 93 |
| CTCGTGGAGGTGGGGAATAAAGG | 94 |
| TGATCTGTGCCCCGAGAGTGAGG | 95 |
| TGAATTAATAGGACATGGGGAGG | 96 |
| ACTCTCGGGGCACAGATCACTGG | 97 |
| GACCACTGGTCCCATTCTACAGG | 98 |
| TGAGGACCATCTTGTATTGCCGG | 99 |
| AGAATCCGTCGTCCTGGGCTGG | 100 |
| TGACGTGTCAGCCTTCCAGGTGG | 101 |
| AAAAGCATCCCGAATCCAGAAGG | 102 |
| TTTTCCCGAGGCCACACTCAGGG | 103 |
| AGCGCCCTGCACCAGGTCAGCGG | 104 |
| TGAGTCGCCCAGGGTCCTGGTGG | 105 |
| CACGTCAGGCCTGAGGTCACAGG | 106 |
| GTTTTCCCGAGGCCACACTCAGG | 107 |
| GAGTCGCCCAGGGTCCTGGTGGG | 108 |
| GAATCCGTCTGTCCTGGGCTGGG | 109 |
| CCGGGGAGGGAGGATGCTCGGGG | 110 |
| GAGCCGAGAATTGAATTAATAGG | 111 |
| GTGACCCGTGCTGTCCGCTGTGG | 112 |
| GGGGGCGTCAAGTCAGAGCTGGG | 113 |
| CGCGCTGTCACCGCTCTCCCCGG | 114 |
| TGCTGCCCAAATATAGTCCATGG | 115 |
| AGTTGAGGAGAAACCTATGGGGG | 116 |
| ATCGTCCTCTATATATAGCAGGG | 117 |
| GAGTTGAGGAGAAACCTATGGGG | 118 |
| AGGGGTACACTGCCTTGGAGGGG | 119 |
| ATAGAGTCCCTCTGGGGACAGGG | 120 |
| CTAGGATGCTCGTGGAGGTGGGG | 121 |
| CGCGGATGACAGGGGCGAGGCGG | 122 |
| AAAACAGAATCCGTCTGTCCTGG | 123 |
| TGCTAGGATGCTCGTGGAGGTGG | 124 |
| GAGTGTGGCCTCGGGAAAACAGG | 125 |

| EXAMPLE 13 - Guide Sequences for AAVS1-Like Region Sequences in CHO (The below guides can be sense guide sequences or antisense guide sequences) | |
| --- | --- |
| | SEQ ID NO |
| CGAGGCGGCCCCTGCAGGGCAGG | 126 |
| CTTACACCCCGTGCCTTTCCAGG | 127 |
| CTGCCCAAATATAGTCCATGGGG | 128 |
| AGGGGCAAAGGACCCTCCTGAGG | 129 |
| TCTCACCATAGAGTCCCTCTGGG | 130 |
| AGTGTACCCCTTTGTTCCCCTGG | 131 |
| GTTGAGGAGAAACCTATGGGGGG | 132 |
| CACAGTGTCTGAGTCGCCCAGGG | 133 |
| TCCTCTTGCTAGGATGCTCGTGG | 134 |
| CACATGATCACCAAAGTCCCTGG | 135 |
| AAACAGAATCCGTCTGTCCTGGG | 136 |
| GTGCAGGGCGCTGATGCCGTCGG | 137 |
| CAGCACGGACTTTTTTTGTTTGG | 138 |
| CAGCCGACCCCGGGGATCCCGGG | 139 |
| TTTGGTCAAGATTTTGCAACTGG | 140 |
| TTGGTCAAGATTTTGCAACTGGG | 141 |
| CCTGTCAGAGAGGATGCTCTAGG | 142 |
| TGGGTTGTCGTCCTCTTGCTAGG | 143 |
| CTCACCATAGAGTCCCTCTGGGG | 144 |
| AGACGCTGACACCCTGAGTGTGG | 145 |
| GGTGGAGCGCCTCTTCTCCAGGG | 146 |
| AACAAAGGGGTACACTGCCTTGG | 147 |
| CTGTCCCCAGAGGGACTCTATGG | 148 |
| GTCTCTGACCCCCTCATTTGTGG | 149 |
| GTCTGAGTCGCCCAGGGTCCTGG | 150 |
| GCCTGACGTGTCAGCCTTCCAGG | 151 |
| ATGTCCCACACAGCTCACGCCGG | 152 |
| GGCTGTGCCGCAGGCTTCCAGGG | 153 |
| CACCCCGTGCCTTTCCAGGCTGG | 154 |
| TCACCAAGGTGTCTGCATGGCGG | 155 |
| GAATTGAATTAATAGGACATGGG | 156 |
| AATATAGTCCATGGGGTGGTAGG | 157 |
| CAGGGCATAGTTTTTAAAGCAGG | 158 |
| CGGCATCAGCGCCCTGCACCAGG | 159 |
| GCAGCCGACCCCGGGGATCCCGG | 160 |
| ACAGGACCTGTATTTGAGGTTGG | 161 |

EXAMPLE 13 - Guide Sequences for
AAVS1-Like Region Sequences in CHO
(The below guides can be sense guide
sequences or antisense guide
sequences)

| | SEQ ID NO |
|---|---|
| GGGGCGAGGCGGCCCCTGCAGGG | 162 |
| AACCTACCCCACCAGGACCCTGG | 163 |
| GCACCGCTCGGGCAGGCGGCGGG | 164 |
| TGGAAGCCTGCGGCACAGCCAGG | 165 |
| GAACCAACACTGTGGCCAGGAGG | 166 |
| AGCAGGGTCCTGTTTTCCCGAGG | 167 |
| TGGGTGGCAAGATCACCAAAAGG | 168 |
| AGCCGACCCCGGGGATCCCGGGG | 169 |
| CATGGCAACTTCCATCTCCTGGG | 170 |
| ACAGCACGGGTCACAGGAAGTGG | 171 |
| GGGGGCCGCTGACCTGGTGCAGG | 172 |
| AGGGGCGAGGCGGCCCCTGCAGG | 173 |
| GTGGTCACCCCTGTCCCCAGAGG | 174 |
| TGGGGCCGGCGTGAGCTGTGTGG | 175 |
| GGAAGCCTGCGGCACAGCCAGGG | 176 |
| CCTGAGCTGATCTCCTGGACTGG | 177 |
| ATCCAAAGCTGGCATTGTCAGG | 178 |
| CTCTCACCATAGAGTCCCTCTGG | 179 |
| GGGGGGCGTCAAGTCAGAGCTGG | 180 |
| GGGTGGAAATCTAAGAGACAGGG | 181 |
| CGGGGAGAGCGGTGACAGCGCGG | 182 |
| AGAATTGAATTAATAGGACATGG | 183 |
| CCATAAAGGAAGTTTTCCACAGG | 184 |
| AGTGAACCAACACTGTGGCCAGG | 185 |
| GTTGGGAGGGAACTCTTGGGAGG | 186 |
| CGGGTCACAGGAAGTGGGGTAGG | 187 |
| GGCCTGGCTAGCCTCAGAGGAGG | 188 |
| GGTAGGTTCTAGAAGGTGACAGG | 189 |
| ACAAGATGGTCCTCACTCTCGGG | 190 |
| CAAGGTGTCTGCATGGCGGGAGG | 191 |
| TGTTTCACTCATCCAGGCAGAGG | 192 |
| TGTGGAAAACTTCCTTTATGGGG | 193 |
| GAGGACGACAACCCAGGAGATGG | 194 |
| GGGTGGCAAGATCACCAAAAGGG | 195 |
| CTGGTGGGGTAGGTTCTAGAAGG | 196 |

| | SEQ ID NO |
|---|---|
| ACTCTTCAGGCCTTTGCAGGAGG | 197 |
| CAGAGGGACTCTATGGTGAGAGG | 198 |
| AGCACGGGTCACAGGAAGTGGGG | 199 |
| CTATGGTGAGAGGCGTCCTGTGG | 200 |
| CAGCACGGGTCACAGGAAGTGGG | 201 |
| ATGGGATGGGGCCCAACAGACGG | 202 |
| CTCCCGCCATGCAGACACCTTGG | 203 |
| GGGGATCCCGGGGACCCCGGGGG | 204 |
| TGTCCGCTGTGGCCTCAGGAGGG | 205 |
| GCAGTTGGGAGGGAACTCTTGGG | 206 |
| GCCTGGCTAGCCTCAGAGGAGGG | 207 |
| GAGAGTTGAGGAGAAACCTATGG | 208 |
| ACCTGTATTTGAGGTTGGCCTGG | 209 |
| TCGGGCAGGCGGCGGGACGCCGG | 210 |
| TAGAGTCCCTCTGGGGACAGGGG | 211 |
| GAAGTGACACTGAAGGGCCTGGG | 212 |
| AGCAGCCTGAGCTGATCTCCTGG | 213 |
| TCATGGCAACTTCCATCTCCTGG | 214 |
| GTCACAGGTTCCTGTCAGAGAGG | 215 |
| CACCAAGGTGTCTGCATGGCGGG | 216 |
| GTAGGTTCTAGAAGGTGACAGGG | 217 |
| AATTGAATTAATAGGACATGGGG | 218 |
| TTCCAAGCACCTGATTTCTGTGG | 219 |
| CTGTCAGAGAGGATGCTCTAGGG | 220 |
| GTGCTGTCCGCTGTGGCCTCAGG | 221 |
| CCCGGGGAGGGAGGATGCTCGGG | 222 |
| GGGGTGGCTCGGGGGGCCCCGGG | 223 |
| GTCAAGTCAGAGCTGGGCCCTGG | 224 |
| GACACTGAAGGGCCTGGGCCTGG | 225 |
| CTGAAAGTGAACCAACACTGTGG | 226 |
| AAAGGGGTACACTGCCTTGGAGG | 227 |
| TCTGGAAACTTCTAAGCATTCGG | 228 |
| AGAGTTGAGGAGAAACCTATGGG | 229 |
| CTCTGAGGCTAGCCAGGCCCAGG | 230 |
| AGGGGTGGCTCGGGGGGCCCCGG | 231 |
| TCCACATTGATTTGCCTTTCTGG | 232 |

-continued

-continued

| EXAMPLE 13 - Guide Sequences for AAVS1-Like Region Sequences in CHO (The below guides can be sense guide sequences or antisense guide sequences) | |
| --- | --- |
| | SEQ ID NO |
| AGGGTGGAAATCTAAGAGACAGG | 233 |
| CTGTCCGCTGTGGCCTCAGGAGG | 234 |
| AGACACAGGACCTGTATTTGAGG | 235 |
| GGGTGGCTCGGGGGGCCCCGGGG | 236 |
| TGGCTGTGCCGCAGGCTTCCAGG | 237 |
| TCCAGAAAGGCAAATCAATGTGG | 238 |
| CACCAGCCTGGAAAGGCACGGGG | 239 |
| CGGGGTCCCCGGGATCCCCGGGG | 240 |
| ACACTGCCTTGGAGGGGCAAAGG | 241 |
| TGACAGGAACCTGTGACCTCAGG | 242 |
| TCTCATGTGGGCTATCAAGATGG | 243 |
| GGGAACTCTTGGGAGGGCCAGGG | 244 |
| GAGGCCACAGCGGACAGCACGGG | 245 |
| TGTCCTATTAATTCAATTCTCGG | 246 |
| AGGGAACTCTTGGGAGGGCCAGG | 247 |
| GCACCTGATTTCTGTGGTATTGG | 248 |
| GTATCTTGAGTGTCTTTTCTCGG | 249 |
| CTGTGGAAAACTTCCTTTATGGG | 250 |
| GGGACCTCCAGCAGATGCAGAGG | 251 |
| CTGGGGACAGGGGTGACCACTGG | 252 |
| TTCAGTGTCACTTCTTTTGGGGG | 253 |
| TCCCTCCTCTGAGGCTAGCCAGG | 254 |
| GGCGCCGGGATCGGGGCCCCCGG | 255 |
| GGTTCTAGAAGGTGACAGGGTGG | 256 |
| TTGGGAGGGAACTCTTGGGAGGG | 257 |
| ATCAGGTGCTTGGAAAGTAGAGG | 258 |
| CGGGGAGGGAGGATGCTCGGGGG | 259 |
| TGAGGCCACAGCGGACAGCACGG | 260 |
| TGGTCACCCCTGTCCCCAGAGGG | 261 |
| TCCCCGCCTCCTGCCCTGCAGGG | 262 |
| GGCTGCCCTGGCTGTGCCGCAGG | 263 |
| TCCAAAAGCTGGCATTGTCAGGG | 264 |
| CAATGCCAGCTTTTGGATGACGG | 265 |
| CTGGGCCTGGCTAGCCTCAGAGG | 266 |
| GGTTCACTTTCAGTCTTTCATGG | 267 |

| EXAMPLE 13 - Guide Sequences for AAVS1-Like Region Sequences in CHO (The below guides can be sense guide sequences or antisense guide sequences) | |
| --- | --- |
| | SEQ ID NO |
| AGGAGAAACCTATGGGGGGTGGG | 268 |
| TCTAAAAGACAGCCCAGCCCAGG | 269 |
| CGGGGATCCCGGGGACCCCGGGG | 270 |
| TCTTCTCCAGGGGAACAAAGGGG | 271 |
| ACTGACACAAAAAGTCAGCACGG | 272 |
| CCTGAAGAGTCAGGTCACCAAGG | 273 |
| GGAGGAGAGTCCCACCTGGAAGG | 274 |
| GGGCAGCCACCAGCCTGGAAAGG | 275 |
| AGCCCTATTTCTCTCTCCTCTGG | 276 |
| GCCACCAGCCTGGAAAGGCACGG | 277 |
| TGACACCCTGAGTGTGGCCTCGG | 278 |
| AATTAATAGGACATGGGGAGGGG | 279 |
| GGCTCGGGGGGCCCCGGGGAGGG | 280 |
| TAATAGGACATGGGGAGGGGAGG | 281 |
| CTCTTCTCCAGGGGAACAAAGGG | 282 |
| TCGGGGCCCCCGGGGTCCCCGGG | 283 |
| TCCCTGACAATGCCAGCTTTTGG | 284 |
| GAATTAATAGGACATGGGGAGGG | 285 |
| AATGAGGGGGTCAGAGACACAGG | 286 |
| GAAAACTTCCTTTATGGGGCCGG | 287 |
| CTTGGGAGGGCCAGGGACTTTGG | 288 |
| CCCCTGCAGGGCAGGAGGCGGGG | 289 |
| TCAGTGTCACTTCTTTTGGGGGG | 290 |
| ATCCCCGTTCTTCTTCCTCCTGG | 291 |
| CTTCCTCCTGGCCACAGTGTTGG | 292 |
| TGCAGTTGGGAGGGAACTCTTGG | 293 |
| TGGCTCGGGGGGCCCCGGGGAGG | 294 |
| CTGCAAAGGCCTGAAGAGTCAGG | 295 |
| CCGTGTGCGGAAGACGCCGCCGG | 296 |
| CCCCGGGGAGGGAGGATGCTCGG | 297 |
| TTCCAGGCTGGTGGCTGCCCTGG | 298 |
| AGGTCACCAAGGTGTCTGCATGG | 299 |
| GGCGGCCCCTGCAGGGCAGGAGG | 300 |
| TCGGGGGGGCCCCGGGGAGGGAGG | 301 |
| CCAAAAGAAGTGACACTGAAGGG | 302 |
| GGCCAGGAGGAAGAAGAACGGGG | 303 |

165

-continued

| EXAMPLE 13 - Guide Sequences for AAVS1-Like Region Sequences in CHO (The below guides can be sense guide sequences or antisense guide sequences) | |
|---|---|
| | SEQ ID NO |
| GCCCAGGGTCCTGGTGGGGTAGG | 304 |
| GCTAGCCTCAGAGGAGGGAGTGG | 305 |
| GAGGGTCCTTTGCCCCTCCAAGG | 306 |
| CCACCAGCCTGGAAAGGCACGGG | 307 |
| GATTTCTGTGGTATTGGGGTTGG | 308 |
| CTAGCCTCAGAGGAGGGAGTGGG | 309 |
| CCCGGGGTCCCCGGGATCCCCGG | 310 |
| CATGGGGTGGTAGGTGGAGTGGG | 311 |
| AATGCCAGCTTTTGGATGACGGG | 312 |
| GCCCCTGCAGGGCAGGAGGCGGG | 313 |
| GAGGAGAAACCTATGGGGGGTGG | 314 |
| AGAAGTGACACTGAAGGGCCTGG | 315 |
| CCTCCAGCAGATGCAGAGGAAGG | 316 |
| CCTCTTCTCCAGGGGAACAAAGG | 317 |
| CCGGGGTCCCCGGGATCCCCGGG | 318 |
| TAGCCTCAGAGGAGGGAGTGGG | 319 |
| CAGAGGAAGGGGATGCAGTTGGG | 320 |
| CTCCAGCAGATGCAGAGGAAGGG | 321 |
| GATTCTGTTTTTCCTCTGCCTGG | 322 |
| CTTCAGTGTCACTTCTTTTGGGG | 323 |
| CATAGAGTCCCTCTGGGGACAGG | 324 |
| GGACCCTCCTGAGGCCACAGCGG | 325 |
| CCATGGGGTGGTAGGTGGAGTGG | 326 |
| GACACCCTGAGTGTGGCCTCGGG | 327 |
| ATGCTTAGAAGTTTCCAGAAAGG | 328 |
| AGCTGGGCCCTGGAAGCCTGCGG | 329 |
| TACCACAGAAATCAGGTGCTTGG | 330 |
| ACCCCAATACCACAGAAATCAGG | 331 |
| TTCTACAGGTAAAAAAACTAAGG | 332 |
| GGCCCCTGCAGGGCAGGAGGCGG | 333 |
| CTCCCCGCCTCCTGCCCTGCAGG | 334 |
| TCTCTGACCCCCTCATTTGTGGG | 335 |
| GGAGAAACCTATGGGGGGTGGGG | 336 |
| ACAGCCCAGCCCAGGACAGACGG | 337 |
| CCTGTATTTGAGGTTGGCCTGGG | 338 |

| EXAMPLE 13 - Guide Sequences for AAVS1-Like Region Sequences in CHO (The below guides can be sense guide sequences or antisense guide sequences) | |
|---|---|
| | SEQ ID NO |
| AGCCAGGGCAGCCACCAGCCTGG | 339 |
| AGCCTCAGAGGAGGGAGTGGGGG | 340 |
| GTTCAGTGTTTCACTCATCCAGG | 341 |
| CTGACTCTTCAGGCCTTTGCAGG | 342 |
| ATCCCCCACTCCCTCCTCTGAGG | 343 |
| CCCAAAAGAAGTGACACTGAAGG | 344 |
| TGGCCAGGAGGAAGAAGAACGGG | 345 |
| GGGAGGAAGGTTATGGGATGGGG | 346 |
| CCTGAGGCTTCCTGCACTCTAGG | 347 |
| TAGTTTTTTTACCTGTAGAATGG | 348 |
| AAGTGGGGTAGGGAACAAGGTGG | 349 |
| GGGTCACAGGAAGTGGGGTAGGG | 350 |
| CACCTGATTTCTGTGGTATTGGG | 351 |
| TTTGCAACTGGGTCTCATGTGGG | 352 |
| GAGAAACCTATGGGGGGTGGGGG | 353 |
| GAGGGAGGAGGGGTGGCTCGGGG | 354 |
| GCCTGTAATCCCACAAATGAGGG | 355 |
| GCAGAGGAAGGGGATGCAGTTGG | 356 |
| ACCTGATTTCTGTGGTATTGGGG | 357 |
| AAACCAGAGGAGAGAGAAATAGG | 358 |
| AACCAGAGGAGAGAGAAATAGGG | 359 |
| GAGGAGAGAGAAATAGGGCTTGG | 360 |
| CTGCAGGGCAGGAGGCGGGGAGG | 361 |
| AGGAAGGGGATGCAGTTGGGAGG | 362 |
| GGTATTGGGGTTGGAACCTGAGG | 363 |
| TTTTGCAACTGGGTCTCATGTGG | 364 |
| GGGAGGAGGGGTGGCTCGGGGGG | 365 |
| TCCCCTTCCTCTGCATCTGCTGG | 366 |
| AGGAAGTGGGGTAGGGAACAAGG | 367 |
| AGGGGAGGAAGGTTATGGGATGG | 368 |
| CCTGTAATCCCACAAATGAGGGG | 369 |
| AGTTTTTTTACCTGTAGAATGG | 370 |
| AGGAAGAAGAACGGGGATGGGGG | 371 |
| TGCAGGGCAGGAGGCGGGGAGGG | 372 |
| GGAAGGGGATGCAGTTGGGAGGG | 373 |
| CAAAGTCACTGTGTAGATGAAGG | 374 |

-continued

-continued

| EXAMPLE 13 - Guide Sequences for AAVS1-Like Region Sequences in CHO (The below guides can be sense guide sequences or antisense guide sequences) | |
|---|---|
| | SEQ ID NO |
| GTGGCCAGGAGGAAGAAGAACGG | 375 |
| TCCAGCAGATGCAGAGGAAGGGG | 376 |
| AGGGAGGAGGGGTGGCTCGGGGG | 377 |
| AACCTATGGGGGGTGGGGGTGGG | 378 |
| GGGGAGGGGAGGAAGGTTATGGG | 379 |
| CACCCACCCCCACCCCCCATAGG | 380 |
| AAACCTATGGGGGGTGGGGGTGG | 381 |
| GGAGGAAGAAGAACGGGGATGGG | 382 |
| GAGGAAGAAGAACGGGGATGGGG | 383 |
| GGAGGGAGGAGGGGTGGCTCGGG | 384 |
| GGTTGGCCTGGGCTACACAGGGG | 385 |
| AGAGGAGGGAGTGGGGGATTGGG | 386 |
| GAGGTTGGCCTGGGCTACACAGG | 387 |
| AGGTTGGCCTGGGCTACACAGGG | 388 |
| TGGGGAGGGGAGGAAGGTTATGG | 389 |
| GAAAGTAGAGGCAGGAGGGTTGG | 390 |
| GAGGAGGGAGTGGGGGATTGGGG | 391 |
| GGGGAGGAAGGTTATGGGGATGGG | 392 |
| AGAGTGCTTGCCTAGAGTGCAGG | 393 |
| AGGAGGGAGTGGGGGATTGGGGG | 394 |
| CAGAGGAGGGAGTGGGGGATTGG | 395 |
| AGGAGGAAGAAGAACGGGGATGG | 396 |
| TTTTTTCCCCTGTGTAGCCCAGG | 397 |
| GGTGCTTGGAAAGTAGAGGCAGG | 398 |
| CTTGGAAAGTAGAGGCAGGAGGG | 399 |

| EXAMPLE 13 - Guide Sequences for AAVS1-Like Region Sequences in CHO (The below guides can be sense guide sequences or antisense guide sequences) | |
|---|---|
| | SEQ ID NO |
| CTGTAATCCCACAAATGAGGGGG | 400 |
| AGGACATGGGGAGGGGAGGAAGG | 401 |
| TCATCTACACAGTGACTTTGAGG | 402 |
| GAGGGAGTGGGGGATTGGGGGGG | 403 |
| GGGAGGGAGGAGGGGTGGCTCGG | 404 |
| AGGGAGTGGGGGATTGGGGGGGG | 405 |
| AACAACAAAAACAAAACCAGAGG | 406 |
| CTATGGGGGGTGGGGGTGGGTGG | 407 |
| GGAGGGAGTGGGGGATTGGGGGG | 408 |
| TGCCTGTAATCCCACAAATGAGG | 409 |
| GAGTGGGGGATTGGGGGGGGGGG | 410 |
| AGGGCAGGAGGCGGGGAGGGAGG | 411 |
| CAGGAGGCGGGGAGGGAGGAGGG | 412 |
| AGGAGGGGGGAGGGAGGAGGGG | 413 |
| GGAGTGGGGGATTGGGGGGGGGG | 414 |
| GGGAGTGGGGGATTGGGGGGGGG | 415 |
| GCAGGAGGCGGGGAGGGAGGAGG | 416 |
| AGGCGGGGAGGGAGGAGGGGTGG | 417 |
| GCTTGGAAAGTAGAGGCAGGAGG | 418 |
| GAGAGAGAGAGAGAGAGTTGAGG | 419 |

It is to be understood that the description, specific examples and data, while indicating exemplary embodiments, are given by way of illustration and are not intended to limit the present inventions. Various changes and modifications within the present inventions, including combining embodiments in whole and in part, will become apparent to the skilled artisan from the discussion, disclosure and data contained herein, and thus are considered part of the inventions.

What is claimed is:

1. A mammalian cell comprising a site for integration of a gene of interest, wherein the cell comprises a first Stable Integration Site located in a Genomic Safe Harbor and a second Stable Integration Site that is not located in the Genomic Safe Harbor, wherein the first Stable Integration Site comprises a DNA polynucleotide comprising in 5' to 3' order a first recombinase recognition site (RRS), a first reporter gene encoding a first reporter protein, a Cas9 gene and a second RRS; and wherein the second Stable Integration Site comprises a DNA polynucleotide comprising in 5' to 3' order a first Genomic Safe Harbor homology arm containing a CRISPR single guide RNA (sgRNA) target site, a third RRS, a second reporter gene encoding a second reporter protein, a fourth RRS and a second Genomic Safe Harbor homology arm containing an CRISPR sgRNA target site, wherein the first RRS, the second RRS, the third RRS and the fourth RRS are different, and wherein the first reporter protein and the second reporter protein are different.

2. The mammalian cell according to claim 1, wherein the second Stable Integration Site is located in a second Genomic Safe Harbor that is different from the first Genomic Safe Harbor.

3. A mammalian cell comprising a site for integration of a gene of interest, wherein the cell comprises a first Stable Integration Site located in a Genomic Safe Harbor and a second Stable Integration Site that is not located in the Genomic Safe Harbor, wherein the first Stable Integration Site comprises a first DNA polynucleotide encoding a first reporter protein, wherein the first DNA polynucleotide comprises in 5' to 3' order a first recombinase recognition site (RRS), a first reporter gene encoding the first reporter protein, a Cas9gene and a second RRS; and wherein the second Stable Integration Site comprises a second DNA polynucleotide encoding a second reporter protein, wherein the second DNA polynucleotide comprises in 5' to 3' order a first Genomic Safe Harbor homology arm containing a CRISPR single guide RNA (sgRNA) target site, a third RRS, a second reporter gene encoding the second reporter protein, a fourth RRS and a second Genomic Safe Harbor homology arm containing an CRISPR sgRNA target site, and wherein the first RRS, the second RRS, the third RRS and the fourth RRS are different.

4. The mammalian cell according to claim 3, wherein the second Stable Integration Site is located in a second Genomic Safe Harbor that is different from the first Genomic Safe Harbor.

5. The mammalian cell according to claim 3, wherein the mammalian cell is a human cell.

6. The mammalian cell according to claim 3, wherein the mammalian cell is selected from the group consisting of a Human Amniotic Epithelial Cell, a HEK293 Cell, a BHK cell, and a CHO cell.

7. The mammalian cell according to claim 1, wherein the mammalian cell is selected from the group consisting of a Human Amniotic Epithelial Cell, a HEK293 Cell, a BHK cell, and a CHO cell.

8. The mammalian cell according to claim 1, wherein the Cas9 gene can be removed using a recombinase.

9. The mammalian cell according to claim 1, wherein the Cas9 gene encodes Cas9 protein, wherein the Cas9 protein is used to produce at least one Stable Integration Site in the Genomic Safe Harbor for stable integration of DNA polynucleotides.

10. The mammalian cell according to claim 9, wherein the mammalian cell can have more than one Stable Integration Site for stable integration.

11. The mammalian cell according to claim 1, wherein the mammalian cell further comprises a DNA polynucleotide encoding a repressor under the control of a promoter.

12. The mammalian cell according to claim 11, wherein the repressor is a Tet repressor.

13. The mammalian cell according to claim 1, wherein the mammalian cell comprises a DNA polynucleotide encoding a repressor protein and a polyadenylation signal under transcriptional control of a promoter, wherein the DNA polynucleotide encoding the repressor protein is randomly or site-specifically inserted in the cell genome.

14. The mammalian cell according to claim 1, wherein the integrated Cas9 gene is under the control of a promoter.

15. The mammalian cell according to claim 1, wherein the expression of Cas9 gene increases the efficiency of homology arm integration into a Genomic Safe Harbor by increasing the occurrence of cuts in genomic DNA caused by Cas9 endonuclease.

16. The mammalian cell according to claim 9, wherein the integrated Cas9 gene provides greater homology directed repair efficiency than homology directed repair without an integrated Cas9 gene.

17. The mammalian cell according to claim 16, wherein the integrated Cas9 gene provides $10, 10^2, 10^3, 10^4, 10^5, 10^6, 10^7, 10^8, 10^9,$ or $10^{10}$ greater homology directed repair efficiency than homology directed repair without an integrated Cas9 gene.

18. The mammalian cell according to claim 1 further comprising a CMV promoter operably linked to a Tet operator to control transcription of the Cas9 gene.

19. The mammalian cell according to claim 1, wherein the first and second Genomic Safe Harbor homology arms each contain a region with a sequence alteration to avoid recreating a targetable site.

20. The mammalian cell according to claim 1, wherein the first and second Genomic Safe Harbor homology arms can target a sequence according to SEQ ID NO:2.

21. The mammalian cell according to claim 20, wherein the first and second Genomic Safe Harbor homology arms each contain a region with a sequence alteration to avoid recreating a targetable site.

22. The mammalian cell according to claim 1, wherein a gene of interest can be inserted between the third RRS and the fourth RRS.

23. The mammalian cell according to claim 3, wherein the Cas9 gene can be removed using a recombinase.

24. The mammalian cell according to claim 3, wherein the Cas9 gene encodes Cas9 protein, wherein the Cas9 protein is used to produce at least one Stable Integration Site in the Genomic Safe Harbor for stable integration of DNA polynucleotides.

25. The mammalian cell according to claim 24, wherein the mammalian cell can have more than one Stable Integration Site for stable integration.

26. The mammalian cell according to claim 3, wherein the mammalian cell further comprises a DNA polynucleotide encoding a repressor under the control of a promoter.

27. The mammalian cell according to claim 26, wherein the repressor is a Tet repressor.

28. The mammalian cell according to claim 3, wherein the mammalian cell comprises a DNA polynucleotide encoding a repressor protein and a polyadenylation signal under transcriptional control of a promoter, wherein the DNA polynucleotide encoding the repressor protein is randomly or site-specifically inserted in the cell genome.

29. The mammalian cell according to claim 3, wherein the integrated Cas9 gene is under the control of a promoter.

30. The mammalian cell according to claim 3, wherein the expression of Cas9 gene increases the efficiency of homology arm integration into a Genomic Safe Harbor by increasing the occurrence of cuts in genomic DNA caused by Cas9 endonuclease.

31. The mammalian cell according to claim 24, wherein the integrated Cas9 gene provides greater homology directed repair efficiency than homology directed repair without an integrated Cas9 gene.

32. The mammalian cell according to claim 31, wherein the integrated Cas9 gene provides $10, 10^2, 10^3, 10^4, 10^5, 10^6, 10^7, 10^8, 10^9,$ or $10^{10}$ greater homology directed repair efficiency than homology directed repair without an integrated Cas9 gene.

33. The mammalian cell according to claim 3 further comprising a CMV promoter operably linked to a Tet operator to control transcription of the Cas9 gene.

34. The mammalian cell according to claim 3, wherein the first and second Genomic Safe Harbor homology arms each contain a region with a sequence alteration to avoid recreating a targetable site.

35. The mammalian cell according to claim 3, wherein the first and second Genomic Safe Harbor homology arms can target a sequence according to SEQ ID NO:2.

36. The mammalian cell according to claim 35, wherein the first and second Genomic Safe Harbor homology arms each contain a region with a sequence alteration to avoid recreating a targetable site.

37. The mammalian cell according to claim 3, wherein a gene of interest can be inserted between the third RRS and the fourth RRS.

\* \* \* \* \*

SEQUENCE LISTING

```
Sequence total quantity: 419
SEQ ID NO: 1           moltype = DNA  length = 4067
FEATURE                Location/Qualifiers
misc_feature           1..4067
                       note = Human AAVS1
source                 1..4067
                       mol_type = genomic DNA
                       organism = Homo sapiens
SEQUENCE: 1
gaattcctaa ctgccccggg gcagtctgct attcatcccc tttacgcggt gctacacaca  60
cttgctagta tgccgtgggg acccctccgg cctgtagact ccatttccca gcattccccg  120
gaggaggccc tcatctggcg atttccactg ggggcctcgg agctgcggac ttcccagtgt  180
gcatcggggc acagcgactc ctggaagtgg ccacttctgc taatggactc catttcccag  240
gctcccgcta cctgcccagc acaccctggg gcatccgtga cgtcagcaag ccgggcgggg  300
```

-continued

```
accggagatc cttgggcgg tggggggcca gcggcagttc ccaggcggcc cccggggcgg   360
gcgggcgggc gggtggtggc ggcggttggg gctccgggcg cgtcgctcgc tcgctcgctg   420
ggcgggcggg cggtgcgatg tccggagagg atggccggcg gctggcccgg gggcggcggc   480
gcggctgccc gggagcggcg acgggagcag ctgcggcagt ggggcgcggg cgggcgccga   540
gcctggcccc ggagagcgcc gcgcccgcac cgtccgcttc gagcgcgccg gcgagttcct   600
ggcggcctgt gcgggcggcg acctggacga ggcgcgtctg atgctgcgcg ccgccgaccc   660
tggccccggc gccggagctc gaccccgccg gccgccgccc gcccgcgccg tgctggactc   720
caccaacgcc gacggtatca gcgccctgca ccaggtcagc gcccccgcg gcgtctcccg   780
gggccaggtc caccctctgc gccacctggg gcatcctcct tccccgttgc cagtctcgat   840
ccgcccgtc gttactggcc ctgggtttnc accctatgct gacaccccgt tccagtcccc   900
ttaccattcc cttcgaccac cccacttccg aattggagcg cttcaactgg ctgggctagc   960
actctgtgtg acactctgaa gctctacatt cccttcgacc tactctcttc gattggagtc  1020
gctttaactg gccctggctt tggcagcctg tgctgaccca tcgagtcctc cttaccatcc  1080
ctccctcgac ttcccctctt ccgatgttga gccccctccag ccggtcctgg actttgtctc  1140
cttccctgcc ctgccctctc ctgaacctga gccagctccc atagctcagg tctggtctat  1200
ctgcctggcc ctggccattg tcactttgcg ctgccctcct ctcgccccg agtgcccttg  1260
ctgtgccgcc ggaactctgc cctctaacgc tgccgtgccg tctctctcct gagtccggac  1320
cactttgagc tctactggct tctgcgcgcc tctggcccac tgtttccct tcccaggcag  1380
gtcctgcttt ctctgaccag cattctctcc cctgggcctg tgccgctttc tgtctgcagc  1440
ttgtggcctg ggtcacctct acggctggcc caagatcctt ccctgccgcc tccttcaggt  1500
tccgtcttcc tccactccct cttccccttg ctctctgctg tgttgctgcc caaggatgct  1560
ctttccggag cacttccttc tcggcgctgc accacgtgat gtcctctgag cggatcctcc  1620
ccgtgtctgg gtcctctccg ggcatctctc ctccctcacc caaccccatg ccgtgttcac  1680
tcgctgggtt ccctttcct tctccttctg gggcctgtgc catctctcgt ttcttaggat  1740
ggccttctcc gacggatgtc tcccttgcgt cccgcctccc cttcttgtag gcctgcatca  1800
tcaccgtttt tctggacaac cccaaagtac cccgtcctcc tggcttagca cctctccatc  1860
ctcttgcttt ctttgcctgg acaccccgtt ctcctgtgga ttcgggtcac ctctcactcc  1920
tttcatttgg gcagctcccc tacccccctt acctctctag tctgtgctag ctcttccagc  1980
ccctgtcat ggcatcttcc aggggtccga gagctcagct agtcttcttc ctccaacccg  2040
ggccctatgt ccacttcagg acagcatgtt tgctgcctcc agggatcctg tgtccccgag  2100
ctgggaccac cttatattcc cagggccggt taatgtggct ctggttctgg gtacttttat  2160
ctgtcccctc caccccacag tggggccact agggacagga ttggtgacag aaaagcccc  2220
atccttaggc ctcctccttc ctagtctcct gatattcgtc taaccccac ctcctgttag  2280
gcagattcct tatctggtga cacaccccca tttcctggag ccatctctct ccttgccaga  2340
acctctaagg tttgcttacg atggagccag agaggatcct gggagggaga cttggcaggg  2400
ggtgggaggg aagggggggga tgcgtgacct gcccggttct cagtggccac cctgcgctac  2460
cctctcccag aacctgagct gctctgacgc ggctgtctgg tgcgtttcac tgatcctggt  2520
gctgcagctt ccttacactt cccaagagga gaagcagttt ggaaaaacaa aatcagaata  2580
agttggtcct gagttctaac tttggctctt cacctttcta gnccccaatt tatattgttc  2640
ctccgtgcgt cagtttttacc tgtgagataa ggccagtagc caccccccgtc ctggcagggc  2700
tgtggtgagg agggggggtgt ccgtgtggaa aactccctttt gtgagaatgg tgcgtcctag  2760
gtgttcacca ggtcgtggcc gcctctactc ccttctctctt tctccatcca tccttctttc  2820
cttaaagagc ccccagtgct atctggacat attcctccgc ccagagcagg gtccgcttcc  2880
ctaaggccct gctctgggct tctgggtttg agtccttgca agcccaggag agcgctagct  2940
tccctgtccc ccttcctcgt ccaccatctc atgccctggc tctcctgccc cttcctacag  3000
gggttcctgg ctctgctctt cagactgagc cccgttcccc tgcatccccg ttccctgca  3060
tcccccttcc cctgcatccc ccagagcccc aggccaccta cttggcctgg aaccccacga  3120
gaggccaccc cagccctgtc taccaggctg acctttgg tgattctcct ccaactgtgg  3180
ggtgactgct tgggcaaact cactcttcgg ggtatcccag gaggcctgga gcattggggt  3240
gggctggggt tcagagagga gggattccct ccaggttacg tggccaagaa gcaggggagc  3300
tgggtttggg tcaggctggg tgtggggtga ccagcttatg ctgtttgccc aggacagcct  3360
agttttagcg ctgaaaccct cagtcctagg aaaacaggga tggttggtca ctgtctctgg  3420
gtgactcttg attcccggcc agtttctcca cctggggctg tgtttctcgt cctgcatcct  3480
tctccaggca ggtccccaag catcgccccc ctggctgttc ccaagttctt aggtaccca  3540
cgtggtttta tgaaccactt ggtgaggctg gtaccctgcc cccattcctg caccccaatt  3600
gccttagtgg ctaggggggtt gggggctaga gtaggagggg ctggagccag gattcttagg  3660
gctgaacaga gccgagctgg gggcctgggc tcctgggttt gagagaggag gggctggggc  3720
ctggactcct gggtccgagg gaggaggggc tggggcctgg actcctgggt ctgagggtgg  3780
agggactggg ggcctggact cctgggtccg agggaggagg ggctgggggcc tggactcgtg  3840
ggtctgaggg aggaggggtc gggggtctgg acttctgggt cttagggagg cggggctggg  3900
cctgaccccc tgggtctgaa tggggagagg ctgggggcct ggactccttc atctgagggc  3960
ggaagggctg gggcctggcc tcctgggttg aatggggagg ggttgggcct ggactctgga  4020
gtccctggtg cccaggcctc aggcatcttt cacaggggatg cctgtac           4067
```

```
SEQ ID NO: 2              moltype = DNA   length = 44232
FEATURE                   Location/Qualifiers
misc_feature             1..44232
                          note = Synthetic: CHO AAVS1-Like Sequence
source                   1..44232
                          mol_type = other DNA
                          organism = synthetic construct
SEQUENCE: 2
ccagcaccca catggtggct cacaactgtc cgtaactcca gttccagagg atctgatgcc   60
ctcttctgtc tcccgcgagc acctggcaca cacgtgatgc acacttaaac acatgcaagc  120
aaaccatcag acacataact ttttttttcca attttttaaa gatttagtta ttattattta  180
cttaataaat atttattata tttattacat atacagtttc tgcctacatg ccagcagagg  240
gcaccagatt gaattgtaga tggttgtgag ccaccatgtg gttgctggga attgaactca  300
ggaccccctg aagagcagtc agtgctctta acctctgagc catctctcca gccccctccat  360
tttttttttt ttaaataaag aaatgtaatg tcctaagtgg ggcttagaga gtggaagcag  420
```

```
ataaagaaag atggagttaa gaattttaag aagccagttg gcggttgtgc atgccagcac   480
tcaggaggca gaggcaggtg gatggatctc tatgagttcg aggccagcct ggtctacaga   540
gagagagttc caggacagac ttctccaaag ctacagagaa accctgtctg aacccaccac   600
gaccaccaca aagaaaaaaa ggatttcaag aggagagcca ggtttatagc aagagagaaa   660
gttgtgaact aatgcccagg gcttagtgtg gcctacctct gggctgggtc tctctctgaa   720
cacaggtgg agctgccccg ggaggaagaa gcggctccgt acagtcccga attctacagt   780
ggctgggagc ctcccgccac tgacccgcag ggccgcgcct gggaggaccc ggtgggaaaa   840
cagctacagc atgagaagag gcgcaggcag gtgaggcagg gttgccgggg gagcactggg   900
ctccccgttt ctgcacaaca tgggcgagca ggacgtctga ggtctagcct gcctgacccc   960
aagctctctc tcttcccgca gcaaagcgcc ccccagatcg ctgtcaatgg gtgagtgacc  1020
gctgcagggt ggccagggat ggggttggga ggactgagtc ccgggtcac cccggctctg   1080
actccgaccc tccccctttt ttcttgtctt tttttttttt tttttttttt tttaaacctc  1140
tgccttcccg gctctttgca ggtgggtgag gtggtgagga ggcggggctg gggtgggggt  1200
gggggaggag ccaggaggga ggggggagg agcccagaac tctgggtcca agggaagagg  1260
gaaaggaggc ttagtttgct gaagcatga gagttagggg ctgaaagtgg gtgggtctaa  1320
aggcttggac cccacacccc caccccggc atcctcaaaa gattgaaaag gtgcagtttg  1380
gtgttctagg acctgggaga gcaccatgct tgagtcccca gagcacagag cactgggtgt  1440
cagagaaaaa aaaaaaatgg agaccaaaaa gcagggttgg gacttccgag gattcaggga  1500
caagtttgag gaaacgtgag aaagtgctgg catccctgga ccactaactg aggtgtgggact  1560
tccggcttcc taatgcgcaa aggaatagca cgtactgagc aaactggaat gctcccaggg  1620
ctgaaagaat ggaggaaatt gaaggtcaag gcacggactc ctgcctaggt ccctgggaag  1680
gaaagaacta gggacctaaa tttacagttc taccaaacta tggaagctga gggctgcagg  1740
tccaggtgag gaagtgatgg agaggggtc acagccctag gatccttggg gaaatagggg  1800
ccaggagtgg agggcgtgga tgtggcttga gaacaaaatg atagacttgg aggagaggaa  1860
ttgggggcct aggtgagagc cccagcagag ggtctcagca gggacggcat actgggagct  1920
gtcagtccca cacatggggc gccgagcc tgaaagagtcc cctcctccct tccacaggta  1980
ggcctgatcc gggatgaggt ctctcttgct gggggcgcca gagctaatcg tcccccaggc  2040
tgcctggtgc tgcagggccc tcttgtctgt ctgtctgctt ctgaatcttg ggctcagcac  2100
ctgcaagctg tttactcgcc ttctctggct gtaatttctt tgcctggaag ggtgaggact  2160
ctctggcgct gtaaggggct tgcaaagagc tcagtgccgt gactcagcct gagttcaaat  2220
ccagctgcat gaagaacagt acagagtgac cctgacaagg gcagcctagg gccagctcag  2280
tcacaccttt ctctttcttg tgcactggcc gttactacag tatccctcgg ttccttcata  2340
tagaaagaga aatagtgagc cgggcagtgg tggcgcacac ctttaatccc agcacttggg  2400
aggcaaaggc aggtggacct ctgtgagttc aagaccagcc tggtctacaa gagctagttc  2460
caggatagtc tccaaagcca cagagaaacc ctgtctcgaa aaaccaaaaa agaaaaaaga  2520
aagaaagaga aatagtgaga ccggcagtgg tggtgcacgt ctttagtccc agcactgggg  2580
aggcagaggc agccggattt ctgtgagttc aaggatagac tggtctacag agtgagttcc  2640
aagacagcca gaactaaaca gtgaaaccct gtcttggaaa aaaaaaaag tgaaataatg  2700
gccatattct ggtgatggtg taggcctgtg gtcccagcta ctcagagaca tgaagcagga  2760
gaataaaaat caaggcctgc tttgactaca aagtgagctt caaaggccag cctgggcaaa  2820
gcaacaaggc cttgcctcaa aatgaaaaaa taaaaataaa agaggctgga gaaatggctt  2880
agtggttaag agtactggcc gctcttccag gggaccaggg ttcaattccc agcacccaga  2940
catacagcag ctcacaactc cagtttcagg gaatccggtg ttctctctgg tctctgtagg  3000
caccaggcac tcaagttgtg cagacataaa ataacacaga gggctgggct ggggctcagt  3060
ggcaggcatt tgcccagaat ccccagtaa agacatagct cagtgaatcc agagctgagg  3120
ggctgggcgt atattaatgg tggaatcctt gcctagaatt caaccagcga agggctgtgg  3180
ccgtggctcg gctgtgagaac cctgtcctgg tatctaccat gaagggctgg gacatggctc  3240
agagataaaa cacttgccta gactctaccg ctgagagcct ggggtgtgga tcagtggaca  3300
gtgcccgcct agcatgcaca aggccctg gttcaatccc ctgtaccaca aaaaaaaggg  3360
ggggtggagg gagggtaaga gtgagatctc aggagaagga aggaaccaaa ttcatggaac  3420
tacaaggaa ctccaggaga atcgaagcgt ttctggcgta cgttgctgtg taagcacaag  3480
ggtcggctat ttttgcaccc tgttcattat cctagcgggt gatgggaata gatctgctgt  3540
ctctagccga ttcctcatga tcctcactga tgaaaatgca ggtgagggc tggagagatt  3600
aagaacactg tctgctctgg cactggacct aggttcattc agctccccac agcacatggt  3660
ggcccacaaa tatctgtaac tccagctcta agaacccagg tctaggacac cctctcctgg  3720
actctgtggc tactcacac aggtgatgca catacacaca catgcatgca ggcaacacac  3780
acacacacac acacacacac acacacacac acacaatgca tgtgaacgac tggggatgaa  3840
gctcggaagc taagcacttc cctggcatgc acgggccctg ggttcaatcc ccagcacccc  3900
ataatgaatt aaatcgttat catgatacgt tgtgtttact gcatggtgcc aggcaaggaa  3960
atgagctaac tccattcaag tcgtgactcc agtgtcaagc ctgtattaac atattaacct  4020
gggcctctgc tctgacccc tgcttggctc taaccccacc tcacaccttta gagtccagac  4080
cagcagggct ggctacctcc taatctcctg ctggtttctt tctccccagt catcaagatc  4140
cagacctgga agccgccgag ctagaagaga gagccagaaa gtgggttctg tgtaactatg  4200
acttccaggc ccgaaatagc agcgagctgt ctgtcaagca cggagatgtg ttggaggtta  4260
gcggtgtggg gggcctgaga ccctgaaatt ggtcaattta gccctaggta tagaaccgga  4320
gcgtgaattc tctccttata cgccacctag gtcctggatg acaggcgcaa gtggtggaag  4380
gttcgggacc atcagggaca ggagggttat gtacccata acatcctgac accccaccct  4440
ggacctcagg tgcaccgcag ccaaagtcct gcaggaaacc tagtaagtcg gcgtgttctt  4500
gcttcttcgg ggagaaaggg gggcaagatc ctaggtcctg gggatgagga cagagaaaat  4560
caggtgtgaa ggttgctgtt tggaaagggg gggggtggt cagatgttta ttgggaaagg  4620
agctggaagc ctctcttcat tcccttccag gagacgagta ctcctcctcc cccacccgca  4680
ccagctccag ccectgctca ggtgcgaccc cactgggaca gttgcgacag tctcaacaat  4740
ttggacccca gcgagaaggg tgagtggtgg acgtcactc tgggaagtga tccttgtctt  4800
cgcttttcag gctccaccct gggcacccta gcggctccca gcccctgac cccagaaccc  4860
ctgagcgcgc actcccctcc gccccccccc ctcacggttt cgcttctgca gagaaattct  4920
cccagatgct cagtgtcaat gaggagctgc aggcgcgcct tgcgcagggc cgttcgggtc  4980
ccagccgggt agcccggga ccccgcgccc cggagcctca gctcagcccg cgctctgagg  5040
cctcggtggt ccgtgcctgg ctgcagacca agggcttag ctcggggtga gtggggctcc  5100
ccccgggggct agtctgaaga gacctgtgct tgaactgaaa ggcgaggtt ccattggtcc  5160
```

-continued

```
aggggtgggg gcgtggaaac tgtggagcag gcccaaattg caacgcccaa tgcccaggga    5220
caggctccaa acggaggcca caggaaagga agtcccatcc cctttccgaa gccccaaatc    5280
tccaagagtt tgaacatccc ccctccccc cagcttcctt gtttgagaac tctgattgca    5340
caagcagcta ggtaggtgtg gcgtgattgg tggagggccg agggagcttg atgagctgtg    5400
atggcccctg ctgcctcgct caggactgtg gacgcgctcg gcgtgctgac cggagcacag    5460
ctcttctcgc tgcaaaagga agagttgcgg gcggtgtgcc ccgaggaagg ggcgcgggtg    5520
tacagccaag tcaccgtgca gcgcgcgctg ctggaggtga gcgaatcctt ggggccggac    5580
aaggcgacgg agggtagggt ggggatgggg gacctggggg gaggggtcg tccagggttc    5640
acatactaag atcttgattt ctacccgct ctgcaggaca gagaaaaagt gtcggagctg    5700
gagccgtgat ggagaagcaa aagaaaaaag tggaaggcga gaccaaaaca gaagttattt    5760
gatccttcct gactcggtca caaaacgtga tggcatggcg gggctcccag cgcccctag    5820
gacaacagtc gccagactcc tccccgtgac cggggacagt agatgtcccg aaggatcgcc    5880
caccctcatc tcccggctca ctcgctcgct cgctctcctg gcgggcaggc tgcgctgaca    5940
gtgccggctg gaatccttcc gggggacctc agactgacgg ggacgggac gggacgggg    6000
acggggacgg agcatacaga cactaccaga gaggcacgcc caagaggcgc acggagggag    6060
ggccctgggc gtcgtgacgt gctataaaca gcctcctttc tagaccatgc gtgtcacctg    6120
ctgtcccctt ctctcgccgg ctacccagga gccaggaatc tgagagatgc cccacgcttc    6180
ctccccataa acctggagag tccagcccag gcttcctaat caccagtcta tcctcgcact    6240
ggccccatct acatcccttc tcctgttcaa aaccctcgcc tggctggctc ctcgttgttc    6300
tcagtcctgt ctcctggtgt ttaaggcctg ggcttttctc attgtctccg cccacctgc     6360
atttcggccc agccgctcca gaccacaagc ggtttgcact taacgcttct gagggttgga    6420
gcggcccca tcaccctggc tcggctctcc tagccacacc gtggacaccc gtgtccagcc    6480
tctaaggacc ggccatgcag atctggacgc tcccggggca tgccacgggc tcttggttct    6540
tcctggcccc tcaacaactt tctccctgcc aagccctgca acttgtccag gttatgcagg    6600
tggatggtaa gagccggttt tctcatccgc gctaggttta tctaaggcct ttcttttccc    6660
tgcatccttg gaacactccc aagagtccca ccgttgcagt cggcctctgc tccccgccca    6720
gctcagtcct tacctgggcc accaggtggc gcacctcgaa tctgacccag gagggccagc    6780
cttgggctga cttcactaag cccccttttcc ttctggaaca ctgtagcgtt ccagtaagcc    6840
tttagtgtcc attcccttgg tttctcctgg tacatgagat aaaacctaac tccagcatga    6900
cagccgatgg cctgtgaccc ctatgggctc aggtcgccct tcctctctgt tcgggactcc    6960
aggcactggt ccatgctgtt ggttctgttg ggatgtcttg gctccatggt gtcttatcac    7020
tgcctggggc gtcatttctt atgtcgcgct tggttggttt gttggaggcc gtctgggtac    7080
agccccaaac tctcggtcct ccagtttcag tttcctgcat gtggggatat tggcaggcgc    7140
cctgctgcca ccctcttttc taatcgagaa accaaaagta caagcagttg cccaagctgt    7200
tttgattccg gcagtgaggt cccagactac agactgaaat gccagcagga gccatctggc    7260
ttgctgggac atcaggtgat caggtgcctg tggctggctc tctgtggttt ggagtctgac    7320
ctttttcatcc tgacttgacc ctctgtcgat cactttgtcc atccatcact ccccaagtct    7380
acatccagcc aggggcacct gtcagagctc aagccggatg gtaacctggt ggtcaggcct    7440
cccagctcag gtggagctca agttcttaac agagccatga tcacacacaa agccatcacc    7500
tcagcgccac agcacgccag gcctgctcta ccccacgctg cacacggttc tcatcatcat    7560
gcaaaaggtg cttccttcag atacagggct caccgtcacc ttctagcatc tgtctgtgca    7620
gcttgtcatg gggcctactt ttgactgtca taaacaccac acacgcacat atatatacac    7680
accagataca cacacaccac acacatgccc aatacactgt gcatgcgcac acacaaacac    7740
acacacatac ctcatacacc atacacccta taacccacac cagccatacc acacaccaca    7800
tatacacagt tcacctcaga cagcatggca caccacacac acacacacac acacacac     7860
gcgcgcgcgc gcacacacac acacacacac acacacacac tccgcactct cccctttctcc   7920
acagcactgt agctgaaatc cacacagtgg caaccttcct cagtgtactg gctgctggac    7980
caagctgttc actcctgtga cgccagctgg cagaacagcc cattcctgac tgtcaggatg    8040
gaggaggcac cacgcgatcc atctcaagac tgattcctgg ctctgcccca gtcactgtgg    8100
ccacgaagga ctacttacca tcacctactc ctttcccaga aaacctagac ttgcggtttc    8160
ctatgttggc catcctacct tttcaatgtt aagccactga ctccgctcac ttccaaagca    8220
ctgagggtca atgtgagcac ccggatcagg tcacaggctt ccttctgacc cccctacct    8280
cacctggggc tctttctctc cagctgctca ctcgagcaag ctcccctccc cacacctgtg    8340
agcaagctcc cagccaccca ctggccctca tccaaatgga tgagcggttt cagtcagata    8400
cacaggctga gtatacaagc aggaaccagt gccccacacc caggggggaga caagtcactg    8460
agtggcaatg tcacgacttt atttgtggtg cctgtgcttt gtctcaaaaa taccttctcc    8520
ccctccccag acaatgggtg ggaaggaggc agcaaaaata gaagcaaacc ctccctattg    8580
cacacggacc ctatatacag gcccacctgg cagaggccag tggggctctt ggcacattcc    8640
tggatccctg ctggggaggg aagggatact gggtagcatc acacgtgagg tgggcccggg    8700
gcagccactc tgctcctgga tactgatcct ggcttccttg gtccttgctt ccttcctggt    8760
cccatctctg gtgcctgccc actctcggca acatttccct acctggctca gcctcccacc    8820
tccaccctgg ttctgtgggac tctgtgcttt cctccgggtt ctgaggtccc gagaggaggt    8880
tatggcttct caacaacttc ccccggagcc ctgtcactca tgttcactcg ggggaagggg    8940
tgcgtgtgtc aaaagcagct gtataaatac ggtgcgggaa ccctccaga gtcacttgga    9000
gagcttgcta atgacgcgga tcagtgctgc attctcatcc ttgagccgct ggttgtcagc    9060
gcggaggtcg gacagggcct aggggcaggg gtggagtcag ctgggcaggg cggggcaggg    9120
tgggctctgg ccaccgccct tcacaagctc gttaccttca gctcctcctc cagctctgcg    9180
gccttgcgct ccagggccct gcgctcctgc aggaatgggc tgggctcaga agcagggtaa    9240
gggcagggga cagggcaagg gcgggacacc accccagggg cccaaactca cgaatctctc    9300
cagctccagg agggcgggcc tctcggcaaa gcgttcctgc cgctggtaag ggcagagaag    9360
actgggcgtc aggagctgct tcttacccct aggacatcag agccctgccc cccccccccg    9420
agtggggac ctccaacctc ccagccacgg ccaggcccct tgccactggg gctctgactc     9480
ccactgcccc aacagctggt tcttaggtct cagtatctgc acctgcgtgg cccgctcaag    9540
ctccaccttg agctgtgcca gccgcagggt ggtctgtgtc agggcctcac gaagccgctc    9600
gttctccctc cgaagctcca tgtacagcta gggacacaga ggaagcaggc aggctcagaa    9660
gggcccggga aggggccagg acagggtggg gtggggcagg aggtagcatg cggcaccttc    9720
cggaagcttc catcgggttc ttcctgttcc tgcttggatt ctggattgag gtctctctgc    9780
aaacgctgtc tacgggcagt ggagccgcca tccacggtgc tggacagaaa ttcaggcctt    9840
agggcccagg ccctgcccga ggggtgcccc agccccacg catgacccgg cctacctgca     9900
```

-continued

```
ctccaggctc cgttctgccg gccccgcctc ctcccctgc agaagagccc tgagagttca    9960
gtctccatgc aacgtcctcc ctccagcccg cccggcctcc acacagcatc ctcacctccg   10020
cggcccctcc ctccagcccg cccggcctcc acacagcatc ctcacctccg cgggcccctc   10080
cctccagccc gccgggcctc cacacagcat cctcacctcc gcggcccctc cctccagccc   10140
gcccggcctc cacacagcat cctcacctcc gcggcccctc cctccagccc gcccggcctc   10200
cacacagcat cctcacctcc gcggcccctc cctccagccc cgcccggcct ccacacagca   10260
tcctcaccct ccgctgcccc tccctccagc ccgccccgc ctccacacag catcctcacc    10320
tccgcggccc tccctccagc ccgcccggcc tccacacagc atcctcacct ccgcgggccc   10380
tccctccagc ccgcccggcc tccacacagc agcatcctca cctccgcggg ccctccctcc   10440
agcccgcccg gcctccacac agcatcctca cctccgcggc ccctccctcc agcccgcccg   10500
gcctccacac agcatcctca cctccgcggc ccctccctcc agcccgcccc cgcctccaca   10560
cagcatcctc acctccgcgg ccctccctc cagcccgccc ggcctccaca cagcatcctc    10620
acctccgcgg ccctccctc cagcccgccc cgcctccaca cagcatcctg acctccgcgg    10680
ccctccctcc agcccgcccg gcctccacac agcatcctca cctccgcggg ccctccctcc   10740
agcccccccc cccccgcctc cacacagcag catcctcacc tccgcggccc ctccctccag   10800
cccgcccccg gcctccacac agcagcatcc tcacctccgc ggcccctcc ctccagctcc    10860
gcccggcctc cacacagcat cctcacctcc tcggcccctc cctccagccg ccccccccc    10920
gcctccacac agcatcctca cctccgcggg ccctccctcc agcccgccgg cctccacaca   10980
gcagcatcct cacctccgcg ggcctccctc cagcccgccc ggcctccaca cagcatcctc   11040
acctccgcgg ccctccctc cagcccgccc cggcctccha cacagcatcc tcacctccgc    11100
ggcccctccc tccccgcccg gcctccacac agcatcctca cctccgcggg ccctccctcc   11160
agcccgcccg gcctccacac agcatcctca cctccgcggc ccctccctcc agccggcc     11220
cccccccccc accccgccc tccacacagc atcctcacct ccgcgggccc tccctccagc    11280
ccgcccgcct ccacacagca tcctcacctc cgcgggccct ccctcagcc cgccccgcct    11340
ccacacagca gcatctcacc tccgcggccc ctccctccag cccgccccgg cctccacaca   11400
gcagcatcct cacctccgcg ccccctccct cagcccgccc cgcctccac acagcagcat    11460
cctcacctct gcggcccctc cctccagccc gcccggcctc cacacagcat cctcacctcc   11520
gcggcccctc cctccagccc gccccggcct ccacacagca tcctcacctc tgcggcccct   11580
ccctccagcc cgcccggcct ccacacagca tcctcacctc cgcgggcccc cttcgctcgt   11640
ggcgacctt tcgatgctcc ctggccgcct gtggtccctg agccgtccct gcgggcgcct   11700
ctgctgggga accagtggga atcagctcag acaccaccat aggggcccct gtctactgtg   11760
cagggaacct gacttagccc ccagtgaaca aagacacttt atggggagac aggatggctc   11820
cctgggagc gacttcccag aaagccgacc tcacctctct gggcagggcc ctcagcgttc    11880
tccacgccag ggacccgagg tctccgagaa gggtcctgcc ggggaggagc acagtcagaa   11940
acagggagac gggtccaccc gccccagttc acctgaccct gctcaccagg ctgggcaggg   12000
caggctgctc tggctctgga gccttccctg ccacctcct tgcttccttc aagtctgtca    12060
aggtcacgcc ctagtgtaga gaactcggtc aaggaaaaag ggcctagact tccacaggac   12120
tcaagttcaa gaccccggcc ctcctccctc agacccggga gcacagcccc agcccatcc    12180
cacacctgtg tagacctccg agactggcgc ataaggcggg agcgagcctt ccgctgagac   12240
tcggactctt catcacgcac aggcatctgg taggacctga gtggagaatg tcccttggg    12300
tgctgtcgca ctgtgaatga caccttaggg gagtgcacat tctggcagag aacgtgtcaa   12360
ctgggcaaac aggaccccag gagcctaccc agagcccag agaccctaa acactgtctt     12420
ccctagcct ctttacctcc gccgatccct ggagtcaggt agggctgctg cagaggctgc    12480
gagggcattt ggcttcactg gggatccagg ctccctcctg gaggatgggg cggagtgatc   12540
cgaagaagga ggcatggcag cctcacacct gtatggattc attcattcat cagcaaatat   12600
tcctcaagcc cgcattctgt gtcaggcata ggagagacca cagagaagga gccaatcatg   12660
gctgctgatg agccatttct gggcaaaaca gataaaacaa acagcagcca aagagaccag   12720
tgtggagctt ggggagaaaa ggtgcttgga aaaaataaag agaataagca attatttgat   12780
gcaccctaag ggctttctca gatctcaaat gccaggatgg caccagacct gtccccttgc   12840
cccagccact ggtacttaca gggtagaggg ctctggcact ttctgggcag gggtagggggt  12900
tattctggca agacggggtt ccctggcctg tgggagacagg agagaagcaa aggaggcact   12960
gtctgcccca aggcaggagc ctgtacccca cacacttcac ggcacctacc tgagaggagg   13020
cctttttctag gagggaggag gaggctgagc gctgcagacc gagaaccccc tctgcaccc    13080
tcctctctga gggacccagg gcaccagagc ttcctgtctt ctggagaccg ccgcgcctgg   13140
agaaggagc ctcttctggc ggctgggaga ggaagaaggt cttcattact gagcaaagca   13200
atgaccctc tcctcagagc ctacgcgtgt aactccaggg gaattacagt aaaccacagc     13260
caaagcaatg accctcctcc tcagagccta cgcgtgtaac tccaggagaa tcacagtaaa   13320
ccacagccaa agcaatggcc cttctcctca gagcctacgc gtgtagctcc aggggaatca   13380
cagtaaacca cagccaaagc aatgaccctt ctcctcacgc gtg tagctccagg            13440
ggaatcacag taaaccacag ccaaagcaat ggcccttctc ctcagagcct acgcgtgtag   13500
ctccagggga attacagtaa accacagcca aagcaatgac ccttctcctc agagcctacg   13560
cgtgtaactc caggagaatc acagtaaacc acagccaaag caatggccct tctcctcaga   13620
gcctacgcgt gtaactccag gagaatcaca gtaaaccaca gccaaagcaa tggcccttct   13680
cctcagagcc tacgcgtgta actccaggag aatcacagca gccaaagcaa tggcccttct   13740
cccttctcct cagagcctac gcgtgtagct ccaggggaat tacagtaaac cacagccaaa   13800
gcaatgaccc ttctcctcag agcctacgcg tgtaactcca ggagaatcac agtaaaccac   13860
agccaaagca atgacccttc tcttcagagc ctaagagtgt aactccagga gaatcacagt   13920
aaaccacagc ccaggcaggt gccaccaaaa aaaaaaaaaa aaaaaacatt acttcttggt   13980
ccacaaggac ctaagaacca agtcaaaaag ccactttcct cagcggaagc agaagtattt   14040
accgtatccc acccgctgcc ccaaacctca catctgctca gggcgctcag gctcaccaca   14100
gggctcttgg ggctggagga cacaggagaa gacacgccat tgagggctct tggttgcaca   14160
ggagggtgat ctgtgtgcag gaacaggaga ggggggtcac aggagaggcc ggcgcctct    14220
gagattgggg acccacaagt ccagctcctt cctcagaccc agggtccagc atccctacca   14280
gctgcctctt cttctcccctc atcctcatcc ccaagagagg gccgccggc cccaccaggc   14340
cggcgctcct tcgacagatc ctgcaggag atcttctcac ggctgctcaa acgacacacg    14400
gagctcctag gaggacaggg tgtccgtgtc caagtctggg ggcgagtccg acccacccca   14460
ggcctaggca tctcttacct tctgtgcttg ctgttggagg gcacctgtgg ctcttggcct   14520
cggctctgag aggcttcctt ttggttccga agctacaag atggaaggg gcaactgggg    14580
aggggcagag agcacaagcc ctccagggtc tcctggccgc cccctctgtg ccacctctcc   14640
```

```
acctcgaggg ccatcacgca taactgggct agtcacactt tatgcagggt cctgcaaaca 14700
tgggggactc agtaacccgg cagcacactg gctctggggc ttattcaggc tctcccaggc 14760
ttggcctggt ccagctgtca ctgcctccag cctcattccc aggggggattc gtcttcttcc 14820
caggagcgag caccttgctc agacttcccc ctaccctcca gcacatccag ggcaggacag 14880
ggcaggtggc tcttttctggt tatcacaggc cagctctcag ctcaaggaca acggccaccg 14940
tcccatacta agcagtctgg tgtcgtaacc ccaggaacac ctcttgccca tgccctcctt 15000
gcatcccagt gtgccacggg actcctctct ggacaatgtt cccgatggt ccacgaggcc 15060
cgggccacct cactaaataa tggaattgca gccatgccgt ctgcttgggg ccacacccat 15120
gatgcctcac tctccacttt cctagcaaaa gtgctaacta gagtgggggg ggggtagata 15180
caggttcaac ctgtgtcaca cacagctgtc ttcccaagcg agcaggcagg aaactctggg 15240
catagcctca agtcctccag atatggaggt gcctctgttc ttagccctcc accagagctg 15300
ggctgacagg tgggaatagc gggtctcagt actgagggtg tcaagggaca aagactgtca 15360
gccctcccgg ttactgttac ctcctcagag ctgccaagta aagaggcaaa ctagagtcga 15420
gactcacgtc ctcctgtttc tgggccagtt cctccaaaag gttcatcact tcctcatcag 15480
ccaggtcaca gggccgctgc ccctgagtag gagaaggagg cagatgacgg tgatggtggt 15540
ggtgtagtag gggctccccc gccaccctgc cccaccatct gagatggccc ttaccgcatg 15600
ggtcagcgaa tccatgcccc caccgtgctc agccaggaga cggcaggcgt cctccacacc 15660
ccagtgggct gctgcgtgca acggtgtcca gccatctcca tcccggagct ctgtgtcgta 15720
gccagcttgg agtagcagcc taagggccag ggaggcttgg gtcagatggc aagctaggcc 15780
aatggctgat ctcaacttct gttctgtggc cacaggacta ctgatcaata cccaagcgtt 15840
actagtttta ccagcaacca gccccacccc aagctcaact gagccctccc ttggaccagc 15900
agctactaat gaaaaagctc cctcatacca cagggatccc actcctcagg ccccagggta 15960
aagggttagg gcagtggtga ggcgatgagg tggatgcagg actcccact aacgcaagcc 16020
catggagagg atggaccctg aaggggctgt gatgctggaa ccactggaac cacgcggttt 16080
taggacacgg atcctcaaca gtgtcaagca gctctcacac cctctctaca actggagaca 16140
tcaccactag aatcctaact tacgggtaca agcaggaagc accagtgtgt gggagctgga 16200
gaggctgctc aaccccctcc cacgcacagg acagccctac cacagcacgg taagacccca 16260
aacatcacag tgccggagga gagcgagcct ggctcagcct tccagaaggt aacaacctgg 16320
agctctcaaa actcagcatg gcacgaggcg aggcctcttt tggaagcagt gtgatgaggt 16380
cctgtgtcag tgaggaaggc ttcaagccca gggaggcagg ggtacaaggc aacaaggtgct 16440
gtgtggccct gggaccctcc tccctcacac ttcccaagat tcccctgtcc ccttgcagca 16500
gggcacgctg ggcttcttgt tacattccca catgccaggg tctctagcca gctgtgcgct 16560
ccttctggtc agtatcctag gagcctgaag cgtgccaccc agccacaccc cctagtccat 16620
cagcacttcc tcacctggca gtttcttcac caccatctct gccaggggc ctccctactg 16680
cccactagtt atagcctccc aaggccaagg tttttctttgt ataagcttag tgttatttac 16740
cattagtgtg tgtgtctgtg tgtgtgtgtg tgtgtgtgtg tgtgtgtgtg tgtctgtgtg 16800
tgtgtgtgtg tctgtgtgtg tctgtgtgtg tctatgtgtg tgtgtgtctg tgtgtgtctg 16860
tgtgtgtgtg tgtctgtgtg tgtgtgtgtg tgtctatgtg tgtgtgtgtc tgcgtgtctg 16920
tgtttgtgtg tgtgtgtgtg tctgtgtctg tgtgttgtgc ataaatgcca acacacatgc 16980
cccagtatga agatcatgga tgaagatcag aggacatatt caggattcac tttctccttc 17040
caccaccggt tccaggacct aacacaagtc accaggctct tgtgtggcca acactttac 17100
ctctgagcta tctcactggt ctagaagcca acgtttgcag ctggaccctg ctactcccca 17160
gaggacctgt ggcaatgtct acagtcatca cacaactggg tcagaggtgc tgcaatggac 17220
tggacagcca tcagaataga atgacccagc ccatcaagtc tctcattggc tacggtgggt 17280
acacatctga aacaccacga ccagcccagg aggctagccc ctaacagaca ccaatattta 17340
cctgtacttc aatgagtaca atcatagaag acttttaata cagtcagaaa caatagataa 17400
ctataaattc agtgaacagg agtctaaacg caaactcaca caaagggtac catcacaaaa 17460
ttacaaaatt cagtatgatg gctcacacct gcaatcccag aacacagaag ctgaggcagg 17520
aggacagctg tgagtgcaag gccaacctag gctatctatc cagtaccagg ctagtcagga 17580
ctacatagca agaccttgtc tccattagaa aagaaagaag ccagaggga gggaggcaag 17640
catggtggct ctcacctcta tcccacagga aggtgaagga acaaagagta gaaattcaag 17700
accagtgaac tagaggcgat catgaccgac atgagctatt tatggaagag gccaaataaa 17760
caaacacaaa agttgtcatc agtgcatttt tttttttcagg gctgggactg gaacccagaa 17820
cgctaggcaa gtgctctatc cctgaggcac ccccccccttc cctcacgggt agacaccagg 17880
gaagcatcta tctacctatg gcctgcgacc acagcccagt gcttcagttc tgggacaagt 17940
attggctcac tttctctact aactagcccc ccggaccctat gcaggtgaca ccggggaaag 18000
catttaagca caaagacagg aaggagttct gatcaccaga atccacttaa aaactcagtg 18060
gatagctgtt ataaaaaaat gacatcaggg tggagagaga tagatggctc tgctcttcca 18120
gagacccggg ttcaattccc agcacccaca cggcagctcc aggggttctg accccctcaca 18180
ctgacataac acagacaggc aaagcactaa ttaatgcaca ttaaaaaaaa taacatcatg 18240
aaatctgcag gcaaatggat ggaactggaa aaaaaaaaaa aaaaaaaaaa catcctgggt 18300
gaggtaaccc agcccagaa agacaaacat ggtgtgtact catttacaag tgcacattag 18360
ctgttcagtg aaggacaatc gtgctacaat ccacagaccc agagaggcta ggtaacaagg 18420
agggctccgg ggagggacgg tgcacggatg ccccagggaa agggaaagag aaaagacttt 18480
gcagatggaa tgggcaggta gggatggaaa caggagaggt ggggagaggg agtgaggggg 18540
aaatactggg gggggtggct gcaatgggggg ctcacttttgg gggtgttaag gaaacccagc 18600
acagtgggaa ctcctggact ctgcaagggt ggacctagcc aagtaacgag ggacacagag 18660
tctgaaccgg ctactttggg taacaggcaa ggctcccagc agtgggacat caacccggcc 18720
acaaaacttt tgacctacga tgtgccctgc ctgcaaggtg tggtaggta atggtggcgc 18780
agagcttgtg ggagtggcca accaatgaca ggtccagctt gaggtccatg ccacaagagg 18840
gagcccacgc ctgacacagc cttgatggcc aggagcctgg atagcccgag acctgggta 18900
gaaccaaata caattggggg aaaagaaaaa aaggcaagaa acaattctta atgatattct 18960
gctgttctca tggatctgtg gctagcccaa ctgtcgtcag agagcttttt ccagcagttg 19020
acgggacgag atgcagagac ccacagctca gggaacccca caggaaggat tatggggggg 19080
gggggcgcga ggacaccagg agaacaaagc ccacagaatc aactaagcag ggctccttgg 19140
ggctcatgga gactgaagga gctagccatc aggacctgta tgggtctgcg ctgggtcctc 19200
gcctggtgct cttgcgggac tccttaacac tgggactgga gctgtcgctg actcttgtgc 19260
ctgtttgggg acccagacaa gcataactgg ttacgctgtg cttggctgtc atctctgaga 19320
tgcctgttct tttctgaagg gaaacagagg actggatctg gaggaggggt ggaggggaac 19380
```

-continued

```
agggcagagg ggagggagga atgtaatatg agaggaaaaa acaacaacta caattattga 19440
gtggacatgg cagcccatct gcagagacag gccaccctca gacggagatg gcagctaaac 19500
ttgccaaaaa ggcaagctga gggatcggcc agaggccctg cctcaatatt agagtggaga 19560
gcaaccagag aaagtactac atgccaacac acacacgagt gtgaacacac acacacacac 19620
aagtcatacc catacacatg cacacgcgcg cgcgcacaca cacacacaca ccacaaccgt 19680
taaccagaca tatagttgtg tggaaacaaa cctagttttc cttgcaacta ggactggcca 19740
atggtgagaa ctgggttaat ggaacacaga tattaaatat gcacacttct ggaatgttct 19800
cctgaaaagt aatagacatt cgctcccttt gcctctgctt cccaccaact tgagatatag 19860
acgcaaaggc aggtgaggca agtcaccctc aagtgagagg caccgctaga gcagggcgca 19920
agctctgcac tcggagattt agggcatcct gtcccccaaa aggaatgggc tcagagcgca 19980
ctgggactca tgctgtaact acagagactg atgcccctcc cccaggagca caactatgca 20040
ggcaggctgt aagtctgggg gtggcacgag gtcttaaatc ctgctggaga aaacctgcct 20100
gcaaccttac cagtatgaaa agcagagagg ttcatcttaa ttcaatttgg gtctttgttt 20160
ttttgttgtt tttttttaca acaggatccc tctataaagc actagcctca cactcagtat 20220
atagacaaat ctatcctgga attccagtaa tcctcctgcc tctgattctc aagtgtaatt 20280
atagacatat aacaccgtat caagcaagca agtgcacaca cgcacgcaca cgctcttgtt 20340
acatagcctg ggctagccta caactcacag caatcctgcc tcgacctccc aagtgaggaa 20400
attaaaagcg tataccacca tgcctggctt aatgccattt ttttaggttg gtattatttt 20460
tatgcgtata tgttttgcct acatgtatgt atgcatacaa atacacacag acacagagat 20520
aaataaatgt aattttaaa cctctttggc tttaggtatg taaaccagga gaagaaaagg 20580
acaagagccc cgaaaagctt ccagacacaa aacaatcact ctggcctcgc tcacctcatc 20640
acctcgatgt agcccttggc ggcagccaca tgcagggcag aggccccggt ccgggggtgg 20700
cgggcctctg gcatggcacc cccattcagc cagcaccttg tgtcatgaag cagcagttct 20760
tcttcagccc gcttggctgc ctcgacatcc acacctggga gaatgagagg tgacaggtgg 20820
actcacacag ggtggcctag gaaaccccgg ctgcggtctc aactagtcac agcccggccc 20880
cgtgactcat caagtctctg gaccactcag gagaccgggt ctgcccgagt gtttcccaac 20940
tgtgctccct gaagacctgg gcaccaccga gggggccaag acaggccagg aatggaaacc 21000
acaggtcctg acccctgtgg gtcagtatcc tctttatgtt tttctaatag aaaaacccac 21060
accggattcc atctaggttt tcctacccct ccagctataa gctaaagcca gcgcccttcac 21120
acaatgtcac tgctggttct tctcccttg aagtacgata ggccaaacaa aacttcacta 21180
cggcgttgta cgtggtggct ccggcctcta ttccagatct cagccttggc aggatgaccg 21240
gtggcctcga atctgagaac agcctgagct acatacatgg tgtcaagcca accaggacta 21300
gagagacaga ctctgtctta gacaacagta aaaactaaaa ctcaaaagct tctgggcggt 21360
ggtgcacacc attaatccca gcactcggga ggcagaggca ggcggatctc tgtgagttcg 21420
agaccagcct ggtctccaga gtgagtgcca ggataggctc caaagctaca cagagaaacc 21480
ctgtctcgag aaaaaaaaaa aaaaaaaaaa aaaagctatt tcccaaacta tttgcatgca 21540
tagtttcatt cttgcccaga tgtccaggca tttgacacct cgctggccca cgacagaagt 21600
gagaagtgag tgactgcctt ggcactttgt gcttatgcgg gtatgctgca tgcctgtgac 21660
cccaacacag gcaagaggca agagaccagc agggctccac agggacccty agtcaaaaga 21720
caaacagagg gggaggggct ggagagatgg tttagaggat gaagtgccaa gcccgatgac 21780
ccaagttcaa tcctgggaac tcatgaggca aaggaaagaa tcaagttgca caaggggttt 21840
ccctttgtga acccagcttg gcctcaaact cacagcaatc ctcagtctct ggaaagctga 21900
gattaagagg gggtttttt gttgtttatt tgtttttttt ggttttggtt ttacgagaca 21960
gggtttctct gtgtatcttt ggagcctatc ctggcactcg ctctggagac caggctggtc 22020
tccaactcac agagatccac ctgcctctgc ctcccgagtg ctgggattaa aggcgtgcac 22080
caccaacacc tggctaagat taagagttac acaccacacc tgtactccct gcactcaaag 22140
aggctgaggc aggaggattg ctccaagtcc aaggtcaggc tgggcgccag catgagagcc 22200
tgtctcaaac acctcagggg ggaaacagaa agccaggcag actagctgag gctgaagcac 22260
tccagccctc actgtgaccc tcatccctta aagcacccct aactcactga gaccacagca 22320
aaatggcctc tgctgaataa cttcctcctg ggaaggttat tactgcccat gcttttgcag 22380
ttgtgaaact cttgacttgc cgaagttcct cagagttgag ctgttgtatc cagtagccgg 22440
cagctatgtg gaactgccga gcgagcactc gaaactgaga catgctgtga acgtcaagtg 22500
cactcgggat ttcaaaacac aggaaaaggt aagggctctc gtggacagtt gtctctaaac 22560
tgttttgtgc acacgtgcat ggcagcgtgg tcagggggca attctgagga gccgagtcct 22620
gcttcccacc ttgctgaggc tgggtctctg gattctgcgg ctgtgctgtg tactctaggc 22680
tacccggccc acagggcgtc cccacagttc tcccaccttc ctctaggacc tgggagtacg 22740
gacgtgcacc agtgccgccg ccggcttttt acaagggttc tagaggtggt aacttgggtg 22800
catctaacat ctttactggc tgagctatct ccccagttcc ccttactgtg ttgattgcac 22860
ccaacggaat actgggtttg tttttttgttc tggagcgtgc gtgagagaga gagagagaga 22920
gagagagaga gagagagaga gagagagaga gagagagata gagagagata cagacacaga 22980
atcttaacag agagacagag tcttacatta tatagtggag gctgaatatc tagtcttcct 23040
gcctcccaag tactatggga tagtccttct gtacgctacg aatatggact cttctcattg 23100
gttaataata aagctgagtt ggcccacagc caggcagaat aagggtaggc gggaaagcca 23160
aacagagata cagggagaaa gaagggcaga gttgagtaga acgtaagcag ccaccaggga 23220
agcaagatgc caggtgacag gtaaagccac gagccatgtg gcaaaacaca ggctaataga 23280
aatgggttga tttaagttgt aagagctagt tagtaataag cctgagctat aagccgagca 23340
ttccgtaatc aatacgagct cttgtgtatt tatttggggc ctggcgattg gaactaaagg 23400
gaagcttaga ctacggactt gcacctccat gcttagttta tgggttcaga ggaccatgct 23460
aatggataag cactctacca actaagctac accccccagcc tatggcttgc aagtttcaaa 23520
ctacatctgt ggctcattca ggatttccac tgggcgtcac tggcaaaggc cttcaggtcc 23580
cacctggagc gctggctcag ccattagagc cattaatggt agactcacaa cctacacaag 23640
agacaaaaac ccacacaagg ggtggaatgc agagactcaa ccagttccaa gccagccggg 23700
actaacaaag caagatcctg gctcataaac ccaggagcag ggtttagccc agtggtggta 23760
tgcctgcctg gaaagggatg gcccccaggtt caggcctca cacagaggc tgctttcctc 23820
accacactcc ctcttaacca aggtgagcag ccgctcccct cagcacacac attgtacact 23880
gccaccataa agctttacat gggacccaag aaacagtcct gaaagctggt tcgggatgtt 23940
ctttctcatt gcaggcaag gccaactcca tgcggacacc ggctgcagct tggtgctacc 24000
tggcggcagc cgggtcctag ctccttgtgt ctcctgccca actagggttt cccttgtggt 24060
ggcagagttc aagaatgcat ggcgaaagtc cacccgcagc acagtcacag ggaacagggc 24120
```

-continued

```
agggagggcc aggcccgccc tcgtcctcca gactcctgct tccttaaagg gagtctccca  24180
cagttccacc tactgtgggg ggaagggaa ggggaagggc ggagctcct tgctgttctt  24240
caaccaccag ccagtactcc cgtgcaggct caagggcagc ctgtgctctc cacacagcca  24300
agacctgctt gcttgttact cagtttttct tacacaggcc gttagctgat taattgggtt  24360
tttattttat gtgtatggat gtgttgcctg tgtgcatgaa tgtatacatg tgtgctggtg  24420
cccgaaaagg ccagaagagg gtgtcagatt cctctggaaa tggagttaca ggtgtcatgt  24480
gggtgctaga gttgaacccg agtcttaacc accgaggcat agccactgat tcagccagac  24540
tgaccagcct gcaaacccca gggatcctct gtatcggcct tgccccacac ctgctaggat  24600
tacaggtggt ggtgggcttg gctttgtggt tgctggggaa ctgaacttaa gacctcagta  24660
tgtgcaccaa acccttctac tgacttagca acattcccgt ggaagtcctg aaaatgaagg  24720
acgggggggaa ggatactgac tctgctgtaa gaaaattctt acatttatgt tattgtgtgg  24780
atgtgtgtgc actcaagcac aaatgagagc tagagagggc ctgcagaagt cacttctctc  24840
ctcccaccaa gcggatccca gggactgagc ccaggggtca ggcttggtgg tgagcgcctt  24900
cgcccactga agcacctcac cagcctgaaa ataaagctct catggcaccc agccacgtct  24960
gcttttctc atcccgtcgc tggctcattt cccccgatag cagctggtag agtcattata  25020
gcaagaccgt gcaccctgta aggcctgaaa cacatactga ccagccctcc acaggtccca  25080
gctgactcct gctgggacca ctgagttata aatcagagcg tcatctaccg gctgcagagg  25140
cgacagcttt ttggtgtcac caacagcaaa cactgtgctg tattcctgtg cactcaccac  25200
ctgtgagaaa atgcaccagg gcaggagctc aggcctgcag cttcagccag gttaaggccg  25260
gcctgagctc tccttccagg cacagccttg cactactcta gctggcatct gtaactaccg  25320
cagtccactg tgcccatctc tgcatgctac agccctcact gtccttcctg gatgtcagtt  25380
tccatgggag acagcttcgc ctttctccaa agcacatcct aagtctcctt cctaccctgt  25440
ccccccaagg ggggctcctc ctccacggac actgtgcttt cagtctttgc caggggtctg  25500
acctaggcct gggccgcacc aacactgcta ggacctggca gcaccactc ttcctccttc  25560
aggaaccacg tcctgacttt cctcgcccac agggcttcag tgtgacactt gtcacaaggt  25620
gacaagtcct cctgcacact ggtggggctct gggactgaca tgagatcatg tgccagtgtc  25680
acacagagag ctgtgtgctca gccactgagg ggggtagggc tactgtaccc cacctaggca  25740
ttagccctgc taagcaccac agggagagac cagaccccac caggaggcca aagcggctgg  25800
tggcattagg gatccactgc caaagactgg aactctaggg cttggacaga cagatggctc  25860
agttggtaaa gtgttcacca cacaagctgc aaacctgagt tcaaccccca gcacccatgt  25920
aaaatgccag gcatggtgga gcatgtgtaa tcccagtact ggggaggtag agactggagg  25980
acaaccgggg ttcactggcc agccaaacta gcccaatcgt ggaagctact gagacaccct  26040
gactcaaaaa tcaaggtaga cggctcctga cgaacattcg attgacctct ggtctccaaa  26100
cacacctgtg cacgcacaca tgcacacaca aacatatgaa ggactgagat tctgcatacg  26160
ttaaacagca actctctcct ccccctttt attgcattca tttactggtg tgtgtggctg  26220
agaacaatct atgggtcag ttctctggtc caccaagtgg gtccaaggaa tcagactcag  26280
ttgtaggctt ggcagcaagc accttgaccc actgagccat ccagccaact ctctttttg  26340
tttgtttagt ttgttgggtc agaatctctc tgtgtagtcg tggctgtcct ggaagccact  26400
ctgtagacca ggctggcctc aaactcagag attcacctgt ctctgcctcc agtgctggga  26460
ataaggcatg tgatagggtt aaacccacca cacccagctc tactcccagg gttgttagcg  26520
cctgaaaacc acattggatg ctctgtggct atgactttgg gagcgctatt attttcatta  26580
cgcttggtgt ctcacacaaa tggaaacctc gcacttgtct ttgagtggct gacttgctcc  26640
atgtagggtcc ttaagtctca tccaaatctg gcaggcggtg gtggcgcacg cctttagtcc  26700
cagtactcag gaggcagagg caggcggagt tcgaagccag cctggtctac agagacagtt  26760
ccaggacagg ctccaaagca atacagaaa accctgcctc aaaaaaccaa aaaaaaaaaa  26820
aaaaaaaaaa aaaaaaaaaa aaaaaaaaag aaagaaaaag tttcatccac atcgttagac  26880
gtgttggttt ccttccctgt ttaaggatgag cagcattctt ttatctgtat agaccacatt  26940
ttgcttatcc agccagtgat ggacttccta ccctccctgg tcctgaggct ggaattctca  27000
taccagacca agtgccacag gctggagtac taagcaacac ccaagtccta ggctactgta  27060
aatacgcctg caggtggctt tctctttgcc caacaccaca aaacataaag aagggagcca  27120
gacatagagg caactactac aatccagacc ctcaagaggc tgaagcagaa ggatccaaaa  27180
ccgtactaca gtcagtttcg ccgcagccga ggccaactaa ctaattaatt aacaaaataa  27240
tacgtattgt gggtgtgcat cttgcgatgc ttgtgttgtg gtgtggggat tgaacctgcc  27300
tacgctcagc aaacgctctg ccagtatgaa gtgtccagtc ctctcccaca cacacgcgaa  27360
cacacgcgaa cacacgggaa cacacgcaca cacacacaca cacacacaca cacacacaca  27420
cacacacacg cacacgtata tttaagatct ttcctctctc tctctctctc tctctcacac  27480
acacacacac acacagggtt agttaagacc ttatttgtat tacttttaat tgtgtgtgcg  27540
tgtgtctgtg cagggcacgc acacacgtgt ttcagtaccg gaagaggtgt gggatccccc  27600
aggtgctgga gctacagtga gccagacact ggtgctctga actgaactga atcctctgcc  27660
aaagcagaaa gcactctctg gactcctgct tttgttggtt ttgttttgtt ttgttttgtt  27720
ttgtttttgtt ttctttgtac ttttcaacag attctcacta aactgtccaa gttggcttga  27780
actccctctg tagttcaggc aggccttgaa ctcacaattc ctcaggcctg ggagagcgga  27840
atcttttcgt caagaaaaca ccccatttga aaactgagga atgctgtatc agcacaggaa  27900
gggggaagct caggccttgt ggcttagaga agcggccttg tgccatgggg ttaagagccc  27960
caggctgccc catctcgttg gctgagggag gcgcttcccg ttatctgagc agagcttcca  28020
gcatcagcaa catagtctcc aagtggctga ggaatggaag gaggatggac tggaaaggag  28080
aaaacaggaa gggtactgcc gcctgtgtgt ggggaaaggg gcagagctgg acaaaacagt  28140
aaaggcgtct atttaaagtg tgcgattcca tctgcacgaa atgtccgcaa cagacagatc  28200
cctaatgaga gaaaccttag aggcttgccc agggatggga caggggacta gacttttgag  28260
ggtgactttta aaatgctctg aaatcaatgt ggcatcgact ccgacaactc tgtggaccac  28320
agcacaacca ggaagtgcac tttggatggg caaacttctg ggcatattaa ttacagcccc  28380
aaaggctgct ttgttataaa aagcactggt gggctggccg gctagctcag caggtcaggc  28440
gcttgccacc aacaacctga gtcccagacc aaggccacat ggtggaagga gaggcctgcc  28500
agaaattgcc ctctgacccc cacagtgccg agcactcaca ctcatgataa actaaataaa  28560
tctaaaaaac aaaacaagac ttcaaaagca gcagatggag cgctgacaca gacactcggg  28620
aggcttgggc aggacggctc caaattcaag gccagcctga tctacgcagt gagtaccaag  28680
ccagccagga cttcgtagca agaccctgtc tcaaagacat aaacagggct aaagggctgc  28740
ctcagtggtt aacagcgctg gatgctcttc ctgaagaccc aggttcaatt cccagcaccc  28800
cgggcaggca gctcacaacc atctgtaact acactcccag ggatccagtg ccatcttcta  28860
```

-continued

```
gcctccgcag acaccaggca cacatggaac aaaataccgg gacataaaga acacactgtg   28920
tggtgaagcc cagggaagga tctgtggtgg ctgtcacagt accgaggcga ctcttctgag   28980
tttgaatcag gggacgggaa ggagagctca gctcaaccgc tgctacctgt ggctcctgac   29040
cactgccctt cagctcttgg tgcccactgg ctaccaagca ttcccaagtg actcgcagtc   29100
acctgaaatt caatatgcca acatggtgaa cccactgtct ctccatcctg cgtagcaaca   29160
cgcaaggacg gggagccaag actatgcctc ccatgaacta tctgtcctct gtccccgctt   29220
atctcctaac tggacagtcc ccagtctgga actggtgcct tatgttcctg gagagcctgc   29280
aaagctgcct gtttgctgat cccttttctt ccagaccctg cactacgag ctgagagcca    29340
cccagctata acccagtgtt tcgtttgtag ctgacaggga ctcacagagc ccaggctgct   29400
cacaaactta ctatgtgggg aagcctgacc taaactcctg atcttcctgc cctgcctccc   29460
aaggctggct gggattacag gcctgtgccg ggacacctgg ccgggacact agcttgtcag   29520
gcaggcagag agggctctca agccctgtta agaacttgct attgggaaca cacacgcccc   29580
acccaggaaa atgaatagga cccaacatgg agtttcaagg ggcatgatgg gagctcagga   29640
gagaatcctc tgcatgctcc agtgcctcct aacacgagct gggtctagcc atcttgctgc   29700
ttactcctcg acaggccctt gctgacagca cctccctcct tcagttcctc agacactcac   29760
agcagttggg gctcttactc tgtgtctggc agtgtctcac tagaccccttg gcaacccacc   29820
ctggggacac gtaccacccc cacttcacag ggaaggaaac tgaggcacaa agagcaagag   29880
tacaaggaaa tgggctgggc ctttgagccc agactcccag acgccaaagc tctcgatccc   29940
acaggcccac ctcggcgggc gatctccgcc ttcagcagcc cctccatggc atccgactca   30000
gccaggtcca aagacaggtc tccatcactg ttgacggcgg cgatgttggc cccatggctc   30060
aggaggtacc tagggggcagg ggaaggtcag agccaccagg cctggaccta acgcctaacc   30120
caagccctgc ccttcaaccc cagcctcacc tggcaatgtc caagtaccca caggaggctg   30180
ccacatgcag cggcgtccag ccctcgttgt ccgcctggtt cacagtagca ccctgctcca   30240
ccaggaagcg caccacctcc aggttctcgt ctatgcaggc ctggggacgg ggacaggccc   30300
atcagctccc ggccgggcca atgagaggtg tggaaagcaa cgccgatggg ctgcagcaca   30360
gattccaggg gccctctggt cagtggccgc ctaaaatatg cctcgttacc catgcttggg   30420
taatctatgc atgcagagct catggagact agagcaggct ccaaaaggca gattgaaaag   30480
gcgaccaggg aagaggcgga gctgccatcc ctgcatgtga ctgctgaaca taccctatga   30540
ggcagaggaa ccccagagcc cagccatgtt cttccaaggg gcagggcaag gctaggttga   30600
ggcaaaacgc tcacctagcc ctgggttcca tccacaacac aggaaaaaga gagatcacca   30660
caaagagaca cacgcacatc ccagagttga gggcttgggg cacagttccc aaaaagggatg   30720
agtaggctat gttcccggtg tccagggatc caagcagacc aagctctggg tcactgaggg   30780
cctaccgtgc acaggtctcc tcagaacttc ttttctaaac accccacacc acactaatcc   30840
cccacctcct cacccttcga accaacagct caggagagga aggcctcacc ctagccagcca  30900
cagcacccag ggccacaaga gagctggtct caatccctga tgacactgct tggacactgg   30960
aaccactgag tctagggagg gggttaggtc cggactcctg ggtcctcatg aaaattaacc   31020
cccttctaca agcgcgacca tctggagaaa gagggaagga agctacgagg gccaagtgca   31080
tgaagtcatg gaaatttagg ctgggggggg gggcacgtgc cctgggaacg ggatgaactc   31140
tgggcttcac tctgggctca gtttatttcc accctgttgt catggtgatg ggagggggggg  31200
caaggaggca gatgggcctt tccctttcaa ggacctggcc gggtacgggc atccatgtga   31260
aagatgcctg aggctgggca ctggggaccc aagaatcctc ctccctcaga tgtagaactc   31320
tagccaatcc tctttcctta gacccaggga tccagacttg gccctcctcc ctcaggccca   31380
ggtgctaggg ctccccatct ctcccctgct caaacctagg actcttaact cccagcccta   31440
cctactccag acccaactca tagccattat tggacaaggc aattattgga caagggaaag   31500
aggaaggaat gtccctgcct tgctaaggca gaggctgggg cttaggaaat gtcattgcag   31560
gaggctgatg ccccaaggag ggtctagaac cggaaacact aaaaagtctg aggtgtagaa   31620
atcaccacag actgggtggc tcaatgcccc tgctttcctg ggactgaaac tagtttcagg   31680
agttttcact gctgaagcca gggcagtggt actaggaggt gatgctacgt acgcaccact   31740
ccaaaccocca gcccctctg cgttctggcc ctgaaagcca aatgatctca ctgaatctga    31800
tctccagtct cccaagcctc ctgcaaaggc ctgaagagtc aggtcaccaa ggtgtctgca   31860
tggcgggagg agagtcccac ctggaaggct gacacgtcag gcctgaggtc acaggttcct   31920
gtcagagagg atgctctagg gacctccagc agatgcagag gaagggggatg cagttgggag   31980
ggaactcttg ggagggccag ggactttggt gatcatgtga gcagcctgag ctgatctcct   32040
ggactggtca aagacgctga caccctgagt gtggcctcgg gaaaacagga ccctgctata   32100
tatagaggac gatgtcccac acagctcacg ccggcccat aaaggaagtt ttccacagga    32160
cgcctctcac catagagtcc ctctggggac aggggtgacc actggtccca ttctacaggt   32220
aaaaaaacta aggcgcaccg agaaaagaca ctcaagatac aagacacaag aagcagactg   32280
acacaaaaag tcagcacgga ctttttttgt ttggtcaaga ttttgcaact gggtctcatg   32340
tgggctatca agatggcctc aaagtcactg tgtagatgaa ggtgacactg aattccaacc   32400
ctcctgcctc tactttccaa gcacctgatt tctgtggtat tggggttgga acctgaggct   32460
tcctgcactc taggcaagca ctctgtctaa aagacagccc agcccaggac agacggattc   32520
tgtttttcct ctgcctggat gagtgaaaca ctgaacctTt attccccacc tccacgagca   32580
tcctagcaag aggacgacaa cccaggagat ggaagttgcc atgaaagact gaaagtgaac   32640
caacactgtg gccaggagga agagaacgg ggatggggtc tctgctgtga ctaatcttgt    32700
ccctgacaat gccagctttt ggatgacggg gagataaaag catcccgaat ccagaaggat   32760
cccggcaata caagatggtc ctcactctcg ggcacagat cactggaaaa agataatcac    32820
agtgtctgag tcgcccaggg tcctggtggg gtaggttcta gaaggtgaca gggtggaaat   32880
ctaagagaca gggcatagtt tttaaagcag gatgctgccc aaatatagtc catggggtgg   32940
taggtggagt gggcatgcct gtaatccac aaatgagggg gtcagagaca caggacctgt    33000
atttgaggtt ggcctgggct acacagggga aaaaacaaaa aacaacaaca aaaacaaaac   33060
cagagagag agaaataggg cttggaagac cgaatgctta gaagtttcca gaaaggcaaa   33120
tcaatgtgga cacagagaga gaaagacaga gagagagaga gagagagaga gagagagaga   33180
gagagagaga gagagagaga gttgaggaga aacctatggg gggtgggggt gggtggcaag   33240
atcaccaaaa gggggatggc cgagaattga attaatagga catggggagg ggaggaaggt   33300
tatgggatgg ggcccaacag acggtggagc gcctcttctc caggggaaca aaggggtaca   33360
ctgccttgga ggggcaaagg accctcctga ggccacagcg gacagcacgg gtcacaggaa   33420
gtggggtagg aacaaggtg gaccccccaa aagaagtgac actgaagggc ctgggcctgg    33480
ctagcctcag aggaggaggt gggggggattgg gggggggggc gtcaagtcag agctgggccc   33540
tggaagcctg cggcacagcc agggcagcca ccagcctgga aaggcacggg gtgtaagcca   33600
```

```
tccgtgtgcg gaagacgccg ccggggagag cggtgacagc gcggatgaca ggggcgaggc    33660
ggcccctgca gggcaggagg cggggaggga ggaggggtgg ctcggggggc cccgggggagg   33720
gaggatgctc gggggccgct gacctggtgc agggcgctga tgccgtcggc gttggtggag     33780
tcgagcaccg ctcgggcagg cggcgggacg ccggcgtccg attccccgct ggcgccggga    33840
tcggggcccc cggggtcccc gggatccccg gggtcggctg cgcgaagcat caggcgagcc    33900
tcatccagat cgccgcccgc acaggccgcc aggaactcgg cggcgcgctc gaagcgcacg    33960
gtgcgagcac gacgctcccc ggggcccggc tcagcccccg cccgcgcccc ccaccgccgc    34020
agctgctcct gccgccgctc gcgggctgcc gccgccgccg aagacgacga cgacgacgac    34080
gacgacgacg acgccgcccc ggggccgtcc tcgcccgaca tcgcgcccca caccgggccg    34140
ctcgcccgct cacccaccga gcgagcgagc gagcgagctg agcgagcgcc cgcccgaagg    34200
ccggccggcg acgaacagcc gccacccgcc cgctcgctcg ctcgcccgcc cgcccgccag    34260
ccccggggggc cgccgggaac cgccgccgcc gccgccgccg ccgccacaag caccgcccccg   34320
aggctcaggc tgggcccccac ccctcccccc acggacgggc gttgacgtca cgacgctgcc   34380
ccacagccct ctgggaaatg gagtcctccg ttgagaagcc cgcagggttt tttcagcaga    34440
ctcgctaact gctgagggaa cggtcggggt ggcacggaag ccgccagcag gcgcgcctac    34500
agcccccagc acctgagagg caaactgctc tctcgagttc gaggtcagcc tgggctacag    34560
aggcagtgcc agggtagcac caattgccta aagcaggaca cgcccccccc cgggaatgct    34620
ggaaatctga gtttagaggc gggacgggat gcccgggggg atgctgggag atgtagtttt    34680
tttggtaaag cggcgcaaag gatggcgcgt gggaaatgat ggcgtgtagc ggaacccgag     34740
agacgcagaa ataagactcg cgtactttca gttgtgtttt tgctgtgaga tgggtttgcc    34800
ctcgagctcg ctgtgtgact gcgattgtct gttttaaact cccgaccttc ctgcctccgt     34860
ctcctaattg ctggggttgc agacgtttgt ttggggtttttg ttggtttggt ttggggttggg 34920
tttttttcttg ggggcggggg tattttgttg ttttgttttt gttttttgttt tgagacagcg  34980
tctcactatg tagccctgcc tggcctgaaa ctcgctacgt agaccaggct ggcctcgaac    35040
tcatagagac tcctcccccc acacttctgc ctggtatgaa gggggcgcca ccaggtcccg    35100
cttgttttgg ttttggaatc tgcccctccc tccctcccca tcaacacccg atgaaggaca    35160
aggatttgtg aatgaatgaa tgaatgcatg agtgcatgaa tgaatgggct ccccaagacg    35220
tcgggggagac caggggccca cgggaaactg agtcctgaaa ccagattaaa caccaatcgc   35280
cgccaaactc ctctgggtaa ctaaggttcc cgtgcaaaat ccaagggtat cgggtagcat    35340
ggggcaagct gggaaatgta gtcccagggc cacgcctcct aaagagttca gcccccagac   35400
ttccaaaact gcctgagatg ccaaggtacc ccggaaagtc agtttccaga tgaagacaag    35460
cctccggtct ccagcggtaa tcccttgagc acccgggaag aagggtcccc aaagaaccac    35520
acatttctcc ttagcccact cggggctgcg ggggacgcta ggagatgctc tcccggctgc    35580
atcaatgctc tcctggaatt ctgggatcgg tagcacaaaa tgtgatgcctc cgataggttt   35640
ggaagttttg ttagtagacc caacagataa aagaacacct tgatctttca agaatcttcc    35700
ccccacccccc accccacccc ccacctccac cccaaaaatt gcaatttgag aaggacagaa    35760
acacttttga gacaggaaca cagactcaca cacacacaca caaaaaagta gaacagaaag    35820
ctgtcaagtt tatagagaga aaacacgtct tcctaagggt cgttagggca gccccgttca    35880
cactgtgacc cttggatttg tgaatgagag ataaattaca gaccctggca gagtctaggg    35940
aataacgacc ataaatccaa aaggataacc ctgtggtttt taagatgtga gatcacacac    36000
acacacacac acacacacac acacacacac acacacacac cattcttccc caaggcaaga    36060
aatcagatat ttcaacccct ggggtccaga aggaaggagg tcgctgactc caaaaactgt    36120
cttctgattt ccaccatgga tttccacaca cacacaccct atcaacacac acactaaata    36180
gacgtttata aaatgatcca caaaataagg ctacaccaac acacagaggt aagactgttg    36240
ttagacagtt ttggtctggt tgggttttttt tttttttttt tttttttttt gagtagcctt    36300
ctcctgtccc atttctcatg cctctacaca cacctggcct ctgggtgtgt tattttaaaa   36360
catccttaga agaattaatg accttgtaca accagtttaa atgcaagagg caattaattt    36420
tgttttgttt tgttttttcga dacagggttt ctctgtgtag ctttggagcc tgtcctggca    36480
ctcgttctgt agaccaggct gacctcgaac tcacagagat ccccctgcct ctgcctcccg    36540
agtgctggga ttaaaggcga gcccggcagc actggagatt taactcaagg tctcctgagt    36600
gctcgacaag ctactcccag ccatgaactt gatatctctt taatggcagc tgatgtctct    36660
cccgggcaac atggagctgt ccagccaagc cgcacagcca gccacgcata atgacaacac    36720
ggaagaactc aagcggatgt ctggagggcc tttattttga gttacagatg ggggacacac    36780
tccagaggct cccaggctcc atgcagtggg gcgtgtcctg gcagtctcac ttccagcggc    36840
ctccaactcg acccttccca gccccctttc ggctgtggga gaagaaggtg gagtcaggaa    36900
gaagcccgga gcctccgaga taagcttaac acagtccctt taaaattaag gaagtccacc   36960
aaatacccac ccccacccag agggaagaga gagcagaggt cagcgagagct gtttttttttt  37020
gtttgttttt tgggtttttt ttttgcagta gtgagcataa agtcaaggcc tcacacgtgc   37080
taagtatgtt ctgtacactg agccacgccc cttgcctctc actggcgatt ctaagcaagg   37140
gctctaccac tgagccacat ccccagcccc tcactggggg attccaggca ggggctctac    37200
cactgagcca cgccccagc ccctcctcac tgggggatt ctaggtaggg gctccaccac      37260
tgagccacac ccccagcccc tcctcactgg ggggattcta ggcaggggct ccaccactga   37320
gccacgcccc cagcccctcc tcactggggg gactctaggc aggggctcta ccactgagcc    37380
acgcccccag cccctcctca ctggggggac tctaggcagg ggctctacca ctgagccacg    37440
cccccagccc ctcactgggg gattctaggc aggggctcca ccactgagcc acacccagcc    37500
cctcactggg ggattctagg caggggctat accactgagc cacaccccca gcccctcact    37560
ggggggattct aggcaggggc tccaccactg agccacgccc ccagcccctc actggggat     37620
tctaggcagg ggctctacca ctgagccaca ccccagcccc ctcactgggg gattctaggc    37680
aggggctcca ccactgagcc acgcccccat taagggcatc tctttcagat aattcccagt    37740
aggggggttgg tggccatgtt ggagttgact ttcttgggtt agttcggaga acacatgcaa    37800
atttatgagt aagggccctg agggagaagg aagggtgagc tggagttggt gacttgcatg    37860
caacaatgtt gagtgaggct ggaacagtac agaaaatgct agaaaaggc agagactgag     37920
cagtgagcgg cctggatacg gtggagcaca tcggtaatct ctgcactctg aaggggatga    37980
ggcaggagga tcaccgagag tttgaggaca acctgggcta tatagcaaga gcctgactca    38040
aatgaaaaca acaacaacag caaaaaagtc gggtatgatg gctctgtaat ccctgaactt     38100
gggaagcaga ggcaggaaag tgtcaggagt tcaaggacac cctcaactac aaatggagtt    38160
caaggtcatt cacgcttaca ggagaccttg tcttaaagca agaaatagaa ggaaaagggg    38220
caggaagtgg acagacagat ggagaagggg ggaggggggga aagaaaggaa gaaagagaga    38280
gagagagaga gagagagaga gagagagaga gagagaaaga aaggcagaca gagggggggca   38340
```

-continued

```
ctgagatggc tcagcaggta aaggagcttg cagccaagcc taggccctga gtttcaactc  38400
tgggacccac atgatagaag gagaaaaccg acttgttcga gtcatccttc ggccacatct  38460
gcaccataac agcacacaca cacacacaca cacacacaca cacacacaca cgcacgcacg  38520
cacgcacgca cgcacgcgcg cgcacacaca cacacacact atgcggtgtg atatgataca  38580
aaaaaaagtg taaaagaaaa tgtactcaga aagaaagggt tggagggagg cagagagggcg  38640
gggagattga gaccaaagag ttgataaaga gaagcaagag attgggagtgc aggccaataa  38700
acacagcact cagcaggctg aagccagggg accaggagga gttcaaggtc agcctcagct  38760
acctagtgag actgggctgc atgaaacctt gccttaaaaa taaatagaca gagccgggca  38820
gtgatgcgca cgcctttaat cccagcactt gggaggcaga ggcaggcgga tctctgtgag  38880
ttcgagacca gcctggtcta cagagctagt tccaggacag cctccaaagc cacagagaaa  38940
ccctgtctcg aaaaaaccaa aaaataaatg aatacataaa taaataaata aatagacata  39000
ccaaaaaaaa aaaaaaaaac aggaacagtg agtcatgcca atcatcccca catacatggg  39060
attaaagcaa gaggatctcc tacaggttca aagaaagcct ggtctacata gtgagtacca  39120
ggccagcctg ggctacaaag taagacttcc tcgaaataat aaacaaacta aacaaacaaa  39180
caaacaaata aataaacaaa cccgagagaa cagatacaga aaggatgtct cagggagcaa  39240
ggaacaaaga catataagat gccaaaagga gggctggaga gatggctcag cagttaagag  39300
cactggctgc tgttctggag gtcctgagtt caattcccag caaccatatg gtggctcaca  39360
gccatctata atgagatctg gtgccctctt ctggcctgca ggcaggcata caagctggca  39420
gaacactgca tacataaata aataaatcaa aaaaagataa cactttaaag aaaatgatac  39480
tttgagaatt ctatgtatag agccaggcgg tggtggcgca cgcctttaat ctaggtcctc  39540
aggaggcaga ggcaggagga tctctgtgag ttcgaggcca gcctggtcta ctgagcaagt  39600
tccaggacag gctccaaagc tacagagaaa ccctgtctca gaagaagaaa aaataaaaga  39660
tcccaaaggg cagtggtatg cagaagacag ggaggaaggg aggaggggag ggacagaggg  39720
agggacagag ggaggacagc aggcctttg tggaagcagc acttacaatt tctgggcatg  39780
gctgattcgg ttgtacagca cattgatctg tagaacgaga agccaggcta ggtgcagatg  39840
tccaaccaaa gccctgccct gcctatcacc cctgtcaccc aggcctggac cccaacagag  39900
gcaggtccca cctcgtattt ctgttgcttc agtttctcca tcagatcaaa tttctctgac  39960
tcgagctggt ggatccattc cgacagctcc tgggccttct ccctggcaga atgagaataa  40020
ctgggatgca gcgagactat gttctgggcc cagaaaggtt gagacaccta ccccaagcct  40080
caaggcaagt ctctctgagc ttgatacagt tggtatgcta agccactatg agcctgatac  40140
agttggtatg ttgtgtgaatg ttactttaac tatgtaaaga tgccttacat ttgtttactt  40200
tgtggaatgt tactttaact atgtaaagat gcgttacatt tgtttacttt gtggaatgtt  40260
actttaacta tgtaaagatg agttacattt gtttacgctg tggaatgtta ctataactat  40320
gtaaagatgc gttacatttg tttatattgt ggaatgttac tttaactatg taaagatgca  40380
ttacatttgt ttacgttgtg gaatgttact ataactatgt aaagatgcgt tacatttgtt  40440
taggttgtgg aatgttactt taactatgta aagatgcgtt acatttgttt actttgtgga  40500
atgttactct aactatggga aggtgtgttg catttgtttc tgctgcattt gttgagttgg  40560
ataaaggtgt gttgctgttt caccttgcct gcctaaggca cctgattggt ctaataaaaa  40620
gccgaacagc caatagctag gcaggagagg gataagcggg gctggcaggc agagagaata  40680
agtaggagga ggaatctagg atgcaggag ggagaccaag ggagaaagag agggagatgc  40740
ctggagccaa ccagacatgg agtagtcaaa atgcagatga agagaaacag gttaatttaa  40800
gttataagag ctggtaggac aagcataagc taaggccaag cttttcataac taaattatct  40860
ctccacgtct tgatttgcga accggttggt ggcccgaaag gaaggcagct acactggtaa  40920
attcttgtta agattggagg ctgaagtttt aaaatatggc cactttctga aacgagggtc  40980
tcccaaagga gagaaggaag tgatgactgg gagccccaga atcggaaaga tgtttggttt  41040
ttatttattg cttatgtagt gtgtgtgtgt gtgtgcgtgt gtgtgtgttt aattttgatt  41100
tctgagacaa ggtctcgtgt aacccaagct tcaatatata ggagaggatg acccagaact  41160
tctgatcctc ctgcctcccc ctcctgagtg ctaagattcc acctaaatga gggagagagc  41220
actgtcaatg ccagactcca caggccatgc caggcacagg acagattgca cccgagtgac  41280
attttgaaca gagaaagcaa cagtggccca gaaaaggaat gtcacttgcc taaagtgaca  41340
cagcaccaag gctcacacct ggaacatcac ccacggaaac cttaggagag ccacaggtgt  41400
tgctgtagtt ccttgtccca ccaggtccct tcgtccttct cagccccaaa taaacacaca  41460
gatacttata ttaattataa aactgttggc tgatggctag ggcttcttat tggccagctc  41520
tgtcttaatt gacccatttc tataactcta tgtatctcca cgtggtcttg gcttaccgga  41580
gaatggccgg acctgttact cctttttggca gctacatggt gtcttccctg tggcccctct  41640
ctacctacct ttcccagaat cctcctcgtc tcctagcccc gcctatcttg ctgcctttat  41700
tggccaagca gtgtttcatt catcaaccaa taagagaaac acatatacag aaaggcatcc  41760
cccatcacac aggcacttac cggagttggt cctcccccat gtagtcgatg ttcaggggtt  41820
ttttcctctc agacaggatc ctgagcttca tctcccggcc ggtctgccgc ttcccacgtt  41880
tctgctcagc ctggagggg aggaatccca agccagggat gggacctgga ggccaaatcc  41940
actcagggtc ctacagtcat ggccagggc tccaccactt gcaaggggcc caggctgcag  42000
ccctcctccc ccagacccag gaatccaagc tccatgcctc ctccatcaga cacgggagta  42060
caggcccact cttcccttgc acccaggcac caccagaatg ttatctaaag cgacagctgc  42120
cccccccttac ccaaacccca acgggatcca ggctcagtgc ggctcagtgt gaccagcact  42180
ctgcagctcc ccttccctcc tccttgtaaa cgcagacacc cccccccag ggctagactc  42240
accttgacca ggtagccccc aaaatgagcc cccatgttgg agagaacctt cttcttcttg  42300
gcatcgtcct cggctcgctt cttggcttcc tcctcctctt tgcgcatctt ctcttcctgt  42360
gaaaacagag gggttccctc catgtggccc tactaaggaa ggcacgagcc tgggtagtgc  42420
atggctaggc tccatagacg gggccgcaga gggatccact cctaaacttg atatatagtt  42480
caccgagccc tcaggttggc agaaatcctc ctgcctcagc ttctccaggg ctgggatcac  42540
aggtctgagc ccaccgcagg cagcaaagct cagtcattgt gctatggttt tgagtctctt  42600
gatccagcca tgcctgaact tttttaaaatt tatatgcagt tcatcctttc actaggaaaa  42660
acaaaaaaca aaaacaaaaa caaaaaaacc ttgcgctgta cattacaggg actttctgag  42720
aaccacgggca gacatcaacg gcaggaaagg aaagtattcg tctccaagaa agggggcagac  42780
acctaccgcc agcttggcct gccgctcccg ctccttttcg gttctgaatc gctgctgctc  42840
agctctctct gcacgacgcc tctcctgggg tggggttggg gatggaagag aggaagatag  42900
cggaggggga ttggaggcta ccctctcccc cagtttatcc ctccctccac cagtagacag  42960
caagagaggt aagtgcggtt tcttttgttt tcttttcctt ttttgagata gtctcagaga  43020
gcccaggctg gtctcaaatt cgtggcaatc taccttcctt gtccctctaa gagcacgcct  43080
```

-continued

```
ggccgaaata cgcattggag tgcaaccacc cggtgtcccc attgtttctc ccggagaccc   43140
caaagcactt cacggaggaa gggacgagga gggaccgaag gacccggcct ccccggcctc   43200
cccggcctcc caggctcacg atgcgatctt tcagcgcaat gagctcctct tcctcctttt   43260
tgcgctgctc gaagtgcacg tcaatcagag tctgcagctc cagtaagtct ttctccatgc   43320
gcttccggtg gatgtcctgc agagggagcc cgtgaggcag agggaccaga ccctagagcc   43380
gcccctctcc ggcccaggg gatgatgatt gacagccagc tgggacggct tccagcagag   43440
gtcagcaaag cattcctggc tggcaacagg gcaccgaggt aaatgcaggc attttcaaga   43500
aaggagcaaa gagggcgcc tatcagaatg ggctcaaggc gctgaggagc cagcaagtat   43560
gtctggggtg ggacacctgt cgcttacatc aaagtccaca cgctcccctt ctgggatctt   43620
gggggggatc aaaggaggca ccacaggacg gctgtcggga cagaaatggg aagagatcat   43680
tagcaggctg gcctcctcat cccccctcac cacagacagt tcaaagtgac agctgccct   43740
gagtctaagc agagaccagt cagaaagtac accgtctgag catgttgggt ttaataaaac   43800
gtgtaagacg gtgtgtgttttg cctgtttttga catacttgta aaaaaaaaaa aaaaatggac   43860
agagcctgat ggcacaaacc tgtcacccga tctacttggg aatcagagac aagttccggg   43920
cctgcctgat ctacagtaaa gctaaagcca tccctggaaa cttgtgagac ccggcctcaa   43980
actaaaaagt aaaaacagga ctgggactgt ggctcagggg tagagcccct gcctagaatc   44040
ccccagtgag gggctggggt gtggctcagt ggtggagccc ctgcctagaa tccccagtg   44100
aggggctcgg gtgtggctca gtggtagagc ccctgcctag aattccccag tgaggggctg   44160
gggtgtggct caagacggag cccttgtgtc aaacatataa ggccacaggt tggacactgg   44220
acattaaaag gg                                                        44232

SEQ ID NO: 3            moltype = DNA  length = 22144
FEATURE                 Location/Qualifiers
misc_feature            1..22144
                        note = CCR5 sequence
source                  1..22144
                        mol_type = genomic DNA
                        organism = Homo sapiens
SEQUENCE: 3
gtaaacagag tcctgtaatg caaggtccgg ccttggcagc cccagcctgg agccacagtg   60
agatgtgagc cgaggggttat gctgggaaaa acctctccct cccagcacct gaaaggctct   120
gcaggcccag cagctcagca agcaagggta agggcatgga ctaacatctt atttcatact   180
atcccttata acacatccta atgtaatcag ctcacaatat gaaattattt catttctctc   240
cagtcattgt ttcaatgggg ccttagggtt gactggattc tggagggccc tgcctagagg   300
aggggggtgca ttctgtccct atgtcccctc ctgctccatc ctccacagca cgtgcctagt   360
ggtctacctt gtggggaatt cttgtacctc cctcttctag gcatggacta gcattgagaa   420
gtgggagagg agtgttagga aaaagggcaa atatagacat accttgtctt attgtgcttt   480
acagatattg ttttttgttgt tgttgttgtt gtttacaaat tgaaggtttg tggcaaccct   540
gcctcgagca agtctattgg tgctgttttt ccaacagcat gtgcttgttt tacatctctg   600
tgtcacattt tggtaattct cccaatattt caaactttgt cattatttct atatctgtta   660
tggtaatctg tgatcagtga tctttgatgt cactattgta gttgtttggg ggcaccatga   720
agtgcaccca tgtaagatgg caaacaatca ataaatgttg tgtgtgttct gactgctcca   780
tggactgcct gttcctgaga cacaataatg tatatataac aattatatat atatatattt   840
ataacaatta tatatatata tatatatatt ttttttttga ggcagagtcg cactctgatt   900
gcccaggctg gagtgcaatg atgtgatttc agctcactgc aacctctgcc tccccaggct   960
caggtgattc tcccacttca gcctcccaag ctgggactac aggtgtgcac catcacaccc   1020
ggctaatttt tttttttgtat ttttaggaga gacagggttt tgccatgttg cccaggctgg   1080
ccttaaactc ctagactcaa acaatccacc tgcctcagct tcccaaaggg ctgggattac   1140
aggcatgagc cactgtgccc agcccaagac acaataatat tgaaattaag ccaattaata   1200
accctacaat ggcctctaag tgttcaagtg aagggaaaag tcccacgtct ctcactttaa   1260
atcaaaatct agaaatgatt aagcttagta aggaggacat attgaaagtc aaggccaaaa   1320
gctcacctct gcaccagtta gccaaattgc gacttcacag gaaaagttct tgaaggatat   1380
ttaagctcta ctccagggaa catgcaaatg aagagaaaac aaagcagcca tattgctaat   1440
atggagaaag tttgagtggt ctggagaaaa gatccaacca gccacaacat ttccttaagt   1500
caaagcctaa tccagagcaa gactctaact ctcttcaatg ctatgaaggc gggagagagg   1560
gaggaagctg cagaagaaaa gtttgaagct agcggaggtt ggtttgtgag gtttaatgaa   1620
agacaacatc tccataacat aaaaatgcaa gatgaagcag caagtgcaaa gggagaaagct   1680
gtggcaagtt atccagaaaa tctagataag ataattgatg aaagtgtcta cacgaaacaa   1740
cagattttca gtgtagacaa aacagtctta tgttggaaga agatgccatc caggactttc   1800
acagctagag aggagatgtc aaggcaagct gcaaagctcc acaggacagg ctgactctct   1860
ttttagaggt gaatgcagct gatgacttta agttgaagta aatgttcatt tactattttg   1920
taaatcctgg tgtcattaag aattatgcga aatctactct atctgtgctc cataaatgga   1980
acaataaagc ctggatgaca acacatctgt ttacagcatg gtttactgaa tatttcaagc   2040
ccactattga gaactattgc tcagaaaaaa agattcctta caaaatatta ctgctctgca   2100
ccatgtcgat caagagctgt gttggagatg tacgagaata ttcatgttgt tttcatccct   2160
gctaacacaa acatccattc tgcagtccat ggaccaagac tttcaagtct tattaagaaa   2220
tatatttcat aaggctatta agaaatagct atatatat atatagcctt atatagttta   2280
tatagctacc attgatagtg attccattga tggatctgag caaagcaaat tgaaaagctt   2340
ctggaaagta gtcattattc tagatgccat taggaacatt tgtaattcat gggaggaggt   2400
caaaatacca acattaacag gagtgtgaaa gacattgatt ccaaccccca tagatgactt   2460
tcaggggttc acgtcttcag tggaggaagt cgctgtagat gtggtggaaa cagcaagaga   2520
actagaacta gaagtggagc ctgaagttgt gactgaattg ccgcactctc atgatcaaac   2580
ttgaacagat gaagagttgc ttcttacata tgagcagtga aagtggtctc ttgagatgga   2640
atctcctcct ggtgaaatg ctgtgaacac ggttaaaatg acaacaatcg atttagaata   2700
ttacataaat ttagttaata aagcagtggc agggtttgag aggattgact ccaatttga   2760
aagaagtggg taaatgcta tcaaatagca tcacatggta tggagaaatc ttttgtgaag   2820
ggaagagtcg accaaggtgg caaattgcat tgtcatctta tttttaagaaa ttgccacagc   2880
cacccccagc tttagcaacc accaccctga tcagtaagca gccatcaaca tcaaaacaag   2940
accgccatcc tcttcagcaa aaacactatg acttgctgaa ggctcagatg atggttagca   3000
```

-continued

```
ttttttagcaa tacaatattt ttaattaagg tatgcacatt ggttttttctg acataatact   3060
attgcatact taatagacta cagtatagga taaacacaac tttttatatgc actgggaaac   3120
caaaaaggtt attttttgaga tatttgcttt actgtggtgg tctgaagctg aactcacaat   3180
ctcaccaagg tgtgcctgaa cctcttttagc taactggcca ctgccacagt ccactctgtg   3240
ttggtcaaga tgcccagag tggcaggcac actgtgtgat cacatccaag ggcctagata   3300
tggtggggggc tccaaatgga tctagatatg tgagatctct cttttgatttg acttcttcca   3360
acccaccatt ttctgggtgc tgggctcatc tcacccagaa agtaggaccc aatgtgacag   3420
ttcctgccca gttccctcct gtggtagcca cttgacccag gggcactctt gatccttgca   3480
gcctcactta cacaccctat ctctacccct attaactctc tccaatcccc actcccccctg   3540
ctcagcttgt ctgctgccca gtgggggccc cacccatgct ggcctctcct tttgcaagtc   3600
cccattcctc atatggtttc ttcagagccc cttttcttttgg ctttgaggag agatgccctc   3660
actcgcttcc ccaccaatcc tgcccacttc tacaatccat tcattatcct aattgcctcc   3720
gtatacagac tggagtgaga ggagttgatg tgatgggtgt ggatacaggg ctggtgctgt   3780
catcttctag taagccctgg gagaggtgtc tgagcccagg tgtcagtggt ttttcttttgga   3840
actgtgagtg cataacactt ctttgccttc agccttaggc catagttgct agttctggga   3900
caaccagaaa agccctacat aatctcgtgt tatgtgcaga gctgagtata gagctccagg   3960
tatgatctga ctcacttaag atcacagtga gtctattgta ttgttgaact gttagcttag   4020
acatctgtta ctgtacctac atggcactag cctcacgcct agacaccgat ctgaaagaaa   4080
tccccctaaat gcatagagaa gacttctcag ctgagctaag gggctcccac caggtttgag   4140
cctatctaat gaatccatga ggtagacagc ctgcacatgt ccacttggtt tgatgaattg   4200
cacaaatccc tatgggggat gtggttcatg ggctgggaag tgggttaccc tgggaaaggt   4260
ctacaggaca gaggcaggga tggagacaac agcatggtga gttcccaacc cacccacgat   4320
gataggtgtc tgaggcagaa ggtaaagagg ctgtcacctg gtgggtgtca taagactcaa   4380
gtgtcattgt tgaggcacat gggtaacaaa gcgtggcact ggatgggggt agattcttcc   4440
tatttctgtg aggatcaggg ggactccctg gctctcctgc taaaggtggc tctagggaca   4500
ggaagagtgt acttcttgac agggatgtca gagcactgat ggtgacaatc agtgtgacac   4560
tgctcacatg actgaacaac cgagaagagc ccgactgtct actgaacaac gggaagagcc   4620
cgactgtcaa tgacggagct ctgttaaata tagttaaggc tattttgttg aatgaatgaa   4680
gccagacagg aaagaggaca gtatctttaa tccatttata gaagttaaag acaggcttat   4740
ttaatctcta tgaagacaga gtggcccctta cctctgggtg gagcaaaagg caccttctga   4800
agtgataggg atgttcctta tcatcttgat ccggagtggt agttacatgc atgtgtgcat   4860
atcaaaactc accaagctgt accactaagt gtgttcttcc tcaataaaaa taataaagaa   4920
ctacacttat aaagaatttt ttaataatat aggaaaatgt ctacactata atctttagct   4980
aaaaaaaaaaa aaaaaagaag ccgcctacag aatggtatat gcatgagaac aattaatcga   5040
aaagtgcatg ggaaaagtca ggattgaaac atcatgtttt aaaagacatt gttttgatac   5100
tgtgagaatg tacctaagtt ttttccttttt tctgttttttc ccaattttat acaatgagca   5160
tgtgttggtt ttataattag acattttgtt tgtttggttt ggttttgaga cacagcttgc   5220
tgtcacccag gttggagtgc aatggcccaa tcttggttca ctgcaacctc catctcctgg   5280
gttcaagaga ttctcccact tcagcctcct gagtagctgg gactataggg gcgcaccacc   5340
acatccagct aattttgtgt attttttagta gagatgggg ttcaccatgc tggccaggtt   5400
ggtctcaaac tcctgacctc aagttatcca ctcgccttgg cttcccaaag tgctgggatt   5460
ataggcatga gccaccgcac ttggcctaga catttgtttt taaaaataaa agattcattt   5520
gctcttttta cagcccgtct cactgttgac tgatattgac caggagtcaa ctcaggcccc   5580
agggattttc acaacagctg ctgtatggca gggtttctgc tcactgtgct catgtagttg   5640
gcccttgcac ccaaagtgaa taattaacat tctcccatc ctgttgacga tgctctgaaa   5700
atatggtcca gaaatggtgt gagcaaggag acagcaaagc aatgcttgga acataggtgc   5760
agtgactaga catggggcag ctgtttaaag acaaaaaggc cccaaaaagg agggatggca   5820
cgaaacaccc tccaatatgg gcatggagtc tagagtgaca aagtgatcaa aagttcattt   5880
cctatggggt gtccgaatgt acttaataat aaaaagagaa caagagccat gcaaactgag   5940
agggacaaag tagaaagagt agcagacacc aagcaactaa gtcacagcat gataagctgc   6000
tagcttgttg tcattattgt atccagaaca acatttcatt taaatgctga agaatttccc   6060
atgggtcccc actttcttgt gaatccttgg gctgaacccc cctgtcctga gtggttacta   6120
gaacacacct ctggaccaga aacacaaaag tggagtaacg cacactgcaa agctgtgctt   6180
ccttgtttca gcctgtgaat cctcacccttg tttcccatct agcctatatt tttcaaacta   6240
acttggccat agaatcatgt agtatttagg gtggaagctg ccccaggtct agcacgtcat   6300
ttaacagatg aggaaatgga agcttgggca gtggaagtat cttgccgagg tcacacagca   6360
agtcagcagc acagcgtgtg tgactccgag cctgctccgc tagcccacat tgccctctgg   6420
gggtgagtat gtcttcacat cctccaatac cctaatgaca gacaaacaga acatggcaaa   6480
gcctcagctc tgcatggtga aagtaagaac cagcaattgc cacaaacaga aatacagtgt   6540
tggtccggca gcctccgggg gttctgcaca agtggattac cagtgaatac aaggctatct   6600
atctttcgaa aaaccaaagt tgtatttatg ctatctattt tctataaaat tttatattaa   6660
tttatttgtt acctattttt gaactcttttc aaaagcacac tttatatttc cctgcttaaa   6720
cagtcccccg agggtgggtg cccaaaaggc tctacacttg ttatcattcc ctctccacca   6780
caggcatatt gagtaagttt gtatttgggt tttttttaaaa cctccactct acagttaaga   6840
aaactaaggc acagagcttc aataaatttgg tcagagccaa gtagcagtaa tgaagctgga   6900
ggttaaaccc agcagcatga ctgcagttct taatcaatgc cttttgaatt gcacatatgg   6960
gatgaactag aacattttct cgatgattcg ctgtccttgt tatgattatg ttactgagct   7020
ctgttgtagc acagacatat gtccctatat ggggcggggg tggggggtgtc ttgatcgctg   7080
ggctatttct atactgttct ggcttttccc aagcagtcat ttctttctat tctccaagca   7140
ccagcaatta gctttacctt ttcagcttct agtttgctga aactaatctg ctatagacag   7200
agactccggt gaaccaattt tattaggatt tgatcaaata aactctctct gacaaaggac   7260
tgctgaaaga gtaactaaga gtttgatgtt tactgagtgc atagtatgtg ctagatgctg   7320
gccgtggatg cctcatagaa tcctcccaac aactcatgaa atgactactg tcattcagcc   7380
caatacccag acgagaaagc tgagggtaag acaggtttca agttggcag tctgactaca   7440
gaggccactg gcttagcccc tgggttagtc tgcctctgta ggattggggg cacgtaattt   7500
tgctgtttgg ggtctcattt gccttcttag agatcacaag ccaaagcttt ttattctaga   7560
gccaaggtca cggaagccca gagggcatct tgtggctcgg gagtagctct ctgctgtctt   7620
ctcagctctg ctgacaatac ttgagatttt cagatgtcac caaccgccaa gagagcttga   7680
tatgactgta tatagtatag tcataaagaa cctgaacttg accatatact tatgtcatgt   7740
```

-continued

```
ggaaaatttc tcatagcttc agatagaatta tatctggagt gaagaatcct gccacctatg   7800
tatctggcat agtgtgagtc ctcataaatg cttactggtt tgaagggcaa caaaatagtg   7860
aacagagtga aaatccccac taagatcctg ggtccagaaa aagatgggaa acctgtttag   7920
ctcacccgtg agcccatagt taaaactctt tagacaacag gttgtttccg tttacagaga   7980
acaataatat tgggtggtga gcatctgtgt gggggttggg gtgggatagg ggatacgggg   8040
agagtggaga aaaaggggac acaggggttaa tgtgaagtcc aggatccccc tctacatttta  8100
aagttggttt aagttggctt taattaatag caactcttaa gataatcaga attttcttaa   8160
cctttttagcc ttactgttga aaagccctgt gatcttgtac aaatcatttg cttcttggat   8220
agtaatttct tttactaaaa tgtgggcttt tgactagatg aatgtaaatg ttcttctagc   8280
tctgatatcc tttattctt atattttcta acagattctg tgtagtggga tgagcagaga   8340
acaaaaacaa aataatccag tgagaaaagc ccgtaaataa accttcagac cagagatcta   8400
ttctctagct tattttaagc tcaacttaaa aagaagaact gttctctgat tctttttcgcc   8460
ttcaatacac ttaatgattt aactccaccc tccttcaaaa gaaacagcat ttcctacttt   8520
tatactgtct atatgattga tttgcacagc tcatctggcc agaagagctg agacatccgt   8580
tcccctacaa gaaactctcc ccggtaagta acctctcagc tgcttggcct gttagttagc   8640
ttctgagatg agtaaaagac tttacaggaa acccatagaa gacatttggc aaacaccaag   8700
tgctcataca attatcttaa aatataatct ttaagataag gaaagggtca cagtttggaa   8760
tgagtttcag acggttataa catcaaagat acaaaacatg attgtgagtg aaagacttta   8820
aagggagcaa tagtatttta ataactaaca atccttacct ctcaaaagaa agatttgcag   8880
agagatgagt cttagctgaa atcttgaaat cttatcttct gctaaggaga actaaaccct   8940
ctccagtgag atgccttctg aatatgtgcc cacaagaagt tgtgtctaag tctgttctc   9000
ttttttctt ttcctccaga caagagggaa gcctaaaaat ggtcaaaatt aatattaaat   9060
tacaaacgcc aaataaaatt ttcctctaat atatcagttt catggcacag ttagtatata   9120
attctttatg gttcaaaatt aaaaatgagc ttttctaggg gcttctctca gctgcctagt   9180
ctaaggtgca gggagtttga gactcacagg gtttaataag agaaaattct cagctagagc   9240
agctgaactt aaatagacta ggcaagacag ctggttataa gaactaaacta cccagaatgc  9300
atgacattca tctgtggtgg cagacgaaac attttttatt atattatttc ttgggtatgt   9360
atgcaaactc ttaattgtgg caactcagaa actacaaaca caaacttcac agaaaatgtg   9420
aggatttttac aattggctgt tgtcatctat gaccttccct gggacttggg cacccggcca   9480
tttcactctg actacatcat gtcaccaaac atctgatggt cttgccttt aattctcttt   9540
tcgaggactg agaggagggg tagcatggta gttaagagtg caggcttccc gcattcaaaa   9600
tcggttgctt actagctgtg tggctttgag caagttactc accctctctg tgcttcaagg   9660
tccttgtctg caaaatgtga aaaatatttc ctgcctcata aggttgccct aaggattaaa   9720
tgaatgaatg ggtatgatgc ttagaacagt gattggcatc cagtatgtgc cctcgaggcc   9780
tcttaattat tactggcttg ctcatagtgc atgttcttg tgggctaact ctagcgtcaa   9840
taaaaatgtt aagactgagt tgcagccggg catggtggct catgcctgta atcccagcat   9900
tctaggaggc tgaggcagga ggatcgcttg agcccaggag ttcgagacca gcctgggcaa   9960
catagtgtga tcttgtatct ataaaaataa acaaaattag cttggtgtgg tggcgcctgt   10020
agtccccagc cacttggagg ggtgaggtga gaggattgct tgagcccggg atggtccagg   10080
ctgcagtgag ccatgatcgt gccactgcac tccagcctgg gcgacagagt gagaccctgt   10140
ctcacaacaa caacaacaac aacaaaaagg ctgagctgca ccatgcttga cccagtttct   10200
taaaattgtt gtcaaagctt cattcactcc atggtgctat agagcacaag atttttatttg  10260
gtgagatggt gctttcatga attcccccaa cagagccaag ctctccatct agtggacagg   10320
gaagctagca gcaaaccttc ccttcactac aaaaacttcat tgcttggcca aaaagagagt   10380
taattcaatg tagacatcta tgtaggcaat taaaaaccta ttgatgtata aaacagtttg   10440
cattcatgga gggcaactaa atacattcta ggactttata aaagatcact tttatttat   10500
gcacagggtg gaacaagatg gattatcaag tgtcaagtcc aatctatgac atcaattatt   10560
atacatcgga gccctgccaa aaaatcaatg tgaagcaaat cgcagcccgc ctcctgcctc   10620
cgctctactc actggtgttc atctttggtt ttgtgggcaa catgctggtc atcctcatcc   10680
tgataaactg caaaaggctg aagagcatga ctgacatctca cctgctcaac ctggccatct  10740
ctgacctgtt tttccttctt actgtcccct tctgggctca ctatgctgcc gcccagtggg   10800
actttggaaa tacaatgtgt caactcttga cagggctcta ttttataggc ttcttctctg   10860
gaatcttctt catcatcctc ctgacaatcg ataggtacct ggctgtcgtc catgctgtgt   10920
ttgctttaaa agcccaggac gtcacctttg gggtggtgac aagtgtgatc acttgggtgg   10980
tggctgtgtt tgcgtctctc ccaggaatca tcttaccag atctcaaaaa gaaggtcttc   11040
attacacctg cagctctcat tttccataca gtcagtatcca attctggaag aatttccaga  11100
cattaaagat agtcatcttg gggctggtcc tgccgctgct tgtcatggtc atctgctact   11160
cgggaatcct aaaaactctg cttcggtgtc gaaatgagaa gaagaggcac agggctgtga   11220
ggcttatctt caccatcatg attgtttatt ttctcttctg ggctccctac aacattgtcc   11280
ttctcctgaa cacccttcag gaattctttg gcctgaataa ttgcagtagc tctaacaggt   11340
tggaccaagc tatgcaggtg acagagactc ttgggatgac gcactgctgc atcaacccca   11400
tcatctatgc ctttgtcggg gagaagttca gaaaactacct cttagtcttc ttccaaaagc  11460
acattgccaa acgcttctgc aaatgctgtt ctattttcca gcaagaggct cccgagcgag   11520
caagctcagt ttacacccga tccactgggg agcaggaaat atctgtggcc ttgtgacacg   11580
gactcaagtg ggctggtgac ccagtcagag ttgtgcacat ggcttagttt tcatacacag   11640
cctgggctgg gggtgggggtg ggagaggtct ttttttaaaag gaagttactg ttatagaggg  11700
tctaagattc atccatttat ttggcatctg tttaaagtag attagatctt ttaagcccat   11760
caattataga aagccaaatc aaaatatgtt gatgaaaaat agcaacctt ttatctcccc   11820
ttcacatgca tcaagttatt gacaaactct ccctttcactc cgaaagttcc ttatgtatat   11880
ttaaaagaaa gcctcagaga attgctgatt cttgagtttta gtgatctgaa cagaaatacc   11940
aaaattattt cagaaatgta caactttta cctagtacaa ggcaacatat aggttgtaaa   12000
tgtgtttaaa acaggtctt gtcttgctat ggggagaaaa gacatgaata tgattagtaa   12060
agaaatgaca ctttttcatgt gtgatttccc ctccaaggta tggttaataa gtttcactga   12120
cttagaacca ggcgagagac ttgtggcctg ggagagctca ggagagcttct taaatgagaa   12180
ggaatttgag ttggatcatc tattgctggc aaagacagaa gcctcactgc aagcactgca   12240
tgggcaagct tggctgtaga aggagacaga gctggttggg aagacatggg gaggaaggac   12300
aaggctagat catgaagaac cttgacggca ttgctccgtc taagtcatga gctgagcagg   12360
gagatcctgg ttggtgttgc agaaggttta ctctgtggcc aaaggagggt caggaaggat   12420
gagcatttag ggcaaggaga ccaccaacag ccctcaggtc agggtgagga tggcctctgc   12480
```

-continued

```
taagctcaag gcgtgaggat gggaaggagg gaggtattcg taaggatggg aaggagggag    12540
gtattcgtgc agcatatgag gatgcagagt cagcagaact ggggtggatt tgggttggaa    12600
gtgagggtca gagaggagtc agagagaatc cctagtcttc aagcagattg gagaaaccct    12660
tgaaaagaca tcaagcacag aaggaggagg aggaggttta ggtcaagaag aagatggatt    12720
ggtgtaaaag gatgggtctg gtttgcagag cttgaacaca gtctcaccca gactccaggc    12780
tgtctttcac tgaatgcttc tgacttcata gatttccttc ccatcccagc tgaaatactg    12840
aggggtctcc aggaggagac tagatttatg aatacacgag gtatgaggtc taggaacata    12900
cttcagctca cacatgagat ctaggtgagg attgattacc tagtagtcat ttcatgggtt    12960
gttgggagga ttctatgagg caaccacagg cagcatttag cacatactac acattcaata    13020
agcatcaaac tcttagttac tcattcaggg atagcactga gcaaagcatt gagcaaaggg    13080
gtcccataga ggtgagggaa gcctgaaaaa ctaagatgct gcctgcccag tgcacacaag    13140
tgtaggtatc attttctgca tttaaccgtc aataggcaaa gggggaagg gacatattca     13200
tttggaaata agctgccttg agccttaaaa cccacaaaag tacaatttac cagcctccgt    13260
atttcagact gaatggggt ggggggggcg ccttaggtac ttattccaga tgccttctcc     13320
agacaaacca gaagcaacag aaaaaatcgt ctctccctcc ctttgaaatg aatatacccc    13380
ttagtgtttg ggtatattca tttcaaaggg agagagagag gtttttttct gttctgtctc    13440
atatgattgt gcacatactt gagactgttt tgaatttggg ggatggctaa aaccatcata    13500
gtacaggtaa ggtgagggaa tagtaagtgg tgagaactac tcagggaatg aaggtgtcag    13560
aataataaga ggtgctactg actttctcag cctctgaata tgaacggtga gcattgtggc    13620
tgtcagcagg aagcaacgaa gggaaatgtc tttccttttg ctcttaagtt gtggagagtg    13680
caacagtagc ataggaccct accctctggg ccaagtcaaa gacattctga catcttagta    13740
tttgcatatt cttatgtatg tgaaagttac aaattgcttg aaagaaaata tgcatctaat    13800
aaaaaacacc ttctaaaata attcattata ttcttgctct ttcagtcaag tgtacattta    13860
gagaatagca cataaaactg ccagagcatt ttataagcag ctgtttttctt ccttagtgtg    13920
tgtgcatgtg tgtgtgatgt atacaaagag agagataatt gtatttttgt attttctttt    13980
aaataatttt taaaattgac cctttttcctg agacaaattg ccagaatagt ttgtatttag    14040
agatggtacc tctaagagta aggttgctgg ttgctgagca attgacttga aaacttttaa    14100
aattcaaatt ttaattccac tactcaaaag aattgccatg ttttaaaaaa gagaattggt    14160
gccataagtt agttgtctat gtttgaaaat gaagaagata tgcaacgtca tggcctggtc    14220
acttacccgc agccctgagt tgtaggcaca tcatatgtga gaatgaggat gcttttcttt    14280
catttaaaat ccctccccaa aacttggctc taattgcagt catgacaatc atgtacattt    14340
ggatttatgt gcacgagtct cttaccctga gagaggacag gtgctacagg tggaggggac    14400
ccgtctgggt cacgttcaca ttttgaacat gctggttttc agtcactgca cactcatctc    14460
ccagcacagg tcatgggcag cagatgcaaa agctgcccgt ggtccctattt ggaggtgcat    14520
gaaatgagca gaagacagaa cagcttgatc tgactagaag ggcagcttgt ccctaccaag    14580
acttgaagga ttgcctttca tctgttaggg taaaaggtag aatgaaccaa ggaagggcag    14640
gagggggctg gggttagggt agaaggaagg ggccatggag aagggagatc catcccatag    14700
gaggaaggca gtgcggcagg gaggtttgaa ggtatcagct tttgtggctg acatacatgc    14760
agtcatgtca attgctcgtt tttccttttc catcttatta aatgtcttcc aacgttagca    14820
cgaagaaaag ctatttgcag tgttgccagc ctttccagag cccgtcccca ttacctcccc    14880
aggcccatgc ctttactcct tggagtttca actcacgacc ttcaggatct gactttattc    14940
accaactctg gggtgaacgt accttctgtc tccacccaga ggtctctatc aaagaggaga    15000
ttgcatgcca tggataaagt caaagtagag gtgactgtcc ttaggaagag taatgtgaaa    15060
attcataaac tgggattctg tttacatttt gtactccagg ggttcttagt ttaaatcgct    15120
ctgaataaat taagatgcaa tggcatttca actgttatga ttaaatttac aaatcattta    15180
ttttctatca cggggagaga tagagctcca aatgcaaaca taactgctca agtgttaaca    15240
cttataatga aaacataaga attaccacca actaccctgg gggctagaag cagaaatgtg    15300
aaccagaaaa caaatcatga actttccttt tttttttttga gatggagtct cgctctgttg    15360
cccaggctgg agtgcaatgg tgcgatctcg gctcactgca accactgcct cccgggttca    15420
agcaattctc ctgcctcagc ctcctgagta gctgggacta caggcatgca ccaccacgcc    15480
tgggtaattt tttgtatttt tagtagagac agggtttcac cgtattagcc aggatgctct    15540
cgatctcctg acctcgtgat ctgcccgcct cggcctccca ccgaagtgct gggattacag    15600
gcatgagcca ctgtgcccgg ccaacaaatc atgaactttc taactgcagt tccttgtagc    15660
ttgttaacac atccacttac ttattgtcag agtacgtgga gattttccac aaccctcggg    15720
gataaggctg aacagaagag gcaaaaacgt gaaaacattt cgatagctcc tatactttga    15780
aataaaattc actgtaaaag ttgcttgtat ttttccaaaa cagagtcaac ccttaatatt    15840
taagattctg tatacaaata catatttta tataattaat atatattgtc atatgacata      15900
tatctttata ttaatatgca tgcatataat atatatttcc ttcctaattt tctataagca    15960
attttacaag actgacttct atttgcctcc ttattgttac tacgtggttt gataatccgt    16020
tttgtgtcat tgtgattctg tcatgttttg gggacttatt tttgtttctc tgggtggtca    16080
ctagtttttt taaagcattc atggaagagt gtgaatcttt tacaagctag gaagccatgg    16140
caagccttgg gtcatactgc ccccgcgagg ccacattggc aaaccagcaa gggtgttcaa    16200
cttccagact tggccatgga gaagacacac gaggaggctt ttcacattca gctctttaat    16260
gtttgtctct gccggcacca tcccagttgt gaaaaagagg tatttccaca gccggcccagg    16320
gtaggtagtg cacagctcac attcatcatt tctgaaaacc gagaggagtc tccattcggg    16380
gtacaggttg atgcctgtcg tggaatgaag gttccaacac ccagaccaat ctctgcagtg    16440
tgctgctctc atgagcttgc aacaagatca gaaaatgttt tgtgactaag catttttcat    16500
attgcataaa atgcttcaag ctcctccctt gtttctctct ataatcctgt atatctgatg    16560
attgtgggta ccaagtgttt gaaataatca aatgtgattt gatgttggta aatttcttttt    16620
ttttttttttt tttacttcta ttttttttat tatactttaa gttttagggt acatgtgcac    16680
attgtgcagg ttagttacat atgtatacat gtgccatgct ggtgcgctgc acccactaac    16740
tcgtcatcta gcattaggta tatctcccaa tgctatccct cccccctccc cccacccac    16800
cacagtcccc aaagtgtgat attccccttc ctatgtccat gtgatctcat tgttcaattc    16860
ccacctatga gtgagaatat gcggtgtttg gttttttgtt cttgcgatag tttactgaga    16920
atgatggttt ccaatttcat ccatgtccct acaaaggaca tgaacatagc aaagacttgg    16980
aaccaaccca aatgtccaac aatgatagac tggattaaga aaatgtggca catatacacc    17040
atggtaaatt tctttatcat tcgcactctc ctttctctat tattgttatt gtaactgaac    17100
cgcagattag tcactcattg cttgcagaat ccaattaaca agagcgaggt cagatataaa    17160
gaaaatgatt tattccaaac ctccttcagg gaagaggtgc agcctcctgc ctctaaatgc    17220
```

-continued

```
actgcttcgc caggcgtggt ggctcacacc tgtaatccca gcactttggg agaccgagga   17280
gggcagatca cttaaggtca ggagttcaag accggcctgg ccaatatagt gaaacccctg   17340
cctctactaa aaatacaaaa aattagccag acgtggtggc gggtgcttgt aatcccagct   17400
actcgggagg ctgaggcagg agaatcgctt gaacctggga ggtggaagtt gcagtgagct   17460
gacatctagc cactgcactc cagcctgggt gacagagtga gactctgtct caaaataaat   17520
aaataaataa ataaataaat aaataaataa atagtaaatg cactgctttg cttttggagc   17580
agaaagcagg cactttgaaa aggcagggga ggaagtgagc aagggcaggg ggtctgcaca   17640
ctggcatggt gcctgatcta tccaggcagt tgaattggca cttttcatagg cagaaataag   17700
ttgaaaaagt ggcctaaaac tctctaggtg ggagtggata gtgggcatgc cttcaacctg   17760
cctttctgga gggtgagttc catggcaacc ccctgaaggg tgagagttcc atggagatca   17820
tgctttggtc tgtaaatcag ctgttaactc tctagaaagt tctgtcttgg agcatatagt   17880
tagatgaact tgccctgtaa agaatgtctg gtgaagggga agtaaaaggt gagatttgca   17940
tttctaaagg gctaagtaga aagtggggta caagaggaaa ggagaaaaga gaaaataatt   18000
taaaaaataa ttgtaactta ttcccttttta cttagaaaaa agggaatact cagttacatt   18060
atcacctcgt ttacatcaaa ccctcttatg gaatcctatg gtttgaaaac aaaaaggttg   18120
ttgaggacca gtgagcccaa cccccttgct ttataaatga agagcattgc ctgccctaag   18180
ccccagagac tctgatgtcg tgggtctgga gtgggctcca acagcggcat gttttgatgg   18240
tgcttcccag tggcacgcca gcgatgagcc tttgagtagg gaaagtagga gcactcgtga   18300
ctcccttcac gatcagcacc tgtgtgctaa taaattcaca aaagccaaca tattggagtc   18360
actcaggag ttttacaaat agtgaggtta aatccaacct caaatagttc tgattcgatc   18420
tgcctgcatt gctgccctgt ggttccccac tgtagaagct ccccaggtga ttctaagtgt   18480
agccaagtct gagaaatact gcctaaagcc tgttggactg acagcaaggg ctgttgtctg   18540
agcaagactt tgcctggcct ggggtggcat gtgcaccagg aagagtctca actttccataa   18600
cagaacattc cccaagctgg tttttttaaa gcatgtgaat ctagacttca ttggcaatac   18660
caaagatctg tatttgaggc tccaagtatt tcactttcat ttttggtttt gggttatgtt   18720
ttcacccttc ctttccaagt gaaaagtaaa cagaagtggg atgtctggcg cccatgctga   18780
gcttggcaac ttcaaattca atagagaaga agtctcttgt atagaaaagg gcctgtctga   18840
gatgtttctc aaataaatat agattttgct tatgtggcta aaggattctt ctccccccat   18900
ttccttatcc ctgcagtgag ccatccttct taactctttc catgaaagca ttattcctga   18960
agaactggga actcatgcca gccctgatca ggcaatgata attctgcaga gaattagaat   19020
ttagatttaa attgtcaact cttatacatc ctggcatatg gtttaaacac atgtacacac   19080
acacaaacac ctcctactat ttactgaaga gcagatatct gataacttaa tcttttttggt   19140
tttgagtcaa gacaattcct ccttttgaaa ctgcataccg ctgaatataa taaaatgtaa   19200
ttaagattaa aaataagaaa ctaatgggag aatttcaata ttgtctatgt tcactttaaa   19260
attcctctac ttaggtttac tgccattacc aaagactatt caaaaatcct ttttaggaga   19320
atcctaatgg tttcctgaca tataatcaaa taaggactct gttgattggc taactcaatc   19380
ttcctgtgcc aaaaagcaga gcccagcaga gaagagggca gggacttgaa agtcagactg   19440
actcgagttc cagccttggg gctgtgggag cttgggcaag tgacttaacg tctctggctc   19500
tcaggatcta aaaggatttc cagtagtaat ttggggtgtt actgatacag gagctaaaaa   19560
gaaattattt aggtggttag tgagggtcag agagtcctcg gtaagatttg cctttttaaca   19620
aaaagcagcc ccaaaatcat ttgtttgcta acaaagagaa gcctgtaaaa ttgagctgca   19680
gacatagata agcaagctgg aagcttgcac gggtgaatgc cggcagctgt gccaatagga   19740
aaaggctatc tgggggccag gcatgttcaa catggattct ccatcttccc tttttctttgt   19800
caaccaagtg tacagtaaag gaacaggcaa catggcacgg gccaggtaga gaaccccttct   19860
gcataataaa agattagggt gagatggcca gcttcttccc gtgctatgta aatggcatac   19920
ctggtccaac cagtctttttg ggccctgtgt aaatcagaca ccgcctcctc aagttagtct   19980
ataaaacccc atgcattttta ccgtgaaact gggagatcca ctcggaaccc cctcctgcac   20040
gagagacctt ttctctttttg cctattacac ttccgctctt aaactcactg ctcatgtgtt   20100
agcatccttg atttccttgg catgaggcaa cgaaccttgt gtattacccc atacaaatga   20160
tgctgcttca ttactaatag caacctgaca gggttgtgtt ggggtataaa ttatctagac   20220
cagggagatc caatataatt tttttgtaat gacgggaatg ctttgtatct gcatcatcca   20280
aaatggtagc caccaggcca gggtgaaatg tggccagtgt gactgaggaa ctgaatgttt   20340
tccatgattt aatttaaatg tggccaatgg ctactgtagg agacagtgtg agtctggcat   20400
attataaata ataaatatta atataatttg aactttggca tcagtgtttc ctagatttga   20460
attactatgc aagttgctta ctgtttccaa gcctcagctt tctaatctgt aattggggct   20520
aataatagta tctgccttac aggtttgttc agaggataaa tgagaaattg catgttgagg   20580
gcttaacaca gtgcctggca cataaaagct ctggtaacag ttagccactt taataatttg   20640
ctaataatgg ctatttcttc ttcagattag gatgtgctcc cccaaacagt gcacttagac   20700
atagcgggca atccagctca ctctctgcag tgagagagaa gcactggccg accagagtca   20760
gccaggggct catgggtatg aaatcaacag catgatttg taagtaatgg atggaaaggg   20820
cctcacaact ttatggcact gtgttcaatt tgcttggtct tctgtagctc cttttgaaag   20880
ccttttaggg tggattaacc tgctaccaat aattctggtc agatgtagac tccatagctc   20940
aaagcaaact gagagagtga gggcagcagg ccaattcccc accccttcct tctggactct   21000
gacagaagct tacactcaag gaagagcaag taggaattaa cgtgttaaga gctaggtaag   21060
caaaacccaa tgagaagttc tggcaaagcc ccatggcag gggtggctta ggcacaggaa   21120
acaagtagga tttcatacca cgcgcctcag tctacttccg gggccctcat cctcagctgt   21180
gcctatgcaa aggagagcaa ccaataaacc ccaccgccac tctcctactg tggaggccag   21240
ggatggccag gggtaagaga gggatgggaa gtgtttcctc cagccgtcct ctgagaagga   21300
gaggaaactg gacagagctt ctgtcctcct tcaagcagaa acagaaacaa aagaaacccc   21360
taagggggtt cttacttccc ctctagttca gttgtgcact aaccatctgc agctcaacat   21420
tcagcattca ttcattgatt cagcaaacat tgaaggaggg ccagctatgt gccagatgcc   21480
aactcatgcc atgaaagaga gtccctgtcc ttatgaaatt cactatttag agagaaaagc   21540
aagcaaaaag gcaaagtttg aaaagtactg ttgaagtggc atcattgtct ggggtgaata   21600
cctgaggttt gtggtctcac gccaagggaa tcaaggactc aggcacacaa gaagtgagtt   21660
taagacagca ggtttaatag gcaaaagaaa gagaaaaaag aatagctctc ttgcctgcac   21720
agagagaggg gcacctgagt ggatcttcct gtttttgtggt gaaatgcaag gcattttata   21780
gacgagcttg aggaagtggt gtctgattta cttaggaccc gagagattgg tcagaccagg   21840
tgtgatgttt acatagcata caaagaagct ggccatccca tcctaatctt ttattacgca   21900
gacgggggtct atacctggct ggtgccatgt tgtctgttcc ttactgtaca cgtggttgac   21960
```

-continued

```
aaagaaaagg gaagatgaag aatccatgtt gaacatgcct ggcccccaga tagtcttttc  22020
ctattggcac agctgccggc attcactctt gcaagcttcc agattgctta tctatgtctg  22080
cagcccaatt ttacaggttg ctctttgcta gaaaagaaat gatttggggg ctgcttttca  22140
ttaa                                                                22144
```

```
SEQ ID NO: 4            moltype = DNA   length = 20020
FEATURE                 Location/Qualifiers
misc_feature            1..20020
                        note = Synthetic: hRosa26 sequence
source                  1..20020
                        mol_type = other DNA
                        organism = synthetic construct
SEQUENCE: 4
accatttaaa cctcaaatta agcaacccac agaaccagga agttcaagga ccatgtctgt   60
tttcaccacg atgtctttcc ccaccccccc accccccact ccaccccca ctaagggcag   120
ggtattgtat ctgccagact gggtatttgt tgaacaagcg agtattttcg cctattagct   180
tagtttttaa ggaaatcatt tttttacttga ttcatcatag ctttaattct attacatact   240
acaataaaaa tttgacaaga ctgatacaaa tatgtagtgg gcaatagttt gccgtcttct   300
tccctagtat ggtgttttc aatctggtga ctagaatagg cagtgggcta taagcaggat   360
tcataaggcc tggagctgag ttatatgtga cactgccacc tattcattgt gtgaccttgg   420
ttttaacctt caaagtgggt ctcctggact aaaagaatgt gaaaagatgg ggaaataaat   480
ctgtaatctg aacatggaat gacttagtta cagaccagat attgttac tgggaatgaa   540
aaagtcaata tatttgaggg gaaaaaaatg taaataaata ttgagaaaga ttttacaaat   600
ctaattaggg gaagatagtt atctcccaat actagagggt accagagtgc ttttaagggg   660
aacatttggt taccctatt tctttaaaaa atggcagttt aggaaattct gccctaactg   720
tagtcccaat gtcagatagg actcaggtct ccactgcaag gaccaaaatg ttaagttgaa   780
gactgaaaat gggaaaattt ggaaatgtct ttggaacctc aagtacataa aagcctgtaa   840
gtgcttcata ctcattaaca acataggcat agaaaaaaga tatccttatt ctcaagcata   900
gccttttcta ataagttcat gttagatgtc atgaagttta gtgaggagtg aaaatctatg   960
aggaaaaaca tgaaccattc tactctggca aaagttcagg acaaacacca taggcctgta   1020
taccaaattt taaaccatgt tgaataaatgt gaaaaaaagc atcacattgc ttatgaaagg   1080
ctttcctgtc gcccttaat acttctgtct caggctaaca tgtttgttaa tgagttacag   1140
tggtgaagtt aaggaaatct gcttcctgtc ctagcatgcc cattatccca gccatacaga   1200
tttaatacca ggagtcactt taactccatg aagtcattca acaggtactt gagtatttac   1260
tatgtgcgtt tgtgctagag tagccatttc ttaaactttg tggcctcaga gaatcccttc   1320
acattcttaa agattgaggg ccccaaatca ctttactagt atcttaccat attagaaagt   1380
aaaatattta aatattatag caacaaatgc atatttttaa aaaaataggt gcattgtttt   1440
acattttggc aattgtttcc ctaaatgtct gacttaaata gaagacaact gaattgtttc   1500
ttttgcattc aattggttac aatgttacta gcagttttct ataatctcac gtattagtca   1560
ttaggaaaat atagcttcac tgagttatgt caatctccca aatgttggcc cattttactg   1620
tatactacct aaaatatcat tggccgggca cagtggctta aacctgtaat cctagcactt   1680
tgggaggcca aggtggatca cctgaggtca ggagttcaag accaccctgg ccaacatggt   1740
gaaaccccat ctctactaaa aatacaaaaa ttagccggat acagtggtac acacctgtag   1800
tcccagttat gcaggaggct gaggcaggag aattgcttga acccaggaga cagaggttgc   1860
agtcagccag atgtcccaaa aaaaaaaaaa aattatttc aatatcacta tctcatgaag   1920
tattgggaag ctgtcaagtt cctgatatta gacacaagtt ttcccgaaat tctgattttg   1980
actcaacgtt tggattttat cattgaaaac aattgctgtc agttgttagg ctccaaggaa   2040
atagcagata attcagctta catgagtgct ttttcttgag acaaccattt caaaaagtta   2100
tgtactgtag ggtttaagat ttaacaaaat gtcactgctt tcacaaggac attcttgagt   2160
gaaactggtt ttttttcttt gtggggggttc acaccacaaa tgcatggcag tgaaaaataa   2220
cttagagttt gatgccactg ccacagtttg tgccaaggtg cctgaaattt tacttttaca   2280
tactgttgcc ttatcaccac tcttatgtca acatatagtt tagcataaac catgagattt   2340
taaaaagtta ttctacactt gcattatttc aggacatgtg tttgttgcca agctttcacg   2400
taagagtatc tttaactagt tggtgctgat gcctggcaaa tacaagccaa gtaacaagtc   2460
cagccatgtt tatgcacgca tccattgata acgtattagc acagtcagcc ctccatatcc   2520
tcaggttctg catctgcaga ttcaaccaaa tgtgcttgaa aatatttgag aatatttaat   2580
acaatagtac aaatataagt acacaatgta caaactattt atatagcatt cacattgtat   2640
gaagtataag aaatctggaa atgatttaaa gtatatggga ggatgtgtgt aagttgtatg   2700
cagatacagc gccattttat aaaagggaat tcaacatcct tgggtttttgg tgtccttggc   2760
aaatggccag caagggtggg ggagtgctgt ccagaaacca atcccaaagc aagggacaaa   2820
tatatacttc tacagatgag atattaactc agaatccatg tctgcacaca catctttaat   2880
gacaagttgc tttatcactc aacagcggca ctactatgat cttttactta cacttcagcc   2940
agcagagaca ttcagcagtg tgagattttt taagtttttc agctattgtg tatgtttcta   3000
gtgtataata aagtaactta tcctttaaga tacttaagta gcttttcatt tctagcttta   3060
aaacctgttt ttttttttt cccagtagtg gcatacctgc attaaaaaat aatgccttac   3120
caaaaaaagc actctgaatg attggtttca aaatgatgcc acaacatagg tggcaccaac   3180
actattcaag atcattccat tcccatctct aaaaaaattt ttggctgggt atggtggctc   3240
acgcctatta actcaacatt ttgagaggcc caaagcaaga tcactcaggg ctaggagttg   3300
aagactagcc tgagcaacat ggcaagatcc tgtctcaaaa ttcttttaa aatttttta   3360
aaagcccagg cttggtggcg catgcctata gttccagcta ctcaggaggc tgaggcagaa   3420
ggatctcttg aacccaggag tttcaggctg tagttcacta tgatggcagc tgtgaatagc   3480
ctgggcaaca cagcaagacc tcatctccaa aaaaagacaa aagaactaaa ttattctact   3540
gcagaacatg attaggtaaa tatctccaaa gcagaaagac aggtttcata ttttcgttag   3600
tttgagtcag tccttccaaa tcaaatcttg tttttttatta gtatacagat ggtatagcca   3660
gtaagtaaat gagaagcagt ctttttaagc cgatccattc ttaaatgaaa aaatatataa   3720
atattttaga ataaatttat taaattctaa agttgtagaa tttttaaatt tggatatttt   3780
gggaaaatat ttaaaccact attgcaaaca aaacaacaaa atgtacttat gtttatactt   3840
aggcacaaag aaaactacag tattttaaag taaccattac acaatattga ggttgcaaag   3900
attactgaag gcataaccta aaaaatgagt tgatttctaa aaatgggaaa aaggaaaaaa   3960
```

```
ataatttcta aaaacaagta tgcataccta aacctaccta atgacacctt agaaaattca  4020
agtatagcac cattcattaa catcaatgag gatgtcatca cacatcatgt agcctctgca  4080
caccgtgaga ataaatgaaa aagacaggca tcttgctatc atgacaatag ttttgacctc  4140
gcagacctct ctgtgcttac gcaacggata aagccataag aactgtcctg ccctcaagga  4200
gcaacctaaa gtaggaaaaa aaaaacaaaa ttacacaatt attatttaca attgtgagaa  4260
gagctcttga caacattcaa atggaggata cagtgtagta agggtgaggg tatcaaggct  4320
tccttgagaa gtgatgtttt gaggccattc tttcttctca ataactggta tttggttcct  4380
gaatcctta acttccttac cattgtcact cctaagccaa atctcattac gtcatgtcta  4440
gactactgtt aagagaacca cttaagtggt ctctgcagcc ctcaatttat tggtgttatc  4500
tatgggaaaa ttgctcaaac tctaagcctt agtttcctac cctataaaat ggggtttat  4560
atacaaggaa catactaaat acacaggtat acctcagaaa cacggcaggc tcaattccag  4620
agcactacaa taaagcgaat ctcatgaatt tgttggtttc ccagtgcata aattatggtt  4680
acactatacc atagtctatt aagaagtgta caatagcatt atgtataatt gataaaatca  4740
tcactgctaa aaaaatgcta acaatctttt tgctggtgga gggtcttacg ccaacgttaa  4800
cgatggctac tgactcatca gggtggtggt ggttgaagat tacgatagct gtggcaattt  4860
cttaaaagac aatgaagttt gccacactga catcctttca caagacttct ctgtagcatg  4920
tgatgctgtt tgatagcatg atagcatttt acccacagta gaactttttt ttccttttcc  4980
ttttttttt tttttaaacg caaggtctca ctctgtcacc caggctggag tgcaggggcg  5040
ccatctcggc ttactgcaac ctcctcctcc ctggttcaag agattctcct gcctcagctt  5100
cccaagtagc tgggactaca ggtgtgcacc acacctggct aatttggtag aggtggggtt  5160
tcaccatgtt ggcaaggctg gtcttgaact cctgacctca aatgatctac cagtctcggc  5220
ctcctaaagt actgggattg caggtgtgag ccaccacacc agccagtgg aacttatttc  5280
aaaattgaag tcaactctct cacacctggg cactgcttta tcaaccaggt ttctgtaatt  5340
cctaaatcct ttattggcat tttaacaatg ttcacagcaa cttcaccagt agattccatc  5400
tcgagaaacc actttctttg ctcatcccta aaaagcaact cctcatccat tcaaatttga  5460
tcatgagatt gcagcaattc agtcacatct tcaatgcttt acttccagtt ctagttctct  5520
tcctgtttcc acacctgcag tacacaaaaa gcattcaata actattactt catttcttct  5580
acctatgttt ccattagctt ttgcctatag tacgcactag agtatgttac cattatttgt  5640
tataagtagt acctcattat tacactattc gtaagcaata cctcaaggtc taagattaga  5700
ttttaaatca aggtcagtaa aaatagaaaa ggctgtgaaa actgttgact gactttacca  5760
gaatccatac actagaggtg agattagtta ggtgatgaaa taaccattct ataaacatga  5820
tctgaaactc tgttactgtt gtcagcagga aaagccaatg ttacatatgt ttaaaaaaga  5880
aaaaaaaaac ccaaaaccag aaaacaaaag gtgacaaagt atcaagacaa aaggtcactg  5940
atgactgatc tctaggaaaa gctggaaagc aggattatta aatgtaacca cgactaagat  6000
aaaaatcaga gacagaaaag tctttgtcac caagaagata tactccatga gagagcagaa  6060
acaattcatc aggtttaacc ctgctctaga taaaataaaa ctatctgatt caatactcac  6120
acttctctaa taatccaata cattatccca tctcaagaag agagagtcac agataagaaa  6180
aaaaaggctt cttgagaagt atgtgctcta atataaacta atatgccact aagaaagcaa  6240
cctgcaaagt ccagtaccag acttctggat ttgtgaccta acaaggtgct ctacaattaa  6300
cctaacagtc aaaccagagt gttgtaaaag agaattatgt aattatgcca aacctccact  6360
cacaaaaaat atatggaagt aacctaagtt tacattttgc aaatctcaca cacacactag  6420
ccctgacaaa agtttcacca gctttctcat ccaagtacaa gcgtgtaata tacttaataa  6480
atttgtctta taagggtaag aaatagtatg taactacttg aaaaggagat aggtagctgg  6540
ttaatttaaa caaaaagccc aaggaagtaa ggtgcaggaa aaggataact gcaatgatta  6600
gtacaggaaa cccaaagaag aactgaatgg tgggatagat gtactcagag accatgaggc  6660
atcagtttcc tctatgaata gaatattagg agatgtaggt taaatgggac cctgaagtct  6720
ctcccaaaaa gccttgttta tatgtttct gagcttaact attacttgag aatcaatttc  6780
acgtataaac caacaaaact aacatttatt gagcttccag ctctgtgctt aggcactgaa  6840
aaatcacttt ccttaaggat tgcaattaag caggagaaac acaaataagg tgaacttctc  6900
ttgttcgaaa gaatatattt caacattcct tttaaaagga aaacctgacc tgcaagtttc  6960
caaaaatatt aattactatt cctctcttgcc tctcaaaatt ccattctgt tattttttag  7020
gaggaggaaa aaacagttca tttgaggaaa aattgagggt cacatactat acaattgaga  7080
agagtttctc tgaaactgta atcatttttg gcaggtaaat aggcatatcc gagtcagcaa  7140
atgaacttga agatactgag ttatactgcc tgccctgtgg ggttccacct tccccaaaag  7200
aattcagaat ttttgggtga tctgagaatc tacattaaga caactgtctc cacacacagg  7260
aggcctgaag atcgctgaca taagggtctt tttaaaaagt atatttaatg gcctagggcg  7320
gtggctcaca cctgtaatcc caggactttg ggaagcttag ggcaggaaga tcacttgagc  7380
ccaggagttc taacctgtgc agcacagcaa aaacccatct ctacaaaaaa aaaaacacaa  7440
aaaaattagc tgggcatgga agcgtgtgcc tgtagttcca gctactcagg aggctgaggc  7500
aggaggatca cttgagccca ggaagtcaag gctgcgtgag ccatgatcat gccattgcaa  7560
tccagtatgt gacactaaga ctccgtctca aaaaaaaaaa aaagataatt aaaatgtgta  7620
agatactgta ttagcaatat aaaaagcatt tggtgttaaa atgttggtat tataattcct  7680
caggataaaa cttactttgt gattgttttc tataactcaa gatatgatgc ttagagctcc  7740
tccaatcaag tgtttccagg aagtgaaaac ttgtaggaca gaaatttagg ctgggttcat  7800
ttgtatcaca cagacctatt cttcattcaa gttctgatat atttaactat gtagctcctg  7860
taacagttta atggaatctc acctccctaa aattcattat gcattttttt ttgaaatcca  7920
aactcattaa cgcttgcttt cactgttgtc caaggcaggc acatctttaa aaatggtttg  7980
ttggacttag cttttcagcta aatatataat aaataaaaca aaacaagcag ttaaatgaaa  8040
tgtaatgggc cagagagctt cagctttat ttccttactg ctcagtaaaa agagaaaacc  8100
atcaatgtcc acgtattctg taatccacag aacaagtccg gggctacagc tatactgtcc  8160
acagttgcaa ttcaaattag ataaaaaata aaaattcagt tctttagtca taccagccac  8220
ttttccaatg ctcaagatta ataaaaatgtc aaaccataaa gacatttaca tgtcgctcac  8280
tccatttact taaagttggc tagacatcag agtatactag gagctcagga gtacaagaca  8340
ctattccttc aaaaagctca gaatagttaa ggtaatttaa atcagcaatg acaacaaccc  8400
cagaattact atgacccacg cagtacaaac tgctcaggag tcagaagaaa actgcttttt  8460
taaaagggca gtttgggtca tagaacaaca gaccatggaa ggcatgacca aaggggagat  8520
gacatttgaa tctgcaggat taaaagcagc aagggtagca ttccaaaaag aaccacccca  8580
caaagatata tgacgtctct atgatttggg taactgcaat tcattccatg tgacttcagg  8640
agagaggtca tatttgtgtg tgtagtatgt ggaaaatagt gaaaaatgaa aaagctgtta  8700
```

```
aattgaggaa agtctatcca gggacccttat gcatcacatt cacgagaaca gaattcatcc   8760
tgtaaaccag gggtgtccaa tctttcggct tccctgggcc acactgcaag aactgtcttg   8820
ggccacatat aaaggacagc tgatgagcaa aaaaaaaaaa cagacaacaa caacaaaaaa   8880
aacaccccgc aaaaaaaact cctaaaactt taagaaagtt tacgaatttg tgttgggtcg   8940
cattcaaagc tgtcctgggg cccatgcggc ccgcgggtta gacaacttgc tgtaaacagt   9000
acaagccagt aatggagttt cacctgtcat tttcatgctc tatcttcctt taggacaatc   9060
atcctaacaa gatgtaagat ggatcaaaag ataacactaa agacagagac agcaatttgg   9120
aagctatcac acaggcatct gagatcagtt actaactggt aagaacagaa atgagaggta   9180
tttagaggaa gaaaaaggga gatgttgcct aacctcagat ccaattctct gtaaagcagt   9240
agtcaagatc acctggactg tgaagacggt cagggacaga atcccagcta aggaaaaagg   9300
ataaaatgaa aatcaagata aacatttaag aacgtgaact agggaggaat aaaagcactg   9360
ctgggtaaga gtcaagcccc agctcaagcc ttaatttgtg gtggaaccaa tctgtctggt   9420
ttcgcgagac accaggctac ccaagatcaa gagagggaga aagctagtgc tatgtctgaa   9480
tactagagga gcaagtacaa caaatggaaa atgggatcaa gtatgagtga gagttgctaa   9540
gatgcctggt agggatgcaa aggggtagag agcctgggga gagagggtga gggagggaag   9600
cactggtttc tcaagcaaaa gctaaaattt ttctattaag atttaacctg atgctacact   9660
ttggtggtgc agcaagggtc tcaaatggta taaaactcag gtgatcatgc tttatgtctg   9720
tctctagaaa aatgctccaa aaatgataag tagtgataat ccgcagtctc gttgcataaa   9780
atcagcccca ggtgaatgac taagctccat ttccctaccc caccctttatt acaataacct   9840
cgacaccaac tctagtccgt gggaagataa actaatcgga gtcgcccctc aaatcttaca   9900
gctgctcact cccctgcagg gcaacgccca gggaccaagt tagcccctta agcctaggca   9960
aaagaatccc gcccataatc gagaagcgac tcgacatgga ggcgatgacg agatcacgcg   10020
aggaggaaag gagggagggc ttcttccagg cccaggcgg tccttacaag acgggaggca   10080
gcagagaact cccataaagg tattgcggca ctcccctccc cctgcccaga agggtgcggc   10140
cttctctcca cctcctccac cgcagctccc tcaggattgc agctcgcgcc ggttttggga   10200
gaacaagcgc ctcccaccca caaaccagcc ggaccgaccc cgctcctcc cccaccccca   10260
cgagtgcctg tagcaggtcg ggcttgtctc gcccttcagg cggtgggaac ccggggcgga   10320
gccgcggccg ccgccatcca gaagtctcgg ccggcagccc gccccccgcct ccagcgcgcg   10380
cttcctgcca cgttgcgcag gggcgcgggg ccagacactg cggcgctcgg cctcgggggag   10440
gaccgtacca acgcccgcct cccccgccacc cccgcgccacc gcgcagtgt ttcgctcatg   10500
tgagactcga gccagtagca agggcccggt cccacagctt cgacagccaa tcaggtgtcg   10560
aagacaagca ggcggcgggt aaaccgactc ccccgaagga aggggagggt gggaggacgc   10620
ccgcgccaga gccgatttca ctgaccctcc cctcccgccg caggaggccg gccgcgcccg   10680
cacacccagc atctctacac cccacctacc tacccgcccc acccaggggg caacgcgaga   10740
gtcgctaagc ggctgcgtac tcccgacggc gtaactgaca ggagctttac tccaaccaga   10800
atacgccatt tgtgtttca cacacggcgg gaggagaaac ggccaatcgg cgacaagagg   10860
ctagccggaa gcgctcctcc ctctgcgaga gcaatggctc cgtccggttt cgagcatttt   10920
ccgctccctt ctccctcccc ctccggttgc cgcaggcgcg gcctccctcc cgcctgcatc   10980
cagccacccc tttccctccc aacgtaacaa acattatgtt ccgacttcc cacgggaaag   11040
gcaaccccccg caagccacca gacggccccc ctagccaccc atcccccccag tgtaccgcac   11100
ctcccctccc accagagttc cgctcccta cctagccgag gctctctgag gagccggagc   11160
gccgaagcac agcctcttct ctaggcggcc ccggcggctt ccgctgattg gcggcgagtg   11220
ggccaatggg tgcgggggcgg tgggcggaga ggccaatggc gcggcggggga gggcgtgatc   11280
ccgggtgccc ctggcgccgg cgctgggaat ccccgtgcgg tcagtggcgt ttccgctcgg   11340
gcagcgggct gagtgcagctg ccgccgccgc cgccgccgcc gccgccgccg ccgctgccgg   11400
gggaggggcg gccgccgccc gcctgcgctc agagactcac gcagcccccag tcccgccagt   11460
ccgccaacac agtagtgccg gcccccctct ttccctggcc ctgccccccc tccccgcctt   11520
tggctcgctc cgcctttctg cccccccaccc ccacctcacg ggtacgggcc attcccggcc   11580
aggaaacgcc gtggcgccgc gttgggccta actcgagtcc tgccgcctcc cgggagtgcc   11640
gtgcgccgca gcccggggccc aggccccggc agcgcctggg acaaggtaag ggtccgacag   11700
aaaagagacc gaacctcacg atcgggcccc aggggagggga agggtcacct cctccgtctc   11760
cccgcgctcg ctctccttgg gtcgtgggcc tggccctccc caagctctta ggaggatgct   11820
gccacttctc acccccctcg ccgccttgca cacaccgttg caaacacccca ttttcccagg   11880
gagagagatc ccccctctaat ctaggcgacc caactccccc tttcatgttt ttcctgggtc   11940
aggacgcttc ccctcccccca acgcctcttc accccctttc ctgggaactg cctactccac   12000
gtttacctttt cccttgagga gaggcctctt gctgccctcc gctcgaaata cacaggcata   12060
cttttttttct ctcccgatc ccccactccc taccccgtt ctcgcggcct tgtgacagac   12120
aactctgatc gctctggggg ccgcgatctc ccctccgtaa tcttcctgga cgccttccct   12180
ctcgttttct ggcttccac ctcagatggc tgcttcccaa aggcattacc ttcgccaccc   12240
ccaccacacg ttctctggct ccccgtggcg tgtgccacag cgtgtctgag atagcctcgt   12300
tgaatgtgta gggttcgagc ctggagttga gccagattgt gtcgtttac ttgccttggg   12360
cgtgagaac gatcttgtga gaatatcttc aaaggcagaa aaatattccc tttatgaatt   12420
ctctttccct ctgcgtgtaa gtcgggaatg tgaagaggag tgtaggaaag agccctggtt   12480
caagtaggta aatcgcatga gagggaaagt taaactgttg ggaaagcccc ttctatgcta   12540
attgattcta tagagtcctt gcttgtctca cttcttgggc gtcagtggtc tttctcttgg   12600
atatggatgc tgcagtcagc tctgctggtc tgggtcaggg gtgcgtgtat gacctgcatt   12660
ttctgctttc tcatgttact tgtgcaatgt attcaccggt aactcatttc tttcccagac   12720
ctctgggttc cactgggctt tgtctatatt taagttcatt tctccagttt ccttcctgca   12780
cataggtact gaacgaatcc ccaagttctg tgctaaattac cttcatcagt tgactaaaca   12840
agttttttaga tgacatattt gtgaccaagg tcatatttac atttctttgt tggacagatg   12900
ttacatagct atacttgtga ttggggagga tccagctgag tggagtgtgc tgagcttttt   12960
aggagagtgt gtactcccta tttgaaatta ttttttggtt gttaattta tattattaat   13020
gttttaggt cacagaaagt tctaagtggt aattttagat gtgtgggatc tgagctagga   13080
ctaaagcaga gaatacccac gtaatcagag gtttctgggc tccatagagg acgtagggct   13140
ttttttttttc tattggattt cttccagttt tctcaggatc attagttctc ttctgtagcc   13200
aaaaattctg gcctgttatg ggattagagt ctttaaggtt tactcagact gtcattatgt   13260
gtagaaaaat gaattatgcc ctttggtagg acatgacaca aggctctgtt tctagctgca   13320
aatttaaatt agattgtaga gtgcttggga aattggcttt caaaagacca aagcttaatc   13380
ttcactccta aactgctggc ttaattaaaa tggatattta gaatttggta aatgttgatt   13440
```

-continued

```
tttctaataa aaggccttgg tttaaaaggg tgaccttagg attgtttctt tcttaaaagc   13500
ataattccag cccttctggc atggagcact ggtccaaaaa aaaaaaaaaa aagtgtgtgt   13560
aaggagtggg ggtggggtaa agagaaggtt gttcctttgg gttggatcac aggggtgagt   13620
atacaaggca gcagcagctg ctggctctgg agctctggtt gctacgtgag aagcttgagt   13680
agtgctggct gctgtctcca gggaaggaca gcagtgcagc gtccattaat gctgctggct   13740
gcagggagca gcacttaggc gatggctgct tcaggactaa gaagaaacct tgcttttctg   13800
ggaattttca ctgctgagct ggtttgcttt ttattggtgg ggagatggga attagtaatt   13860
cataatctcc tacccattta tggatattgg catctggaaa ctggatcatg gttaaagcct   13920
ttcttttttt gtttgtttga tttgattttt gtttttttggc agattttttgt tttttatcta   13980
gacatttgtg cttggatagg actaaaagtt ccattagagt tttaattttt caatcagttt   14040
aaaaacccaa gtaataattt taagaatctt tctgataacc acaataggaa gaaaataaca   14100
ggaatttttt cctgcagctc acatatcatg ccttcctcca tctctttaat catagaatca   14160
attcttatta ttttgttatg tgtctccatc cttttcgatta gaccacattt accttataga   14220
cgatttgcta aacattttac taagcttgaa ctcttaaact ctaaaaaggt gccattttgg   14280
agtggtttct aaataaatat ttttaatttg tatattagta ataaacttct ccagattaga   14340
tattttctttt ggagtttgac ttataagatt gattcattat atacatgttg gatatagcct   14400
tctgacatca caaatatatg tctttggcca taatccatct gaaatgtagg acagaccaga   14460
agaaaatgc agaaatcgaa taagtctagt tcaggatact gagaagatgg cctctgagcc   14520
ccttaggtga tctcccctcc cccacaactc ctgaacatta ggatgatctc tgattaagca   14580
aaacagtctg agcgtggaaa aacttgaagg agaaccacca ccaccaatta tatgcaatac   14640
tggacatatt cctgtgtgct gtttttcttc cccaagactc gtgtatccta tacttttttc   14700
tctcagaatt ttgatttgtt catttccgtg taaatgtact taaatctcac aaacatctat   14760
aatttgtagt atcactctgg catttgtggc agagaaccaa aaagaatgga aatgagtttt   14820
gtcattcaca aatgtggctc acattgtttt cccagtaata aaagcagacc aatgaaacag   14880
aacctttaat ggatactatt ttaggaggtt ccaattctta ttactatcac atagataaga   14940
tgcaatagca gataaaatatg atttcaatgta tactggctgt ttgacatact tagggtttaa   15000
gataaaaatg tttgtagttt tttactctgt ggcttaagtt gctatataaa ataattgctt   15060
ttacactcga atttcctgtt gtttggaacc ttttgtgctc ttgatattat cattttttag   15120
aggatcatac aggccctttt catagaagga tttacttaag ttatacccctt gaaaactttt   15180
ttatatcttt tgatactgtt ttgtgtccag gaactgactt tctgaaatta ttctggcttt   15240
tctggggaga atgactattt cattttttacc tttgaatggg gaaataataa agtgcaaagt   15300
acagatttgc agataaattac ttttgcttta tcctctccat gttgaaataa cttatgaaaa   15360
attaggccat agttaacagc agtcaatgac tattggatac attttatcag aggggaactg   15420
gatcatgaat aaaataaaat tttaaaaata attttggct gaactctggt gattcatcag   15480
tttaatttga agtcagaagg tctagcagtg aattttattt ataaaaattg tatttcaagt   15540
gttgaaaact gaaacttctt gaccagtata ttttgtttga ggcatcaaac tttgcaaaat   15600
gtgcatcgta tatttagtga tataactggt agtcatttgt aatttaaagt attctttcaa   15660
aggcactctt tagaaagtaa tgtagtgtac ccgtgatggg cagggattgg taccattcct   15720
tactgccaaa aattccaaaa tatgtggcaa aatgattgat ttatcttgtg ggtgggattc   15780
tgggaagttc atgaaaggtg gagagaatat agtttccttc acttgtctat atacattttg   15840
ttaaataagt cttaggaaaa ctgtttttatt gtatctttaa ttatgaattg cgtaaaagat   15900
acccagtaac tttgggggga ggtgctgtta gaaagcatta cattggagag aattccccta   15960
ccctgggaca aaatgcattc tgtctttaat acttagcgaa gggaactatg ggataaaata   16020
aacaatgaag gtaagctcag tctgcttat atgtgcccctc actgagcaag gaatttgtaa   16080
tcgcatcgtg cctcattcgt ttataccatc atattgattt tgtttgctga gtacctgagg   16140
gaataccttca cttaatgtaa ggtcacatta agtatgtttg atatgaagac agggaaagga   16200
attttctgct tcttggaagta atgtcttagt attttaaaa cacttaagtt tttacatcag   16260
gccagttttg cctgatgctc atgtctgttg ctttggttgg gctgctgctt tctcttctgt   16320
gttcttatgg gttcgttgtg gtataaggat tcccacagct ttcatggcag tatgaagtaa   16380
tgagaagcat tgcctagcc atgttagtta catgtatact tttggcctat gttatgaatc   16440
acaaaaagcg gtagctatag gaatgtatac aaaatagatt tctgtctggg gaatcaagtt   16500
tttgatttgt gctacctaat ggaggggaaa atgctgaatt tcttgctgct ctgtttgaga   16560
aatagatgga agcatgggag gagccagaga cctctgcagc aggatttggt ctaagtagaa   16620
aaggaagatt tttgtttcaa attgccagct gcttatgtca gactgactcc cttattatgc   16680
ctccagtagg cctgtcaata tggccaaaca gctagataag tgcggggcag gacaaagggc   16740
tctttgcaca gcagggaggc aatgttggtg ggggaggggc aggaggtagg aaaggcaaga   16800
ggaggaggtt ctttttccctg ggagattatt cagtttggca tacaattaaa gaaatcattt   16860
ttagttccca ctcaagcatt gaattttttgc caaccacata ctattaaccc caaatttgat   16920
acatttcaga atatcttgta gggatccatt ctcgccaagg aaaaataaaa aaataaataa   16980
agctctgtat aggttaaaat aaaataaatc ccacactctg caccctccta ggtgcaagtc   17040
acctcccgag gagaccccgtt ctagagctga attctcatta agaaatggaa aagaatactc   17100
tatctgaata aaaacacatt gtaatacaat gtgtttattt gggttgggat tggacctgaa   17160
catgtagaat aatttgtttc cctttatgaa atagttgctc gtagttgtct acaattttat   17220
ttcattaaga taggtagcac attacagctt tcatgtgttg ggttgccata tgtaaaatgc   17280
taactgaaga aaggctactt tttaatttca gcctcatcct tagttcctgg agaacctgat   17340
atttcctgga gattactccc tccccccacct tttagtttag gcaacctctt ttgatacatt   17400
tgtgttcagc tcgcatacaa gtgggatagt tgcatccagt ttattaagac ttagtatgaa   17460
tcatagagtt ggaaaagatc tgttggttat ctggtccttt aaaccaaaat cataatgaaa   17520
tattttgaaa tttgggtccc tattgaagtt ttcattaaaa tgttaaagga tcggtgttct   17580
gaacaacatt tttagttact tttaaaataa atgtttgcg tcagttcttt ttttaaaaat   17640
aaagaatttc atttataggc aaattagctg gcaattattt gaattgtgat aggatttctc   17700
ttttatgaag gaatatatga caaggttttt caaaatgctt aatatatttt aaaagacttt   17760
aattttttaga aataattggt ttgaacagtt ttccaagagc acatttgttg cttgggttga   17820
ggtaccacct atattgcaat gttactaaac tagccttaaa gttttcccctt ctgtctatac   17880
tgcatgcaac aataaaggga actggaatgt taatttccat ttatggatta gcagaggaga   17940
tgttttaacc gattaataac caaaaaactg cctttcgtac acgtaatatt aagcaagcct   18000
gaccaagttt tgtgttattt ctctctgtta aagaaaactg gatgtgttac tacttaacat   18060
tatattgtta tttaatggtc ttggcagtaa tgatataata tttcgaccaa aagaaatttt   18120
gagtaattaa ttattattgt aattagttgg aagtttctca tcagtaaaat agcaacagca   18180
```

```
ttaacacaaa atctagtgag ctatatttta tattactaca gaaatttagg gtagtcattt   18240
ctttctttat aatttattca catggattat ttccataaat ttgtgggact aaaatagaag   18300
ccatctagtc aagcaccagt ctccatacca gacagttttc tctgcatgtg ctatgaccca   18360
cattgccagt attaaacatc ctttacaccc tcccccttcc cagataatta gaaatctctt   18420
cagggtagct tccattgctc ctattacctg gatcttgcta gaggctctaa gaagttcctg   18480
gtaaaagtga gacagtaagg gaccacattt tgattccaaa ggtttttgata actgttaggg   18540
ctccccaaac agctaatctc attttcacca agacttagcc agcagagggc tggaatggag   18600
gtgaaacaca agcactgtac ctcatcttgc ctgtgcagct gctccacctt atttcctgct   18660
attattatct caacacgcct cctcccatca aaaagaaact aggacaaagg gggaaaattg   18720
gatgggctaa tgtgattttt attatgctag gttgtgggct tgtttatatg tacttaaata   18780
caaagctaat ttgccccatt cttaaaagtc tttagtgata gagattttgt aacttctgta   18840
tcttctactt tctttcttga taaaccattt cagattctca gccttacaga aagaaaggtt   18900
ttaagcatac ttaattttcg ttggccgttc acagtcatta ttaccaccag atgccactgt   18960
attattagct tgaagaaagg tgggctctct tctgtacata atatctgcaa tttgttttgg   19020
aaaatactaa tttgtataaa tctgatttat gactaaaata aggttaaaaa ttagacctct   19080
atgtatgttt accctattac cttagtgggg gtgaaattaa ttagctcttt gaacataaat   19140
ttttcatgtc ttagagttct ttttttcaagc tgcataattt atgttcttca agccattttt   19200
atcccatacc accccacaa aggggaaat tttattttt atcattttta ttgtctttca   19260
atggtgagat tttcgccacc ccactcctga aatgtgaaga ctcaaataaa actgagtaat   19320
ctaataaggt atatgcgttg ctgaatgtag taagatgatt gtttcatcat tcttagatat   19380
tatgatctag tttgaatctg gtttccagta tcatgttagc atatttaata ctgttgatat   19440
gttaatttta atacatgccc aggtggatct ccttgcttc tatttgtgcc ccttgtttgt   19500
cgtttttgtat gaagggggtt tttgttgttg gattttcttc cccatctctg tgtcctgtta   19560
tgttctttgg cttatgtttc aaaaattctg tttcctacca ccaacctctg tacatgccac   19620
aacacataca atttgtactt tcacagtttc tgtgaagtag gatgatctgc agttaataat   19680
caactgtttg ggcattcttg gtatccaagg aaggtttac ttagaaggaa gaacctggaa   19740
ggacctgttg gcaattagac tacttctgcg tttattttac attttcccctt attaacgtag   19800
gctgttgaga gttgacttgt tttataagag aaaccagatt gacagagaag accccccaatc   19860
agatagagtt attttaaaaa taaatgtgtt tattatggta acatttgggg tagaatctaa   19920
agggcatatt tttaaaaaaa cttttagttc taaagacaaa agagtttaac ctaaaacaga   19980
acaaagagaa gggcctttga agcagtatga ttgattatat                         20020
```

```
SEQ ID NO: 5         moltype = DNA  length = 6473
FEATURE              Location/Qualifiers
source               1..6473
                     mol_type = genomic DNA
                     organism = Cricetulus griseus
SEQUENCE: 5
tctagaaaca aaaccaaaaa tattaagtca ggcttggctt caggtgctgg ggtggagtgc   60
tgacaaaaat acacaaattc ctggctttct aaggctttt cggggattca ggtattgggt   120
gatggtagaa taaaaatctg aaacataggt gatgtatctg ccatactgca tgggtgtgta   180
tgtgtgtgta tgtgtgtctg tgtgtgtgcc cagacagaaa taccatgaag gaaaaaaaca   240
cttcaaagac aggagagaag agtgacctgg gaaggactcc ccaatgagat gagaactgaa   300
cacatgccag aggaggtgag gactgaacca ttcaacacaa gtggtgaata gtcctgcaga   360
cacagagagg gccagaagca ctcagaactc caggggtca ggagtggttc tctgaggct   420
tctgcccttg gaggttcctg aggaggaggc ttccatattg aaaatgtagt tagtggccgt   480
ttccattagt acagtgacta gagagagctg agggaccact ggactgaggc ctagatgctc   540
agtcagatgg ccatgaaagc ctagacaagc acttccgggt ggaaaggaaa cagcaggtgt   600
gaggggtcag gggcaagtta gtgggagagg tcttccagat gaagtagcag gaacggagac   660
gcactggatg gcccccacttg tcaaccagca aaagcttgga tcttgttcta agaggccagg   720
gacatgacaa gggtgatctc ggttttttaaa aggctttgtg ttacctaatc acttctatta   780
gtcagatact ttgtaacaca aatgagtact tggcctgtat tttagaaact tctgggatcc   840
tgaaaaaaca caatgacatt ctggctgcaa cacctggaga ctcccagcca ggccctggac   900
ccgggtccat tcatgcaaat actcagggac agattcttca ctaggtactg atgagctgtc   960
ttggatgcaa atgtggcctc ttcattttac tacaagtcac catgagtcag gaggtgctgt   1020
ttgcacagtg tgactaagtg atggagtgtt gactgcagcc attcccggcc ccagcttgtg   1080
agagagatcc tttaaattg aaagtaagct caaagttacc acgaagccac acatgtataa   1140
actgtgtgaa taatctgtgc acatacacaa accatgtgaa taatctgtgt acatgtataa   1200
actgtgtgaa taatctgtgt gcagcctttc cttacctact accttccagt gatcaggttt   1260
ggactgcctg tgtgctactg gaccctgaat gtcccaccg ctgtcccctg tcttttacga   1320
ttctgacatt tttaataaat tcagcggctt cccctctgct ctgtgcctag ctataccttg   1380
gtactctgca ttttggtttc tgtgacattt ctctgtgact ctgctacatt ctcagatgac   1440
atgtgacaca gaaggtgttc cctctggaga catgtgatgt ccctgtcatt agtggaatca   1500
gatgccccca aactgttgtc cagtgtttgg gaaagtgaca cgtgaaggag gatcaggaaa   1560
agaggggtgg aaatcaagat gtgtctgagt atctcatgtc cctgagtggt ccaggctgct   1620
gacttcactc ccccaagtga gggaggccat ggtgagtaca cacacctcac acatactata   1680
tccaacacac acacacacac acacacacac acgcacgcac gcacgcacgc acgcacacat   1740
gcacacacac gaactacatt tcacaaacca catcgcata ttacacccca aacgtatcac   1800
ctatacatac cacacacataca caccctcca cacatcacac acataccaca cccacacaca   1860
gcacacacat acatagggcac acattcacac accacacata tacatttgtg tatgcataca   1920
tgcatacaca cacaggcaca cagacaccac acacatgcat tgtgtacgca cacatgcata   1980
cacacacata ggcacacatt gagcacacac atacatttgt gtacgcacac tacatagaca   2040
tatatgcatt tgtatatgca cacatgcatg cacacataca taggcacaca tagagcacac   2100
acatacatt gtgtatgcac acatgcacac accaatcaca tgggaagact caggttcttc   2160
actaaggttc acatgaactt agcagttcct ggttatctcg tgaaacttgg aagattgctc   2220
tggagaagag gaagcgttgg cttgagccct ggcagcaatt aaccccgccc agaagaagta   2280
ggtttaaaaa tgagagggtc tcaatgtgga acccgcaggg cgccagttca gagaagagac   2340
ctacccaagc caactgagag caaaggcaga gggatgaacc tgggatgtag tttgaacctc   2400
tgtaccagct gggcttcatg ctattttgtt atatcttat taaatattct tttagtttta   2460
```

-continued

```
tgtgcgtgaa taccttgctt gcataaatgt atgggcactg tatgtgttct tggtgccggt    2520
ggaggccagg agagggcatg gatcctccgg agctggcgtt tgagacagtt gtgacccaca    2580
gtgtgggggtc tgggaactgg gtcttagtgt tccgcaagtg cagctggggc tcttaacctc    2640
tgagccatcc ctccagcttc aagaaactta tttttcttagg acatggggga agggatccag    2700
ggctttaggc ttgtttgttc agcaaatact cttttcgtgt attttgaatt ttattttatt    2760
ttactttttt gggatagaat cacattctgc agctcaggct gggcctgaac tcatcaaaat    2820
cctcctgtct cagtctacca ggtgataaga ttactgatgt gagcctggct ttgacaagca    2880
ctttagagtc cccagcccctt ctggacactt gttccaagta taatatatat atatatatat    2940
atatatat atatatatat atatattgtg tgtgtgtgt tgtgtgtgta tgagacactt    3000
gctctaaggg tatcatatat atccttgatt tgctttaat ttattttta attaaaaatg    3060
attagctaca tgtcacctgt atgcgtctgt atcatctata tatccttcct tccttctctc    3120
tctttctctc ttcttcttct caccccaag catctatttt caaatccttg tgccgaggag    3180
atgccaagag tctcgttggg ggagatggtg agggggcgat acaggggaag agcaggagga    3240
aaggggggaca gactggtgtg ggtctttgga gagctcagga gaatagcagc gatcttccct    3300
gtccctggtg tcacctctta cagccaacac cattttgtgg cctggcagaa gagttgtcaa    3360
gctggtcgca ggtctgccac acaaccccaa tctggcccca agaaaaggca cctgtgtgtg    3420
actctggggt taaaggcgct gcctggtcgt ctccagctgg acttgaaact cccgtttaat    3480
aaagagttct gcaaaataat acccgcagag tcacagtgcc aggttcccgt gctttcctga    3540
agcgccaggc acgggttccc taggaaatgg ggccttgctt gccaagctcc cacggcttgc    3600
cctgcaaacg gcctgaatga tctgtgcactc tgcgttgcca ctgggatgaa atggaaaaaa    3660
gaaaaagaag aagtgtctct ggaagcgggc gcgctcacac aaacccgcaa cgattgtgta    3720
aacactctcc attgagaatc tggagtgcgg ttgccctcta ctggggagct gaagacagct    3780
agtgggggcg gggggaggac cgtgctagca tccttccacg gtgctcgctg gctgtggtgc    3840
atgccgggaa ccgaaacgcg gaactaaagt caagtcttgc tttggtggaa ctgacaatca    3900
acgaaatcac ttcgattgtt ttcctctttt tactggaatt cttggatttg atagatgggg    3960
gaggatcaga gggggagggg aggggcgggg agacgggagg gaggggagga    4020
gggggaggagg ggaggagggg aagggatgga ggaaaatact aacttttcta attcaacatg    4080
acaaagattc ggagaaagtg caccgctagt gaccgggagg aggaatgccc tattgggcat    4140
tatattccct gtcgtctaat ggaatcaaac tcttggttcc agcaccaagg attctgagcc    4200
tatcctattc aagacagtaa ctacagccca cacggaagag gctatacaac tgaagaaata    4260
aaattttcac tttatttcat ttctgtgact gcatgttcac atgtagagag ccacctgtgt    4320
ctaggggctg atgtgctggg cagtagagtt ctgagcccgt taactggaac aacccagaac    4380
tcccaccaca gttagagctt gctgagagag ggaggcccctt ggtgagattt ctttgtgtat    4440
ttatttagag acagggtctc atactgtagt ccaagctcagc ctccagctca cagaaattct    4500
cctgttccgg tttccaaagt actggagtta tgagtgtgtg ttaattgaac gctaagaatt    4560
tgctgattga agaaaacctc aagtgggttt ggctaatccc cacgacccca gaggctgagg    4620
caggaggaat gagagaattc aaggtttgcc agagccacag ggtgagctca atgtggagac    4680
tgtgagggtg agctcaatgt ggagactgtg agggtgagct caatgtggag actgtgaggg    4740
tgagctcaat gtggagactg tgagggtgag ctcaatgtgg agactgtggg ggtgagctca    4800
atgtggagac ctgtatcaag ataataatag tagtagtaac aatgcaggcg agggtgtggt    4860
tgagtggtag agcagttagt tgatttgaca tgcttgaggt ctcccggtcc atctgtggcc    4920
ctgcaacagg aagggaggga ggaagggggg gaacgagaga gaggaaagag agacagaagc    4980
taagataggg aatgagagag gaaggaagaa acgggaagaa attcagactc cttcctgagt    5040
tccgccaacg cctagtgaca tcctgtgcac accctaaggt ggcctttgtg tggcactggc    5100
ttgggtggtc gggaaaggca ttttcagctt gttgcagaac tgccacagta gcatgctggg    5160
tccgtgaaag tttctgcccg ttaacaagaa gtctctacta cttgtgacct caccagtgaa    5220
aatttcttta attgtctcct ggtgttctgg gttttgcatt tttgtttcta aggatacatt    5280
cctgggtgat gtcatgaagt ccccaaagac acagtggggc tgtgttggat tgggaaagat    5340
gatttatctg gggtgtcaaa aggaaaagaa gggaaacagg cacttgggaa aatgtcctcc    5400
cgcccacccg aattttggct tggcaaccgt ggtggaggag caagaaacac gtggacgttt    5460
gaggaggcat ggggtcctag gaggacagga agcagaagga gagagctggg ctgacagcct    5520
gcaggcattg cacagtttca gaaggagatt acagcatgac tgagttttta gggatccaac    5580
agggacctgg gtagagattc tgtgggctct gaggcaactt gacctcagcc agatggtatt    5640
tgaataacct gctcttagag ggaaaacaga catagcaaac agagccacgt ttagtgatga    5700
aactctcact ttgcctgagt catgtgcggc catgcccagg ggtcaggctg acactcaact    5760
caaaaacaag tgagaaattg aagacaatcc gtggtggcag ctactggaag ggccaccaca    5820
tccccagaaa gagtggagct gctaaaaagc catttgtgat aggcacagtt atcttgaatg    5880
catggagcag agattacgga aaaatcgaga atgttaatga ggcaacattc gagttgagtc    5940
attcagtgtg ggaaacccag acgcttccat cccctaaaag gaacatcttg ctctcagtca    6000
aaatggaaat aaaaattggg gcttgaattt ggcaaatgat tcagaactct gtgtaggtat    6060
tttcacacgc acagtggata attttcatgt tggagtttat ttgtgctaaa aggcagaaaa    6120
gggtaaaaag cacatcttaa gagttatgag gttctacgaa taaaaataat gttacttaca    6180
gctattcctt aattagtacc cccttccacc tgtggtaatt tcctgagata gtcagtgggg    6240
aaaagatctc tccttctctt ctttctcccc ctccctcct ctccctcctc ccctcccctc    6300
ctccctcctc tccctccctc ccccttttcct tctttctttg ctccttctcc tctgcctcct    6360
tctccctttc ttcttcattt attctaagta gcttttaaca gcacaccaat tacctgtgta    6420
taacgggaaa acacaggctc aagcagctta gagaagattg atctgtgttc act           6473
```

```
SEQ ID NO: 6          moltype = DNA  length = 7045
FEATURE               Location/Qualifiers
source                1..7045
                      mol_type = genomic DNA
                      organism = Cricetulus griseus
SEQUENCE: 6
actagcgtgc aattcagagg tgggtgaaga taaaaggcaa acatttgagg ccatttcctt     60
atttggcacg gcacttagga agtggaacat gcctaatcta ctggtttgta ccacctttcc    120
ctataatgga ctgtttggga agctcctggg caaccgattc tggcatctca ttggtcagag    180
gcctgttaaa tggtactctt atttgcaaag aaggctgtaa cttgtagctt taaaagcctc    240
tcctcaagaa agaagggaga aaggatatgg ctagacatat ctaatagact taaccactgt    300
```

```
gaaaagcctt agtatgaatc agatagaacc tatttttaac tcagtttga aaaaaataat    360
ctttatattt atttgtgtgt gtgtgtgtgt gtgtgtgtgt gtgtgtgtgt gtgtgtgtgt    420
gaaccacatg tagcaggtgc tggaggaggc cagaagaggg caccagatct cctggaactg    480
acaccacaca tggttatgag ctgcctgatg tgggtgctgg gaactgaact ctcgtgttct    540
gcaagagcag caactgttct cttaactgat gagccatctc tccagccccc cccataattt    600
taattgttca ttttagtaaa ttttattcat aatcaattat cacagtataa aacaatgatt    660
ttatatat catatacata tcaaggatga cagtgagggg gatatgtgtg tgtgtgtgtg    720
tgtgtgtgtg tgtgtgtgtg tgtgttattt gtgtgtgtgc tttttaagaa ggtgccatag    780
tcactgcatt tctctgaagg atttcaaagg aatgagacat gtctgtctgc caggaaccct    840
atcttcctct ttgggaatct gacccaaatg aggtattctg aggaactgaa tgaagagctc    900
aagtagcagt gtcttaaacc caaatgtgct gtctagagaa agtcaacgtc atcagtgagc    960
tgaggagaga tttactgagc ggaagacaag cgctctttga tttaagtggc tcgaacagtc   1020
acggctgtgg agtggagcct gtgctcaggt ctgaggcagt ctttgctagc cagctgtgat   1080
gagcagtgaa gaaaggtgg agatggaggc agggtgggag cagggctatg gttcagacta   1140
ggtatcgtga gcacaccagc tggttgactt gtggtctgtg ggtcaggcgt tgtaaacgcc   1200
ctcagggtca ggcagtcaca ttgcttgaag ctgaatgggt gaggcaacac agagagtgca   1260
aagaaggcaa agtaccacct cttccccgac ccaggtcact tctgggttat agctgagact   1320
ccggacagca tgcaaccagc tggttagagc ttcaggaaa acttgatgtc tgcatgttgc   1380
tatgaaatgt gattcggtac atctggagaa aatttataat gctggctcag tcaagcactg   1440
aacaaaggta ccttggcttt gggagctaca tgacattgac ttgtaggcag acttttttt   1500
ttctgcccgc caattcccag ataaccaata tggaggctca atattaatta taaatgctcg   1560
gctgatagct caggcttgtt actagctaac tcttccaact taaatgaacc catttctatt   1620
atctacattc tgccacgtga ctttacctg tacttcctgt ttcctctcct tgtctgactc   1680
tgcccttctg cttcccagag tccttagtct ggttctcctg cctaacctta tcctgcccag   1740
ctgctgacca agcatttata attaatatta agtctcccag tgagactctc atccaggag   1800
gacttgggtg ctcccccctc ctcattgcca tccgtgtctt cctcttccct cgcttcccgc   1860
tcctcttcct gctcttcctc ctccacccct cctttcatag tattgatggc aagggtgttc   1920
tagaatggag gagtgcccat aggcatgcaa agaaaccagt taggatgctc tgtgaggggt   1980
tgtaatcata agcgatggac acaattcaag ccacagagtg aagacggaag gatgcactgt   2040
gctctagagc aacttctggg gcagaatcac agggtgagtt tctgacttga gggcgaaagag   2100
gccacgagga agggagtgag tttgtctgag ctagaagtca cggcccacct cttggtagca   2160
gacctgccca caagcatgct ttgttaatca tgtgggatct gattttcctc taaatctatg   2220
ttcaactctt aagaaaatgt gaattctcac attaaaattt agatatacgt cttttggtgg   2280
gggggggtgta aaaatcctc aagaatatgg atttctgggg gccggagaga tggctcagaa   2340
gttaagagaa ctggttgctc ttctagacat tctgagtctca attcccagca accacatggt   2400
ggctcacaac catctgtaat gcgacctggt gccatcttct gacatgcatg gatacatgca   2460
ggcagaaagc tgtatacata gtaaattgat aaatctttt ttaaaaagag tatggattct   2520
gccgggtgtt ggtggcgcac gcctttaatc ccagcactct ggaggcagag gcaggtggat   2580
ctctgtgagt tcgagaccag cctggtctat aagagctagt tccaggacag cctccaaagc   2640
cacagagaaa ccctgtctcg aaaaaccaaa aaaaaaaaaa aaaaaaaaaa aaaaaaaga   2700
gtatggattc taagaaagcc gtaacagctg gagctgtgta cggagttcag cgtggtacta   2760
gaagaacaga cattcatgat gaaacacccc aggattttta cttagtatct agtttccatt   2820
gttgttttga gaccggcct tatgctctcc aggctggcct caaactgctg atcttcccgc   2880
ctctacctct caagtcctgg gactacttgg ctcataaaac agtttttgtc gggctccctg   2940
aagttatggt tgtacaaacc gtgggggtca atatactcac ttgggcagag agagaaggtc   3000
tgaatcccag acaatgactg catctcagga cagttgggaa gaggacaatg gcagaaggac   3060
ttagaaaaga tagactggag ggtggaaaag cagcaggaac agagaaacaa aacaggaagc   3120
ttgctatcca gggccactct ggagtcctgt ggcaagatgg aagcgggcta ggggaataca   3180
tttgtgctac tgtgtgtgtg tgtgtgtgtg tgtgtgtgtg tgtgtgtgat caatgcctat   3240
caatgttgaa gggaaatat gtataccaca ttgattctgg gagcaattct cagtatctgg   3300
cctagagaaa ggaatggccc ctgcagaata gacagagtga atggtgccct ttatcatttg   3360
ctaaagtgaa ggagaaataa acatccttcc atagagtttc aggtaaatga accccacagt   3420
tcatctgtgc cgtggtggag gcctggccaa cagttaaaaa gattagacac ggacaaagtc   3480
tgaaggaaac acctcgaata ggaagaggag agccacctca ttctgtaact ttcctcaagg   3540
ggaagatgtt ccaagagtgg gaataaatgg tcaaaggggg gatttttaat taggaaaacg   3600
atttcctgta tcacttgtga aactggaggt tgatttgggg cataggacaa tagatttgat   3660
gctttgcaaa aagctgtttc aaagcagaga aatggaatag agacaattat gtagcgagga   3720
gggagggtgg ggcgaagatg gagacagaga agtggaagct gactttaggg aagaggaaca   3780
tagaccacag gggcggggcg gggggcaggg gcgggggcg gggctcaaag gaggcagtgg   3840
gaacgttgct agtgttcgca gcgtaagcgt gaatgtgcaa gcgtctttgt ggtgtgtgac   3900
caggagtagc gtggctggct tgtgtgctgc ttgtaatccc agtctttgag gtttccacac   3960
tgttccacag tgggtgtgat tttccctcgg agagcatgag ggctctgctt tccccacatc   4020
ctccccagcg ttcgttggta tttgtttcca agatgttagt gggtgagaca aagcctctct   4080
gttgatttgc ctttaacagg tgacaaaaaa agctcaacca ggagacattt ttgccttctt   4140
ggaaggtaat gctccatgt agagcaatgg gacccatctc taaggtgagg ctactcttgc   4200
agtttgcacc cagctcttct gatgcaggaa ggaagttggt gggcaagcaa gactgtttgc   4260
ttcttgcgat ggacacattc tgcacacaaa ggctcaggag gggagaaggc tgtttgatgt   4320
ttagcactca ggaaggcccc tgatgcatct gtgattagct gtctcatct gtggagcaga   4380
cacggactaa ctaaaaacca gtgtttttaa attgtcaaga ctttaaggtg aggaaattga   4440
cttattgtgc tgggccatac gtagagcaag tgctctgcat tgggccaacc cccggctctg   4500
gtttctaggc accagaatgg cctagaacta actcacaatc ctcccattcc aggtctcagg   4560
tgctagaatg aaccactata ccagcctgcc tgcctgccta cctgccttcc taaattttaa   4620
atcatgggga gtaggggaga atacacttat cttagttagg gtttctattg ctgtgaagag   4680
acaccatgag catggcaact cttataaagg aaaacattta gttgggtggc agtttcagaa   4740
gtttttagtac attgtcatca tggctgggaa catgatggca tgcagacaga catggtgctg   4800
gagaaaggga tgagagtcct acatcttgca ggcaacagga cctcagctga gacactggct   4860
ggtaccctga gcataggaaa cctcacagcc caccctcaca gtgacatatt tccttcaaca   4920
aagccatacc tcctaatagt gccactccct atgagatgac agggccaatt acattcaaac   4980
tgctataaca cttttaaagta ttttatttttt attattgtaa attatgtatg tagctgggtg   5040
```

-continued

```
gtggcagccg aggtgcacgc ctttaatccc agcacttggg aggcagaggc agatggatct    5100
ctgtgagttc aagaccagcc tggtctataa gagctagttg caaggaagga tatacaaaga    5160
acagttctag gatagccttc aaagccacag agaagtgctg tcttgaaaac caaaaattgt    5220
gctgggacct gtctctgctt tggttgcttc ccactccccc agagctggac tcttggtcaa    5280
cactgaatca gctgcaaaat aaactcctgg attcctctct tgtaacagga gcccgaagtc    5340
aggcgcccac ttgtcttctc gcaggattgc catagacttt ttctgtgtgc ccaccattcc    5400
agactgaagt agagatggca gtggcagaga ctgggaaggc tgcaacgaaa acaggaagtt    5460
attgcaccct gggaatagtc tggaaatgaa gcttcaaaac ttgcttcatg ttcagttgta    5520
cacagactca ctcccaggtt gactcacacg tgtaaatatt cctgactatg tctgcactgc    5580
ttttatctga tgcttccttc ccaaaatgcc aagtgtacaa ggtgagggaa tcacccttgg    5640
attcagagcc cagggtcgtc ctccttaacc tggacttgtc tttctccggc agcctctgac    5700
accccctcccc ccattttctc tatcagaagg tctgagcaga gttggggcac gctcatgtcc    5760
tgatacactc cttgtcttcc tgaagatcta acttctgacc cagaaagatg gctaaggtgg    5820
tgaagtgttt gacatgaaga cttggtctta agaactggga caggggaaaa aagtcggatg    5880
tggcagcatg taccgaaat cccagaactg gggaggtaga gacggatgag tgcccggggc    5940
tagctggctg ctcagccagc ctagctgaat tgccaaattc caactcctat tgaaaaacct    6000
ttaccaaaca aacaaacaaa caaataataa caacaacaac aacaacaaac taccccatac    6060
aaggtgggcg gctcttggct cttgaggaat gactcaccca aacccaaagc ttgccacagc    6120
tgttctctgg cctaaatggg gtggggtgg ggcagagaca gagacagaga gagacatgac    6180
ttcctgggct gggctgtgtg ctctaggcca ccaggaactt tcctgtcttg ctctctgtct    6240
ggcacagcca gagcaccagc acccagcagg tgcacacacc tccctccgtg cttcttgagc    6300
aaacacaggt gccttggtct gtctattgaa ccggagtaag ttcttgcaga tgtatgcatg    6360
gaaacaacat tgtcctggtt ttatttctac tgttgtgata aaaaccgggg aactccagga    6420
agcagctgag gcagaggcaa atgcaaggaa tgctgcctcc tagcttgctc cccatggctt    6480
gccgggcctg ctttctgcaa gccctttctct ccccattggc atgcctgaca tgaacagcgt    6540
ttgaaatgct ctcaaatgtc actttcaaag aaggcttctc tgatcttgct aactaaatca    6600
gaccatgttt caccgtgcat tatctttctg ctgtctgtct gtctgtctgt ctgtctatct    6660
gtctatcatc tatcaatcat ctatctatct atcttctatt tatctaccta tcattcaatc    6720
atctatcttc taactagtta tcatttattt atttgtttac ttacttttt tatttgagac    6780
agtatttctc tgagtgacag ccttggctgt cctggaaccc attctgtaac caggctgtcc    6840
tcaaactcac agagatccaa ctgcctctgc ctctctggtg ctggggttaa agacgtgcac    6900
caccaacgcc ccgctctatc atctatttat gtacttatta ttcagtcatt atctatcctc    6960
taactatcca tcatctgtct atccatcatc tatctatcta tctatctatc tatctatcta    7020
tctatcatcc atctataatc aattg                                          7045
```

```
SEQ ID NO: 7             moltype = DNA  length = 6473
FEATURE                  Location/Qualifiers
source                   1..6473
                         mol_type = genomic DNA
                         organism = Cricetulus griseus
SEQUENCE: 7
agtgaacaca gatcaatctt ctctaagctg cttgagcctg tgttttcccg ttatacacag    60
gtaattggtg tgctgttaaa agctacttag aataaatgaa gaagaaaggg agaaggaggc   120
agaggagaag gagcaaagaa agaaggaaag ggggagggag ggagaggagg gaggggagga   180
gggagggagg gagaggaggg gagggggaga aagaagagaa ggagagatct tttccccact   240
gactatctca ggaaattacc acaggtggaa ggggtacta attaaggaat agctgtaagt   300
aacattattt ttattcgtag aacctcataa ctcttaagat gtgcttttta ccctttttctg   360
ccttttagca caaataaact ccaacatgaa aattatccac tgtgcgtgtg aaaataccta   420
cacagagttc tgaatcattt gccaaattca agccccaatt tttatttcca ttttgactga   480
gagcaagatg ttccttttag gggatggaag cgtctgggtt tcccacactg aatgactcaa   540
ctcgaatgtt gcctcattaa cattctcgat ttttccgtaa tctctgctcc atgcattcaa   600
gataactgtg cctatcacaa atggcttttt agcagctcca ctctttctgg ggatgtggtg   660
gcccttccag tagctgccac cacggattgt cttcaatttc tcacttgttt ttgagttgag   720
tgtcagcctg acccctgggc atggccgcac atgactcagg caaagtgaga gtttcatcac   780
taaacgtggc tctgtttgct atgtctgttt tccctctaag agcaggttat tcaaatacca   840
tctggctgag gtcaagttgc ctcagagccc acagaatctc tacccaggtc cctgttggat   900
ccctaaaaac tcagtcatgc tgtaatctcc ttctgaaact gtgcaatgcc tgcaggctgt   960
cagcccagct ctctccttct gcttcctgtc ctcctaggac cccatgcctc ctcaaacgtc  1020
cacgtgtttc ttgctcctcc accacggttg ccaagccaaa attcgggtgg gcgggaggac  1080
attttcccaa gtgcctgttt cccttctttt cctttgaca ccccagataa atcatctttc  1140
ccaatccaac acagcccac tgtgtctttg gggacttcat gacatcaccc aggaatgtat  1200
ccttagaaac aaaaatgcaa aacccagaac accaggagac aattaaagaa attttcactg  1260
gtgaggtcac aagtagtaga gacttcttgt taacgggcag aaactttcac ggacccagca  1320
tgctactgtg gcagttctgc aacaagctga aaatgccttt cccgaccacc caagccagtg  1380
ccacacaaag gccaccttag ggtgtgcaca ggatgtcact aggcgttggc ggaactcagg  1440
aaggagtctg aatttcttcc cgtttcttcc ttcctctctc attccctatc ttagcttctg  1500
tctctctttc ctctctctcg ttccccccct tcctccctcc cttcctgttg cagggccaca  1560
gatggaccgg gagacctcaa gcatgtcaaa tcaactaact gctctaccac tcaaccacac  1620
cctcgcctgc attgttacta ctactattat tatcttgata caggtctcca cattgagctc  1680
accctcacag tctccacatt gagctcaccc tcacagtctc cacattgagc tcaccctcac  1740
agtctccaca ttgagctcac cctcacagtc tccacattga gctcaccctc acagtctcca  1800
cattgagctc accctgtggc tctggcaaac cttgaattct ctcattcctc ctgcctcagc  1860
ctctggggtc gtggggatta gccaaaccca cttgaggttt tcttcaatca gcaaattctt  1920
agcgttcaat taacacacac tcataactcc agtactttgg aaaccggaac aggagaattt  1980
ctgtgagctg gaggctagct tggactacag tatgagaccc tgtctctaaa taaatacaca  2040
aagaaatctc accaagggcc tccctctctc agcaagctct aactgtggtg ggagttctgg  2100
gttgttccag ttaacgggct cagaactcta ctgcccagca catcagcccc tagacacagg  2160
tggctctcta catgtgaaca tgcagtcaca gaaatgaaat aaagtgaaaa ttttatttct  2220
tcagttgtat agcctcttcc gtgtgggctg tagttactgt cttgaatagg ataggctcag  2280
```

```
aatccttggt gctggaacca agagtttgat tccattagac gacagggaat ataatgccca  2340
atagggcatt cctcctcccg gtcactagcg gtgcactttc tccgaatctt tgtcatgttg  2400
aattagaaaa gttagtattt tcctccatcc cttcccctcc tcccctcctc ccctcctccc  2460
ctcctcccct cctccctccg tctccccgcc cctcccctcc ccctctgatc ctcccccatc  2520
tatcaaatcc aagaattcca gtaaaaagag gaaaacaatc gaagtgattt cgttgattgt  2580
cagttccacc aaagcaagac ttgactttag ttccgcgttt cggttcccgg catgcaccac  2640
agccagcgag caccgtggaa ggatgctagc acggtcctcc ccccgcccc actagctgtc   2700
ttcagctccc cagtagaggg caaccgcact ccagattctc aatggagagt gtttacacaa  2760
tcgttgcggg tttgtgtgag cgcgcccgct tccagagaca cttcttcttt ttcttttttc  2820
catttcatcc cagtggcaac gcagagtgcc agatcattca ggccgtttgc agggcaagcc  2880
gtgggagctt ggcaagcaag gccccatttc ctagggaacc cgtgcctggc gcttcaggaa  2940
agcacgggaa cctggcactg tgactctgcg ggtattattt tgcagaactc tttattaaac  3000
gggagtttca agtccagctg gagacgacca ggcagcgcct ttaaccccag agtcacacac  3060
aggtgccttt tcttggggcc agattggggt tgtgtggcag acctgcgacc agcttgacaa  3120
ctcttctgcc aggccacaaa atggtgttgg ctgtaagagg tgacaccagg gacagggaag  3180
atcgctgcta ttctcctgag ctctccaaag acccacacca gtctgtcccc ctttcctcct  3240
gctcttcccc tgtatcgccc cctcaccatc tcccccaacg agactcttgg catctcctcg  3300
gcacaaggat ttgaaaatag atgcttgggg gtgagaagaa gaagagagaa agagagagaa  3360
ggaaggaagg atatatagat gatacagacg catacaggtg acatgtagct aatcattttt  3420
aattaaaaaa taaattaaaa gcaaatcaag gatatatatg ataccttag agcaagtgtc   3480
tcatacacac acaaacacac acacacaata tatatatata tatatatata tatatatata  3540
tatatatata ttatacttgg aacaagtgtc cagaagggct ggggactcta aagtgcttgt  3600
caaagccagg ctcacatcag taatcttatc acctggtaga ctgagacagg aggattttga  3660
tgagttcagg cccagcctga gctgcagaat gtgattctat cccaaaaaag taaaataaaa  3720
taaaattcaa aatacacgaa aagagtattt gctgaacaaa caagcctaaa gccctggatc  3780
ccttcccca tgtcctaaga aaataagttt cttgaagctg gagggatggc tcagaggtta   3840
agagccccag ctgcacttgc ggaacactaa gacccagttc ccagacccca cactgtgggt  3900
cacaactgtc tcaaacgcca gctccggagg atccatgccc tctcctggcc tccaccggca  3960
ccaagaacac atacagtgcc catacattta tgcaagcaag gtattcacgc acataaaact  4020
aaaagaatat ttaataaaga tataacaaaa tagcatgaag cccagctggt acagaggttc  4080
aaactacatc ccaggttcat ccctctgcct ttgctctcag ttggcttggg taggtctctt  4140
ctctgaactg gcgccctgcg ggttccacat tgagaccctc tcatttttaa acctacttct  4200
tctgggcggg gttaattgct gccagggctc aagccaacgc ttcctcttct ccacagcaat  4260
cttccaagtt tcacgagata accaggaact gctaagttca tgtgaacctt agtgaagaac  4320
ctgagtcttc ccatgtgatt ggtgtgtgca tgtgtgcata cacaaatgta tgtgtgtgct  4380
ctatgtgtgc ctatgtatgt gtgcatgcat gtgtgcatat acaaatgcat atatgtctat  4440
gtagtgtgcg tacacaaatg tatgtgtgtg ctcaatgtgt gcctatgtgt gtgtatgcat  4500
gtgtgcgtac acaatgcatg tgtgtggtgt ctgtgtgcct gtgtgtgtat gcatgtatgc  4560
atacacaaat gtatatgtgt ggtgtgtgaa tgtgtgccta tgtatgtgtg tgctgtgtgt  4620
gggtgtggta tgtgtgtgat gtgtggaggg gtgtgtatgt gtggtatgta taggtgatac  4680
gtttgggtg taatatgcgt atgtggtttg tgaaatgtag ttcgtgtgtg tgcatgtgtg   4740
cgtgcgtgcg tgcgtgcgtg cgtgtgtgtg tgtgtgtgtg tgtgtgtgtt ggatatagta  4800
tgtgtgaggt gtgtgtactc accatggcct ccctcacttg ggggagtgaa gtcagcagcc  4860
tggaccactc agggacatga gatactcaga cacatcttga tttccacccc tcttttcctg  4920
atcctccttc acgtgtcact ttcccaaaca ctggacaaca gtttgggggc atctgattcc  4980
actaatgaca gggacatcac atgtctccag agggaacacc ttctgtgtca catgtcatct  5040
gagaatgtag cagagtcaca gagaaatgtc acagaaacca aaatgcagag taccaaggta  5100
tagctaggca cagagcagag gggaagccgc tgaatttatt aaaaatgtca gaatcgtaaa  5160
agacagggga cagcggtggg gacattcagg gtccagtagc acacaggcag tccaaacctg  5220
atcactggaa ggtagtaggt aaggaaaggc tgcacacaga ttattcacac agtttataca  5280
tgtacacaga ttattcacat ggtttgtgta tgtgcacaga ttattcacac agtttataca  5340
tgtgtggctt cgtggtaact ttgagcttac tttcaattta aaaggatctc tctcacaagc  5400
tggggccggg aatggctgca gtcaacactc catcacttag tcacactgtg caaacagcac  5460
ctcctgactc atggtgactt gtagtaaaat gaagaggcca catttgcatc caagacagct  5520
catcagtacc tagtgaagaa tctgtccctg agtatttgca tgaatggacc cgggtccagg  5580
gcctggctgg gagtctccag tgttgcagc cagaatgtca ttgtgttttt tcaggatccc   5640
agaagtttct aaaatacagg ccaagtactc atttgtgtta caaagtatct gactaataga  5700
agtgattagg taacacaaag ccttttaaaa accgagatca cccttgtcat gtccctggcc  5760
tcttagaaca agatccaagc ttttgctggt tgacaagtgg ggcatccag tgcgtctccg    5820
ttcctgctac ttcatctgga agacctctcc cactaacttg ccctgaccc ctcacacctg    5880
ctgtttcctt tccacccgga agtgcttgtc taggctttca tggccatctg actgagcatc  5940
taggcctcag tccagtggtc cctcagctct ctctagtcac tgtactaatg gaaacggcca  6000
ctaactacat tttcaatatg gaagcctcct cctcaggaac ctccaagggc agaagcctcc  6060
agagaaccac tcctgacccc ctggagttct gagtgcttct gtgtctgcag ggctctctgg  6120
gactattcac cacttgtgtt gaatggttca gtcctcacct cctctggcat gtgctcagtt  6180
ctcatctcat tggggagtcc ttcccaggtc actcttctct cctgtctttg aagtgttttt  6240
ttccttcatg gtatttctgt ctgggcacac acacagacac acatacacac acatacacac  6300
ccatgcagta tggcagatac atcacctatg tttcagattt ttattctacc atcacccaat  6360
acctgaatcc ccgaaaaagc cttagaaagc caggaatttg tgtattttg tcagcactcc    6420
accccagcac ctgaagccaa gcctgactta atattttgg ttttgtttct aga            6473
```

SEQ ID NO: 8          moltype = DNA   length = 7045
FEATURE               Location/Qualifiers
source                1..7045
                      mol_type = genomic DNA
                      organism = Cricetulus griseus
SEQUENCE: 8
caattgatta tagatggatg atagatagat agatagatag atagatagat agatagatga  60
tggatagaca gatgatggat agttagagga tagataatga ctgaataata agtacataaa  120

-continued

```
tagatgatag agcggggcgt tggtggtgca cgtctttaac cccagcacca gagaggcaga    180
ggcagttgga tctctgtgag tttgaggaca gcctggttac agaatgggtt ccaggacagc    240
caaggctgtc actcagagaa atactgtctc aaataaaaaa agtaagtaaa caaataaata    300
aatgataact agttagaaga tagatgattg aatgataggt agataaatag aagatagata    360
gatagatgat tgatagatga tagacagata gacagacaga cagacagaca gacagcagaa    420
agataatgca cggtgaaaca tggtctgatt tagttagcaa gatcagagaa gccttctttg    480
aaagtgacat ttgagagcat ttcaaacgct gttcatgtca ggcatgccaa tggggagaga    540
agggcttgca gaaagcaggc ccggcaagcc atggggagca agctaggagg cagcattcct    600
tgcatttgcc tctgcctcag ctgcttcctg gagttccccg gtttttatca caacagtaga    660
aataaaacca ggacaatgtt gtttccatgc atacatctgc aagaacttac tccggttcaa    720
tagacagacc aaggcacctg tgtttgctca agaagcacgg agggaggtgt gtgcacctgc    780
tgggtgctgg tgctctggct gtgccagaca gagagcaaga caggaaagtt cctggtggcc    840
tagagcacac agcccagccc aggaagtcat gtctctctct gtctctgtct ctgccccacc    900
cccacccat ttaggccaga gaacagctgt ggcaagcttt gggtttgggt gagtcattcc    960
tcaagagcca agagccgccc accttgtatg gggtagtttg ttgttgttgt tgttgttatt   1020
atttgtttgt ttgtttgttt ggtaaaggtt tttcaatagg agttggaatt tggcaattca   1080
gctaggctgg ctgagcagcc agctagcccc gggcactcat ccgtctctac ctccccagtt   1140
ctgggatttc gggtacatgc tgccacatcc gacttttttc ccctgctcca gttcttaaga   1200
ccaagtcttc atgtcaaaca cttcaccacc ttagccatct ttctgggtca gaagttagat   1260
cttcaggaag acaaggagtg tatcaggaca tgagcgtgcc ccaactctgc tcagaccttc   1320
tgatagaaa aatggggggga ggggtgtcag aggctgccgg agaaagacaa gtccaggtta   1380
aggaggacga ccctgggctc tgaatccaag ggtgattccc tcaccttgta cacttggcat   1440
tttgggaagg aagcatcaga taaaagcagt gcagacatag tcaggaatat ttacacgtgt   1500
gagtcaacct gggagtgagt ctgtgtacaa ctgaacatga agcaagtttt gaagcttcat   1560
ttccagacta ttcccagggt gcaataactt cctgttttcg ttgcagcctt cccagtctct   1620
gccactgcca tctctacttc agtctggaat ggtgggcaca cagaaaaagt ctatggcaat   1680
cctgcgagaa gacaagtggg cgcctgactt cgggctcctg ttacaagaga ggaatccagg   1740
agtttatttt gcagctgatt cagtgttgac caagagtcca gctctggggg agtgggaagc   1800
aaccaaagca gagacaggtc ccagcacaat ttttggtttt caagacagca cttctctgtg   1860
gctttgaagg ctatcctaga actgttcttt gtatatcctt ccttgcaact agctcttata   1920
gaccaggctg gtcttgaact cacagagatc catctgcctc tgcctcccaa gtgctgggat   1980
taaaggcgtg cacctcggct gccaccaccc agctacatac ataatttaca ataataaaaa   2040
taaaatactt taaagtgtta tagcagtttg aatgtaattg gccctgtcat ctcatacggga  2100
gtggcactat taggaggtat ggctttgttg aaggaaatat gtcactgtga gggtgggctg   2160
tgaggtttcc tatgctcagg gtaccagcca gtgtctcagc tgaggtcctg ttgcctgcaa   2220
gatgtaggac tctcatccct ttctccagca ccatgtctgt ctgcatgcca tcatgttccc   2280
agccatgatg acaatgtact aaaacctctg aaactgccac ccaactaaat gttttccttt   2340
ataagagttg ccatgctcat ggtgtctctt cacagcaata gaaaccctaa ctaagataag   2400
tgtattctcc cctactcccc atgatttaaa atttaggaag gcaggtaggc aggcaggcag   2460
gctggtatag tggttcattc tagcacctga gacctggaat gggaggattg tgagttagtt   2520
ctaggccatt ctggtgccta gaaaccagag ccggggggttg gcccaatgca gagcacttgc   2580
tctacgtatg gcccagcaca ataagtcaat ttcctcacct taaaggcttg acaatttaaa   2640
aacactggtt tttagttagt ccgtgtctgc tccacagatg gagacagcta atcacagatg   2700
catcaggggc cttcctgagt gctaaacatc aaacagcctt ctccctcct gagcctttgt    2760
gtgcagaatg tgtccatcgc aagaagcaaa cagtcttgct tgcccaccaa cttccttcct   2820
gcatcagaag agctgggtgc aaactgcaag agtagcctca ccttagagat gggtcccatt   2880
gctctacatg ggagcattac cttccaagaa ggcaaaaatg tcctggtt gagcttttt     2940
tgtcacctgt taaaggcaaa tcaacagaga ggctttgtct cacccactaa catcttggaa   3000
acaaatacca acgaacgctg gggaggatgt ggggaaagca gagccctcat gctctccgag   3060
ggaaaatcac acccactgtg gaacagtgtg gaaacctcaa agactgggat tacaagcagc   3120
acacaagcca gccacgctac tcctggtcac acaccacaaa gacgcttgca cattcacgct   3180
tacgctgcga acactagcaa cgttcccact gcctcctttg agcccgccc ccgcccctg     3240
cccccgccc cgcccctgtg gtctatgttc ctcttccta aagtcagctt ccacttctct     3300
gtctccatct tcgcccaccc ctcccctcctc gctacataat tgtctctatt ccatttctct   3360
gctttgaaac agctttttgc aaagcatcaa atctattgtc ctatgcccca aatcaacctc   3420
cagtttcaca agtgatacag gaaatcgttt tcctaattaa aaatcccccc tttgaccatt   3480
tattcccact cttggaacat cttccccttg aggaaagtta cagaatgagg tggctctcct   3540
cttcctattc gaggtgtttc cttcagactt tgtccgtgtc taatctttt aactgttggc    3600
caggcctcca ccacggcaca gatgaactgt ggggttcatt tacctgaaac tctatggaag   3660
gatgtttatt tctccttcac tttagcaaat gataaaggggc accattcact ctgtctattc   3720
tgcaggggcc attcctttct ctaggccaga tactgagaat tgctcccaga atcaatgtgg   3780
tatacatatt tcccccttcaa cattgatagg cattgatcac acacacacac acacacacac  3840
acacacacac acacagtagc acaaatgtat tcccctagcc cgcttccatc ttgccacagg   3900
actccagagt ggcctggat agcaagcttc ctgtttttgt tctctgttcc tgctgctttt    3960
ccaccctcca gtctatcttt tctaagtcct tctgccattg tcctcttccc aactgtcctg   4020
agatgcagtc attgtctggg attcagacct tctctctctg cccaagtgag tatattgacc   4080
cccacgtttt gtacaaccat aacttcaggg agcccgacaa aaactgtttt atgagccaag   4140
tagtcccagg acttgagagg tagaggcggg aagatcagca gtttgaggcc agcctggaga   4200
gcataagagc cggtctcaaa acaacaatgg aaactagata ctaagtaaaa atcctggggt   4260
gtttcatcat gaatgtctgt tcttctagta ccacgctgaa ctccgtacac agctccagct   4320
gttacggctt tcttagaatc catactcttt tttttttttt tttttttttt tttttttgg   4380
tttttcgaga cagggtttct ctgtggcttt ggaggctgtc ctggaactag ctcttataga   4440
ccaggctggt ctcgaactca cagagatcca cctgcctctg cctccagagt gctgggatta   4500
aaggcgtgcg ccaccaacac cggcagaat ccatactctt tttaaaaaaa gatttatcaa    4560
tttactatgt atacagcttt ctgcctgcat gtatccatgc atgtcagaag atggcaccag   4620
gtcgcattac agatggttgt gagccaccat gtggttgctg ggaattgaac tcagaatgtc   4680
tagaagagca accagttctc ttaacctctg agccatctct ccggcccca gaaatccata    4740
ttcttgagga tttttttacac cccccccacc aaaagacgta tatctaaatt ttaatgtgag   4800
aattcacatt ttcttaagag ttgaacatag atttagagga aaatcagatc ccacatgatt   4860
```

-continued

```
aacaaagcat gcttgtgggc aggtctgcta ccaagaggtg ggccgtagct tctagctcag 4920
acaaactcac tcccttcctc gtggcctctt cgccctcaag tcagaaactc accctgtgat 4980
tctgccccag aagttgctct agagcacagt gcatccttcc gtcttcactc tgtggcttga 5040
attgtgtcca tcgcttatga ttacaacccc tcacagagca tcctaactgg tttctttgca 5100
tgcctatggg cactcctcca ttctagaaca cccttgccat caatactatg aaaggagggg 5160
tggaggagga agagcaggaa gaggaggggg aagcgaggga agaggaagac acggatgggc 5220
atgaggaggg gggagcaccc aagtcctccc tggatgagag tctcactggg agacttaata 5280
ttaattataa atgcttggtc agcagctggg caggataagg ttaggcagga gaaccagact 5340
aaggactctg ggaagcagaa gggcagagtc agacaaggag aggaaacagg aagtacaagg 5400
taaagtcacg tggcagaatg tagataaatag aaatgggttc atttaagttg gaagagttag 5460
ctagtaacaa gcctgagcta tcagccgagc atttataatt aatattgagc ctccatattg 5520
gttatctggg aattggcggg cagaaaaaaa aaagtctgcc tacaagtcaa tgtcatgtag 5580
ctcccaaagc caaggtacct ttgttcagtg cttgactgag ccagcattat aaattttctc 5640
cagatgtacc gaatcacatt tcatagcaac atgcagacat caagtttttcc ctgaagctct 5700
aaccagctgg ttgcatgctg tccggagtct cagctataac ccagaagtga cctgggtcgg 5760
ggaagaggtg gtactttgcc ttctttgcac tctctgtgtt gcctcaccca ttcagcttca 5820
agcaatgtga ctgcctgacc ctgagggcgt ttacaacgcc tgacccacag accacaagtc 5880
aaccagctgg tgtgctcacg atacctagtc tgaaccatag ccctgctccc accctgcctc 5940
catctccacc ctttcttcac tgctcatcac agctggctag caaagactgc ctcagacctg 6000
agcacaggct ccactccaca gccgtgactg ttcgagccac ttaaatcaaa gagcgcttgt 6060
cttccgctca gtaaatctct cctcagctca ctgatgacgt tgactttctc tagacagcac 6120
atttgggttt aagacactgc tacttgagct cttcattcag ttcctcagaa tacctcattt 6180
gggtcagatt cccaaagagg aagatagggt tcctggcaga cagacatgtc tcattccttt 6240
gaaatccttc agagaaatgc agtgactatg gcaccttctt aaaaagcaca cacacaaata 6300
acacacacac acacacacac acacacac acacacacac atatccccct cactgtcatc 6360
cttgatatgt atatgatata tataaaatca ttgtttatata ctgtgataat tgattatgaa 6420
taaaatttac taaaatgaac aattaaaatt atgggggggg ctggagagat ggctcatcag 6480
ttaagagaac agttgctgct cttgcagaac acgagagttc agttcccagc acccacatca 6540
ggcagctcat aaccatgtgt ggtgtcagtt ccaggagatc tggtgccctc ttctggcctc 6600
ctccagcacc tgctacatgt ggttcacaca cacacacaca cacacacaca cacacacaca 6660
cacacacaca caaataaaata taaagattat ttttttcaaa actgagttaa aaataggttc 6720
tatctgattc atactaaggc ttttcacagt ggttaagtct attagatatg tctagccata 6780
tcctttctcc cttctttctt gaggagaggc ttttaaagct acaagttaca gccttctttg 6840
caaataagag taccatttaa caggcctctg accaatgaga tgccagaatc ggttgcccag 6900
gagcttccca aacagtccat tatagggaaa ggtggtacaa accagtagat taggcatgtt 6960
ccacttccta agtgccgtgc caaataagga aatggcctca aatgtttgcc ttttatcttc 7020
acccacctct gaattgcacg ctagt 7045
```

```
SEQ ID NO: 9            moltype = DNA   length = 13515
FEATURE                 Location/Qualifiers
source                  1..13515
                        mol_type = genomic DNA
                        organism = Cricetulus griseus
SEQUENCE: 9
tctagaaaca aaaccaaaaa tattaagtca ggcttggctt caggtgctgg ggtggagtgc 60
tgacaaaaat acacaaattc ctggctttct aaggctttt cggggattca ggtattgggt 120
gatggtagaa taaaaatctg aaacataggt gatgtatctg ccatactgca tgggtgtgta 180
tgtgtgtgta tgtgtgtctg tgtgtgtgcc cagacagaaa taccatgaag gaaaaaaaca 240
cttcaaagac aggagagaag agtgacctgg gaaggactcc ccaatgagat gagaactgag 300
cacatgccag aggaggtgag gactgaacca ttcaacacaa gtggtgaata gtcctgcaga 360
cacagagagg gccagaagca ctcagaactc caggggggtca ggagtggttc tctgaggct 420
tctgcccttg gaggttcctg aggaggaggc ttccatattg aaaatgtagt tagtggccgt 480
ttccattagt acagtgacta gagagagctg agggaccact ggactgaggc ctagatgctc 540
agtcagatgc ccatgaaagc ctagacaagc acttccgggt ggaaaggaaa cagcaggtgt 600
gagggggtcag gggcaagtta gtgggagagg tcttccagat gaagtagcag gaacggagac 660
gcactggatg gcccccacttg tcaaccagca aaagcttgga tcttgttcta agaggccagg 720
gacatgacaa gggtgatctc ggttttttaaa aggcttgtg ttacctaatc acttctatta 780
gtcagatact ttgtaacaca aatgagtact tggcctgtat tttagaaact tctgggatcc 840
tgaaaaaaca caatgacatt ctggctgcaa cacctggaga ctcccagcca ggccctggac 900
ccgggtccat tcatgcaaat actcaggggac agattcttca ctaggtactg atgagctgtc 960
ttggatgcaa atgtggcctc ttcatttttac tacaagtcac catgagtcag gaggtgctgt 1020
ttgcacagtg tgactaagtg atggagtgtt gactgcagcc attcccggcc ccagcttgtg 1080
agagagatcc tttttaaattg aaagtaagct caaagttacc acgaagccac acatgtataa 1140
actgtgtgaa taatctgtgc acatacacaa accatgtgaa taatctgtgt acatgtataa 1200
actgtgtgaa taatctgtgt gcagcctttc cttacctact accttccagt gatcaggttt 1260
ggactgcctg tgtgctactg gaccctgaat gtcccaccg ctgtccctg tcttttacga 1320
ttctgacatt tttaataaat tcagcggctt ccctctgct ctgtgcctag ctataccttg 1380
gtactctgca tttttggtttc tgtgacattt ctctgtgact ctgctacatt ctcagatgac 1440
atgtgacaca gaaggtgttc cctctggaga catgtgatgt ccctgtcatt agtggaatca 1500
gatgcccca aactgttgtc cagtgttttgg gaaagtgaca cgtgaaggag gatcaggaaa 1560
agaggggtgg aaatcaagat gtgtctgagt atctcatgtc cctgagtggt ccaggctgct 1620
gacttcactc ccccaagtga gggaggccat ggtgagtaca cacacctcac acatactata 1680
tccaacacac acacacacac acacacacac acgcacgcac gcacgcacgc acgcacacat 1740
gcacacacac gaactacatt tcacaaacca catcgcacta ttacacccca aacgtatcac 1800
ctatacatac cacacataca cacccctcca cacatcacac acataccaca cccacacaca 1860
gcacacacat acataggcac acattcacac accacacata tacatttgtg tatgcataca 1920
tgcatacaca cacaggcaca cagacaccac acacatgcat tgtgtacgca cacatgcata 1980
cacacacata ggcacacatt gagcacacac atacatttgt gtacgcacac tacatagaca 2040
tatatgcatt tgtatatgca cacatgcatg cacacataca taggcacaca tagagcacac 2100
```

-continued

```
acatacattt gtgtatgcac acatgcacac accaatcaca tgggaagact caggttcttc 2160
actaaggttc acatgaactt agcagttcct ggttatctcg tgaaacttgg aagattgctg 2220
tggagaagag gaagcgttgg cttgagccct ggcagcaatt aaccccgccc agaagaagta 2280
ggtttaaaaa tgagagggtc tcaatgtgga acccgcaggg cgccagttca gagaagagac 2340
ctacccaagc caactgagag caaaggcaga gggatgaacc tgggatgtag tttgaacctc 2400
tgtaccagct gggcttcatg ctattttgtt atatctttat taaatattct tttagtttta 2460
tgtgcgtgaa taccttgctt gcataaatgt atgggcactg tatgtgttct tggtgccggt 2520
ggaggccagg agagggcatg gatcctccgg agctggcgtt tgagacagtt gtgacccaca 2580
gtgtggggtc tgggaactgg gtcttagtgt tccgcaagtg cagctggggc tcttaacctc 2640
tgagccatcc ctccagcttc aagaaactta tttttcttagg acatgggga agggatccag 2700
ggctttaggc ttgtttgttc agcaaatact cttttcgtgt attttgaatt ttattttatt 2760
ttactttttt gggatagaat cacattctgc agctcaggct gggcctgaac tcatcaaaat 2820
cctcctgtct cagtctacca ggtgataaga ttactgatgt gagcctggct ttgacaagca 2880
ctttagagtc cccagccctt ctggacactt gttccaagta taatatatat atatatatat 2940
atatatatat atatatatat atatattgtg tgtgtgtgtt tgtgtgtgta tgagacactt 3000
gctctaaggg tatcatatat atccttgatt tgctttttaat ttattttta attaaaaatg 3060
attagctaca tgtcacctgt atgcgtctgt atcatctata tatccttcct tccttctctc 3120
tctttctctc ttcttcttct caccccccaag catctatttt caaatccttg tgccgaggag 3180
atgccaagag tctcgttggg ggagatggtg aggggggcgat acagggggaag agcaggagga 3240
aaggggggaca gactggtgtg ggtctttgga gagctcagga gaatagcagc gatcttccct 3300
gtccctggtg tcacctctta cagccaacac cattttgtgg cctggcagaa gagttgtcaa 3360
gctggtcgca ggtctgccac acaacccaa tctggcccca agaaaaggca cctgtgtgtg 3420
actctggggt taaaggcgct gcctggtcgt ctccagctgg acttgaaact cccgtttaat 3480
aaagagttct gcaaaataat acccgcagag tcacagtgcc aggttcccgt gctttcctga 3540
agcgccaggc acgggttccc taggaaatgg ggccttgctt gccaagctcc cacggcttgc 3600
cctgcaaacg gcctgaatga tctggcactc tgcgttgcca ctgggatgaa atggaaaaaa 3660
gaaaaagaag aagtgtctct ggaagcgggc gcgctcacac aaacccgcaa cgattgtgta 3720
aacactctcc attgagaatc tggagtgcgg ttgccctcta ctggggagct gaagacagct 3780
agtggggggcg ggggaggac cgtgctagca tccttccacg gtgctcgctg gctgtggtgc 3840
atgccgggaa ccgaaacgcg gaactaaagt caagtcttgc tttggtggaa ctgacaatca 3900
acgaaatcac ttcgattgtt ttcctctttt tactggaatt cttggatttg atagatgggg 3960
gaggatcaga gggggagggg aggggcgggg agacggaggg aggaggggag gaggggagga 4020
ggggaggagg ggaggagggg aagggatgga ggaaaatact aacttttcta attcaacatg 4080
acaaagattc ggagaaagtg caccgctagt gaccgggagg aggaatgccc tattgggcat 4140
tatattccct gtcgtctaat ggaatcaaac tcttggttcc agcaccaagg attctgagcc 4200
tatcctattc aagacagtaa ctacagccca cacggaagag gctatacaac tgaagaaata 4260
aaattttcac tttatttcat ttctgtgact gcatgttcac atgtagagag ccacctgtgt 4320
ctaggggctg atgtgctggg cagtagagtt ctgagcccgt taactggaac aacccagaac 4380
tcccaccaca gttagagctt gctgagagag ggaggcccct ggtgagattt ctttgtgtat 4440
ttatttagag acagggtctc atactgtagt ccaagctagc ctccagctca cagaaattct 4500
cctgttccgg tttccaaagt actggagtta tgagtgtgtg ttaattgaac gctaagaatt 4560
tgctgattga agaaaacctc aagtgggttt ggctaatccc cacgaccccca gaggctgagg 4620
caggaggaat gagagaattc aaggtttgcc agagccacag ggtgagctca atgtggagac 4680
tgtgagggtg agctcaatgt ggagactgtg agggtgagct caatgtggag actgtgaggg 4740
tgagctcaat gtggagactg tgagggtgag ctcaatgtgg agactgtgag ggtgagctca 4800
atgtggagac ctgtatcaag ataataatag tagtagtaac aatgcaggcg agggtgtggt 4860
tgagtggtag agcagttagt tgatttgaca tgcttgaagt ctcccggtcc atctgtggcc 4920
ctgcaacagg aagggaggga ggaaggggg gaacgagaga gaggaaagag agacagaagc 4980
taagataggg aatgagagag gaaggaagaa acgggaagaa attcagactc cttcctgagt 5040
tccgccaacg cctagtgaca tcctgtgcac accctaaggt ggcctttgtg tggcactggc 5100
ttgggtggtc gggaaaggca tttttcagctt gttgcagaac tgccacagta gcatgctggg 5160
tccgtgaaag tttctgcccg ttaacaagaa gtctctacta cttgtgacct caccagtgaa 5220
aatttctttta attgtctcct ggtgttctgg gttttgcatt tttgtttcta aggatacatt 5280
cctgggtgat gtcatgaagt cccaaagac acagtggggc tgtgttggat tgggaaagat 5340
gatttatctg gggtgtcaaa aggaaaagaa gggaaacagc cacttgggaa aatgtcctcc 5400
cgcccacccg aattttggct tggcaaccgt ggtggaggag caagaaacac gtggacgttt 5460
gaggaggcat ggggtcctag gaggacagga agcagaagga gagagctggg ctgacagcct 5520
gcaggcattg cacagtttca gaaggagatt acagcatgac tgagttttta gggatccaac 5580
agggacctgg gtagagattc tgtgggctct gaggcaactt gacctcagcc agatggtatt 5640
tgaataacct gctcttagag ggaaaacaga catagcaaac agagccacgt ttagtgatga 5700
aactctcact ttgcctgagt catgtgcggc catgcccagg ggtcaggctg acactcaact 5760
caaaaacaag tgagaaattg aagacaatcc gtggtggcag ctactggaag ggccaccaca 5820
tccccagaaa gagtggagct gctaaaaagc catttgtgat aggcacagtt atcttgaatg 5880
catggagcag agattacgga aaaatcgaga atgttaatga ggcaacattc gagttgagtc 5940
attcagtgtg ggaaacccag acgcttccat cccctaaaag gaacatcttg ctctcagtca 6000
aaatggaaat aaaaattggg gcttgaattt ggcaaatgat tcagaactct gtgtaggtat 6060
tttcacacgc acagtggata attttcatgt tggagtttat ttgtgctaaa aggcagaaaa 6120
gggtaaaaag cacatcttaa gagttatgag gttctacgaa taaaaataat gttacttaca 6180
gctattcctt aattagtacc cccttccacc tgtggtaatt tcctgagata gtcagtgggg 6240
aaaagatctc tccttctctt ctttctcccc ctcccctcct ctccctccct ccctccctcc 6300
ctccctcctc tccctccctc cccctttcct tcttctcttg ctccttctcc tctgcctcct 6360
tctcccttc ttcttcattt attctaagta gcttttaaca gcacaccaat tacctgtgta 6420
taacgggaaa acacaggctc aagcagctta gagaagattc atctgtgttc actagcgtgc 6480
aattcagagg tgggtgaaga taaaaggcaa acatttgagg ccatttcctt atttggcacg 6540
gcacttagga agtggaacat gcctaatcta ctggtttgta ccacctttcc ctataatgaa 6600
ctgtttggga agctcctggg caaccgattc tggcatctca ttggtcagag gcctgttaaa 6660
tggtactctt atttgcaaag aaggctgtaa cttgtagctt taaaagcctc tcctcaagaa 6720
agaagggaga aaggatatgg ctagacatat ctaatagact taaccactgt gaaaagcctt 6780
agtatgaatc agatagaacc tattttttaac tcagtttga aaaaaataat ctttatattt 6840
```

```
atttgtgtgt gtgtgtgtgt gtgtgtgtgt gtgtgtgtgt gtgtgtgtgt gaaccacatg  6900
tagcaggtgc tggaggaggc cagaagaggg caccagatct cctggaactg acaccacaca  6960
tggttatgag ctgcctgatg tgggtgctgg gaactgaact ctcgtgttct gcaagagcag  7020
caactgttct cttaactgat gagccatctc tccagccccc cccataattt taattgttca  7080
ttttagtaaa ttttattcat aatcaattat cacagtataa aacaatgatt ttatatatat  7140
catatacata tcaaggatga cagtgagggg gatatgtgtg tgtgtgtgtg tgtgtgtgtg  7200
tgtgtgtgtg tgtgttattt gtgtgtgtgc tttttaagaa ggtgccatag tcactgcatt  7260
tctctgaagg atttcaaagg aatgagacat gtctgtctgc caggaaccct atcttcctct  7320
ttgggaatct gacccaaatg aggtattctg aggaactgaa tgaagagctc aagtagcagt  7380
gtcttaaacc caaatgtgct gtctagagaa agtcaacgtc atcagtgagc tgaggagaga  7440
tttactgagc ggaagacaag cgctctttga tttaagtggc tcgaacagtc acggctgtgg  7500
agtggagcct gtgctcaggt ctgaggcagt ctttgctagc cagctgtgat gagcagtgaa  7560
gaaagggtgg agatggaggc agggtgggag cagggctatg gttcagacta ggtatcgtga  7620
gcacaccagc tggttgactt gtggtctgtg ggtcaggcgt tgtaaacgcc ctcagggtca  7680
ggcagtcaca ttgcttgaag ctgaatgggt gaggcaacac agagagtgca aagaaggcaa  7740
agtaccacct cttccccgac ccaggtcact tctgggttat agctgagact ccggacagca  7800
tgcaaccagc tggttagagc ttcagggaaa acttgatgtc tgcatgttgc tatgaaatgt  7860
gattcggtac atctggagaa aatttataat gctggctcag tcaagcactg aacaaaggta  7920
ccttggcttt gggagctaca tgacattgac ttgtaggcag actttttttt ttctgcccgc  7980
caattcccag ataaccaata tggaggctca atattaatta taaatgctcg gctgatagct  8040
caggcttgtt actagctaac tcttccaact taaatgaacc catttctatt atctacattc  8100
tgccacgtga ctttaccttg tacttcctgt ttcctctcct tgtctgactc tgcccttctg  8160
cttcccagag tccttagtct ggttctcctg cctaacctta tcctgcccag ctgctgacca  8220
agcatttata attaatatta agtctcccag tgagactctc atccaggag gacttggtg   8280
ctcccccctc ctcattgcca tccgtgtctt cctcttccct cgcttccccc tcctcttcct  8340
gctcttcctc ctccaccccct cctttcatag tattgatggc aagggtgttc tagaatggag  8400
gagtgcccat aggcatgcaa agaaaccagt taggatgctc tgtgaggggt tgtaatcata  8460
agcgatggac acaattcaag ccacagagtg aagacggaag gatgcactgt gctctagagc  8520
aacttctggg gcagaatcac agggtgagtt tctgacttga gggcgaagag gccacgagga  8580
agggagtgag tttgtctgag ctagaagcta cggcccacct cttggtagca gacctgccca  8640
caagcatgct ttgttaatca tgtgggatct gattttcctc taaatctatg ttcaactctt  8700
aagaaaatgt gaattctcac attaaaattt agatatacgt cttttggtgg ggggggtgta  8760
aaaaatcctc aagaatatgg atttctgggg gccggagaga tggctcagag gttaagagaa  8820
ctggttgctc ttctagacat tctgagttca attcccagca accacatggt ggctcacaac  8880
catctgtaat gcgacctggt gccatcttct gacatgcatg gatacatgca ggcagaaagc  8940
tgtatacata gtaaattgat aaatctttt ttaaaaagag tatggattct gccgggtgtt   9000
ggtggcgcac gcctttaatc ccagcactct ggaggcagag gcaggtggat ctctgtgagt  9060
tcgagaccag cctggtctat aagagctagt tccaggacag cctccaaagc cacagagaaa  9120
ccctgtctcg aaaaaccaaa aaaaaaaaaa aaaaaaaaaa aaaaaaaaga gtatggattc  9180
taagaaagcc gtaacagctg gagctgtgta cggagttcag cgtggtacta gaagaacaga  9240
cattcatgat gaaacacccc aggattttta cttagtatct agtttccatt gttgtttga   9300
gaccggctct tatgctctcc aggctggcct caaactgctg atcttcccgc ctctacctct  9360
caagtcctgg gactacttgg ctcataaaac agtttttgtc ggctccctg aagttatggt   9420
tgtacaaacc gtgggggtca atatactcac ttgggcagag agagaaggtc tgaatcccag  9480
acaatgactg catctcagga cagttgggaa gaggacaatg gcagaaggac ttagaaaaga  9540
tagactggag ggtggaaaag cagcaggaac agagaaacaa aacaggaagc ttgctatcca  9600
gggccactct ggagtcctgt ggcaagatgg aagcgggcta gggggaataca tttgtgctac  9660
tgtgtgtgtg tgtgtgtgtg tgtgtgtgtg tgtgtgtgat caatgcctat caatgttgaa  9720
ggggaaatat gtataccaca ttgattctgg gagcaattct cagtatctgg cctagagaaa  9780
ggaatggccc ctgcagaata gacagagtga atggtgccct ttatcatttg ctaaagtgaa  9840
ggagaaataa acatccttcc atagagtttc aggtaaatga accccacagt tcatctggtgc  9900
cgtggtggag gcctgccaa cagttaaaaa gattagacac ggacaaagtc tgaaggaaac   9960
acctcgaata ggaagaggag agccacctca ttctgtaact ttcctcaagg ggaagatgtt  10020
ccaagagtgg gaataaatgg tcaaaggggg gattttttaat taggaaaacg atttcctgta  10080
tcacttgtga aactggaggt tgatttgggg cataggacaa tagatttgat gctttgcaaa  10140
aagctgtttc aaagcagaga aatgaatag agacaattat gtagcgagga gggagggtgg   10200
ggcgaagatg gagacagaga agtggaagct gactttaggg aagaggaaca tagaccacag  10260
gggcggggcg gggggcaggg gcgggggggcg gggctcaaag gaggcagtgg gaacgttgct  10320
agtgttcgca gcgtaagcgt gaatgtgcaa gcgtctttgt ggtgtgtgac caggagtagc  10380
gtggctggct tgtgtgctgc ttgtaatccc agtctttgag gtttccacac tgttccacag  10440
tgggtgtgat tttccctcgg agagcatgag ggctctgctt tccccacatc ctccccagcg  10500
ttcgttggta tttgtttcca agatgttagt gggtgagaca aagcctctct gttgatttgc  10560
ctttaacagg tgacaaaaaa agctcaacca ggagacattt ttgccttctt ggaaggtaat  10620
gctcccatgt agagcaatgg gacccatctc taaggtgagg ctactcttgc agtttgcaaa  10680
cagctcttct gatgcaggaa ggaagttggt gggcaagcaa gactgtttgc ttcttgcgat  10740
ggacacattc tgcacacaaa ggctcaggag gggagaaggc tgtttgatgt ttagcactca  10800
ggaaggcccc tgatgcatct gtgattagct gtctccatct gtggagcaga cacggactaa  10860
ctaaaaacca gtgtttttaa attgtcaagc ctttaaggtg aggaaattga cttattgtgc  10920
tgggccatac gtagagcaag tgctctgcat tgggccaacc cccggctctg gtttctaggc  10980
accagaatgg cctagaacta actcacaatc ctcccattcc aggtctcagg tgctagaatg  11040
aaccactata ccagcctgcc tgcctgccta cctgccttcc taaattttaa atcatgggga  11100
gtaggggaga atacacttat cttagttagg gtttctattg ctgtgaagag acaccatgag  11160
catggcaact cttataaagg aaaacattta gttgggtggc agtttcagag gttttagtac  11220
attgtcatca tggctgggaa catgatggca tgcagacaga caggatgctg gagaaaggga  11280
tgagagtcct acatcttgca ggcaacagga cctcagctga gacactggct ggtaccctga  11340
gcataggaaa cctcacagcc caccctcaca gtgacatatt tccttcaaca aagccatacc  11400
tcctaatagt gccactccct atgagatgac agggccaatt acattcaaac tgctataaca  11460
ctttaaagta tttttatttt tattattgtaa attatgtatg tagctgggtg gtggcagccg  11520
aggtgcacgc ctttaatccc agcacttggg aggcagaggc agatggatct ctgtgagttc  11580
```

-continued

```
aagaccagcc tggtctataa gagctagttg caaggaagga tatacaaaga acagttctag  11640
gatagccttc aaagccacag agaagtgctg tcttgaaaac caaaaattgt gctgggacct  11700
gtctctgctt tggttgcttc ccactccccc agagctggac tcttggtcaa cactgaatca  11760
gctgcaaaat aaactcctgg attcctctct tgtaacagga gcccgaagtc aggcgcccac  11820
ttgtcttctc gcaggattgc catagacttt ttctgtgtgc ccaccattcc agactgaagt  11880
agagatggca gtggcagaga ctgggaaggc tgcaacgaaa acaggaagtt attgcaccct  11940
gggaatagtc tggaaatgaa gcttcaaaac ttgcttcatg ttcagttgta cacagactca  12000
ctcccaggtt gactcacacg tgtaaatatt cctgactatg tctgcactgc ttttatctga  12060
tgcttccttc ccaaaatgcc aagtgtacaa ggtgagggaa tcacccttgg attcagagcc  12120
cagggtcgtc ctccttaacc tggacttgtc tttctccggc agcctctgac accctccc    12180
ccattttctc tatcagaagg tctgagcaga gttggggcac gctcatgtcc tgatacactc  12240
cttgtcttcc tgaagatcta acttctgacc cagaaagatg gctaaggtgg tgaagtgttt  12300
gacatgaaga cttggtctta agaactggag caggggaaaa aagtcggatg tggcagcatg  12360
tacccgaaat cccagaactg gggaggtaga gacggatgag tgcccggggc tagctggctg  12420
ctcagccagc ctagctgaat tgccaaattc caactcctat tgaaaaacct ttaccaaaca  12480
aacaaacaaa caaataataa caacaacaac aacaacaaac taccccatac aaggtgggcg  12540
gctcttggct cttgaggaat gactcaccca aacccaaagc ttgccacagc tgttctctgg  12600
cctaaatggg gtgggggtgg ggcagaagca gagacagaga gagacatgac ttcctgggct  12660
gggctgtgtg ctctaggcca ccaggaactt tcctgtcttg ctctctgtct ggcacagcca  12720
gagcaccagc acccagcagg tgcacacacc tccctccgtg cttcttgagc aaacacaggt  12780
gccttggtct gtctattgaa ccggagtaag ttcttgcaga tgtatgcatg gaaacaacat  12840
tgtcctggtt ttatttctac tgttgtgata aaaaccgggg aactccagga agcagctgag  12900
gcagaggcaa atgcaaggaa tgctgcctcc tagcttgctc cccatggctt gccgggcctg  12960
ctttctgcaa gcccttctct ccccattggc atgcctgaca tgaacagcgt ttgaaatgct  13020
ctcaaatgtc actttcaaag aaggcttctc tgatcttgct aactaaatca gaccatgttt  13080
caccgtgcat tatctttctg ctgtctgtct gtctgtctgt ctgtctatct ctgtctatca  13140
tatcaatcat ctatctatct atcttctatt tatctaccta tcattcaatc atctatcttc  13200
taactagtta tcatttattt atttgtttac ttactttttt tatttgagac agtatttctc  13260
tgagtgacag ccttggctgt cctggaaccc attctgtaac caggctgtcc tcaaactcac  13320
agagatccaa ctgcctctgc ctctctggtg ctggggttga agacgtgcac caccaacgcc  13380
ccgctctatc atctatttat gtacttatta ttcagtcatt atctatcctc taactatcca  13440
tcatctgtct atccatcatc tatctatcta tctatctatc tatctatcta tctatcatcc  13500
atctataatc aattg                                                  13515
```

```
SEQ ID NO: 10          moltype = DNA  length = 14553
FEATURE                Location/Qualifiers
source                 1..14553
                       mol_type = genomic DNA
                       organism = Mus musculus
SEQUENCE: 10
cttgaagaac acatgttttc caagagggag cacccatgtt ggaatgacaa tgtagttagt  60
gctcctctcc tgtaggttag tgctcctttg ctataggtaa gtgctcctct cctataggtc  120
agtgctcctc tcctataggt tagtgctcct ctcctatagg ttagtgctcc tctcctacag  180
gttagtgctc ctctgctcta ggttagtcct gctctcctat agtacctaga gagctagggc  240
aaatgggcta ggcccgaagt gcagagacaa acagctatgg aagactgggt aagcacttcc  300
aagctacgaa agagcagtgt gaagggtcag ggcttgtgca gttagtaggg gagatcttcc  360
agttgaagaa acagaagaac tgagagccac tgggtatcat cctcctgcgc catgccttcc  420
tggatactgc catgctccca ccttgatgat aatggaatga acctctgaac ctgtaagcca  480
gccccaatga aatattgttt ttatgagagt tgccttggtc atgctgtctg ttcacagcag  540
taaaacccta aataaggcag aagttggtac cagtattgct gtgatagacc tgaccatgct  600
ttcctttgaa agaatgtgga tttggtgact ttggatttgc aacacagtgg aatgctttaa  660
atggagatta atgggtcatc aattcctagt aggaatatgg aagactttgt tgctgggagt  720
atttgaactg tgttgacctg gcctaagaga tttcaaagga gaagaatttc agaatgtggc  780
ataaagacag tttttgtggt attttggtga agaatgtggc tactttttgc ccttgtctga  840
aaagtctgcc tgagactaaa gtgaagagaa tcagattaat tgcattgaca agggaagttt  900
gtggctgcgc tatctggaaa cttacagcca gcctcttgga cctcgggtga cttacgcaaa  960
tactcaggga cagagatgct tgactctgta ctgatgagtt gtcttggatg caaatatggg  1020
ctcttcattt gactacatgt cacgatgagt caggagctgc tctctccaga gtgtgacaaa  1080
gcgaggggat gctgacggta gctgttctag ctttgaaggt aagcctgcac ttatgctaaa  1140
gtcacacata cacgagccgg gtggagaacc tgtctgtgtg gagacacctt tcattacctg  1200
tggcatccag cctctcaagc ttggactgcc tgtgtgctcc tggactctgg aggtcccact  1260
gctctgtcct ctgctgctta tgatactgac attttaaaag aatccagtgg ttcccccctg  1320
tactcggtgt ctacttctac ctggatgttc ctcatttatg ttctgtgaca cttctctgtg  1380
actctgctgc attcctgggt gacatgtgga caccctgtcc ctttgcagac catgatgtca  1440
ctgtcactag tggaatcaga tgccccaagt gttgtcctgt gtttgggaac gtgacaggca  1500
gtacagaagc agaagaggaa gggtgaaaac ggaaatgtca cagcagcatc tgatgtgtgc  1560
ctcagtcacg catgctgctg attggaacta ctcagcatga gagagggcca tggtgaatac  1620
acaaccctat acacactgtg tccatttctc tctctctctt acacagagag agagggagga  1680
gggggaggga gaggcggaga gggaggggga gggagaggga gtggggaggg gagaggggaga  1740
gggagaggga gagggagagg gagagggaga gggagagttt aatgtctgtg aagagatacc  1800
atgaccaaag caactcttat aaaggacaac atttaattgg ggctggctta caggttcaga  1860
aattcagtcc attctcacca tggtgggaag catgcaggta gatgtggtgc tggaggaacc  1920
aagagttcta tatcctgatc tgaaggcagc caggagaaga ctgcctcttc tgcacagggc  1980
agagcttgag catagaacat caaagccctt ccccacactt cctccaacaa ggtcatacat  2040
acttcaacaa agacacacct cctaacggtg ccactccctg tggaccaacc atttaaacgc  2100
atgagtctat gagggtcaaa gctcttcaaa ccaccacact catgtacaca cacacacaca  2160
cacacacaca ctctcataca cacacacaca cacactcaca cacacacaca cacacacaca  2220
cacacacaca ccacacacac acacacacac agagttctat tttgcactgt ttcactgtca  2280
caaggttcta cttatctcag acacactgcc aggaattgtg tgggaagact ttcagtttct  2340
```

-continued

```
ttgggttcac atggacttag cagttcttgg tgatcctgaa agatttctgc agaaagaagc    2400
caaagtgttg agcccaaggc ctggccacac attagtcctg tctagatgaa caggggttta    2460
aaaataaggg ggcatcaagg tgaagccagc aggggctgac ttagagagga gacccaccca    2520
agccaactgc tcgaagtcaa aagcgatgaa tccccatatc cagctgtgcc cggtgctgtc    2580
ttgctacatc tttagtaaat gttcttttag ttgtatgcgt atgaatattt tgcttgcata    2640
tatttgtgta caccataggt gttcctaggg cctatggagg ccagaagagg gcatcagatc    2700
ctttggaact ggaattatag acacttgtta cccatagagt agattgtggg aaatgagcct    2760
ttagtcttcg agagcggcca gtgctcttaa cctttggtcg tttctccagg tctttgagac    2820
tttattttct tggacatcag gacaggatcc agggctttga gcttgtttct tcagccagct    2880
ttcttttcat gtatattaaa ttttatgtta ttttgctttc tttttcccca agacagaatc    2940
acactctata tagctcaggc tgggtttgaa ttcagtttcc ctgtctcagt ctaccgggta    3000
atatgattac agatgtgagt ctgactttgg tatcaaagtc cccagccctt ctggatatgt    3060
gttttaagga tatcagatat atccttgatt tgctttgaat tttctttttta gttacaacat    3120
aattagttcc gtgtcacctg aatatgtgta tgtcacctac atagtcttcc ttcttctctt    3180
cttccctctc ccaccttccc aggtacctgt ctgtcttcat atccttgtgc tgagagtctt    3240
gttgagggag atgatgaccg agacagagcc actgggggaag ggagatgggc tagtgcaggt    3300
cttcagagag gagctcgtga atattgtagc ccctttagtc cctggcatgt cctcttgtat    3360
agccaccgcc atgctgtggc ctggcagaag tgaataagtt gtccagctgt tgacaggcct    3420
gccctccaga cccagtctga tcccaagaaa gggcatctgt gtctgtctct gaggccgtaa    3480
gtgctgcctg gttgtctcca gcttgacttg acactccctc cttaataaga gtaccacaga    3540
acagggtctg cagagtccct gggccaggtc cctgtgctgt cctggaatgc caggcgtgaa    3600
tttcctgtga agtaggactt tgctcgccaa gctcccacgg cttgcccttc agatagccag    3660
aattatctgg taccctgcat tgccgttcaa tacgcagagt atcactggaa gcgcgcgcgc    3720
gcacacacac acacacac acacacac acacacac acacgcccac tccatctttta    3780
aacccccaccc cccagcaacg gcggtgtaaa cactctccat caggaagctg aaacgcagtt    3840
gccctctgct ggggagatga aggcagcttg ctgggggcga ggaccgtgct agcaaccttc    3900
cctggtgcac acgggctctg gtgcatgacg ggaacggaaa cgcggaacta aagtcagtcc    3960
tgcttttttt tttttttttt ttttttttttt ttttttttttt ggcgttggtg    4020
gtggactgag tgacaatcag tgaaatcact taggttgttt ttctcttctt cgttgggttt    4080
gatagacggt gggagagggt cagaggagga ggggagggat ggggagagag ggaggagggga    4140
ggggcgggag gcgggggggcg aggaaaacgt gctaacttct ccaatcctac aagacaaagg    4200
tttggagaaa gccgcactga gtgacccagc agaaggaatc caggaatgtc cgctggaatc    4260
tgactgttga ttccagcgcc atgcagagaa tctaggctgg taggaacatt ctttgtccta    4320
tccgacataa taactccaac caacacggaa aagaaaggct atacaagtga agaaatggca    4380
ttttcacttt catgactata caatcacttc caggtagtaa cacgtgtcta gcacagcggt    4440
tctcaacctg ggggtcacga tccccccactt ttctgcatat cagacatttt tacgttgtta    4500
ttcataacag tagcaaaatt gcagctatga agtaacaatg aaatgcattt atggtgcgtg    4560
tgtgtgtgtg tggggggggta tcaccttaac atttactgta agaaggttga gaatactgct    4620
ccagcagcta gtgtgttgga cttaggttct gggtatatta ttagcaatag ccaaccagaa    4680
tccccacccca ccacagcatt gaggccccat gcagggcttg ctgggagagg cactgataag    4740
acttctttat gtatttatt agagacgaat actcattagg taggccaagc tagcgtcaaa    4800
ctcatggcaa ttctcctcct ccagtttcct aagtactgga ctcaggagtg tgttgccatc    4860
atatacagta aggatttatt gactgaagaa aatctcaagt ggctttggtt aatccctact    4920
acgccagagg ctgaggcagg aggcgcgcaa ggtcaaggct tgcctgggct acatatagag    4980
tgagctcaat tttgacactt ggtgcggtgt tagtagtaat agtaaagatg aaggtgtggc    5040
tcaggtgggg ccggtgattg gacacacttg gggtctcctg gtccatctgc agctgtgcaa    5100
caggagagc ggagaatgag aggaaagaga gaaaagacag aatgagagag agggaggaag    5160
agagaaaaag gaaaagagag aggaaaggaa aaaggaaaat gaggaaagcg agaaagaaga    5220
aatgagaaag aggaaaggga gaaagaaatg agagagagaa aagaaaagac agaatgcgag    5280
agagggagga agagagaaaa aggaaagaga gaggaaagag aaaaaggaaa atgaggaaag    5340
cgagaaagaa gaaatgagaa agaggaaagg gagaaagaaa tgagacaagag aaaagaaaga    5400
acagaatgcg agagagggag gaagagagaa aaggaaaaga agagaggaag ggaaaaagga    5460
aaatgaggaa agcgagaaag aagaaatgag aaagaggaaa gggagaaaga aatgagagag    5520
agaaaagaaa agacagaatg cgagagaggg aggaagagag aaaaaggaaa agagagagga    5580
agggaaaaag gaaaatgagg aaagcgagaa agaagaaatg aggaggaaga agaaaaaagga    5640
gaaatgagag agagaaaaga aaagacagaa tgcgagagag ggaggaagag aaaaaaagga    5700
aaagagagag gaagggaaaa tggaaaatga ggaaagcgag aaagaagaaa tgagaaagag    5760
gaaagggaga aagaaatgag cgagataaaa gacagaattt gagagaggga ggaagaaata    5820
ggaaagaga ggaaaggatg gagaaaagag agaaagaag agaaagatga gagagaaagg    5880
agaaatgaaa tgagagagag agagagacac aaagagccag agagagaaga aaaaagggga    5940
aagagaaaga gaaagaggaa ggctcctctt ggacacatct tcctttatct ttccctgggg    6000
accgccaaag cctggtggca tactgtacat tctgtacact gttcattcaa aacaggctct    6060
gtcttaaaga tggtctgagc ggtcagaaaa gggtattgtt aacttgtttg caaaactgcc    6120
tcaggagagt gctgagtgcg tgaaagttgc tgcccgttaa ggagaagtct ctactacttg    6180
tgatctcacc atcgaaaatt tctttaattg tctcctggtg ttctgggttt tgcagttttg    6240
tttctaagga tacattcttg ggtgatgtca caaagtcccc aaagacacgg tggagctgtg    6300
ttagatgggg aaagacagtc tgctgaggat ttatctggaa ctgtcagaag gaaaagaagg    6360
taaatgggc acttgggaaa gtggcctcta gtttgacttc tggcttagca aaggttgtgg    6420
ggagataagg catacacagt agttagcagg aggcaacagg gcctgggag gacgcgaggc    6480
agaaggagag gctgggctga cagcatgcaa tcattgcata gtctccaaag gagattgcaa    6540
catggctgag ttttcagagg tcctacagag cccgtggtag agattctgtg ggttctgaga    6600
caacttgact ttagccagat ggtatttgag taatctggga gagagaaaac agctacagca    6660
aacagggcca catttagtga cgaaactctc actttgactg ttgagtcatt tgcagtgggc    6720
cctgaggtca ggctggccct cagctcaaaa acaagcgagg aactgaagca attactcagg    6780
taatccacag ccacagccac tggaaagggc cacatcccca gagacagcac agcagggggtg    6840
ggggtggggc tatgagaaag ttagtgattg tagcagttat ctagaatgtg cggagcagag    6900
gaggttacac aaaaacctag aatgtcattc aatgtgggaa accgagaggc tcccaagccc    6960
taaaaggaac agtttgcttt cagccaaaat ggaaataaaa tttggggctt aaatctggca    7020
aatgattcag accttctgtg taggtgtctt taaatgcaca gcagattgat tttcatgttg    7080
```

-continued

```
gagtttattt gaactaaaag acagaaatgg tgaaaagcac acctgaagaa attgagatgc      7140
tatgaataaa atcatttact tacagctatc acttaattag tacctccttc caccttgctg      7200
atttattggg ctagtcaagg aagaaaagat cttccctcct ccttctctcc tcctcccct      7260
cctctcctcc tcccctcccc tccttgacct tcctctcctc cttttccctc ctccccctct      7320
tcttctcttc acccctcct cccctccct cctctgtact cctccccttt cctcccaatc      7380
tcttttttct cccccttctt ctctttctct ccccctcctct tccctcctct tcctccctcc     7440
ctccctcctc ctcctcatcc tcctcttcct cttcatcctc ttctccttcc tccctctcct      7500
cctcctcctt ttccagccct acctaccttc cctttcttct tcatttattc aaagtagctt       7560
tgaacagcac tactcggttt agttgtgtat aaaaggaaaa tgcaggtcca agcagcttgg      7620
ggaagattgc tttttgctct ctggaggcag atgatgacag ttcaagatca ttccttttgc      7680
tccatgtcac aggaaggggg acatgccgaa tctaccagtt tgcagccacc tacacaggat      7740
ccaccttcac ttctcaaggaa atgtttggga agctacctac caaccacttc tggcatctca      7800
tgggctagag gactcttaaa tggcactctt atttgtttaa taaaggaggt tgtgacgtgt      7860
agttttaaat cccttccaca caacaattgc tactctctga ccaaaaaaga agggagacag     7920
gatacggcta ggtgtctagt agactttacc actttgaaaa gccttaatat aaatcaggta      7980
gatacatctt tttaacttat tcttgtaaag acaaaaacaa aactttattt ttatttgtgt      8040
gtatgcttgt gtgtgtgtgc ctgtgtgtat accacatgtc gctggtgccg gagaacacca      8100
gaagaggga cctgatctcc tggagctaaa gctatccatg gttctgagct gcctgatgtg       8160
ggtgctggga acagaactct ggtcttctgc aagagcaaca agcctcctct taactacgaa      8220
tctcctcccc atccccccaa atacatttaa ttattcattt tagcagcttt atttcgtaac      8280
tacttatcac agcataaaac aaggatttta tatatattac atgcaatcga ggataagagt      8340
tgaggggaga tgcgtgtgct ccttctgggt gtctgtgctt ttgaagaatg taagcagtgc      8400
acaagggacc gaggcgtgcc tgtctgccag gagctgtctt cttcccttgg actctgagct      8460
gagtgcagtg ctccgaagaa gtaaaagacg acctcatgaa gcaatgtctt caacccaaac      8520
atgctgtcca gacaaagtcc agcttcatta gtgctctgag gagagactta ctgagcctca      8580
ggaaagcccc cctcagcatg gcgaaagtcc actttgattg aagtgactcg aaagccatgg      8640
cagtgcggcg gcggccgcgt ggagcttgtg ctcgagtcgg aagcggcatc tttgtcaggc      8700
ggctgtgatt agcacgggga ggcaggactg gagtgaagga agagttgggg gcggggctta      8760
gcgctctggt ctcctaagct gtagtcagcg cctcaagatt tgtaacctgc cttctgcctt     8820
cccagccagg cagtcaagtg gctccaagct gaagactgca aagtgcccct aaccttttgc      8880
ttatagcgag gctgaagaca ccgtgctctt tcatgaaagc cggatgtctg aaatccgatt     8940
tgataaatat ggataaaacg tataacgctc gatcaatcga atcgaaggag ctcacgattg      9000
gcaccacggc tttggggaca acagagtact gactcgttgg gaggacttgg atacttcccc      9060
tcctcttcca tctcttcccc tttcctcact tcctcctcct tccttctcca ctttctccct      9120
cttcactgtt tcttactatt tttacaaaag attttatttg tttatttatt tatttatttta     9180
tttatttatt tatttatttta tttatttaat gtatgcgagt acactgtagc tgtcttcaga     9240
cacaccagaa gagggcgtca agttccatta gagatggttt cgagccacca tgtggttgct      9300
gggggcctctg gaaggaccgc cagtgctctt aaccctgag ccatttctcc agtaccttc       9360
tcaccgtttc tcttcaatct tcttcctctt ccttctccac tttccttgtc ttcttggttt      9420
cattatcttt ctccctttct tcctcttctc cccttcttcc tcctccactg tagtttttcct     9480
tccctactct tttcctgcct ccctcctcct ccccctctcat tcccccctcct ctttcctcct    9540
tctccctcct cctccttcct tctccctctc ccctctcccc tctcccttct cccttctccc      9600
cctcctcttc ctctttctcc ttctccaccc ctcctgtcac agtatcaatg gcaagggtgg      9660
tctagaatgg aggagtgtcc cctaggcact aacgaaagcc agttaggatg ctctgagacg      9720
ggtacaattc agggagggcc gtggggatgg aaggggttgtg ctgcgattca ttctggagca     9780
acccccaggc agaatcatga ggttggttcc ggattcgcag ggcacaattc agaagaggaa      9840
ggtttcagga aggacgagtt tgtctgagat aggagttaca ttctgatgtct tggcagcaga     9900
gccactgtac aagcgtgctt tattaaccac gtgggattaa atcttctttt aaatttattt      9960
tcaactctta aggaaacgtg aactttcaca ttcaaattta gacttgcagc tcttatgggg     10020
aaaaaaaggg gatcttaaga atattaagca taggcggctg gagagatggc tcagcggtta     10080
agagcactct ctgctctccc agaggtcctg agttcaattc ctagcaacca cataatagtt     10140
aacaacagtc tttaatgaat tctaatgccc tcttctggtg tgtctgaaga cagttacagt     10200
gtactcatat aaataaaata aagaaattta aaaaaatgaa tattaggcat agattcctgg      10260
atcctaagaa agccatcaga gctggagcca tgtgtgggat cctgcttggt gctggagggg     10320
cagagttcat gcccccgggg tttttactta ttatcacatt ttcatcgttg ttttgaaaca     10380
gggtcttgtg tggtccaggc tggccttgaa ctcatctttc agcctctacc tcacaggttc     10440
tgggattact tggttcctaa aagtatctcc gtcaagctcc ctggtgttat ggctgtgcca     10500
accaggaggg tctatacact cgctcaggta gagggagaag atccgaatct ctgacaggga     10560
ctgctgcctc tcggggcaaa tggagtgaag gacagcggca gaaggattta ggaaagatgg     10620
acgggagagt ggaaatgctg cagaagccag aaaacaaagc aggaagcctg ctgtccagtg     10680
gggctcaaga gcggagggat gcgagggggc tgcgcaggaa catttagcgt ctgcgtctat     10740
gggggtaggg gcggggtgcc agcacctagt cacctgaagg ggaaatgctt gcccagggag     10800
caggtctcag tagctgacct agagaaagga gcggcccta cagaggagac acgggtcact      10860
gtttgttaaa gtgaaggaga aataaatatt ctttcaaaga gttctaggtg agcccagttc     10920
atctgcgctg tggaggcctg gggaacagtt aaaaagaccc tgacacacac ccaaggcaaa     10980
caagcaacac acggctcctt ccgtaagggt ccatgattct ctgaagaatc agccccggaa     11040
tcagccccg aatcaggtag tccgtaaaca caatgagtgt tttactctgc agaagtccag      11100
cctgctggcg tctcccatta ccaaaataga gggatagtca cgtgagctca ccggctcgat     11160
ttaaggcacg tggttttcca gggtagatga gctttggctt ctggaaccat tatggggcac     11220
gaaggatgga gccaggattt tttttttttt ttttttttt tattagcaat tgatttgctt       11280
gggcttggct ggacttgccc agttcttagg cccagtcttc ttaactgccg atctgaagtc     11340
tgtcatggag tcagcctagc cttctcactt cccttcagct cgaataggaa gaggaggtgc      11400
acaccagatg gtctgagagc agggataaat ggtgtgcctt tgtctttcag tatttcgtta     11460
ttttaagtag gaagatgctt ttctgtatta cattgcttgt gaaccggaa gttgattcgg       11520
ggcacaggac aatggatttg gtgtttttgca aggactgttt cagaagagag aggagtggaa     11580
gggtggttag agtgaggagt ggggtggggac gggatggggg aagagaagga agggccagac     11640
aggctaggta gggctgagag gaggcggtgg gaacttcttg agttagcgca gcagtaaact     11700
tggatgtgcg tgtatctttg tgatatatga cccggagccg tgtagctggc tccgatagta     11760
ctgctaatgt cagtgtcggg ggggggggggt cccatactgt tccacagggg ctgcacattc     11820
```

```
ccatcgagag caggagggct cctctctcca tacatcctcg ccagcattcc ttgttgtttc    11880
tgtgatgaca gggggtggga tgaaatctct ctgttggttt gagagaccgt gaagaagctc    11940
aaccccagga cattttgcag tcttggaagg cagtgcctcc atgtggagcc gtggagccca    12000
tctctgagtc caggtcactc ttgcagttcg cactcagctc ttcagatgca ggagagacgt    12060
tggtgggaaa gcaagattgt ttgcttgttg agatagacac attctccaca caaaggctca    12120
cgtgggggcaa aggctgattg acgtacagcg ttcaggaacg cctgtggtag agctatgatt    12180
agctgtctcc atctatgaag cagacaaaga gttataaaaa aaatcaatgt tttcaaattg    12240
tcaaactttt aacccgacag caagcgctct gtccctgggc taatccctag ccctggtttc    12300
ttgagatggg gtcttttgtg cactagactg gcctagaact cacgatctta gtgttccagc    12360
ctcccagctg ctgggatgag ccgctataac cagtctgcct gccttcctaa attttaagtg    12420
atgggaagtg ggggagaata cagtttaaag tatgcagatc tgagagcagg aacctggcaa    12480
agccaagggg ccggagttac aggcggctaa catgggtgct gggaactgac ccaggtcctt    12540
gagaggagca gtgtgtactc ttgaccaaac aggtccgtct ctccagtccc cgtagtatta    12600
aaaataggta ctacgggcat ggtggtgcac acctttaatc ccagcactag ggaggcagag    12660
gcaggtggat ttctgagttt gaggccagcc tggtctacaa aatgagttcc aggacagcca    12720
cggctataca gagaaaccct gtcttgaaaa caaaacaaca acaaaatagg tactacaaag    12780
cgatgtaatt gtgctcaaac atgcaaaccg aggggactgt atgcataaga aagagaaaga    12840
cggccacact ggttctatct gggtgacagg aaatcagtat tttattttt cacattcatt    12900
tttttgttgt tgttgttgac acagtgattt ttctatcaaa aacattattt cttttatagt    12960
tcccctgagg agctgttttt aaagccgtgc tttgaaaaac cattgaagga gcagaggcag    13020
ggagactcct gtgtggcagt cggtgaagca ggccctctgc aggcaggctg gccctggact    13080
tgggagtctc tttccctccc tcctgtgctc aaatagcaaa tgtcaggctt caatgtagct    13140
agaaggttct agaatgatta agtttccaag gctgaagagc ttccctgttt gcctttcact    13200
tccctgagaa ggtcgttgtg tgttccggag tctgcaaggt gcctttggtg atgcgggtgg    13260
ttcatctcgg gagattccgc ctggaggacc caagttcaag ccctgcctga gctacagagt    13320
gactttcagg tcttctgcgc aattcagtga gacccagtct acaaataaaa agtaaaaaga    13380
aggctgtgga tggaactcgg tggtagagtt ctgggtttac tccctagagg aggggagaag    13440
gaggaggagg gaggaggaag aggaagaaag aagaagagaa gggaagagga gaaggaaggg    13500
agggaagggg ctgacaagaa gagagaagag ggagggaggg gagggaaagg aagggaaag    13560
gaagggaggg aagggggctga caagaagaga gaaggaaggg ggaggggggag gaaggaaggg    13620
ggaaagaaga gaagggtaag aagaaactgt tccaatggtc tgggccacag agtgatggcc    13680
ttttgtggtg atcagctgta atccttgatt tgacacaacc tagaatctgg gaagcgagtt    13740
tctgtgaagg agcattcaca ctggctggcc tgtgggcgtg catgtgggag actgtcataa    13800
ttaggttcat taatacagga agtcccagcc cactacaaat ggcttcgttc catacccaag    13860
agatgctaac tgtagacggt tggagaaagc aagcaagctg tggatacccc acgctctttc    13920
acctcggctc ctgggggggtg ggtgcactgt gtctcttggt attttaaagt cctgccttga    13980
cgtccctgct gtgacagact gtaactggaa ttgtgagctt tagtccttta gttttctacg    14040
ttggttttc tcaggatatt ttatcgcagt aacagaaaca agaccaggac acttgatctc    14100
ctctgatcaa cactgaagag ttacaaaaca ggctgaggaa acaaactttc ttctccctct    14160
ccccttctg tccctcccct tccttctcgc tccctccctt gccccctctc tccctgtctc    14220
tgtctctgtc tctgtctctg tctgtctctc tgtctctgcc tctccctcc cctcccctcc    14280
ctctgtctct gtctctgtct ctgtctctgt ctctgtctct gtctcgtcc ctttctcctc    14340
tatctcctaa atggctggag gccatgctag tcaatgttag aactttgaac acgtatttag    14400
gaaatctttg ttcttaacag ttctgaagtg ctgaagtggg ggtttagtct ctcggcctga    14460
caagctcact tcctctcact ctgtcttaat gaccaaatct gccatttccc taaaacagca    14520
caggctccag ctccaggttg ctccggagcg gag                                 14553
```

```
SEQ ID NO: 11          moltype = DNA   length = 4001
FEATURE                Location/Qualifiers
source                 1..4001
                       mol_type = genomic DNA
                       organism = Cricetulus griseus
SEQUENCE: 11
ccaagatgcc catcaactga ttaatagatg ataaaattat tgtacatttc agtgtaatat     60
tattcagttt ttaagaaaaa tgaaatttatg taataagcat gtaaatggat atatcttgaa    120
acaaccattc cccattatat tacctaaaca ttgaaagtcc aaaatcatat gatcttttta    180
gtggatctac taatcttttg ctatatgtat tttattgaac tacccatgga tgtgagataa    240
ttggtaacaa cagcacatgg gagagcatgg gatcattcaa ggaagattag agagaatgca    300
tttttagga gataatggag gagcaataga aaggattaaa tgaggttact gatgaaagtg    360
atggttagag aaggcaatat gaggagggat aactagcact taggggcctt tgaaaaagac    420
atagagaaaa tactattgta gaaacttcct ataattggtg tatagttata tacaccaaag    480
agctcagatg gagttaccct ataatggaaa tattaactac tttttatcac tgtgataaaa    540
catcctgaac agagcaacat agattgggaa gcatttactt tggcttacag ttctaacggg    600
ataaaaattc atgatgaaag aatgaaatat tcagcaaaca gcagtagcaa tggcctgaga    660
agcaggtgag agctcacatc ttgaagtgta agaatgtagc agagagaaca aactgcaaat    720
gaccagaaaa tgcttttgga tcagagccca taccctctg actgacttct ccagaaaattc    780
tgaacaaata aaactcccca aacagagcca taactgaagg tccagtgtct gagactacta    840
ggggtatttc ttattcaaac cactacaatg gggtggggggg agcaatcctc caagtaggca    900
ctacacacag acaaataaaa actctagtaa ctggaatgga ttgacttatt tgaattactt    960
gccagtggag ctacatagag cacaattatt gtatttaaat tacccttat gatcttacaa    1020
aacttgacag taagatcata ttgctaaaga aaccacatat ttgaatcagg aacatggtg    1080
atatctagtt gttcttcaac tggaaacttc atgctttctg cccagcattc atgttgctgg    1140
aaagagcaat gtacactacc agtgtagaaa ttaaatcatc aatcttatca agatgtggat    1200
cctataagtt acaataaaaa ttagcctgat aagtatcacc caccagagaa atattcacat    1260
aaatgctatg ggagcaacaa gctattttct aaattagctt taatcctatt ctacaagaga    1320
gaatccatat ctagaatagt tatagggatc aagaacccat ggcttgattg gtcataggcc    1380
caatgggaga tcctaatatt attgttctac aaaatgaaaa taactcctaa tgacttgttg    1440
ctgcagtaat aagttagtat gttgctcaac tctcacaaga gaagttttgt cttacaataa    1500
atggcaatta aagcagcccc acaagattta tatcataccg atctcctcat ggcctatgca    1560
```

```
tctagaagct aggaaacaaa gaggacccta agagagacat acatggtccc cctggagaag    1620
gggaaggggg caagacctcc aaagctaatt gggagcatgg gggaggggag agggagttag    1680
aagaaagaga aggggataaa aggagggaga ggaggacaag agagagaagg aagatctagt    1740
caagagaaga tagaggagag caagaaaaga gataccatag tagagggagc cttgtatgtt    1800
taaatagaaa actggcacta gggaattgtc caaagatcca caaggtccaa ctaataatct    1860
aagcaatagt cgagaggcta ccttaaaagc ctttctctga taatgagatt gatgactacc    1920
ttatatacca tcctagagcc ttcatccagt agctgatgga agcagaagca gacatctaca    1980
gctaaacact gagctagttg cagacaggga ggagtgatga gcaaagtcaa gaccaggctg    2040
gagaaacaca cagaaacagc agacctgaaa aaaatgttgc acatggaccc cagactgata    2100
gctgggagtc cagcatagga cttttctaga aaccctgaat gaggatatca gtttggaggt    2160
ctggttaatc tatggggaca ctggtagtgg atcaatattt atccctagtt catgactgga    2220
atttgggtac ccattccaca tggaggaatt ctctgtcagc ctagacacat gggggaggtt    2280
ctaggtcctg ctccaaataa tgtgttagac tttgaagaac tcccttgaga agactcaccc    2340
tccctgggga gcagaaaggg gatgggatga gggttggtga gggacaggag aggaggggag    2400
ggtgagggaa ctgggattga caagtaaatg atgcttgttt ctaatttaaa tgaataaagg    2460
aaaagtaaaa gaagaaaaga aaacaggcca aaagattata aaagacagag gtggtgggtg    2520
actataaaga aacactatta tctaaataaa aacatgtcag aagcacacat gaacttatag    2580
tgtttatgaa agtatgtata ataactacat aatctcaagc caagaaaaaa atatcatctt    2640
tcagtgatga aggtgatttt atttctccca gaattaaagc caaagaccta atgaaagtaa    2700
ttatcttcaa aaggttgaaa atacatactt tgcaatacac agatctgcct agaaatctca    2760
tgttcacaat acacatgatg ctcaattgaa ttccattcaa tgttacagtt tagataaaca    2820
gtttgtagat aaactcacaa tgtatcattt ctttttattt tttgaccaaa cagcttctca    2880
tctgttattc agaataaatc ctcgatggca ggatatccat cccaattggg ggaaggggag    2940
aatttgaaga aaacctagac cacatacata tttgccattg ggaaacaaag tctaaaatga    3000
tgttgttcac atcttctcta ctagtcctct ccccgtccca aagaaccttg gtatatgtgc    3060
ctcattttac agagagagga aagcaggaac tgagcatccc ttacttgcca tcctcaaccc    3120
aaaatttgca tcattgctca gctctgccct tctcatatga cagttacaag tcaaggcttc    3180
caaagtccct ctgtcatgtt tggtgtcaat agtttataca gatgacttca tgtcttcata    3240
tctaatgtct tatatagatt aatattaaac aatgttattt ctctaaccac attttaaatt    3300
aatttaaaaa tccattaatt gtgtctataa aatgcagaca gagtgctgag acacaatata    3360
agcctgatga tctgaatttg aaactcacac ccaccacatg gagaatcaac ttccaaaaat    3420
tttcctatta cttccacact tacaccattg tacaaacaca ataataatga acaaaatgaa    3480
atgaaataaa aaattaagtc tctgtaggta atgctactgt gcagcaaaag taaaaatggc    3540
agcttaagct tgctttatgg ttacacttta ccatcttcca ttaattataa ggacttcaat    3600
catggcagaa ctatgctgtt attgtctcag tgtaacctaa ccaggtgttc cagatgttct    3660
taatgtggac acctaaacta tttgatattt gggttaagat ctttccctct ttcagaagaa    3720
acctcaggac agagggaatc ttgtctttta attttgagtc tgtagacttt ttccatttca    3780
aatatacatg aaacaagtga tgaagaaaat taatcaaaag gtgggaattg caatgatatt    3840
aggttcaata ttaagcttca atattatcat ggaatcgcct gttatacact gagtgtttgg    3900
caataaggga ttttttagaag aaggagtttt tattctcaac aggttcctta agtttagctc    3960
aaataaatct aagcaatcca ctctagaatt aaatagtttc c                       4001
```

```
SEQ ID NO: 12          moltype = DNA   length = 14931
FEATURE                Location/Qualifiers
source                 1..14931
                       mol_type = genomic DNA
                       organism = Cricetulus griseus
SEQUENCE: 12
catgtacact tatgcaagta tgatatggcc caacacagta ttttacacca attttttatct    60
ataaaatata catgtacatc aaaatatatt attaataata acatcattat tctttctttc    120
caagtaataa acacatacac tgaaattttg gttcttgtgg ataattttaa tgaaacagga    180
aatgcaaatt tatcttagca tgtttacttc actttctttg catagataac cagtaatcac    240
attgatggat catgttagtga aatgtatttt taggtatcta aggaattttg gcttcgtttt    300
gtgcttgttg acactgaatt ctattcctaa caacagtgtg taaggattct gtctgatttc    360
ttttaccagt atttgtccat ttgcatttc tttattattc atggctgctg ttctagaaag    420
tggaaggtag tgtgtcaagt ctgtttaaca tgtttccctg atgatcagtg tcttaacacc    480
tctctgagta catgttggcc aatgtcgttt ctagacccat ctattcttgc ttgacttatc    540
ctggtacatg cctgccaaga aatttctcct catcctttct gtctcttcac tgatttactt    600
gatgtgtgga tttcacattg atcatatgga aatagaagat acaattttct ttattcacag    660
tttggaagac tttcaatctc atagatcatc attatttttt gctactgttc cctatgctat    720
ggtgaaattt ccatttgaat aattgcttaa acaattaaca agaaagaatc tatttttact    780
tgcaataact tccatttcag aacatttact acactgttac tatatccaaa aactagtttt    840
atatatcatg tgagaaatga ctaattcata atttggccat gacatttttt tcagaaacag    900
aaaaagtgac caatacatac acaatgctat aaatattaaa acttcagcaa attaaatatt    960
tattcatgat atcacataaa attcatttat tatgtttat ttaaatgtgt ttttaaaaca    1020
gtggtatcac taaatattaa gttagatgtg tttatgtgct taatgaattt atattttaga    1080
atgttataag ttgtatatag tcaaatatgt aataaatttt attttttagg tctttctcat    1140
taaggtattt taattttggg tccctttcc agagtgactc tagctcatga tgagttgaca    1200
taaaaactaa acagtacaaa atgtacattg cattcagtat tgcacttgat ctttgcactg    1260
aagtttgagt cagttcatac atttagtact tgggaagtac attaagctaa ctttcattgc    1320
tctggcaaaa tgctcgataa gataaagagtc tattgtggaa agccatggca gcaggaaagt    1380
aagactgctg atgatgttta atccatagtc aagacgcaga aggagatgaa tgctggtatc    1440
caacattttt tgctgttcat tttctctaga accctagtcc ataaagatgt atgacttgca    1500
ttcaaaatgc gtcccttca gttgttcaac ttttctgtaa atatccttc aggcatgtct    1560
agaagattgt ttcgcaaata cttctcaatc cattcaagtt gatagtgcag attaatcact    1620
gcagaataaa agcctgtaac ttggctcacg tgccaaggaa tatgcacact cctgacacat    1680
caataagtaa atcaaagtgt agcttttgcc tttaacattg ccagactat gtaatgttct    1740
gcacgttctt cctccatcac ttttttattct aatggtgttt ccttgacatt gaatcacgct    1800
gtggaagctg cttagaatta acattgaaat ctactgatat atttatgatg cagcaattta    1860
```

-continued

```
gatttactat tttacttaga atttttttata attgagagaa tataatattt tcacagttat   1920
ctatctgctg taaatagagg attttaaaaa aaatctctat aacttttttt tacaacacac   1980
agtaaaatta agttaaaatt taataaagtc actatgttga tttcaaagtg tgctacgccc   2040
acggtggtca cgcaggtgta gcagaagatg ccactaaggt gggctaaggc cgatgggttg   2100
gggtctgcgc tccctggaga tgagccccag gcggttccct ggcaatcagc tgcgatcatg   2160
atgcccgatg agccannnnn nnnnnnnnnn nnnnnnnnnn nnnnnnnnnn nnnnnnnnnn   2220
nnnnnnnnnn nnnnnnnnnc tgggtgactt tatggaaaga atttgataga tttcatgatg   2280
tagaagaatt ttattaggct tattttacag gagactaaga ccctgggacc taaagatatc   2340
tgggtcctga gaatcaggaa atgggtagag acgtggttga tggtatgaga cagattttag   2400
agaactctta gatcatgggc aatgaccgca atctgatgct tagaatagat catctataaa   2460
caattatgct gttctttttc tttctgttgt atgatctgat gatgtagccc ccttgccaag   2520
ttccctgatc ccccttgcca agttccctga ttgtaacagt atataagcat tgcttgagag   2580
catattcaac tacattgagt gtgtctgtct gtcatttcct cgccgattcc tgatttctcc   2640
ttgagccttt tcccttgttc tccctcggtc ggtggtctcc acgagaggcg gtccgtggca   2700
aaagtgtata aatgttctaa aacatttgaa ctctaaaaca tgcaaaatga aaaattaaaa   2760
taaataaaca tgaaaattaa aatatattag ctgctaaaag ttaaacaata ctatataata   2820
ttttgttatt agaattcaaa atcacattag ttggatttaa tttgaacatt gcattctttc   2880
aataataatt tcaataaaaa aagtttcccc atgatagtag aaaataataa catatgtatc   2940
tatctattta tttaactaca catatatagc atttgtttca actaaaataa atgaatgagc   3000
aaagcaccta agtaattggt gtctattata tttatgaagc caatagtttc aaataaaatta   3060
tcatgcataa ggaggtattg caaatgttaa acctttttg aaacagatat tcccagttac   3120
agaaattata atttctaatc tttcctataa gtagaatgat gataattaat ataggccatt   3180
tgtaaataat gttcagatta aaatattctc tatttcacta gagaagaatg atattaaatg   3240
tattatattt tatttcccat tttgtttgca ccactattct atatccctca gcagtttaaa   3300
tttgtttcac catatgtgtg tgtgtttgta tcttaaatat ggcactaaaa ttagaataat   3360
ttaatataaa tctttaggag aaaagatatt gaatttattt atgttgatag gaaaatatct   3420
tttaattgtc caagaatact ttttcttcta ttttaggact gatcagaccc aggactaata   3480
ttttatatgt actaattcta tgtaccaaaa tatgttatta tctcatgaat tctgtctcaa   3540
tattgaggta ataaaaatag tccatcatga actttaaaat taaaataatg attaattaat   3600
ttttattcat attttgtttg tatgaatggt tatacatcac atgtgtgcct ggtgactgtg   3660
aatgtcagga gaaggtatga aagccactgg aattggaata agagataata tttgagatgt   3720
tatgtgggtg ctgagaatta gacgcaagcc atcttcaaga atagccagca tactatacca   3780
ctgagtaatc cattcatccc tcaataatta tctttgtaga cagtaaatat atttctaaac   3840
tataaatgac cagaaaaatt aatgtattat taatgaagac attcatctca tgtgacacac   3900
ttcacctgtc taaatcagta acactctctc cactaattaa gattttctaa gtgcatgaca   3960
cttactattt ctaaagctgt ccaatggggg ccagtcccca gtcagcaccc agtgagataa   4020
tccatgaatg catttatatc ttaggaaaaa ttcttatcta tgtagtattt agaacatttt   4080
catgtgaggg gataaacaag gaagcacaga tgctttctga tagaaacttt ctctttaatt   4140
catctagaaa aaaaaaacct ctcaggaaaa tctctcttgc tctcctccca atgctctatt   4200
cagcatcttc tccctactta attctagatc tttttctcta tgcctccttg ctgctgccct   4260
gctggctctg ctctatgcct ccccatgtca cttttctttg ctatctcacc gttaccttct   4320
ctgcctcact ctctgccttc ttctctgctt ctcacatggc caggctctgg acaattatag   4380
ttatatgtta cattctcata acacatgata tgtcacatag tttctctcag gctagggata   4440
tcacaatgac tggccaatga gcaagtggcc ttgcatgtag ctctaagttg gtgatggttc   4500
ccagacagta agtagccatt tggttgaaat ttgaggttgg gtagtacatg aagactgaat   4560
tttcttcaaa ctctggcctt gaaatagtaa aacaacacct atgaaaatga cgacctgtat   4620
ttgtctttag aggcaaccac atattgtctg cagggcctgc tttgaatttg ctctgaagtt   4680
agcttgtttg tgtaaaagga agaatcctat atcagcctga gaaatgtaaa atatcctagc   4740
atttcaagtc atcaaaatta tatggagagt ataaatcatc cttctgacta ttcatagtca   4800
tatttgtgtc caccaagtat aaaacacact accaaagggc tgtggaaaaa atcgccataa   4860
ctgttcttat tagggaggca tagcagtggt acctgaggaa gttacagcaa caaccagtca   4920
tccagtcaat aaccccatgg ctttgccact tggaggtacc caataatgtt tggctttgcc   4980
gagtaggact ccaacaaatt cagagggtca atttttaaat gctggttgtc actgctgaac   5040
agtcccattg ccctctgcat aattccacaa tggaaagctt tttacactga ttgccaatca   5100
ttaaacagcc tactcagcat aaacaggtat gatattattc tgcattttgt tacattacta   5160
gatgaattcc tatttcttcc tacaatagtg gaactgaaaa aagatacaca atcatactac   5220
ccctctacta atcttatgac ttatatcatt tcaatttttca gaccataatg caaactattg   5280
accaaaacat gtgaagatga aaaatagaaa tgtagaataa tattacatat aaaaagaaaa   5340
ggcggactta ttttgtttta tttcttagca tgcatagcaa tacatgattt gaggtttata   5400
taataaaggg acaataaatc ttcaagaaac ttacccctac tgaattaaaa tattaaagaa   5460
ggtcacacat ttactcaaat atattagact actgggcaaa tagacatgaa aagtagagtt   5520
aatattgagg taggccttct gtgaaatgtc taaggaaatt atgtttcata cagtgtgtaa   5580
ccaagtggga atcatatcag aaagcagtca aaagcttata ttacaagtaa cagatgcttg   5640
gttatatgac ctcccagagc ttgactgtct atacacaaa agtggtgtta ataaactgt   5700
aatttgggct atgttttttt aaatggcttc accaacatga aaggaaggga atgagcatgt   5760
catggatgct tagagattat gcttccagca agaagaattg agctttggct cttattacag   5820
aaacatgaca aggtgtgagt tttatttatt agaaattata taatatttta agctggggac   5880
taaaaatttt attgaaacaa acaggcaagg gataggcatg tactagaagc aaaaatagga   5940
tgtcaatgct gtaatgttat ttttttggacc aaaatagtat ttcctataga aatgacaatg   6000
atcttaggtt attattcttc ataaagatga caagttcaca agatatccta gttcattaaa   6060
atcgtttttag tcatttaata gagtgctgtg atagattaca caaaggaaag cacttacgat   6120
gagaaataat gatatccaca attattttct taattcttag aaacattcta ttgttatatc   6180
tcaatctcag aagccactta ttgctttatt attgaaacat atgaaattgt aagttatata   6240
ttgtctatgg tgacatttca aagaacatgt gacgtacagt gtagcacaga taaagaacat   6300
aactgcagct gaatcagtaa ctaaacttac atacattaaa tctgccatgt tggcaacagt   6360
gtgtgcacta ccaaaggatg tactaatgct cacgacactc ccctatgtca ccctttgttc   6420
atcattacat cataggtcta ttttgtttgc ttttgaaatc tagaccaagt cttttgtgtc   6480
tttccaagca cagagctcat taatttacct catagacttg ttaaacttct tctggttcat   6540
caattgaata gaaatactca ctactaatta tgtgagaccc tgccagtacc atagcacatg   6600
```

-continued

```
gataattttt acataaaaca tgcatacaag taagattatt cagactgaac atgaatttta    6660
gagaaatcag gaaggagtat atgggagtgg ttggagtgag actagagaaa tgtaattaaa    6720
ctataatctc aatacaaaga tctactaagc aaaaaacatg aaacattgtc attcaagtga    6780
aacatcagtc ttcaaattgg aaagatattt ttactaggaa aatgtctggt agatggttat    6840
tatctagaaa acacaaaaat tagaaaacgg taaactttaa taaaaagaat aatacaatga    6900
gactacatga aaagttctta actaatgaaa caaatatctt gaaactttt tcttaaaagt    6960
ttaatatcaa taaccatcat ggaaattcaa attaaaacta tttacatatt acccctgaaa    7020
taataactaa tacccaataa aaataatata aacaaaaaat ggcaatgcat gccatcatgg    7080
atttgggaga gagaatgttc attgcagttc tgaatggata ctggtgccac cacggtgaaa    7140
atctctgtat aggtccttcc aaaagctgaa aatagacata tcacaagacc tgccacacat    7200
ttttcaagca aatacccaaa ggactctacc tgactgcaga gacactttct cataaaatat    7260
tattgttgat ctattcataa tatctggaaa atagaaacag ccaagatgcc catcaactga    7320
ttaatagatg ataaaattat tgtacatttc agtgtaatat tattcagttt ttaagaaaaa    7380
tgaaattatg taataagcat gtaaatggat atatcttgaa acaaccattc cccattatat    7440
tacctaaaca ttgaaagtcc aaaatcatat gatctttttta gtggatctac taatctttttg    7500
ctatatgtat tttattgaac tacccatgga tgtgagataa ttggtaacaa cagcacatgg    7560
gagagcatgg gatcattcaa ggaagattag agagaatgca tttttttagga gataatggag    7620
gagcaataga aaggattaaa tgaggttact gatgaaagtg atggttagga aaggcaatat    7680
gaggagggat aactagcact tagggccttt tgaaaaagac atagagaaaa tactattgta    7740
gaaacttcct ataattggtg tatagttata tacaccaaag agctcagatg gagttaccct    7800
ataatggaaa tattaactac ttttttatcac tgtgataaaa catcctgaac agagcaacat    7860
agattgggaa gcatttactt tggcttacag ttctaacggg ataaaaattc atgatgaaag    7920
aatgaatatg tcagcaaaca gcagtagcaa tggcctgaga agcaggtgag agctcacatc    7980
ttgaagtgta agaatgtagc agagagaaca aactgcaaat gaccagaaaa tgctttttgga    8040
tcagagccca tacccctctg actgacttct ccagaaattc tgaacaaata aaactcccca    8100
aacagagcca taactgaagg tccagtgtct gagactacta gggtatttc ttattcaaac    8160
cactacaatg gggtggggggg agcaatcctc caagtaggca ctacacacag acaaataaaa    8220
actctagtaa ctggaatgga ttgacttatt tgaattactt gccagtggag ctacatagag    8280
cacaattatt gtatttaaat tacccttttat gatcttacaa aacttgacag taagatcata    8340
ttgctaaaga aaccacatat ttgaatcagg gaacatggtg atatctagtt gttcttcaac    8400
tggaaacttc atgctttctg cccagcattc atgttgctgg aaagagcaat gtacactacc    8460
agtgtagaaa ttaaatcatc aatcttatca agatgtggat cctataagtt acaataaaaa    8520
ttagcctgat aagatatccc caccagaaga atattcacat aaatgctatg ggagcaacaa    8580
gctattttct aaattagctt taatcctatt ctacaagaga gaatccatat ctagaatagt    8640
tatagggatc aagaacccat ggcttgattg gtcataggcc caatgggaga tcctaatatt    8700
attgttctac aaaatgaaaa taactcctaa tgacttgttg ctgcagtaat aagttagtat    8760
gttgctcaac tctcacaaga gaagttttgt cttacaataa atggcaatta aagcagcccc    8820
acaagattta tatcataccg atctcctcat ggcctatgca tctagaagct aggaaacaaa    8880
gaggaccta agagagacat acatggtccc cctggagaag gggaaggggg caagacctcc    8940
aaagctaatt gggagcatgg gggagggggag agggagttag aagaaagaga aggggataaa    9000
aggagggaga ggaggacaag agagagaagg aagatctagt caagagaaga tagaggagag    9060
caagaaaaga gataccatag tagagggagc cttgtatgtt taaatagaaa actggcacta    9120
gggaattgtc caaagatcca caaggtccaa ctaataatct aagcaatagt cgagaggcta    9180
ccttaaaagc ctttctctga taatgagatt gatgactacc ttatatacca tcctagagcc    9240
ttcatccagt agctgatgga agcagaagca gacatctaca gctaaacact gagctagttg    9300
cagacaggga ggagtgatga gcaaagtcaa gaccaggctg gagaaacaca cagaaacagc    9360
agacctgaaa aaaatgttgc acatggaccc cagactgata gctgggagtc cagcatagga    9420
cttttctaga aaccctgaat gaggatatca gtttggaggt ctggttaatc tatggggaca    9480
ctggtagtgg atcaatattt atccctagtt catgactgga atttgggtac ccattccaca    9540
tggaggaatt ctctgtcagc ctagacacat gggggaggtt ctaggtcctg ctccaaataa    9600
tgtgttagac tttgaagaac tcccttgaga agactcaccc tccctgggga gcagaaaggg    9660
gatgggatga gggttggtga gggacaggag aggaggggag ggtgagggaa ctgggattga    9720
caagtaaatg atgcttgttt ctaatttaaa tgaataaagg aaaagtaaaa gaagaaaaga    9780
aaacaggcca aaagattata aaagacagag gtggtgggtg actataaaga aacactatta    9840
tctaaataaa aatatgtcag aagcacacat gaacttatag tgtttatgaa agtatgtata    9900
ataactacat aatctcaagc caagaaaaaa atatcatctt tcagtgatga aggtgatttt    9960
atttctccca gaattaaaagc caaagaccta atgaaagtaa ttatcttcaa aaggttgaaa    10020
atacatactt tgcaatacac agatctgcct agaaatctca tgttcacaat acacatgatg    10080
ctcaattgaa ttccattcaa tgttacagtt tagataaaca gtttgtagat aaactcacaa    10140
tgtatcattt ctttttatttt tttgaccaaa cagcttctca tctgttattc agaataaattc    10200
ctcgatggca ggatatccat cccaattggg ggaaggggag aatttgaaga aaacctagac    10260
cacatacata tttgccattg ggaaacaaag tctaaaatga tgttgttcac atcttctcta    10320
ctagtcctct ccccgtccca aagaaccttg gtatatgtgc ctcattttac agagagagga    10380
aagcaggaac tgagcatccc ttacttgcca tcctcaaccc aaaatttgca tcattgctca    10440
gctctgccct tctcatatga cagttacaag tcaaggcttc caaagtccct ctgtcatgtt    10500
tggtgtcaat agtttataca gatgacttca tgtcttcata tctaatgtct tatatagatt    10560
aatattaaac aatgttattt ctctaaccac attttaaatt aatttaaaaa tccattaatt    10620
gtgtctataa aatgcagaca gagtgctgag acacaatata agcctgatga tctgaatttg    10680
aaactcacac ccaccacatg gagaatcaac ttccaaaaat tttcctatta cttccacact    10740
tacaccattg tacaaacaca ataataatga acaaaatgaa atgaaataaa aaattaagtc    10800
tctgtaggta atgctactgt gcagcaaaag taaaaatggc agcttaagct tgctttatgg    10860
ttacacttta ccatcttcca ttaattataa ggacttcaat catggcagaa ctatgctgtt    10920
attgtctcag tgtaacctaa ccaggtgttc cagatgttct taatgtggac acctaaacta    10980
tttgatattt gggttaagat cttteectct ttcagaagaa acctcaggac agagggaatt    11040
ttgtctttta attttgagtc tgtagacttt ttccatttca aatatacatg aaacaagtga    11100
tgaagaaaat taatcaaaag gtgggaattg caatgatatt aggttcaata ttaagcttca    11160
atattatcat ggaatcgcct gttatacact gagtgtttgg caataaggga ttttttagaag    11220
aaggagtttt tattctcaac aggttcctta agtttagctc aaataaatct aagcaatcca    11280
ctctagaatt aaatagtttc ctaagggcac agctatgaat agagctcaat ttacatataa    11340
```

```
aattttgttc accatttatg tcattccagt tttcattagt acaaggaaaa tacaaaatat    11400
ttagatgtca atatcaagtg aatagttcat ctcctttttt aatatatatc acctaaatca    11460
ccattttctc agaaaaatct ggcctgaagt tctgtctgga acttcaacat gaaaaatatg    11520
cacagcttgc tattataaat cctagttgat tttttaagatt catgtctggt gtctgactca   11580
gaggggccag aggctagaca aatatttttt gaatcttcat tgtgaagatt tttaatgatt    11640
attttaatat aaataacaaa gatgatggat aatgtaactt tgtacagttc atagacgctg    11700
aactactttg tgcttaaaat gttagttccc tatcataaat gataggtgat aagtgtatgt     11760
ttaatacttt ccctctgagc tatattcatg tactagagaa ttattttaaa catgaaaaga    11820
ctgtgtttat agtctcagct cctgagaact ggtccaacct taggcaggtg aatgccagga    11880
gcaacgtttt tcttctacag aggatgcttt gctgccaagc aacctggttg tgtggaaatg     11940
ttcctttttt aatcaagttt aaagggtctt catcatgctg ttgctccaca tattttcagg    12000
ttagagcttg gtccttggag tattatcttt taccagaaaa ttcatagtat tctttcaata    12060
actaacaact aaacttttcg ataaaaaaga attggaattt caattttaaa gcctgagtaa     12120
aattcttgtg aatcaggata ttttatttta agtcttatct tttaaaaagt tattttattt    12180
tttaaaaaat tataatatac tttcataatt tccctccttc acttttcttt acaaacactt    12240
ctatagatca ccatgtgttt tttttttttac atttatggcc tctttctgtt cattgttatt   12300
acatacaaat agtcttgcct atagaagaac accacaattg gttacctgat aacaaattat     12360
caacccttaa aacctacaaa ctattgatat tactgaaaag actatactta tagatgtaaa    12420
gatatatgtg tgtgcacata tatagataca catatatgta ggattttttaa ttttagattt   12480
tagacatcaa aattatttat atgactgaga aactagacac tataaatgag cattcagtat    12540
tcaacaccgt gattttagat attgtcacaa tgacagaaaa ttttcttata gaaaatttta     12600
agttttgtga ttgctctgtg cacttagtga agtctcacag aaaaagaatc atagtatttt    12660
tagtttataa taaaaagtac atataattaa aatggttggc acaaacaac atttgagcat      12720
ttttcctatt tactatcaag tagtatcatt ttgaaataat aatttgacta gtttcaaaaa    12780
tgaaaacaaa atttaaacta aatgcctaat ctagcctgat aacatttta tgaatgaaat     12840
tattcaatag tgttatcaat taggggccca aaactttcc taaaataaaa cttttaattt     12900
ttttccattt ttatttaaat tagaaacaaa attgtttttac atgtaaatca gagtttcctc    12960
accctcccct tctccctgtc cctcactaac accctacttg tcccatacca tttctgctcc    13020
ccagggaggg tgaggccttc catggggaaa cttcagagtc tgtctatcct ttcggatagg    13080
gcctaggccc tcacccattt gtctaggcta aggctcacaa agtttactcc tatgctagtg    13140
ataagtactg atctactaca agagacacca tagatttcct aggcttcctc actgacaccc    13200
atgttcatgg ggtctggaac aatcatatgc tagtttccta ggtatcagtc tggggaccat    13260
gagctccccc ttgttcaggt caactgtttc tgtgggtttc accaccctgg tcttgactgc    13320
tttgctcatc actcctccct ttctgtaact gggttccagt acaattccgt gtttagctgt    13380
gggtgtctac ttctactttc atcagcttct gggatggagc ctctaggata gcatacaatt     13440
agtcatcatc tcattatcag ggaagggcat ttaaagtagc ctctccattg ttgcttggat     13500
tgttagttgg tgtcatcttt gtagatctct ggacatttcc ctagtgccag atatctcttt    13560
aaacctacaa gactacctct attatggtat ctctttcctt gctctcgtct attcttccag    13620
acaaaatctt cctgctccct tatattttcc tctccccccc tcttctcccc ttctcattct    13680
cctagatcca tcttcccttc ccccatgctc ccaagagaga tgttgctcag gagatcttgt    13740
tccttaaccc ttttcttggg gatctgtctc tcttagggtt gtccttgttt cctagcttct    13800
ctggaagtgt ggattgtaag ctggtaatca tttgctccat gtctaaaatc catatatgag    13860
tgatgtttgt cttttttgtga ctgggttacc tcactcaaaa tggtttcttc catatgtctg   13920
tggatttcaa tagcacaaac aacatacagt atcttggggc aacactaacc aaacaagtga    13980
aagaccagta tagcaagaac tttgagttta aagaaagaaa ttaaagaaga taccagaaaa    14040
tggaaagatc tcccatgctc tttgatagc agaatcaaca tagtaaaaat ggcaatcttg     14100
ccaaaatcca tctacagact caatgcaatc cccattaaat accagcacac ttcttcacag    14160
acctgaaaga ataatactta actttatatg gagaaacaaa agacccagga taggccaaac    14220
aaccctgtac aatgaaggca cttccagagg catccccatc cctgacttca agctctatta    14280
tagagtaata atcctgaaaa cagcttggta atggcacaaa aatagacagg tagaccaatg    14340
gaattgagtt gaaaaccctg atattaaccc acatatctat gaacacctga ctttgacaaa    14400
gaagctaagg ttatacaatg taagaaagaa agcatcttca acaaatcgtg ctggcataac    14460
tggatgctgg catgtagaag actgcagata gatccatgtc taatgccatg cacaaaactt    14520
aagtccaaat ggatcaaaaa cctcaacata aatccagcca cactgaacct catagaagag    14580
aaagtgggaa gtatccttga ataaattggt acaggagacc acatcttgaa cttaacacca   14640
gtagcacaga caatcagatc aataatcaat aaatgggacc tcctgaaact gagaagcttc   14700
tgtaaggcaa tggataagtc aacaggacaa aatggcagcc cacggaatgg gaaaagatat    14760
tcaccaatcc tatatctgac agagggctgc tctctatttg caaagaacac aataagctag   14820
tttttaaaac accaattaat ccgattataa agtttgggtag agaactaaat aaagaattgt   14880
taacagagca atctcaacttg gcagaaagac acataagaaa gtgctcacca t            14931
```

```
SEQ ID NO: 13          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 13
ccccgctggc gccgggatcg ggg                                             23

SEQ ID NO: 14          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
```

-continued

```
                        organism = synthetic construct
SEQUENCE: 14
gagtcgagca ccgctcgggc agg                                           23

SEQ ID NO: 15          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 15
ttccccgctg gcgccgggat cgg                                           23

SEQ ID NO: 16          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 16
gtgtgcggaa gacgccgccg ggg                                           23

SEQ ID NO: 17          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 17
cggtgacagc gcggatgaca ggg                                           23

SEQ ID NO: 18          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 18
cagcgcggat gacaggggcg agg                                           23

SEQ ID NO: 19          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 19
gccggcgtcc gattccccgc tgg                                           23

SEQ ID NO: 20          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 20
cgtgtgcgga agacgccgcc ggg                                           23

SEQ ID NO: 21          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 21
```

```
gaggcgctcc accgtctgtt ggg                                                  23

SEQ ID NO: 22        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 22
gtccgattcc ccgctggcgc cgg                                                  23

SEQ ID NO: 23        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 23
gaccccgggg gccccgatcc cgg                                                  23

SEQ ID NO: 24        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 24
cggcgtcttc cgcacacgga tgg                                                  23

SEQ ID NO: 25        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 25
tcgagcaccg ctcgggcagg cgg                                                  23

SEQ ID NO: 26        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 26
agctcacgcc ggccccataa agg                                                  23

SEQ ID NO: 27        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 27
catcgtcctc tatatatagc agg                                                  23

SEQ ID NO: 28        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 28
agaggcgctc caccgtctgt tgg                                                  23
```

-continued

```
SEQ ID NO: 29           moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 29
ggtcggctgc gcgaagcatc agg                                               23

SEQ ID NO: 30           moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 30
tgcttcgcgc agccgacccc ggg                                               23

SEQ ID NO: 31           moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 31
ggccccgatc ccggcgccag cgg                                               23

SEQ ID NO: 32           moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 32
tccgattccc cgctggcgcc ggg                                               23

SEQ ID NO: 33           moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 33
tcccggcgcc agcggggaat cgg                                               23

SEQ ID NO: 34           moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 34
tggtggagtc gagcaccgct cgg                                               23

SEQ ID NO: 35           moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 35
caagatggtc ctcactctcg ggg                                               23

SEQ ID NO: 36           moltype = DNA   length = 23
FEATURE                 Location/Qualifiers
```

-continued

```
misc_feature          1..23
                      note = Synthetic: Guide Sequence for AAVS1- Like Sequence
                       in CHO
source                1..23
                      mol_type = other DNA
                      organism = synthetic construct
SEQUENCE: 36
gcttcgcgca gccgaccccg ggg                                        23

SEQ ID NO: 37         moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 37
gtggagcgcc tcttctccag ggg                                        23

SEQ ID NO: 38         moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 38
gacgtgtcag ccttccaggt ggg                                        23

SEQ ID NO: 39         moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 39
gccagcgggg aatcggacgc cgg                                        23

SEQ ID NO: 40         moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 40
tctccccgtc atccaaaagc tgg                                        23

SEQ ID NO: 41         moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 41
ggtggagtcg agcaccgctc ggg                                        23

SEQ ID NO: 42         moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 42
gctgcccaaa tatagtccat ggg                                        23

SEQ ID NO: 43         moltype = DNA   length = 23
FEATURE               Location/Qualifiers
misc_feature          1..23
                      note = Synthetic: Guide Sequence for AAVS1- Like Sequence
```

-continued

```
                           in CHO
source                     1..23
                           mol_type = other DNA
                           organism = synthetic construct
SEQUENCE: 43
atgcttcgcg cagccgaccc cgg                                    23

SEQ ID NO: 44             moltype = DNA  length = 23
FEATURE                   Location/Qualifiers
misc_feature              1..23
                           note = Synthetic: Guide Sequence for AAVS1- Like Sequence
                           in CHO
source                     1..23
                           mol_type = other DNA
                           organism = synthetic construct
SEQUENCE: 44
gcggtgacag cgcggatgac agg                                    23

SEQ ID NO: 45             moltype = DNA  length = 23
FEATURE                   Location/Qualifiers
misc_feature              1..23
                           note = Synthetic: Guide Sequence for AAVS1- Like Sequence
                           in CHO
source                     1..23
                           mol_type = other DNA
                           organism = synthetic construct
SEQUENCE: 45
atgctcgggg gccgctgacc tgg                                    23

SEQ ID NO: 46             moltype = DNA  length = 23
FEATURE                   Location/Qualifiers
misc_feature              1..23
                           note = Synthetic: Guide Sequence for AAVS1- Like Sequence
                           in CHO
source                     1..23
                           mol_type = other DNA
                           organism = synthetic construct
SEQUENCE: 46
ttgtattgcc gggatccttc tgg                                    23

SEQ ID NO: 47             moltype = DNA  length = 23
FEATURE                   Location/Qualifiers
misc_feature              1..23
                           note = Synthetic: Guide Sequence for AAVS1- Like Sequence
                           in CHO
source                     1..23
                           mol_type = other DNA
                           organism = synthetic construct
SEQUENCE: 47
tccccgctgg cgccgggatc ggg                                    23

SEQ ID NO: 48             moltype = DNA  length = 23
FEATURE                   Location/Qualifiers
misc_feature              1..23
                           note = Synthetic: Guide Sequence for AAVS1- Like Sequence
                           in CHO
source                     1..23
                           mol_type = other DNA
                           organism = synthetic construct
SEQUENCE: 48
ctcgactcca ccaacgccga cgg                                    23

SEQ ID NO: 49             moltype = DNA  length = 23
FEATURE                   Location/Qualifiers
misc_feature              1..23
                           note = Synthetic: Guide Sequence for AAVS1- Like Sequence
                           in CHO
source                     1..23
                           mol_type = other DNA
                           organism = synthetic construct
SEQUENCE: 49
ggtggcaaga tcaccaaaag ggg                                    23

SEQ ID NO: 50             moltype = DNA  length = 23
FEATURE                   Location/Qualifiers
misc_feature              1..23
                           note = Synthetic: Guide Sequence for AAVS1- Like Sequence
                           in CHO
source                     1..23
```

-continued

```
                        mol_type = other DNA
                        organism = synthetic construct
SEQUENCE: 50
ggcgctgatg ccgtcggcgt tgg                                        23

SEQ ID NO: 51          moltype = DNA   length = 23
FEATURE                Location/Qualifiers
misc_feature           1..23
                        note = Synthetic: Guide Sequence for AAVS1- Like Sequence
                         in CHO
source                 1..23
                        mol_type = other DNA
                        organism = synthetic construct
SEQUENCE: 51
tccacgagca tcctagcaag agg                                        23

SEQ ID NO: 52          moltype = DNA   length = 23
FEATURE                Location/Qualifiers
misc_feature           1..23
                        note = Synthetic: Guide Sequence for AAVS1- Like Sequence
                         in CHO
source                 1..23
                        mol_type = other DNA
                        organism = synthetic construct
SEQUENCE: 52
aggctgacac gtcaggcctg agg                                        23

SEQ ID NO: 53          moltype = DNA   length = 23
FEATURE                Location/Qualifiers
misc_feature           1..23
                        note = Synthetic: Guide Sequence for AAVS1- Like Sequence
                         in CHO
source                 1..23
                        mol_type = other DNA
                        organism = synthetic construct
SEQUENCE: 53
gggtgtaagc catccgtgtg cgg                                        23

SEQ ID NO: 54          moltype = DNA   length = 23
FEATURE                Location/Qualifiers
misc_feature           1..23
                        note = Synthetic: Guide Sequence for AAVS1- Like Sequence
                         in CHO
source                 1..23
                        mol_type = other DNA
                        organism = synthetic construct
SEQUENCE: 54
aggatcccgg caatacaaga tgg                                        23

SEQ ID NO: 55          moltype = DNA   length = 23
FEATURE                Location/Qualifiers
misc_feature           1..23
                        note = Synthetic: Guide Sequence for AAVS1- Like Sequence
                         in CHO
source                 1..23
                        mol_type = other DNA
                        organism = synthetic construct
SEQUENCE: 55
ggatggggcc caacagacgg tgg                                        23

SEQ ID NO: 56          moltype = DNA   length = 23
FEATURE                Location/Qualifiers
misc_feature           1..23
                        note = Synthetic: Guide Sequence for AAVS1- Like Sequence
                         in CHO
source                 1..23
                        mol_type = other DNA
                        organism = synthetic construct
SEQUENCE: 56
gaggaccatc ttgtattgcc ggg                                        23

SEQ ID NO: 57          moltype = DNA   length = 23
FEATURE                Location/Qualifiers
misc_feature           1..23
                        note = Synthetic: Guide Sequence for AAVS1- Like Sequence
                         in CHO
source                 1..23
                        mol_type = other DNA
                        organism = synthetic construct
```

-continued

```
SEQUENCE: 57
agtcgcccag ggtcctggtg ggg                                                 23

SEQ ID NO: 58          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 58
ggcgggagga gagtcccacc tgg                                                  23

SEQ ID NO: 59          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 59
acctacccca ccaggaccct ggg                                                  23

SEQ ID NO: 60          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 60
tcagcgtctt tgaccagtcc agg                                                  23

SEQ ID NO: 61          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 61
cgtcccgccg cctgcccgag cgg                                                  23

SEQ ID NO: 62          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 62
gtccccggga tccccggggt cgg                                                  23

SEQ ID NO: 63          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 63
agcaccgctc gggcaggcgg cgg                                                  23

SEQ ID NO: 64          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 64
cggtggagcg cctcttctcc agg                                                  23
```

```
SEQ ID NO: 65          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 65
gccccgatcc cggcgccagc ggg                                                    23

SEQ ID NO: 66          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 66
atcggggccc ccggggtccc cgg                                                    23

SEQ ID NO: 67          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 67
attctcggct catccccttt tgg                                                    23

SEQ ID NO: 68          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 68
accaccccat ggactatatt tgg                                                    23

SEQ ID NO: 69          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 69
tagcaagagg acgacaaccc agg                                                    23

SEQ ID NO: 70          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 70
gctgatgccg tcggcgttgg tgg                                                    23

SEQ ID NO: 71          moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 71
tacaagatgg tcctcactct cgg                                                    23

SEQ ID NO: 72          moltype = DNA  length = 23
```

```
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 72
tgccgggatc cttctggatt cgg                                                        23

SEQ ID NO: 73        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 73
cccaaatata gtccatgggg tgg                                                        23

SEQ ID NO: 74        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 74
tacctgtaga atgggaccag tgg                                                        23

SEQ ID NO: 75        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 75
tcttgctagg atgctcgtgg agg                                                        23

SEQ ID NO: 76        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 76
atgccagctt ttggatgacg ggg                                                        23

SEQ ID NO: 77        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 77
atagtccatg gggtggtagg tgg                                                        23

SEQ ID NO: 78        moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 78
caggaccctg ctatatatag agg                                                        23

SEQ ID NO: 79        moltype = DNA   length = 23
FEATURE              Location/Qualifiers
misc_feature         1..23
```

```
                          note = Synthetic: Guide Sequence for AAVS1- Like Sequence
                          in CHO
source                    1..23
                          mol_type = other DNA
                          organism = synthetic construct
SEQUENCE: 79
ggggccggcg tgagctgtgt ggg                                              23

SEQ ID NO: 80             moltype = DNA   length = 23
FEATURE                   Location/Qualifiers
misc_feature              1..23
                          note = Synthetic: Guide Sequence for AAVS1- Like Sequence
                          in CHO
source                    1..23
                          mol_type = other DNA
                          organism = synthetic construct
SEQUENCE: 80
acctggaagg ctgacacgtc agg                                              23

SEQ ID NO: 81             moltype = DNA   length = 23
FEATURE                   Location/Qualifiers
misc_feature              1..23
                          note = Synthetic: Guide Sequence for AAVS1- Like Sequence
                          in CHO
source                    1..23
                          mol_type = other DNA
                          organism = synthetic construct
SEQUENCE: 81
cagcggacag cacgggtcac agg                                              23

SEQ ID NO: 82             moltype = DNA   length = 23
FEATURE                   Location/Qualifiers
misc_feature              1..23
                          note = Synthetic: Guide Sequence for AAVS1- Like Sequence
                          in CHO
source                    1..23
                          mol_type = other DNA
                          organism = synthetic construct
SEQUENCE: 82
cgccgggatc ggggcccccg ggg                                              23

SEQ ID NO: 83             moltype = DNA   length = 23
FEATURE                   Location/Qualifiers
misc_feature              1..23
                          note = Synthetic: Guide Sequence for AAVS1- Like Sequence
                          in CHO
source                    1..23
                          mol_type = other DNA
                          organism = synthetic construct
SEQUENCE: 83
gcgccgggat cggggccccc ggg                                              23

SEQ ID NO: 84             moltype = DNA   length = 23
FEATURE                   Location/Qualifiers
misc_feature              1..23
                          note = Synthetic: Guide Sequence for AAVS1- Like Sequence
                          in CHO
source                    1..23
                          mol_type = other DNA
                          organism = synthetic construct
SEQUENCE: 84
gccgggatcc ttctggattc ggg                                              23

SEQ ID NO: 85             moltype = DNA   length = 23
FEATURE                   Location/Qualifiers
misc_feature              1..23
                          note = Synthetic: Guide Sequence for AAVS1- Like Sequence
                          in CHO
source                    1..23
                          mol_type = other DNA
                          organism = synthetic construct
SEQUENCE: 85
gctgtcaccg ctctccccgg cgg                                              23

SEQ ID NO: 86             moltype = DNA   length = 23
FEATURE                   Location/Qualifiers
misc_feature              1..23
                          note = Synthetic: Guide Sequence for AAVS1- Like Sequence
                          in CHO
```

-continued

```
source                    1..23
                          mol_type = other DNA
                          organism = synthetic construct
SEQUENCE: 86
ggtgacagcg cggatgacag ggg                                              23

SEQ ID NO: 87             moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 87
gaagacgccg ccggggagag cgg                                              23

SEQ ID NO: 88             moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 88
aaggggtaca ctgccttgga ggg                                              23

SEQ ID NO: 89             moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 89
cttctagaac ctaccccacc agg                                              23

SEQ ID NO: 90             moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 90
ggggccgctg acctggtgca ggg                                              23

SEQ ID NO: 91             moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 91
tcccgaatcc agaaggatcc cgg                                              23

SEQ ID NO: 92             moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 92
tcacagtgtc tgagtcgccc agg                                              23

SEQ ID NO: 93             moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
```

```
                          organism = synthetic construct
SEQUENCE: 93
gctaggatgc tcgtggaggt ggg                                        23

SEQ ID NO: 94            moltype = DNA  length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 94
ctcgtggagg tggggaataa agg                                        23

SEQ ID NO: 95            moltype = DNA  length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 95
tgatctgtgc cccgagagtg agg                                        23

SEQ ID NO: 96            moltype = DNA  length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 96
tgaattaata ggacatgggg agg                                        23

SEQ ID NO: 97            moltype = DNA  length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 97
actctcgggg cacagatcac tgg                                        23

SEQ ID NO: 98            moltype = DNA  length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 98
gaccactggt cccattctac agg                                        23

SEQ ID NO: 99            moltype = DNA  length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 99
tgaggaccat cttgtattgc cgg                                        23

SEQ ID NO: 100           moltype = DNA  length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 100
```

-continued

```
agaatccgtc tgtcctgggc tgg                                               23

SEQ ID NO: 101          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 101
tgacgtgtca gccttccagg tgg                                               23

SEQ ID NO: 102          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 102
aaaagcatcc cgaatccaga agg                                               23

SEQ ID NO: 103          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 103
ttttcccgag gccacactca ggg                                               23

SEQ ID NO: 104          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 104
agcgccctgc accaggtcag cgg                                               23

SEQ ID NO: 105          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 105
tgagtcgccc agggtcctgg tgg                                               23

SEQ ID NO: 106          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 106
cacgtcaggc ctgaggtcac agg                                               23

SEQ ID NO: 107          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 107
gttttcccga ggccacactc agg                                               23
```

```
SEQ ID NO: 108        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 108
gagtcgcccca gggtcctggt ggg                                          23

SEQ ID NO: 109        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 109
gaatccgtct gtcctgggct ggg                                          23

SEQ ID NO: 110        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 110
ccggggaggg aggatgctcg ggg                                          23

SEQ ID NO: 111        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 111
gagccgagaa ttgaattaat agg                                          23

SEQ ID NO: 112        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 112
gtgacccgtg ctgtccgctg tgg                                          23

SEQ ID NO: 113        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 113
gggggcgtca agtcagagct ggg                                          23

SEQ ID NO: 114        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 114
cgcgctgtca ccgctctccc cgg                                          23

SEQ ID NO: 115        moltype = DNA   length = 23
FEATURE               Location/Qualifiers
```

-continued

```
misc_feature           1..23
                       note = Synthetic: Guide Sequence for AAVS1- Like Sequence
                        in CHO
source                 1..23
                       mol_type = other DNA
                       organism = synthetic construct
SEQUENCE: 115
tgctgcccaa atatagtcca tgg                                            23

SEQ ID NO: 116          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 116
agttgaggag aaacctatgg ggg                                            23

SEQ ID NO: 117          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 117
atcgtcctct atatatagca ggg                                            23

SEQ ID NO: 118          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 118
gagttgagga gaaacctatg ggg                                            23

SEQ ID NO: 119          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 119
aggggtacac tgccttggag ggg                                            23

SEQ ID NO: 120          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 120
atagagtccc tctggggaca ggg                                            23

SEQ ID NO: 121          moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 121
ctaggatgct cgtggaggtg ggg                                            23

SEQ ID NO: 122          moltype = DNA   length = 23
FEATURE                Location/Qualifiers
misc_feature           1..23
                       note = Synthetic: Guide Sequence for AAVS1- Like Sequence
```

-continued

```
                          in CHO
source                    1..23
                          mol_type = other DNA
                          organism = synthetic construct
SEQUENCE: 122
cgcggatgac aggggcgagg cgg                                                   23

SEQ ID NO: 123           moltype = DNA  length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 123
aaaacagaat ccgtctgtcc tgg                                                   23

SEQ ID NO: 124           moltype = DNA  length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 124
tgctaggatg ctcgtggagg tgg                                                   23

SEQ ID NO: 125           moltype = DNA  length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 125
gagtgtggcc tcgggaaaac agg                                                   23

SEQ ID NO: 126           moltype = DNA  length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 126
cgaggcggcc cctgcagggc agg                                                   23

SEQ ID NO: 127           moltype = DNA  length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 127
cttacacccc gtgcctttcc agg                                                   23

SEQ ID NO: 128           moltype = DNA  length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 128
ctgcccaaat atagtccatg ggg                                                   23

SEQ ID NO: 129           moltype = DNA  length = 23
FEATURE                  Location/Qualifiers
misc_feature             1..23
                          note = Synthetic: Guide Sequence for AAVS1- Like Sequence
                          in CHO
source                    1..23
```

-continued

```
                         mol_type = other DNA
                         organism = synthetic construct
SEQUENCE: 129
aggggcaaag gaccctcctg agg                                        23

SEQ ID NO: 130          moltype = DNA   length = 23
FEATURE                 Location/Qualifiers
misc_feature            1..23
                         note = Synthetic: Guide Sequence for AAVS1- Like Sequence
                          in CHO
source                  1..23
                         mol_type = other DNA
                         organism = synthetic construct
SEQUENCE: 130
tctcaccata gagtccctct ggg                                        23

SEQ ID NO: 131          moltype = DNA   length = 23
FEATURE                 Location/Qualifiers
misc_feature            1..23
                         note = Synthetic: Guide Sequence for AAVS1- Like Sequence
                          in CHO
source                  1..23
                         mol_type = other DNA
                         organism = synthetic construct
SEQUENCE: 131
agtgtacccc tttgttcccc tgg                                        23

SEQ ID NO: 132          moltype = DNA   length = 23
FEATURE                 Location/Qualifiers
misc_feature            1..23
                         note = Synthetic: Guide Sequence for AAVS1- Like Sequence
                          in CHO
source                  1..23
                         mol_type = other DNA
                         organism = synthetic construct
SEQUENCE: 132
gttgaggaga aacctatggg ggg                                        23

SEQ ID NO: 133          moltype = DNA   length = 23
FEATURE                 Location/Qualifiers
misc_feature            1..23
                         note = Synthetic: Guide Sequence for AAVS1- Like Sequence
                          in CHO
source                  1..23
                         mol_type = other DNA
                         organism = synthetic construct
SEQUENCE: 133
cacagtgtct gagtcgccca ggg                                        23

SEQ ID NO: 134          moltype = DNA   length = 23
FEATURE                 Location/Qualifiers
misc_feature            1..23
                         note = Synthetic: Guide Sequence for AAVS1- Like Sequence
                          in CHO
source                  1..23
                         mol_type = other DNA
                         organism = synthetic construct
SEQUENCE: 134
tcctcttgct aggatgctcg tgg                                        23

SEQ ID NO: 135          moltype = DNA   length = 23
FEATURE                 Location/Qualifiers
misc_feature            1..23
                         note = Synthetic: Guide Sequence for AAVS1- Like Sequence
                          in CHO
source                  1..23
                         mol_type = other DNA
                         organism = synthetic construct
SEQUENCE: 135
cacatgatca ccaaagtccc tgg                                        23

SEQ ID NO: 136          moltype = DNA   length = 23
FEATURE                 Location/Qualifiers
misc_feature            1..23
                         note = Synthetic: Guide Sequence for AAVS1- Like Sequence
                          in CHO
source                  1..23
                         mol_type = other DNA
                         organism = synthetic construct
```

-continued

```
SEQUENCE: 136
aaacagaatc cgtctgtcct ggg                                              23

SEQ ID NO: 137       moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 137
gtgcagggcg ctgatgccgt cgg                                              23

SEQ ID NO: 138       moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 138
cagcacggac tttttttgtt tgg                                              23

SEQ ID NO: 139       moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 139
cagccgaccc cggggatccc ggg                                              23

SEQ ID NO: 140       moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 140
tttggtcaag attttgcaac tgg                                              23

SEQ ID NO: 141       moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 141
ttggtcaaga ttttgcaact ggg                                              23

SEQ ID NO: 142       moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 142
cctgtcagag aggatgctct agg                                              23

SEQ ID NO: 143       moltype = DNA   length = 23
FEATURE              Location/Qualifiers
misc_feature         1..23
                     note = Synthetic: Guide Sequence for AAVS1- Like Sequence
                      in CHO
source               1..23
                     mol_type = other DNA
                     organism = synthetic construct
SEQUENCE: 143
tgggttgtcg tcctcttgct agg                                              23
```

-continued

```
SEQ ID NO: 144          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 144
ctcaccatag agtccctctg ggg                                          23

SEQ ID NO: 145          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 145
agacgctgac accctgagtg tgg                                          23

SEQ ID NO: 146          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 146
ggtggagcgc ctcttctcca ggg                                          23

SEQ ID NO: 147          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 147
aacaaagggg tacactgcct tgg                                          23

SEQ ID NO: 148          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 148
ctgtccccag agggactcta tgg                                          23

SEQ ID NO: 149          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 149
gtctctgacc ccctcatttg tgg                                          23

SEQ ID NO: 150          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 150
gtctgagtcg cccagggtcc tgg                                          23

SEQ ID NO: 151          moltype = DNA   length = 23
```

-continued

```
FEATURE            Location/Qualifiers
misc_feature       1..23
                   note = Synthetic: Guide Sequence for AAVS1- Like Sequence
                    in CHO
source             1..23
                   mol_type = other DNA
                   organism = synthetic construct
SEQUENCE: 151
gcctgacgtg tcagccttcc agg                                              23

SEQ ID NO: 152     moltype = DNA  length = 23
FEATURE            Location/Qualifiers
misc_feature       1..23
                   note = Synthetic: Guide Sequence for AAVS1- Like Sequence
                    in CHO
source             1..23
                   mol_type = other DNA
                   organism = synthetic construct
SEQUENCE: 152
atgtcccaca cagctcacgc cgg                                              23

SEQ ID NO: 153     moltype = DNA  length = 23
FEATURE            Location/Qualifiers
misc_feature       1..23
                   note = Synthetic: Guide Sequence for AAVS1- Like Sequence
                    in CHO
source             1..23
                   mol_type = other DNA
                   organism = synthetic construct
SEQUENCE: 153
ggctgtgccg caggcttcca ggg                                              23

SEQ ID NO: 154     moltype = DNA  length = 23
FEATURE            Location/Qualifiers
misc_feature       1..23
                   note = Synthetic: Guide Sequence for AAVS1- Like Sequence
                    in CHO
source             1..23
                   mol_type = other DNA
                   organism = synthetic construct
SEQUENCE: 154
caccccgtgc ctttccaggc tgg                                              23

SEQ ID NO: 155     moltype = DNA  length = 23
FEATURE            Location/Qualifiers
misc_feature       1..23
                   note = Synthetic: Guide Sequence for AAVS1- Like Sequence
                    in CHO
source             1..23
                   mol_type = other DNA
                   organism = synthetic construct
SEQUENCE: 155
tcaccaaggt gtctgcatgg cgg                                              23

SEQ ID NO: 156     moltype = DNA  length = 23
FEATURE            Location/Qualifiers
misc_feature       1..23
                   note = Synthetic: Guide Sequence for AAVS1- Like Sequence
                    in CHO
source             1..23
                   mol_type = other DNA
                   organism = synthetic construct
SEQUENCE: 156
gaattgaatt aataggacat ggg                                              23

SEQ ID NO: 157     moltype = DNA  length = 23
FEATURE            Location/Qualifiers
misc_feature       1..23
                   note = Synthetic: Guide Sequence for AAVS1- Like Sequence
                    in CHO
source             1..23
                   mol_type = other DNA
                   organism = synthetic construct
SEQUENCE: 157
aatatagtcc atggggtggt agg                                              23

SEQ ID NO: 158     moltype = DNA  length = 23
FEATURE            Location/Qualifiers
misc_feature       1..23
```

-continued

```
                         note = Synthetic: Guide Sequence for AAVS1- Like Sequence
                          in CHO
source                   1..23
                         mol_type = other DNA
                         organism = synthetic construct
SEQUENCE: 158
cagggcatag tttttaaagc agg                                        23

SEQ ID NO: 159          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 159
cggcatcagc gccctgcacc agg                                        23

SEQ ID NO: 160          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 160
gcagccgacc ccggggatcc cgg                                        23

SEQ ID NO: 161          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 161
acaggacctg tatttgaggt tgg                                        23

SEQ ID NO: 162          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 162
ggggcgaggc ggcccctgca ggg                                        23

SEQ ID NO: 163          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 163
aacctacccc accaggaccc tgg                                        23

SEQ ID NO: 164          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 164
gcaccgctcg ggcaggcggc ggg                                        23

SEQ ID NO: 165          moltype = DNA  length = 23
FEATURE                 Location/Qualifiers
misc_feature            1..23
                        note = Synthetic: Guide Sequence for AAVS1- Like Sequence
                         in CHO
```

-continued

```
source                  1..23
                        mol_type = other DNA
                        organism = synthetic construct
SEQUENCE: 165
tggaagcctg cggcacagcc agg                                          23

SEQ ID NO: 166          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 166
gaaccaacac tgtggccagg agg                                          23

SEQ ID NO: 167          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 167
agcagggtcc tgttttcccg agg                                          23

SEQ ID NO: 168          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 168
tgggtggcaa gatcaccaaa agg                                          23

SEQ ID NO: 169          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 169
agccgacccc ggggatcccg ggg                                          23

SEQ ID NO: 170          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 170
catggcaact tccatctcct ggg                                          23

SEQ ID NO: 171          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 171
acagcacggg tcacaggaag tgg                                          23

SEQ ID NO: 172          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
```

```
                        organism = synthetic construct
SEQUENCE: 172
ggggccgct gacctggtgc agg                                            23

SEQ ID NO: 173          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 173
aggggcgagg cggccctgc agg                                            23

SEQ ID NO: 174          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 174
gtggtcaccc ctgtccccag agg                                           23

SEQ ID NO: 175          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 175
tggggccggc gtgagctgtg tgg                                           23

SEQ ID NO: 176          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 176
ggaagcctgc ggcacagcca ggg                                           23

SEQ ID NO: 177          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 177
cctgagctga tctcctggac tgg                                           23

SEQ ID NO: 178          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 178
atccaaaagc tggcattgtc agg                                           23

SEQ ID NO: 179          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 179
```

```
ctctcaccat agagtccctc tgg                                            23

SEQ ID NO: 180        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 180
ggggggcgtc aagtcagagc tgg                                            23

SEQ ID NO: 181        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 181
gggtggaaat ctaagagaca ggg                                            23

SEQ ID NO: 182        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 182
cggggagagc ggtgacagcg cgg                                            23

SEQ ID NO: 183        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 183
agaattgaat taataggaca tgg                                            23

SEQ ID NO: 184        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 184
ccataaagga agttttccac agg                                            23

SEQ ID NO: 185        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 185
agtgaaccaa cactgtggcc agg                                            23

SEQ ID NO: 186        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 186
gttgggaggg aactcttggg agg                                            23
```

-continued

```
SEQ ID NO: 187        moltype = DNA  length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 187
cgggtcacag gaagtggggt agg                                         23

SEQ ID NO: 188        moltype = DNA  length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 188
ggcctggcta gcctcagagg agg                                         23

SEQ ID NO: 189        moltype = DNA  length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 189
ggtaggttct agaaggtgac agg                                         23

SEQ ID NO: 190        moltype = DNA  length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 190
acaagatggt cctcactctc ggg                                         23

SEQ ID NO: 191        moltype = DNA  length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 191
caaggtgtct gcatggcggg agg                                         23

SEQ ID NO: 192        moltype = DNA  length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 192
tgtttcactc atccaggcag agg                                         23

SEQ ID NO: 193        moltype = DNA  length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 193
tgtggaaaac ttcctttatg ggg                                         23

SEQ ID NO: 194        moltype = DNA  length = 23
FEATURE               Location/Qualifiers
```

-continued

```
misc_feature            1..23
                        note = Synthetic: Guide Sequence for AAVS1- Like Sequence
                         in CHO
source                  1..23
                        mol_type = other DNA
                        organism = synthetic construct
SEQUENCE: 194
gaggacgaca acccaggaga tgg                                          23

SEQ ID NO: 195          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 195
gggtggcaag atcaccaaaa ggg                                          23

SEQ ID NO: 196          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 196
ctggtggggt aggttctaga agg                                          23

SEQ ID NO: 197          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 197
actcttcagg cctttgcagg agg                                          23

SEQ ID NO: 198          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 198
cagagggact ctatggtgag agg                                          23

SEQ ID NO: 199          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 199
agcacgggtc acaggaagtg ggg                                          23

SEQ ID NO: 200          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 200
ctatggtgag aggcgtcctg tgg                                          23

SEQ ID NO: 201          moltype = DNA   length = 23
FEATURE                 Location/Qualifiers
misc_feature            1..23
                        note = Synthetic: Guide Sequence for AAVS1- Like Sequence
```

-continued

```
                          in CHO
source                    1..23
                          mol_type = other DNA
                          organism = synthetic construct
SEQUENCE: 201
cagcacgggt cacaggaagt ggg                                  23

SEQ ID NO: 202           moltype = DNA   length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 202
atgggatggg gcccaacaga cgg                                  23

SEQ ID NO: 203           moltype = DNA   length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 203
ctcccgccat gcagacacct tgg                                  23

SEQ ID NO: 204           moltype = DNA   length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 204
ggggatcccg gggaccccgg ggg                                  23

SEQ ID NO: 205           moltype = DNA   length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 205
tgtccgctgt ggcctcagga ggg                                  23

SEQ ID NO: 206           moltype = DNA   length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 206
gcagttggga gggaactctt ggg                                  23

SEQ ID NO: 207           moltype = DNA   length = 23
FEATURE                  Location/Qualifiers
misc_feature             1..23
                          note = Synthetic: Guide Sequence for AAVS1- Like Sequence
                          in CHO
source                    1..23
                          mol_type = other DNA
                          organism = synthetic construct
SEQUENCE: 207
gcctggctag cctcagagga ggg                                  23

SEQ ID NO: 208           moltype = DNA   length = 23
FEATURE                  Location/Qualifiers
misc_feature             1..23
                          note = Synthetic: Guide Sequence for AAVS1- Like Sequence
                          in CHO
source                    1..23
```

```
                          mol_type = other DNA
                          organism = synthetic construct
SEQUENCE: 208
gagagttgag gagaaaccta tgg                                              23

SEQ ID NO: 209          moltype = DNA   length = 23
FEATURE                 Location/Qualifiers
misc_feature            1..23
                          note = Synthetic: Guide Sequence for AAVS1- Like Sequence
                          in CHO
source                  1..23
                          mol_type = other DNA
                          organism = synthetic construct
SEQUENCE: 209
acctgtattt gaggttggcc tgg                                              23

SEQ ID NO: 210          moltype = DNA   length = 23
FEATURE                 Location/Qualifiers
misc_feature            1..23
                          note = Synthetic: Guide Sequence for AAVS1- Like Sequence
                          in CHO
source                  1..23
                          mol_type = other DNA
                          organism = synthetic construct
SEQUENCE: 210
tcgggcaggc ggcgggacgc cgg                                              23

SEQ ID NO: 211          moltype = DNA   length = 23
FEATURE                 Location/Qualifiers
misc_feature            1..23
                          note = Synthetic: Guide Sequence for AAVS1- Like Sequence
                          in CHO
source                  1..23
                          mol_type = other DNA
                          organism = synthetic construct
SEQUENCE: 211
tagagtccct ctggggacag ggg                                              23

SEQ ID NO: 212          moltype = DNA   length = 23
FEATURE                 Location/Qualifiers
misc_feature            1..23
                          note = Synthetic: Guide Sequence for AAVS1- Like Sequence
                          in CHO
source                  1..23
                          mol_type = other DNA
                          organism = synthetic construct
SEQUENCE: 212
gaagtgacac tgaagggcct ggg                                              23

SEQ ID NO: 213          moltype = DNA   length = 23
FEATURE                 Location/Qualifiers
misc_feature            1..23
                          note = Synthetic: Guide Sequence for AAVS1- Like Sequence
                          in CHO
source                  1..23
                          mol_type = other DNA
                          organism = synthetic construct
SEQUENCE: 213
agcagcctga gctgatctcc tgg                                              23

SEQ ID NO: 214          moltype = DNA   length = 23
FEATURE                 Location/Qualifiers
misc_feature            1..23
                          note = Synthetic: Guide Sequence for AAVS1- Like Sequence
                          in CHO
source                  1..23
                          mol_type = other DNA
                          organism = synthetic construct
SEQUENCE: 214
tcatggcaac ttccatctcc tgg                                              23

SEQ ID NO: 215          moltype = DNA   length = 23
FEATURE                 Location/Qualifiers
misc_feature            1..23
                          note = Synthetic: Guide Sequence for AAVS1- Like Sequence
                          in CHO
source                  1..23
                          mol_type = other DNA
                          organism = synthetic construct
```

-continued

```
SEQUENCE: 215
gtcacaggtt cctgtcagag agg                                          23

SEQ ID NO: 216         moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 216
caccaaggtg tctgcatggc ggg                                          23

SEQ ID NO: 217         moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 217
gtaggttcta gaaggtgaca ggg                                          23

SEQ ID NO: 218         moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 218
aattgaatta ataggacatg ggg                                          23

SEQ ID NO: 219         moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 219
ttccaagcac ctgatttctg tgg                                          23

SEQ ID NO: 220         moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 220
ctgtcagaga ggatgctcta ggg                                          23

SEQ ID NO: 221         moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 221
gtgctgtccg ctgtggcctc agg                                          23

SEQ ID NO: 222         moltype = DNA  length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 222
cccggggagg gaggatgctc ggg                                          23
```

```
SEQ ID NO: 223          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 223
ggggtggctc gggggcccc ggg                                             23

SEQ ID NO: 224          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 224
gtcaagtcag agctgggccc tgg                                            23

SEQ ID NO: 225          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 225
gacactgaag ggcctgggcc tgg                                            23

SEQ ID NO: 226          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 226
ctgaaagtga accaacactg tgg                                            23

SEQ ID NO: 227          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 227
aaaggggtac actgccttgg agg                                            23

SEQ ID NO: 228          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 228
tctggaaact tctaagcatt cgg                                            23

SEQ ID NO: 229          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 229
agagttgagg agaaacctat ggg                                            23

SEQ ID NO: 230          moltype = DNA  length = 23
```

-continued

```
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 230
ctctgaggct agccaggccc agg                                             23

SEQ ID NO: 231          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 231
aggggtggct cggggggccc cgg                                             23

SEQ ID NO: 232          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 232
tccacattga tttgcctttc tgg                                             23

SEQ ID NO: 233          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 233
agggtggaaa tctaagagac agg                                             23

SEQ ID NO: 234          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 234
ctgtccgctg tggcctcagg agg                                             23

SEQ ID NO: 235          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 235
agacacagga cctgtatttg agg                                             23

SEQ ID NO: 236          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 236
gggtggctcg gggggccccg ggg                                             23

SEQ ID NO: 237          moltype = DNA   length = 23
FEATURE                 Location/Qualifiers
misc_feature            1..23
```

-continued

```
                      note = Synthetic: Guide Sequence for AAVS1- Like Sequence
                       in CHO
source                1..23
                      mol_type = other DNA
                      organism = synthetic construct
SEQUENCE: 237
tggctgtgcc gcaggcttcc agg                                              23

SEQ ID NO: 238        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 238
tccagaaagg caaatcaatg tgg                                              23

SEQ ID NO: 239        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 239
caccagcctg gaaaggcacg ggg                                              23

SEQ ID NO: 240        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 240
cggggtcccc gggatccccg ggg                                              23

SEQ ID NO: 241        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 241
acactgcctt ggaggggcaa agg                                              23

SEQ ID NO: 242        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 242
tgacaggaac ctgtgacctc agg                                              23

SEQ ID NO: 243        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 243
tctcatgtgg gctatcaaga tgg                                              23

SEQ ID NO: 244        moltype = DNA   length = 23
FEATURE               Location/Qualifiers
misc_feature          1..23
                      note = Synthetic: Guide Sequence for AAVS1- Like Sequence
                       in CHO
```

-continued

```
source              1..23
                    mol_type = other DNA
                    organism = synthetic construct
SEQUENCE: 244
gggaactctt gggagggcca ggg                                       23

SEQ ID NO: 245      moltype = DNA  length = 23
FEATURE             Location/Qualifiers
misc_feature        1..23
                    note = Synthetic: Guide Sequence for AAVS1- Like Sequence
                      in CHO
source              1..23
                    mol_type = other DNA
                    organism = synthetic construct
SEQUENCE: 245
gaggccacag cggacagcac ggg                                       23

SEQ ID NO: 246      moltype = DNA  length = 23
FEATURE             Location/Qualifiers
misc_feature        1..23
                    note = Synthetic: Guide Sequence for AAVS1- Like Sequence
                      in CHO
source              1..23
                    mol_type = other DNA
                    organism = synthetic construct
SEQUENCE: 246
tgtcctatta attcaattct cgg                                       23

SEQ ID NO: 247      moltype = DNA  length = 23
FEATURE             Location/Qualifiers
misc_feature        1..23
                    note = Synthetic: Guide Sequence for AAVS1- Like Sequence
                      in CHO
source              1..23
                    mol_type = other DNA
                    organism = synthetic construct
SEQUENCE: 247
agggaactct tgggagggcc agg                                       23

SEQ ID NO: 248      moltype = DNA  length = 23
FEATURE             Location/Qualifiers
misc_feature        1..23
                    note = Synthetic: Guide Sequence for AAVS1- Like Sequence
                      in CHO
source              1..23
                    mol_type = other DNA
                    organism = synthetic construct
SEQUENCE: 248
gcacctgatt tctgtggtat tgg                                       23

SEQ ID NO: 249      moltype = DNA  length = 23
FEATURE             Location/Qualifiers
misc_feature        1..23
                    note = Synthetic: Guide Sequence for AAVS1- Like Sequence
                      in CHO
source              1..23
                    mol_type = other DNA
                    organism = synthetic construct
SEQUENCE: 249
gtatcttgag tgtcttttct cgg                                       23

SEQ ID NO: 250      moltype = DNA  length = 23
FEATURE             Location/Qualifiers
misc_feature        1..23
                    note = Synthetic: Guide Sequence for AAVS1- Like Sequence
                      in CHO
source              1..23
                    mol_type = other DNA
                    organism = synthetic construct
SEQUENCE: 250
ctgtggaaaa cttcctttat ggg                                       23

SEQ ID NO: 251      moltype = DNA  length = 23
FEATURE             Location/Qualifiers
misc_feature        1..23
                    note = Synthetic: Guide Sequence for AAVS1- Like Sequence
                      in CHO
source              1..23
                    mol_type = other DNA
```

```
                        organism = synthetic construct
SEQUENCE: 251
gggacctcca gcagatgcag agg                                          23

SEQ ID NO: 252          moltype = DNA  length = 23
FEATURE                 Location/Qualifiers
misc_feature            1..23
                        note = Synthetic: Guide Sequence for AAVS1- Like Sequence
                        in CHO
source                  1..23
                        mol_type = other DNA
                        organism = synthetic construct
SEQUENCE: 252
ctggggacag gggtgaccac tgg                                          23

SEQ ID NO: 253          moltype = DNA  length = 23
FEATURE                 Location/Qualifiers
misc_feature            1..23
                        note = Synthetic: Guide Sequence for AAVS1- Like Sequence
                        in CHO
source                  1..23
                        mol_type = other DNA
                        organism = synthetic construct
SEQUENCE: 253
ttcagtgtca cttcttttgg ggg                                          23

SEQ ID NO: 254          moltype = DNA  length = 23
FEATURE                 Location/Qualifiers
misc_feature            1..23
                        note = Synthetic: Guide Sequence for AAVS1- Like Sequence
                        in CHO
source                  1..23
                        mol_type = other DNA
                        organism = synthetic construct
SEQUENCE: 254
tccctcctct gaggctagcc agg                                          23

SEQ ID NO: 255          moltype = DNA  length = 23
FEATURE                 Location/Qualifiers
misc_feature            1..23
                        note = Synthetic: Guide Sequence for AAVS1- Like Sequence
                        in CHO
source                  1..23
                        mol_type = other DNA
                        organism = synthetic construct
SEQUENCE: 255
ggcgccggga tcggggcccc cgg                                          23

SEQ ID NO: 256          moltype = DNA  length = 23
FEATURE                 Location/Qualifiers
misc_feature            1..23
                        note = Synthetic: Guide Sequence for AAVS1- Like Sequence
                        in CHO
source                  1..23
                        mol_type = other DNA
                        organism = synthetic construct
SEQUENCE: 256
ggttctagaa ggtgacaggg tgg                                          23

SEQ ID NO: 257          moltype = DNA  length = 23
FEATURE                 Location/Qualifiers
misc_feature            1..23
                        note = Synthetic: Guide Sequence for AAVS1- Like Sequence
                        in CHO
source                  1..23
                        mol_type = other DNA
                        organism = synthetic construct
SEQUENCE: 257
ttgggaggga actcttggga ggg                                          23

SEQ ID NO: 258          moltype = DNA  length = 23
FEATURE                 Location/Qualifiers
misc_feature            1..23
                        note = Synthetic: Guide Sequence for AAVS1- Like Sequence
                        in CHO
source                  1..23
                        mol_type = other DNA
                        organism = synthetic construct
SEQUENCE: 258
```

-continued

```
atcaggtgct tggaaagtag agg                                              23

SEQ ID NO: 259           moltype = DNA   length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 259
cggggaggga ggatgctcgg ggg                                              23

SEQ ID NO: 260           moltype = DNA   length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 260
tgaggccaca gcggacagca cgg                                              23

SEQ ID NO: 261           moltype = DNA   length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 261
tggtcacccc tgtccccaga ggg                                              23

SEQ ID NO: 262           moltype = DNA   length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 262
tccccgcctc ctgccctgca ggg                                              23

SEQ ID NO: 263           moltype = DNA   length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 263
ggctgccctg gctgtgccgc agg                                              23

SEQ ID NO: 264           moltype = DNA   length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 264
tccaaaagct ggcattgtca ggg                                              23

SEQ ID NO: 265           moltype = DNA   length = 23
FEATURE                  Location/Qualifiers
misc_feature             1..23
                         note = Synthetic: Guide Sequence for AAVS1- Like Sequence
                          in CHO
source                   1..23
                         mol_type = other DNA
                         organism = synthetic construct
SEQUENCE: 265
caatgccagc ttttggatga cgg                                              23
```

-continued

```
SEQ ID NO: 266        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 266
ctgggcctgg ctagcctcag agg                                           23

SEQ ID NO: 267        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 267
ggttcacttt cagtctttca tgg                                           23

SEQ ID NO: 268        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 268
aggagaaacc tatgggggt ggg                                            23

SEQ ID NO: 269        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 269
tctaaaagac agcccagccc agg                                           23

SEQ ID NO: 270        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 270
cggggatccc ggggacccg ggg                                            23

SEQ ID NO: 271        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 271
tcttctccag gggaacaaag ggg                                           23

SEQ ID NO: 272        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 272
actgacacaa aaagtcagca cgg                                           23

SEQ ID NO: 273        moltype = DNA   length = 23
FEATURE               Location/Qualifiers
```

-continued

```
misc_feature          1..23
                      note = Synthetic: Guide Sequence for AAVS1- Like Sequence
                       in CHO
source                1..23
                      mol_type = other DNA
                      organism = synthetic construct
SEQUENCE: 273
cctgaagagt caggtcacca agg                                          23

SEQ ID NO: 274        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 274
ggaggagagt cccacctgga agg                                          23

SEQ ID NO: 275        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 275
gggcagccac cagcctggaa agg                                          23

SEQ ID NO: 276        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 276
agccctattt ctctctcctc tgg                                          23

SEQ ID NO: 277        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 277
gccaccagcc tggaaaggca cgg                                          23

SEQ ID NO: 278        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 278
tgacaccctg agtgtggcct cgg                                          23

SEQ ID NO: 279        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 279
aattaatagg acatggggag ggg                                          23

SEQ ID NO: 280        moltype = DNA   length = 23
FEATURE               Location/Qualifiers
misc_feature          1..23
                      note = Synthetic: Guide Sequence for AAVS1- Like Sequence
```

-continued

```
                                in CHO
source                          1..23
                                mol_type = other DNA
                                organism = synthetic construct
SEQUENCE: 280
ggctcggggg gccccgggga ggg                                            23

SEQ ID NO: 281         moltype = DNA  length = 23
FEATURE                Location/Qualifiers
misc_feature          1..23
                                note = Synthetic: Guide Sequence for AAVS1- Like Sequence
                                in CHO
source                          1..23
                                mol_type = other DNA
                                organism = synthetic construct
SEQUENCE: 281
taataggaca tggggagggg agg                                            23

SEQ ID NO: 282         moltype = DNA  length = 23
FEATURE                Location/Qualifiers
misc_feature          1..23
                                note = Synthetic: Guide Sequence for AAVS1- Like Sequence
                                in CHO
source                          1..23
                                mol_type = other DNA
                                organism = synthetic construct
SEQUENCE: 282
ctcttctcca ggggaacaaa ggg                                            23

SEQ ID NO: 283         moltype = DNA  length = 23
FEATURE                Location/Qualifiers
misc_feature          1..23
                                note = Synthetic: Guide Sequence for AAVS1- Like Sequence
                                in CHO
source                          1..23
                                mol_type = other DNA
                                organism = synthetic construct
SEQUENCE: 283
tcggggcccc cgggtccccc ggg                                            23

SEQ ID NO: 284         moltype = DNA  length = 23
FEATURE                Location/Qualifiers
misc_feature          1..23
                                note = Synthetic: Guide Sequence for AAVS1- Like Sequence
                                in CHO
source                          1..23
                                mol_type = other DNA
                                organism = synthetic construct
SEQUENCE: 284
tccctgacaa tgccagcttt tgg                                            23

SEQ ID NO: 285         moltype = DNA  length = 23
FEATURE                Location/Qualifiers
misc_feature          1..23
                                note = Synthetic: Guide Sequence for AAVS1- Like Sequence
                                in CHO
source                          1..23
                                mol_type = other DNA
                                organism = synthetic construct
SEQUENCE: 285
gaattaatag gacatgggga ggg                                            23

SEQ ID NO: 286         moltype = DNA  length = 23
FEATURE                Location/Qualifiers
misc_feature          1..23
                                note = Synthetic: Guide Sequence for AAVS1- Like Sequence
                                in CHO
source                          1..23
                                mol_type = other DNA
                                organism = synthetic construct
SEQUENCE: 286
aatgaggggg tcagagacac agg                                            23

SEQ ID NO: 287         moltype = DNA  length = 23
FEATURE                Location/Qualifiers
misc_feature          1..23
                                note = Synthetic: Guide Sequence for AAVS1- Like Sequence
                                in CHO
source                          1..23
```

-continued

```
                              mol_type = other DNA
                              organism = synthetic construct
SEQUENCE: 287
gaaaacttcc tttatggggc cgg                                                23

SEQ ID NO: 288           moltype = DNA   length = 23
FEATURE                  Location/Qualifiers
misc_feature             1..23
                         note = Synthetic: Guide Sequence for AAVS1- Like Sequence
                           in CHO
source                   1..23
                         mol_type = other DNA
                         organism = synthetic construct
SEQUENCE: 288
cttgggaggg ccagggactt tgg                                                23

SEQ ID NO: 289           moltype = DNA   length = 23
FEATURE                  Location/Qualifiers
misc_feature             1..23
                         note = Synthetic: Guide Sequence for AAVS1- Like Sequence
                           in CHO
source                   1..23
                         mol_type = other DNA
                         organism = synthetic construct
SEQUENCE: 289
cccctgcagg gcaggaggcg ggg                                                23

SEQ ID NO: 290           moltype = DNA   length = 23
FEATURE                  Location/Qualifiers
misc_feature             1..23
                         note = Synthetic: Guide Sequence for AAVS1- Like Sequence
                           in CHO
source                   1..23
                         mol_type = other DNA
                         organism = synthetic construct
SEQUENCE: 290
tcagtgtcac ttcttttggg ggg                                                23

SEQ ID NO: 291           moltype = DNA   length = 23
FEATURE                  Location/Qualifiers
misc_feature             1..23
                         note = Synthetic: Guide Sequence for AAVS1- Like Sequence
                           in CHO
source                   1..23
                         mol_type = other DNA
                         organism = synthetic construct
SEQUENCE: 291
atccccgttc ttcttcctcc tgg                                                23

SEQ ID NO: 292           moltype = DNA   length = 23
FEATURE                  Location/Qualifiers
misc_feature             1..23
                         note = Synthetic: Guide Sequence for AAVS1- Like Sequence
                           in CHO
source                   1..23
                         mol_type = other DNA
                         organism = synthetic construct
SEQUENCE: 292
cttcctcctg gccacagtgt tgg                                                23

SEQ ID NO: 293           moltype = DNA   length = 23
FEATURE                  Location/Qualifiers
misc_feature             1..23
                         note = Synthetic: Guide Sequence for AAVS1- Like Sequence
                           in CHO
source                   1..23
                         mol_type = other DNA
                         organism = synthetic construct
SEQUENCE: 293
tgcagttggg agggaactct tgg                                                23

SEQ ID NO: 294           moltype = DNA   length = 23
FEATURE                  Location/Qualifiers
misc_feature             1..23
                         note = Synthetic: Guide Sequence for AAVS1- Like Sequence
                           in CHO
source                   1..23
                         mol_type = other DNA
                         organism = synthetic construct
```

-continued

```
SEQUENCE: 294
tggctcgggg ggccccgggg agg                                           23

SEQ ID NO: 295          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 295
ctgcaaaggc ctgaagagtc agg                                           23

SEQ ID NO: 296          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 296
ccgtgtgcgg aagacgccgc cgg                                           23

SEQ ID NO: 297          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 297
ccccggggag ggaggatgct cgg                                           23

SEQ ID NO: 298          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 298
ttccaggctg gtggctgccc tgg                                           23

SEQ ID NO: 299          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 299
aggtcaccaa ggtgtctgca tgg                                           23

SEQ ID NO: 300          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 300
ggcggcccct gcagggcagg agg                                           23

SEQ ID NO: 301          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 301
tcggggggcc ccggggaggg agg                                           23
```

-continued

```
SEQ ID NO: 302          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 302
ccaaaagaag tgacactgaa ggg                                               23

SEQ ID NO: 303          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 303
ggccaggagg aagaagaacg ggg                                               23

SEQ ID NO: 304          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 304
gcccagggtc ctggtggggt agg                                               23

SEQ ID NO: 305          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 305
gctagcctca gaggagggag tgg                                               23

SEQ ID NO: 306          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 306
gagggtcctt tgcccctcca agg                                               23

SEQ ID NO: 307          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 307
ccaccagcct ggaaaggcac ggg                                               23

SEQ ID NO: 308          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 308
gatttctgtg gtattggggt tgg                                               23

SEQ ID NO: 309          moltype = DNA   length = 23
```

-continued

```
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 309
ctagcctcag aggagggagt ggg                                            23

SEQ ID NO: 310            moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 310
cccgggtcc ccgggatccc cgg                                             23

SEQ ID NO: 311            moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 311
catggggtgg taggtggagt ggg                                            23

SEQ ID NO: 312            moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 312
aatgccagct tttggatgac ggg                                            23

SEQ ID NO: 313            moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 313
gcccctgcag ggcaggaggc ggg                                            23

SEQ ID NO: 314            moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 314
gaggagaaac ctatgggggg tgg                                            23

SEQ ID NO: 315            moltype = DNA   length = 23
FEATURE                   Location/Qualifiers
misc_feature              1..23
                          note = Synthetic: Guide Sequence for AAVS1- Like Sequence
                           in CHO
source                    1..23
                          mol_type = other DNA
                          organism = synthetic construct
SEQUENCE: 315
agaagtgaca ctgaagggcc tgg                                            23

SEQ ID NO: 316            moltype = DNA   length = 23
FEATURE                   Location/Qualifiers
misc_feature              1..23
```

-continued

```
                            note = Synthetic: Guide Sequence for AAVS1- Like Sequence
                            in CHO
source                      1..23
                            mol_type = other DNA
                            organism = synthetic construct
SEQUENCE: 316
cctccagcag atgcagagga agg                                         23

SEQ ID NO: 317              moltype = DNA  length = 23
FEATURE                     Location/Qualifiers
misc_feature                1..23
                            note = Synthetic: Guide Sequence for AAVS1- Like Sequence
                            in CHO
source                      1..23
                            mol_type = other DNA
                            organism = synthetic construct
SEQUENCE: 317
cctcttctcc aggggaacaa agg                                         23

SEQ ID NO: 318              moltype = DNA  length = 23
FEATURE                     Location/Qualifiers
misc_feature                1..23
                            note = Synthetic: Guide Sequence for AAVS1- Like Sequence
                            in CHO
source                      1..23
                            mol_type = other DNA
                            organism = synthetic construct
SEQUENCE: 318
ccggggtccc cgggatcccc ggg                                         23

SEQ ID NO: 319              moltype = DNA  length = 23
FEATURE                     Location/Qualifiers
misc_feature                1..23
                            note = Synthetic: Guide Sequence for AAVS1- Like Sequence
                            in CHO
source                      1..23
                            mol_type = other DNA
                            organism = synthetic construct
SEQUENCE: 319
tagcctcaga ggagggagtg ggg                                         23

SEQ ID NO: 320              moltype = DNA  length = 23
FEATURE                     Location/Qualifiers
misc_feature                1..23
                            note = Synthetic: Guide Sequence for AAVS1- Like Sequence
                            in CHO
source                      1..23
                            mol_type = other DNA
                            organism = synthetic construct
SEQUENCE: 320
cagaggaagg ggatgcagtt ggg                                         23

SEQ ID NO: 321              moltype = DNA  length = 23
FEATURE                     Location/Qualifiers
misc_feature                1..23
                            note = Synthetic: Guide Sequence for AAVS1- Like Sequence
                            in CHO
source                      1..23
                            mol_type = other DNA
                            organism = synthetic construct
SEQUENCE: 321
ctccagcaga tgcagaggaa ggg                                         23

SEQ ID NO: 322              moltype = DNA  length = 23
FEATURE                     Location/Qualifiers
misc_feature                1..23
                            note = Synthetic: Guide Sequence for AAVS1- Like Sequence
                            in CHO
source                      1..23
                            mol_type = other DNA
                            organism = synthetic construct
SEQUENCE: 322
gattctgttt ttcctctgcc tgg                                         23

SEQ ID NO: 323              moltype = DNA  length = 23
FEATURE                     Location/Qualifiers
misc_feature                1..23
                            note = Synthetic: Guide Sequence for AAVS1- Like Sequence
                            in CHO
```

-continued

```
source                1..23
                      mol_type = other DNA
                      organism = synthetic construct
SEQUENCE: 323
cttcagtgtc acttcttttg ggg                                        23

SEQ ID NO: 324        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 324
catagagtcc ctctggggac agg                                        23

SEQ ID NO: 325        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 325
ggaccctcct gaggccacag cgg                                        23

SEQ ID NO: 326        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 326
ccatggggtg gtaggtggag tgg                                        23

SEQ ID NO: 327        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 327
gacaccctga gtgtggcctc ggg                                        23

SEQ ID NO: 328        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 328
atgcttagaa gtttccagaa agg                                        23

SEQ ID NO: 329        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 329
agctgggccc tggaagcctg cgg                                        23

SEQ ID NO: 330        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
```

-continued

```
                              organism = synthetic construct
SEQUENCE: 330
taccacagaa atcaggtgct tgg                                         23

SEQ ID NO: 331              moltype = DNA   length = 23
FEATURE                     Location/Qualifiers
misc_feature               1..23
                           note = Synthetic: Guide Sequence for AAVS1- Like Sequence
                            in CHO
source                     1..23
                           mol_type = other DNA
                           organism = synthetic construct
SEQUENCE: 331
accccaatac cacagaaatc agg                                         23

SEQ ID NO: 332              moltype = DNA   length = 23
FEATURE                     Location/Qualifiers
misc_feature               1..23
                           note = Synthetic: Guide Sequence for AAVS1- Like Sequence
                            in CHO
source                     1..23
                           mol_type = other DNA
                           organism = synthetic construct
SEQUENCE: 332
ttctacaggt aaaaaaacta agg                                         23

SEQ ID NO: 333              moltype = DNA   length = 23
FEATURE                     Location/Qualifiers
misc_feature               1..23
                           note = Synthetic: Guide Sequence for AAVS1- Like Sequence
                            in CHO
source                     1..23
                           mol_type = other DNA
                           organism = synthetic construct
SEQUENCE: 333
ggcccctgca gggcaggagg cgg                                         23

SEQ ID NO: 334              moltype = DNA   length = 23
FEATURE                     Location/Qualifiers
misc_feature               1..23
                           note = Synthetic: Guide Sequence for AAVS1- Like Sequence
                            in CHO
source                     1..23
                           mol_type = other DNA
                           organism = synthetic construct
SEQUENCE: 334
ctccccgcct cctgccctgc agg                                         23

SEQ ID NO: 335              moltype = DNA   length = 23
FEATURE                     Location/Qualifiers
misc_feature               1..23
                           note = Synthetic: Guide Sequence for AAVS1- Like Sequence
                            in CHO
source                     1..23
                           mol_type = other DNA
                           organism = synthetic construct
SEQUENCE: 335
tctctgaccc cctcatttgt ggg                                         23

SEQ ID NO: 336              moltype = DNA   length = 23
FEATURE                     Location/Qualifiers
misc_feature               1..23
                           note = Synthetic: Guide Sequence for AAVS1- Like Sequence
                            in CHO
source                     1..23
                           mol_type = other DNA
                           organism = synthetic construct
SEQUENCE: 336
ggagaaacct atggggggtg ggg                                         23

SEQ ID NO: 337              moltype = DNA   length = 23
FEATURE                     Location/Qualifiers
misc_feature               1..23
                           note = Synthetic: Guide Sequence for AAVS1- Like Sequence
                            in CHO
source                     1..23
                           mol_type = other DNA
                           organism = synthetic construct
SEQUENCE: 337
```

-continued

```
acagcccagc ccaggacaga cgg                                                23

SEQ ID NO: 338        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 338
cctgtatttg aggttggcct ggg                                                23

SEQ ID NO: 339        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 339
agccagggca gccaccagcc tgg                                                23

SEQ ID NO: 340        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 340
agcctcagag gagggagtgg ggg                                                23

SEQ ID NO: 341        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 341
gttcagtgtt tcactcatcc agg                                                23

SEQ ID NO: 342        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 342
ctgactcttc aggcctttgc agg                                                23

SEQ ID NO: 343        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 343
atcccccact ccctcctctg agg                                                23

SEQ ID NO: 344        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 344
cccaaaagaa gtgacactga agg                                                23
```

-continued

```
SEQ ID NO: 345        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 345
tggccaggag gaagaagaac ggg                                              23

SEQ ID NO: 346        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 346
gggaggaagg ttatgggatg ggg                                              23

SEQ ID NO: 347        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 347
cctgaggctt cctgcactct agg                                              23

SEQ ID NO: 348        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 348
tagttttttt acctgtagaa tgg                                              23

SEQ ID NO: 349        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 349
aagtggggta gggaacaagg tgg                                              23

SEQ ID NO: 350        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 350
gggtcacagg aagtggggta ggg                                              23

SEQ ID NO: 351        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 351
cacctgattt ctgtggtatt ggg                                              23

SEQ ID NO: 352        moltype = DNA   length = 23
FEATURE               Location/Qualifiers
```

-continued

```
misc_feature          1..23
                      note = Synthetic: Guide Sequence for AAVS1- Like Sequence
                       in CHO
source                1..23
                      mol_type = other DNA
                      organism = synthetic construct
SEQUENCE: 352
tttgcaactg ggtctcatgt ggg                                                  23

SEQ ID NO: 353        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 353
gagaaaccta tggggggtgg ggg                                                  23

SEQ ID NO: 354        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 354
gagggaggag gggtggctcg ggg                                                  23

SEQ ID NO: 355        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 355
gcctgtaatc ccacaaatga ggg                                                  23

SEQ ID NO: 356        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 356
gcagaggaag gggatgcagt tgg                                                  23

SEQ ID NO: 357        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 357
acctgatttc tgtggtattg ggg                                                  23

SEQ ID NO: 358        moltype = DNA   length = 23
FEATURE               Location/Qualifiers
misc_feature          1..23
                      note = Synthetic: Guide Sequence for AAVS1- Like Sequence
                       in CHO
source                1..23
                      mol_type = other DNA
                      organism = synthetic construct
SEQUENCE: 358
aaaccagagg agagagaaat agg                                                  23

SEQ ID NO: 359        moltype = DNA   length = 23
FEATURE               Location/Qualifiers
misc_feature          1..23
                      note = Synthetic: Guide Sequence for AAVS1- Like Sequence
```

-continued

```
                            in CHO
source                      1..23
                            mol_type = other DNA
                            organism = synthetic construct
SEQUENCE: 359
aaccagagga gagagaaata ggg                                   23

SEQ ID NO: 360              moltype = DNA   length = 23
FEATURE                     Location/Qualifiers
misc_feature                1..23
                            note = Synthetic: Guide Sequence for AAVS1- Like Sequence
                             in CHO
source                      1..23
                            mol_type = other DNA
                            organism = synthetic construct
SEQUENCE: 360
gaggagagag aaatagggct tgg                                   23

SEQ ID NO: 361              moltype = DNA   length = 23
FEATURE                     Location/Qualifiers
misc_feature                1..23
                            note = Synthetic: Guide Sequence for AAVS1- Like Sequence
                             in CHO
source                      1..23
                            mol_type = other DNA
                            organism = synthetic construct
SEQUENCE: 361
ctgcagggca ggaggcgggg agg                                   23

SEQ ID NO: 362              moltype = DNA   length = 23
FEATURE                     Location/Qualifiers
misc_feature                1..23
                            note = Synthetic: Guide Sequence for AAVS1- Like Sequence
                             in CHO
source                      1..23
                            mol_type = other DNA
                            organism = synthetic construct
SEQUENCE: 362
aggaagggga tgcagttggg agg                                   23

SEQ ID NO: 363              moltype = DNA   length = 23
FEATURE                     Location/Qualifiers
misc_feature                1..23
                            note = Synthetic: Guide Sequence for AAVS1- Like Sequence
                             in CHO
source                      1..23
                            mol_type = other DNA
                            organism = synthetic construct
SEQUENCE: 363
ggtattgggg ttggaacctg agg                                   23

SEQ ID NO: 364              moltype = DNA   length = 23
FEATURE                     Location/Qualifiers
misc_feature                1..23
                            note = Synthetic: Guide Sequence for AAVS1- Like Sequence
                             in CHO
source                      1..23
                            mol_type = other DNA
                            organism = synthetic construct
SEQUENCE: 364
ttttgcaact gggtctcatg tgg                                   23

SEQ ID NO: 365              moltype = DNA   length = 23
FEATURE                     Location/Qualifiers
misc_feature                1..23
                            note = Synthetic: Guide Sequence for AAVS1- Like Sequence
                             in CHO
source                      1..23
                            mol_type = other DNA
                            organism = synthetic construct
SEQUENCE: 365
gggaggaggg gtggctcggg ggg                                   23

SEQ ID NO: 366              moltype = DNA   length = 23
FEATURE                     Location/Qualifiers
misc_feature                1..23
                            note = Synthetic: Guide Sequence for AAVS1- Like Sequence
                             in CHO
source                      1..23
```

-continued

```
                        mol_type = other DNA
                        organism = synthetic construct
SEQUENCE: 366
tccccttcct ctgcatctgc tgg                                            23

SEQ ID NO: 367          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 367
aggaagtggg gtagggaaca agg                                            23

SEQ ID NO: 368          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 368
aggggaggaa ggttatggga tgg                                            23

SEQ ID NO: 369          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 369
cctgtaatcc cacaaatgag ggg                                            23

SEQ ID NO: 370          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 370
agttttttta cctgtagaat ggg                                            23

SEQ ID NO: 371          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 371
aggaagaaga acggggatgg ggg                                            23

SEQ ID NO: 372          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 372
tgcagggcag gaggcgggga ggg                                            23

SEQ ID NO: 373          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
```

-continued

```
SEQUENCE: 373
ggaaggggat gcagttggga ggg                                                  23

SEQ ID NO: 374         moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 374
caaagtcact gtgtagatga agg                                                  23

SEQ ID NO: 375         moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 375
gtggccagga ggaagaagaa cgg                                                  23

SEQ ID NO: 376         moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 376
tccagcagat gcagaggaag ggg                                                  23

SEQ ID NO: 377         moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 377
agggaggagg ggtggctcgg ggg                                                  23

SEQ ID NO: 378         moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 378
aacctatggg gggtgggggt ggg                                                  23

SEQ ID NO: 379         moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 379
ggggagggga ggaaggttat ggg                                                  23

SEQ ID NO: 380         moltype = DNA   length = 23
FEATURE                Location/Qualifiers
misc_feature           1..23
                       note = Synthetic: Guide Sequence for AAVS1- Like Sequence
                        in CHO
source                 1..23
                       mol_type = other DNA
                       organism = synthetic construct
SEQUENCE: 380
cacccacccc caccccccat agg                                                  23
```

-continued

```
SEQ ID NO: 381          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 381
aaacctatgg ggggtggggg tgg                                              23

SEQ ID NO: 382          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 382
ggaggaagaa gaacggggat ggg                                              23

SEQ ID NO: 383          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 383
gaggaagaag aacggggatg ggg                                              23

SEQ ID NO: 384          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 384
ggagggagga ggggtggctc ggg                                              23

SEQ ID NO: 385          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 385
ggttggcctg ggctacacag ggg                                              23

SEQ ID NO: 386          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 386
agaggaggga gtgggggatt ggg                                              23

SEQ ID NO: 387          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 387
gaggttggcc tgggctacac agg                                              23

SEQ ID NO: 388          moltype = DNA   length = 23
```

```
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 388
aggttggcct gggctacaca ggg                                              23

SEQ ID NO: 389          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 389
tggggagggg aggaaggtta tgg                                              23

SEQ ID NO: 390          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 390
gaaagtagag gcaggagggt tgg                                              23

SEQ ID NO: 391          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 391
gaggagggag tggggattg ggg                                               23

SEQ ID NO: 392          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 392
ggggaggaag gttatgggat ggg                                              23

SEQ ID NO: 393          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 393
agagtgcttg cctagagtgc agg                                              23

SEQ ID NO: 394          moltype = DNA   length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 394
aggagggagt gggggattgg ggg                                              23

SEQ ID NO: 395          moltype = DNA   length = 23
FEATURE                 Location/Qualifiers
misc_feature            1..23
```

-continued

```
                          note = Synthetic: Guide Sequence for AAVS1- Like Sequence
                           in CHO
source                    1..23
                          mol_type = other DNA
                          organism = synthetic construct
SEQUENCE: 395
cagaggaggg agtgggggat tgg                                               23

SEQ ID NO: 396           moltype = DNA  length = 23
FEATURE                  Location/Qualifiers
misc_feature             1..23
                          note = Synthetic: Guide Sequence for AAVS1- Like Sequence
                           in CHO
source                    1..23
                          mol_type = other DNA
                          organism = synthetic construct
SEQUENCE: 396
aggaggaaga agaacgggga tgg                                               23

SEQ ID NO: 397           moltype = DNA  length = 23
FEATURE                  Location/Qualifiers
misc_feature             1..23
                          note = Synthetic: Guide Sequence for AAVS1- Like Sequence
                           in CHO
source                    1..23
                          mol_type = other DNA
                          organism = synthetic construct
SEQUENCE: 397
ttttttcccc tgtgtagccc agg                                               23

SEQ ID NO: 398           moltype = DNA  length = 23
FEATURE                  Location/Qualifiers
misc_feature             1..23
                          note = Synthetic: Guide Sequence for AAVS1- Like Sequence
                           in CHO
source                    1..23
                          mol_type = other DNA
                          organism = synthetic construct
SEQUENCE: 398
ggtgcttgga aagtagaggc agg                                               23

SEQ ID NO: 399           moltype = DNA  length = 23
FEATURE                  Location/Qualifiers
misc_feature             1..23
                          note = Synthetic: Guide Sequence for AAVS1- Like Sequence
                           in CHO
source                    1..23
                          mol_type = other DNA
                          organism = synthetic construct
SEQUENCE: 399
cttggaaagt agaggcagga ggg                                               23

SEQ ID NO: 400           moltype = DNA  length = 23
FEATURE                  Location/Qualifiers
misc_feature             1..23
                          note = Synthetic: Guide Sequence for AAVS1- Like Sequence
                           in CHO
source                    1..23
                          mol_type = other DNA
                          organism = synthetic construct
SEQUENCE: 400
ctgtaatccc acaaatgagg ggg                                               23

SEQ ID NO: 401           moltype = DNA  length = 23
FEATURE                  Location/Qualifiers
misc_feature             1..23
                          note = Synthetic: Guide Sequence for AAVS1- Like Sequence
                           in CHO
source                    1..23
                          mol_type = other DNA
                          organism = synthetic construct
SEQUENCE: 401
aggacatggg gaggggagga agg                                               23

SEQ ID NO: 402           moltype = DNA  length = 23
FEATURE                  Location/Qualifiers
misc_feature             1..23
                          note = Synthetic: Guide Sequence for AAVS1- Like Sequence
                           in CHO
```

-continued

```
source                  1..23
                        mol_type = other DNA
                        organism = synthetic construct
SEQUENCE: 402
tcatctacac agtgactttg agg                                            23

SEQ ID NO: 403          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 403
gagggagtgg gggattgggg ggg                                            23

SEQ ID NO: 404          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 404
gggagggagg aggggtggct cgg                                            23

SEQ ID NO: 405          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 405
agggagtggg ggattggggg ggg                                            23

SEQ ID NO: 406          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 406
aacaacaaaa acaaaaccag agg                                            23

SEQ ID NO: 407          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 407
ctatggggg tggggtggg tgg                                              23

SEQ ID NO: 408          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 408
ggagggagtg ggggattggg ggg                                            23

SEQ ID NO: 409          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
```

-continued

```
                            organism = synthetic construct
SEQUENCE: 409
tgcctgtaat cccacaaatg agg                                      23

SEQ ID NO: 410          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 410
gagtggggga ttgggggggg ggg                                      23

SEQ ID NO: 411          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 411
agggcaggag gcgggagggg agg                                      23

SEQ ID NO: 412          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 412
caggaggcgg ggagggagga ggg                                      23

SEQ ID NO: 413          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 413
aggaggcggg gagggaggag ggg                                      23

SEQ ID NO: 414          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 414
ggagtggggg attggggggg ggg                                      23

SEQ ID NO: 415          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 415
gggagtgggg gattggggggg ggg                                     23

SEQ ID NO: 416          moltype = DNA  length = 23
FEATURE                 Location/Qualifiers
misc_feature            1..23
                        note = Synthetic: Guide Sequence for AAVS1- Like Sequence
                         in CHO
source                  1..23
                        mol_type = other DNA
                        organism = synthetic construct
SEQUENCE: 416
```

-continued

```
gcaggaggcg gggagggagg agg                                        23

SEQ ID NO: 417         moltype = DNA  length = 23
FEATURE                Location/Qualifiers
misc_feature           1..23
                       note = Synthetic: Guide Sequence for AAVS1- Like Sequence
                       in CHO
source                 1..23
                       mol_type = other DNA
                       organism = synthetic construct
SEQUENCE: 417
aggcggggag ggaggagggg tgg                                        23

SEQ ID NO: 418         moltype = DNA  length = 23
FEATURE                Location/Qualifiers
misc_feature           1..23
                       note = Synthetic: Guide Sequence for AAVS1- Like Sequence
                       in CHO
source                 1..23
                       mol_type = other DNA
                       organism = synthetic construct
SEQUENCE: 418
gcttggaaag tagaggcagg agg                                        23

SEQ ID NO: 419         moltype = DNA  length = 23
FEATURE                Location/Qualifiers
misc_feature           1..23
                       note = Synthetic: Guide Sequence for AAVS1- Like Sequence
                       in CHO
source                 1..23
                       mol_type = other DNA
                       organism = synthetic construct
SEQUENCE: 419
gagagagaga gagagagttg agg                                        23
```